(12) United States Patent
Tamaki et al.

(10) Patent No.: US 7,923,573 B2
(45) Date of Patent: Apr. 12, 2011

(54) BENZENE COMPOUND HAVING 2 OR MORE SUBSTITUENTS

(75) Inventors: Kazuhiko Tamaki, Tokyo (JP);
Takahiro Yamaguchi, Tokyo (JP); Kozo Oda, Tokyo (JP); Naoki Terasaka, Tokyo (JP); Daisuke Nakai, Tokyo (JP); Masakazu Nakadai, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 865 days.

(21) Appl. No.: 11/577,822

(22) PCT Filed: Oct. 26, 2005

(86) PCT No.: PCT/JP2005/019676
§ 371 (c)(1),
(2), (4) Date: May 30, 2007

(87) PCT Pub. No.: WO2006/046593
PCT Pub. Date: May 4, 2006

(65) Prior Publication Data
US 2008/0004301 A1    Jan. 3, 2008

(30) Foreign Application Priority Data

Oct. 27, 2004  (JP) ................................. 2004-311821
Jun. 28, 2005  (JP) ................................. 2005-187686

(51) Int. Cl.
*C07C 69/76*    (2006.01)
*C07C 69/00*    (2006.01)
*A01N 31/14*    (2006.01)

(52) U.S. Cl. ............... 560/61; 560/64; 560/65; 514/717

(58) Field of Classification Search .................. None
See application file for complete search history.

(56) References Cited

U.S. PATENT DOCUMENTS

| | | |
|---|---|---|
| 4,231,938 A | 11/1980 | Monaghan et al. |
| 4,287,341 A | 9/1981 | Hess et al. |
| 4,294,846 A | 10/1981 | Albers-Schonberg et al. |
| 4,294,926 A | 10/1981 | Monaghan et al. |
| 4,319,039 A | 3/1982 | Albers-Schonberg |
| 4,342,767 A | 8/1982 | Albers-Schonberg et al. |
| 4,346,227 A | 8/1982 | Terahara et al. |
| 4,420,491 A | 12/1983 | Albers-Schonberg et al. |
| 4,444,784 A | 4/1984 | Hoffman et al. |
| 4,739,073 A | 4/1988 | Kathawala |
| 5,006,530 A | 4/1991 | Angerbauer et al. |
| 5,120,738 A | 6/1992 | Ikawa et al. |
| 5,260,440 A | 11/1993 | Hirai et al. |
| 5,270,317 A | 12/1993 | Bernhart et al. |
| 5,273,995 A | 12/1993 | Roth |
| 5,352,788 A | 10/1994 | Bernhart et al. |
| 5,399,578 A | 3/1995 | Buhlmayer |
| 5,409,947 A | 4/1995 | Tomiyama |
| 5,459,148 A | 10/1995 | Yanagisawa et al. |
| 5,475,130 A | 12/1995 | Sato et al. |
| 5,491,172 A | 2/1996 | Lee et al. |
| 5,559,233 A | 9/1996 | Bernhart et al. |
| 5,591,762 A | 1/1997 | Havel et al. |
| 5,594,003 A | 1/1997 | Havel et al. |
| 5,602,127 A | 2/1997 | Havel et al. |
| 5,614,519 A | 3/1997 | Havel et al. |
| 5,633,287 A | 5/1997 | Lee et al. |
| 5,733,931 A | 3/1998 | Yamada et al. |
| 5,772,629 A | 6/1998 | Kaplan |
| 5,849,732 A | 12/1998 | Suzuki et al. |
| 5,854,259 A | 12/1998 | Fujikawa et al. |
| 5,856,336 A | 1/1999 | Fijikawa et al. |
| 5,965,592 A | 10/1999 | Buhlmayer |

(Continued)

FOREIGN PATENT DOCUMENTS

EP    0253310 A    1/1988

(Continued)

OTHER PUBLICATIONS

Vanags et al., Berichte der Deutschen Chemischen Gesellschaft [Abteilung] B: Abhandlungen (1943), 76B, 479-83, Database CAS abstract No. 1943:42208.*

(Continued)

*Primary Examiner* — Karl J Puttlitz
(74) *Attorney, Agent, or Firm* — Brandon T. Schurter; Locke Lord Bissell & Liddell

(57) ABSTRACT

A superior LXR modulator is provided. A compound represented by the general formula (I):

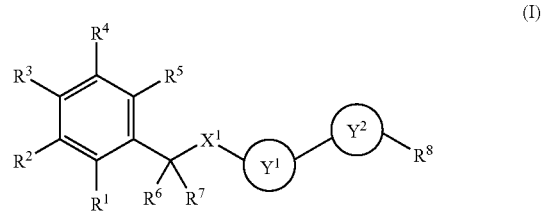

[wherein $R^1$: —$COR^9$ (wherein $R^9$: alkyl, optionally substituted alkoxy or optionally substituted amino); $R^2$: H, OH, alkoxy, optionally substituted amino, etc.; $R^3$: H, optionally substituted alkyl, cycloalkyl, optionally substituted alkoxy, optionally substituted amino, halogeno, etc.; $R^4$ and $R^5$: H, optionally substituted alkyl, halogeno, etc.; $R^6$ and $R^7$: H, alkyl; $R^8$: —$X^2R^{10}$ [wherein $R^{10}$: —$COR^{11}$ (wherein $R^{11}$: OH, optionally substituted alkoxy, optionally substituted amino, etc.), —$SO_2R^{12}$ (wherein $R^{12}$: optionally substituted alkyl, optionally substituted amino, etc.), tetrazol-5-yl, etc.; $X^2$: single bond, optionally substituted alkylene, etc.]; $X^1$: —NH—, —O—, —S—, etc.; $Y^1$: optionally substituted phenyl, optionally substituted 5- to 6-membered aromatic heterocyclyl; $Y^2$: optionally substituted aryl, optionally substituted heterocyclyl, etc.] and the like is provided.

75 Claims, No Drawings

U.S. PATENT DOCUMENTS

| | | | |
|---|---|---|---|
| 5,990,150 A | 11/1999 | Matsui et al. | |
| 5,990,173 A | 11/1999 | Patoiseau et al. | |
| 6,063,806 A | 5/2000 | Kamiya et al. | |
| 6,093,719 A | 7/2000 | Bocan | |
| 6,124,309 A | 9/2000 | Bocan | |
| 6,127,403 A | 10/2000 | Matsui et al. | |
| 6,143,755 A | 11/2000 | Bocan | |
| 6,200,988 B1 | 3/2001 | Kamiya et al. | |
| 6,316,503 B1 | 11/2001 | Li et al. | |
| 6,426,365 B1 | 7/2002 | Shinkai et al. | |
| 6,753,346 B2 | 6/2004 | Shinkai et al. | |
| 7,005,440 B1 | 2/2006 | Joyyosi | 514/375 |
| 7,271,196 B2 | 9/2007 | Shinkai et al. | |
| 7,579,379 B2 | 8/2009 | Shinkai et al. | |
| 2003/0073614 A1 | 4/2003 | Schulman | |
| 2003/0086923 A1 | 5/2003 | Sparrow | |
| 2004/0152681 A1 | 8/2004 | Liao | |
| 2004/0214888 A1 | 10/2004 | Matsuura | 560/1 |
| 2007/0105959 A1 | 5/2007 | Kusuda | 514/367 |

FOREIGN PATENT DOCUMENTS

| | | |
|---|---|---|
| EP | 0403159 A | 12/1990 |
| EP | 0443983 A | 8/1991 |
| EP | 0459136 A | 12/1991 |
| EP | 0502314 A | 9/1992 |
| EP | 0511767 | 11/1992 |
| EP | 0520423 | 12/1992 |
| EP | 0987254 | 3/2000 |
| EP | 1 382 336 | 1/2004 |
| JP | 56122375 A | 9/1981 |
| JP | 57002240 A | 1/1982 |
| JP | 57163374 | 10/1982 |
| JP | 60500015 A | 1/1985 |
| JP | 1279866 A | 11/1989 |
| JP | 3058967 A | 3/1991 |
| JP | 5078328 A | 3/1993 |
| JP | 5178841 A | 7/1993 |
| JP | 5320139 A | 12/1993 |
| JP | 11049743 A | 2/1999 |
| JP | 1216974 A | 8/1999 |
| JP | 11222428 A | 8/1999 |
| JP | 2006-001926 | 1/2006 |
| JP | 2006-45203 | 2/2006 |
| WO | WO 91/14679 | 10/1991 |
| WO | WO 92/09561 | 6/1992 |
| WO | WO 96/10559 | 4/1996 |
| WO | WO 96/26948 | 9/1996 |
| WO | WO 97/28137 | 8/1997 |
| WO | WO 00/17164 | 3/2000 |
| WO | WO 00/54759 | 9/2000 |
| WO | WO 01/41704 | 6/2001 |
| WO | WO 01/60818 | 8/2001 |
| WO | WO 02/24632 | 3/2002 |
| WO | WO 02/46141 | 6/2002 |
| WO | WO 02/46172 | 6/2002 |
| WO | WO 02/46181 | 6/2002 |
| WO | WO 02/062302 | 8/2002 |
| WO | WO 03/031408 | 4/2003 |
| WO | WO 03/039480 | 5/2003 |
| WO | WO 03/045382 | 6/2003 |
| WO | WO 03/048140 | 6/2003 |
| WO | WO 03/053352 | 7/2003 |
| WO | WO 03/059874 | 7/2003 |
| WO | WO 03/059884 | 7/2003 |
| WO | WO 03/063576 | 8/2003 |
| WO | WO 03/063796 | 8/2003 |
| WO | WO 03-074101 | 9/2003 |
| WO | WO 03/082192 | 10/2003 |
| WO | WO 03/082205 | 10/2003 |
| WO | WO 03/082802 | 10/2003 |
| WO | WO 03/084544 | 10/2003 |
| WO | WO 03-090732 | 11/2003 |
| WO | WO 03/090732 | 11/2003 |
| WO | WO 03/090746 | 11/2003 |
| WO | WO 03/090869 | 11/2003 |
| WO | WO 03/099769 | 12/2003 |
| WO | WO 03/099775 | 12/2003 |
| WO | WO 03/103651 | 12/2003 |
| WO | WO 03/106435 | 12/2003 |
| WO | WO 2004/007464 | 1/2004 |
| WO | WO 2004/009091 | 1/2004 |
| WO | WO 2004/011448 | 2/2004 |
| WO | WO 2004/024161 | 3/2004 |
| WO | WO 2004/024162 | 3/2004 |
| WO | WO 2004/026816 | 4/2004 |
| WO | WO 2004/043939 | 5/2004 |
| WO | WO 2004/072041 | 8/2004 |
| WO | WO 2004-072042 | 8/2004 |
| WO | WO 2004/072042 | 8/2004 |
| WO | WO 2004/072046 | 8/2004 |
| WO | WO 2004/076418 | 9/2004 |
| WO | WO 2004/103376 | 12/2004 |
| WO | WO 2005/005416 | 1/2005 |
| WO | WO 2005/005417 | 1/2005 |
| WO | WO 2005/016277 | 2/2005 |
| WO | WO 2005/023188 | 3/2005 |
| WO | WO 2005/023196 | 3/2005 |
| WO | WO 2005/023247 | 3/2005 |
| WO | WO 2005/023782 | 3/2005 |
| WO | WO 2005/077124 | 8/2005 |
| WO | WO 2005-101011 | 10/2005 |
| WO | WO 2005/113499 | 12/2005 |
| WO | WO 2006/109633 | 10/2006 |
| WO | WO 2006/003923 | 12/2006 |

OTHER PUBLICATIONS

Askam, V. et al., "Oxidation and Claisen Condensation Products of 3-Nitro-o-xylene", J. Chem. Soc. C, 1969, 1935-1936.

Dawson, M. I. et al., "Conformationally Restricted Retinoids", J. Med. Chem., 1984, vol. 27, 1516-1531.

Desolms. et al., "Dual Protein Farnesyltransferase-Geranylgeranyltransferase-I Inhibitors as Potential Cancer Chemotherapeutic Agents", J. Med. Chem., 2003, vol. 46, 2973-2984.

Gu, Y. G. ; Bayburt, E. K., "Synthesis of 4-Alkyl-3,5-dibromo-, 3-Bromo-4,5-dialkyl- and 3,4,5-Trialkylpyridines via Sequential Metalation and Metal-Halogen Exchange of 3,5-Dibromopyridine", Tetrahedron Lett., 1966, vol. 37, 2565-2568.

Hanessian, S. et al., "Synthesis of Functionally Diverse and Conformationally Constrained Polycyclic Analogues of Proline and Prolinol", J. Org. Chem., 2003, vol. 68, 7204-7218.

Hofsløkken, N. U. et al., "Convenient Method for the ortho-Formylation of Phenols", Acta Chem. Scand., 1999, vol. 53, 258-262.

Jackson, P. M., "Preparation and Diels-Alder Reactivity of Thieno[2,3-c]-and Thieno[3,2-c]-pyran-3-ones, Stable 2,3-Dimethylenethiophene Derivatives; Synthesis of Benzothiophenes", J. Chem. Soc., Perkin Trans. 1, 1990, vol. 11, 2909-2918.

James, R. et al., "Synthesis, Biological Evaluation, and Preliminary Structure-Activity Considerations of a Series of Alkylphenols as Intravenous Anesthetic Agents", J. Med Chem., 1980, vol. 23, 1350-1357.

Larock, R. C. "Condensation Reaction", Chapter 5 in Comprehensive Organic Transformations. John Wiley & Sons, Inc, 1999.

Miller, J. A. et al., "Synthesis of 2,6-Bis(trifluoromethyl)phenol and Its Elaboration Into 'Metabolism-Resistant' Analogs of Tebufelone", J. Org. Chem., 1993, vol. 58, 2637-2639.

Fu, Y. et al., "Synthesis of a Sialyl Lewis$^x$ Mimetic Conjugated with DTPA, Potential Ligand of New Contrast Agents for Medical Imaging", Eur. J. Org. Chem., 2002, vol. 23, 3966-3973.

Nishide, H. et al., "Synthesis of and Ferromagnetic Coupling in Poly(phenylenevinylene)s Bearing Built-in-$t$-Butyl Nitroxides", Bull. Chem. Soc. Jpn., 1996, vol. 69, 499-508.

Tsuji. J., Palladium Reagents and Catalysis: New perspectives for the 21st Century. John Wiley & Sons, Inc, 2004.

Watanabe, T. et al., "Synthesis and Biological Evaluation of Phenylacetyl Derivatives Having Low Central Nervous System Permeability as Potent and Selective $M_2$ Muscarinic Receptor Antagonists[1)]", Chem. Pharm. Bull., 1998, vol. 46, 53-68.

Corey, E. J. et al., "Protection of Hydroxyl Groups as *tert*-Butyldimethylsilyl Derivatives", *J. Am. Chem. Soc.*, 1972, vol. 94, 6190-6191.

Green, T.H. et al., "Protective Groups in Organic Synthesis" John Wiley & Sons, Inc, 1999 (in particular Chapters 2, 3, 5, 7 and 10).

Harvison, P. J. et al., "Synthesis of 11H-Pyridocarbazoles and Derivatives. Comparison of Their DNA Binding and Antitumor Activity of 6H- and 7H-Pyridocarbazoles", J. Med. Chem., 1986, vol. 29, 1737-1743.

Menke, "A Novel Liver X Receptor Agonist Establishes Species Differences in the Regulation of Cholesterol 7a-Hydroxylase (CYP7a)", Endocrinology, 2002, vol. 143, 2548-2558.

Winkle, M. R. et al., "Regioselective Metalation Reactions of Some Substituted (Methoxymethoxy)areness", J. Org. Chem., 1982, vol. 47, 2101-2108.

Lescot, Elie et al., "Synthesis of 11H-Pyridocarbazoles and Derivatives. Comparison of Their DNA Binding and Antitumor Activity with Those of 6H- and 7H-Pyridocarbazoles", J. Med. Chem. 1986, 29, 1731-1737.

Casscells, W., "Mechnaisms of restenosis", TX Heart Inst J. 21, 68-77 (1994).

Bauters, C., "Mechanisms and prevention of restenosis: from experimental models to clinical practice", Cardiovasc. Res. 31, 835-846 (1996).

Chen, X., "Restenosis: emerging molecular targets going beyond drug-eluting stents", Drug Disc Today: Disease Mech 2, 1-9 (2005).

Elisaf, M., "Effects of Fibrates on Serum Metabolic Parameters", Current Medical Research and Opinion, vol. 18, No. 5, pp. 269-276, 2002.

Kastrati, A., "Sirolimus-eluting stent or paclitaxel-eluting stent vs. balloon angioplasty for prevention of recurrences in patients with coronary in-stent restenosis",. JAMA 293, 165-171 (2005).

Konigsberg, W., "The TF:VIIa complex: clinical significance, structure-function relationships and its role in signaling and metastasis", Thromb Haemost 86, 757-771 (2001).

Lefkovis, J., "Pharmacological approaches for the prevention of restenosis after percutaneous coronary intervention", Prog Cardiovasc Diseases 40, 141-158 (1997).

Losordo, D., "Endothelial Recovery: the next target in restenosis prevention", Circ 107, 2635-2637 (2003).

Mackman, N., "Regulation of the tissue factor gene", FASEB J 9, 883-889 (1995).

Merriam Webster's Collegiate Dictionary, entries 1. inhibit; 2. prohibit; and 3. prophylaxis (1996 edition).

Fu, Y. et al., "Intravascular tissue factor initiates coagulation via circulating microvesicles and platelets", FASEB J. 17, 476-478 (2003).

Sheppard, R., "Intracoronary radiotherapy for restenosis", NEJM 344, 295-297 (2001).

Spencer, et al., "Pharmacophore Analysis of the Nuclear Oxysterol Receptor LXRa," J. Med. Chem., vol. 44, 886-897, (2001).

Terasaka, N. et al., "Liver X Receptor Agonists Inhibit Tissue Factor Expression in Macrophages", FEBS Journal, vol. 272, pp. 1546-1556, 2005.

Wilcox, J., "Localization of tissue factor in the normal vessel wall and in the atherosclerotic plaque", PNAS 86, 2839-2843 (1989).

International Search Report for International Application No. PCT/JP2005/012185.

Ross, R., "Cell Biology of Atherosclerosis", Annu. Rev. Phyisol., 57, pp. 791-804, 1995.

Steinberg, D., "Low Density Lipoprotein Oxidation and Its Pathobiological Significance", J. Biol. Chem., 272, pp. 20963-20966, 1997.

Janowski, B.A. et al., "An oxysterol signaling pathway mediated by the nuclear receptor LXRα", Nature, 383, pp. 728-731, 1996.

Lu, T.T. et al., "Orphan Nuclear Receptors as eLiXiRs and FiXeRs of Sterol Metabolism", J. Biol. Chem., 276, pp. 37735-37738, 2001.

Repa, J.J. et al., "Regulation of Absorption and ABC1-Mediated Efflux of Cholesterol by RXR Heterdimers", Science, 289, pp. 1524-1529, 2002.

Ross, R., "The Pathogenesis of Atherosclerosis", N. Engl. J. Med., 314, pp. 488-500, 1986.

Manglesdorf, D.J. et al., "Reciprocal regulation of inflammation and lipid metabolism by liver X receptors", Nat. Med., 9, pp. 213-219, 2003.

Fowler, A.J. et al., "Liver X Receptor Activators Display Anti-Inflammatory Activity in Irritant and Allergic Contact Dermatitis Models: Liver-X-Receptor-Specific Inhibition of Inflammation and Primary Cytokine Production", J. Invest. Dermatol., 120, pp. 246-255, 2003.

English publication of International Search Report for Application No. PCT/JP2005/019676, filed Oct. 26, 2005, completed international search on Dec. 20, 2005 and mailed on Jan. 17, 2006.

English language abtract WO 2004/007464; Publication Date: Jan. 22, 2004.

English language abstract of WO 2003/048140; Published Date: Jun. 12, 2003.

Bennett, D. et al., "Liver X Receptor Agonists As A Treatment for Atherosclerosis", Expert Opin. Ther. Patents, ISSN: 1354-3776, 14:7, pp. 967-982, Jan. 1, 2004.

European Supplementary Search Report and the European Search Opinion, for EP application No. EP 05799391.7, mailed on Mar. 3, 2010.

Muller I., "Intravascular tissue factor initiates coagulation via circulating microvesicles and platelets." Faseb J., 17, 476-478 (2003).

Rauch et al. Thrombus Formation on Atherosclerotic Plaques: Pathogenesis and Clinical Consequences. Ann. Intern. Med. 134, 224-238 (2001).

Supplemental Search Report and Search Opinion for EP05755860 as issued in the related EP case, dated Jun. 14, 2010.

* cited by examiner

BENZENE COMPOUND HAVING 2 OR MORE SUBSTITUENTS

This application claims the benefit of International Application Number PCT/JP2005/019676, filed on Oct. 26, 2005 under 35 USC §371, entitled, "Benzene Compound Having 2 or More Substituents," which claims the benefit of Japanese Patent Application Number 2004-311821, filed on Oct. 27, 2004 and Japanese Patent Application Number 2005-187686, filed on Jun. 28, 2005 all of which are hereby incorporated by reference.

TECHNICAL FIELD

The present invention relates to a benzene compound having two or more substituents or a pharmacologically acceptable salt or ester thereof, which demonstrates superior anti-arteriosclerotic and anti-inflammatory effects by regulating the function of liver X receptors (LXR), improving lipid metabolism disorders or controlling the formation of inflammatory mediators.

Moreover, the present invention relates to an LXR modulator, an LXR agonist or an LXR antagonist comprising a benzene compound having two or more substituents or a pharmacologically acceptable salt or ester thereof, preferably an LXR modulator or an LXR agonist, and more preferably an LXR modulator.

Moreover, the present invention relates to a pharmaceutical composition comprising as an active ingredient a benzene compound having two or more substituents, or a pharmaceutical acceptable salt or ester thereof, preferably a pharmaceutical composition for treating or preventing arteriosclerosis, atherosclerosis, arteriosclerosis caused by diabetes, hyperlipemia, hypercholesterolemia, lipid-associated diseases, inflammatory disease, auto-immune disease, arteriosclerotic heart disease, cardiovascular disease, coronary artery disease, cerebrovascular disease, kidney disease, diabetes, diabetic complications, obesity, nephritis, hepatitis, cancer or Alzheimer's disease; more preferably a pharmaceutical composition for treating or preventing arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease or diabetes; even more preferably a pharmaceutical composition for treating or preventing arteriosclerosis, atherosclerosis, arteriosclerosis caused by diabetes, arteriosclerotic heart disease, cardiovascular disease or coronary artery disease; still more preferably a pharmaceutical composition for treating or preventing arteriosclerosis, atherosclerosis or arteriosclerotic heart disease; and most preferably a pharmaceutical composition for treating or preventing arteriosclerosis. In addition, the present invention relates to a pharmaceutical composition for inducing ABCA1 expression or promoting reverse cholesterol transport comprising as an active ingredient a benzene compound having two or more substituents or a pharmacologically acceptable salt or ester thereof.

Moreover, the present invention relates to the use of a benzene compound having two or more substituents or a pharmacologically acceptable salt or ester thereof, for preparing a pharmaceutical composition, preferably a pharmaceutical composition for treating or preventing the aforementioned diseases.

Moreover, the present invention relates to a method for treating or preventing a disease, preferably for treating or preventing the aforementioned diseases, by administering a pharmacologically effective amount of a benzene compound having two or more substituents or a pharmacologically acceptable salt or ester thereof, to a warm-blooded animal (particularly a human).

Moreover, the present invention relates to a method for preparing a benzene compound having two or more substituents or a pharmacologically acceptable salt or ester thereof.

BACKGROUND OF THE ART

Circulatory diseases caused by hypertension, hyperlipemia or hyperglycemia and so forth (such as heart disease, cerebrovascular disease or kidney disease) are becoming a serious problem in advanced countries. An antihypertensive medicine, an antihyperlipemic medicine and an antidiabetic medicine are used for the treatment of hypertension, hyperlipemia and hyperglycemia, respectively. In the clinical setting, α- and β-blockers, diuretics, calcium antagonists, ACE inhibitors, A-II antagonists and so forth are used as an antihypertensive medicine; HMG-CoA reductase inhibitors, anion exchange resins, nicotinic acid derivatives, probucol, fibrates and so forth are used as an antihyperlipidemic medicine; and insulin, sulfonylureas, metformin, glitazones and so forth are used as an antidiabetic medicine. These medicines contribute to regulation of blood pressure and lipid or glucose levels in the blood. However, since the use of these medicines has not resulted in a remarkable improvement of the mortality rates due to heart disease, cerebrovascular disease and kidney disease, there is a need for the development of a superior therapeutic medicine for these diseases.

A direct risk factor of circulatory disease is arteriosclerosis accompanying hypertrophy of artery walls, and the cause of this hypertrophy is the formation of plaque resulting from accumulation of oxidized low-density lipoprotein cholesterol (LDL-C) on artery walls (Ross, R., Annu. Rev. Physiol., 57, pp. 791-804, 1995; Steinberg, D., J. Biol. Chem., 272, pp. 20963-20966, 1997). This plaque inhibits the flow of blood and promotes the formation of thrombi.

The nuclear receptor, LXR, has recently been determined to play an important role in the regulation of lipid metabolism (Janowski, B. A., Willy, P. J., Falck, J. R., Mangelsdorf, D. J., Nature, 383, pp. 728-731, 1996). LXR has two types of isoforms consisting of LXRα and LXRβ. LXRα is highly distributed in the liver of mammals and only distributed in small amounts in the kidney, small intestine, spleen and adrenals, while LXRβ is distributed in organs and tissues throughout the body. LXR is subject to regulation of transcription by oxidized sterol present in macrophages of vascular walls, induces an expression of ABCA1 (ATP binding cassette transporter-1) and ApoE (apolipoprotein E), and promotes extraction of cholesterol from vascular walls and reverse cholesterol transport to the liver (Lu, T. T., Repa, J. J., Mangelsdorf, D. J., J. Biol. Chem., 276, pp. 37735-37738, 2001). In addition, LXR induces expression of ABCA1 in the small intestine, and inhibits absorption of dietary cholesterol from the digestive tract (Repa, J. J., Turley, S. D., Lobaccaro, J. A., Medina, J., Li, L., Lustig, K., Shan, B., Heyman, R. A., Dietschy, J., Mangelsdorf, D. J., Science, 289, pp. 1524-1529, 2002). In consideration of the importance of LXR in cholesterol metabolism, medicines which regulate LXR can be expected to be useful in the treatment or prevention of arteriosclerosis, atherosclerosis, arteriosclerosis caused by diabetes, hyperlipemia, lipid-associated diseases, arteriosclerotic heart disease, cardiovascular disease or coronary artery disease.

Atherosclerosis is also considered to be a chronic inflammatory disease (Ross, R., N. Engl. J. Med., 314, pp. 488-500, 1986). LXR has recently been reported to play an important role in the control of immune functions by regulating the expression of inflammatory mediators such as nitric oxide synthase, cyclooxygenase-2 (COX-2) and interleukin-6 (IL-6) (Mangelsdorf, D. J., Tontonoz, P., et al., Nat. Med., 9, pp. 213-219, 2003). Thus, in addition to improving lipid metabolism, LXR modulators are expected to inhibit the onset and progression of arteriosclerosis by improving lipid metabolism as well as anti-inflammatory action. Moreover, naturally-occurring and synthetic LXR activators have been shown to reduce chemically-induced dermatitis in animal models (Fowler, A. J., et al., J. Invest. Dermatol., 120, pp. 246-255, 2003). In this manner, LXR modulators are expected to be useful for the treatment of various inflammatory diseases.

Although benzene compounds having two or more substituents showing an LXR regulatory effect (namely, having an effect on the expression of ABCA1) are known, their structures differ to that of the compound of the present invention (see Patent documents 1 and 2).
[Patent Document 1]
International Patent Publication No. 2004/026816 pamphlet
[Patent Document 2]
International Patent Publication No. 2002/024632 pamphlet

DISCLOSURE OF THE INVENTION

Object of the Invention

As a result of conducting extensive studies on the synthesis and pharmacological activity of benzene compounds having two or more substituents to find a compound having superior binding activity to LXR, the inventors of the present invention found that a specific benzene compound having two or more substituents has superior binding activity to LXR, thereby leading to completion of the present invention.

Means for Achieving the Object

The present invention provides a benzene compound having two or more substituents or a pharmacologically acceptable salt or ester thereof, which demonstrates superior anti-arteriosclerotic and anti-inflammatory effects by regulating the function of LXR, improving lipid metabolism disorders or controlling the formation of inflammatory mediators.

Moreover, the present invention provides an LXR modulator, an LXR agonist or an LXR antagonist comprising a benzene compound having two or more substituents or a pharmacologically acceptable salt or ester thereof, preferably an LXR modulator or an LXR agonist, and more preferably an LXR modulator.

Moreover, the present invention provides a pharmaceutical composition comprising as an active ingredient a benzene compound having two or more substituents or a pharmacologically acceptable salt or ester thereof, preferably a pharmaceutical composition for treating or preventing arteriosclerosis, atherosclerosis, arteriosclerosis caused by diabetes, hyperlipemia, hypercholesterolemia, lipid-associated diseases, inflammatory disease, auto-immune disease, arteriosclerotic heart disease, cardiovascular disease, coronary artery disease, cerebrovascular disease, kidney disease, diabetes, diabetic complications, obesity, nephritis, hepatitis, cancer or Alzheimer's disease; more preferably a pharmaceutical composition for treating or preventing arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease or diabetes; even more preferably a pharmaceutical composition for treating and or preventing arteriosclerosis, atherosclerosis, arteriosclerosis caused by diabetes, arteriosclerotic heart disease, cardiovascular disease or coronary artery disease; still more preferably a pharmaceutical composition for treating or preventing arteriosclerosis, atherosclerosis or arteriosclerotic heart disease; and most preferably a pharmaceutical composition for treating or preventing arteriosclerosis. In addition, the present invention provides a pharmaceutical composition for inducing ABCA1 expression or promoting reverse cholesterol transport comprising as an active ingredient a benzene compound having two or more substituents or a pharmacologically acceptable salt or ester thereof.

Moreover, the present invention provides the use of a benzene compound having two or more substituents or a pharmacologically acceptable salt or ester thereof, for preparing a pharmaceutical composition, preferably a pharmaceutical composition for treating or preventing the aforementioned diseases.

Moreover, the present invention provides a method for treating or preventing a disease, preferably for treating or preventing the aforementioned diseases, by administering a pharmacologically effective amount of a benzene compound having two or more substituents or a pharmacologically acceptable salt or ester thereof, to a warm-blooded animal (particularly a human).

Moreover, the present invention provides a method for preparing a benzene compound having two or more substituents or a pharmacologically acceptable salt or ester thereof. The present invention provides
(1) a compound represented by the general formula (I) or a pharmacologically acceptable salt or ester thereof:

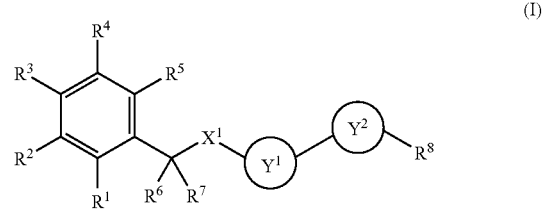

(I)

[wherein $R^1$ represents a group having the formula —$COR^9$ [wherein $R^9$ represents a $C_1$-$C_{10}$ alkyl group, a $C_1$-$C_{10}$ alkoxy group, a halogeno $C_1$-$C_{10}$ alkoxy group (wherein said halogeno $C_1$-$C_{10}$ alkoxy group represents a $C_1$-$C_{10}$ alkoxy group substituted with 1 to 7 halogeno groups), a phenyl-($C_1$-$C_{10}$ alkoxy) group, a $C_1$-$C_{10}$ alkylamino group or a di($C_1$-$C_{10}$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)];

$R^2$ represents a hydrogen atom, a halogeno $C_1$-$C_4$ alkyl group (wherein said halogeno $C_1$-$C_4$ alkyl group represents a $C_1$-$C_4$ alkyl group substituted with 1 to 5 halogeno groups), a hydroxyl group, a $C_1$-$C_4$ alkoxy group, an amino group, a $C_1$-$C_4$ alkylamino group, a di($C_1$-$C_4$ alkyl)amino group (wherein said alkyl groups may be the same or different) or a halogeno group;

$R^3$ represents a hydrogen atom, a $C_1$-$C_6$ alkyl group, a halogeno $C_1$-$C_6$ alkyl group (wherein said halogeno $C_1$-$C_6$ alkyl group represents a $C_1$-$C_6$ alkyl group substituted with 1 to 7 halogeno groups), a ($C_1$-$C_4$ alkoxy)-($C_1$-$C_4$ alkyl) group, a ($C_1$-$C_4$ alkylthio)-($C_1$-$C_4$ alkyl) group, a ($C_1$-$C_4$ alkylsulfinyl)-($C_1$-$C_4$ alkyl) group, a ($C_1$-$C_4$ alkylsulfonyl)-$C_1$-$C_4$ alkyl) group, a ($C_1$-$C_4$ alkylamino)-($C_1$-$C_4$ alkyl) group, a [di($C_1$-$C_4$ alkyl)amino]-($C_1$-$C_4$ alkyl) group (wherein said alkyl groups may be the same or different), a $C_3$-$C_6$ cycloalkyl group, a $C_2$-$C_6$ alkenyl group, a $C_2$-$C_6$ alkynyl group, a hydroxyl group, a $C_1$-$C_6$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a ($C_1$-$C_6$ alkoxy)carbonyl group, a cyano group, a nitro group or a halogeno group;

$R^4$ and $R^5$ may be the same or different and each represents a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_6$ cycloalkyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups) or a halogeno group;

$R^6$ and $R^7$ may be the same or different and each represents a hydrogen atom or a $C_1$-$C_3$ alkyl group;

$R^8$ represents a group having the formula —$X^2R^{10}$ [wherein $R^{10}$ represents a group having the formula —$COR^{11}$ [wherein $R^{11}$ represents a $C_1$-$C_6$ alkyl group, a hydroxyl group, a $C_1$-$C_1$ alkoxy group, a ($C_3$-$C_8$ cycloalkyl)-($C_1$-$C_6$ alkyl)oxy group, a $C_3$-$C_8$ cycloalkyloxy group, an amino group, a $C_1$-$C_6$ alkylamino group, a [($C_3$-$C_8$ cycloalkyl)-($C_1$-$C_6$ alkyl)]amino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di[($C_3$-$C_8$ cycloalkyl)-($C_1$-$C_6$ alkyl)]amino group, a di($C_3$-$C_8$ cycloalkyl)amino group, a N—[($C_3$-$C_8$ cycloalkyl)-($C_1$-$C_6$ alkyl)]-N—($C_1$-$C_6$ alkyl)amino group, a N—($C_3$-$C_8$ cycloalkyl)-N—($C_1$-$C_6$ alkyl)amino group, a N—[($C_3$-$C_8$ cycloalkyl)-($C_1$-$C_6$ alkyl)]-N—($C_3$-$C_8$ cycloalkyl)amino group, a hydroxylamino group or a hydroxyl($C_1$-$C_6$ alkyl)amino group], a group having the formula —$SO_2R^{12}$ [wherein $R^{12}$ represents a $C_1$-$C_6$ alkyl group, a ($C_3$-$C_8$ cycloalkyl)-($C_1$-$C_6$ alkyl) group, a $C_3$-$C_8$ cycloalkyl group, an amino group, a $C_1$-$C_6$ alkylamino group, a [($C_3$-$C_8$ cycloalkyl)-($C_1$-$C_6$ alkyl)] amino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di[($C_3$-$C_8$ cycloalkyl)-($C_1$-$C_6$ alkyl)]amino group, a di($C_3$-$C_8$ cycloalkyl)amino group, a N—[($C_3$-$C_8$ cycloalkyl)-($C_1$-$C_6$ alkyl)]-N—($C_1$-$C_6$ alkyl)amino group, a N—($C_3$-$C_8$ cycloalkyl)-N—($C_1$-$C_6$ alkyl)amino group or a N—[($C_3$-$C_8$ cycloalkyl)-($C_1$-$C_6$ alkyl)]-N—($C_3$-$C_8$ cycloalkyl)amino group], a group having the formula —N($R^{13}$)$COR^{14}$ [wherein $R^{13}$ represents a hydrogen atom, a $C_1$-$C_6$ alkyl group, a ($C_3$-$C_8$ cycloalkyl)-($C_1$-$C_6$ alkyl) group or a $C_4$-$C_8$ cycloalkyl group, and $R^{14}$ represents a hydrogen atom, a $C_1$-$C_6$ alkyl group, a ($C_3$-$C_8$ cycloalkyl)-($C_1$-$C_6$ alkyl) group or a $C_3$-$C_8$ cycloalkyl group], a group having the formula —N($R^{13}$)$SO_2R^{15}$ [wherein $R^{13}$ is the same as previously defined, and $R^{15}$ represents a $C_1$-$C_6$ alkyl group, a ($C_3$-$C_3$ cycloalkyl)-($C_1$-$C_6$ alkyl) group or a $C_3$-$C_6$ cycloalkyl group], or a tetrazol-5-yl group, and $X^2$ represents a single bond, a $C_1$-$C_4$ alkylene group or a substituted $C_1$-$C_4$ alkylene group (wherein said substituents may be the same or different and are one or two groups selected from Substituent group γ, or two of said substituents may together form a methylene group, an ethylene group or a trimethylene group)];

$X^1$ represents a group having the formula —NH— or —$NR^{16}$— (wherein $R^{16}$ represents a $C_1$-$C_4$ alkyl group), —O—, —S—, —SO— or —$SO_2$—;

$Y^1$ represents a phenyl group, a substituted phenyl group (wherein said substituents may be the same or different and are 1 to 3 groups selected from Substituent group α), a 5- or 6-membered aromatic heterocyclyl group or a substituted 5- or 6-membered aromatic heterocyclyl group (wherein said substituents may be the same or different and are 1 to 3 groups selected from Substituent group α);

$Y^2$ represents a 6- to 10-membered aryl group, a substituted 6- to 10-membered aryl group (wherein said substituents may be the same or different and are 1 to 3 groups selected from Substituent group β), a 9- or 10-membered unsaturated cyclic hydrocarbon group (provided that $Y^1$ is bonded to a benzene ring part in said unsaturated cyclic hydrocarbon group), a substituted 9- or 10-membered unsaturated cyclic hydrocarbon group (provided that $Y^1$ is bonded to a benzene ring part in said unsaturated cyclic hydrocarbon group, and said substituents may be the same or different and are 1 to 3 groups selected from Substituent group β), a 5- to 10-membered aromatic heterocyclyl group or a substituted 5- to 10-membered aromatic heterocyclyl group (wherein said substituents may be the same or different and are 1 to 3 groups selected from Substituent group β), a 9- or 10-membered unsaturated heterocyclyl group (provided that $Y^1$ is bonded to an aromatic ring part in said unsaturated heterocyclyl group) or a substituted 9- or 10-membered unsaturated heterocyclyl group (provided that $Y^1$ is bonded to an aromatic ring part in said unsaturated heterocyclyl group, and said substituents may be the same or different and are 1 to 3 groups selected from Substituent group β);

Substituent group α represents the group consisting of a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a hydroxyl group, a $C_1$-$C_4$ alkoxy group and a halogeno group;

Substituent group β represents the group consisting of a $C_1$-$C_6$ alkyl group, a hydroxy($C_1$-$C_6$ alkyl) group, a carboxy ($C_1$-$C_6$ alkyl) group, a ($C_1$-$C_6$ alkoxy)carbonyl-($C_1$-$C_6$ alkyl) group, a halogeno $C_1$-$C_6$ alkyl group (wherein said halogeno $C_1$-$C_6$ alkyl group represents a $C_1$-$C_6$ alkyl group substituted with 1 to 7 halogeno atoms), a ($C_3$-$C_8$ cycloalkyl)-($C_1$-$C_6$ alkyl) group, a $C_2$-$C_7$ alkenyl group, a $C_2$-$C_7$ alkynyl group, a $C_3$-$C_8$ cycloalkyl group, a hydroxyl group, a $C_1$-$C_6$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di($C_3$-$C_8$ cycloalkyl)amino group, a N—($C_3$-$C_8$ cycloalkyl)-N—($C_1$-$C_6$ alkyl)amino group, a formylamino group, a ($C_1$-$C_6$ alkyl)carbonylamino group, a ($C_3$-$C_8$ cycloalkyl)carbonylamino group, a N—[($C_1$-$C_6$ alkyl)carbonyl]-N—($C_1$-$C_6$ alkyl)amino group, a N—[($C_3$-$C_8$ cycloalkyl)carbonyl]-N—($C_1$-$C_6$ alkyl)amino group, a $C_1$-$C_6$ alkylsulfonylamino group, a N—($C_1$-$C_6$ alkylsulfonyl)-N—($C_1$-$C_6$ alkyl)amino group, a N—($C_1$-$C_6$ alkylsulfonyl)-N—($C_3$-$C_8$ cycloalkyl)amino group, a formyl group, a ($C_1$-$C_6$ alkyl)carbonyl group, a carboxyl group, a ($C_1$-$C_6$ alkoxy)carbonyl group, a carbamoyl group, a ($C_1$-$C_6$ alkylamino)carbonyl group, a ($C_3$-$C_8$ cycloalkylamino)carbonyl group, a di($C_1$-$C_6$ alkyl)aminocarbonyl group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a N—($C_3$-$C_8$ cycloalkyl)-N—($C_1$-$C_6$ alkyl)aminocarbonyl group, a cyano group, a nitro group and a halogeno group; and, Substituent group γ represents the group consisting of a $C_1$-$C_6$ alkyl group, a hydroxy($C_1$-$C_6$ alkyl) group, a ($C_1$-$C_6$ alkoxy)-($C_1$-$C_6$ alkyl) group, a mercapto($C_1$-$C_6$ alkyl) group, a ($C_1$-$C_6$ alkylthio)-($C_1$-$C_6$ alkyl) group, a ($C_1$-$C_6$ alkylsulfinyl)-($C_1$-$C_6$ alkyl) group, a ($C_1$-$C_{16}$ alkylsulfonyl)-($C_1$-$C_6$ alkyl) group, an amino($C_1$-$C_6$ alkyl) group, a ($C_1$-$C_6$ alkylamino)-($C_1$-$C_6$ alkyl) group, a ($C_3$-$C_8$ cycloalkylamino)-($C_1$-$C_6$ alkyl) group, a di($C_1$-$C_6$ alkyl)amino-($C_1$-$C_6$ alkyl) group (wherein said alkyl groups may be the same or different and two of said alkyl groups of the di($C_1$-$C_6$ alkyl)amino moiety may, together with the nitrogen atom of said amino group, form a 5- to 7-membered saturated heterocyclyl group containing 1 to 3 atoms selected from the group consisting of a nitrogen atom, an oxygen atom and a sulfur atom), a di($C_3$-$C_8$ cycloalkyl)amino-($C_1$-$C_6$ alkyl) group, a [N—($C_3$-$C_8$, cycloalkyl)-N—($C_1$-$C_6$ alkyl)amino]-($C_1$-$C_6$ alkyl) group, a hydroxyl group, a $C_1$-$C_6$ alkoxy group, a $C_3$-$C_8$ cycloalkyloxy group, a mercapto group, a $C_1$-$C_6$ alkylthio group, a $C_3$-$C_8$ cycloalkylthio group, a $C_1$-$C_6$ alkylsulfinyl group, a $C_3$-$C_8$ cycloalkylsulfinyl group, a $C_1$-$C_6$ alkylsulfonyl group, a $C_3$-$C_8$ cycloalkylsulfonyl group, an amino group, a $C_1$-$C_6$ alkylamino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di($C_3$-$C_8$ cycloalkyl)amino group, a N—($C_3$-$C_8$ cycloalkyl)-N—($C_1$-$C_6$ alkyl) amino group and a halogeno group].

In addition, the present invention provides an LXR modulator, an LXR agonist or an LXR antagonist comprising a benzene compound having two or more substituents or a pharmacologically acceptable salt or ester thereof, preferably an LXR modulator or an LXR agonist, and more preferably an LXR modulator.

In addition, the present invention provides a pharmaceutical composition comprising an effective amount of a compound represented by the aforementioned general formula (I) or a pharmacologically acceptable salt or ester thereof having a pharmacological activity, and a vehicle or diluent. In particular, the present invention provides the aforementioned pharmaceutical composition for treating or preventing a disease in a warm-blooded animal, and said warm-blooded animal may be a human having a disease which can be treated or prevented by regulating LXR function in a warm-blooded animal. Said disease may be a disease which can be treated or prevented by regulating LXR function, and preferably is a disease selected from the group consisting of arteriosclerosis, atherosclerosis, arteriosclerosis caused by diabetes, hyperlipemia, hypercholesterolemia, lipid-associated diseases, inflammatory disease, auto-immune disease, arteriosclerotic heart disease, cardiovascular disease, coronary artery disease, cerebrovascular disease, kidney disease, diabetes, diabetic complications, obesity, nephritis, hepatitis, cancer and Alzheimer's disease; more preferably a disease selected from the group consisting of arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease and diabetes; even more preferably a disease selected from the group consisting of arteriosclerosis, atherosclerosis, arteriosclerosis caused by diabetes, arteriosclerotic heart disease, cardiovascular disease and coronary artery disease; still more preferably a disease selected from the group consisting of arteriosclerosis, atherosclerosis and arteriosclerotic heart disease; and most preferably arteriosclerosis. The present invention also provides a pharmaceutical composition for inducing ABCA1 expression or promoting reverse cholesterol transport: comprising as an active ingredient a compound represented by the aforementioned general formula (I) or a pharmacologically acceptable salt or ester thereof.

In addition, the present invention provides a compound represented by the aforementioned general formula (I) or a pharmacologically acceptable salt or ester thereof, for use as a pharmaceutical.

In addition, the present invention provides the use of one or more of the compounds represented by the aforementioned general formula (I) or a pharmacologically acceptable salt or ester thereof, in the production of a pharmaceutical for treating or preventing a disease in a warm-blooded animal, and said warm-blooded animal may be a human having a disease which can be treated or prevented by regulating LXR function in a warm-blooded animal. Said disease may be the same as those indicated above.

In addition, the present invention provides a method for treating or preventing a disease in a warm-blooded animal by administering an effective amount of a compound represented by the aforementioned general formula (I) or a pharmacologically acceptable salt or ester thereof, to a warm-blooded animal, and said warm-blooded animal may be a human having a disease which can be treated or prevented by regulating LXR function in a warm-blooded animal. Said disease may be the same as those indicated above.

In addition, the present invention provides a pharmaceutical composition comprising a compound represented by the aforementioned general formula (I) or a pharmacologically acceptable salt or ester thereof; one or more pharmaceuticals selected from the group consisting of an HMG-CoA reductase inhibitor, HMG-CoA synthase inhibitor, serum HDL enhancer, cholesterol biosynthesis inhibitor, squalene epoxidase inhibitor, squalene synthase inhibitor, hypercholesterolemia therapeutic drug, acyl coenzyme A, cholesteryl ester transfer protein inhibitor (hereinafter abbreviated as CETP inhibitor), ACAT inhibitor, probucol, cholesterol absorption inhibitor, bile acid adsorption ion exchange resin, fibrate-based medicine, nicotinic acid derivative, niacin amide, LDL receptor inducing substance, vitamin $B_6$, vitamin $B_{12}$, anti-oxidative vitamin, angiotensin II inhibitor, angiotensin converting enzyme inhibitor, β-blocker, fibrinogen inhibitor, aspirin and diuretic; and a vehicle or diluent.

In a compound of the present invention represented by the general formula (I) or a pharmacologically acceptable salt or ester thereof described in (1) above, a preferred compound is (2) a compound described in (1), wherein $R^1$ is a group having the formula —$COR^{9a}$ [wherein $R^{9a}$ represents a $C_1$-$C_6$ alkyl group, a $C_1$-$C_8$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylamino group or a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], (3) a compound described in (1), wherein $R^1$ is a group having the formula —$COR^{9b}$ [wherein $R^{9b}$ represents a $C_1$-$C_6$ alkoxy group or a halogeno $C_1$-$C_4$ alkoxy group (wherein said halogeno $C_1$-$C_4$ alkoxy group represents a $C_1$-$C_4$ alkoxy group substituted with 1 to 5 halogeno groups)], (4) a compound described in (1), wherein $R^1$ is a group having the formula —$COR^{9c}$ (wherein $R^{9c}$ represents a $C_3$-$C_5$ alkoxy group), (5) a compound described in (1), wherein $R^1$ is a group having the formula —$COR^{9d}$ (wherein $R^{9d}$ represents a 2-methyl-2-propoxy group), (6) a compound described in any one of (1) to (5), wherein $R^2$ is a hydrogen atom, a trifluoromethyl group, a 2,2,2-trifluoroethyl group, a pentafluoroethyl group, a hydroxyl group, a fluoro group or a chloro group, (7) a compound described in any one of (1) to (5), wherein $R^2$ is a hydrogen atom or a hydroxyl group, (8) a compound described in any one of (1) to (5), wherein $R^2$ is a hydroxyl group, (9) a compound described in any one of (1) to (8), wherein $R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_2$-$C_4$ alkenyl group, a $C_2$-$C_4$ alkynyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a fluoro group, a chloro group or a bromo group,

(10) a compound described in any one of (1) to (8), wherein $R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_2$-$C_4$ alkenyl group, a $C_1$-$C_4$ alkoxy group, a fluoro group or a chloro group,

(11) a compound described in any one of (1) to (8), wherein $R^3$ is a methyl group, an ethyl group, a 2-propyl group, a 2-methyl-2-propyl group, a trifluoromethyl group, a 2,2,2-trifluoroethyl group, a methoxy group, a fluoro group or a chloro group,

(12) a compound described in any one of (1) to (8), wherein $R^3$ is a 2-propyl group, a 2-methyl-2-propyl group, a trifluoromethyl group or a chloro group,

(13) a compound described in any one of (1) to (8), wherein $R^3$ is a trifluoromethyl group,

(14) a compound described in any one of (1) to (13), wherein $R^4$ and $R^5$ may be the same or different and each is a hydrogen atom, a methyl group, an ethyl group, a trifluoromethyl group, cyclopropyl group, a hydroxyl group, a methoxy group, a fluoro group, a chloro group or a bromo group,

(15) a compound described in any one of (1) to (13), wherein $R^4$ is a hydrogen atom, and $R^5$ is a hydrogen atom or a hydroxyl group,

(16) a compound described in any one of (1) to (13), wherein $R^4$ and $R^5$ are hydrogen atoms,

(17) a compound described in any one of (1) to (16), wherein $R^6$ and $R^7$ may be the same or different and each is a hydrogen atom or a methyl group,

(18) a compound described in any one of (1) to (16), wherein $R^6$ and $R^7$ are hydrogen atoms,

(19) a compound described in any one of (1) to (11), wherein $R^8$ is a group having the formula —$X^{2a}R^{10a}$ [wherein $R^{10a}$ represents a group having the formula —$COR^{11a}$ [wherein, $R^{11a}$ represents a hydroxyl group, a $C_1$-$C_4$ alkoxy group, a ($C_3$-$C_6$ cycloalkyl)-($C_1$-$C_4$ alkyl)oxy group, a $C_3$-$C_6$ cycloalkyloxy group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a hydroxylamino group or a hydroxyl($C_1$-$C_4$ alkyl)]amino group], a group having the formula —$SO_2R^{12a}$ [wherein $R^{12a}$ represents a $C_1$-$C_4$ alkyl group, a ($C_3$-$C_6$ cycloalkyl)-($C_1$-$C_4$ alkyl) group, a $C_3$-$C_6$ cycloalkyl group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group or a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], a group having the formula —$N(R^{13a})COR^{14a}$ [wherein $R^{13a}$ represents a hydrogen atom, a $C_1$-$C_4$ alkyl group, a ($C_3$-$C_5$ cycloalkyl)-($C_1$-$C_2$ alkyl) group or a $C_3$-$C_5$ cycloalkyl group, and $R^{14a}$ represents a hydrogen atom, a $C_1$-$C_4$ alkyl group, a ($C_3$-$C_5$ cycloalkyl)-($C_1$-$C_2$ alkyl) group or a $C_3$-$C_5$ cycloalkyl group], a group having the formula —$N(R^{13a})SO_2R^{15a}$ [wherein $R^{13a}$ is the same as previously defined, and $R^{15a}$ represents a $C_1$-$C_4$ alkyl group, a ($C_3$-$C_5$ cycloalkyl)-($C_1$-$C_2$ alkyl) group or a $C_3$-$C_5$ cycloalkyl group], or a tetrazol-5-yl group, and $X^{2a}$ represents a single bond, a $C_1$-$C_2$ alkylene group or a substituted $C_1$-$C_2$ alkylene group (wherein said substituents may be the same or different and are one or two groups selected from Substituent group γ1, or two of said substituents may together form a methylene group, an ethylene group or a trimethylene group)]; and, Substituent group γ1 is the group consisting of a methyl group, an ethyl group, a hydroxymethyl group, a hydroxyethyl group, a methoxymethyl group, a methoxyethyl group, a methylthiomethyl group, a methylthioethyl group, an aminomethyl group, an aminoethyl group, a methylaminomethyl group, an ethylaminomethyl group, a methylaminoethyl group, a cyclopropylaminomethyl group, a cyclopropylaminoethyl group, a dimethylaminomethyl group, a dimethylaminoethyl group, a (N-methyl-N-ethylamino)methyl group, a dicyclopropylaminomethyl group, a hydroxyl group, a methoxy group, an ethoxy group, a cyclopropyloxy group, a methylthio group, an ethylthio group, a cyclopropylthio group, an amino group, a methylamino group, an ethylamino group, a cyclopropylamino group, a cyclobutylamino group, a dimethylamino group, a diethylamino group, a dicyclopropylamino group, a N-cyclopropyl-N-methylamino group, a fluoro group and a chloro group,

(20) a compound described in any one of (1) to (18), wherein $R^8$ is a group having the formula $—X^{2b}R^{10b}$ [wherein $R^{10b}$ represents a group having the formula $—COR^{11b}$ [wherein, $R^{11b}$ represents a hydroxyl group, a $C_1$-$C_4$ alkoxy group, a ($C_1$-$C_4$ cycloalkyl)-($C_1$-$C_2$ alkyl)oxy group, a $C_3$-$C_5$ cycloalkyloxy group, an amino group, a methylamino group, an ethylamino group, a dimethylamino group, a diethylamino group, a methylethylamino group or a hydroxylamino group], a group having the formula $—SO_2R^{12b}$ [wherein $R^{12b}$ represents a $C_1$-$C_4$ alkyl group, a ($C_3$-$C_5$ cycloalkyl)-($C_1$-$C_2$ alkyl) group or a $C_3$-$C_5$ cycloalkyl group], or a tetrazol-5-yl group, and $X^{2b}$ represents a single bond, a methylene group, an ethylene group or a substituted methylene group or a substituted ethylene group (wherein said substituents may be the same or different and are one or two groups selected from Substituent group γ2, or two of said substituents may together form an ethylene group or a trimethylene group)]; and, Substituent group γ2 represents the group consisting of a methyl group, an ethyl group, a hydroxymethyl group, a methoxymethyl group, an aminomethyl group, a methylaminomethyl group, a dimethylaminomethyl group, a (N-methyl-N-ethylamino)methyl group, a methoxy group, an ethoxy group, a methylamino group, a dimethylamino group, a fluoro group and a chloro group,

(21) a compound described in any one of (1) to (18), wherein $R^8$ is a group having the formula $—X^{2c}R^{10c}$ [wherein $R^{10c}$ represents a group having the formula $—COR^{11c}$ (wherein $R^{11c}$ represents a hydroxyl group or a methoxy group), or a group having the formula $—SO_2R^{12c}$ (wherein $R^{12c}$ represents a methyl group), and $X^{2c}$ represents a single bond, a methylene group or a substituted methylene group (wherein said substituent is a group selected from Substituent group γ3, or two of said substituents may together form an ethylene group)]; and, Substituent group γ3 is the group consisting of a methyl group, an ethyl group, a hydroxymethyl group, a dimethylaminomethyl group, a methoxy group and an ethoxy group,

(22) a compound described in any one of (1) to (18), wherein $R^8$ is a group having the formula $—X^{2d}R^{10d}$ [wherein $R^{10d}$ represents a group having the formula $—COR^{11d}$ (wherein $R^{11d}$ represents a hydroxyl group), and $X^{2d}$ represents a methylene group or a substituted methylene group (wherein said substituent is a group selected from Substituent group γ4, or two of said substituents may together form an ethylene group)]; and, Substituent group γ4 is the group consisting of a methyl group, an ethyl group and a hydroxymethyl group,

(23) a compound described in any one of (1) to (18), wherein $R^8$ is a group having the formula $—X^{2e}R^{10e}$ [wherein $R^{10e}$ represents a group having the formula $—COR^{11e}$ (wherein $R^{11e}$ represents a hydroxyl group), and $X^{2e}$ represents a methylene group or a substituted methylene group (wherein said substituent is a methyl group)],

(24) a compound described in any one of (1) to (18), wherein $R^8$ is a group having the formula $—X^{2f}R^{10f}$ [wherein $R^{10f}$ represents a group having the formula $—SO_2R^{12f}$ (wherein $R^{12f}$ represents a methyl group), and $X^{2f}$ represents a single bond],

(25) a compound described in any one of (1) to (24), wherein $X^1$ is a group having the formula $—NH—$, $—O—$ or $—S—$,

(26) a compound described in any one of (1) to (24), wherein $X^1$ is a group having the formula $—O—$,

(27) a compound described in any one of (1) to (26), wherein $Y^1$ is a phenyl group, a substituted phenyl group (wherein said substituents may be the same or different and are one or two groups selected from Substituent group α1), a 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyridazinyl group) or a substituted 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyridazinyl group, and said substituents may be the same or different and are one or two groups selected from Substituent group α1), and Substituent group α1 is the group consisting of a methyl group, an ethyl group, a trifluoromethyl group, a methoxy group, an ethoxy group, a fluoro group and a chloro group,

(28) a compound described in any one of (1) to (26), wherein $Y^1$ is a phenyl group (wherein the substitution positions where $X^1$ and $Y^2$ are bonded to said phenyl group are the 1 and 3 positions or the 1 and 4 positions, respectively), a substituted phenyl group (wherein said substituent is a group selected from Substituent group α2, and the substitution positions where $X^1$ and $Y^2$ are bonded to said phenyl group are the 1 and 3 positions or the 1 and 4 positions, respectively), a thienyl group (wherein the substitution positions where $X^1$ and $Y^2$ are bonded to said thienyl group are the 2 and 5 positions, respectively), a substituted thienyl group (wherein said substituent is a group selected from Substituent group α2, and the substitution positions where $X^1$ and $Y^2$ are bonded to said thienyl group are the 2 and 5 positions, respectively), a pyridyl group (wherein the substitution positions where $X^1$ and $Y^2$ are bonded to said pyridyl group are the 2 and 5 positions or the 5 and 2 positions, respectively) or a substituted pyridyl group (wherein said substituent is a group selected from Substituent group α2, and the substitution positions where $X^1$ and $Y^2$ are bonded to said pyridyl group are the 2 and 5 positions or the 5 and 2 positions, respectively), and Substituent group α2 is the group consisting of a methyl group, a fluoro group and a chloro group,

(29) a compound described in any one of (1) to (26), wherein $Y^1$ is a phenyl group (wherein the substitution positions where $X^1$ and $Y^2$ are bonded to said phenyl group are the 1 and 4 positions, respectively) or a pyridyl group (wherein the substitution positions where $X^1$ and $Y^2$ are bonded to said pyridyl group are the 5 and 2 positions, respectively),

(30) a compound described in any one of (1) to (26), wherein $Y^1$ is a phenyl group (wherein the substitution positions where $X^1$ and $Y^2$ are bonded to said phenyl group are the 1 and 4 positions),

(31) a compound described in any one of (1) to (30), wherein $Y^2$ is a phenyl group, a substituted phenyl group (wherein said substituents may be the same or different and are 1 to 3 groups selected from Substituent group β1), an indanyl group or a tetrahydronaphthyl group (provided that $Y^1$ is bonded to a benzene ring part in said indanyl or tetrahydronaphthyl group), a substituted indanyl group or a substituted tetrahydronaphthyl group (provided that $Y^1$ is bonded to a benzene ring part in said indanyl or tetrahydronaphthyl group, and said substituents may be the same or different and are 1 to 3 groups selected from Substituent group β1), a 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyrimidinyl group), a substituted 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyrimidinyl group, and said substituents may be the same or different and are 1 to 3 groups selected from Substituent group β1), a 9- or 10-membered unsaturated heterocyclyl group (provided that $Y^1$ is bonded to an aromatic ring part in said unsaturated heterocyclyl group, and said unsaturated heterocyclyl group represents an indolinyl group, a dihydrobenzofuryl group, a dihydrobenzothienyl group, a tetrahydroquinolyl group or a chromanyl group) or a substituted 9- or 10-membered unsaturated heterocyclyl group (provided that $Y^1$ is bonded to an aromatic ring part in said unsaturated heterocyclyl group, said unsaturated heterocyclyl group represents an indolinyl group, a dihydrobenzofuryl group, a dihydrobenzothienyl group, a tetrahydroquinolyl group or a chromanyl group, and said substituents may be the same or different and are 1 to 3 groups selected from Substituent group β1); and, Substituent group β1 is the group consisting of a $C_1$-$C_6$ alkyl group, a hydroxy($C_1$-$C_4$ alkyl) group, a carboxy($C_1$-$C_4$ alkyl) group, a ($C_1$-$C_4$ alkoxy)carbonyl-($C_1$-$C_4$ alkyl) group, a halogeno $C_1$-$C_4$ alkyl group (wherein said halogeno $C_1$-$C_4$ alkyl group represents a $C_1$-$C_4$ alkyl group substituted with 1 to 5 halogeno atoms), a ($C_3$-$C_6$ cycloalkyl)-($C_1$-$C_4$ alkyl) group, a $C_1$-$C_4$ alkenyl group, a $C_2$-$C_5$ alkynyl group, a $C_3$-$C_6$ cycloalkyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a $C_3$-$C_8$ cycloalkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a formylamino group, a ($C_1$-$C_4$ alkyl)carbonylamino group, a ($C_3$-$C_6$ cycloalkyl)carbonylamino group, a N—[($C_1$-$C_4$ alkyl)carbonyl]-N—($C_1$-$C_4$ alkyl)amino group, a N—[($C_3$-$C_6$ cycloalkyl)carbonyl]-N—($C_1$-$C_4$ alkyl)amino group, a $C_1$-$C_4$ alkylsulfonylamino group, a N—($C_1$-$C_4$ alkylsulfonyl)-N—($C_1$-$C_4$ alkyl)amino group, a formyl group, a ($C_1$-$C_4$ alkyl)carbonyl group, a carboxyl group, a ($C_1$-$C_4$ alkoxy)carbonyl group, a carbamoyl group, a ($C_1$-$C_4$ alkylamino)carbonyl group, a di($C_1$-$C_4$ alkyl)aminocarbonyl group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a cyano group, a nitro group, a fluoro group, a chloro group and a bromo group,

(32) a compound described in any one of (1) to (30), wherein $Y^2$ is a phenyl group (wherein the substitution positions where $Y^1$ and $R^6$ are bonded to said phenyl group are the 1 and 3 positions or the 1 and 4 positions, respectively), a substituted phenyl group (wherein said substituents may be the same or different and represent one or two groups selected from Substituent group β2, and the substitution positions where $Y^1$ and $R^8$ are bonded to said phenyl group are the 1 and 3 positions or the 1 and 4 positions, respectively), a thienyl group (wherein the substitution positions where $Y^1$ and $R^8$ are bonded to said thienyl group are the 2 and 5 positions, respectively), a substituted thienyl group (wherein said substituents may be the same or different and are one or two groups selected from Substituent group β2, and the substitution positions where $Y^1$ and $R^8$ are bonded to said thienyl group are the 2 and 5 positions, respectively), a thiazolyl group (wherein the substitution positions where $Y^1$ and $R^8$ are bonded to said thiazolyl group are the 2 and 5 positions, respectively), a substituted thiazolyl group (wherein said substituents may be the same or different and are one or two groups selected from Substituent group β2, and the substitution positions where $Y^1$ and $R^8$ are bonded to said thiazolyl group are the 2 and 5 positions, respectively), a pyridyl group (wherein the substitution positions where $Y^1$ and $R^8$ are bonded to said pyridyl group are the 2 and 5 positions or the 3 and 5 positions, respectively) or a substituted pyridyl group (wherein said substituents may be the same or different and are one or two groups selected from Substituent group β2, and the substitution positions where $Y^1$ and $R^8$ are bonded to said pyridyl group are the 2 and 5 positions or the 3 and 5 positions, respectively); and, Substituent group β2 is the group consisting of a $C_1$-$C_4$ alkyl group, a hydroxymethyl group, a 1-hydroxyethyl group, a trifluoromethyl group, a 2,2,2-trifluoroethyl group, a pentafluoroethyl group, a $C_2$-$C_4$ alkenyl group, a $C_2$-$C_4$ alkynyl group, a $C_3$-$C_4$ cycloalkyl group, a hydroxyl group, a methoxy group, an ethoxy group, a methanesulfonyl group, an ethanesulfonyl group, an amino group, a methylamino group, an ethylamino group, a dimethylamino group, a diethylamino group, a formyl group, a methylcarbonyl group, an ethylcarbonyl group, a cyano group, a nitro group, a fluoro group and a chloro group,

(33) a compound described in any one of (1) to (30), wherein $Y^2$ is a phenyl group (wherein the substitution positions where $Y^1$ and $R^8$ are bonded to said phenyl group are the 1 and 4 positions, respectively), a substituted phenyl group (wherein said substituents may be the same or different and are one or two groups selected from Substituent group β3, and the substitution positions where $Y^1$ and $R^8$ are bonded to said phenyl group are the 1 and 4 positions, respectively), a thienyl group (wherein the substitution positions where $Y^1$ and $R^8$ are bonded to said thienyl group are the 2 and 5 positions, respectively), a substituted thienyl group (wherein said substituents may be the same or different and are one or two groups selected from Substituent group β3, and the substitution positions where $Y^1$ and $R^8$ are bonded to said thienyl group are the 2 and 5 positions, respectively), a pyridyl group (wherein the substitution positions where $Y^1$ and $R^8$ are bonded to said pyridyl group are the 2 and 5 positions, respectively) or a substituted pyridyl group (wherein said substituents may be the same or different and are one or two groups selected from Substituent group β3, and the substitution positions where $Y^1$ and $R^8$ are bonded to said pyridyl group are the 2 and 5 positions, respectively); and, Substituent group β3 is the group consisting of a methyl group, an ethyl group, a 2-propyl group, a hydroxymethyl group, a trifluoromethyl group, a cyclopropyl group, a methoxy group, a methanesulfonyl group, an amino group, a methylamino group, a dimethylamino group, a methylcarbonyl group, an ethylcarbonyl group, a cyano group, a nitro group, a fluoro group and a chloro group,

(34) a compound described in any one of (1) to (30), wherein $Y^2$ is a phenyl group (wherein the substitution positions where $Y^1$ and $R^6$ are bonded to said phenyl group are the 1 and 4 positions, respectively), a substituted phenyl group (wherein said substituents may be the same or different and are a group selected from Substituent group β3 or two groups selected from Substituent group β4, and the substitution positions where $Y^1$ and $R^8$ are bonded to said phenyl group are the 1 and 4 positions, respectively), a thienyl group (wherein the substitution positions where $Y^1$ and $R^8$ are bonded to said thienyl group are the 2 and 5 positions, respectively) or a substituted thienyl group (wherein said substituents may be the same or different and are a group selected from Substituent group β3 or two groups selected from Substituent group β4, and the substitution positions where $Y^1$ and $R^8$ are bonded to said thienyl group are the 2 and 5 positions, respectively); and, Substituent group β4 is the group consisting of a methyl group, an ethyl group and a fluoro group,

(35) a compound described in any one of (1) to (30), wherein $Y^2$ is a phenyl group (wherein the substitution positions where $Y^1$ and $R^8$ are bonded to said phenyl group are the 1 and 4 positions, respectively), or a substituted phenyl group (wherein said substituent is a group selected from Substituent group β5, two methyl groups or two fluoro groups, and the substitution positions where $Y^1$ and $R^8$ are bonded to said phenyl group are the 1 and 4 positions, respectively); and, Substituent group β5 is the group consisting of a methyl group, an ethyl group, a 2-propyl group, a trifluoromethyl group, a nitro group, a fluoro group and a chloro group,

(36) a compound described in any one of (1) to (30), wherein $Y^2$ is a phenyl group (wherein the substitution positions where $Y^1$ and $R^8$ are bonded to said phenyl group are the 1 and 3 positions, respectively), a substituted phenyl group (wherein said substituent is a group selected from Substituent group β6, and the substitution positions where $Y^1$, $R^8$ and the substituent are bonded to said phenyl group are the 1, 3 and 2 positions, respectively), a pyridyl group (wherein the substitution positions where $Y^1$ and $R^8$ are bonded to said pyridyl group are the 3 and 5 positions, respectively) or a substituted pyridyl group (wherein said substituent is a group selected from Substituent group β6, and the substitution positions where $Y^1$, $R^8$ and the substituent are bonded to said pyridyl group are the 3, 5 and 4 positions, respectively); and, Substituent group β6 is the group consisting of a $C_1$-$C_4$ alkyl group, a methoxy group, a fluoro group and a chloro group, or

(37) a compound described in any one of (1) to (30), wherein $Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β7, and the substitution positions where $Y^1$, $R^6$ and the substituent are bonded to said phenyl group are the 1, 3 and 2 positions, respectively); and, Substituent group β7 is the group consisting of a methyl group, an ethyl group, a methoxy group and a fluoro group.

In a compound represented by the general formula (I) or a pharmacologically acceptable salt or ester thereof of the present invention described in (1) above, compounds obtained by optional combining of $R^1$ selected from (2) to (5), $R^2$ selected from (6) to (8), $R^3$ selected from (9) to (13), $R^4$ and $R^5$ selected from (14) to (16), $R^6$ and $R^7$ selected from (17) and (18), $R^8$ selected from (19) to (24), $X^1$ selected from (25) and (26), $Y^1$ selected from (27) to (30), and $Y^2$ selected from (31) to (37) are preferred. In addition, compounds obtained according to the following combinations are more preferred;

(i) $R^8$ selected from (22) and (23) and $Y^2$ selected from (33) to (35);
(ii) $R^8$ represented in (23) and $Y^2$ selected from (36) and (37), and
(iii) $R^8$ represented in (24) and $Y^2$ selected from (36) and (37).

Examples of such preferred compounds include the following:

(38) a compound described in (1), wherein $R^1$ is a group having the formula —$COR^{9a}$ [wherein $R^{9a}$ represents a $C_1$-$C_6$ alkyl group, a $C_1$-$C_8$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylamino group or a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)];

$R^2$ is a hydrogen atom, a trifluoromethyl group, a 2,2,2-trifluoroethyl group, a pentafluoroethyl group, a hydroxyl group, a fluoro group or a chloro group;

$R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_1$-$C_4$ alkenyl group, a $C_2$-$C_4$ alkynyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a fluoro group, a chloro group or a bromo group;

$R^4$ and $R^5$ may be the same or different and each is a hydrogen atom, a methyl group, an ethyl group, a trifluoromethyl group, a cyclopropyl group, a hydroxyl group, a methoxy group, a fluoro group, a chloro group or a bromo group;

$R^6$ and $R^7$ may be the same or different and each is a hydrogen atom or a methyl group;

$R^8$ is a group having the formula —$X^{2a}R^{10a}$ [wherein $R^{10a}$ represents a group having the formula —$COR^{11a}$ [wherein $R^{11a}$ represents a hydroxyl group, a $C_1$-$C_4$ alkoxy group, a ($C_3$-$C_6$ cycloalkyl)-($C_1$-$C_4$ alkyl)oxy group, a $C_3$-$C_6$ cycloalkyloxy group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a hydroxylamino group or a hydroxyl($C_1$-$C_4$ alkyl)amino group], a group having the formula —$SO_2R^{12a}$ [wherein $R^{12a}$ represents a $C_1$-$C_4$ alkyl group, a ($C_3$-$C_6$ cycloalkyl)-($C_1$-$C_4$ alkyl) group, a $C_3$-$C_6$ cycloalkyl group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group or a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], a group having the formula —N(R$^{13a}$)COR$^{14a}$ [wherein R$^{13a}$ represents a hydrogen atom, a C$_1$-C$_4$ alkyl group, a (C$_3$-C$_5$ cycloalkyl)-(C$_1$-C$_2$ alkyl) group or a C$_3$-C$_8$ cycloalkyl group, and R$^{14a}$ represents a hydrogen atom, a C$_1$-C$_4$ alkyl group, a (C$_3$-C$_5$ cycloalkyl)-(C$_1$-C$_2$ alkyl) group or a C$_3$-C$_5$ cycloalkyl group], a group having the formula —N(R$^{13a}$)SO$_2$R$^{15a}$ [wherein R$^{13a}$ is the same as previously defined, and R$^{15a}$ represents a C$_1$-C$_4$ alkyl group, a (C$_3$-C$_5$ cycloalkyl)-(C$_1$-C$_2$ alkyl) group or a C$_3$-C$_5$ cycloalkyl group], or a tetrazol-5-yl group, and X$^{2a}$ represents a single bond, a C$_1$-C$_2$ alkylene group or a substituted C$_1$-C$_2$ alkylene group (wherein said substituents may be the same or different and are one or two groups selected from Substituent group γ1, or two of said substituents may together form a methylene group, an ethylene group or a trimethylene group)];

X$^1$ is a group having the formula —NH—, —O— or —S—;

Y$^1$ is a phenyl group, a substituted phenyl group (wherein said substituents may be the same or different and are one or two groups selected from Substituent group α1), a 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyridazinyl group) or a substituted 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyridazinyl group, said substituents may be the same or different and are one or two groups selected from Substituent group α1); and, Y$^2$ is a phenyl group, a substituted phenyl group (wherein said substituents may be the same or different and are 1 to 3 groups selected from Substituent group β1), an indanyl group or a tetrahydronaphthyl group (provided that Y$^1$ is bonded to a benzene ring part in said indanyl or tetrahydronaphthyl group), a substituted indanyl group or a substituted tetrahydronaphthyl group (provided that Y$^1$ is bonded to a benzene ring part in said indanyl or tetrahydronaphthyl group, and said substituents may be the same or different and are 1 to 3 groups selected from Substituent group β1), a 5- or 6-membered aromatic heterocyclyl group (wherein said heterocyclyl group represents a pyrrolyl group, a furyl group, a thienyl group, an imidazolyl group, an oxazolyl group, a thiazolyl group, a pyridyl group or a pyrimidinyl group), a substituted 5- or 6-membered aromatic heterocyclyl group (wherein, said heterocyclyl group represents a pyrrolyl group, a furyl group, a thienyl group, an imidazolyl group, an oxazolyl group, a thiazolyl group, a pyridyl group or a pyrimidinyl group, said substituents may be the same or different and are 1 to 3 groups selected from Substituent group β1), a 9- or 10-membered unsaturated heterocyclyl group (provided that Y$^1$ is bonded to an aromatic ring part in said unsaturated heterocyclyl group, and said unsaturated heterocyclyl group represents an indolinyl group, a dihydrobenzofuryl group, a dihydrobenzothienyl group, a tetrahydroquinolyl group or a chromanyl group) or a substituted 9- or 10-membered unsaturated heterocyclyl group (provided that Y$^1$ is bonded to an aromatic ring part in said unsaturated heterocyclyl group, said unsaturated heterocyclyl group represents an indolinyl group, a dihydrobenzofuryl group, a dihydrobenzothienyl group, a tetrahydroquinolyl group or a chromanyl group, and said substituents may be the same or different and are 1 to 3 groups selected from Substituent group β1),

(39) a compound described in (1), wherein R$^1$ is a group having the formula —COR$^{9b}$ [wherein R$^{9b}$ represents a C$_1$-C$_6$ alkoxy group or a halogeno C$_1$-C$_4$ alkoxy group (wherein said halogeno C$_1$-C$_4$ alkoxy group represents a C$_1$-C$_4$ alkoxy group substituted with 1 to 5 halogeno groups)];

R$^2$ is a hydrogen atom or a hydroxyl group;

R$^3$ is a hydrogen atom, a C$_1$-C$_4$ alkyl group, a halogeno C$_1$-C$_4$ alkyl group (wherein said halogeno C$_1$-C$_4$ alkyl group represents a C$_1$-C$_4$ alkyl group substituted with 1 to 5 halogeno groups), a C$_3$-C$_5$ cycloalkyl group, a C$_3$-C$_5$ alkenyl group, a C$_1$-C$_4$ alkoxy group, a fluoro group or a chloro group;

R$^4$ is a hydrogen atom and R$^5$ is a hydrogen atom or a hydroxyl group;

R$^6$ and R$^7$ are hydrogen atoms;

R$^8$ is a group having the formula —X$^{2b}$R$^{10b}$ [wherein R$^{10b}$ represents a group having the formula —COR$^{11b}$ [wherein R$^{11b}$ represents a hydroxyl group, a C$_1$-C$_4$ alkoxy group, a (C$_3$-C$_5$ cycloalkyl)-(C$_1$-C$_2$ alkyl)oxy group, a C$_3$-C$_5$ cycloalkyloxy group, an amino group, a methylamino group, an ethylamino group, a dimethylamino group, a diethylamino group, a methylethylamino group or a hydroxylamino group], a group having the formula —SO$_2$R$^{12b}$ [wherein R$^{12b}$ represents a C$_1$-C$_4$ alkyl group, a (C$_3$-C$_5$ cycloalkyl)-(C$_1$-C$_2$ alkyl) (group or a C$_3$-C$_5$ cycloalkyl group], or a tetrazol-5-yl group, and X$^{2b}$ represents a single bond, a methylene group, an ethylene group or a substituted methylene group or a substituted ethylene group (wherein said substituents may be the same or different and are one or two groups selected from Substituent group γ2, or two of said substituents may together form an ethylene group or a trimethylene group)];

X$^1$ is a group having the formula —O—;

Y$^1$ is a phenyl group (wherein the substitution positions where X$^1$ and Y$^2$ are bonded to said phenyl group are the 1 and 3 positions or the 1 and 4 positions, respectively), a substituted phenyl group (wherein said substituents represent a group selected from Substituent group α2, and the substitution positions where X$^1$ and Y$^2$ are bonded to said phenyl group are the 1 and 3 positions or the 1 and 4 positions, respectively), a thienyl group (wherein the substitution positions where X$^1$ and Y$^2$ are bonded to said thienyl group are the 2 and 5 positions, respectively), a substituted thienyl group (wherein said substituent is a group selected from Substituent group α2, and the substitution positions where X$^1$ and Y$^2$ are bonded to said thienyl group are the 2 and 5 positions, respectively), a pyridyl group (wherein the substitution positions where X$^1$ and Y$^2$ are bonded to said pyridyl group are the 2 and 5 positions or the 5 and 2 positions, respectively) or a substituted pyridyl group (wherein said substituent is a group selected from Substituent group α2, and the substitution positions where X$^1$ and Y$^2$ are bonded to said pyridyl group are the 2 and 5 positions or the 5 and 2 positions, respectively); and, Y$^2$ is a phenyl group (wherein the substitution positions where Y$^1$ and R$^8$ are bonded to said phenyl group are the 1 and 3 positions or the 1 and 4 positions, respectively), a substituted phenyl group (wherein said substituents may be the same or different and are one or two groups selected from Substituent group β2, and the substitution positions where Y$^1$ and R$^8$ are bonded to said phenyl group are the 1 and 3 positions or the 1 and 4 positions, respectively), a thienyl group (wherein the substitution positions where Y$^1$ and R$^8$ are bonded to said thienyl group are the 2 and 5 positions, respectively), a substituted thienyl group (wherein said substituents may be the same or different and are one or two groups selected from Substituent group β2, and the substitution positions where $Y^1$ and $R^8$ are bonded to said thienyl group are the 2 and 5 positions, respectively), a thiazolyl group (wherein the substitution positions where $Y^1$ and $R^8$ are bonded to said thiazolyl group are the 2 and 5 positions, respectively), a substituted thiazolyl group (wherein said substituents may be the same or different and are one or two groups selected from Substituent group β2, and the substitution positions where $Y^1$ and $R^8$ are bonded to said thiazolyl group are the 2 and 5 positions, respectively), a pyridyl group (wherein the substitution positions where $Y^1$ and $R^8$ are bonded to said pyridyl group are the 2 and 5 positions or the 3 and 5 positions, respectively) or a substituted pyridyl group (wherein said substituents may be the same or different and are one or two groups selected from Substituent group β2, and the substitution positions where $Y^1$ and $R^8$ are bonded to said pyridyl group are the 2 and 5 positions or the 3 and 5 positions, respectively),

(40) a compound described in (1), wherein $R^1$ is a group having the formula —$COR^{9c}$ (wherein $R^{9c}$ represents a $C_3$-$C_5$ alkoxy group);

$R^2$ is a hydroxyl group;

$R^3$ is a methyl group, an ethyl group, a 2-propyl group, a 2-methyl-2-propyl group, a trifluoromethyl group, a 2,2,2-trifluoroethyl group, a methoxy group, a fluoro group or a chloro group;

$R^4$ and $R^5$ are hydrogen atoms;

$R^6$ and $R^7$ are hydrogen atoms;

$R^8$ is a group having the formula —$X^{2c}R^{10c}$ [wherein $R^{10c}$ represents a group having the formula —$COR^{11c}$ (wherein $R^{11c}$ represents a hydroxyl group or a methoxy group), or a group having the formula —$SO_2R^{12c}$ (wherein $R^{12c}$ represents a methyl group), and $X^{2c}$ represents a single bond, a methylene group or a substituted methylene group (wherein said substituent is a group selected from Substituent group γ3, or two of said substituents may together form an ethylene group)];

$X^1$ is a group having the formula —O—;

$Y^1$ is a phenyl group (wherein the substitution positions where $X^1$ and $Y^2$ are bonded to said phenyl group are the 1 and 4 positions, respectively) or a pyridyl group (wherein the substitution positions where $X^1$ and $Y^2$ are bonded to said pyridyl group are the 5 and 2 positions, respectively); and, $Y^2$ is a phenyl group (wherein the substitution positions where $Y^1$ and $R^8$ are bonded to said phenyl group are the 1 and 3 positions or the 1 and 4 positions, respectively), a substituted phenyl group (wherein said substituents may be the same or different and are one or two groups selected from Substituent group β2, and the substitution positions where $Y^1$ and $R^8$ are bonded to said phenyl group are the 1 and 3 positions or the 1 and 4 positions, respectively), a thienyl group (wherein the substitution positions where $Y^1$ and $R^8$ are bonded to said thienyl group are the 2 and 5 positions, respectively), a substituted thienyl group (wherein said substituents may be the same or different and are one or two groups selected from Substituent group β2, and the substitution positions where $Y^1$ and $R^8$ are bonded to said thienyl group are the 2 and 5 positions, respectively), a thiazolyl group (wherein the substitution positions where $Y^1$ and $R^8$ are bonded to said thiazolyl group are the 2 and 5 positions, respectively), a substituted thiazolyl group (wherein said substituents may be the same or different and are one or two groups selected from Substituent group β2, and the substitution positions where $Y^1$ and $R^8$ are bonded to said thiazolyl group are the 2 and 5 positions, respectively), a pyridyl group (wherein the substitution positions where $Y^1$ and $R^8$ are bonded to said pyridyl group are the 2 and 5 positions or the 3 and 5 positions, respectively) or a substituted pyridyl group (wherein said substituents may be the same or different and are one or two groups selected from Substituent group β2, and the substitution positions where $Y^1$ and $R^8$ are bonded to said pyridyl group are the 2 and 5 positions or the 3 and 5 positions, respectively),

(41) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a 2-propyl group, a 2-methyl-2-propyl group, a trifluoromethyl group or a chloro group;

$R^4$ and $R^5$ are hydrogen atoms;

$R^6$ and $R^7$ are hydrogen atoms;

$R^8$ is a group having the formula —$X^{2d}R^{10d}$ [wherein $R^{10d}$ represents a group having the formula —$COR^{11d}$ (wherein $R^{11d}$ represents a hydroxyl group), and $X^{2d}$ is a methylene group or a substituted methylene group (wherein said substituent is a group selected from Substituent group γ4, or two of said substituents may together form an ethylene group)];

$X^1$ is a group having the formula —O—;

$Y^1$ is a phenyl group (wherein the substitution positions where $X^1$ and $Y^2$ are bonded to said phenyl group are the 1 and 4 positions, respectively) or a pyridyl group (wherein the substitution positions where $X^1$ and $Y^1$ are bonded to said pyridyl group are the 5 and 2 positions, respectively); and, $Y^2$ is a phenyl group (wherein the substitution positions where $Y^1$ and $R^8$ are bonded to said phenyl group are the 1 and 4 positions, respectively), a substituted phenyl group (wherein said substituents may be the same or different and are one or two groups selected from Substituent group β3, and the substitution positions where $Y^1$ and $R^8$ are bonded to said phenyl group are the 1 and 4 positions, respectively), a thienyl group (wherein the substitution positions where $Y^1$ and $R^8$ are bonded to said thienyl group are the 2 and 5 positions, respectively), a substituted thienyl group (wherein said substituents may be the same or different and are one or two groups selected from Substituent group β3, and the substitution positions where $Y^1$ and $R^8$ are bonded to said thienyl group are the 2 and 5 positions, respectively), a pyridyl group (wherein the substitution positions where $Y^1$ and $R^8$ are bonded to said pyridyl group are the 2 and 5 positions, respectively) or a substituted pyridyl group (wherein said substituents may be the same or different and are one or two groups selected from Substituent group β3, and the substitution positions where $Y^1$ and $R^8$ are bonded to said pyridyl group are the 2 and 5 positions, respectively),

(42) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a trifluoromethyl group;

$R^4$ and $R^5$ are hydrogen atoms;

$R^6$ and $R^7$ are hydrogen atoms;

$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];

$X^1$ is a group having the formula —O—;

$Y^1$ is a phenyl group (wherein the substitution positions where $X^1$ and $Y^2$ are bonded to said phenyl group are the 1 and 4 positions); and, $Y^2$ is a phenyl group (wherein the substitution positions where $Y^1$ and $R^8$ are bonded to said phenyl group are the 1 and 4 positions, respectively), a substituted phenyl group (wherein said substituents may be the same or different and are a group selected from Substituent group β3 or two groups selected from Substituent group β4, and the substitution positions where $Y^1$ and $R^8$ are bonded to said phenyl group are the 1 and 4 positions, respectively), a thienyl group (wherein the substitution positions where $Y^1$ and $R^8$ are bonded to said thienyl group are the 2 and 5 positions, respectively), a substituted thienyl group (wherein said substituents may be the same or different and are a group selected from Substituent group β3 or two groups selected from Substituent group β4, and the substitution positions where $Y^1$ and $R^8$ are bonded to said thienyl group are the 2 and 5 positions, respectively),

(43) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a trifluoromethyl group;

$R^4$ and $R^5$ are hydrogen atoms;

$R^6$ and $R^7$ are hydrogen atoms;

$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];

$X^1$ is a group having the formula —O—;

$Y^1$ is a phenyl group (wherein the substitution positions where $X^1$ and $Y^2$ are bonded to said phenyl group are the 1 and 4 positions); and, $Y^2$ is a phenyl group (wherein the substitution positions where $Y^1$ and $R^8$ are bonded to said phenyl group are the 1 and 4 positions, respectively) or a substituted phenyl group (wherein said substituent is a group selected from Substituent group β5, two methyl groups or two fluoro groups, and the substitution positions where $Y^1$ and $R^8$ are bonded to said phenyl group are the 1 and 4 positions, respectively),

(44) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a trifluoromethyl group;

$R^4$ and $R^5$ are hydrogen atoms;

$R^6$ and $R^7$ are hydrogen atoms;

$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];

$X^1$ is a group having the formula —O—;

$Y^1$ is a phenyl group (wherein the substitution positions where $X^1$ and $Y^2$ are bonded to said phenyl group are the 1 and 4 positions); and, $Y^2$ is a phenyl group (wherein the substitution positions where $Y^1$ and $R^8$ are bonded to said phenyl group are 1 and 3 positions, respectively), a substituted phenyl group (wherein said substituent is a group selected from Substituent group β6, and the substitution positions where $Y^1$, $R^8$ and the substituent are bonded to said phenyl group are the 1, 3 and 2 positions, respectively), a pyridyl group (wherein the substitution positions where $Y^1$ and $R^8$ are bonded to said pyridyl group are the 3 and 5 positions, respectively) or a substituted pyridyl group (wherein said substituent is a group selected from Substituent group β6, and the substitution positions where $Y^1$, $R^8$ and the substituent are bonded to said pyridyl group are the 3, 5 and 4 positions, respectively),

(45) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a trifluoromethyl group;

$R^4$ and $R^5$ are hydrogen atoms;

$R^6$ and $R^7$ are hydrogen atoms;

$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];

$X^1$ is a group having the formula —O—;

$Y^1$ is a phenyl group (wherein the substitution positions where $X^1$ and $Y^2$ are bonded to said phenyl group are the 1 and 4 positions); and, $Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β7, and the substitution positions where $Y^1$, $R^8$ and the substituent are bonded to said phenyl group are the 1, 3 and 2 positions, respectively),

(46) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a trifluoromethyl group;

$R^4$ and $R^5$ are hydrogen atoms;

$R^6$ and $R^7$ are hydrogen atoms;

$R^8$ is a group having the formula —$X^{2f}R^{10f}$ [wherein $R^{10f}$ represents a group having the formula —$SO_2R^{12f}$ (wherein $R^{12f}$ represents a methyl group), and $X^{2f}$ represents a single bond];

$X^1$ is a group having the formula —O—;

$Y^1$ is a phenyl group (wherein the substitution positions where $X^1$ and $Y^1$ are bonded to said phenyl group are the 1 and 4 positions); and, $Y^2$ is a phenyl group (wherein the substitution positions where $Y^1$ and $R^8$ are bonded to said phenyl group are the 1 and 3 positions, respectively), a substituted phenyl group (wherein said substituent is a group selected from Substituent group β6, and the substitution positions where $Y^1$, $R^8$ and the substituent are bonded to said phenyl group are the 1, 3 and 2 positions, respectively), a pyridyl group (wherein the substitution positions where $Y^1$ and $R^8$ are bonded to said pyridyl group are the 3 and 5 positions, respectively) or a substituted pyridyl group (wherein said substituent is a group selected from Substituent group β6, and the substitution positions where $Y^1$, $R^8$ and the substituent are bonded to said pyridyl group are the 3, 5 and 4 positions, respectively),

(47) a compound described in (1), wherein $R^1$ is a group having the formula —$COR^{9d}$ (wherein $R^{9d}$ represents a 2-methyl-2-propoxy group);

$R^2$ is a hydroxyl group;

$R^3$ is a trifluoromethyl group;

$R^4$ and $R^5$ are hydrogen atoms;

$R^6$ and $R^7$ are hydrogen atoms;

$R^8$ is a group having the formula —$X^{2f}R^{10f}$ [wherein $R^{10f}$ represents a group having the formula —$SO_2R^{12f}$ (wherein $R^{12f}$ represents a methyl group), and $X^{2f}$ represents a single bond];

$X^1$ is a group having the formula —O—;

$Y^1$ is a phenyl group (wherein the substitution positions where $X^1$ and $Y^2$ are bonded to said phenyl group are the 1 and 4 positions); and, $Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β7, and the substitution positions where $Y^1$, $R^8$ and the substituent are bonded to said phenyl group are the 1, 3 and 2 positions, respectively),

(48) a compound described in (1) selected from the group consisting of (4'-{[2-(tert-butoxycarbonyl)-3-hydroxy-4-(trifluoromethyl)benzyl]oxy}-1,1'-biphenyl-4-yl)acetic acid, 2-(4'-{[2-(tert-butoxycarbonyl)-3-hydroxy-4-(trifluoromethyl)benzyl]oxy}-1,1'-biphenyl-4-yl)propanoic acid, 1-(4'-{[2-(tert-butoxycarbonyl)-3-hydroxy-4-(trifluoromethyl)benzyl]oxy}-1,1'-biphenyl-4-yl)cyclopropanecarboxylic acid, 2-(4'-{[2-(tert-butoxycarbonyl)-3-hydroxy-4-(trifluoromethyl)benzyl]oxy}-1,1'-biphenyl-4-yl)-3-hydroxypropanoic acid, 2-[4'-{[2-(tert-butoxycarbonyl)-3-hydroxy-4-(trifluoromethyl)benzyl]oxy}-1,1'-biphenyl-4-yl]butanoic acid, (4'-{[2-(tert-butoxycarbonyl)-3-hydroxy-4-(trifluoromethyl)benzyl]oxy}-2-methyl-1,1'-biphenyl-3-yl)acetic acid, (4'-{[2-(tert-butoxycarbonyl)-3-hydroxy-4-(trifluoromethyl)benzyl]oxy}-2-methyl-1,1'-biphenyl-4-yl)acetic acid, (4'-{[2-(tert-butoxycarbonyl)-3-hydroxy-4-(trifluoromethyl)benzyl]oxy}-2-chloro-1,1'-biphenyl-4-yl)acetic acid, (4'-{[2-(tert-butoxycarbonyl)-3-hydroxy-4-(trifluoromethyl)benzyl]oxy}-3-fluoro-1,1'-biphenyl-4-yl)acetic acid, (4'-{[2-(tert-butoxycarbonyl)-3-hydroxy-4-(trifluoromethyl)benzyl]oxy}-3-chloro-1,1'-biphenyl-4-yl)acetic acid, 2-(4'-{[2-(tert-butoxycarbonyl)-3-hydroxy-4-(trifluoromethyl)benzyl]oxy}-2-methoxy-1,1'-biphenyl-3-yl)propanoic acid, 2-(4'-{[2-(tert-butoxycarbonyl)-3-hydroxy-4-(trifluoromethyl)benzyl]oxy}-3-fluoro-1,1'-biphenyl-4-yl)propanoic acid, 1-(4'-{[2-(tert-butoxycarbonyl)-3-hydroxy-4-(trifluoromethyl)benzyl]oxy}-3-fluoro-1,1'-biphenyl-4-yl)cyclopropanecarboxylic acid, (4'-{[2-(tert-butoxycarbonyl)-3-hydroxy-4-(trifluoromethyl)benzyl]oxy}-3-methoxy-1,1'-biphenyl-4-yl)acetic acid, (4'-{[2-(tert-butoxycarbonyl)-3-hydroxy-4-(trifluoromethyl)benzyl]oxy}-2-trifluoromethyl-1,1'-biphenyl-4-yl)acetic acid, (4'-{[2-(tert-butoxycarbonyl)-3-hydroxy-4-(trifluoromethyl)benzyl]oxy}-2-ethyl-1,1'-biphenyl-4-yl)acetic acid, tert-butyl 6-[({2'-ethyl-4'-[(methoxycarbonyl)methyl]-1,1'-biphenyl-4-yl}oxy)methyl]-2-hydroxy-3-(trifluoromethyl)benzoate, (4'-{[2-(tert-butoxycarbonyl)-3-hydroxy-4-(trifluoromethyl)benzyl]oxy}-2-nitro-1,1'-biphenyl-4-yl)acetic acid, (2-amino-4'-{[2-(tert-butoxycarbonyl)-3-hydroxy-4-(trifluoromethyl)benzyl]oxy}-1,1'-biphenyl-4-yl)acetic acid, (4'-{[2-(tert-butoxycarbonyl)-3-hydroxy-4-(trifluoromethyl)benzyl]oxy}-2-isopropyl-1,1'-biphenyl-4-yl)acetic acid, (4'-{[2-(tert-butoxycarbonyl)-3-hydroxy-4-(trifluoromethyl)benzyl]oxy}-2-formyl-1,1'-biphenyl-4-yl)acetic acid, (4'-{[2-(tert-butoxycarbonyl)-3-hydroxy-4-(trifluoromethyl)benzyl]oxy}-2-(hydroxymethyl)-1,1'-biphenyl-4-yl)acetic acid, (4'-{[2-(tert-butoxycarbonyl)-3-hydroxy-4-(trifluoromethyl)benzyl]oxy}-2-cyano-1,1'-biphenyl-4-yl)acetic acid, (4'-{[2-(tert-butoxycarbonyl)-3-hydroxy-4-(trifluoromethyl)benzyl]oxy}-2-cyclopropyl-1,1'-biphenyl-4-yl)acetic acid, (4'-{[2-(tert-butoxycarbonyl)-3-hydroxy-4-(trifluoromethyl)benzyl]oxy}-3-ethyl-1,1'-biphenyl-4-yl)acetic acid, (4'-{[2-(tert-butoxycarbonyl)-3-hydroxy-4-(trifluoromethyl)benzyl]oxy}-2-ethyl-1,1'-biphenyl-3-yl)acetic acid, 2-(4'-{[2-(tert-butoxycarbonyl)-3-hydroxy-4-(trifluoromethyl)benzyl]oxy}-3-fluoro-1,1'-biphenyl-4-yl)-3-(dimethylamino)propanoic acid, 2-(4'-{[2-(tert-butoxycarbonyl)-3-hydroxy-4-(trifluoromethyl)benzyl]oxy}-2-ethyl-1,1'-biphenyl-4-yl)propanoic acid,

[5-(4-{[2-(tert-butoxycarbonyl)-3-hydroxy-4-(trifluoromethyl)benzyl]oxy}phenyl)-4-methyl-2-thienyl]acetic acid, 2-(4'-{[2-(tert-butoxycarbonyl)-3-hydroxy-4-(trifluoromethyl)benzyl]oxy}-2-nitro-1,1'-biphenyl-4-yl)propanoic acid, 2-[4-(5-{[2-(tert-butoxycarbonyl)-3-hydroxy-4-(trifluoromethyl)benzyl]oxy}-2-pyridinyl)-3-methylphenyl]propanoic acid, 2-(4'-{[2-(tert-butoxycarbonyl)-3-hydroxy-4-(trifluoromethyl)benzyl]oxy}-2-isopropyl-1,1'-biphenyl-4-yl)propanoic acid, 2-(4'-{[2-(tert-butoxycarbonyl)-3-hydroxy-4-(trifluoromethyl)benzyl]oxy}-2,3-dimethyl-1,1'-biphenyl-4-yl)propanoic acid, and 2-(4'-{[2-(tert-butoxycarbonyl)-3-hydroxy-4-(trifluoromethyl)benzyl]oxy}-2-cyclopropyl-1,1'-biphenyl-4-yl)propanoic acid.

In addition, the present invention provides:

(49) a compound or a pharmacologically acceptable salt or ester thereof described in (1), wherein $R^{11}$ in the group having the formula —$COR^{11}$ represented in $R^{10}$ of the group having the formula —$X^2R^{10}$ in $R^8$ is a hydroxyl group, a $C_1$-$C_6$ alkoxy group, a ($C_3$-$C_8$ cycloalkyl)-($C_1$-$C_6$ alkyl)oxy group, a $C_3$-$C_8$ cycloalkyloxy group, an amino group, a $C_1$-$C_6$ alkylamino group, a [($C_3$-$C_8$ cycloalkyl)-($C_1$-$C_6$ alkyl)]amino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di[($C_3$-$C_8$ cycloalkyl)-($C_1$-$C_6$ alkyl)]amino group, a di($C_3$-$C_8$ cycloalkyl)amino group, a N—[($C_3$-$C_8$ cycloalkyl)-($C_3$-$C_8$ alkyl)]-N—($C_1$-$C_6$ alkyl)amino group, a N—($C_3$-$C_8$ cycloalkyl)-N—($C_1$-$C_6$ alkyl)amino group, a N—[($C_3$-$C_8$ cycloalkyl)-($C_1$-$C_6$ alkyl)]-N—($C_3$-$C_8$ cycloalkyl)amino group, a hydroxylamino group or a hydroxyl($C_1$-$C_6$ alkyl)amino group, and $X^2$ in the group having the formula —$X^2R^{10}$ in $R^8$ is a single bond, a $C_1$-$C_4$ alkylene group or a substituted $C_1$-$C_4$ alkylene group (wherein said substituents may be the same or different and are one or two groups selected from Substituent group γ, or two of said substituents may together form an ethylene group or a trimethylene group), and

(50) a compound or a pharmacologically acceptable salt or ester thereof described in (1), wherein $R^8$ is a group having the formula —$X^{2g}R^{10g}$ [wherein $R^{10g}$ represents a group having the formula —$COR^{11g}$ [wherein $R^{11g}$ represents a hydroxyl group, a $C_1$-$C_6$ alkoxy group, an amino group, a $C_1$-$C_6$ alkylamino group or a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], or a tetrazol-5-yl group, and $X^{2g}$ represents a single bond, a $C_1$-$C_4$ alkylene group or a substituted $C_1$-$C_4$ alkylene group (wherein said substituents may be the same or different and are one or two groups selected from a group consisting of a $C_1$-$C_4$ alkyl group and a halogeno group, and two of said substituents may together form a methylene group or a trimethylene group)];

$Y^1$ is a phenyl group, a substituted phenyl group (wherein said substituents may be the same or different and are 1 to 3 groups selected from Substituent group δ), a 5- or 6-membered aromatic heterocyclyl group or a substituted 5- or 6-membered aromatic heterocyclyl group (wherein said substituents may be the same or different and are 1 to 3 groups selected from Substituent group δ)

$Y^2$ is a phenyl group, a substituted phenyl group (wherein said substituents may be the same or different and are 1 to 3 groups selected from Substituent group δ), a 5- or 6-membered aromatic heterocyclyl group or a substituted 5- or 6-membered aromatic heterocyclyl group (wherein said substituents may be the same or different and are 1 to 3 groups selected from Substituent group δ); and, Substituent group δ is the group consisting of a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group (wherein said alkyl groups may be the same or different), a carboxyl group, a ($C_1$-$C_4$ alkoxy) carbonyl group, a cyano group and a halogeno group.

Moreover, the present invention provides:

(51) a pharmaceutical composition comprising as an active ingredient a compound represented by the general formula (I) or a pharmacologically acceptable salt or ester thereof described in any one of (1) to (50); and one or more pharmaceutical(s) selected from the group consisting of an HMG-CoA reductase inhibitor, CETP inhibitor, ACAT inhibitor, cholesterol absorption inhibitor, bile acid adsorption ion exchange resin, fibrate-based medicine, nicotinic acid derivative, angiotensin II inhibitor and diuretic,

(52) a pharmaceutical composition containing as an active ingredient a compound represented by the general formula (I) or a pharmacologically acceptable salt or ester thereof described in any one of (1) to (50); and one or more pharmaceutical(s) selected from the group consisting of an HMG-CoA reductase inhibitor, CETP inhibitor and cholesterol absorption inhibitor,

(53) a pharmaceutical composition containing as an active ingredient a compound represented by the general formula (I) or a pharmacologically acceptable salt or ester thereof described in any one of (1) to (50) and an HMG-CoA reductase inhibitor,

(54) a pharmaceutical composition described in (53), wherein the HMG-CoA reductase inhibitor is pravastatin, lovastatin, simvastatin, fluvastatin, cerivastatin, atorvastatin, pitavastatin or rosuvastatin, and

(55) the pharmaceutical composition described in (53), wherein the HMG-CoA reductase inhibitor is pravastatin, atorvastatin or rosuvastatin.

In the compound represented by the formula (I) of the present invention, respective substituents are defined as follows.

The "$C_1$-$C_{10}$ alkyl group" in $R^9$ of the formula (I) is a straight or branched chain alkyl group having from 1 to 10 carbon atoms and can include a methyl group, an ethyl group, a 1-propyl group, a 2-propyl group, a 1-butyl group, a 2-butyl group, a 2-methyl-1-propyl group, a 2-methyl-2-propyl group, a 1-pentyl group, a 2-pentyl group, a 3-pentyl group, a 2-methyl-2-butyl group, a 3-methyl-2-butyl group, a 1,1-dimethyl-1-propyl group, a 1-hexyl group, a 2-hexyl group, a 3-hexyl group, a 2-methyl-1-pentyl group, a 3-methyl-3-pentyl group, a 2-ethyl-1-butyl group, a 2,3-dimethyl-1-butyl group, a 3-heptyl group, a 4-heptyl group, a 3-methyl-3-hexyl group, a 3-ethyl-3-pentyl group, a 3-octyl group, a 4-octyl group, a 3-ethyl-3-hexyl group, a 4-nonyl group, a 5-nonyl group, a 4-ethyl-4-heptyl group, a 4-decyl group, a 5-decyl group or a 4-(1-propyl)-4-heptyl group, preferably, a $C_1$-$C_6$ alkyl group, more preferably a $C_2$-$C_6$ alkyl group, further preferably a $C_3$-$C_5$ alkyl group.

The "$C_1$-$C_{10}$ alkoxy group" in $R^9$ of the formula (I) is a hydroxyl group substituted by a $C_1$-$C_{10}$ alkyl group described above and can include a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group, a 3-methyl-2-butoxy group, a 2-methyl-2-butoxy group, a 1-hexyloxy group, a 2-hexyloxy group, a 3-hexyloxy group, a 2-methyl-1-pentyloxy group, a 3-methyl-3-pentyloxy group, a 2-ethyl-1-butoxy group, a 2,3-dimethyl-1-butoxy group, a 1-heptyloxy group, a 3-heptyloxy group, a 4-heptyloxy group, a 3-methyl-3-hexyloxy group, a 3-ethyl-3-pentyloxy group, a 3-octyloxy group, a 4-octyloxy group, a 3-ethyl-3-hexyloxy group, a 4-nonyloxy group, a 5-nonyloxy group, a 4-ethyl-4-heptyloxy group, a 4-decyloxy group, a 5-decyloxy group or 4-(1-propyl)-4-heptyloxy group, preferably a $C_1$-$C_8$ alkoxy group, more preferably a $C_1$-$C_6$ alkoxy group, further preferably a $C_2$-$C_6$ alkoxy group, further more preferably a $C_3$-$C_6$ alkoxy group, particularly preferably a $C_3$-$C_5$ alkoxy group (particularly a 2-propoxy group, a 2-methyl-2-propoxy group or a 2-methyl-2-butoxy group), most preferably a 2-methyl-2-propoxy group.

The "$C_1$-$C_4$ alkyl group" in $R^4$, $R^5$, $R^{16}$ and Substituent group α or the like of the formula (I) is a straight or branched chain alkyl group having from 1 to 4 carbon atoms and can include a methyl group, an ethyl group, a 1-propyl group, a 2-propyl group, a 1-butyl group, a 2-butyl group, a 2-methyl-1-propyl group or a 2-methyl-2-propyl group, preferably a $C_1$-$C_3$ alkyl group, more preferably a methyl group or an ethyl group, most preferably a methyl group.

The "$C_1$-$C_4$ alkoxy group" in $R^2$, $R^4$, $R^5$ and Substituent group α of the formula (I) is a hydroxyl group substituted by one $C_1$-$C_4$ alkyl group described above and can include a methoxy group, an ethoxy group, a 1-propoxy group, a 2-propoxy group, a 1-butoxy group, a 2-butoxy group or a 2-methyl-2-propoxy group, preferably a $C_1$-$C_3$ alkoxy group, more preferably a methoxy group or an ethoxy group, most preferably a methoxy group.

The "halogeno $C_1$-$C_{10}$ alkoxy group" in $R^9$ of the formula (I) is a $C_1$-$C_{10}$ alkoxy group described above substituted by 1 to 7 halogeno groups described below and can include a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a 2,2,2-trichloroethoxy group, pentafluoroethoxy group, a 3,3,3-trifluoro-1-propoxy group, a 1,1,1-trifluoro-2-propoxy group, a 1,1,1-trichloro-2-propoxy group, a 4,4,4-trifluoro-1-butoxy group, a 4,4,4-trifluoro-2-butoxy group, a 2-trifluoromethyl-1-propoxy group, a 2-trifluoromethyl-2-propoxy group, a 5,5,5-trifluoro-1-pentyloxy group, 5,5,5-trifluoro-2-pentyloxy group, a 1,1,1-trifluoro-3-pentyloxy group, a 4,4,4-trifluoro-2-methyl-2-butoxy group, a 4,4,4-trifluoro-3-methyl-2-butoxy group, a 4,4,4-trifluoro-2-methyl-2-butoxy group, a 6,6,6-trifluoro-1-hexyloxy group, a 6,6,6-trifluoro-2-hexyloxy group, a 6,6,6-trifluoro-3-hexyloxy group, a 5,5,5-trifluoro-2-methyl-1-pentyloxy group, a 1,1,1-trifluoro-3-methyl-3-pentyloxy group, a 6,6,6-trifluoro-2-ethyl-1-butoxy group, a 6,6,6-trifluoro-2,3-dimethyl-1-butoxy group, a 7,7,7-trifluoro-1-heptyloxy group, a 7,7,7-trifluoro-3-heptyloxy group, a 1,1,1-trifluoro-4-heptyloxy group, a 6,6,6-trifluoro-3-methyl-3-hexyloxy group, a 1,1,1-trifluoro-3-ethyl-3-pentyloxy group, a 8,8,8-trifluoro-3-octyloxy group, a 8,8,8-trifluoro-4-octyloxy group, a 6,6,6-trifluoro-3-ethyl-3-hexyloxy group, a 9,9,9-trifluoro-4-nonyloxy group, a 9,9,9-trifluoro-5-nonyloxy group, a 1,1,1-trifluoro-4-ethyl-4-heptyloxy group, a 9,9,9-trifluoro-4-decyloxy group, a 9,9,9-trifluoro-5-decyloxy group or a 1,1,1-trifluoro-4-(1-propyl)-4-heptyloxy group, preferably a halogeno $C_1$-$C_6$ alkoxy group (said halogeno $C_1$-$C_6$ alkoxy group represents a $C_1$-$C_6$ alkoxy group substituted by 1 to 7 halogeno groups), more preferably a halogeno $C_1$-$C_4$ alkoxy group (said halogeno $C_1$-$C_4$ alkoxy group represents a $C_1$-$C_4$ alkoxy group substituted by 1 to 5 halogeno group), further preferably a halogeno $C_3$-$C_4$ alkoxy group (said halogeno $C_3$-$C_4$ alkoxy group represents a $C_3$-$C_4$ alkoxy group substituted by 1 to 5 halogeno groups), most preferably a 1,1,1-trifluoro-2-propoxy group or a 2-trifluoromethyl-2-propoxy group.

The "phenyl-($C_1$-$C_{10}$ alkoxy) group" in $R^9$ of the formula (I) is a $C_1$-$C_{10}$ alkoxy group described above substituted by one phenyl group and can include a phenylmethoxy group, a phenylethoxy group, a 3-phenyl-1-propoxy group, a 1-phenyl-2-propoxy group, a 4-phenyl-1-butoxy group, a 1-phenyl-2-butoxy group, a 3-phenyl-2-methyl-1-propoxy group, a 1-phenyl-2-methyl-2-propoxy group, a 5-phenyl-1-pentyloxy group, a 5-phenyl-2-pentyloxy group, a 1-phenyl-3-pentyloxy group, a 4-phenyl-2-methyl-2-butyoxy group, a 4-phenyl-3-methyl-2-butoxy group, a 4-phenyl-2-methyl-2-butoxy group, a 6-phenyl-1-hexyloxy group, a 6-phenyl-2-hexyloxy group, a 6-phenyl-3-hexyloxy group, a 5-phenyl-2-methyl-1-pentyloxy group, a 1-phenyl-3-methyl-3-pentyloxy group, a 4-phenyl-2-ethyl-1-butoxy group, a 4-phenyl-2,3-dimethyl-1-butoxy group, a 7-phenyl-1-heptyloxy group, a 7-phenyl-3-heptyloxy group, a 1-phenyl-4-heptyloxy group, a 6-phenyl-3-methyl-3-hexyloxy group, a 1-phenyl-3-ethyl-3-pentyloxy group, a 8-phenyl-3-octyloxy group, a 8-phenyl-4-octyloxy group, a 6-phenyl-3-ethyl-3-hexyloxy group, a 9-phenyl-4-nonyloxy group, a 1-phenyl-5-nonyloxy group, a 1-phenyl-4-ethyl-4-heptyloxy group, a 9-phenyl-4-decyloxy group, a 1-phenyl-5-decyloxy group or a 1-phenyl-4-(1-propyl)-4-heptyloxy group, preferably a phenyl-($C_1$-$C_6$ alkoxy) group, more preferably a phenyl-($C_1$-$C_4$ alkoxy) group, further preferably a phenyl-($C_1$-$C_3$ alkoxy) group, most preferably a phenylmethoxy group or a 1-phenylethoxy group.

The "$C_1$-$C_{10}$ alkylamino group" in $R^9$ of the formula (I) is an amino group substituted by one $C_1$-$C_{10}$ alkyl group described above and can include a methylamino group, an ethylamino group, a 1-propylamino group, a 2-propylamino group, 1-butylamino group, a 2-butylamino group, a 2-methyl-1-propylamino group, a 2-methyl-2-propylamino group, a 1-pentylamino group, a 2-pentylamino group, a 3-pentylamino group, 2-methyl-2-butylamino group, a 3-methyl-2-butylamino group, a 2-methyl-2-butylamino group, a 1-hexylamino group, a 2-hexylamino group, a 3-hexylamino group, a 2-methyl-1-pentylamino group, a 3-methyl-3-pentylamino group, a 2-ethyl-1-butylamino group, a 2,3-dimethyl-1-butylamino group, a 1-heptylamino group, a 3-heptylamino group, a 4-heptylamino group, a 3-methyl-3-hexylamino group, a 3-ethyl-3-pentylamino group, a 3-ocytylamino group, a 4-octylamino group, a 3-ethyl-3-hexylamino group, a 4-nonylamino group, a 5-nonylamino group, a 4-ethyl-4-heptylamino group, a 4-decylamino group, a 5-decylamino group or a 4-(1-propyl)-4-heptylamino group, preferably a $C_1$-$C_6$ alkylamino group, more preferably a $C_2$-$C_6$ alkylamino group, further preferably a $C_3$-$C_6$ alkylamino group, further more preferably a $C_3$-$C_5$ alkylamino group (particularly a 2-propylamino group, a 2-methyl-2-propylamino group or a 2-methyl-2-butylamino group), most preferably a 2-methyl-2-propylamino group.

The "di-($C_1$-$C_{10}$ alkyl)amino group" in $R^9$ of the formula (I) is an amino group substituted by the same or different two $C_1$-$C_{10}$ alkyl groups described above and can include a dimethylamino group, a methylethylamino group, a methylpropylamino group [for example, a N-(1-propyl)-N-methylamino group or the like], a methylbutylamino group [for example, a N-(1-butyl)-N-methylamino group, a N-methyl-N-(2-methyl-2-propyl)amino group or the like], a N-methyl-N-(2-methyl-2-butyl)amino group, a N-methyl-N-(3-methyl-3-pentyl)amino group, a N-methyl-N-(3-ethyl-3-pentyl)amino group, a N-methyl-N-(3-ethyl-3-hexyl)amino group, a N-methyl-N-(4-ethyl-4-heptyl)amino group, a N-methyl-N-[4-(1-propyl)-4-heptyl]amino group, a diethylamino group, an ethylpropylamino group [for example an N-(1-propyl)-N-ethylamino group or the like], a N-ethyl-N-(2-methyl-2-propyl)amino group, a N-ethyl-N-(2-methyl-2-butyl)amino group, a N-ethyl-N-(3-methyl-3-pentyl)amino group, a N-ethyl-N-(3-ethyl-3-pentyl)amino group, a dipropylamino group [for example, a di(1-propyl)amino group, a di(2-propyl)amino group or the like], a N-(1-propyl)-N-(2-methyl-2-propyl)amino group, a dibutylamino group [for example, a di(1-butyl)amino group, a di(2-butyl)amino group or the like], a di(2-methyl-1-propyl)amino group, a di(2-methyl-2-propyl)amino group, a N-(1-butyl)-N-(2-methyl-2-propyl)amino group, a dipentylamino group [for example, a di(1-pentyl)amino group, a di(2-pentyl)amino group, a di(3-pentyl)amino group or the like], a di(2-methyl-1-butyl)amino group, a di(2-ethyl-1-propyl)amino group, a N-(1-pentyl)-N-(2-methyl-2-propyl)amino group, a dihexylamino group [for example, a di(1-hexyl)amino group, di(2-hexyl)amino group, di(3-hexyl)amino group or the like], a di(2-methyl-1-pentyl) amino group, a di(3-methyl-1-pentyl)amino group, a di(4-methyl-1-pentyl)amino group, a di(2-methyl-2-pentyl)amino group, a di(3-methyl-2-pentyl)amino group, a di(4-methyl-2-pentyl)amino group, a di(2,2-dimethyl-1-butyl)amino group, a di(3,3-dimethyl-1-butyl)amino group, a di(2,3-dimethyl-1-butyl)amino group, a di(2-ethyl-1-butyl)amino group, a N-(1-hexyl)-N-(2-methyl-2-propyl)amino group, a diheptylamino group [for example, a di(1-heptyl)amino group, a di(2-heptyl)amino group or the like], a di(3-ethyl-3-pentyl) amino group, a dioctylamino group [for example, a di(1-octyl)amino group, a di(2-octyl)amino group, a di(4-octyl) amino group or the like], a di(3-ethyl-3-hexyl)amino group, a dinonylamino group [for example, a di(5-nonyl)amino group or the like], a di(4-ethyl-4-heptyl)amino group, a didecylamino group [for example, a di(5-decyl)amino group or the like] or a di[4-(1-propyl)-4-heptyl]amino group, preferably a di($C_1$-$C_6$ alkyl)amino group, more preferably a di($C_2$-$C_6$ alkyl)amino group or a N—($C_1$-$C_4$ alkyl)-N—($C_2$-$C_6$ alkyl) amino group, further preferably a di($C_3$-$C_6$ alkyl)amino group or a N—($C_1$-$C_4$ alkyl)-N—($C_3$-$C_6$ alkyl)amino group, further more preferably a di($C_3$-$C_5$ alkyl)amino group or a N—($C_1$-$C_4$ alkyl)-N—($C_1$-$C_8$ alkyl)amino group, most preferably a N-methyl-N-(2-methyl-2-propyl)amino group, a N-ethyl-N-(2-methyl-2-propyl)amino group, a N-(1-propyl)-N-(2-methyl-2-propyl)amino group, a N-(1-butyl)-N-(2-methyl-2-propyl)amino group or a di(2-methyl-2-propyl)amino group. Further, in the "di($C_1$-$C_{10}$ alkyl)amino group", said two alkyl groups together with the nitrogen atom of said amino group may form a 5- to 7-membered saturated heterycyclyl group containing 1 to 3 atoms selected from the group consisting of a nitrogen atom, an oxygen atom and a sulfur atom and the 5- to 7-membered saturated heterocyclyl group can include a pyrrolidinyl group, a piperidyl group, a piperazinyl group, a morpholinyl group, a thiomorpholinyl group or a perhydroazepinyl group, preferably a 5- or 6-membered saturated heterocyclyl group containing 1 or 2 atoms selected from the group consisting of a nitrogen atom, an oxygen atom and a sulfur atom, more preferably a pyrrolidinyl group, a piperidyl group, a morpholinyl group or a thiomorpholinyl group, and further preferably a piperidyl group or a morpholinyl group.

The "halogeno $C_1$-$C_4$ alkyl group" in $R^2$, $R^4$, $R^5$ and Substituent group α of the general formula (I) is a $C_1$-$C_4$ alkyl group described above substituted by 1 to 5 halogeno groups described below and can include a fluoromethyl group, a difluoromethyl group, a dichloromethyl group, a dibromomethyl group, a trifluoromethyl group, a trichloromethyl group, a 2-fluoroethyl group, a 2-bromoethyl group, a 2-chloroethyl group, a 2-iodoethyl group, a 2,2-difluoroethyl group, a 2,2,2-trifluoroethyl group, a 2,2,2-trichloroethyl group, a pentafluoroethyl group, a 3-fluoropropyl group, a 3-chloropropyl group, a 3,3,3-trifluoropropyl group, a 4-fluorobutyl group or a 4,4,4-trifluorobutyl group, preferably a halogeno $C_1$-$C_2$ alkyl group (said halogeno $C_1$-$C_2$ alkyl group represents a $C_1$-$C_2$ alkyl group substituted by 1 to 5 halogeno groups), more preferably a trifluoromethyl group, a 2,2,2-trifluoroethyl group or a pentafluoroethyl group, and most preferably a trifluoromethyl group.

The "$C_1$-$C_4$ alkylamino group" in $R^2$ of the general formula (I) is an amino group substituted by one $C_1$-$C_4$ alkyl group described above and can include a methylamino group, an ethylamino group, a propylamino group (for example, a 1-propylamino group, a 2-propylamino group), a 1-butylamino group, a 2-butylamino group, a 2-methyl-1-propylamino group or a 2-methyl-2-propylamino group, preferably a $C_1$-$C_3$ alkylamino group, more preferably a methylamino group or an ethylamino group, and most preferably a methylamino group.

The "di($C_1$-$C_4$ alkyl)amino group" in $R^2$ of the general formula (I) is an amino group substituted by the same or different two $C_1$-$C_4$ alkyl groups described above and can include a dimethylamino group, a methylethylamino group, a methylpropylamino group [for example, a N-(1-propyl)-N-methylamino group or the like], a methylbutylamino group [for example, a N-(1-butyl)-N-methylamino group or the like], a diethylamino group, an ethylpropylamino group [for example, a N-(1-propyl)-N-ethylamino group or the like], a dipropylamino group [for example, a di(1-propyl)amino group, a di(2-propyl)amino group or the like], a di(1-butyl) amino group, a di(2-butyl)amino group, a di(2-methyl-1-propyl)amino group or a di(2-methyl-2-propyl)amino group, preferably a di($C_1$-$C_3$ alkyl)amino group (said alkyl groups are the same or different), more preferably a dimethylamino group, methylethylamino group, a methylpropylamino group, a diethylamino group, an ethylpropylamino group or a dipropylamino group, further preferably a dimethylamino group or a diethylamino group, and most preferably a dimethylamino group.

The "halogeno group" in $R^2$, $R^3$, $R^4$, $R^5$, Substituent group α, Substituent group β and Substituent group γ of the general formula (I) can include a fluoro group, a chloro group, a bromo group or a iodo group, preferably a fluoro group, a chloro group or a bromo group, more preferably a fluoro group or a chloro group, and most preferably a fluoro group.

The "$C_1$-$C_6$ alkyl group" in $R^3$, $R^{11}$, $R^{12}$, $R^{13}$, $R^{14}$, $R^{15}$, Substituent group β and Substituent group γ of the general formula (I) is a straight or branched chain alkyl group having from 1 to 6 carbon atoms and can include a methyl group, an ethyl group, a 1-propyl group, a 2-propyl group, a 1-butyl group, a 2-butyl group, a 2-methyl-1-propyl group, a 2-methyl-2-propyl group, a 1-pentyl group, a 2-pentyl group, a 3-pentyl group, a 2-methyl-2-butyl group, a 3-methyl-2-butyl group, a 1-hexyl group, a 2-hexyl group, a 3-hexyl group, a 2-methyl-1-pentyl group, a 3-methyl-1-pentyl group, a 2-ethyl-1-butyl group, a 2,2-dimethyl-1-butyl group or a 2,3-dimethyl-1-butyl group, preferably a $C_1$-$C_4$ alkyl group, more preferably a $C_1$-$C_3$ alkyl group (particularly a methyl group, an ethyl group or a propyl group), further preferably a methyl group or an ethyl group, and most preferably a methyl group.

The "halogeno $C_1$-$C_6$ alkyl group" in $R^3$ and Substituent group β of the general formula (I) is a $C_1$-$C_6$ alkyl group described above substituted by 1 to 7 halogeno groups described above and can include a fluoromethyl group, a difluoromethyl group, a dichloromethyl group, a dibromomethyl group, a trifluromethyl group, a trichloromethyl group, a trifluoromethyl group, a trichloromethyl group, a 2-fluoroethyl group, a 2-bromoethyl group, a 2-chloroethyl group, a 2-iodoethyl group, a 2,2-difluoroethyl group, a 2,2,2-trifluoroethyl group, a trichloroethyl group, a pentafluoroethyl group, a 3-fluoropropyl group, a 3-chloropropyl group, a 3,3,3-trifluoropropyl group, a 4-fluorobutyl group, a 4,4,4-trifluorobutyl group, a 5-fluoropentyl group, a 5,5,5-trifluoropentyl group, a 6-fluorohexyl group or a 6,6,6-trifluorohexyl group, preferably a halogeno $C_1$-$C_4$ alkyl group (said halogeno $C_1$-$C_4$ alkyl group represents a $C_1$-$C_4$ alkyl group substituted by 1 to 5 halogeno groups), more preferably a halogeno $C_1$-$C_4$ alkyl group (said halogeno $C_1$-$C_4$ alkyl group represents a $C_1$-$C_4$ alkyl group substituted by 1 to 5 fluoro, chloro or bromo groups), further more preferably a trifluoromethyl group, a 2,2,2-trifluoroethyl group or a pentafluoroethyl group, particularly preferably a trifluoromethyl group or a 2,2,2-trifluoroethyl group, and most preferably a trifluoromethyl group.

The "($C_1$-$C_4$ alkoxy)-($C_1$-$C_4$ alkyl) group" in $R^3$ of the general formula (I) is a $C_1$-$C_4$ alkyl group described above substituted by one $C_1$-$C_4$ alkoxy group described above and can include a methoxymethyl group, an ethoxymethyl group, a (1-propoxy)methyl group, a (2-propoxy)methyl group, a (1-butoxy)methyl group, a (2-butoxy)methyl group, a (2-methyl-2-propoxy)methyl group, a methoxyethyl group, an ethoxyethyl group, a (1-propoxy)ethyl group, a (2-propoxy) ethyl group, a (1-butoxy)ethyl group, a (2-butoxy)ethyl group, a (2-methyl-2-propoxy)ethyl group, a methoxy(1-propyl) group, an ethoxy(1-propyl) group, a (1-propoxy)-(1-propyl) group, a (1-butoxy)-(1-propyl) group, a methoxy(1-butyl) group, an ethoxy(1-butyl) group, a (1-propoxy)-(1-butyl) group or a (1-butoxy)-(1-butyl) group, preferably a ($C_1$-$C_2$ alkoxy)-($C_1$-$C_2$ alkyl) group, more preferably a methoxymethyl group or an ethoxymethyl group, and most preferably a methoxymethyl group.

The $C_1$-$C_4$ alkylthio moiety of the "($C_1$-$C_4$ alkylthio)-($C_1$-$C_4$ alkyl) group" in $R^3$ of the general formula (I) is a mercapto group substituted by one $C_1$-$C_4$ alkyl group described above and can include a methylthio group, an ethylthio group, a 1-propylthio group, a 2-propylthio group, a 1-butylthio group, a 2-butylthio group or a 2-methyl-2-propylthio group, preferably a $C_1$-$C_3$ alkylthio group, more preferably a methylthio group or an ethylthio group, and most preferably a methylthio group.

The "($C_1$-$C_4$ alkylthio)-($C_1$-$C_4$ alkyl) group in $R^3$ of the general formula (I) is a $C_1$-$C_4$ alkyl group described above substituted by one $C_1$-$C_4$ alkylthio group described above and can include a methylthiomethyl group, an ethylthiomethyl group, a (1-propylthio)methyl group, a (2-propylthio)methyl group, a (1-butylthio)methyl group, a (2-butylthio)methyl group, a (2-methyl-2-propylthio)methyl group, a methylthioethyl group, an ethylthioethyl group, a (1-propylthio)ethyl group, a (2-propylthio)ethyl group, a (1-butylthio)ethyl group, a (2-butylthio)ethyl group, a (2-methyl-2-propylthio) ethyl group, a methylthio(1-propyl) group, an ethylthio(1-propyl) group, a (1-propylthio)-(1-propyl) group, a (1-butylthio)-(1-propyl) group, a methylthio(1-butyl) group, an ethylthio(1-butyl) group, a (1-propylthio)-(1-butyl) group or a (1-butylthio)-(1-butyl) group, preferably a ($C_1$-$C_2$ alkylthio)-($C_1$-$C_2$ alkyl) group, more preferably a methylthiomethyl group or an ethylthiomethyl group, and most preferably a methylthiomethyl group.

The $C_1$-$C_4$ alkylsulfinyl moiety of the "($C_1$-$C_4$ alkylsulfinyl)-($C_1$-$C_4$ alkyl) group" in $R^3$ of the general formula (I) is a sulfinyl group (—SO—) substituted by one $C_1$-$C_4$ alkyl group described above and can include a methylsulfinyl group, an ethylsulfinyl group, a 1-propylsulfinyl group, a 2-propylsulfinyl group, a 1-butylsulfinyl group, a 2-butylsulfinyl group or a 2-methyl-2-propylsulfinyl group, preferably a $C_1$-$C_3$ alkylsulfinyl group, more preferably a methylsulfinyl group or an ethylsulfinyl group, and most preferably a methylsulfinyl group.

The "($C_1$-$C_4$ alkylsulfinyl)-($C_1$-$C_4$ alkyl) group" in $R^3$ of the general formula (I) is a $C_1$-$C_4$ alkyl group described above substituted by one $C_1$-$C_4$ alkylsulfinyl group described above and can include a methylsulfinylmethyl group, an ethylsulfinylmethyl group, a (1-propylsulfinyl)methyl group, a (2-propylsulfinyl)methyl group, a (1-butylsulfinyl)methyl group, a (2-butylsulfinyl)methyl group, a (2-methyl-2-propylsulfinyl) methyl group, a methylsulfinylethyl group, an ethylsulfinylethyl group, a (1-propylsulfinyl)ethyl group, a (2-propylsulfinyl)ethyl group, a (1-butylsulfinyl)ethyl group, a (2-butylsulfinyl)ethyl group, a (2-methyl-2-propylsulfinyl) ethyl group, a methylsulfinyl(1-propyl) group, an ethylsulfinyl(1-propyl) group, a (1-propylsulfinyl)-(1-propyl) group, a (1-butylsulfinyl)-(1-propyl) group, a methylsulfinyl(1-butyl) group, an ethylsulfinyl(1-butyl) group, a (1-propylsulfinyl)-(1-butyl) group or a (1-butylsulfinyl)-(1-butyl) group, preferably a ($C_1$-$C_2$ alkylsulfinyl)-($C_1$-$C_2$ alkyl) group, more preferably a methylsulfinylmethyl group or an ethylsulfinylmethyl group, and most preferably a methylsulfinylmethyl group.

The $C_1$-$C_4$ alkylsulfonyl moiety of the "($C_1$-$C_4$ alkylsulfonyl)-($C_1$-$C_4$ alkyl) group" in $R^3$ of the general formula (I) is a sulfonyl group (—$SO_2$—) substituted by one $C_1$-$C_4$ alkyl group described above and can include a methanesulfonyl group, an ethanesulfonyl group, a 1-propanesulfonyl group, a 2-propanesulfonyl group, a 1-butanesulfonyl group, a 2-butanesulfonyl group or a 2-methyl-2-propanesulfonyl group, preferably a $C_1$-$C_3$ alkylsulfonyl group, more preferably a methanesulfonyl group or an ethanesulfonyl group, and most preferably a methanesulfonyl group.

The "($C_1$-$C_4$ alkylsulfonyl)-($C_1$-$C_4$ alkyl) group" in $R^3$ of the general formula (I) is a $C_1$-$C_4$ alkyl group described above substituted by one $C_1$-$C_4$ alkylsulfonyl group described above and can include a methanesulfonylmethyl group, an ethanesulfonylmethyl group, a (1-propanesulfonyl)methyl group, a (2-propanesulfonyl)methyl group, a (1-butanesulfonyl)methyl group, a (2-butanesulfonyl)methyl group, a (2-methyl-2-propanesulfonyl)methyl group, a methanesulfonylethyl group, an ethanesulfonylethyl group, a (1-propanesulfonyl)ethyl group, a (2-propanesulfonyl)ethyl group, a (1-butanesulfonyl)ethyl group, a (2-butanesulfonyl)ethyl group, a (2-methyl-2-propanesulfonyl)ethyl group, a methanesulfonyl(1-propyl) group, an ethanesulfonyl(1-propyl) group, a (1-propanesulfonyl)-(1-propyl) group, a (1-butanesulfonyl)-(1-propyl) group, a methanesulfonyl(1-butyl) group, an ethanesulfonyl(1-butyl) group, a (1-propanesulfonyl)-(1-butyl) group or a (1-butanesulfonyl)-(1-butyl) group, preferably a ($C_1$-$C_2$ alkylsulfonyl)-($C_1$-$C_2$ alkyl) group, more preferably a methanesulfonylmethyl group or an ethanesulfonylmethyl group, and most preferably a methanesulfonylmethyl group.

The "($C_1$-$C_4$ alkylamino)-($C_1$-$C_4$ alkyl) group" in $R^3$ of the general formula (I) is a $C_1$-$C_4$ alkyl group described above substituted by one $C_1$-$C_4$ alkylamino group described above and can include a methylaminomethyl group, an ethylaminomethyl group, a (1-propylamino)methyl group, a (2-propylamino)methyl group, a (1-butylamino)methyl group, a (2-butylamino)methyl group, a (2-methyl-2-propylamino) methyl group, a methylaminoethyl group, an ethylaminoethyl group, a (1-propylamino)ethyl group, a (2-propylamino)ethyl group, a (1-butylamino)ethyl group, a (2-butylamino)ethyl group, a (2-methyl-2-propylamino)ethyl group, a methylamino(1-propyl) group, a ethylamino(1-propyl) group, a (1-propylamino)-(1-propyl) group, a (1-butylamino)-(1-propyl) group, a methylamino(1-butyl) group, an ethylamino(1-butyl) group, a (1-propylamino)-(1-butyl) group or a (1-butylamino)-(1-butyl) group, preferably a ($C_1$-$C_2$ alkylamino)-($C_1$-$C_2$ alkyl) group, more preferably a methylaminomethyl group or an ethylaminomethyl group, and most preferably a methylaminomethyl group.

The "di($C_1$-$C_4$ alkylamino)-($C_1$-$C_4$ alkyl) group" in $R^3$ of the general formula (I) is a $C_1$-$C_4$ alkyl group described above substituted by the same or different two $C_1$-$C_4$ alkylamino groups described above and can include a dimethylaminomethyl group, a methylethylaminomethyl group, a methylpropylaminomethyl group [for example, a [N-(1-propyl)-N-methylamino]methyl group or the like], a methylbutylaminomethyl group [for example, a [N-(1-butyl)-N-methylamino]methyl group or the like], a diethylaminomethyl group, an ethylpropylaminomethyl group [for example, a [N-(1-propyl)-N-ethylamino]methyl group or the like], a dipropylaminomethyl group [for example, a di(1-propyl) aminomethyl group, a di(2-propyl)aminomethyl group or the like], a dibutylaminomethyl group [for example, a di(1-butyl) aminomethyl group, a di(2-butyl)aminomethyl group], a di(2-methyl-1-propyl)aminomethyl group, a di(2-methyl-2-propyl)aminomethyl group, a dimethylaminoethyl group [for example, a 2-dimethylamonoethyl group or the like], a methylethylamonoethyl group [for example, a 2-(N-methyl-N-ethylamino)ethyl group or the like], a methylpropylaminoethyl group [for example, a 2-[N-methyl-N-(1-propyl)amino] ethyl group or the like], a methylbutylaminoethyl group [for example, a 2-[N-methyl-N-(1-butyl)amino]ethyl group or the like], a diethylaminoethyl group (for example, a 2-diethylaminoethyl group or the like), an ethylpropylaminoethyl group [for example, a 2-[N-(1-propyl)-N-ethylamino]ethyl group or the like], a dipropylaminoethyl group [for example, a 2-[di(1-propyl)amino]ethyl group or the like], a dibutylaminoethyl group [for example, a 2-di(1-butyl)aminoethyl group or the like], a di(2-methyl-1-propyl)aminoethyl group [for example, a 2-di(2-methyl-1-propyl)aminoethyl group or the like], a di(2-methyl-2-propyl)aminoethyl group [for example, a 2-di(2-methyl-2-propyl)aminoethyl group or the like], a dimethylaminopropyl group [for example, a 3-dimethylamino-1-propyl group or the like], a methylethylaminopropyl group [for example, a 3-(N-methyl-N-ethylamino)-1-propyl group or the like], a diethylaminopropyl group [for example, a 3-diethylamino-1-propyl group or the like], a dipropylaminopropyl group [for example, a 3-di(1-propyl) amino-1-propyl group or the like], a dibutylaminopropyl group [for example a 3-di(1-butyl)amino-1-propyl group or the like], a dimethylaminobutyl group [for example, a 4-dimethylamino-1-butyl group or the like], a methylethylaminobutyl group [for example, a 4-(N-methyl-N-ethylamino)-1-butyl group or the like], a diethylaminobutyl group [for example, a 4-diethylamino-1-butyl group or the like], a dipropylaminobutyl group [for example, a 4-di(1-propyl)amino-1-butyl group or the like] or a dibutylaminobutyl group [for example, a 4-di(1-butyl)amino-1-butyl group or the like], preferably a di($C_1$-$C_2$ alkylamino)-($C_1$-$C_2$ alkyl) group, more preferably a dimethylamino group or a diethylaminomethyl group, and most preferably a dimethylaminomethyl group.

The "$C_3$-$C_6$ cycloalkyl group" in $R^3$, $R^4$ and $R^5$ of the general formula (I) is a cyclic alkyl group having 3 to 6 carbon atoms and can include a cyclopropyl group, a cyclobutyl group, a cyclopentyl group or a cyclohexyl group, preferably a $C_3$-$C_5$ cycloalkyl group, more preferably a $C_3$-$C_4$ cycloalkyl group, and most preferably a cyclopropyl group.

The "$C_2$-$C_6$ alkenyl group" in $R^3$ of the general formula (I) is an alkenyl group having 1 or 2 carbon-carbon double bonds and 2 to 6 carbon atoms and can include a vinyl group, a 2-propenyl group, a 2-butenyl group, a 1,3-butadien-1-yl group, a 2-methyl-2-propenyl group, a 2-pentenyl group, a 2-methyl-2-butenyl group or a 2-hexenyl group, preferably a $C_2$-$C_4$ alkenyl group, more preferably a $C_2$-$C_3$ alkenyl group, and most preferably a vinyl group.

The "$C_2$-$C_6$ alkynyl group" in $R^3$ of the general formula (I) is an alkynyl group having 1 or 2 carbon-carbon triple bonds and from 2 to 6 carbon atoms and can include an ethynyl group, a 1-propynyl group, a 1-butynyl group, a 1,3-butadyn-1-yl group, a 1-pentynyl group or a 1-hexynyl group, preferably a $C_1$-$C_4$ alkynyl group, more preferably a $C_2$-$C_3$ alkynyl group, and most preferably an ethynyl group.

The "$C_1$-$C_6$ alkoxy group" in $R^3$, $R^{11}$, Substituent group β and Substituent group γ of the general formula (I) is a hydroxyl group substituted by one $C_1$-$C_6$ alkyl group described above and can include a methoxy group, an ethoxy group, a 1-propoxy group, a 2-propoxy group, a 1-butoxy group, a 2-butoxy group, a 2-methyl-1-propoxy group, a 2-methyl-2-propoxy group, a 1-pentyloxy group, a 2-pentyloxy group, a 3-pentyloxy group, a 2-methyl-2-butoxy group, a 3-methyl-2-butoxy group, a 1-hexyloxy group, a 2-hexyloxy group, a 3-hexyloxy group, a 2-methyl-1-pentyloxy group, a 3-methyl-1-pentyloxy group, a 2-ethyl-1-butoxy group, a 2,2-dimethyl-1-butoxy group or a 2,3-dimethyl-1-butoxy group, preferably a $C_1$-$C_4$ alkoxy group, more preferably a $C_1$-$C_3$ alkoxy group (particularly a methoxy group, an ethoxy group or a propoxy group), further preferably a methoxy group or an ethoxy group, and most preferably a methoxy group.

The "halogeno $C_1$-$C_6$ alkoxy group" in $R^3$ and Substituent group β of the general formula (I) is a $C_1$-$C_6$ alkyl group described above substituted by 1 to 7 halogeno groups described above and can include a fluoromethoxy group, a difluoromethoxy group, a dichloromethoxy group, a dibromomethoxy group, a trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a 2,2,2-trichloroethoxy group, a pentafluoroethoxy group, a 3,3,3-trifluoro-1-propoxy group, a 1,1,1-trifluoro-2-propoxy group, a 1,1,1-trichloro-2-propoxy group, a 4,4,4-trifluoro-1-butoxy group, a 4,4,4-trifluoro-2-butoxy group, a 2-trifluoromethyl-1-propoxy group, a 2-trifluoromethyl-2-propoxy group, a 5,5,5-trifluoro-1-pentyloxy group, a 5,5,5-trifluoro-2-pentyloxy group, a 1,1,1-trifluoro-3-pentyloxy group, a 4,4,4-trifluoro-2-methyl-2-butoxy group, a 4,4,4-trifluoro-3-methyl-2-butoxy group, a 4,4,4-trifluoro-2-methyl-2-butoxy group, a 6,6,6-trifluoro-1-hexyloxy group, a 6,6,6-trifluoro-2-hexyloxy group, a 6,6,6-trifluoro-3-hexyloxy group, a 5,5,5-trifluoro-2-methyl-1-pentyloxy group, a 1,1,1-trifluoro-3-methyl-3-pentyloxy group, a 6,6,6-trifluoro-2-ethyl-1-butoxy group or a 6,6,6-trifluoro-2,3-dimethyl-1-butoxy group, preferably a halogeno $C_1$-$C_4$ alkoxy group (said halogeno $C_1$-$C_4$ alkoxy group represents a $C_1$-$C_4$ alkoxy group substituted by 1 to 5 halogeno groups), more preferably a halogeno $C_1$-$C_2$ alkoxy group (said halogeno $C_1$-$C_2$ alkoxy group represents a $C_1$-$C_2$ alkoxy group substituted by 1 to 5 fluoro, chloro or bromo groups), further more preferably a trifluoromethoxy group, a 2,2,2-trifluoroethoxy group or a pentafluoroethoxy group, and most preferably a trifluoromethoxy group.

The "$C_1$-$C_6$ alkylthio group" in $R^3$, Substituent group β and Substituent group γ of the general formula (I) is a mercapto group substituted by one $C_1$-$C_6$ alkyl group described above and can include a methylthio group, an ethylthio group, a 1-propylthio group, a 2-propylthio group, a 1-butylthio group, a 2-butylthio group, a 2-methyl-1-propylthio group, a 2-methyl-2-propylthio group, a 1-pentylthio group, a 2-pentylthio group, a 3-pentylthio group, a 2-methyl-2-butylthio group, a 3-methyl-2-butylthio group, a 1-hexylthio group, a 2-hexylthio group, a 3-hexylthio group, a 2-methyl-1-pentylthio group, a 3-methyl-1-pentylthio group, a 2-ethyl-1-butylthio group, a 2,2-dimethyl-1-butylthio group or a 2,3-dimethyl-1-butylthio group, preferably a $C_1$-$C_4$ alkylthio group, more preferably a $C_1$-$C_3$ alkylthio group (particularly a methylthio group, an ethylthio group or a propylthio group), further preferably a methylthio group or an ethylthio group, and most preferably a methylthio group.

The "$C_1$-$C_6$ alkylsulfinyl group" in $R^3$, Substituent group β and Substituent group γ of the general formula (I) is a sulfinyl group (—SO—) substituted by one $C_1$-$C_6$ alkyl group described above and can include a methylsulfinyl group, an ethylsulfinyl group, a 1-propylsulfinyl group, a 2-propylsulfinyl group, a 1-butylsulfinyl group, a 2-butylsulfinyl group, a 2-methyl-1-propylsulfinyl group, a 2-methyl-2-propylsulfinyl group, a 1-pentylsulfinyl group, a 2-pentylsulfinyl group, a 3-pentylsulfinyl group, a 2-methyl-2-butylsulfinyl group, a 3-methyl-2-butylsulfinyl group, a 1-hexylsulfinyl group, a 2-hexylsulfinyl group, a 3-hexylsulfinyl group, a 2-methyl-1-pentylsulfinyl group, a 3-methyl-1-pentylsulfinyl group, a 2-ethyl-1-butylsulfinyl group, a 2,2-dimethyl-1-butylsulfinyl group or a 2,3-dimethyl-1-butylsulfinyl group, preferably a $C_1$-$C_4$ alkylsulfinyl group, more preferably a $C_1$-$C_3$ alkylsulfinyl group (particularly a methylsulfinyl group, an ethylsulfinyl group or a propylsulfinyl group), further preferably a methylsulfinyl group or an ethylsulfinyl group, and most preferably a methylsulfinyl group.

The "$C_1$-$C_6$ alkylsulfonyl group" in $R^3$, Substituent group β and Substituent group γ of the general formula (I) is a sulfonyl group (—$SO_2$—) substituted by one $C_1$-$C_6$ alkyl group described above and can include a methanesulfonyl group, an ethanesulfonyl group, a 1-propanesulfonyl group, a 2-propanesulfonyl group, a 1-butanesulfonyl group, a 2-butanesulfonyl group, a 2-methyl-1-propanesulfonyl group, a 2-methyl-2-propanesulfonyl group, a 1-pentanesulfonyl group, a 2-pentanesulfonyl group, a 3-pentanesulfonyl group, a 2-methyl-2-butanesulfonyl group, a 3-methyl-2-butanesulfonyl group, a 1-hexanesulfonyl group, a 2-hexanesulfonyl group, a 3-hexanesulfonyl group, a 2-methyl-1-pentanesulfonyl group, a 3-methyl-1-pentanesulfonyl group, a 2-ethyl-1-butanesulfonyl group, a 2,2-dimethyl-1-butanesulfonyl group or a 2,3-dimethyl-1-butanesulfonyl group, preferably a $C_1$-$C_4$ alkylsulfonyl group, more preferably a $C_1$-$C_3$ alkylsulfonyl group (particularly a methanesulfonyl group, an ethanesulfonyl group or a propanesulfonyl group), further preferably a methanesulfonyl group or an ethanesulfonyl group, and most preferably a methanesulfonyl group.

The "$C_1$-$C_6$ alkylamino group" in $R^3$, $R^{11}$, $R^{12}$, Substituent group β and Substituent group γ of the general formula (I) is an amino group substituted by one $C_1$-$C_6$ alkyl group described above and can include a methylamino group, an ethylamino group, a propylamino group, a 2-propylamino group, a 1-butylamino group, a 2-butylamino group, a 2-methyl-1-propylamino group, a 2-methyl-2-propylamino group, a 1-pentylamino group, a 2-pentylamino group, a 3-pentylamino group, a 2-methyl-2-butylamino group, a 3-methyl-2-butylamino group, a 1-hexylamino group, a 2-hexylamino group, a 3-hexylamino group, a 2-methyl-1-pentylamino group, a 3-methyl-1-pentylamino group, a 2-ethyl-1-butylamino group, a 2,2-dimethyl-1-butylamino group or a 2,3-dimethyl-1-butylamino group, preferably a $C_1$-$C_4$ alkylamino group, more preferably a $C_1$-$C_3$ alkylamino group (particularly a methylamino group, an ethylamino group or a propylamino group), further preferably a methylamino group or an ethylamino group, and most preferably a methylamino group.

The "di($C_1$-$C_6$ alkyl)amino group" in $R^3$, $R^{11}$, $R^{12}$, Substituent group β and Substituent group γ of the general formula (I) is an amino group substituted by the same or different two $C_1$-$C_6$ alkyl groups described above and can include a dimethylamino group, a methylethylamino group, a methylpropylamino group [for example, a N-(1-propyl)-N-methylamino group or the like], a methylbutylamino group [for example, a N-(1-butyl)-N-methylamino group or the like], a diethylamino group, an ethylpropylamino group [for example, a N-(1-propyl)-N-ethylamino group or the like], a dipropylamino group [for example, a di(1-propyl)amino group, a di(2-propyl)amino group or the like], a dibutylamino group [for example, a di(1-butyl)amino group, a di(2-butyl)amino group or the like], a di(2-methyl-1-propyl)amino group, a dipentylamino group [for example, a di(1-pentyl) amino group, a di(2-pentyl)amino group, a di(3-pentyl) amino group or the like] or a dihexylamino group [for example, a di(1-hexyl)amino group, a di(2-hexyl)amino group, a di(3-hexyl)amino group or the like], preferably a di($C_1$-$C_4$ alkyl)amino group, more preferably a di($C_1$-$C_3$ alkyl)amino group, further preferably a dimethylamino group or a diethylamino group, most preferably a dimethylamino group. Further, in "di-($C_1$-$C_6$ alkyl)amino group", said two alkyl groups together with the nitrogen atom of said amino group may form a 5- to 7-membered saturated heterocyclyl group containing from to 3 atoms selected from the group consisting of a nitrogen atom, an oxygen atom and a sulfur atom and the 5- to 7-membered saturated heterocyclyl group can include a pyrrolidinyl group, a piperidyl group, a piperazinyl group, a morpholinyl group, a thiomorpholinyl group or a perhydroazepinyl group, preferably a 5- or 6-membered saturated heterocyclyl group containing 1 or 2 atoms selected from the group consisting of a nitrogen atom, an oxygen atom and a sulfur atom, more preferably a pyrrolidinyl group, a piperidyl group, a morpholinyl group or a thiomorpholinyl group, and further preferably a piperidyl group or a morpholinyl group.

The "($C_1$-$C_6$ alkoxy) carbonyl group" in $R^3$ and Substituent group β of the general formula (I) is a carbonyl group (—CO—) substituted by one $C_1$-$C_6$ alkoxy group described above and can include a methoxycarbonyl group, an ethoxycarbonyl group, a 1-propoxycarbonyl group, a 2-propoxycarbonyl group, a 1-butoxycarbonyl group, a 2-butoxycarbonyl group, a 2-methyl-1-propoxycarbonyl group, a 2-methyl-2-propoxycarbonyl group, a 1-pentyloxycarbonyl group, a 2-pentyloxycarbonyl group, a 3-pentyloxycarbonyl group, a 2-methyl-2-butoxycarbonyl group, a 3-methyl-2-butoxycarbonyl group, a 1-hexyloxycarbonyl group, a 2-hexyloxycarbonyl group, a 3-hexyloxycarbonyl group, a 2-methyl-1-pentyloxycarbonyl group, a 3-methyl-1-pentyloxycarbonyl group, a 2-ethyl-1-butoxycarbonyl group, a 2,2-dimethyl-1-butoxycarbonyl group or a 2,3-dimethyl-1-butoxycarbonyl group, preferably a ($C_1$-$C_4$ alkoxy)carbonyl group, more preferably a methoxycarbonyl group or an ethoxycarbonyl group, and most preferably a methoxycarbonyl group.

The "halogeno $C_1$-$C_4$ alkoxy group" in $R^4$ and $R^5$ of the general formula (I) is $C_1$-$C_4$ alkoxy group described above substituted by 1 to 5 halogeno groups described above and can include a fluoromethoxy group, a difluoromethoxy group, a dichloromethoxy group, a dibromomethoxy group, trifluoromethoxy group, a trichloromethoxy group, a 2-fluoroethoxy group, a 2-bromoethoxy group, a 2-chloroethoxy group, a 2-iodoethoxy group, a 2,2-difluoroethoxy group, a 2,2,2-trifluoroethoxy group, a 2,2,2-trichloroethoxy group, a pentafluoroethoxy group, a 3,3,3-trifluoro-1-propoxy group, a 1,1,1-trifluoro-2-propoxy group, a 1,1,1-trichloro-2-propoxy group, a 4,4,4-trifluoro-1-butoxy group, a 4,4,4-trifluoro-2-butoxy group, a 2-trifluoromethyl-1-propoxy group or a 2-trifluoromethyl-2-propoxy group, preferably a halogeno $C_1$-$C_2$ alkoxy group (said halogen $C_1$-$C_2$ alkoxy group represents a $C_1$-$C_2$ alkoxy group substituted by 1 to 5 halogeno groups), more preferably a trifluoromethoxy group, a 2,2,2-trifluoroethoxy group or a pentafluoroethoxy group, and most preferably a trifluoromethoxy group.

The "$C_1$-$C_3$ alkyl group" in $R^6$ and $R^7$ of the general formula (I) is a straight or branched chain alkyl group having from 1 to 3 carbon atoms and can include a methyl group, an ethyl group, a 1-propyl group or a 2-propyl group, preferably a methyl group or an ethyl group, and most preferably a methyl group.

The "($C_3$-$C_8$ cycloalkyl)-($C_1$-$C_6$ alkyl)oxy group" in $R^{11}$ of the general formula (I) is a $C_1$-$C_6$ alkoxy group described above substituted by one $C_3$-$C_8$ cycloalkyl group described below and can include a cyclopropylmethoxy group, a cyclobutylmethoxy group, a cyclopentylmethoxy group, a cyclohexylmethoxy group, a cyclohexylmethoxy group, 1-cyclopropylethoxy group, a 2-cyclopropylethoxy group, a 2-cyclobutylethoxy group, a 2-cyclopentylethoxy group, a 2-cyclohexylethoxy group, a 2-cycloheptylethoxy group, a 3-cyclopropyl-1-propoxy group, a 2-cyclopropyl-1-propoxy group, a 2-cyclopropyl-2-propoxy group, a 3-cyclobutyl-1-propoxy group, a 3-cyclopentyl-1-propoxy group, a 3-cyclohexyl-1-propoxy group, a 4-cyclopropyl-1-butoxy group, a 4-cyclopropyl-2-butoxy group, a 3-cyclopropyl-2-methyl-1-propoxy group, a 3-cyclopropyl-2-methyl-2-propoxy group, a 4-cyclobutyl-1-butoxy group, a 5-cyclopropyl-1-pentyloxy group, a 5-cyclopropyl-2-pentyloxy group, a 5-cyclopropyl-3-pentyloxy group, a 4-cyclopropyl-2-methyl-2-butoxy group, a 4-cyclopropyl-3-methyl-2-butoxy group, a 6-cyclopropyl-1-hexyloxy group, a 6-cyclopropyl-2-hexyloxy group, a 6-cyclopropyl-3-hexyloxy group, a 5-cyclopropyl-2-methyl-1-pentyloxy group, a 5-cyclopropyl-3-methyl-1-pentyloxy group, a 4-cyclopropyl-2-ethyl-1-butoxy group, a 4-cyclopropyl-2,2-dimethyl-1-butoxy group or a 4-cyclopropyl-2,3-dimethyl-1-butoxy group, preferably a ($C_3$-$C_6$ cycloalkyl)-($C_1$-$C_4$ alkyl)oxy group, more preferably a ($C_3$-$C_5$ cycloalkyl)-($C_1$-$C_2$ alkyl)oxy group, further preferably a ($C_3$-$C_4$ cycloalkyl)-($C_1$-$C_2$ alkyl)oxy group, and most preferably a cyclopropylmethyloxy group.

The "$C_3$-$C_8$ cycloalkyloxy group" in $R^{11}$ and Substituent group γ of the general formula (I) is a hydroxyl group substituted by one $C_3$-$C_8$ cycloalkyl group described below and can include a cyclopropyloxy group, a cyclobutyloxy group, a cyclopentyloxy group, a cyclohexyloxy group, a cycloheptyloxy group or a cyclooctyloxy group, preferably a $C_3$-$C_6$ cycloalkyloxy group, more preferably a $C_3$-$C_4$ cycloalkyloxy group, and most preferably a cyclopropyloxy group.

The "[($C_3$-$C_8$ cycloalkyl)-($C_1$-$C_6$ alkyl)]amino group" in $R^{11}$ and $R^{12}$ of the general formula (I) is a $C_1$-$C_6$ alkylamino group described above substituted by one $C_3$-$C_8$ cycloalkyl group described below and can include a cyclopropylmethylamino group, a cyclobutylmethylamino group, a cyclopentylmethylamino group, a cyclohexylmethylamino group, a cyclohexylmethylamino group, a 1-cyclopropylethylamino group, a 2-cyclopropylethylamino group, a 2-cyclobutylethylamino group, a 2-cyclopentylethylamino group, a 2-cyclohexylethylamino group, a 2-cycloheptylethylamino group, a 3-cyclopropyl-1-propylamino group, a 2-cyclopropyl-1-propylamino group, a 2-cyclopropyl-2-propylamino group, a 3-cyclobutyl-1-propylamino group, a 3-cyclopentyl-1-propylamino group, a 3-cyclohexyl-1-propylamino group, a 4-cyclopropyl-1-butylamino group, a 4-cyclopropyl-2-butylamino group, a 3-cyclopropyl-2-methyl-1-propylamino group, a 3-cyclopropyl-2-methyl-2-propylamino group, a 4-cyclobutyl-1-butylamino group, a 5-cyclopropyl-1-pentylamino group, a 5-cyclopropyl-2-pentylamino group, a 5-cyclopropyl-3-pentylamino group, a 4-cyclopropyl-2-methyl-2-butylamino group, a 4-cyclopropyl-3-methyl-2-butylamino group, a 6-cyclopropyl-1-hexylamino group, a 6-cyclopropyl-2-hexylamino group, a 6-cyclopropyl-3-hexylamino group, a 5-cyclopropyl-2-methyl-1-pentylamino group, a 5-cyclopropyl-3-methyl-1-pentylamino group, a 4-cyclopropyl-2-ethyl-1-butylamino group, a 4-cyclopropyl-2,2-dimethyl-1-butylamino group or a 4-cyclopropyl-2,3-dimethyl-1-butylamino group, preferably a ($C_3$-$C_6$ cycloalkyl)-($C_1$-$C_4$ alkyl)amino group, more preferably a ($C_3$-$C_5$ cycloalkyl)-($C_1$-$C_2$ alkyl)amino group, further preferably a ($C_3$-$C_4$ cycloalkyl)-($C_1$-$C_2$ alkyl)amino group, and most preferably a cyclopropylmethylamino group.

The "$C_3$-$C_8$ cycloalkylamino group" in $R^{11}$, $R^{12}$, Substituent group β and Substituent group γ of the general formula (I) is an amino group substituted by one $C_3$-$C_8$ cycloalkyl group described below and can include a cyclopropylamino group, a cyclobutylamino group, a cyclopentylamino group, a cyclohexylamino group, a cycloheptylamino group or a cyclooctylamino group, preferably a $C_3$-$C_6$ cycloalkylamino group, more preferably a $C_3$-$C_4$ cycloalkylamino group, and most preferably a cyclopropylamino group.

The "di[($C_3$-$C_8$ cycloalkyl)-($C_1$-$C_6$ alkyl)]amino group" in $R^{11}$ and $R^{12}$ of the general formula (I) is an amino group substituted by the same or different two ($C_3$-$C_8$ cycloalkyl)-($C_1$-$C_6$ alkyl) groups described below and can include a di(cyclopropylmethyl)amino group, a N-cyclopropylmethyl-N-cyclobutylmethylamino group, a N-cyclopropylmethyl-N-cyclopentylmethylamino group, a N-cyclopropylmethyl-N-cyclohexylmethylamino group, a N-cyclopropylmethyl-N-cycloheptylmethylamino group, a N-cyclopropylmethyl-N-cyclooctylmethylamino group, a N-cyclopropylmethyl-N-cyclopropylethylamino group, a N-cyclopropylmethyl-N-(3-cyclopropyl-1-propyl)amino group, a di(cyclobutylmethyl)amino group, a di(cyclopentylmethyl)amino group, a di(cyclohexylmethyl)amino group, a di(cycloheptylmethyl)amino group or a di(cyclooctylmethyl)amino group, preferably a di[($C_3$-$C_6$ cycloalkyl)-($C_1$-$C_4$ alkyl)]amino group, more preferably a di[($C_3$-$C_5$ cycloalkyl)-($C_1$-$C_2$ alkyl)]amino group, further preferably a di[($C_3$-$C_4$ cycloalkyl)-($C_1$-$C_2$ alkyl)]amino group, and most preferably a di(cyclopropylmethyl)amino group.

The "di($C_3$-$C_8$ cycloalkyl)amino group" in $R^{11}$, $R^{12}$, Substituent group β and Substituent group γ of the general formula (I) is an amino group substituted by the same or different two $C_3$-$C_8$ cycloalkyl groups described below and can include a dicyclopropylamino group, a N-cyclopropyl-N-cyclobutylamino group, a N-cyclopropyl-N-cyclopentylamino group, a N-cyclopropyl-N-cyclohexylamino group, a N-cyclopropyl-N-cycloheptylamino group, a N-cyclopropyl-N-cyclooctylamino group, a dicyclobutylamino group, a dicyclopentylamino group, a dicyclohexylamino group, a dicycloheptylamino group or a dicyclooctylamino group, preferably a di($C_3$-$C_6$ cycloalkyl)amino group, more preferably a di($C_3$-$C_4$ cycloalkyl)amino group, and most preferably a dicyclopropylamino group.

The "N—[($C_3$-$C_8$ cycloalkyl)-($C_1$-$C_6$ alkyl)]-N—($C_1$-$C_6$ alkyl)amino group" in $R^{11}$ and $R^{12}$ of the general formula (I) is an amino group substituted by one ($C_3$-$C_8$ cycloalkyl)-($C_1$-$C_6$ alkyl) group described below and one $C_1$-$C_6$ alkyl group described above and can include a N-cyclopropylmethyl-N-methylamino group, a N-cyclopropylmethyl-N-ethylamino group, a N-cyclopropylmethyl-N-propylamino group, a N-cyclopropylmethyl-N-butylamino group, a N-cyclopropylmethyl-N-pentylamino group, a N-cyclopropylmethyl-N-hexylamino group, a N-cyclopropylethyl-N-methylamino group, a N-(3-cyclopropyl-1-propyl)-N-methylamino group, a N-cyclobutylmethyl-N-methylamino group, a N-cyclopentylmethyl-N-methylamino group, a N-cyclohexylmethyl-N-methylamino group, a N-cycloheptylmethyl-N-methylamino group or a N-cyclooctylmethyl-N-methylamino group, preferably a N—[($C_3$-$C_6$ cycloalkyl)-($C_1$-$C_4$ alkyl)]-N—($C_1$-$C_4$ alkyl)amino group, more preferably a N—[($C_3$-$C_4$ cycloalkyl)-($C_1$-$C_2$ alkyl)]-N—($C_1$-$C_2$ alkyl)amino group, further preferably a N—[($C_3$-$C_4$ cycloalkyl)methyl-N-methylamino group, and most preferably a N-cyclopropylmethyl-N-methylamino group.

The "N—($C_3$-$C_8$ cycloalkyl)-N—($C_1$-$C_6$ alkyl)amino group" in $R^{11}$, $R^{12}$, Substituent group β and Substituent group γ of the general formula (I) is an amino group substituted by one $C_3$-$C_8$ cycloalkyl group described above and one $C_1$-$C_6$ alkyl group described above and can include a N-cyclopropyl-N-methylamino group, a N-cyclopropyl-N-ethylamino group, a N-cyclopropyl-N-propylamino group, a N-cyclopropyl-N-butylamino group, a N-cyclopropyl-N-pentylamino group, a N-cyclopropyl-N-hexylamino group, a N-cyclobutyl-N-methylamino group, a N-cyclopentyl-N-methylamino group, a N-cyclohexyl-N-methylamino group, a N-cycloheptyl-N-methylamino group or a N-cyclooctyl-N-methylamino group, preferably a N—($C_3$-$C_6$ cycloalkyl)-N—($C_1$-$C_4$ alkyl)amino group, more preferably a N—($C_3$-$C_4$ cycloalkyl)-N—($C_1$-$C_2$ alkyl)amino group, further preferably a N—($C_1$-$C_4$ cycloalkyl)-N-methylamino group, and most preferably a N-cyclopropyl-N-methylamino group.

The "N—[($C_3$-$C_8$ cycloalkyl)-($C_1$-$C_6$ alkyl)]-N—($C_3$-$C_8$ cycloalkyl)amino group" in $R^{11}$ and $R^{12}$ of the general formula (I) is an amino group substituted by one ($C_3$-$C_8$ cycloalkyl)-($C_1$-$C_6$ alkyl) group described below and one $C_3$-$C_8$ cycloalkyl group described below and can include a N-cyclopropylmethyl-N-cyclopropylamino group, a N-cyclobutylmethyl-N-cyclopropylamino group, a N-cyclopentylmethyl-N-cyclopropylamino group, a N-cyclohexylmethyl-N-cyclopropylamino group, a N-cycloheptylmethyl-N-cyclopropylamino group, a N-cyclooctylmethyl-N-cyclopropylamino group, a N-cyclopropylethyl-N- cyclopropylamino group, a N-(3-cyclopropyl-1-propyl)-N-cyclopropylamino group, a N-cyclopropylmethyl-N-cyclobutylamino group or a N-cyclopropylmethyl-N-cyclopentylamino group, preferably a N—[($C_3$-$C_6$ cycloalkyl)-($C_1$-$C_4$ alkyl)]-N—($C_3$-$C_6$ cycloalkyl)amino group, more preferably a N—[($C_3$-$C_4$ cycloalkyl)-($C_1$-$C_2$ alkyl)]-N—($C_3$-$C_4$ cycloalkyl)amino group, further preferably a N—[($C_3$-$C_4$ cycloalkyl)methyl]-N—($C_3$-$C_4$ cycloalkyl)amino group, and most preferably a N-cyclopropylmethyl-N-cyclopropylamino group.

The "hydroxyl($C_1$-$C_6$ alkyl)amino group" in $R^{11}$ of the general formula (I) is an amino group substituted by one $C_1$-$C_6$ alkyl group described below and one hydroxyl group and can include a hydroxyl(methyl)amino group, a hydroxyl (ethyl)amino group, a hydroxyl(1-propyl)amino group, a hydroxyl(2-propyl)amino group, a hydroxyl(1-butyl)amino group, a hydroxyl(2-butyl)amino group, a hydroxyl(2-methyl-1-propyl)amino group, a hydroxyl(2-methyl-2-propyl)amino group, a hydroxyl(1-pentyl)amino group, a hydroxyl(2-pentyl)amino group, a hydroxyl(3-pentyl)amino group, a hydroxyl(2-methyl-2-butyl)amino group, a hydroxyl(3-methyl-2-butyl)amino group, a hydroxyl(2-methyl-2-butyl)amino group, a hydroxyl(1-hexyl)amino group, a hydroxyl(2-hexyl)amino group, a hydroxyl(3-hexyl)amino group, a hydroxyl(2-methyl-1-pentyl)amino group, a hydroxyl(3-methyl-3-pentyl)amino group, a hydroxyl(2-ethyl-1-butyl)amino group, a hydroxyl (2,3-dimethyl-1-butyl)amino group, a hydroxyl(1-heptyl)amino group, a hydroxyl(3-heptyl) amino group, a hydroxyl(4-heptyl)amino group, a hydroxyl (3-methyl-3-hexyl)amino group, a hydroxyl(3-ethyl-3-pentyl)amino group, a hydroxyl(3-octyl)amino group, a hydroxyl(4-octyl)amino group, a hydroxyl(3-ethyl-3-hexyl) amino group, a hydroxyl(4-nonyl)amino group, a hydroxyl (5-nonyl)amino group, a hydroxyl(4-ethyl-4-heptyl)amino group, a hydroxyl(4-decyl)amino group, a hydroxyl(5-decyl) amino group or a hydroxyl[4-(1-propyl)-4-heptyl]amino group, preferably a hydroxyl($C_1$-$C_4$ alkyl)amino group, more preferably a hydroxyl(methyl)amino group or a hydroxyl (ethyl)amino group, and most preferably a hydroxylmethylamino group.

The "($C_3$-$C_8$ cycloalkyl)-($C_1$-$C_6$ alkyl) group" in $R^{12}$, $R^{13}$, $R^{14}$, $R^{15}$ and Substituent group β of the general formula (I) is a $C_1$-$C_6$ alkyl group described above substituted by one $C_3$-$C_8$ cycloalkyl described below and can include a cyclopropylmethyl group, a cyclobutylmethyl group, a cyclopentylmethyl group, a cyclohexylmethyl group, a cycloheptylmethyl group, a cyclooctylmethyl group, a 1-cyclopropylethyl group, a 2-cyclopropylethyl group, a 2-cyclobutylethyl group, a 2-cyclopentylethyl group, a 2-cyclohexylethyl group, a 2-cycloheptylethyl group, a 3-cyclopropyl-1-propyl group, a 2-cyclopropyl-1-propyl group, a 2-cyclopropyl-2-propyl group, a 3-cyclobutyl-1-propyl group, a 3-cyclopentyl-1-propyl group, a 3-cyclohexyl-1-propyl group, a 4-cyclopropyl-1-butyl group, a 4-cyclopropyl-2-butyl group, a 3-cyclopropyl-2-methyl-1-propyl group, a 3-cyclopropyl-2-methyl-2-propyl group, a 4-cyclobutyl-1-butyl group, a 5-cyclopropyl-1-pentyl group, a 5-cyclopropyl-2-pentyl group, a 5-cyclopropyl-3-pentyl group, a 4-cyclopropyl-2-methyl-2-butyl group, a 4-cyclopropyl-3-methyl-2-butyl group, a 6-cyclopropyl-1-hexyl group, a 6-cyclopropyl-2-hexyl group, a 6-cyclopropyl-3-hexyl group, a 5-cyclopropyl-2-methyl-1-pentyl group, a 5-cyclopropyl-3-methyl-1-pentyl group, a 4-cyclopropyl-2-ethyl-1-butyl group or a 4-cyclopropyl-2,2-dimethyl-1-butyl group or a 4-cyclopropyl-2,3-dimethyl-1-butyl group, preferably a ($C_3$-$C_8$ cycloalkyl)-($C_1$-$C_4$ alkyl) group, more preferably a ($C_3$-$C_5$ cycloalkyl)-($C_1$-$C_2$ alkyl) group, further preferably a ($C_3$-$C_4$ cycloalkyl)-($C_1$-$C_2$ alkyl) group, further more preferably a cyclopropylmethyl group or a cyclopropylethyl group, and most preferably a cyclopropylmethyl group.

The "$C_3$-$C_8$ cycloalkyl group" in $R^{12}$, $R^{13}$, $R^{14}$, $R^{15}$ and Substituent group β of the general formula (I) is a cyclic alkyl group having from 3 to 8 carbon atoms and can include a cyclopropyl group, a cyclobutyl group, a cyclopentyl group, a cyclohexyl group, a cycloheptyl group or a cyclooctyl group, preferably a $C_3$-$C_6$ cycloalkyl group, more preferably a $C_3$-$C_5$ cycloalkyl group, further preferably a $C_3$-$C_4$ cycloalkyl group (a cyclopropyl group or a cyclobutyl group), and most preferably a cyclopropyl group.

The "$C_1$-$C_4$ alkylene group" in $X^2$ of the general formula (I) is an alkylene group having from 1 to 4 carbon atoms and can include a methylene group, an ethylene group [—($CH_2$)$_2$—], a methylmethylene group [—CH(Me)—], a trimethylene group [—($CH_2$)$_3$—], a methylethylene group [—CH(Me)$CH_2$— or —$CH_2$CH(Me)—], a tetramethylene group [—($CH_2$)$_4$—], or a methyltrimethylene group [—CH(Me) $CH_2$$CH_2$—, —$CH_2$CH(Me)$CH_2$— or —$CH_2$$CH_2$CH (Me)—], preferably a $C_1$-$C_3$ alkylene group, more preferably a methylene group or an ethylene group, and most preferably a methylene group.

The "5- or 6-membered aromatic heterocyclyl group" in $Y^1$ of the general formula (I) is a 5- or 6-membered aromatic heterocyclic group containing from 1 to 4 atoms selected from the group consisting of a nitrogen atom, an oxygen atom and a sulfur atom and can include a furyl group, a thienyl group, a pyrrolyl group, an imidazolyl group, a pyrazolyl group, an oxazolyl group, an isoxazolyl group, a thiazolyl group, an isothiazolyl group, a triazolyl group, a tetrazolyl group, an oxadiazolyl group, a thiadiazolyl group, a tetrazolyl group, a pyranyl group, a pyridyl group, a pyridazinyl group, a pyrimidinyl group or a pyrazinyl group, preferably a pyrrolyl group, a furyl group, a thienyl group, an imidazolyl group, an oxazolyl group, a thiazolyl group or a pyridyl group, more preferably a thienyl group or a pyridyl group, and most preferably a pyridyl group.

The "6- to 10-membered aryl group" in $Y^2$ of the general formula (I) is a 6- to 10-membered aromatic hydrocarbon group and can include a phenyl group or a naphthyl group, preferably a phenyl group.

The "9- or 10-membered unsaturated cyclic hydrocarbon group" in $Y^2$ of the general formula (I) is a group which is formed by the 9- or 10-membered aromatic hydrocarbon group being partially reduced, which is not a saturated hydrocarbon group and in which a cyclic group bonded to $Y^1$ is a phenyl group. The 9- or 10-membered unsaturated cyclic hydrocarbon group can include an indanyl group or a tetrahydronaphthyl group, preferably an indanyl group.

The "5- to 10-membered aromatic heterocyclyl group" in $Y^2$ of the general formula (I) is a 5- to 10-membered aromatic heterocyclic group containing from 1 to 4 atoms selected from the group consisting of a nitrogen atom, an oxygen atom and a sulfur atom and can include a furyl group, a thienyl group, a pyrrolyl group, a pyrazolyl group, an imidazolyl group, an oxazolyl group, an isoxazolyl group, a thiazolyl group, an isothiazolyl group, a triazolyl group, an oxadiazolyl group, a thiadiazolyl group, a tetrazolyl group, a pyridyl group, a pyridazinyl group, a pyrimidinyl group, a pyrazinyl group, an azepinyl group, an azosinyl group, an azoninyl group, an indolyl group, a benzofuranyl group, a benzothienyl group, a benzoimidazolyl group, a benzoxazolyl group, a benzisoxazolyl group, a benzothiazolyl group, a benzisothiazolyl group, a quinolyl group, an isoquinolyl group, a quinoxalinyl group or a quinazolinyl group, preferably a 5- or 6-membered aromatic heterocyclyl group, more preferably a pyrrolyl group, a furyl group, a thienyl group, an imidazolyl group, an oxazolyl group, a thiazolyl group, a pyridyl group or a pyrimidinyl group, further preferably a thienyl group, a thiazolyl group or a pyridyl group, and most preferably a pyridyl group.

The "9- or 10-membered unsaturated heterocyclyl group" in $Y^2$ of the general formula (I) is a group which is formed by a 9- or 10-membered aromatic heterocyclyl group being partially reduced, which is not a saturated heterocyclyl group and in which a cyclic group bonded to $Y^1$ is an aromatic ring group. The 9- or 10-membered unsaturated heterocyclyl group can include an indolinyl group, a dihydrobenzofuryl group, a dihydrobenzothienyl group, a tetrahydroquinolyl group or a chromanyl group, preferably an indolinyl group, a dihydrobenzofuryl group or a dihydrobenzothienyl group.

The "hydroxy($C_1$-$C_6$ alkyl) group" in Substituent group β and Substituent group γ of the general formula (I) is a $C_1$-$C_6$ alkyl group described above substituted by one hydroxyl group and can include a hydroxymethyl group, a hydroxyethyl group, a hydroxy(1-propyl) group, a hydroxy(2-propyl) group, a hydroxy(1-butyl) group, a hydroxy(2-butyl) group, a hydroxy(2-methyl-1-propyl) group, a hydroxy(2-methyl-2-propyl) group, a hydroxy(1-pentyl) group or a hydroxy(1-hexyl) group, preferably a hydroxy($C_1$-$C_4$ alkyl) group, more preferably a hydroxy($C_1$-$C_3$ alkyl) group (particularly a hydroxymethyl group, a hydroxyethyl group or a hydroxypropyl group), further preferably a hydroxymethyl group or a hydroxyethyl group, most preferably a hydroxymethyl group.

The "carboxy($C_1$-$C_6$ alkyl) group" in Substituent group β of the general formula (I) is a $C_1$-$C_6$ alkyl group described above substituted by one carboxyl group and can include a carboxymethyl group, a carboxyethyl group, a carboxy(1-propyl) group, a carboxy(2-propyl) group, a carboxy(1-butyl) group, a carboxy(2-butyl) group, a carboxy(2-methyl-1-propyl) group, a carboxy(2-methyl-2-propyl) group, a carboxy(1-pentyl) group or a carboxy(1-hexyl) group, preferably a carboxy($C_1$-$C_4$ alkyl) group, more preferably a carboxy($C_1$-$C_3$ alkyl) group (particularly a carboxymethyl group, a carboxyethyl group or a carboxypropyl group), further preferably a carboxymethyl group or a carboxyethyl group, and most preferably a carboxymethyl group.

The "($C_1$-$C_6$ alkoxy)carbonyl-($C_1$-$C_6$ alkyl) group" in Substituent group β of the general formula (I) is a $C_1$-$C_6$ alkyl group described above substituted by one ($C_1$-$C_6$ alkoxy) carbonyl group described below and can include a methoxycarbonylmethyl group, an ethoxycarbonylmethyl group, a propoxycarbonylmethyl group, a butoxycarbonylmethyl group, a pentyloxycarbonylmethyl group, a hexyloxycarbonylmethyl group, a methoxycarbonylethyl group, a methoxycarbonylpropyl group, a methoxycarbonylbutyl group, a methoxycarbonylpentyl group or a methoxycarbonylhexyl group, preferably a ($C_1$-$C_4$ alkoxy)carbonyl-($C_1$-$C_4$ alkyl) group, more preferably a ($C_1$-$C_2$ alkoxy)carbonyl-($C_1$-$C_2$ alkyl) group, further preferably a methoxycarbonylmethyl group or a methoxycarbonylethyl group, and most preferably a methoxycarbonylmethyl group.

The "$C_2$-$C_7$ alkenyl group" in Substituent group β of the general formula (I) is a straight or branched chain alkenyl group having from 2 to 7 carbon atoms (which may have one or more carbon-carbon double bonds) and can include a vinyl group, a 2-propenyl group (an allyl group), a 2-butenyl group, a 2-pentenyl group, a 3-methyl-2-butenyl group, a 2-hexenyl group, a 3-methyl-2-pentenyl group, a 2-heptenyl group or a 3-ethyl-2-pentenyl group, preferably a $C_2$-$C_5$ alkenyl group, more preferably a $C_2$-$C_4$ alkenyl group, and most preferably a vinyl group or a 2-propenyl group.

The "$C_2$-$C_7$ alkynyl group" in Substituent group β of the general formula (I) is a straight or branched chain alkynyl group having from 2 to 7 carbon atoms (which may have one or more carbon-carbon triple bonds) and can include an ethynyl group, a 2-propynyl group, a 2-butynyl group, a 2-pentynyl group, a 2-hexynyl group or a 2-heptynyl group, preferably a $C_2$-$C_5$ alkynyl group, more preferably a $C_2$-$C_4$ alkynyl group, and most preferably an ethynyl group or a 2-propynyl group.

The "($C_1$-$C_6$ alkyl)carbonylamino group" in Substituent group β of the general formula (I) is a group in which the carbon atom of a carbonylamino group (—CONH—) is substituted by one $C_1$-$C_6$ alkyl group described above and can include a methylcarbonylamino group, an ethylcarbonylamino group, a (1-propyl)carbonylamino group, a (2-propyl) carbonylamino group, a (1-butyl)carbonylamino group, a (2-butyl)carbonylamino group, a (2-methyl-1-propyl)carbonylamino group, a (2-methyl-2-propyl)carbonylamino group, a (1-pentyl)carbonylamino group or a (1-hexyl)carbonylamino group, preferably a ($C_1$-$C_4$ alkyl)carbonylamino group, more preferably a ($C_1$-$C_3$ alkyl)carbonylamino group, further preferably a methylcarbonylamino group or an ethylcarbonylamino group, and most preferably a methylcarbonylamino group.

The "($C_3$-$C_8$ cycloalkyl)carbonylamino group" in Substituent group β of the general formula (I) is a group in which the carbon atom of a carbonylamino group (—CONH—) is substituted by one $C_3$-$C_8$ cycloalkyl group described above and can include a cyclopropylcarbonylamino group, a cyclobutylcarbonylamino group, a cyclopentylcarbonylamino group, a cyclohexylcarbonylamino group, a cycloheptylcarbonylamino group or a cyclooctylcarbonylamino group, preferably a ($C_3$-$C_6$ cycloalkyl)carbonylamino group, more preferably a ($C_3$-$C_5$ cycloalkyl)carbonylamino group, further preferably a ($C_3$-$C_4$ cycloalkyl)carbonylamino group (a cyclopropylcarbonylamino group or a cyclobutylcarbonylamino group), and most preferably a cyclopropylcarbonylamino group.

The "N—[($C_1$-$C_6$ alkyl)carbonyl]-N—($C_1$-$C_6$ alkyl)amino group" in Substituent group β of the general formula (I) is a group in which the nitrogen atom of a ($C_1$-$C_6$ alkyl)carbonylamino group described above is substituted with one $C_1$-$C_6$ alkyl group described above and can include a N-methylcarbonyl-N-methylamino group, a N-ethylcarbonyl-N-methylamino group, a N-propylcarbonyl-N-methylamino group, a N-butylcarbonyl-N-methylamino group, a N-pentylcarbonyl-N-methylamino group, a N-hexylcarbonyl-N-methylamino group, a N-methylcarbonyl-N-ethylamino group, a N-methylcarbonyl-N-propylamino group, a N-methylcarbonyl-N-butylamino group, a N-methylcarbonyl-N-pentylamino group or a N-methylcarbonyl-N-hexylamino group, preferably a N—[($C_3$-$C_8$ alkyl)carbonyl]-N—($C_1$-$C_6$ alkyl) amino group, more preferably a N—[($C_1$-$C_2$ alkyl)carbonyl]-N—($C_1$-$C_2$ alkyl)amino group, further preferably a N-methylcarbonyl-N-methylamino group or a N-ethylcarbonyl-N-methylamino group, and most preferably a N-methylcarbonyl-N-methylamino group.

The "N—[($C_3$-$C_8$ cycloalkyl)carbonyl]-N— ($C_1$-$C_6$ alkyl) amino group" in Substituent group β of the general formula (I) is a group in which the nitrogen atom of a ($C_3$-$C_8$ cycloalkyl)carbonylamino group described above is substituted by one $C_1$-$C_6$ alkyl group described above and can include a N-cyclopropylcarbonyl-N-methylamino group, a N-cyclobutylcarbonyl-N-methylamino group, a N-cyclopentylcarbonyl-N-methylamino group, a N-cyclohexylcarbonyl-N-methylamino group, a N-cycloheptylcarbonyl-N-methylamino group, a N-cyclooctylcarbonyl-N-methylamino group, a N-cyclopropylcarbonyl-N-ethylamino group, a N-cyclopropylcarbonyl-N-propylamino group, a N-cyclopropylcarbonyl-N-butylamino group, a N-cyclopropylcarbonyl-N-pentylamino group or a N-cyclopropylcarbonyl-N-hexylamino group, preferably a N—[($C_3$-$C_6$ cycloalkyl)carbonyl]-N—($C_1$-$C_4$ alkyl)amino group, more preferably a N—[($C_3$-$C_5$ cycloalkyl)carbonyl]-N—($C_1$-$C_2$ alkyl)amino group, further preferably a N—[($C_3$-$C_4$ cycloalkyl)carbonyl]-N—($C_1$-$C_2$ alkyl)amino group, and most preferably a N-cyclopropylcarbonyl-N-methylamino group.

The "$C_1$-$C_6$ alkylsulfonylamino group" in Substituent group β of the general formula (I) is an amino group substituted by one $C_1$-$C_6$ alkylsulfonyl group described above and can include a methanesulfonylamino group, an ethanesulfonylamino group, a 1-propanesulfonylamino group, a 2-propanesulfonylamino group, a 1-butanesulfonylamino group, a 2-butanesulfonylamino group, a 2-methyl-1-propanesulfonylamino group, a 2-methyl-2-propanesulfonylamino group, a 1-pentanesulfonylamino group, a 2-pentanesulfonylamino group, a 3-pentanesulfonylamino group, a 2-methyl-2-butanesulfonylamino group, a 3-methyl-2-butanesulfonylamino group, a 1-hexanesulfonylamino group, a 2-hexanesulfonylamino group, a 3-hexanesulfonylamino group, a 2-methyl-1-pentanesulfonylamino group, a 3-methyl-1-pentanesulfonylamino group, a 2-ethyl-1-butanesulfonylamino group, a 2,2-dimethyl-1-butanesulfonylamino group or a 2,3-dimethyl-1-butanesulfonylamino group, preferably a $C_1$-$C_4$ alkylsulfonylamino group, more preferably a methanesulfonylamino group or an ethanesulfonylamino group, and most preferably a methanesulfonylamino group.

The "N—($C_1$-$C_6$ alkylsulfonyl)-N—($C_1$-$C_6$ alkyl)amino group" in Substituent group β of the general formula (I) is an amino group substituted by one $C_1$-$C_6$ alkylsulfonyl group described above and one $C_1$-$C_6$ alkyl group and can include a N-methanesulfonyl-N-methylamino group, a N-methanesulfonyl-N-ethylamino group, a N-methanesulfonyl-N-propylamino group, a N-methanesulfonyl-N-butylamino group, a N-methanesulfonyl-N-pentylamino group, a N-methanesulfonyl-N-hexylamino group, a N-ethanesulfonyl-N-methylamino group, a N-propanesulfonyl-N-methylamino group, a N-butanesulfonyl-N-methylamino group, a N-pentanesulfonyl-N-methylamino group or a N-hexanesulfonyl-N-methylamino group, preferably a N—($C_1$-$C_4$ alkylsulfonyl)-N—($C_1$-$C_4$ alkyl)amino group, more preferably a N—($C_1$-$C_2$ alkylsulfonyl)-N—($C_1$-$C_2$ alkyl)amino group, further preferably a N-methanesulfonyl-N-methylamino group or a N-ethanesulfonyl-N-methylamino group, and most preferably a N-methanesulfonyl-N-methylamino group.

The "N—($C_1$-$C_6$ alkylsulfonyl)-N—($C_3$-$C_8$ cycloalkyl)amino group" in Substituent group β of the general formula (I) is an amino group substituted by one $C_1$-$C_6$ alkylsulfonyl group described above and one $C_3$-$C_8$ cycloalkyl group and can include a N-methanesulfonyl-N-cyclopropylamino group, a N-methanesulfonyl-N-cyclobutylamino group, a N-methanesulfonyl-N-cyclopentylamino group, a N-methanesulfonyl-N-cyclohexylamino group, a N-ethanesulfonyl-N-cyclopropylamino group, a N-propanesulfonyl-N-cyclopropylamino group, a N-butanesulfonyl-N-cyclopropylamino group, a N-pentanesulfonyl-N-cyclopropylamino group or a N-hexanesulfonyl-N-cyclopropylamino group, preferably a N—($C_1$-$C_4$ alkylsulfonyl)-N—($C_3$-$C_6$ cycloalkyl)amino group, more preferably a N—($C_1$-$C_2$ alkylsulfonyl)-N—($C_3$-$C_4$ cycloalkyl)amino group, further preferably a N-methanesulfonyl-N-cyclopropylamino group or a N-ethanesulfonyl-N-cyclopropylamino group, and most preferably a N-methanesulfonyl-N-cyclopropylamino group.

The "($C_1$-$C_6$ alkyl)carbonyl group" in Substituent group β of the general formula (I) is a carbonyl group (—CO—) substituted by one $C_1$-$C_6$ alkyl group described above and can include a methylcarbonyl group (an acetyl group), an ethylcarbonyl group, a (1-propyl)carbonyl group, a (2-propyl)carbonyl group, a (1-butyl)carbonyl group, a (2-butyl)carbonyl group, a (2-methyl-1-propyl)carbonyl group, a (2-methyl-2-propyl)carbonyl group, a (1-pentyl)carbonyl group or a (1-hexyl)carbonyl group, preferably a ($C_1$-$C_4$ alkyl)carbonyl group, more preferably a ($C_1$-$C_3$ alkyl)carbonyl group, further preferably a methylcarbonyl group or an ethylcarbonyl group, and most preferably a methylcarbonyl group.

The "($C_1$-$C_6$ alkylamino)carbonyl group" in Substituent group β of the general formula (I) is a carbonyl group (—CO—) substituted by one $C_1$-$C_6$ alkylamino group described above and can include a methylaminocarbonyl group, an ethylaminocarbonyl group, a (1-propylamino)carbonyl group, a (2-propylamino)carbonyl group, a (1-butylamino)carbonyl group, a (2-butylamino)carbonyl group, a (2-methyl-1-propylamino)carbonyl group, a (2-methyl-2-propylamino)carbonyl group, a (1-pentylamino)carbonyl group or a (1-hexylamino)carbonyl group, preferably a ($C_1$-$C_4$ alkylamino)carbonyl group, more preferably a ($C_1$-$C_3$ alkylamino)carbonyl group, further preferably a methylaminocarbonyl group or an ethylaminocarbonyl group, and most preferably a methylaminocarbonyl group.

The "($C_3$-$C_8$ cycloalkylamino)carbonyl group" in Substituent group β of the general formula (I) is a carbonyl group (—CO—) substituted by one $C_3$-$C_8$ cycloalkylamino group described above and can include a cyclopropylaminocarbonyl group, a cyclobutylaminocarbonyl group, a cyclopentylaminocarbonyl group, a cyclohexylaminocarbonyl group, a cycloheptylaminocarbonyl group or a cyclooctylaminocarbonyl group, preferably a $C_3$-$C_6$ cycloalkylaminocarbonyl group, more preferably a $C_3$-$C_4$ cycloalkylaminocarbonyl group, and most preferably a cyclopropylaminocarbonyl group.

The "di($C_1$-$C_6$ alkyl)aminocarbonyl group" in Substituent group β of the general formula (I) is a carbonyl group (—CO—) substituted by one di($C_1$-$C_6$ alkyl)amino group described above and can include a dimethylaminocarbonyl group, a (N-methyl-N-ethylamino)carbonyl group, a (N-methyl-N-propylamino)carbonyl group [for example, a [N-(1-propyl)-N-methylamino]carbonyl group or the like], a (N-methyl-N-butylamino)carbonyl group [for example, a [N-(1-butyl)-N-methylamino]carbonyl group or the like], a (N-methyl-N-pentylamino)carbonyl group, a (N-methyl-N-hexylamino)carbonyl group, a diethylaminocarbonyl group, a dipropylaminocarbonyl group [for example, a di(1-propyl)aminocarbonyl group, a di(2-propyl)aminocarbonyl group or the like], a dibutylaminocarbonyl group, a dipentylaminocarbonyl group or a dihexylaminocarbonyl group, preferably a di($C_1$-$C_4$ alkyl)aminocarbonyl group (said alkyl groups are the same or different), more preferably a di($C_1$-$C_2$ alkyl)aminocarbonyl group (said alkyl groups are the same or different), further preferably a dimethylaminocarbonyl group or a diethylaminocarbonyl group, and most preferably a dimethylaminocarbonyl group. Further, in the di($C_1$-$C_6$ alkyl)aminocarbonyl group, said two alkyl groups, together with the nitrogen atom of said amino group, may form a 5- to 7-membered saturated heterocyclyl group containing from 1 to 3 atoms selected from the group consisting of a nitrogen atom, an oxygen atom and a sulfur atom and in this case, the di($C_1$-$C_6$ alkyl)aminocarbonyl group can be, for example, a pyrrolidinylcarbonyl group, a piperidylcarbonyl group, a piperazinylcarbonyl group, a morpholinylcarbonyl group or a thiomorpholinylcarbonyl, preferably a pyrrolidinylcarbonyl group, a piperidylcarbonyl group or a morpholinylcarbonyl group.

The "N—($C_3$-$C_8$ cycloalkyl)-N—($C_1$-$C_6$ alkyl)aminocarbonyl group" in Substituent group β of the general formula (I) is a carbonyl group (—CO—) substituted by one N—($C_3$-$C_8$ cycloalkyl)-N—($C_1$-$C_6$ alkyl)amino group described above and can include a N-cyclopropyl-N-methylaminocarbonyl group, a N-cyclopropyl-N-ethylaminocarbonyl group, a N-cyclopropyl-N-propylaminocarbonyl group, a N-cyclopropyl-N-butylaminocarbonyl group, a N-cyclopropyl-N-pentylaminocarbonyl group, a N-cyclopropyl-N-hexylaminocarbonyl group, a N-cyclobutyl-N-methylaminocarbonyl group, a N-cyclopentyl-N-methylaminocarbonyl group, a N-cyclohexyl-N-methylaminocarbonyl group, a N-cycloheptyl-N-methylaminocarbonyl group or a N-cyclooctyl-N-methylaminocarbonyl group, preferably a N—($C_3$-$C_6$ cycloalkyl)-N—($C_1$-$C_4$ alkyl)aminocarbonyl group, more preferably a N—($C_3$-$C_4$ cycloalkyl)-N—($C_1$-$C_2$ alkyl)aminocarbonyl group, further preferably a N—($C_3$-$C_4$ cycloalkyl)-N-methylaminocarbonyl group, and most preferably a N-cyclopropyl-N-methylaminocarbonyl group.

The "($C_1$-$C_6$ alkoxy)-($C_1$-$C_6$ alkyl) group" in Substituent group γ of the general formula (I) is a $C_1$-$C_6$ alkyl group described above substituted by one $C_1$-$C_6$ alkoxy group described above and can include a methoxymethyl group, an ethoxymethyl group, a propoxymethyl group, a butoxymethyl group, a pentyloxymethyl group, a hexyloxymethyl group, a methoxyethyl group, a methoxypropyl group, a methoxybutyl group, a methoxypentyl group or a methoxyhexyl group, preferably a ($C_1$-$C_4$ alkoxy)-($C_1$-$C_4$ alkyl) group, more preferably a ($C_1$-$C_2$ alkoxy)-($C_1$-$C_2$ alkyl) group, further preferably a methoxymethyl group or a methoxyethyl group, and most preferably a methoxymethyl group.

The "mercapto($C_1$-$C_6$ alkyl) group" in Substituent group γ of the general formula (I) is a $C_1$-$C_6$ alkyl group described above substituted by one mercapto group and can include a mercaptomethyl group, a mercaptoethyl group, a mercapto(1-propyl) group, a mercapto(2-propyl) group, a mercapto(1-butyl) group, a mercapto(2-butyl) group, a mercapto(2-methyl-1-propyl) group, a mercapto(2-methyl-2-propyl) group, a mercapto(1-pentyl) group or a mercapto(1-hexyl) group, preferably a mercapto($C_1$-$C_4$ alkyl) group, more preferably a mercapto($C_1$-$C_3$ alkyl) group (particularly a mercaptomethyl group, a mercaptoethyl group or a mercaptopropyl group), further preferably a mercaptomethyl group or a mercaptoethyl group, and most preferably a mercaptomethyl group.

The "($C_1$-$C_6$ alkylthio)-($C_1$-$C_6$ alkyl) group" in Substituent group γ of the general formula (I) is a $C_1$-$C_6$ alkyl group described above substituted by one $C_1$-$C_6$ alkylthio group described above and can include a methylthiomethyl group, an ethylthiomethyl group, a propylthiomethyl group, a butylthiomethyl group, a pentylthiomethyl group, a hexylthiomethyl group, a methylthioethyl group, a methylthiopropyl group, a methylthiobutyl group, a methylthiopentyl group or a methylthiohexyl group, preferably a ($C_1$-$C_4$ alkylthio)-($C_1$-$C_4$ alkyl) group, more preferably a ($C_1$-$C_2$ alkylthio)-($C_1$-$C_2$ alkyl) group, further preferably a methylthiomethyl group or a methylthioethyl group, and most preferably a methylthioethyl group.

The "($C_1$-$C_6$ alkylsulfinyl)-($C_1$-$C_6$ alkyl) group" in Substituent group γ of the general formula (I) is a $C_1$-$C_6$ alkyl group substituted by one $C_1$-$C_6$ alkylsulfinyl group described above and can include a methylsulfinylmethyl group, an ethylsulfinylmethyl group, a propylsulfinylmethyl group, a butylsulfinylmethyl group, a pentylsulfinylcimethyl group, a hexylsulfinylmethyl group, a methylsulfinylethyl group, a methylsulfinylpropyl group, a methylsulfinylbutyl group, a methylsulfinylpentyl group or a methylsulfinylhexyl group, preferably a ($C_1$-$C_4$ alkylsulfinyl)-($C_1$-$C_4$ alkyl) group, more preferably a ($C_1$-$C_2$ alkylsulfinyl)-($C_1$-$C_2$ alkyl) group, further preferably a methylsulfinylmethyl group or a methylsulfinylethyl group, and most preferably a methylsulfinylmethyl group.

The "($C_1$-$C_6$ alkylsulfonyl)-($C_1$-$C_6$ alkyl) group" in Substituent group γ of the general formula (I) is a $C_1$-$C_6$ alkyl group described above substituted by one $C_1$-$C_6$ alkylsulfonyl group described above and can include a methanesulfonylmethyl group, an ethanesulfonylmethyl group, a propanesulfonylmethyl group, a butanesulfonylmethyl group, a pentanesulfonylcimethyl group, a hexanesulfonylmethyl group, a methanesulfonylethyl group, a methanesulfonylpropyl group, a methanesulfonylbutyl group, a methanesulfonylpentyl group or a methanesulfonylhexyl group, preferably a ($C_1$-$C_4$ alkylsulfonyl)-($C_1$-$C_4$ alkyl) group, more preferably a ($C_1$-$C_2$ alkylsulfonyl)-($C_1$-$C_2$ alkyl) group, further preferably a methanesulfonylmethyl group or a methanesulfonylethyl group, and most preferably a methanesulfonylmethyl group.

The "amino($C_1$-$C_6$ alkyl) group" in Substituent group γ of the general formula (I) is a $C_1$-$C_6$ alkyl group described above substituted by one amino group and can include an aminomethyl group, an aminoethyl group, an amino(1-propyl) group, an amino(2-propyl) group, an amino(1-butyl) group, an amino(2-butyl) group, an amino(2-methyl-1-propyl) group, an amino(2-methyl-2-propyl) group, an amino(1-pentyl) group or an amino(1-hexyl) group, preferably an amino($C_1$-$C_4$ alkyl) group, more preferably an amino($C_1$-$C_3$ alkyl) group (particularly an aminomethyl group, an aminoethyl group or an aminopropyl group), further preferably an aminomethyl group or an aminoethyl group, and most preferably an aminomethyl group.

The "($C_1$-$C_6$ alkylamino)-($C_1$-$C_6$ alkyl) group" in Substituent group γ of the general formula (I) is a $C_1$-$C_6$ alkyl group described above substituted by one $C_1$-$C_6$ alkylamino group described above and can include a methylaminomethyl group, an ethylaminomethyl group, a (1-propylamino)methyl group, a (2-propylamino)methyl group, a (1-butylamino)methyl group, a (2-butylamino)methyl group, a (2-methyl-2-propylamino)methyl group, a methylaminoethyl group, an ethylaminoethyl group, a (1-propylamino)ethyl group, a (2-propylamino)ethyl group, a (1-butylamino)ethyl group, a (2-butylamino)ethyl group, a (2-methyl-2-propylamino)ethyl group, a methylamino(1-propyl) group, an ethylamino(1-propyl) group, a (1-propylamino)-(1-propyl) group, a (1-butylamino)-(1-propyl) group, a methylamino(1-butyl) group, an ethylamino(1-butyl) group, a (1-propylamino)-(1-butyl) group, a (1-butylamino)-(1-butyl) group, a methylamino(1-pentyl) group or a methylamino(1-hexyl) group, preferably a ($C_1$-$C_4$ alkylamino)-($C_1$-$C_4$ alkyl) group, more preferably a ($C_1$-$C_2$ alkylamino)-($C_1$-$C_2$ alkyl) group, further preferably a methyl aminomethyl group, an ethylaminomethyl group or a methylaminoethyl group, and most preferably a methylaminomethyl group.

The "($C_3$-$C_8$ cycloalkylamino)-($C_1$-$C_6$ alkyl) group" in Substituent group γ of the general formula (I) is a $C_1$-$C_6$ alkyl group described above substituted by one $C_3$-$C_8$ cycloalkylamino group described above and can include a cyclopropylaminomethyl group, a cyclobutylaminomethyl group, a cyclopentylaminomethyl group, a cyclohexylaminomethyl group, a cycloheptylaminomethyl group, a cyclooctylaminomethyl group, a cyclopropylaminoethyl group, a cyclopropylaminopropyl group, a cyclopropylaminobutyl group, a cyclopropylaminopentyl group or a cyclopropylaminohexyl group, preferably a ($C_3$-$C_6$ cycloalkylamino)-($C_1$-$C_4$ alkyl)

group, more preferably a ($C_3$-$C_4$ cycloalkylamino)-($C_1$-$C_2$ alkyl) group, further preferably a cyclopropylaminomethyl group or a cyclopropylaminoethyl group, and most preferably a cyclopropylaminomethyl group.

The "di($C_1$-$C_6$ alkyl)amino-($C_1$-$C_6$ alkyl) group" in Substituent group γ of the general formula (I) is a $C_1$-$C_6$ alkyl group substituted by one di($C_1$-$C_6$ alkyl)amino group described above and can include a dimethylaminomethyl group, a (N-methyl-N-ethylamino)methyl group, a (N-methyl-N-propylamino)methyl group, a (N-methyl-N-butylamino)methyl group, a (N-methyl-N-pentylamino)methyl group, a (N-methyl-N-hexylamino)methyl group, a diethylaminomethyl group, a dimethylaminoethyl group, a dimethylaminopropyl group, a dimethylaminobutyl group, a dimethylaminopentyl group or a dimethylaminohexyl group, preferably a di($C_1$-$C_4$ alkyl)amino-($C_1$-$C_4$ alkyl) group (said alkyl groups are the same or different), more preferably a di($C_1$-$C_2$ alkyl)amino-($C_1$-$C_2$ alkyl) group (said alkyl groups are the same or different), further preferably a dimethylaminomethyl group, a dimethylaminoethyl group or a (N-methyl-N-ethylamino)methyl group, further more preferably a dimethylaminomethyl group or a (N-methyl-N-ethylamino) methyl group, and most preferably a dimethylaminomethyl group. Further, in the di($C_1$-$C_6$ alkyl)amino-($C_1$-$C_6$ alkyl) group, said two alkyl groups of the di($C_1$-$C_6$ alkyl)amino moiety, together with the nitrogen atom of said amino group, may form a 5- to 7-membered saturated heterocyclyl group containing from 1 to 3 atoms selected from the group consisting of a nitrogen atom, an oxygen atom and a sulfur atom and in this case, the di($C_1$-$C_6$ alkyl)aminocarbonyl group can be, for example, a pyrrolidinylmethyl group, a piperidylmethyl group, a piperazinylmethyl group, a morpholinylmethyl group or a thiomorpholinylmethyl group, preferably a pyrrolidinylmethyl group, a piperidylmethyl group or a morpholinylmethyl group.

The "di($C_3$-$C_8$ cycloalkyl)amino-($C_1$-$C_6$ alkyl) group" in Substituent group γ of the general formula (I) is a $C_1$-$C_6$ alkyl group substituted by one di($C_3$-$C_8$ cycloalkyl)amino group described above and can include a dicyclopropylaminomethyl group, a (N-cyclopropyl-N-cyclobutylamino)methyl group, a (N-cyclopropyl-N-cyclopentylamino)methyl group, a (N-cyclopropyl-N-cyclohexylamino)methyl group, a (N-cyclopropyl-N-cycloheptylamino)methyl group, a (N-cyclopropyl-N-cyclooctylamino)methyl group, a dicyclobutylaminomethyl group, a dicyclopentylaminomethyl group, a dicyclohexylaminomethyl group, a dicycloheptylaminomethyl group, a dicyclooctylaminomethyl group, a dicyclopropylaminoethyl group, a dicyclopropylaminopropyl group, a dicyclopropylaminobutyl group, a dicyclopropylaminopentyl group or a dicyclopropylaminohexyl group, preferably a di($C_3$-$C_6$ cycloalkyl)amino-($C_1$-$C_4$ alkyl) group, more preferably a di($C_3$-$C_4$ cycloalkyl)amino-($C_1$-$C_2$ alkyl) group, and most preferably a dicyclopropylaminomethyl group.

The "[N—($C_3$-$C_8$ cycloalkyl)-N—($C_1$-$C_6$ alkyl)amino]-($C_1$-$C_6$ alkyl) group" in Substituent group γ of the general formula (I) is a $C_1$-$C_6$ alkyl group substituted by one N—($C_3$-$C_8$ cycloalkyl)-N—($C_1$-$C_6$ alkyl)amino group described above and can include a (N-cyclopropyl-N-methylamino) methyl group, a (N-cyclopropyl-N-ethylamino)methyl group, a (N-cyclopropyl-N-propylamino)methyl group, a (N-cyclopropyl-N-butylamino)methyl group, a (N-cyclopropyl-N-pentylamino)methyl group, a (N-cyclopropyl-N-hexylamino)methyl group, a (N-cyclobutyl-N-methylamino) methyl group, a (N-cyclopentyl-N-methylamino)methyl group, a (N-cyclohexyl-N-methylamino)methyl group, a (N-cycloheptyl-N-methylamino)methyl group, a (N-cyclooctyl-N-methylamino)methyl group, a (N-cyclopropyl-N-methylamino)ethyl group, a (N-cyclopropyl-N-methylamino)propyl group, a (N-cyclopropyl-N-methylamino) butyl group, a (N-cyclopropyl-N-methylamino)pentyl group or a (N-cyclopropyl-N-methylamino)hexyl group, preferably a [N—($C_3$-$C_6$ cycloalkyl)-N—($C_1$-$C_4$ alkyl)amino]-($C_1$-$C_4$ alkyl) group, more preferably a [N—($C_3$-$C_4$ cycloalkyl)-N—($C_1$-$C_2$ alkyl)amino]-($C_1$-$C_2$ alkyl) group, and most preferably a (N-cyclopropyl-N-methylamino)methyl group.

The "$C_3$-$C_8$ cycloalkylthio group" in Substituent group γ of the general formula (I) is a mercapto group substituted by one $C_3$-$C_8$ cycloalkyl group described above and can include a cyclopropylthio group, a cyclobutylthio group, a cyclopentylthio group, a cyclohexylthio group, a cycloheptylthio group or a cyclooctylthio group, preferably a $C_3$-$C_6$ cycloalkylthio group, more preferably a $C_3$-$C_5$ cycloalkylthio group, further preferably a $C_3$-$C_4$ cycloalkylthio group (a cyclopropylthio group or a cyclobutylthio group), and most preferably a cyclopropylthio group.

The "$C_3$-$C_8$ cycloalkylsulfinyl group" in Substituent group γ of the general formula (I) is a sulfinyl group (—SO—) substituted by one $C_3$-$C_8$ cycloalkyl group described above and can include a cyclopropylsulfinyl group, a cyclobutylsulfinyl group, a cyclopentylsulfinyl group, a cyclohexylsulfinyl group, a cycloheptylsulfinyl group or a cyclooctylsulfinyl group, preferably a $C_3$-$C_6$ cycloalkylsulfinyl group, more preferably a $C_3$-$C_5$ cycloalkylsulfinyl group, further preferably a $C_3$-$C_4$ cycloalkylsulfinyl group (a cyclopropylsulfinyl group or a cyclobutylsulfinyl group), and most preferably a cyclopropylsulfinyl group.

The "$C_3$-$C_8$ cycloalkylsulfonyl group" in Substituent group γ of the general formula (I) is a sulfonyl group (—SO—) substituted by one $C_3$-$C_8$ cycloalkyl group described above and can include a cyclopropanesulfonyl group, a cyclobutanesulfonyl group, a cyclopentanesulfonyl group, a cyclohexanesulfonyl group, a cycloheptanesulfonyl group or a cyclooctanesulfonyl group, preferably a $C_3$-$C_6$ cycloalkylsulfonyl group, more preferably a $C_3$-$C_5$ cycloalkylsulfonyl group, further preferably a $C_3$-$C_4$ cycloalkylsulfonyl group (a cyclopropanesulfonyl group or a cyclobutanesulfonyl group), and most preferably a cyclopropanesulfonyl group.

The respective groups in Substituent group δ of the general formula (I) have the same meanings as defined above.

In the formula (I), $X^1$ is preferably a group having the formula —NH—, —O— or —S—, and more preferably a group having the formula —O—.

In the formula (I), when $Y^1$ is a phenyl group or a substituted phenyl group, the substitution positions where $X^1$ and $Y^2$ are bonded to $Y^1$ are preferably the 1 and 3 positions (represented by $Y^{1a}$ described below) or the 1 and 4 positions (represented by $Y^{1b}$ described below), respectively, and more preferably the 1 and 4 positions, respectively. When $Y^1$ is a thienyl group or a substituted thienyl group, the substitution positions of $X^1$ and $Y^2$ are preferably the 2 and 4 positions or the 2 and 5 positions (represented by $Y^{1c}$ described below), respectively, and more preferably the 2 and 5 positions, respectively. When $Y^1$ is a pyridyl group or a substituted pyridyl group, the substitution positions of $X^1$ and $Y^2$ are preferably the 2 and 4 positions, the 2 and 5 positions (represented by $Y^{1d}$ described below), the 3 and 5 positions or the 5 and 2 positions (represented by $Y^{1e}$ described below), respectively, more preferably the 2 and 5 positions or the 5 and 2 positions, respectively, and most preferably the 5 and 2 positions, respectively.

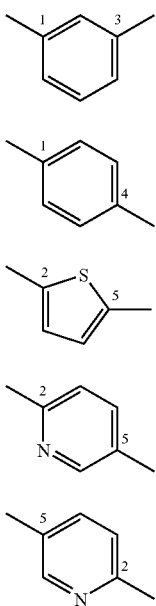

(Y^{1a})

(Y^{1b})

(Y^{1c})

(Y^{1d})

(Y^{1e})

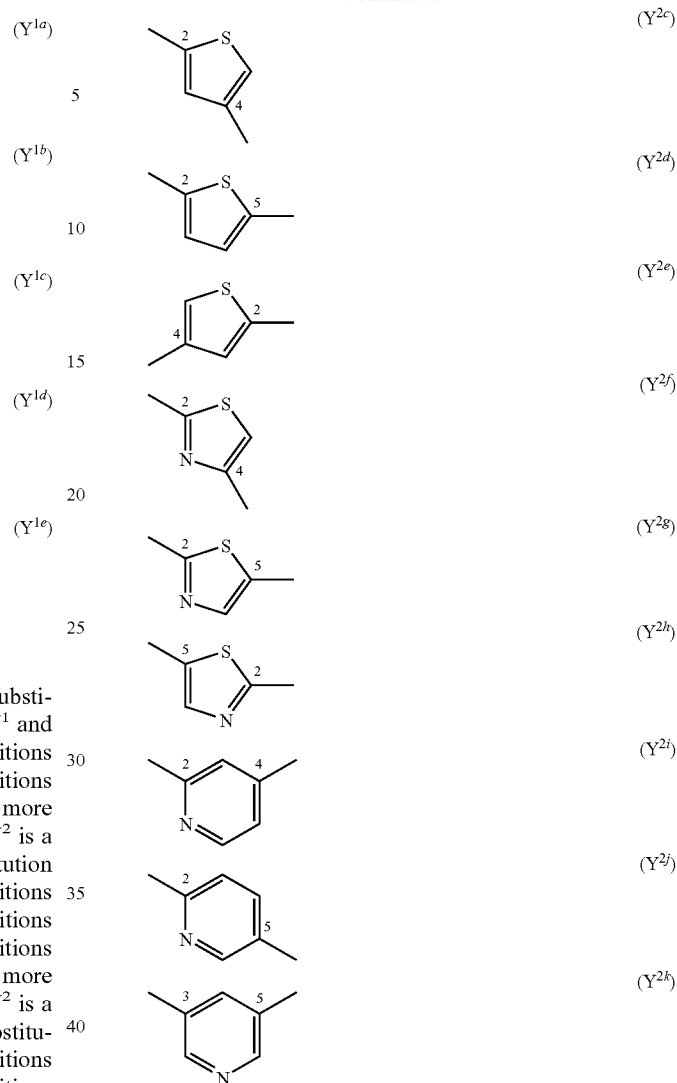

In the formula (I), when $Y^2$ is a phenyl group or a substituted phenyl group, the substitution positions where $Y^1$ and $R^8$ are bonded to $Y^2$ are preferably the 1 and 3 positions (represented by $Y^{2a}$ described below) or the 1 and 4 positions (represented by $Y^{2b}$ described below), respectively, and more preferably the 1 and 4 positions, respectively. When $Y^2$ is a thienyl group or a substituted thienyl group, the substitution position of $Y^1$ and $R^8$ are preferably the 2 and 4 positions (represented by $Y^{2c}$ described below), the 2 and 5 positions (represented by $Y^{2d}$ described below) or the 4 and 2 positions (represented by $Y^{2e}$ described below), respectively, and more preferably the 2 and 5 positions, respectively. When $Y^2$ is a thiazolyl group or a substituted thiazolyl group, the substitution positions of $Y^1$ and $R^8$ are preferably the 2 and 4 positions (represented by $Y^{2f}$ described below), the 2 and 5 positions (represented by $Y^{2g}$ described below) or the 5 and 2 positions (represented by $Y^{2h}$ described below), respectively, and more preferably 2 and 5 positions, respectively. When $Y^2$ is a pyridyl group or a substituted pyridyl group, the substitution positions of $Y^1$ and $R^8$ are preferably the 2 and 4 positions (represented by $Y^{2i}$ described below), the 2 and 5 positions (represented by $Y^{2j}$ described below) or the 3 and 5 positions (represented by $Y^{2k}$ described below), respectively, more preferably the 2 and 5 positions or the 3 and 5 positions, respectively, and most preferably the 3 and 5 positions, respectively.

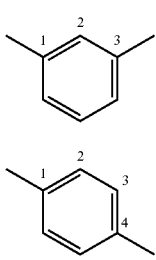

(Y^{2a})

(Y^{2b})

In the formula (I), (i) in the case that $Y^2$ is a substituted phenyl group and the substitution positions where $Y^1$ and $R^8$ are bonded to $Y^2$ are the 1 and 4 positions, respectively;

(ii) in the case that $Y^2$ is a substituted thienyl group and the substitution positions where $Y^1$ and $R^8$ are bonded to $Y^2$ are the 2 and 5 positions, respectively; or (iii) in the case that $Y^2$ is a substituted pyridyl group and the substitution positions where $Y^1$ and $R^8$ are bonded to $Y^2$ are the 2 and 5 positions, respectively, said substituent of $Y^2$ is preferably 1 to 3 groups selected from Substituent group β1, more preferably 1 or 2 groups selected from Substituent group β2, further preferably 1 or 2 groups selected from Substituent group β3, further more preferably one group selected from Substituent group β3 or two groups selected from Substituent group β4, and most preferably one group selected from Substituent group β5, two methyl groups or two fluoro groups. The substitution position of said substituent of $Y^2$ in the case of (i) is preferably the 2 position, the 3 position, the 2 and 3 positions or the 2 and 5 positions, more preferably the 2 position, 3 position or the 2 and 3 positions, and most preferably the 2 position or the 3 position.

In the formula (I), (iv) in the case that $Y^2$ is a substituted phenyl group and the substitution positions where $Y^1$ and $R^8$ are bonded to $Y^2$ are the 1 and 3 positions, respectively; or (v) in the case that $Y^2$ is a substituted pyridyl group and the substitution positions where $Y^1$ and $R^8$ are bonded to $Y^2$ are the 3 and 5 positions, respectively, said substituent of $Y^2$ is preferably 1 to 3 groups selected from Substituent group β1, more preferably 1 or 2 groups selected from Substituent group β2, further preferably one group selected from Substituent group β6, and most preferably one group selected from Substituent group β7. The substitution position of said substituent of $Y^2$ is preferably the 2 position in the case of (iv) and the 4 position in the case of (v).

In the case that a compound represented by the general formula (I) or a pharmacologically acceptable ester thereof of the present invention has a basic group, it can be converted to a salt by reacting it with an acid, and in the case that a compound represented by the general formula (I) or a pharmacologically acceptable ester thereof of the present invention has an acidic group, it can be converted to a salt by reacting it with a base. In the case that these salts are used for treatment of a disease, these must be pharmacologically acceptable.

A salt formed with a basic group of a compound represented by the general formula (I) of the present invention can preferably include an inorganic acid salt such as a hydrohalogenic acid salt including a hydrochloride, a hydrobromide and a hydroiodide; a nitrate; a perchlorate; a sulfate; and a phosphate; an organic acid salt such as a salt with a $C_1$-$C_6$ alkanesulfonic acid which may be substituted by a fluorine atom including a methanesulfonate, a trifluoromethanesulfonate and an ethanesulfonate; a salt with a $C_6$-$C_{10}$ arylsulfonic acid which may be substituted by a $C_1$-$C_4$ alkyl group including a benzenesulfonate and a p-toluenesulfonate; an acetate; a malate; a fumarate; a succinate; a citrate; a tartrate; an oxalate; and a maleate; or an amino acid salt such as a glycine salt, a lysine salt, an arginine salt, an ornithine salt, a glutamate and an aspartate, and more preferably a hydrohalogenic acid salt.

A salt formed with an acidic group of a compound represented by the general formula (I) of the present invention can preferably include a metal salt such as an alkali metal salt including a sodium salt, a potassium salt and a lithium salt; an alkaline earth metal salt including a calcium salt and a magnesium salt; an aluminum salt; an iron salt; a zinc salt; a copper salt; a nickel salt; and a cobalt salt; an amine salt such as an inorganic amine salt including an ammonium salt; and an organic amine salt including a t-octylamine salt, a dibenzylamine salt, a morpholine salt, a glucosamine salt, a phenylglycine alkyl ester salt, an ethylenediamine salt, a N-methylglucamine salt, a guanidine salt, a diethylamine salt, a triethylamine salt, a dicyclohexylamine salt, a N,N'-dibenzylethylenediamine salt, a chloroprocaine salt, a procaine salt, a diethanolamine salt, a N-benzylphenethylamine salt, a piperazine salt, a tetramethylammonium salt, a tris(hydroxymethyl)aminomethane salt, a choline salt, or a trometamine salt [a 2-amino-2-(hydroxymethyl)propan-1,3-diol salt]; or an amino acid salt such as a glycine salt, a lysine salt, an arginine salt, an ornithine salt, a glutamate and an aspartate, and more preferably an alkali metal salt.

A compound represented by the general formula (I) or a pharmacologically acceptable salt or ester thereof of the present invention may form a hydrate by being left to stand in air or by adsorbing moisture at the time of recrystallization and these hydrates are included in the present invention. Further, the compound of the present invention sometimes may form a solvate by incorporating other solvents and these other solvates are also included in the present invention.

In the case that a compound of the present invention has one or more asymmetric centers, an optical isomer (including a diastereomer) can exist and these isomers and a mixture thereof are described by a single formula such as the formula (I). The present invention includes any of the respective isomers and a mixture thereof in any arbitrary ratio (including the racemate).

The present invention includes an ester of a compound represented by the formula (I). These esters are compounds in which a hydroxyl group or a carboxyl group of a compound represented by the general formula (I) is modified by addition of a protective group according to a well-known method in the field (for example, "Protective Groups in Organic Synthesis, Second Edtion", Theodora W. Greene and Peter G. M. Wuts, 1991, John Wiley & Sons, Inc.).

The nature of this protective group is not particularly limited. However, in the case that the ester is used for usage in treatment of a disease, it must be pharmacologically acceptable. For example, the protection group must be eliminated in a metabolic process (for example, hydrolysis) to produce a compound represented by the general formula (I) or a salt thereof when the compound is administered into the living body of a mammal. Namely, a pharmacologically acceptable ester is a "prodrug" of a compound represented by the general formula (I) of the present invention. However, in the case that an ester of a compound represented by the general formula (I) of the present invention is used other than for treatment of a disease (for example, in the case that it is used as an intermediate to prepare another compound), it is not required that the ester is pharmacologically acceptable.

It is easily determined whether or not an ester of a compound represented by the general formula (I) of the present invention is pharmacologically acceptable. A compound is intravenously administered to an experimental animal such as rat or mouse and blood or a body fluid of the animal is measured. In the case that a compound represented by the general formula (I) of the present invention or a pharmacologically acceptable salt thereof is detected, said compound is determined to be a pharmacologically acceptable ester.

A compound represented by the general formula (I) of the present invention can be converted to an ester and the ester can be a compound in which a hydroxyl group of the compound is esterified. When the esterified compound is used as an intermediate, an ester residue can be a general protective group and in a case that the esterified compound is a pharmacologically acceptable compound, it can be a protective group which can be eliminated in a metabolic process (for example, hydrolysis) in the living body.

The general protective group described above is an ester protective group which can be eliminated under a chemical condition such as hydrolysis, hydrogenation decomposition, electrolysis or photolysis. These general protective groups used for preparation of a compound represented by the general formula (I) in which the hydroxyl group is modified can be preferably, for example, the following groups:

(i) an aliphatic acyl group such as an alkylcarbonyl group having from 1 to 25 carbon atoms, an ester formation residue of a saturated or unsaturated $C_2$-$C_{10}$ dicarboxylic acid, a halogeno-alkylcarbonyl group having from 1 to 25 carbon atoms, a lower alkoxyalkylcarbonyl group having from 1 to 25 carbon atoms or an unsaturated alkylcarbonyl group having from 1 to 25 carbon atoms;

(ii) an aromatic acyl group such as an arylcarbonyl group, a halogeno-arylcarbonyl group, a lower alkylarylcarbonyl group, a lower alkoxyarylcarbonyl group, a nitrated arylcarbonyl group, a lower alkoxycarbonylarylcarbonyl group or an arylated arylcarbonyl group;

(iii) an alkoxycarbonyl group such as a ($C_1$-$C_6$ alkoxy)carbonyl group or a ($C_1$-$C_6$ alkoxy)carbonyl group substituted by one or more substituents selected from the group consisting of a halogeno group and a tri($C_1$-$C_6$ alkyl)silyl group;

(iv) a tetrahydropyranyl group or a tetrahydrothiopyranyl group which may be substituted by one or more substituents selected from the group consisting of $C_1$-$C_6$ alkyl, halogeno and $C_1$-$C_6$ alkoxy;

(v) a tetrahydrofuranyl group or a tetrahydrothiofuranyl group which may be substituted by one or more substituents selected from the group consisting of $C_1$-$C_6$ alkyl, halogeno and $C_1$-$C_6$ alkoxy;

(vi) a silyl group such as a tri($C_1$-$C_6$ alkyl)silyl group, a di($C_1$-$C_6$ alkyl)arylsilyl group or a diaryl($C_1$-$C_6$ alkyl)silyl group;

(vii) an alkoxymethyl group such as a ($C_1$-$C_6$ alkoxy)methyl group, a ($C_1$-$C_6$ alkoxy)-($C_1$-$C_6$ alkoxy)methyl group or a ($C_1$-$C_6$ alkoxy)methyl group substituted by a halogeno group;

(viii) a substituted ethyl group such as a ($C_1$-$C_6$ alkoxy)ethyl group or a ($C_1$-$C_6$ alkoxy)ethyl group substituted by a halogeno group;

(ix) an aralkyl group such as a triphenylmethyl group which may be substituted by one or more substituents selected from the group consisting of $C_1$-$C_6$ alkyl, halogeno and $C_1$-$C_6$ alkoxy or a benzyl group which may be substituted by one or more substituents selected from the group consisting of $C_1$-$C_6$ alkyl, $C_1$-$C_6$ alkoxy, nitro, halogeno and cyano;

(x) an alkenyloxycarbonyl group having from 3 to 6 carbon atoms;

(xi) an aralkyloxycarbonyl group which may be substituted by one or more substituents selected from the group consisting of $C_1$-$C_6$ alkyl, $C_1$-$C_6$ alkoxy, nitro, halogeno and cyano;

(xii) an ester formation residue of a $C_1$-$C_{10}$ sulfonic acid;

(xiii) a carbonate ester;

(xiv) an ester with a carbonic acid mono($C_1$-$C_6$ alkyl) ester or a carbonic acid di($C_1$-$C_6$ alkyl) ester;

(xv) an ester with a carbonic acid mono($C_6$-$C_{10}$ aromatic hydrocarbon) ester or a carbonic acid di($C_6$-$C_{10}$ aromatic (xvi) a phosphoric acid ester;

(xvii) an ester with a phosphoric acid mono($C_1$-$C_6$ alkyl) ester or a phosphoric acid di($C_1$-$C_6$ alkyl) ester; or (xviii) an ester with a phosphoric acid mono($C_6$-$C_{10}$ aromatic hydrocarbon) ester or a phosphoric acid di($C_6$-$C_{10}$ aromatic hydrocarbon) ester.

An ester group which can be eliminated in a metabolic process (for example, hydrolysis) in the living body is an ester group which is eliminated in a metabolic process (for example, hydrolysis) to produce a compound represented by the general formula (I) or a salt thereof when the compound is administered into the living body of a mammal. Such protective group as an ester residue can preferably include the following groups:

(i) a 1-(acyloxy)-($C_1$-$C_6$ alkyl) group such as a 1-[($C_1$-$C_6$ alkyl)carbonyloxy]-($C_1$-$C_6$ alkyl) group, a 1-[($C_3$-$C_8$ cycloalkyl)carbonyloxy]-($C_1$-$C_6$ alkyl) group or a 1-[($C_6$-$C_{12}$ aryl)carbonyloxy]-($C_1$-$C_6$ alkyl) group;

(ii) a substituted carbonyloxyalkyl group such as a ($C_1$-$C_6$ alkoxy)carbonyloxyalkyl group or an oxodioxolenylmethyl group which may be substituted (said substituent is a group selected from the group consisting of a $C_1$-$C_6$ alkyl group and an aryl group which may be substituted by $C_1$-$C_6$ alkyl or halogeno);

(iii) a phthalidyl group which may be substituted by $C_1$-$C_6$ alkyl or $C_1$-$C_6$ alkoxy;

(iv) an aliphatic acyl group as described in a general protective group of a hydroxyl group;

(v) an aromatic acyl group as described in a general protective group of a hydroxyl group;

(vi) a half ester residue of succinic acid;

(vii) a phosphoric acid ester residue;

(viii) an ester formation residue of an amino acid such as glutamate and aspartate;

(ix) a carbamoyl group which may be substituted by 1 or 2 $C_1$-$C_6$ alkyl groups; or (x) a 1-(acyloxy)alkoxycarbonyl group (said acyloxy group represents an aliphatic acyloxy group described above or an aromatic acyloxy group described above).

In a protective group described above that is used for producing a compound represented by the general formula (I) in which a hydroxyl group is modified and that can be eliminated in a metabolic process (for example, hydrolysis) in the living body, an aliphatic acyl group (particularly $C_1$-$C_{25}$ alkylcarbonyl group) and a substituted carbonyloxyalkyl group are preferred.

Preferred as compounds represented by the general formula (I) are compounds shown in the following Tables 1 and 2. The compounds of the present invention, however, are not limited to these compounds.

In the following Tables 1, 2 and 3, the following abbreviations are used:

cBu: cyclobutyl
cbx-cBu: 1-carboxy-1-cyclobutyl
cbx-cPr: 1-carboxy-1-cyclopropyl
cPr: cyclopropyl
Dmbu: 2,3-dimethyl-2-butyl
Et: ethyl
Ety: ethynyl
iPr: 2-propyl
Mbu: 2-methyl-2-butyl
Me: methyl
Mpe: 3-methyl-3-pentyl
nPr: 1-propyl
tBu: 2-methyl-2-propyl
Tet: tetrazolyl
Tfe: 2,2,2-trifluoroethyl
Vin: vinyl.

TABLE 1

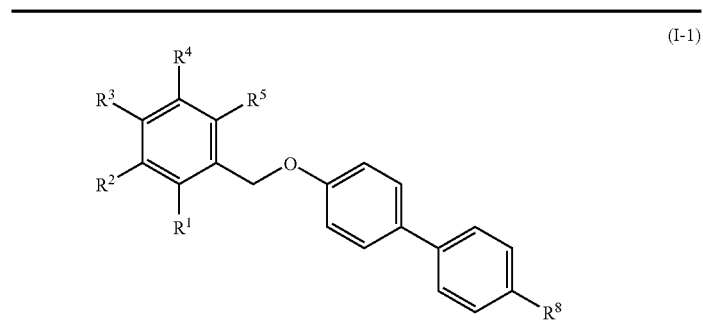
(I-1)

| Exemplification Compound No. | R¹ | R² | R³ | R⁴ | R⁵ | R⁸ |
|---|---|---|---|---|---|---|
| 1-1 | COCH$_2$CMe$_3$ | OH | CF$_3$ | H | H | CH$_2$COOH |
| 1-2 | COCH$_2$CMe$_3$ | OH | CF$_3$ | H | H | cbx-cPr |
| 1-3 | COOiPr | OH | iPr | H | H | CH$_2$COOH |
| 1-4 | COOiPr | OH | tBu | H | H | CH$_2$COOH |
| 1-5 | COOiPr | OH | CF$_3$ | H | H | CH$_2$COOH |
| 1-6 | COOiPr | OH | CF$_3$ | H | H | cbx-cPr |
| 1-7 | COOiPr | OH | CF$_3$ | H | H | CH$_2$COOMe |
| 1-8 | COOtBu | H | Me | H | H | CH$_2$COOH |
| 1-9 | COOtBu | H | Me | H | H | cbx-cPr |
| 1-10 | COOtBu | H | Et | H | H | CH$_2$COOH |
| 1-11 | COOtBu | H | Et | H | H | cbx-cPr |
| 1-12 | COOtBu | H | iPr | H | H | CH$_2$COOH |
| 1-13 | COOtBu | H | iPr | H | H | cbx-cPr |
| 1-14 | COOtBu | H | tBu | H | H | CH$_2$COOH |
| 1-15 | COOtBu | H | tBu | H | H | cbx-cPr |
| 1-16 | COOtBu | H | CF$_3$ | H | H | CH$_2$COOH |
| 1-17 | COOtBu | H | CF$_3$ | H | H | CH$_2$COOMe |
| 1-18 | COOtBu | H | CF$_3$ | H | H | CH(Me)COOH |
| 1-19 | COOtBu | H | CF$_3$ | H | H | C(Me)$_2$COOH |
| 1-20 | COOtBu | H | CF$_3$ | H | H | cbx-cPr |
| 1-21 | COOtBu | H | Tfe | H | H | CH$_2$COOH |
| 1-22 | COOtBu | H | Tfe | H | H | cbx-cPr |
| 1-23 | COOtBu | H | cPr | H | H | CH$_2$COOH |
| 1-24 | COOtBu | H | cPr | H | H | cbx-cPr |
| 1-25 | COOtBu | H | Vin | H | H | CH$_2$COOH |
| 1-26 | COOtBu | H | Vin | H | H | cbx-cPr |
| 1-27 | COOtBu | H | Ety | H | H | CH$_2$COOH |
| 1-28 | COOtBu | H | Ety | H | H | cbx-cpr |
| 1-29 | COOtBu | H | OMe | H | H | CH$_2$COOH |
| 1-30 | COOtBu | H | OMe | H | H | cbx-cPr |
| 1-31 | COOtBu | H | SMe | H | H | CH$_2$COOH |
| 1-32 | COOtBu | H | SMe | H | H | cbx-cPr |
| 1-33 | COOtBu | H | SOMe | H | H | CH$_2$COOH |
| 1-34 | COOtBu | H | SOMe | H | H | cbx-cPr |
| 1-35 | COOtBu | H | SO$_2$Me | H | H | CH$_2$COOH |
| 1-36 | COOtBu | H | SO$_2$Me | H | H | cbx-cPr |
| 1-37 | COOtBu | H | F | H | H | CH$_2$COOH |
| 1-38 | COOtBu | H | F | H | H | cbx-cPr |
| 1-39 | COOtBu | H | Cl | H | H | CH$_2$COOH |
| 1-40 | COOtBu | H | Cl | H | H | cbx-cPr |
| 1-41 | COOtBu | OH | H | H | H | CH$_2$COOH |
| 1-42 | COOtBu | OH | H | H | H | cbx-cPr |
| 1-43 | COOtBu | OH | Me | H | H | CH$_2$COOH |
| 1-44 | COOtBu | OH | Me | H | H | cbx-cPr |
| 1-45 | COOtBu | OH | Et | H | H | CH$_2$COOH |
| 1-46 | COOtBu | OH | Et | H | H | cbx-cPr |
| 1-47 | COOtBu | OH | iPr | H | H | CH$_2$COOH |
| 1-48 | COOtBu | OH | iPr | H | H | cbx-cPr |
| 1-49 | COOtBu | OH | tBu | H | H | CH$_2$COOH |
| 1-50 | COOtBu | OH | tBu | H | H | CH$_2$COOMe |
| 1-51 | COOtBu | OH | tBu | H | H | CH(Me)COOH |
| 1-52 | COOtBu | OH | tBu | H | H | C(Me)$_2$COOH |
| 1-53 | COOtBu | OH | tBu | H | H | cbx-cPr |
| 1-54 | COOtBu | OH | CF$_3$ | H | H | COOH |
| 1-55 | COOtBu | OH | CF$_3$ | H | H | CH$_2$COOH |
| 1-56 | COOtBu | OH | CF$_3$ | H | H | CH$_2$COOMe |
| 1-57 | COOtBu | OH | CF$_3$ | H | H | CH$_2$COOEt |
| 1-58 | COOtBu | OH | CF$_3$ | H | H | CH$_2$COOnPr |
| 1-59 | COOtBu | OH | CF$_3$ | H | H | CH$_2$CONH$_2$ |

TABLE 1-continued (I-1)

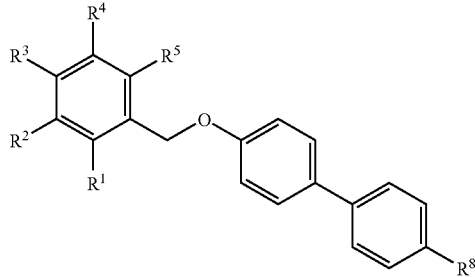

| Exemplification Compound No. | R¹ | R² | R³ | R⁴ | R⁵ | R⁸ |
|---|---|---|---|---|---|---|
| 1-60 | COOtBu | OH | CF₃ | H | H | CH₂CONHMe |
| 1-61 | COOtBu | OH | CF₃ | H | H | CH₂CONMe₂ |
| 1-62 | COOtBu | OH | CF₃ | H | H | CH(Me)COOH |
| 1-63 | COOtBu | OH | CF₃ | H | H | C(Me)₂COOH |
| 1-64 | COOtBu | OH | CF₃ | H | H | cbx-cPr |
| 1-65 | COOtBu | OH | CF₃ | H | H | cbx-cBu |
| 1-66 | COOtBu | OH | CF₃ | H | H | CF₂COOH |
| 1-67 | COOtBu | OH | CF₃ | H | H | (CH₂)₂COOH |
| 1-68 | COOtBu | OH | CF₃ | H | H | 5-Tet |
| 1-69 | COOtBu | OH | CF₃ | F | H | CH₂COOH |
| 1-70 | COOtBu | OH | CF₃ | F | H | cbx-cPr |
| 1-71 | COOtBu | OH | CF₃ | Cl | H | CH₂COOH |
| 1-72 | COOtBu | OH | CF₃ | Cl | H | cbx-cPr |
| 1-73 | COOtBu | OH | Tfe | H | H | CH₂COOH |
| 1-74 | COOtBu | OH | Tfe | H | H | cbx-cPr |
| 1-75 | COOtBu | OH | CH₂OMe | H | H | CH₂COOH |
| 1-76 | COOtBu | OH | CH₂OMe | H | H | cbx-cPr |
| 1-77 | COOtBu | OH | CH₂SMe | H | H | CH₂COOH |
| 1-78 | COOtBu | OH | CH₂SMe | H | H | cbx-cPr |
| 1-79 | COOtBu | OH | cPr | H | H | CH₂COOH |
| 1-80 | COOtBu | OH | cPr | H | H | cbx-cPr |
| 1-81 | COOtBu | OH | Vin | H | H | CH₂COOH |
| 1-82 | COOtBu | OH | Vin | H | H | cbx-cPr |
| 1-83 | COOtBu | OH | Ety | H | H | CH₂COOH |
| 1-84 | COOtBu | OH | Ety | H | H | cbx-cPr |
| 1-85 | COOtBu | OH | OMe | H | H | CH₂COOH |
| 1-86 | COOtBu | OH | OMe | H | H | cbx-cPr |
| 1-87 | COOtBu | OH | SMe | H | H | CH₂COOH |
| 1-88 | COOtBu | OH | SMe | H | H | cbx-cPr |
| 1-89 | COOtBu | OH | SOMe | H | H | CH₂COOH |
| 1-90 | COOtBu | OH | SOMe | H | H | cbx-cPr |
| 1-91 | COOtBu | OH | SO₂Me | H | H | CH₂COOH |
| 1-92 | COOtBu | OH | SO₂Me | H | H | cbx-cPr |
| 1-93 | COOtBu | OH | F | H | H | CH₂COOH |
| 1-94 | COOtBu | OH | F | H | H | cbx-cPr |
| 1-95 | COOtBu | OH | Cl | H | H | CH₂COOH |
| 1-96 | COOtBu | OH | Cl | H | H | cbx-cPr |
| 1-97 | COOCH₂CMe₃ | OH | CF₃ | H | H | CH₂COOH |
| 1-98 | COOCH₂CMe₃ | OH | CF₃ | H | H | cbx-cPr |
| 1-99 | COOMbu | OH | CF₃ | H | H | CH₂COOH |
| 1-100 | COOMbu | OH | CF₃ | H | H | cbx-cPr |
| 1-101 | COOMpe | OH | CF₃ | H | H | CH₂COOH |
| 1-102 | COOMpe | OH | CF₃ | H | H | cbx-cPr |
| 1-103 | COODmbu | OH | CF₃ | H | H | CH₂COOH |
| 1-104 | COODmbu | OH | CF₃ | H | H | cbx-cPr |
| 1-105 | COOC(Et)₃ | OH | CF₃ | H | H | CH₂COOH |
| 1-106 | COOC(Et)₃ | OH | CF₃ | H | H | cbx-cPr |
| 1-107 | COOC(CF₃)Me₂ | OH | CF₃ | H | H | CH₂COOH |
| 1-108 | COOC(CF₃)Me₂ | OH | CF₃ | H | H | cbx-cPr |
| 1-109 | CONHtBu | OH | CF₃ | H | H | CH₂COOH |
| 1-110 | CONHtBu | OH | CF₃ | H | H | cbx-cPr |
| 1-111 | CON(Me)tBu | OH | CF₃ | H | H | CH₂COOH |
| 1-112 | CON(Me)tBu | OH | CF₃ | H | H | cbx-cPr |
| 1-113 | COOtBu | OH | CF₃ | H | H | CH₂SO₂NHMe |
| 1-114 | COOtBu | OH | CF₃ | H | H | CH(CH₂OH)COOH |
| 1-115 | COOtBu | OH | CF₃ | H | H | CH(OH)COOH |
| 1-116 | COOtBu | OH | CF₃ | H | H | CH(OEt)COOH |
| 1-117 | COOtBu | OH | CF₃ | H | H | CH₂CH(OH)COOH |
| 1-118 | COOtBu | OH | CF₃ | H | H | CH₂CON(Me)Et |

TABLE 1-continued (I-1)

Exemplification Compound No.

| No. | R¹ | R² | R³ | R⁴ | R⁵ | R⁸ |
|---|---|---|---|---|---|---|
| 1-119 | COOtBu | OH | CF₃ | H | H | CH₂CONH(iPr) |
| 1-120 | COOtBu | OH | CF₃ | H | H | CH₂SO₂NMe₂ |
| 1-121 | COOtBu | OH | CF₃ | H | H | CH₂CONHEt |
| 1-122 | COOtBu | OH | CF₃ | H | H | CH₂CON(Me)iPr |
| 1-123 | COOtBu | OH | CF₃ | H | H | CH₂SO₂Me |
| 1-124 | COOtBu | OH | CF₃ | H | H | C(COOH)=CH₂ |
| 1-125 | COOtBu | OH | CF₃ | H | H | C(CH₂OH)₂COOH |
| 1-126 | COOCH(Me)CF₃ | OH | CF₃ | H | H | CH₂COOH |
| 1-127 | COOtBu | OH | CF₃ | H | H | CH(CH₂OMe)COOH |
| 1-128 | COOtBu | OH | CF₃ | H | H | CH(CH₂OEt)COOH |
| 1-129 | COOtBu | OH | CF₃ | H | OH | CH₂COOH |
| 1-130 | COOtBu | OH | CF₃ | H | H | CH(OMe)COOH |
| 1-131 | COOtBu | OH | CF₃ | H | H | CH₂(5-Tet) |
| 1-132 | COOtBu | OH | CF₃ | H | H | CH(Et)COOH |

TABLE 2

(I-2)

$Y^1 =$ (Yᵃ), (Yᵇ), (Yᶜ), (Yᵈ), (Yᵉ)

$Y^2 =$ (Yᶠ), (Yᵍ), (Yʰ), (Yⁱ)

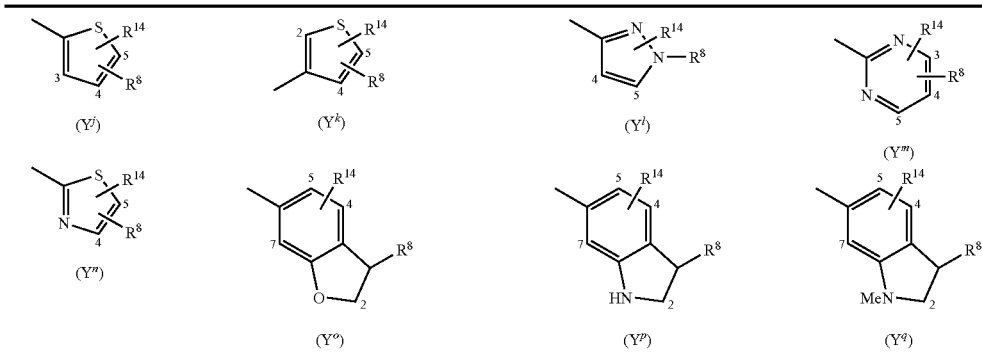

TABLE 2-continued

| Exemplification Compound No. | $R^2$ | $R^3$ | $R^6$ | $R^7$ | $R^8$ | $X^1$ | $Y^1$ | $Y^2$ | $R^{13}$ | $R^{14}$ |
|---|---|---|---|---|---|---|---|---|---|---|
| 2-1 | H | $CF_3$ | H | H | 3-COOH | O | $Y^a$ | $Y^f$ | H | H |
| 2-2 | H | $CF_3$ | H | H | 3-$CH_2$COOH | O | $Y^a$ | $Y^f$ | H | H |
| 2-3 | H | $CF_3$ | H | H | 3-$CH_2$COOH | O | $Y^a$ | $Y^f$ | H | 2-Me |
| 2-4 | H | $CF_3$ | H | H | 3-$CH_2$COOH | O | $Y^a$ | $Y^f$ | H | 2-F |
| 2-5 | H | $CF_3$ | H | H | 3-$CH_2$COOH | O | $Y^a$ | $Y^f$ | H | 2-Cl |
| 2-6 | H | $CF_3$ | H | H | 3-$CH_2$COOH | O | $Y^a$ | $Y^f$ | H | 4-Me |
| 2-7 | H | $CF_3$ | H | H | 3-$CH_2$COOH | O | $Y^a$ | $Y^f$ | H | 4-F |
| 2-8 | H | $CF_3$ | H | H | 3-$CH_2$COOH | O | $Y^a$ | $Y^f$ | H | 4-Cl |
| 2-9 | H | $CF_3$ | H | H | 3-$CH_2$COOH | O | $Y^a$ | $Y^f$ | H | 5-Me |
| 2-10 | H | $CF_3$ | H | H | 3-$CH_2$COOH | O | $Y^a$ | $Y^f$ | H | 5-F |
| 2-11 | H | $CF_3$ | H | H | 3-$CH_2$COOH | O | $Y^a$ | $Y^f$ | H | 5-Cl |
| 2-12 | H | $CF_3$ | H | H | 3-$CH_2$COOH | O | $Y^a$ | $Y^f$ | H | 6-Me |
| 2-13 | H | $CF_3$ | H | H | 3-$CH_2$COOH | O | $Y^a$ | $Y^f$ | H | 6-F |
| 2-14 | H | $CF_3$ | H | H | 3-$CH_2$COOH | O | $Y^a$ | $Y^f$ | H | 6-Cl |
| 2-15 | H | $CF_3$ | H | H | 4-$CH_2$COOH | O | $Y^a$ | $Y^f$ | H | 2-Me |
| 2-16 | H | $CF_3$ | H | H | 4-$CH_2$COOH | O | $Y^a$ | $Y^f$ | H | 2-OMe |
| 2-17 | H | $CF_3$ | H | H | 4-$CH_2$COOH | O | $Y^a$ | $Y^f$ | H | 3-Me |
| 2-18 | H | $CF_3$ | H | H | 4-$CH_2$COOH | O | $Y^a$ | $Y^f$ | H | 3-F |
| 2-19 | H | $CF_3$ | H | H | 4-$CH_2$COOH | O | $Y^a$ | $Y^f$ | H | 3-Cl |
| 2-20 | H | $CF_3$ | H | H | 4-$CH_2$COOH | O | $Y^a$ | $Y^f$ | 3-F | H |
| 2-21 | H | $CF_3$ | H | H | 4-$CH_2$COOH | O | $Y^a$ | $Y^f$ | 3-F | 2-Me |
| 2-22 | H | $CF_3$ | H | H | 4-$CH_2$COOH | O | $Y^a$ | $Y^f$ | 3-F | 3-Me |
| 2-24 | H | $CF_3$ | H | H | 4-$CH_2$COOH | O | $Y^a$ | $Y^f$ | 3-F | 3-F |
| 2-25 | H | $CF_3$ | H | H | 4-$CH_2$COOH | O | $Y^a$ | $Y^f$ | 3-F | 3-Cl |
| 2-26 | H | $CF_3$ | H | H | 5-$CH_2$COOH | O | $Y^a$ | $Y^j$ | H | H |
| 2-27 | H | $CF_3$ | H | H | $CH_2$COOH | O | $Y^a$ | $Y^l$ | H | H |
| 2-28 | OH | $CF_3$ | H | H | 3-COOH | O | $Y^a$ | $Y^f$ | H | H |
| 2-29 | OH | $CF_3$ | H | H | 3-$CH_2$COOH | O | $Y^a$ | $Y^f$ | H | H |
| 2-30 | OH | $CF_3$ | H | H | 3-$CH_2$COOMe | O | $Y^a$ | $Y^f$ | H | H |
| 2-31 | OH | $CF_3$ | H | H | 3-$CH_2$COOH | O | $Y^a$ | $Y^f$ | H | 2-Me |
| 2-32 | OH | $CF_3$ | H | H | 3-$CH_2$COOH | O | $Y^a$ | $Y^f$ | H | 2-F |
| 2-33 | OH | $CF_3$ | H | H | 3-$CH_2$COOH | O | $Y^a$ | $Y^f$ | H | 2-Cl |
| 2-34 | OH | $CF_3$ | H | H | 3-$CH_2$COOH | O | $Y^a$ | $Y^f$ | H | 4-Me |
| 2-35 | OH | $CF_3$ | H | H | 3-$CH_2$COOH | O | $Y^a$ | $Y^f$ | H | 4-F |
| 2-36 | OH | $CF_3$ | H | H | 3-$CH_2$COOH | O | $Y^a$ | $Y^f$ | H | 4-Cl |
| 2-37 | OH | $CF_3$ | H | H | 3-$CH_2$COOH | O | $Y^a$ | $Y^f$ | H | 5-Me |
| 2-38 | OH | $CF_3$ | H | H | 3-$CH_2$COOH | O | $Y^a$ | $Y^f$ | H | 5-F |
| 2-39 | OH | $CF_3$ | H | H | 3-$CH_2$COOH | O | $Y^a$ | $Y^f$ | H | 5-Cl |
| 2-40 | OH | $CF_3$ | H | H | 3-$CH_2$COOH | O | $Y^a$ | $Y^f$ | H | 6-Me |
| 2-41 | OH | $CF_3$ | H | H | 3-$CH_2$COOH | O | $Y^a$ | $Y^f$ | H | 6-F |
| 2-42 | OH | $CF_3$ | H | H | 3-$CH_2$COOH | O | $Y^a$ | $Y^f$ | H | 6-Cl |
| 2-43 | OH | $CF_3$ | H | H | 4-$CH_2$COOH | O | $Y^a$ | $Y^f$ | H | 2-Me |
| 2-44 | OH | $CF_3$ | H | H | 4-$CH_2$COOH | O | $Y^a$ | $Y^f$ | H | 2-OMe |
| 2-45 | OH | $CF_3$ | H | H | 4-$CH_2$COOH | O | $Y^a$ | $Y^f$ | H | 2-F |
| 2-46 | OH | $CF_3$ | H | H | 4-$CH_2$COOH | O | $Y^a$ | $Y^f$ | H | 2-Cl |
| 2-47 | OH | $CF_3$ | H | H | 4-$CH_2$COOH | O | $Y^a$ | $Y^f$ | H | 3-Me |
| 2-48 | OH | $CF_3$ | H | H | 4-$CH_2$COOH | O | $Y^a$ | $Y^f$ | H | 3-F |
| 2-49 | OH | $CF_3$ | H | H | 4-$CH_2$COOH | O | $Y^a$ | $Y^f$ | H | 3-Cl |
| 2-50 | OH | $CF_3$ | H | H | 4-$CH_2$COOH | O | $Y^a$ | $Y^f$ | 2-Me | H |
| 2-51 | OH | $CF_3$ | H | H | 4-$CH_2$COOH | O | $Y^a$ | $Y^f$ | 2-F | H |
| 2-52 | OH | $CF_3$ | H | H | 4-$CH_2$COOH | O | $Y^a$ | $Y^f$ | 2-Cl | H |
| 2-53 | OH | $CF_3$ | H | H | 4-$CH_2$COOH | O | $Y^a$ | $Y^f$ | 3-Me | H |
| 2-54 | OH | $CF_3$ | H | H | 4-$CH_2$COOH | O | $Y^a$ | $Y^f$ | 3-F | H |
| 2-55 | OH | $CF_3$ | H | H | 4-$CH_2$COOH | O | $Y^a$ | $Y^f$ | 3-F | 2-Me |
| 2-56 | OH | $CF_3$ | H | H | 4-$CH_2$COOH | O | $Y^a$ | $Y^f$ | 3-F | 2-Cl |
| 2-57 | OH | $CF_3$ | H | H | 4-$CH_2$COOH | O | $Y^a$ | $Y^f$ | 3-F | 3-Me |
| 2-58 | OH | $CF_3$ | H | H | 4-$CH_2$COOH | O | $Y^a$ | $Y^f$ | 3-F | 3-F |
| 2-59 | OH | $CF_3$ | H | H | 4-$CH_2$COOH | O | $Y^a$ | $Y^f$ | 3-F | 3-Cl |

TABLE 2-continued

| | | | | | | | | | | |
|---|---|---|---|---|---|---|---|---|---|---|
| 2-60 | OH | CF$_3$ | H | H | 4-CH$_2$COOH | O | Y$^a$ | Y$^f$ | 3-Cl | H |
| 2-61 | OH | CF$_3$ | H | H | 4-CH(Me)COOH | O | Y$^a$ | Y$^f$ | H | 2-Me |
| 2-62 | OH | CF$_3$ | H | H | 4-CH(Me)COOH | O | Y$^a$ | Y$^f$ | H | 2-Cl |
| 2-63 | OH | CF$_3$ | H | H | 3-CH(Me)COOH | O | Y$^a$ | Y$^f$ | H | 2-OMe |
| 2-64 | OH | CF$_3$ | H | H | 4-CH(Me)COOH | O | Y$^a$ | Y$^f$ | H | 3-F |
| 2-65 | OH | CF$_3$ | H | H | 4-CH(Me)COOH | O | Y$^a$ | Y$^f$ | H | 3-Cl |
| 2-66 | OH | CF$_3$ | H | H | 4-CH(Me)COOH | O | Y$^a$ | Y$^f$ | 3-F | H |
| 2-67 | OH | CF$_3$ | H | H | 4-cbx-cPr | O | Y$^a$ | Y$^f$ | H | 2-Me |
| 2-68 | OH | CF$_3$ | H | H | 4-cbx-cPr | O | Y$^a$ | Y$^f$ | H | 2-Cl |
| 2-69 | OH | CF$_3$ | H | H | 4-cbx-cPr | O | Y$^a$ | Y$^f$ | H | 3-Me |
| 2-70 | OH | CF$_3$ | H | H | 4-cbx-cPr | O | Y$^a$ | Y$^f$ | H | 3-F |
| 2-71 | OH | CF$_3$ | H | H | 4-cbx-cPr | O | Y$^a$ | Y$^f$ | H | 3-Cl |
| 2-72 | OH | CF$_3$ | H | H | 4-cbx-cPr | O | Y$^a$ | Y$^f$ | 3-F | H |
| 2-73 | OH | CF$_3$ | H | H | 4-cbx-cPr | O | Y$^a$ | Y$^f$ | 3-F | 2-Me |
| 2-74 | OH | CF$_3$ | H | H | 4-cbx-cPr | O | Y$^a$ | Y$^f$ | 3-F | 3-Me |
| 2-75 | OH | CF$_3$ | H | H | 4-cbx-cPr | O | Y$^a$ | Y$^f$ | 3-F | 3-F |
| 2-76 | OH | CF$_3$ | H | H | 4-cbx-cPr | O | Y$^a$ | Y$^f$ | 3-F | 3-Cl |
| 2-77 | OH | CF$_3$ | H | H | 4-CH$_2$COOH | NH | Y$^a$ | Y$^f$ | H | H |
| 2-78 | OH | CF$_3$ | H | H | 4-CH$_2$COOH | NMe | Y$^a$ | Y$^f$ | H | H |
| 2-79 | OH | CF$_3$ | H | H | 4-CH$_2$COOH | S | Y$^a$ | Y$^f$ | H | H |
| 2-80 | OH | CF$_3$ | H | H | 4-CH$_2$COOH | SO | Y$^a$ | Y$^f$ | H | H |
| 2-81 | OH | CF$_3$ | H | H | 4-CH$_2$COOH | SO$_2$ | Y$^a$ | Y$^f$ | H | H |
| 2-82 | OH | CF$_3$ | Me | H | 4-CH$_2$COOH | O | Y$^a$ | Y$^f$ | H | H |
| 2-83 | OH | CF$_3$ | Me | Me | 4-CH$_2$COOH | O | Y$^a$ | Y$^f$ | H | H |
| 2-84 | OH | CF$_3$ | H | H | 4-CH$_2$COOH | O | Y$^a$ | Y$^g$ | H | H |
| 2-85 | OH | CF$_3$ | H | H | 4-CH$_2$COOH | O | Y$^a$ | Y$^g$ | H | 2-Me |
| 2-86 | OH | CF$_3$ | H | H | 4-CH$_2$COOH | O | Y$^a$ | Y$^g$ | H | 3-Me |
| 2-87 | OH | CF$_3$ | H | H | 4-CH$_2$COOH | O | Y$^a$ | Y$^g$ | H | 3-F |
| 2-88 | OH | CF$_3$ | H | H | 4-CH$_2$COOH | O | Y$^a$ | Y$^g$ | H | 3-Cl |
| 2-89 | OH | CF$_3$ | H | H | 4-CH$_2$COOH | O | Y$^a$ | Y$^g$ | 3-F | H |
| 2-90 | OH | CF$_3$ | H | H | 4-cbx-cPr | O | Y$^a$ | Y$^g$ | H | H |
| 2-91 | OH | CF$_3$ | H | H | 4-cbx-cPr | O | Y$^a$ | Y$^g$ | H | 2-Me |
| 2-92 | OH | CF$_3$ | H | H | 4-cbx-cPr | O | Y$^a$ | Y$^g$ | H | 3-Me |
| 2-93 | OH | CF$_3$ | H | H | 4-cbx-cPr | O | Y$^a$ | Y$^g$ | H | 3-F |
| 2-94 | OH | CF$_3$ | H | H | 4-cbx-cPr | O | Y$^a$ | Y$^g$ | H | 3-Cl |
| 2-95 | OH | CF$_3$ | H | H | 3-CH$_2$COOH | O | Y$^a$ | Y$^h$ | H | H |
| 2-96 | OH | CF$_3$ | H | H | 3-cbx-cPr | O | Y$^a$ | Y$^h$ | H | H |
| 2-97 | OH | CF$_3$ | H | H | 3-CH$_2$COOH | O | Y$^a$ | Y$^i$ | H | H |
| 2-98 | OH | CF$_3$ | H | H | 3-cbx-cPr | O | Y$^a$ | Y$^i$ | H | H |
| 2-99 | OH | H | H | H | 5-CH$_2$COOH | O | Y$^a$ | Y$^j$ | H | H |
| 2-100 | OH | H | H | H | 5-cbx-cPr | O | Y$^a$ | Y$^j$ | H | H |
| 2-101 | OH | Me | H | H | 5-CH$_2$COOH | O | Y$^a$ | Y$^j$ | H | H |
| 2-102 | OH | Me | H | H | 5-cbx-cPr | O | Y$^a$ | Y$^j$ | H | H |
| 2-103 | OH | Et | H | H | 5-CH$_2$COOH | O | Y$^a$ | Y$^j$ | H | H |
| 2-104 | OH | Et | H | H | 5-cbx-cPr | O | Y$^a$ | Y$^j$ | H | H |
| 2-105 | OH | iPr | H | H | 5-CH$_2$COOH | O | Y$^a$ | Y$^j$ | H | H |
| 2-106 | OH | iPr | H | H | 5-cbx-cPr | O | Y$^a$ | Y$^j$ | H | H |
| 2-107 | OH | tBu | H | H | 5-CH$_2$COOH | O | Y$^a$ | Y$^j$ | H | H |
| 2-108 | OH | tBu | H | H | 5-cbx-cPr | O | Y$^a$ | Y$^j$ | H | H |
| 2-109 | OH | CF$_3$ | H | H | 4-CH$_2$COOH | O | Y$^a$ | Y$^j$ | H | H |
| 2-110 | OH | CF$_3$ | H | H | 4-CH$_2$COOH | O | Y$^a$ | Y$^j$ | 3-F | H |
| 2-111 | OH | CF$_3$ | H | H | 4-cbx-cPr | O | Y$^a$ | Y$^j$ | H | H |
| 2-112 | OH | CF$_3$ | H | H | 4-cbx-cPr | O | Y$^a$ | Y$^j$ | 3-F | H |
| 2-113 | OH | CF$_3$ | H | H | 5-CH$_2$COOH | O | Y$^a$ | Y$^j$ | H | H |
| 2-114 | OH | CF$_3$ | H | H | 5-CH$_2$COOH | O | Y$^a$ | Y$^j$ | 3-F | H |
| 2-115 | OH | CF$_3$ | H | H | 5-CH$_2$COOMe | O | Y$^a$ | Y$^j$ | H | H |
| 2-116 | OH | CF$_3$ | H | H | 5-CH$_2$COOEt | O | Y$^a$ | Y$^j$ | H | H |
| 2-117 | OH | CF$_3$ | H | H | 5-CH$_2$COOnPr | O | Y$^a$ | Y$^j$ | H | H |
| 2-118 | OH | CF$_3$ | H | H | 5-CH$_2$CONH$_2$ | O | Y$^a$ | Y$^j$ | H | H |
| 2-119 | OH | CF$_3$ | H | H | 5-CH$_2$CONHMe | O | Y$^a$ | Y$^j$ | H | H |
| 2-120 | OH | CF$_3$ | H | H | 5-CH$_2$CONMe$_2$ | O | Y$^a$ | Y$^j$ | H | H |
| 2-121 | OH | CF$_3$ | H | H | 5-CH(Me)COOH | O | Y$^a$ | Y$^j$ | H | H |
| 2-122 | OH | CF$_3$ | H | H | 5-CH(Me)COOH | O | Y$^a$ | Y$^j$ | 3-F | H |
| 2-123 | OH | CF$_3$ | H | H | 5-cbx-cPr | O | Y$^a$ | Y$^j$ | H | H |
| 2-124 | OH | CF$_3$ | H | H | 5-cbx-cPr | O | Y$^a$ | Y$^j$ | 3-F | H |
| 2-125 | OH | Tfe | H | H | 5-CH$_2$COOH | O | Y$^a$ | Y$^j$ | H | H |
| 2-126 | OH | Tfe | H | H | 5-cbx-cPr | O | Y$^a$ | Y$^j$ | H | H |
| 2-127 | OH | cPr | H | H | 5-CH$_2$COOH | O | Y$^a$ | Y$^j$ | H | H |
| 2-128 | OH | cPr | H | H | 5-cbx-cPr | O | Y$^a$ | Y$^j$ | H | H |
| 2-129 | OH | Vin | H | H | 5-CH$_2$COOH | O | Y$^a$ | Y$^j$ | H | H |
| 2-130 | OH | Vin | H | H | 5-cbx-cPr | O | Y$^a$ | Y$^j$ | H | H |
| 2-131 | OH | OMe | H | H | 5-CH$_2$COOH | O | Y$^a$ | Y$^j$ | H | H |
| 2-132 | OH | OMe | H | H | 5-cbx-cPr | O | Y$^a$ | Y$^j$ | H | H |
| 2-133 | OH | SMe | H | H | 5-CH$_2$COOH | O | Y$^a$ | Y$^j$ | H | H |
| 2-134 | OH | SMe | H | H | 5-cbx-cPr | O | Y$^a$ | Y$^j$ | H | H |
| 2-135 | OH | SOMe | H | H | 5-CH$_2$COOH | O | Y$^a$ | Y$^j$ | H | H |
| 2-136 | OH | SOMe | H | H | 5-cbx-cPr | O | Y$^a$ | Y$^j$ | H | H |
| 2-137 | OH | SO$_2$Me | H | H | 5-CH$_2$COOH | O | Y$^a$ | Y$^j$ | H | H |
| 2-138 | OH | SO$_2$Me | H | H | 5-cbx-cPr | O | Y$^a$ | Y$^j$ | H | H |
| 2-139 | OH | F | H | H | 5-CH$_2$COOH | O | Y$^a$ | Y$^j$ | H | H |

TABLE 2-continued

| | | | | | | | | | | |
|---|---|---|---|---|---|---|---|---|---|---|
| 2-140 | OH | F | H | H | 5-cbx-cPr | O | $Y^a$ | $Y^j$ | H | H |
| 2-141 | OH | Cl | H | H | 5-CH$_2$COOH | O | $Y^a$ | $Y^j$ | H | H |
| 2-142 | OH | Cl | H | H | 5-cbx-cPr | O | $Y^a$ | $Y^j$ | H | H |
| 2-143 | OH | CF$_3$ | H | H | 5-CH$_2$COOH | O | $Y^a$ | $Y^k$ | H | H |
| 2-144 | OH | CF$_3$ | H | H | 5-CH$_2$COOH | O | $Y^a$ | $Y^k$ | 3-F | H |
| 2-145 | OH | CF$_3$ | H | H | 5-cbx-cPr | O | $Y^a$ | $Y^k$ | H | H |
| 2-146 | OH | CF$_3$ | H | H | 5-cbx-cPr | O | $Y^a$ | $Y^k$ | 3-F | H |
| 2-147 | OH | CF$_3$ | H | H | CH$_2$COOH | O | $Y^a$ | $Y^l$ | H | H |
| 2-148 | OH | CF$_3$ | H | H | CH$_2$COOH | O | $Y^a$ | $Y^l$ | 3-F | H |
| 2-149 | OH | CF$_3$ | H | H | cbx-cPr | O | $Y^a$ | $Y^l$ | H | H |
| 2-150 | OH | CF$_3$ | H | H | cbx-cPr | O | $Y^a$ | $Y^l$ | 3-F | H |
| 2-151 | OH | CF$_3$ | H | H | 4-CH$_2$COOH | O | $Y^a$ | $Y^m$ | H | H |
| 2-152 | OH | CF$_3$ | H | H | 4-CH$_2$COOH | O | $Y^a$ | $Y^m$ | 3-F | H |
| 2-153 | OH | CF$_3$ | H | H | 4-cbx-cPr | O | $Y^a$ | $Y^m$ | H | H |
| 2-154 | OH | CF$_3$ | H | H | 4-cbx-cPr | O | $Y^a$ | $Y^m$ | 3-F | H |
| 2-155 | OH | CF$_3$ | H | H | 3-CH$_2$COOH | O | $Y^b$ | $Y^f$ | H | H |
| 2-156 | OH | CF$_3$ | H | H | 3-cbx-cPr | O | $Y^b$ | $Y^f$ | H | H |
| 2-157 | OH | CF$_3$ | H | H | 4-CH$_2$COOH | O | $Y^b$ | $Y^f$ | H | H |
| 2-158 | OH | CF$_3$ | H | H | 4-cbx-cPr | O | $Y^b$ | $Y^f$ | H | H |
| 2-159 | OH | CF$_3$ | H | H | 4-CH$_2$COOH | O | $Y^c$ | $Y^f$ | H | H |
| 2-160 | OH | CF$_3$ | H | H | 4-CH$_2$COOH | O | $Y^c$ | $Y^f$ | H | 2-Me |
| 2-161 | OH | CF$_3$ | H | H | 4-CH$_2$COOH | O | $Y^c$ | $Y^f$ | H | 3-Me |
| 2-162 | OH | CF$_3$ | H | H | 4-CH$_2$COOH | O | $Y^c$ | $Y^f$ | H | 3-F |
| 2-163 | OH | CF$_3$ | H | H | 4-CH$_2$COOH | O | $Y^c$ | $Y^f$ | H | 3-Cl |
| 2-164 | OH | CF$_3$ | H | H | 4-CH$_2$COOH | O | $Y^d$ | $Y^f$ | H | H |
| 2-165 | OH | CF$_3$ | H | H | 4-CH$_2$COOH | O | $Y^d$ | $Y^f$ | H | 2-Me |
| 2-166 | OH | CF$_3$ | H | H | 4-CH$_2$COOH | O | $Y^d$ | $Y^f$ | H | 3-Me |
| 2-167 | OH | CF$_3$ | H | H | 4-CH$_2$COOH | O | $Y^d$ | $Y^f$ | H | 3-F |
| 2-168 | OH | CF$_3$ | H | H | 4-CH$_2$COOH | O | $Y^d$ | $Y^f$ | H | 3-Cl |
| 2-169 | OH | CF$_3$ | H | H | 4-CH$_2$COOH | O | $Y^e$ | $Y^f$ | H | H |
| 2-170 | OH | CF$_3$ | H | H | 4-CH$_2$COOH | O | $Y^e$ | $Y^f$ | H | 2-Me |
| 2-171 | OH | CF$_3$ | H | H | 4-CH$_2$COOH | O | $Y^e$ | $Y^f$ | H | 3-Me |
| 2-172 | OH | CF$_3$ | H | H | 4-CH$_2$COOH | O | $Y^e$ | $Y^f$ | H | 3-F |
| 2-173 | OH | CF$_3$ | H | H | 4-CH$_2$COOH | O | $Y^e$ | $Y^f$ | H | 3-Cl |
| 2-174 | OH | CF$_3$ | H | H | 4-CH(Me)COOH | O | $Y^e$ | $Y^f$ | H | H |
| 2-175 | OH | CF$_3$ | H | H | 4-CH(Me)COOH | O | $Y^e$ | $Y^f$ | H | 2-Me |
| 2-176 | OH | CF$_3$ | H | H | 4-CH(Me)COOH | O | $Y^e$ | $Y^f$ | H | 3-Me |
| 2-177 | OH | CF$_3$ | H | H | 4-CH(Me)COOH | O | $Y^e$ | $Y^f$ | H | 3-F |
| 2-178 | OH | CF$_3$ | H | H | 4-CH(Me)COOH | O | $Y^e$ | $Y^f$ | H | 3-Cl |
| 2-179 | OH | CF$_3$ | H | H | 4-cbx-cPr | O | $Y^e$ | $Y^f$ | H | H |
| 2-180 | OH | CF$_3$ | H | H | 4-cbx-cPr | O | $Y^e$ | $Y^f$ | H | 2-Me |
| 2-181 | OH | CF$_3$ | H | H | 4-cbx-cPr | O | $Y^e$ | $Y^f$ | H | 3-Me |
| 2-182 | OH | CF$_3$ | H | H | 4-cbx-cPr | O | $Y^e$ | $Y^f$ | H | 3-F |
| 2-183 | OH | CF$_3$ | H | H | 4-cbx-cPr | O | $Y^e$ | $Y^f$ | H | 3-Cl |
| 2-184 | OH | CF$_3$ | H | H | 4-CH$_2$COOH | O | $Y^a$ | $Y^f$ | H | 3-OMe |
| 2-185 | OH | CF$_3$ | H | H | 4-CH$_2$COOH | O | $Y^a$ | $Y^f$ | H | 2-CF$_3$ |
| 2-186 | OH | CF$_3$ | H | H | 4-CH$_2$COOH | O | $Y^a$ | $Y^f$ | H | 2-Et |
| 2-187 | OH | CF$_3$ | H | H | 5-CH$_2$COOH | O | $Y^a$ | $Y^n$ | H | H |
| 2-188 | OH | CF$_3$ | H | H | 3-SO$_2$Me | O | $Y^a$ | $Y^f$ | H | H |
| 2-189 | OH | CF$_3$ | H | H | 4-CH$_2$COOMe | O | $Y^a$ | $Y^f$ | H | 2-Et |
| 2-190 | OH | CF$_3$ | H | H | 3-NHSO$_2$Me | O | $Y^a$ | $Y^f$ | H | H |
| 2-191 | OH | CF$_3$ | H | H | 4-CH$_2$COOH | O | $Y^a$ | $Y^f$ | H | 2-NO$_2$ |
| 2-192 | OH | CF$_3$ | H | H | 4-CH$_2$COOH | O | $Y^a$ | $Y^f$ | H | 2-NH$_2$ |
| 2-193 | OH | CF$_3$ | H | H | 4-CH$_2$COOH | O | $Y^a$ | $Y^f$ | H | 2-NMe$_2$ |
| 2-194 | OH | CF$_3$ | H | H | 4-CH$_2$COOH | O | $Y^a$ | $Y^f$ | H | 2-COCH$_3$ |
| 2-195 | OH | CF$_3$ | H | H | 4-CH$_2$COOH | O | $Y^a$ | $Y^f$ | H | 2-iPr |
| 2-196 | OH | CF$_3$ | H | H | 4-CH$_2$COOH | O | $Y^a$ | $Y^f$ | H | 3-CF$_3$ |
| 2-197 | OH | CF$_3$ | H | H | 4-CH$_2$COOH | O | $Y^a$ | $Y^f$ | H | 2-CHO |
| 2-198 | OH | CF$_3$ | H | H | 4-CH$_2$COOH | O | $Y^a$ | $Y^f$ | H | 2-CH$_2$OH |
| 2-199 | OH | CF$_3$ | H | H | 4-CH$_2$COOH | O | $Y^a$ | $Y^f$ | H | 2-CN |
| 2-200 | OH | CF$_3$ | H | H | 3-(CH$_2$)$_2$COOH | O | $Y^a$ | $Y^f$ | H | H |
| 2-201 | OH | CF$_3$ | H | H | 3-CH$_2$NHSO$_2$Me | O | $Y^a$ | $Y^f$ | H | H |
| 2-202 | OH | CF$_3$ | H | H | COOH | O | $Y^a$ | $Y^p$ | H | H |
| 2-203 | OH | CF$_3$ | H | H | 4-CH$_2$COOH | O | $Y^a$ | $Y^f$ | H | 3-SO$_2$M |
| 2-204 | OH | CF$_3$ | H | H | 3-N(Me)SO$_2$Me | O | $Y^a$ | $Y^f$ | H | H |
| 2-205 | OH | CF$_3$ | H | H | 3-CH$_2$N(Me)SO$_2$Me | O | $Y^a$ | $Y^f$ | H | H |
| 2-206 | OH | CF$_3$ | H | H | 4-COOH | O | $Y^a$ | $Y^g$ | H | H |
| 2-207 | OH | CF$_3$ | H | H | 4-(CH$_2$)$_2$COOH | O | $Y^a$ | $Y^g$ | H | H |
| 2-208 | OH | CF$_3$ | H | H | 4-CH$_2$COOH | O | $Y^a$ | $Y^f$ | H | 2-nPr |
| 2-209 | OH | CF$_3$ | H | H | 3-COMe | O | $Y^a$ | $Y^f$ | H | H |
| 2-210 | OH | CF$_3$ | H | H | 5-COMe | O | $Y^a$ | $Y^g$ | H | H |
| 2-211 | OH | CF$_3$ | H | H | 4-CH$_2$COOMe | O | $Y^a$ | $Y^f$ | H | 3-Cl |
| 2-212 | OH | CF$_3$ | H | H | 4-CH$_2$COOH | O | $Y^a$ | $Y^f$ | H | 2-COEt |
| 2-213 | OH | CF$_3$ | H | H | COOH | O | $Y^a$ | $Y^o$ | H | H |
| 2-214 | OH | CF$_3$ | H | H | 4-CH$_2$COOH | O | $Y^a$ | $Y^f$ | H | 3-OH |
| 2-215 | OH | CF$_3$ | H | H | 3-SO$_2$Me | O | $Y^a$ | $Y^h$ | H | H |
| 2-216 | OH | CF$_3$ | H | H | 3-CH$_2$COOH | O | $Y^a$ | $Y^h$ | H | 2-Me |
| 2-217 | OH | CF$_3$ | H | H | 4-CH$_2$COOH | O | $Y^a$ | $Y^f$ | H | 2-CONMe$_2$ |
| 2-218 | OH | CF$_3$ | H | H | 4-CH(CH$_2$OH)COOH | O | $Y^a$ | $Y^f$ | H | 2-Et |
| 2-219 | OH | CF$_3$ | H | H | 4-CH(CH$_2$OH)COOH | O | $Y^a$ | $Y^f$ | H | 3-F |

TABLE 2-continued

| 2-220 | OH | CF$_3$ | H | H | 4-CH$_2$COOH | O | Y$^a$ | Y$^f$ | H | 2-OH |
| 2-221 | OH | CF$_3$ | H | H | 4-CH$_2$COOH | O | Y$^a$ | Y$^f$ | H | 2-cPr |
| 2-222 | OH | CF$_3$ | H | H | 4-CH$_2$COOH | O | Y$^a$ | Y$^f$ | H | 3-NO$_2$ |
| 2-223 | OH | CF$_3$ | H | H | 4-CH$_2$COOH | O | Y$^a$ | Y$^f$ | H | 3-Et |
| 2-224 | OH | CF$_3$ | H | H | 4-CH$_2$COOH | O | Y$^a$ | Y$^f$ | H | 3-CN |
| 2-225 | OH | CF$_3$ | H | H | 4-CH$_2$COOH | O | Y$^a$ | Y$^f$ | H | 2-CH(OH)CH$_2$ |
| 2-226 | OH | CF$_3$ | H | H | 4-CH$_2$COOH | O | Y$^a$ | Y$^f$ | H | 3-CONMe$_2$ |
| 2-227 | OH | CF$_3$ | H | H | 3-CH$_2$COOH | O | Y$^a$ | Y$^f$ | H | 2-Et |
| 2-228 | OH | CF$_3$ | H | H | 4-CH$_2$COOH | O | Y$^a$ | Y$^f$ | H | 2,3-di-F |
| 2-229 | OH | CF$_3$ | H | H | 4-CH$_2$COOH | O | Y$^a$ | Y$^f$ | H | 2,3-di-Me |
| 2-230 | OH | CF$_3$ | H | H | 4-CH(CH$_2$NMe$_2$)COOH | O | Y$^a$ | Y$^f$ | H | 3-F |
| 2-231 | OH | CF$_3$ | H | H | 4-CH(Me)COOH | O | Y$^a$ | Y$^f$ | H | 2-Et |
| 2-232 | OH | CF$_3$ | H | H | 5-CH$_2$COOH | O | Y$^a$ | Y$^j$ | H | 3-Me |
| 2-233 | OH | CF$_3$ | H | H | 3-CH(Me)COOH | O | Y$^a$ | Y$^f$ | H | 2-Me |
| 2-234 | OH | CF$_3$ | H | H | 3-CH(Me)COOH | O | Y$^a$ | Y$^f$ | H | 2-Et |
| 2-235 | OH | CF$_3$ | H | H | 4-CH(Me)COOH | O | Y$^a$ | Y$^f$ | H | 2-NO$_2$ |
| 2-236 | OH | CF$_3$ | H | H | 4-CH(Me)COOH | O | Y$^d$ | Y$^f$ | H | 2-Me |
| 2-237 | OH | CF$_3$ | H | H | 4-CH(Me)COOH | O | Y$^a$ | Y$^f$ | H | 3-Et |
| 2-238 | OH | CF$_3$ | H | H | 4-CH(Me)COOH | O | Y$^a$ | Y$^f$ | H | 2,5-di-Me |
| 2-239 | OH | CF$_3$ | H | H | 4-CH$_2$COOH | O | Y$^a$ | Y$^f$ | H | 2,5-di-Me |
| 2-240 | OH | CF$_3$ | H | H | COOH | O | Y$^a$ | Y$^q$ | H | H |
| 2-241 | OH | CF$_3$ | H | H | 4-CH(Me)COOH | O | Y$^a$ | Y$^f$ | H | 2-CF$_3$ |
| 2-242 | OH | CF$_3$ | H | H | 4-CH(Me)COOH | O | Y$^a$ | Y$^f$ | H | 2-iPr |
| 2-243 | OH | CF$_3$ | H | H | 4-CH(Me)COOH | O | Y$^a$ | Y$^f$ | H | 2,3-di-F |
| 2-244 | OH | CF$_3$ | H | H | 4-CH(Me)COOH | O | Y$^a$ | Y$^f$ | H | 2,3-di-Me |
| 2-245 | OH | CF$_3$ | H | H | 4-CH(Me)COOH | O | Y$^a$ | Y$^f$ | H | 2-cPr |
| 2-246 | OH | CF$_3$ | H | H | 3-CH$_2$COOH | O | Y$^a$ | Y$^f$ | H | 2-OMe |

TABLE 3

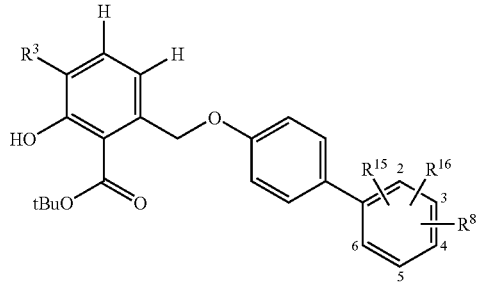

(I-3)

| Exemplification Compound No. | R$^3$ | R$^8$ | R$^{15}$ | R$^{16}$ |
|---|---|---|---|---|
| 3-1 | iPr | 4-CH$_2$COOH | 2-Me | H |
| 3-2 | iPr | 4-CH$_2$COOH | 2-Me | 3-Me |
| 3-3 | iPr | 4-CH$_2$COOH | 2-Me | 5-Me |
| 3-4 | iPr | 4-CH$_2$COOH | 3-Me | H |
| 3-5 | iPr | 4-CH$_2$COOH | 2-Et | H |
| 3-6 | iPr | 4-CH$_2$COOH | 3-Et | H |
| 3-7 | iPr | 4-CH$_2$COOH | 2-iPr | H |
| 3-8 | iBr | 4-CH$_2$COOH | 3-iPr | H |
| 3-9 | iPr | 4-CH$_2$COOH | 2-CH$_2$OH | H |
| 3-10 | iPr | 4-CH$_2$COOH | 2-CF$_3$ | H |
| 3-11 | iPr | 4-CH$_2$COOH | 3-CF$_3$ | H |
| 3-12 | iPr | 4-CH$_2$COOH | 2-cPr | H |
| 3-13 | iPr | 4-CH$_2$COOH | 3-cPr | H |
| 3-14 | iPr | 4-CH$_2$COOH | 2-OMe | H |
| 3-15 | iPr | 4-CH$_2$COCH | 3-OMe | H |
| 3-16 | iPr | 4-CH$_2$COOH | 2-SO$_2$Me | H |
| 3-17 | iPr | 4-CH$_2$COOH | 3-SO$_2$Me | H |
| 3-18 | iPr | 4-CH$_2$COOH | 2-NH$_2$ | H |
| 3-19 | iPr | 4-CH$_2$COOH | 2-NHMe | H |
| 3-20 | iPr | 4-CH$_2$COOH | 2-NMe$_2$ | H |
| 3-21 | iPr | 4-CH$_2$COOH | 2-COMe | H |
| 3-22 | iPr | 4-CH$_2$COOH | 2-COEt | H |
| 3-23 | iPr | 4-CH$_2$COOH | 2-CN | H |
| 3-24 | iPr | 4-CH$_2$COOH | 3-CN | H |
| 3-25 | iPr | 4-CH$_2$COOH | 2-NO$_2$ | H |
| 3-26 | iPr | 4-CH$_2$COOH | 3-NO$_2$ | H |
| 3-27 | iPr | 4-CH$_2$COOH | 2-F | H |

TABLE 3-continued

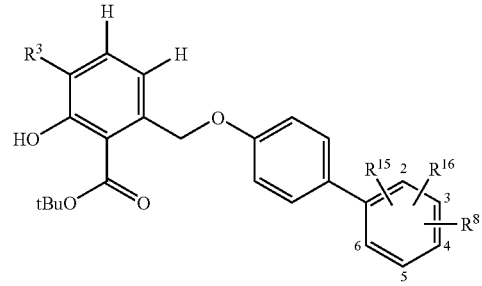

(I-3)

| Exemplification Compound No. | R$^3$ | R$^8$ | R$^{15}$ | R$^{16}$ |
|---|---|---|---|---|
| 3-28 | iPr | 4-CH$_2$COOH | 2-F | 3-F |
| 3-29 | iPr | 4-CH$_2$COOH | 2-F | 5-F |
| 3-30 | iPr | 4-CH$_2$COOH | 3-F | H |
| 3-31 | iPr | 4-CH$_2$COOH | 2-Cl | H |
| 3-32 | iPr | 4-CH$_2$COOH | 3-Cl | H |
| 3-33 | iPr | 3-CH$_2$COOH | 2-Me | H |
| 3-34 | iPr | 3-CH$_2$COOH | 2-Et | H |
| 3-35 | iPr | 3-CH$_2$COOH | 2-OMe | H |
| 3-36 | iPr | 3-CH$_2$COOH | 2-F | H |
| 3-37 | iPr | 3-CH(Me)COOH | 2-Me | H |
| 3-38 | iPr | 3-CH(Me)COOH | 2-Et | H |
| 3-39 | iPr | 3-CH(Me)COOH | 2-OMe | H |
| 3-40 | iPr | 3-CH(Me)COOH | 2-F | H |
| 3-41 | tBu | 4-CH$_2$COOH | 2-Me | H |
| 3-42 | tBu | 4-CH$_2$COOH | 2-Me | 3-Me |
| 3-43 | tBu | 4-CH$_2$COOH | 2-Me | 5-Me |
| 3-44 | tBu | 4-CH$_2$COOH | 3-Me | H |
| 3-45 | tBu | 4-CH$_2$COOH | 2-Et | H |
| 3-46 | tBu | 4-CH$_2$COOH | 3-Et | H |
| 3-47 | tBu | 4-CH$_2$COOH | 2-iPr | H |
| 3-48 | tBu | 4-CH$_2$COOH | 3-iPr | H |
| 3-49 | tBu | 4-CH$_2$COOH | 2-CH$_2$OH | H |
| 3-50 | tBu | 4-CH$_2$COOH | 2-CF$_3$ | H |
| 3-51 | tBu | 4-CH$_2$COOH | 3-CF$_3$ | H |
| 3-52 | tBu | 4-CH$_2$COOH | 2-cPr | H |
| 3-53 | tBu | 4-CH$_2$COOH | 3-cPr | H |
| 3-54 | tBu | 4-CH$_2$COOH | 2-OMe | H |

TABLE 3-continued (I-3)

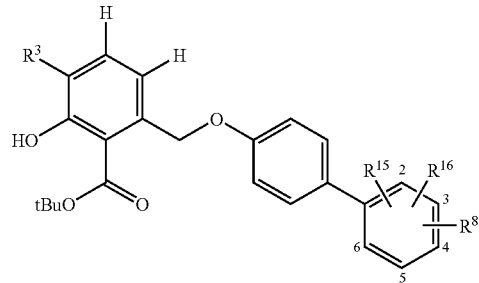

| Exemplification Compound No. | R³ | R⁸ | R¹⁵ | R¹⁶ |
|---|---|---|---|---|
| 3-55 | tBu | 4-CH₂COOH | 3-OMe | H |
| 3-56 | tBu | 4-CH₂COOH | 2-SO₂Me | H |
| 3-57 | tBu | 4-CH₂COOH | 3-SO₂Me | H |
| 3-58 | tBu | 4-CH₂COOH | 2-NH₂ | H |
| 3-59 | tBu | 4-CH₂COOH | 2-NHMe | H |
| 3-60 | tBu | 4-CH₂COOH | 2-NMe₂ | H |
| 3-61 | tBu | 4-CH₂COOH | 2-COMe | H |
| 3-62 | tBu | 4-CH₂COOH | 2-COEt | H |
| 3-63 | tBu | 4-CH₂COOH | 2-CN | H |
| 3-64 | tBu | 4-CH₂COOH | 3-CN | H |
| 3-65 | tBu | 4-CH₂COOH | 2-NO₂ | H |
| 3-66 | tBu | 4-CH₂COOH | 3-NO₂ | H |
| 3-67 | tBu | 4-CH₂COOH | 2-F | H |
| 3-68 | tBu | 4-CH₂COOH | 2-F | 3-F |
| 3-69 | tBu | 4-CH₂COOH | 2-F | 5-F |
| 3-70 | tBu | 4-CH₂COOH | 3-F | H |
| 3-71 | tBu | 4-CH₂COOH | 2-Cl | H |
| 3-72 | tBu | 4-CH₂COOH | 3-Cl | H |
| 3-73 | tBu | 3-CH₂COOH | 2-Me | H |
| 3-74 | tBu | 3-CH₂COOH | 2-Et | H |
| 3-75 | tBu | 3-CH₂COOH | 2-OMe | H |
| 3-76 | tBu | 3-CH₂COOH | 2-F | H |
| 3-77 | tBu | 3-CH(Me)COOH | 2-Me | H |
| 3-76 | tBu | 3-CH(Me)COOH | 2-Et | H |
| 3-79 | tBu | 3-CH(Me)COOH | 2-OMe | H |
| 3-80 | tBu | 3-CH(Me)COOH | 2-F | H |
| 3-81 | CF₃ | 4-CH₂COOH | 3-iPr | H |
| 3-82 | CF₃ | 4-CH₂COOH | 3-cPr | H |
| 3-83 | CF₃ | 4-CH₂COOH | 2-SO₂Me | H |
| 3-84 | CF₃ | 4-CH₂COOH | 2-NHMe | H |
| 3-85 | CF₃ | 4-CH₂COOH | 2-F | 5-F |
| 3-86 | CF₃ | 3-CH(Me)COOH | 2-F | H |
| 3-87 | Cl | 4-CH₂COOH | 2-Me | H |
| 3-88 | Cl | 4-CH₂COOH | 2-Me | 3-Me |
| 3-89 | Cl | 4-CH₂COOH | 2-Me | 5-Me |
| 3-90 | Cl | 4-CH₂COOH | 3-Me | H |
| 3-91 | Cl | 4-CH₂COOH | 2-Et | H |
| 3-92 | Cl | 4-CH₂COOH | 3-Et | H |
| 3-93 | Cl | 4-CH₂COOH | 2-iPr | H |
| 3-94 | Cl | 4-CH₂COOH | 3-iPr | H |
| 3-95 | Cl | 4-CH₂COOH | 2-CH₂OH | H |
| 3-96 | Cl | 4-CH₂COOH | 2-CF₃ | H |
| 3-97 | Cl | 4-CH₂COOH | 3-CF₃ | H |
| 3-98 | Cl | 4-CH₂COOH | 2-cPr | H |
| 3-99 | Cl | 4-CH₂COOH | 3-cPr | H |
| 3-100 | Cl | 4-CH₂COOH | 2-OMe | H |
| 3-101 | Cl | 4-CH₂COOH | 3-OMe | H |
| 3-102 | Cl | 4-CH₂COOH | 2-SO₂Me | H |
| 3-103 | Cl | 4-CH₂COOH | 3-SO₂Me | H |
| 3-104 | Cl | 4-CH₂COOH | 2-NH₂ | H |
| 3-105 | Cl | 4-CH₂COOH | 2-NHMe | H |
| 3-106 | Cl | 4-CH₂COOH | 2-NMe₂ | H |
| 3-107 | Cl | 4-CH₂COOH | 2-COMe | H |
| 3-108 | Cl | 4-CH₂COOH | 2-COEt | H |
| 3-109 | Cl | 4-CH₂COOH | 2-CN | H |
| 3-110 | Cl | 4-CH₂COOH | 3-CN | H |
| 3-111 | Cl | 4-CH₂COOH | 2-NO₂ | H |
| 3-112 | Cl | 4-CH₂COOH | 3-NO₂ | H |
| 3-113 | Cl | 4-CH₂COOH | 2-F | H |

TABLE 3-continued (I-3)

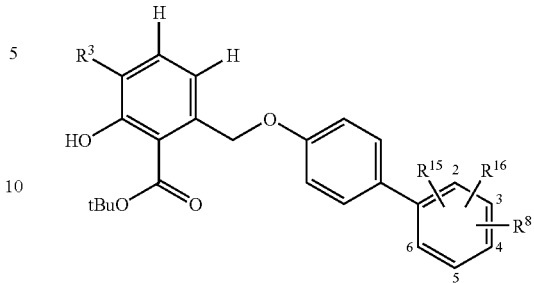

| Exemplification Compound No. | R³ | R⁸ | R¹⁵ | R¹⁶ |
|---|---|---|---|---|
| 3-114 | Cl | 4-CH₂COOH | 2-F | 3-F |
| 3-115 | Cl | 4-CH₂COOH | 2-F | 5-F |
| 3-116 | Cl | 4-CH₂COOH | 3-F | H |
| 3-117 | Cl | 4-CH₂COOH | 2-Cl | H |
| 3-118 | Cl | 4-CH₂COOH | 3-Cl | H |
| 3-119 | Cl | 3-CH₂COOH | 2-Me | H |
| 3-120 | Cl | 3-CH₂COOH | 2-Et | H |
| 3-121 | Cl | 3-CH₂COOH | 2-OMe | H |
| 3-121 | Cl | 3-CH₂COOH | 2-F | H |
| 3-122 | Cl | 3-CH(Me)COOH | 2-Me | H |
| 3-123 | Cl | 3-CH(Me)COOH | 2-Et | H |
| 3-124 | Cl | 3-CH(Me)COOH | 2-OMe | H |
| 3-125 | Cl | 3-CH(Me)COOH | 2-F | H |

In Exemplification compounds described above, preferred compounds are the compounds of Exemplification Compound Nos.: 1-16, 1-55, 1-62, 1-64, 1-114, 1-132, 2-29, 2-31, 2-43, 2-46, 2-47, 2-48, 2-49, 2-54, 2-61, 2-62, 2-63, 2-64, 2-65, 2-70, 2-113, 2-165, 2-184, 2-185, 2-186, 2-188, 2-189, 2-191, 2-192, 2-193, 2-194, 2-195, 2-196, 2-197, 2-198, 2-199, 2-213, 2-216, 2-218, 2-219, 2-221, 2-222, 2-223, 2-227, 2-228, 2-229, 2-230, 2-231, 2-232, 2-233, 2-234, 2-235, 2-236, 2-238, 2-239, 2-241, 2-242, 2-243, 2-244, and 2-245, more preferred compounds are the compounds of Exemplification Compound No. 1-55: (4'-{[2-(tert-butoxycarbonyl)-3-hydroxy-4-(trifluoromethyl)benzyl]oxy}-1,1'-biphenyl-4-yl)acetic acid, Exemplification Compound No. 1-62: 2-(4'-{[2-(tert-butoxycarbonyl)-3-hydroxy-4-(trifluoromethyl)benzyl]oxy}-1,1'-biphenyl-4-yl)propanoic acid, Exemplification Compound No. 1-64: 1-(4'-{[2-(tert-butoxycarbonyl)-3-hydroxy-4-(trifluoromethyl)benzyl]oxy}-1,1'-biphenyl-4-yl)cyclopropane carboxylic acid, Exemplification Compound No. 1-114: 2-(4'-{[2-(tert-butoxycarbonyl)-3-hydroxy-4-(trifluoromethyl)benzyl]oxy}-1,1'-biphenyl-4-yl)-3-hydroxypropanoic acid, Exemplification Compound No. 1-132: 2-[4'-{[2-(tert-butoxycarbonyl)-3-hydroxy-4-(trifluoromethyl)benzyl]oxy}-1,1'-biphenyl-4-yl]butanoic acid, Exemplification Compound No. 2-31: (4'-{[2-(tert-butoxycarbonyl)-3-hydroxy-4-(trifluoromethyl)benzyl]oxy}-2-methyl-1,1'-biphenyl-3-yl)acetic acid, Exemplification Compound No. 2-43: (4'-{[2-(tert-butoxycarbonyl)-3-hydroxy-4-(trifluoromethyl)benzyl]oxy}-2-methyl-1,1'-biphenyl-4-yl)acetic acid, Exemplification Compound No. 2-46: (4'-{[2-(tert-butoxycarbonyl)-3-hydroxy-4-(trifluoromethyl)benzyl]oxy}-2-chloro-1,1'-biphenyl-4-yl)acetic acid, Exemplification Compound No. 2-48: (4'-{[2-(tert-butoxycarbonyl)-3-hydroxy-4-(trifluoromethyl)benzyl]oxy}-3-fluoro-1,1'-biphenyl-4-yl)acetic acid, Exemplification Compound No. 2-49: (4'-{[2-(tert-butoxy-carbonyl)-3-hydroxy-4-(trifluoromethyl)benzyl]oxy}-3-chloro-1,1'-biphenyl-4-yl)acetic acid, Exemplification Compound No. 2-63: 2-(4'-{[2-(tert-butoxy-carbonyl)-3-hydroxy-4-(trifluoromethyl)benzyl]oxy}-2-methoxy-1,1'-biphenyl-3-yl)propanoic acid, Exemplification Compound No. 2-64: 2-(4'-{[2-(tert-butoxy-carbonyl)-3-hydroxy-4-(trifluoromethyl)benzyl]oxy}-3-fluoro-1,1'-biphenyl-4-yl)propanoic acid, Exemplification Compound No. 2-70: 1-(4'-{[2-(tert-butoxy-carbonyl)-3-hydroxy-4-(trifluoromethyl)benzyl]oxy}-3-fluoro-1,1'-biphenyl-4-yl)cyclopropane carboxylic acid, Exemplification Compound No. 2-184: (4'-{[2-(tert-butoxy-carbonyl)-3-hydroxy-4-(trifluoromethyl)benzyl]oxy}-3-methoxy-1,1'-biphenyl-4-yl)acetic acid, Exemplification Compound No. 2-185: (4'-{[2-(tert-butoxy-carbonyl)-3-hydroxy-4-(trifluoromethyl)benzyl]oxy}-2-trifluoromethyl-1,1'-biphenyl-4-yl)acetic acid, Exemplification Compound No. 2-186: (4'-{[2-(tert-butoxy-carbonyl)-3-hydroxy-4-(trifluoromethyl)benzyl]oxy}-2-ethyl-1,1'-biphenyl-4-yl)acetic acid, Exemplification Compound No. 2-189: tert-butyl 6-[({2'-ethyl-4'-[(methoxycarbonyl)methyl]-1,1'-biphenyl-4-yl}oxy)methyl]-2-hydroxy-3-(trifluoromethyl)benzoate, Exemplification Compound No. 2-191: (4'-{[2-(tert-butoxy-carbonyl)-3-hydroxy-4-(trifluoromethyl)benzyl]oxy}-2-nitro-1,1'-biphenyl-4-yl)acetic acid, Exemplification Compound No. 2-192: (2-amino-4'-{[2-(tert-butoxycarbonyl)-3-hydroxy-4-(trifluoromethyl)benzyl]oxy}-1,1'-biphenyl-4-yl)acetic acid, Exemplification Compound No. 2-195: (4'-{[2-(tert-butoxy-carbonyl)-3-hydroxy-4-(trifluoromethyl)benzyl]oxy}-2-isopropyl-1,1'-biphenyl-4-yl)acetic acid, Exemplification Compound No. 2-197: (4'-{[2-(tert-butoxy-carbonyl)-3-hydroxy-4-(trifluoromethyl)benzyl]oxy}-2-formyl-1,1'-biphenyl-4-yl)acetic acid, Exemplification Compound No. 2-198: (4'-{[2-(tert-butoxy-carbonyl)-3-hydroxy-4-(trifluoromethyl)benzyl]oxy}-2-(hydroxymethyl)-1,1'-biphenyl-4-yl)acetic acid, Exemplification Compound No. 2-199: (4'-{[2-(tert-butoxy-carbonyl)-3-hydroxy-4-(trifluoromethyl)benzyl]oxy}-2-cyano-1,1'-biphenyl-4-yl)acetic acid, Exemplification Compound No. 2-221: (4'-{[2-(tert-butoxy-carbonyl)-3-hydroxy-4-(trifluoromethyl)benzyl]oxy}-2-cyclopropyl-1,1'-biphenyl-4-yl)acetic acid, Exemplification Compound No. 2-223: (4'-{[2-(tert-butoxy-carbonyl)-3-hydroxy-4-(trifluoromethyl)benzyl]oxy}-3-ethyl-1,1'-biphenyl-4-yl)acetic acid, Exemplification Compound No. 2-227: (4'-{[2-(tert-butoxy-carbonyl)-3-hydroxy-4-(trifluoromethyl)benzyl]oxy}-2-ethyl-1,1'-biphenyl-3-yl)acetic acid, Exemplification Compound No. 2-230: 2-(4'-{[2-(tert-butoxycarbonyl)-3-hydroxy-4-(trifluoromethyl)benzyl]oxy}-3-fluoro-1,1'-biphenyl-4-yl)-3-(dimethylamino)propanoic acid, Exemplification Compound No. 2-231: 2-(4'-{[2-(tert-butoxycarbonyl)-3-hydroxy-4-(trifluoromethyl)benzyl]oxy}-2-ethyl-1,1'-biphenyl-4-yl)propanoic acid, Exemplification Compound No. 2-232: [5-(4-{[2-(tert-butoxycarbonyl)-3-hydroxy-4-(trifluoromethyl)benzyl]oxy}phenyl)-4-methyl-2-thienyl]acetic acid, Exemplification Compound No. 2-235: 2-(4'-{[2-(tert-butoxycarbonyl)-3-hydroxy-4-(trifluoromethyl)benzyl]oxy}-2-nitro-1,1'-biphenyl-4-yl)propanoic acid, Exemplification Compound No. 2-236: 2-[4-(5-{[2-(tert-butoxycarbonyl)-3-hydroxy-4-(trifluoromethyl)benzyl]oxy}-2-pyridinyl)-3-methylphenyl]propanoic acid, Exemplification Compound No. 2-242: 2-(4'-{[2-(tert-butoxycarbonyl)-3-hydroxy-4-(trifluoromethyl)benzyl]oxy}-2-isopropyl-1,1'-biphenyl-4-yl)propanoic acid, Exemplification Compound No. 2-244: 2-(4'-{[2-(tert-butoxycarbonyl)-3-hydroxy-4-(trifluoromethyl)benzyl]oxy}-2,3-dimethyl-1,1'-biphenyl-4-yl)propanoic acid, and Exemplification Compound No. 2-245: 2-(4'-{[2-(tert-butoxycarbonyl)-3-hydroxy-4-(trifluoromethyl)benzyl]oxy}-2-cyclopropyl-1,1'-biphenyl-4-yl)propanoic acid.

A compound represented by the general formula (I) of the present invention can be prepared according to the following Method A to Method P.

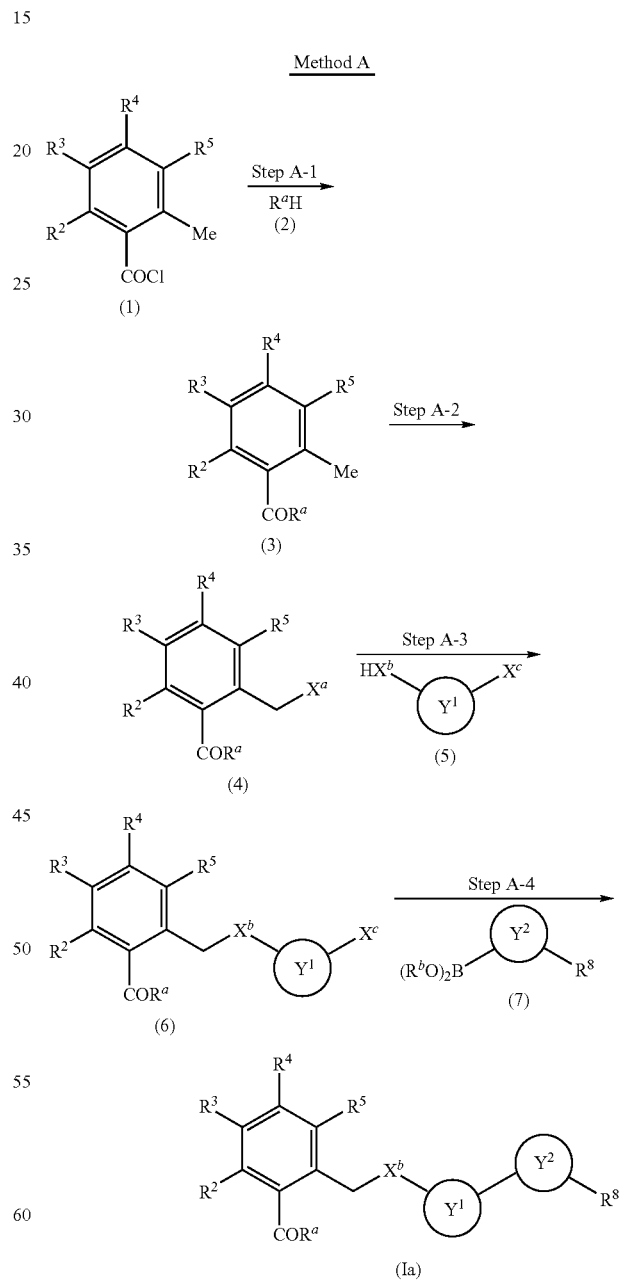

-continued
Method B
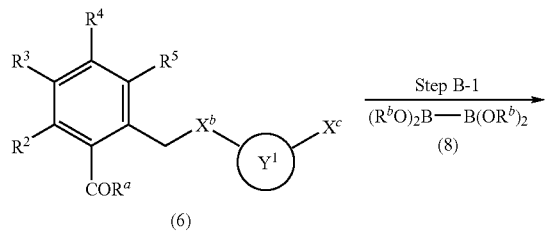
(6) → Step B-1, $(R^bO)_2B\text{—}B(OR^b)_2$ (8)
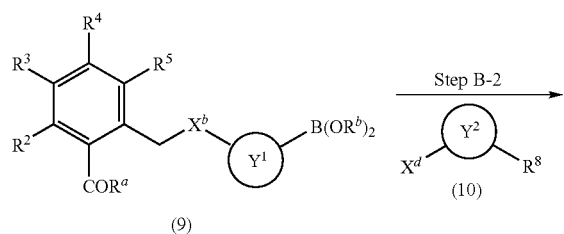
(9) → Step B-2, (10)
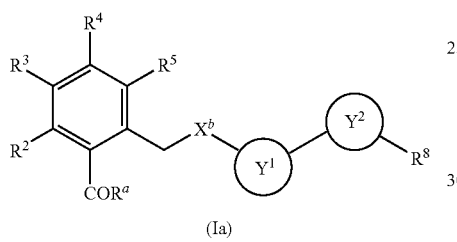
(Ia)
Method C
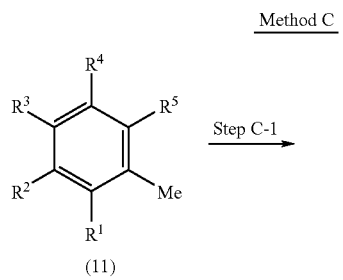
(11) → Step C-1
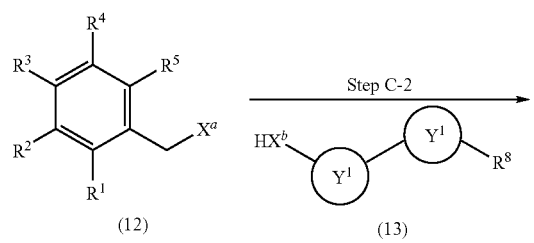
(12) + (13) → Step C-2
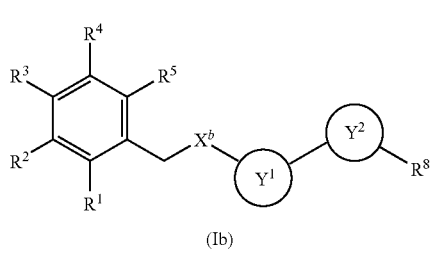
(Ib)
-continued
Method D
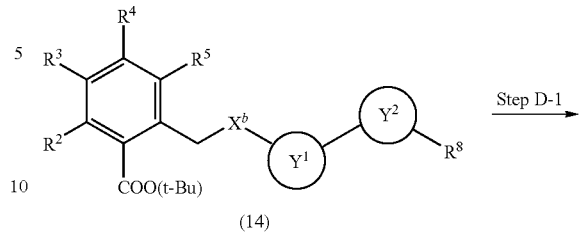
(14) → Step D-1
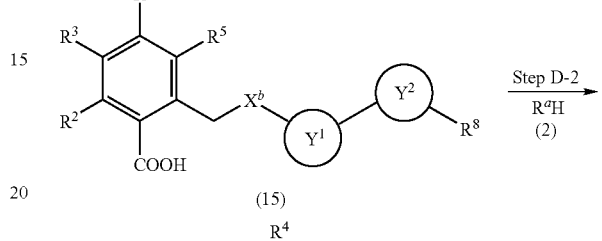
(15) → Step D-2, $R^aH$ (2)
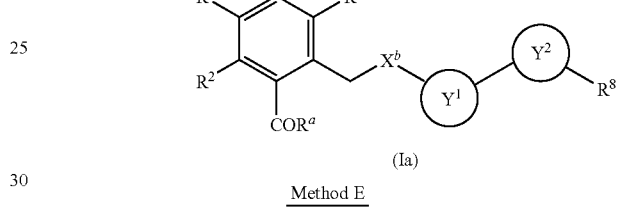
(Ia)
Method E
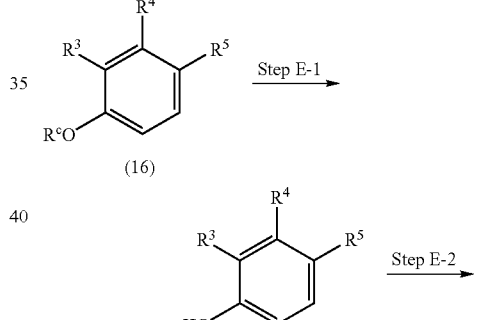
(16) → Step E-1
(17) → Step E-2
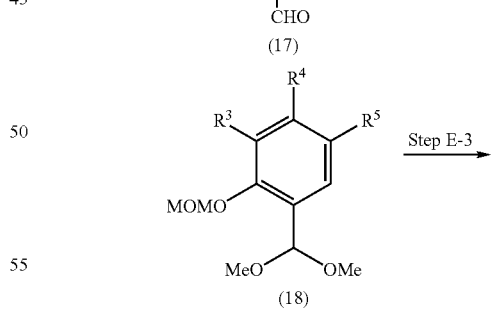
(18) → Step E-3
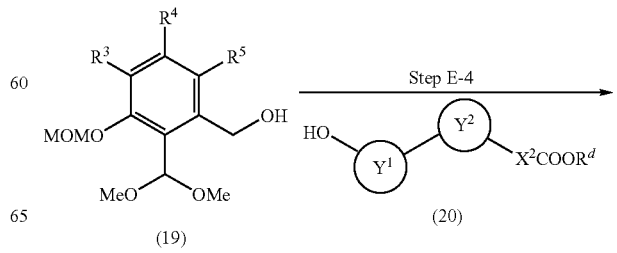
(19) + (20) → Step E-4

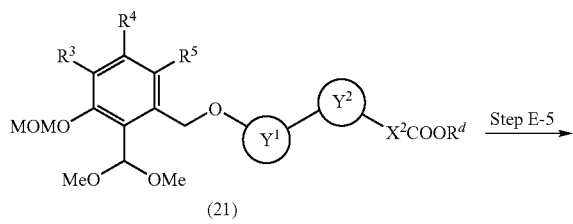
(21)
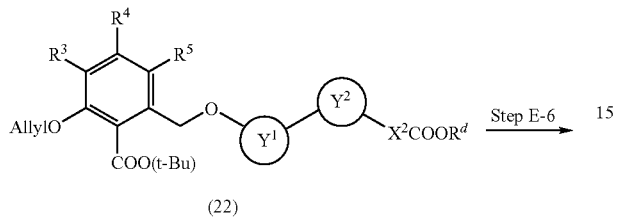
(22)
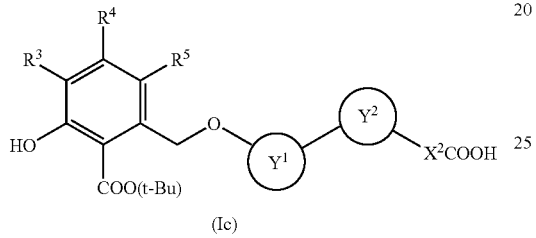
(Ic)
Method F
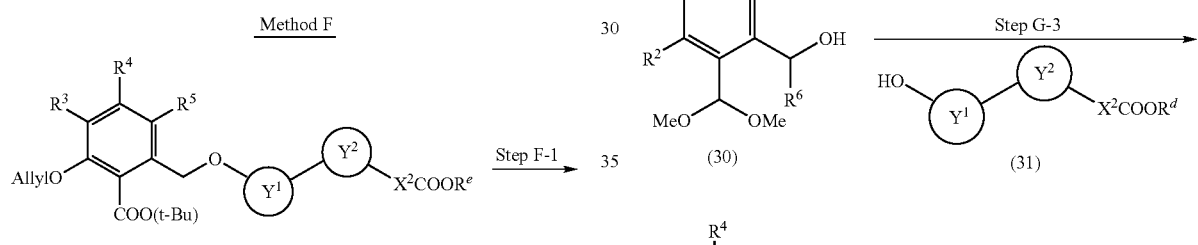
(23)
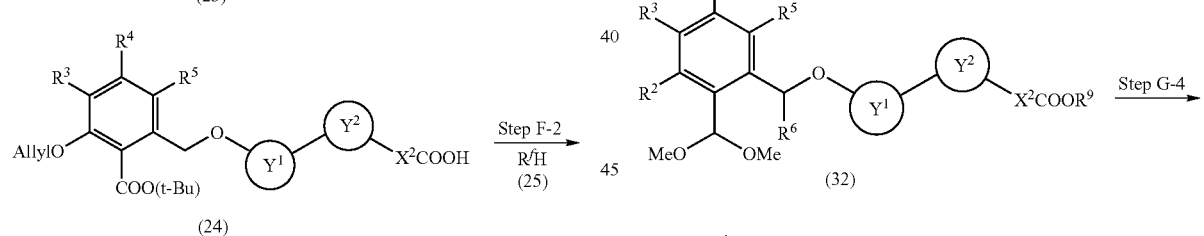
(24)
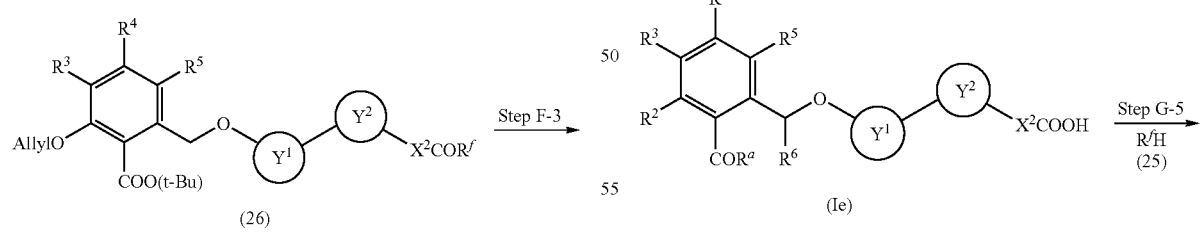
(26)
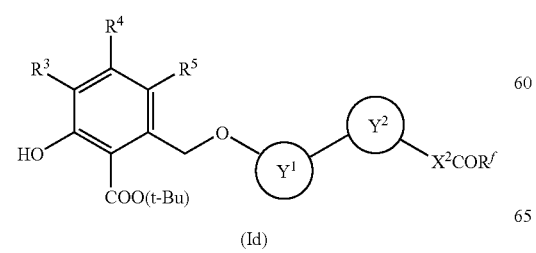
(Id)
Method G
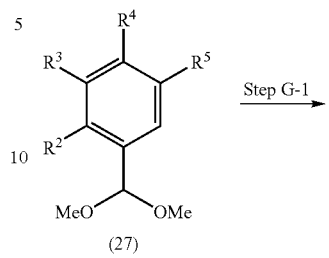
(27)
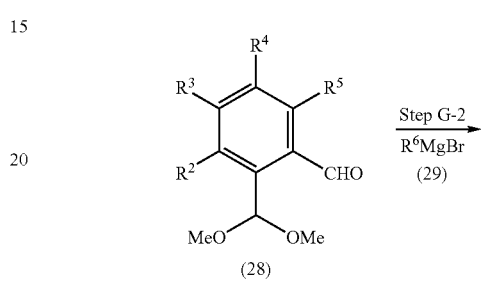
(28)
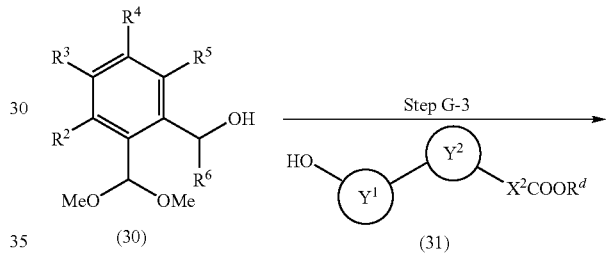
(30) (31)
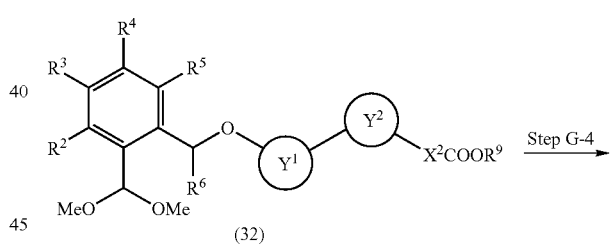
(32)
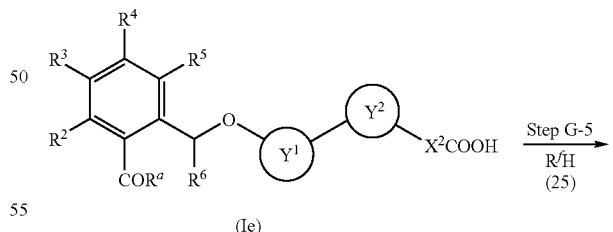
(Ie)
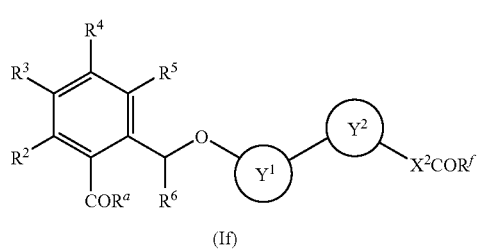
(If)

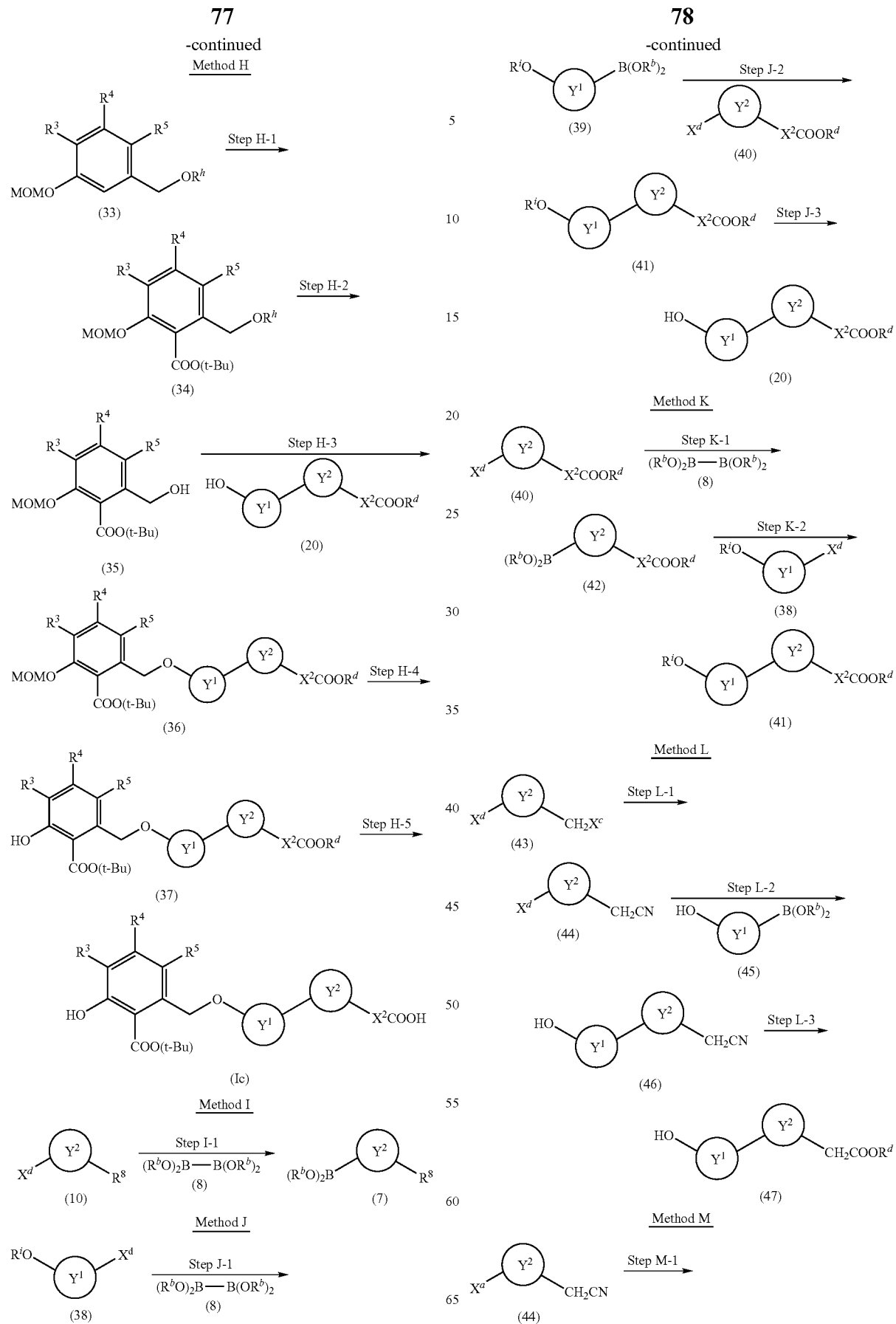

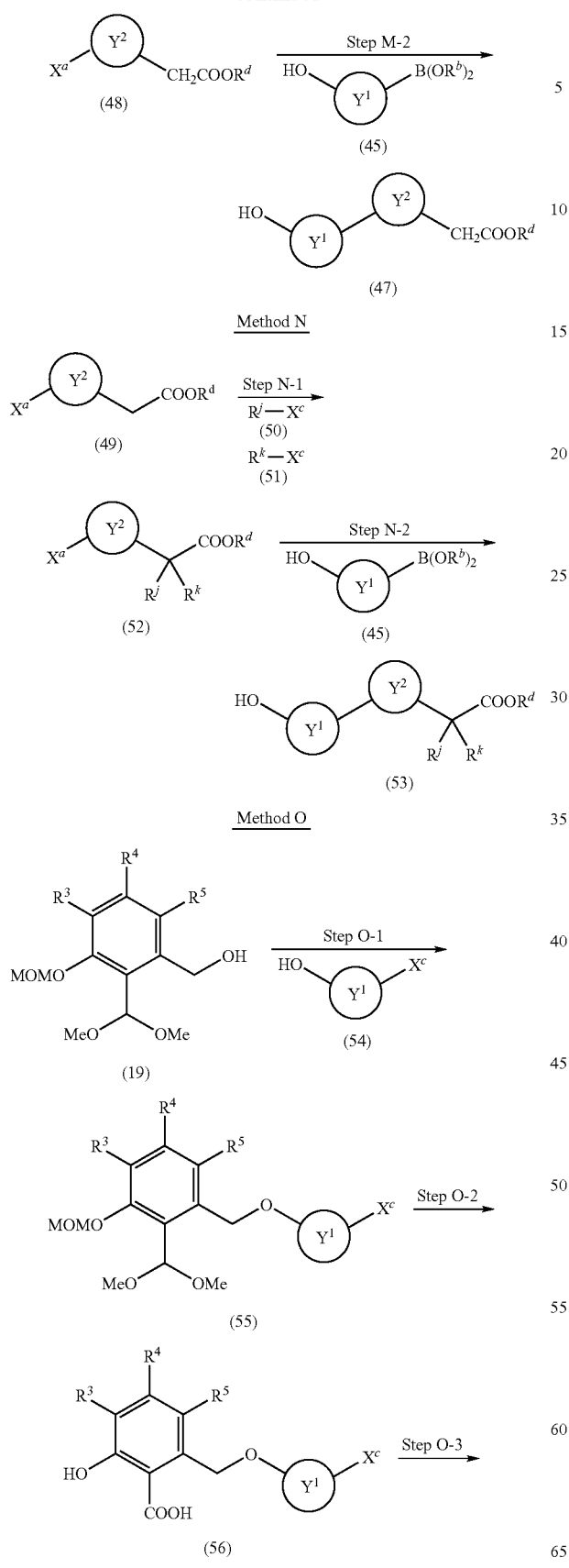
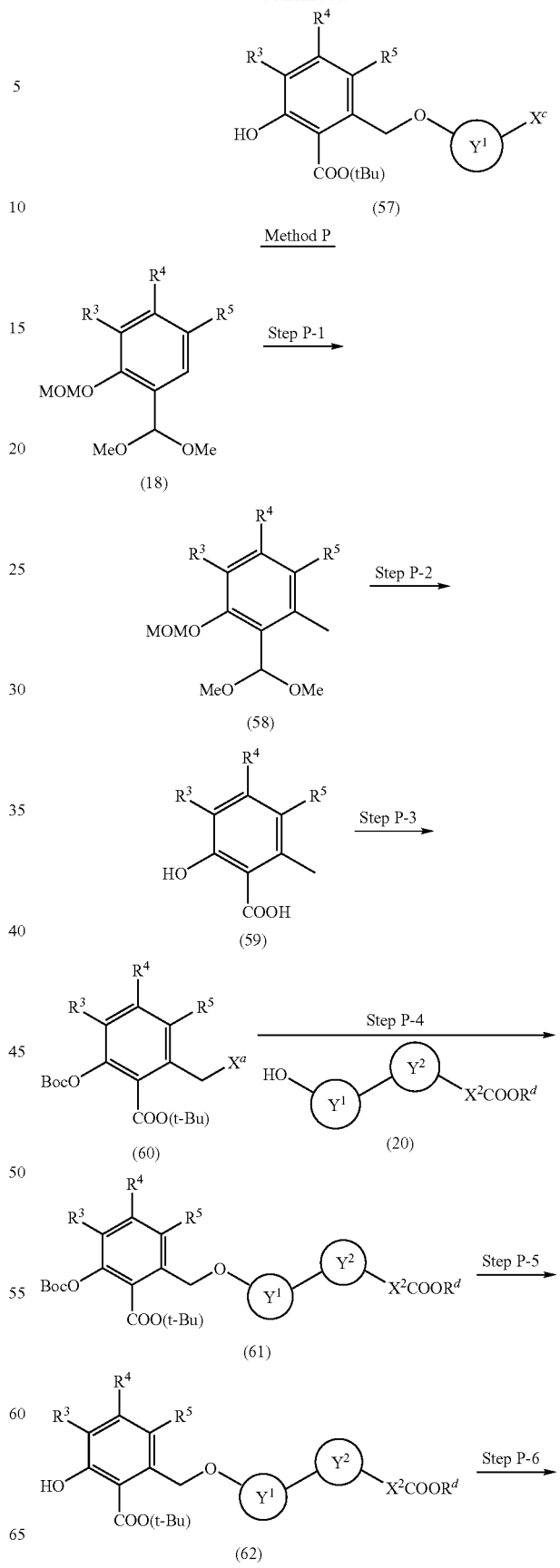

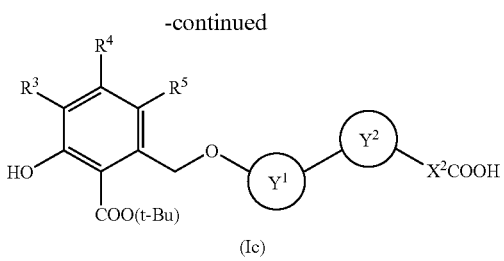

(Ic)

In the structural formulae of the compound of Method A to Method P described above, $R^1$, $R^2$, $R^3$, $R^4$, $R^5$, $R^6$, $R^8$, $X^2$, $Y^1$ and $Y^2$ have the same meanings as defined above, $R^a$ represents a $C_1$-$C_{10}$ alkoxy group, a halogeno $C_1$-$C_{10}$ alkoxy group, a phenyl-($C_1$-$C_{10}$ alkoxy) group, a $C_1$-$C_{10}$ alkylamino group or a di($C_1$-$C_{10}$ alkyl)amino group in $R^9$, $R^b$ represents a hydrogen atom or a $C_1$-$C_6$ alkyl group and two of $R^b$ may together with each other form an ethylene group or a trimethylene group (said ethylene group or said trimethylene group may be substituted by 1 to 4 methyl groups), $R^c$ represents a tetrahydrofuranyl group, a tetrahydropyranyl group or a methoxymethyl group, $R^d$ represents a $C_1$-$C_6$ alkyl group or an allyl group, $R^e$ represents a $C_1$-$C_6$ alkyl group, $R^f$ represents a $C_1$-$C_6$ alkoxy group, an amino group, a $C_1$-$C_6$ alkylamino group or a di($C_1$-$C_6$ alkyl)amino group in $R^{11}$, $R^g$ represents an allyl group, $R^h$ represents a silyl group substituted by three groups selected from the group consisting of a $C_1$-$C_6$ alkyl group and a phenyl group (preferably a tert-butyldimethylsilyl group, a tert-butyldiphenylsilyl group or a triisopropylsilyl group), $R^i$ represents a protective group of a hydroxyl group, and preferably a silyl group substituted by three groups selected from the group consisting of a $C_1$-$C_6$ alkyl group and a phenyl group (particularly a tert-butyldimethylsilyl group, a tert-butyldiphenylsilyl group or a triisopropylsilyl group), a tetrahydrofuranyl group, a tetrahydropyranyl group, a methoxymethyl group or an allyl group, $R^j$ and $R^k$ represent a $C_1$-$C_4$ alkyl group and may together form an ethylene group or a trimethylene group, $X^a$ and $X^c$ represent a chloro group, a bromo group or an iodo group, $X^b$ represents a group having the formula —NH—, —$NR^{12}$—, —O— or —S—, $X^d$ represents a chloro group, a bromo group, an iodo group or a trifluoromethanesulfonyloxy group, Allyl represents an allyl group, Boc represents a tert-butoxycarbonyl group, t-Bu represents a tert-butyl group and MOM represents a methoxymethyl group.

In the reactions of the respective steps of the following Method A to Method P, in the case that a compound as a reaction substrate has a group which inhibits a desired reaction such as an amino group, a hydroxyl group or a carboxyl group, introduction of a protective group to those groups may be appropriately carried out if necessary and removal of the introduced protective group may be appropriately carried out if necessary. Such a protective group is not particularly limited provided it is a group which is usually used for progressing a reaction and can be, for example, a protective group described in T. H. Greene, P. G. Wuts, Protective Groups in Organic Synthesis, Third Edition, 1999, John Wiley & Sons, Inc. or the like. Introduction reactions of those protective groups and removal reactions of said protective groups can be carried out according to usual methods such as a method described in the literature above.

The solvent used in reactions of the respective steps of the following Method A to Method P is not particularly limited provided it does not inhibit the reaction and dissolves a starting material to some extent and is selected from the following solvent group. The solvent group consists of an aliphatic hydrocarbon such as hexane, pentane, petroleum ether and cyclohexane; an aromatic hydrocarbon such as benzene, toluene and xylene; a halogenated hydrocarbon such as methylene chloride, chloroform, carbon tetrachloride, dichloroethane, chlorobenzene and dichlorobenzene; an ether such as diethyl ether, diisopropyl ether, tetrahydrofuran, dioxane, dimethoxyethane and diethylene glycol dimethyl ether; a ketone such as acetone, methyl ethyl ketone, methyl isobutyl ketone and cyclohexanone; an ester such as ethyl acetate, propyl acetate and butyl acetate; a nitrile such as acetonitrile, propionitrile, butyronitrile and isobutyronitrile; a carboxylic acid such as acetic acid and propionic acid; an alcohol such as methanol, ethanol, 1-propanol, 2-propanol, 1-butanol, 2-butanol, 2-methyl-1-propanol and 2-methyl-2-propanol; an amide such as formamide, dimethylformamide, dimethylacetamide, N-methyl-2-pyrrolidone and hexamethylphosphor triamide; a sulfoxide such as dimethyl sulfoxide and sulforane; water; and a mixture of these.

The acid used in reactions of the respective steps of the following Method A to Method P is not particularly limited provided it does not inhibit a reaction and is selected from the following acid group. The acid group consists of an organic acid such as acetic acid, propionic acid, trifluoroacetic acid and pentafluoropropionic acid; an organic sulfonic acid such as p-toluenesulfonic acid, camphorsulfonic acid and trifluoromethanesulfonic acid; and an inorganic acid such as hydrochloric acid, hydrobromic acid, hydroiodic acid, phosphoric acid, sulfuric acid and nitric acid.

The base used in reactions of the respective steps of the following Method A to Method P is not particularly limited provided it does not inhibit the reaction and is selected from the following base group. The base group consists of an alkali metal carbonate such as lithium carbonate, sodium carbonate, potassium carbonate and cesium carbonate; an alkali metal hydrogencarbonate such as lithium hydrogencarbonate, sodium hydrogencarbonate and potassium hydrogencarbonate; an alkali metal hydroxide such as lithium hydroxide, sodium hydroxide and potassium hydroxide; an alkaline earth metal hydroxide such as calcium hydroxide and barium hydroxide; an alkali metal hydride such as lithium hydride, sodium hydride and potassium hydride; an alkali metal amide such as lithium amide, sodium amide and potassium amide; an alkali metal alcoxide such as lithium methoxide, sodium methoxide, sodium ethoxide, sodium tert-butoxide and potassium tert-butoxide; a lithium alkylamide such as lithium diisopropylamide; a lithium silylamide such as lithium bistrimethylsilylamide and sodium bistrimethylsilylamide; an alkyl lithium such as n-butyl lithium, sec-butyl lithium and tert-butyl lithium; and an organic amine such as triethylamine, tributylamine, diisopropylethylamine, N-methylpiperidine, N-methylmorpholine, N-ethylmorpholine, pyridine, picoline, 4-(N,N-dimethylamino)pyridine, 4-pyrrolidinopyridine, 2,6-di(tert-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU).

In the reactions of the respective steps of the following Method A to Method P, the reaction temperature varies depending on the solvent, starting material, reagent or the like and the reaction time varies depending on the solvent, starting material, reagent, reaction temperature or the like.

In the reactions of the respective steps of the following Method A to Method P, after the reaction, the desired compound of the respective steps is isolated from the reaction mixture according to a usual method. For example, the desired compound is obtained by (i) removing insolubles such as a catalyst or the like by filtration if necessary, (ii) adding water and a solvent immiscible with water (for example, methylene chloride, diethyl ether, ethyl acetate or the like) to the reaction mixture to extract the desired compound, (iii) washing the organic layer with water and drying it using a drying agent such as anhydrous magnesium sulfate or the like and (iv) removing the solvent. The obtained desired compound can be further purified, if necessary, by a usual method, for example, recrystallization, reprecipitation or silica gel column chromatography or the like. Further, the desired compound of the respective steps can be used in a subsequent reaction as such without purification.

(Method A)

Method A is a method to prepare compound (Ia) in which $R^1$ is —$COR^a$, $R^6$ and $R^7$ are hydrogen atoms and $X^1$ is $X^b$ in the formula (I).

(Step A-1)

Step A-1 is a step to prepare compound (3) by reacting compound (1) publicly known or easily obtained from a publicly known compound with compound (2) in the presence or absence of a base.

In Step A-1, in the case that $R^a$ of compound (2) is a $C_1$-$C_{10}$ alkoxy group, a halogeno $C_1$-$C_{10}$ alkoxy group or a phenyl-($C_1$-$C_{10}$ alkoxy) group, compound (2a) $R^a X^e$ (wherein $X^e$ represents an alkali metal, preferably sodium or potassium) can be used instead of compound (2) in the absence of a base.

The base used is selected from the above base group, is not particularly limited provided it is usually used for an esterification reaction or an amidation reaction and is preferably an organic amine, more preferably triethylamine.

The solvent used is selected from the above solvent group and is preferably an ether, more preferably tetrahydrofuran.

The reaction temperature is usually from −20 to 100° C., preferably from 0 to 50° C.

The reaction time is usually from 10 minutes to 6 hours, preferably from 30 minutes to 3 hours.

Step A-1 can also be carried out in similar manner to step D-2 using a carboxylic acid compound instead of compound (1).

(Step A-2)

Step A-2 is a step to prepare compound (4) by halogenating compound (3) obtained in Step A-1 with a halogenating reagent.

The halogenating reagent used is not particularly limited provided it is usually used for a halogenation reaction and can include a N-halogenosuccinimide such as N-chlorosuccinimide, N-bromosuccinimide and N-iodosuccinimide or a halogen such as bromine and iodine, preferably a N-halogenosuccinimide, and more preferably N-bromosuccinimide. Step A-2 can be carried out, if necessary, in the presence of a radical reaction initiator such as azoisobutyronitrile (preferably azoisobutyronitrile or benzoyl peroxide).

The solvent used is selected from the above solvent group and is preferably an aromatic hydrocarbon or a halogenated hydrocarbon, more preferably benzene or carbon tetrachloride.

The reaction temperature is usually from 20 to 200° C., preferably from 50 to 150° C.

The reaction time is usually from 30 minutes to 12 hours, preferably from 30 minutes to 6 hours.

(Step A-3)

Step A-3 is a step to prepare the compound (6) by reacting compound (4) obtained in Step A-2 with compound (5) publicly known or easily obtained from a publicly known compound in the presence of a base.

The base used is selected from the above base group, is not particularly limited provided it is usually used for an alkylation reaction of a phenol and is preferably an alkali metal carbonate, an alkali metal hydrogencarbonate or an alkali metal hydride, more preferably potassium carbonate or cesium carbonate.

The solvent used is selected from the above solvent group and is preferably an amide, more preferably dimethylformamide.

The reaction temperature is usually from −20 to 100° C., preferably from 0 to 50° C.

The reaction time is usually from 30 minutes to 48 hours, preferably from 1 hour to 24 hours.

(Step A-4)

Step A-4 is a step to prepare compound (Ia) by reacting compound (6) obtained in Step A-3 with compound (7) in the presence of a palladium catalyst and a base. Compound (7) is publicly known, easily obtained from a publicly known compound or can be prepared by Method I.

The palladium catalyst used is not particularly limited provided it is usually used for a carbon-carbon bond formation reaction and can be a palladium catalyst described in J. Tsuji, Palladium Reagents and Catalysis: New perspectives for the 21$^{st}$ Century, 2004, John Wiley & Sons, Inc. or the like. The palladium catalyst used can include tetrakis(triphenylphosphine)palladium (0), bis[1,2-bis(diphenylphosphino)ethane] palladium (0), tris(dibenzylideneacetone)dipalladium (0), bis(tri-t-butylphosphine)palladium (0), bis(tricyclohexylphosphine)palladium (0), palladium chloride (II), palladium acetate (II), dichlorobis(triphenylphosphine) palladium (II), dichlorobis[methylenebis(diphenylphosphine)]dipalladium-dichloromethane adduct, [1,2-bis(diphenylphosphino)ethane]dichloropalladium (II), [1,1'-bis(diphenylphosphino)ferrocene]dichloropalladium (II)-dichloromethane adduct, palladium (II) acetylacetonate, bis(benzonitrile)palladium (II) chloride, bis(acetate)bis(triphenylphosphine)palladium (II), bis(acetonitrile) dichloropalladium (II), bis(benzonitrile)dichloropalladium (II), trans-benzyl(chloro)bis(triphenylphosphine)palladium (II), palladium-carbon, palladium hydroxide or palladium hydroxide-carbon, and preferably tetrakis(triphenylphosphine)palladium (0), palladium acetate (II), tris(dibenzylideneacetone)dipalladium (0) or [1,1'-bis(diphenylphosphino) ferrocene]dichloropalladium (II)-dichloromethane adduct.

In Step A-4, a phosphine ligand which can coordinate on the palladium catalyst described above may be appropriately used if necessary. The phosphine ligand used can be a phosphine ligand described in J. Tsuji, Palladium Reagents and Catalysis: New perspectives for the 21$^{st}$ Century, 2004, John Wiley & Sons, Inc. or the like. The phosphine ligand used can include triphenylphosphine, tri-o-tolylphosphine, tri-m-tolylphosphine, tri-p-tolylphosphine, tris(2,6-dimethoxyphenyl)phosphine, tris[2-(diphenylphosphino)ethyl]phosphine, bis(2-methoxyphenyl)phenylphosphine, 2-(di-t-butylphosphino)biphenyl, 2-(dicyclohexylphosphino)biphenyl, 2-(diphenylphosphino)-2'-(N,N-dimethylamino)biphenyl, tri-t-butylphosphine, bis(diphenylphosphino)methane, 1,2-bis(diphenylphosphino)ethane, 1,2-bis(dimethylphosphino) ethane, 1,3-bis(diphenylphosphino)propane, 1,4-bis(diphenylphosphino)butane, 1,5-bis(diphenylphosphino)pentane, 1,6-bis(diphenylphosphino)hexane, 1,2-bis(dimethylphosphino)ethane, 1,1'-bis(diphenylphosphino)ferrocene, bis(2-diphenylphosphinoethyl)phenylphosphine, 2-(dicyclohexylphosphino-2',6'-dimethoxy-1,1'-biphenyl (S-PHOS), 2-(dicyclohexylphosphino-2',4',6'-tri-iso-propyl-1,1'-biphenyl (X-PHOS) or bis(2-diphenylphosphinophenyl)ether (DPEphos), and preferably triphenylphosphine, tri-o-tolylphosphine, the 1,3-bis(diphenylphosphino) propane, 2-(dicyclohexylphosphino-2',6'-dimethoxy-1,1'-biphenyl or bis(2-diphenylphosphinophenyl)ether.

The base used can be a base selected from the above base group or an alkali metal phosphate, preferably an alkali metal carbonate or alkali metal phosphate, and more preferably sodium carbonate, potassium carbonate or potassium phosphate.

The solvent used is selected from the above solvent group and is preferably a hydrocarbon, an ether, an alcohol, an amide, water or a mixture of these, more preferably toluene, tetrahydrofuran, ethanol, dimethylacetamide, water or a mixture of these, and most preferably a mixture of toluene and ethanol, a mixture of tetrahydrofuran and water or a mixture of dimethylacetamide and water.

The reaction temperature is usually from 20 to 200° C., preferably from 50 to 150° C.

The reaction time is usually from 1 hour to 48 hours, preferably from 3 hours to 24 hours.
(Method B)

Method B is a method to prepare compound (Ia) in which $R^1$ is $-COR^a$, $R^6$ and $R^7$ are hydrogen atoms and $X^1$ is $X^b$ in the formula (I).
(Step B-1)

Step B-1 is a step to prepare compound (9) by reacting compound (6) obtained in Step A-3 with compound (8) publicly known or easily obtained from a publicly known compound in the presence of a palladium reagent and a base.

The palladium catalyst used can be similar to those shown in Step A-4, preferably [1,1'-bis(diphenylphosphino) ferrocene]dichloropalladium (II)-dichloromethane adduct. Further, the phosphine ligand can be appropriately used, if necessary, similarly to Step A-4.

The base used is a base shown in the above base group or an acetic acid alkali metal salt such as sodium acetate and potassium acetate, preferably an acetic acid alkali metal salt, and more preferably potassium acetate.

The solvent used is selected from the above solvent group and is preferably an ether, a sulfoxide or a mixture of these, more preferably tetrahydrofuran, dioxane, dimethyl sulfoxide or a mixture of these, and further preferably dimethyl sulfoxide or dioxane.

The reaction temperature is usually from 20 to 200° C., preferably from 50 to 150° C.

The reaction time is usually from 30 minutes to 24 hours, preferably from 2 hours to 12 hours.
(Step B-2)

Step B-2 is a step to prepare compound (Ia) by reacting compound (9) obtained in Step B-1 with compound (10) publicly known or easily obtained from a publicly known compound in the presence of a palladium catalyst and a base.

Step B-2 can be carried out in similar manner to Step A-4.
(Method C)

Method C is a method to prepare compound (Ib) in which $R^6$ and $R^7$ are hydrogen atoms and $X^1$ is $X^b$ in the formula (I).
(Step C-1)

Step C-1 is a step to prepare compound (12) by halogenating compound (11) publicly known or easily obtained from a publicly known compound with a halogenating reagent.

Step C-1 can be carried out in similar manner to Step A-2.
(Step C-2)

Step C-2 is a step to prepare compound (Ib) by reacting compound (12) obtained in Step C-1 with compound (13) in the presence of a base. Compound (13) is publicly known, easily obtained from a publicly known compound or can be obtained by Method J, Method L or Method M.

Step C-2 can be carried out in similar manner to Step A-3.

Step C-2 can be also carried out using compound (12a) in which $X^1$ is a methanesulfonyloxy group, a benzenesulfonyloxy group or a p-toluenesulfonyloxy group in compound (12).

Compound (Ib-2) in which $R^6$ and $R^7$ are hydrogen atoms and $X^1$ is a group having the formula $-SO-$ or $-SO_2-$ in the formula (I) can be prepared by oxidizing compound (Ib-1) in which $X^b$ is a group having the formula $-S-$ in compound (Ib) obtained in Step C-2 with 1 or 2 moles of meta-chloroperbenzoic acid in a solvent (preferably methylene chloride or the like).
(Method D)

Method D is a method to prepare compound (Ia) in which $R^1$ is $-COR^a$, $R^6$ and $R^7$ are hydrogen atoms and $X^1$ is $X^b$ in the formula (I).
(Step D-1)

Step D-1 is a step to prepare compound (15) by treating compound (14) obtained by Method A, Method B or Method C with an acid.

The acid used is selected from the above acid group, is not particularly limited provided it is used for an elimination reaction of a tert-butyl group and is preferably trifluoroacetic acid or hydrochloric acid, more preferably trifluoroacetic acid.

The solvent used is selected from the above solvent group and is preferably a halogenated hydrocarbon, more preferably methylene chloride.

The reaction temperature is usually from 0 to 100° C., preferably from 20 to 60° C.

The reaction time is usually from 1 hour to 48 hours, preferably from 1 hour to 24 hours.
(Step D-2)

Step D-2 is a step to prepare compound (Ia) by reacting compound (15) obtained in Step D-1 with compound (2) publicly known or easily obtained from a publicly known compound in the presence of a condensation reagent.

The condensation reagent used is not particularly limited provided it is usually used for the condensation reaction of a carboxylic acid and an amine or a carboxylic acid and an alcohol and can be the condensation reagent described in R. C. Larock, Comprehensive Organic Transformations, Second Edition, 1999, John Wiley & Sons, Inc. or the like. The condensation reagent used can include (i) a combination of phosphates such as diethylphosphoryl cyanide and diphenylphosphoryl azide and a base described below;

(ii) a carbodiimide such as 1,3-dicyclohexylcarbodiimide, 1,3-diisopropylcarbodiimide and 1-ethyl-3-(3-dimethylaminopropyl)carbodiimide (WSC); a combination of a carbodiimide described above and a base described below; and a combination of a carbodiimide described above and a N-hydroxy compound such as N-hydroxysuccinimide, 1-hydroxybenzotriazole and N-hydroxy-5-norbornene-2,3-dicarboxyimide;

(iii) a combination of a disulfide such as 2,2'-dipyridyl disulfide and 2,2'-dibenzothiazolyl disulfide and a phosphine such as triphenylphosphine and tributylphosphine;

(iv) a combination of a 2-halogeno-1-lower alkylpyridinium halide such as 2-chloro-1-methylpyridinium iodide and 2-bromo-1-ethylpyridinium chloride and a base described below;

(v) an imidazole such as 1,1'-oxalyldiimidazole and N,N'-carbonyldiimidazole; or (vi) a combination of a sulfonyl chloride such as p-toluenesulfonyl chloride, 2,4,6-trimethylsulfonyl chloride and 2,4,6-triisopropylsulfonyl chloride and a base described below, preferably a combination of a carbodiimide and a base, a combination of a 2-halogeno-1-lower alkylpyridinium halide and a base or a combination of a sulfonyl chloride and a base, and more preferably a combination of 1-ethyl-3-(3-dimethylaminopropyl)carbodiimide and a base, a combination of 2-chloro-1-methylpyridinium iodide and a base or a combination of the 2,4,6-triisopropylsulfonyl chloride and a base.

The base used in combination with a condensation reagent described above is preferably an organic amine in the above base group, more preferably triethylamine, diisopropylethylamine, pyridine, 4-(N,N-dimethylamino)pyridine or a mixture of these, and most preferably triethylamine, 4-(N,N-dimethylamino)pyridine or a mixture of these. In the case that compound (12) is an amine in Step D-2, an excess amount of compound (12) can also be used as a base.

The solvent used is selected from the above solvent group and is preferably a halogenated hydrocarbon, more preferably methylene chloride.

The reaction temperature is usually from 0 to 100° C., preferably from 20 to 60° C.

The reaction time is usually from 1 hour to 48 hours, preferably from 3 hours to 24 hours.

Further, Step D-2 can be also carried out by converting compound (15) to an acid chloride by oxalyl chloride, thionyl chloride or the like in a solvent (preferably methylene chloride or the like) followed by reacting the acid chloride with compound (2) or compound (2a) described above in the presence of a base (preferably triethylamine or the like).

(Method E)

Method E is a method to prepare compound (Ic) in which $R^1$ is —COO(t-Bu), $R^2$ is a hydroxyl group, $R^6$ and $R^7$ are hydrogen atoms, $X^1$ is a group having the formula —O— and $R^8$ is —$X^2$COOH in the formula (I).

(Step E-1)

Step E-1 is a step to prepare compound (17) by reacting compound (16) publicly known or easily obtained from a publicly known compound with dimethylformamide in the presence of an alkyl lithium and a base.

The alkyl lithium used is selected from an alkyl lithium shown in the above base group and is preferably n-butyl lithium.

The base used can be a base having the nature of coordinating on a lithium ion, preferably tetramethylethylenediamine.

The solvent used is selected from the above solvent group and is preferably an ether, more preferably diethyl ether.

The reaction temperature is usually from –80 to 50° C., preferably from –50 to 20° C.

The reaction time is usually from 10 minutes to 6 hours, preferably from 30 minutes to 3 hours.

In Step E-1, a compound in which the hydroxyl group in compound (17) is —$OR^c$ may be obtained depending on the kind of compound (16). In this case, compound (17) can be obtained by carrying out a removal reaction of $R^7$ by treating the obtained compound with an acid (preferably inorganic acid, more preferably hydrochloric acid).

(Step E-2)

Step E-2 comprises (Step E-2a): a step of reacting compound (17) obtained in Step E-1 with methyl orthoformate in the presence of an acid; and (Step E-2b): a step of preparing compound (18) by reacting the compound obtained in Step E-2a with chloromethyl methyl ether in the presence of a base.

(Step E-2a)

The acid used is selected from the above acid group and is preferably an organic sulfonic acid, more preferably camphorsulfonic acid.

The solvent used is selected from the above solvent group and is preferably an alcohol, more preferably methanol.

The reaction temperature is usually from 0 to 150° C., preferably from 20 to 100° C.

The reaction time is usually from 1 hour to 24 hours, preferably from 2 hours to 12 hours.

(Step E-2b)

The base used is selected from the above base group and is preferably an organic amine, more preferably diisopropylethylamine.

The solvent used is selected from the above solvent group and is preferably a halogenated hydrocarbon, more preferably methylene chloride.

The reaction temperature is usually from –20 to 100° C., preferably from 0 to 50° C.

The reaction time is usually from 1 hour to 48 hours, preferably from 3 hours to 24 hours.

(Step E-3)

Step E-3 comprises (Step E-3a): a step of reacting compound (18) obtained in Step E-2 with dimethylformamide in the presence of an alkyl lithium and a base; and (Step E-3b): a step of preparing compound (19) by reducing the compound obtained in Step E-3a with a reducing reagent.

(Step E-3a)

The alkyl lithium used is selected from an alkyl lithium shown in the above base group and is preferably n-butyl lithium. In Step E-3a, the mole ratio of compound (18) and n-butyl lithium is preferably 1:1 to 1:3, more preferably 1:1.5 to 1:2.5.

The base used can be a base having the nature of coordinating on a lithium ion and is preferably the tetramethylethylenediamine. In Step E-3a, the mole ratio of compound (18) and tetramethylethylenediamine is preferably 1:1 to 1:3, more preferably 1:1 to 1:2.5.

The solvent used is selected from the above solvent group, preferably an ether, more preferably diethyl ether or tetrahydrofuran.

The reaction temperature is usually from –80 to 60° C., preferably from –50 to 40° C.

The reaction time is usually from 30 minutes to 10 hours, preferably from 30 minutes to 6 hours.

(Step E-3b)

The reducing reagent used is not particularly limited provided it is usually used for a reduction reaction of a formyl group and can include an alkali metal borohydride such as sodium borohydride, sodium triacetoxyborohydride, sodium cyanoborohydride and lithium borohydride, preferably sodium borohydride.

The solvent used is selected from the above solvent group and is preferably an ether, an alcohol or a mixture of these, more preferably tetrahydrofuran, methanol or a mixture of these, and most preferably a mixture of tetrahydrofuran and methanol.

The reaction temperature is usually from 0 to 100° C., preferably from 20 to 60° C.

The reaction time is usually from 10 minutes to 6 hours, preferably from 30 minutes to 3 hours.

(Step E-4)

Step E-4 is a step to prepare compound (21) by reacting compound (19) obtained in Step E-3 with compound (20) in the presence of an azodicarboxylate reagent and a phosphine reagent. Compound (20) is publicly known or easily obtained from a publicly known compound or can be obtained by Method J, Method L or Method M.

The azodicarboxylate reagent used is not particularly limited provided it is usually used for the Mitsunobu reaction and can include dialkylazodicarboxylate such as dimethylazodicarboxylate, diethylazodicarboxylate, dipropylazodicarboxylate, diisopropylazodicarboxylate, and di(tert-butyl) azodicarboxylate; bis(2,2,2-trichloroethyl)azodicarboxylate; diphenylazodicarboxylate; 1,1'-(azodicarbonyl)dipiperidine; N,N,N',N'-(tetramethylazodicarboxamide); or dibenzylazodicarboxylate, preferably dialkylazodicarboxylate or 1,1'-(azodicarbonyl)dipiperidine, more preferably diethylazodicarboxylate or 1,1'-(azodicarbonyl)dipiperidine. As the azodicarboxylate reagent, an azodicarboxylate reagent immobilized to a polymer such as polystyrene or the like [preferably an azodicarboxylate reagent immobilized to polystyrene such as ethoxycarbonylazocarboxymethyl polystyrene (Noba-biochem Inc., product number: 01-64-0371)] can be also used.

The phosphine reagent used is not particularly limited provided it is usually used for the Mitsunobu reaction and can include triphenylphospine, tritolylphosphine, tris(methoxyphenyl)phosphine, tris(chlorophenyl)phosphine, tri-n-butylphosphine or 2-(di-t-butylphosphino)biphenyl, preferably triphenylphosphine or tri-n-butylphosphine. As the phosphine reagent, a phosphine reagent immobilized to a polymer such as polystyrene or the like (preferably triphenylphosphine immobilized to polystyrene such as triphenylphosphine polystyrene) can be also used.

The solvent used is selected from the above solvent group and is preferably an aromatic hydrocarbon or an ether, more preferably tetrahydrofuran.

The reaction temperature is usually from 0 to 100° C., preferably from 20 to 60° C.

The reaction time is usually from 10 minutes to 12 hours, preferably from 30 minutes to 6 hours.
(Step E-5)
Step E-5 comprises
(Step E-5a): a step of converting a dimethoxymethyl group to a formyl group and removing a methoxymethyl group in the presence of an acid in compound (21) obtained in Step E-4;
(Step E-5b): a step of reacting a hydroxyl group of the compound obtained in Step E-5a with allyl bromide in the present of a base;
(Step E-5c): a step of oxidizing the compound obtained in Step E-5b by sodium hypochlorite ($NaClO_2$) in the presence of sodium dihydrogenphosphate and 2-methyl-2-butene; and
(Step E-5d): a step of preparing compound (22) by reacting the compound obtained in Step E-5c with N,N-dimethylformamide di-tert-butylacetal [$Me_2NC[O(t-Bu)]_2$].
(Step E-5a)

The acid used is selected from the above acid group and is preferably an organic sulfonic acid or an inorganic acid, more preferably p-toluenesulfonic acid or hydrochloric acid.

The solvent used is selected from the above solvent group and is preferably an ether or a ketone, more preferably tetrahydrofuran or acetone.

The reaction temperature is usually from 0 to 100° C., preferably from 20 to 60° C.

The reaction time is usually from 10 minutes to 24 hours, preferably from 30 minutes to 12 hours.
(Step E-5b)

The base used is selected from the above base grout and is preferably an alkali metal carbonate, more preferably potassium carbonate.

The solvent used is selected from the above solvent group and is preferably an amide, more preferably dimethylformamide.

The reaction temperature is usually from 0 to 100° C., preferably from 20 to 60° C.

The reaction time is usually from 10 minutes to 24 hours, preferably from 30 minutes to 12 hours.
(Step E-5c)

The solvent used is selected from the above solvent group and is preferably an ether, an alcohol, water or a mixture of these, more preferably a mixture of 1,4-dioxane and water, a mixture of 2-methyl-2-propanol and water or a mixture of 1,4-dioxane/2-methyl-2-propanol/water.

The reaction temperature is usually from 0 to 100° C., preferably from 20 to 60° C.

The reaction time is usually from 10 minutes to 6 hours, preferably from 30 minutes to 3 hours.
(Step E-5d)

The solvent used is selected from the above solvent group and is preferably an aromatic hydrocarbon, more preferably toluene.

The reaction temperature is usually from 50 to 200° C., preferably from 80 to 150° C.

The reaction time is usually from 30 minutes to 24 hours, preferably from 1 hour to 12 hours.
(Step E-6)
Step B-5 comprises
(Step E-6a): a step of removing an allyl group in the presence of a palladium reagent in the allyloxy group of compound (22) obtained in Step E-5; and
(Step E-6b): a step of preparing compound (Ic) by hydrolysis in the presence of a base of the compound obtained in Step E-6a.

In Step E-6, in the case that $R^d$ of compound (22) is an allyl group, since $R^d$ is simultaneously eliminated in Step E-6a, it is not required that Step E-6b is carried out.
(Step E-6a)

The palladium reagent used is not particularly limited provided it is usually used for an elimination reaction of an allyl group and can be, for example, similar to those shown in Step A-4, preferably tetrakis(triphenylphosphine)palladium (0).

In Step E-6a, a scavenger can be appropriately used if necessary. The scavenger used can include pyrrolidine, piperidine, morpholine, diethylamine, formic acid, acetic acid, 2-ethylhexanoic acid, sodium 2-methylhexanoate, 5,5-dimethyl-1,3-cyclohexanedione, dimethyl malonate or tributyltin hydride, preferably pyrrolidine or morpholine.

The solvent used is selected from the above solvent group and is preferably an ether or a mixture of an ether and water, more preferably a mixture of dioxane and water.

The reaction temperature is usually from 0 to 100° C., preferably from 20 to 60° C.

The reaction time is usually from 10 minutes to 12 hours, preferably from 30 minutes to 6 hours.
(Step E-6b)

The base used can be an alkali metal hydroxide in the above base group, preferably sodium hydroxide or potassium hydroxide.

The solvent used is selected from the above solvent group and is preferably an ether, an alcohol or a mixture of these, more preferably tetrahydrofuran, methanol or a mixture of these. In Step E-6b, water is necessarily used and only water can also be used as solvent.

The reaction temperature is usually from 0 to 150° C., preferably from 20 to 100° C.

The reaction time is usually from 1 hour to 36 hours, preferably from 2 hours to 24 hours.
(Method F)

Method F is a method to prepare compound (Id) in which $R^1$ is —COO(t-Bu), $R^2$ is a hydroxyl group, $R^6$ and $R^7$ are hydrogen atoms, $X^1$ is a group having the formula —O— and $R^8$ is —$X^2COR^f$ in the formula (I).

(Step F-1)

Step F-1 is a step to prepare compound (24) by carrying out a removal reaction of $R^e$ in compound (23) obtained in Step E-5.

Step F-1 can be carried out in similar manner to Step E-6b.
(Step F-2)

Step F-2 is a step to prepare compound (26) by reacting compound (24) obtained in Step F-1 with compound (25) publicly known or easily obtained from a publicly known compound in the presence of a condensation reagent.

Step F-2 can be carried out in similar manner to Step D-2.
(Step F-3)

Step F-3 is a step to prepare compound (Id) by removing an allyl group in the presence of a palladium reagent in an allyloxy group of compound (26) obtained in Step F-2.

Step F-3 can be carried out in similar manner to Step E-6a.
(Method G)

Method G is a method to prepare compound (Ie) or compound (If) in which $R^1$ is —$COR^a$, $R^7$ is a hydrogen atom, $X^1$ is a group having the formula —O— and $R^6$ is —$X^2COOH$ or —$X^2COR^f$ in the formula (I)
(Step G-1)

Step G-1 is a step to prepare compound (28) by reacting compound (27) publicly known or easily obtained from a publicly known compound with dimethylformamide in the presence of an alkyl lithium and a base.

Step G-1 can be carried out in similar manner to Step E-3a.
(Step G-2)

Step G-2 is a step to prepare compound (30) by reacting compound (28) obtained in Step G-1 with compound (29).

The solvent used is selected from the above solvent group and is preferably an ether, more preferably tetrahydrofuran.

The reaction temperature is usually from 0 to 100° C., preferably from 20 to 60° C.

The reaction time is usually from 30 minutes to 24 hours, preferably from 1 hour to 12 hours.

In Step G-2, compound $R^6MgCl$ can be also used instead of compound (29).
(Step G-3)

Step G-3 is a step to prepare compound (32) by reacting compound (30) obtained in step G-2 with compound (31) in the presence of an azodicarboxylate reagent and a phosphine reagent. Compound (31) is publicly known or easily obtained from a publicly known compound or can be obtained by Method J, Method L or Method M.

Step G-3 can be carried out in similar manner to Step E-4.
(Step G-4)

Step G-4 comprises
(Step G-4a): a step of converting a dimethoxymethyl group to a formyl group in the presence of an acid in compound (32) obtained in Step G-3;
(Step G-4b): a step of oxidizing the compound obtained in Step G-4a with sodium hypochlorite ($NaClO_2$) in the presence of sodium dihydrogenphosphate and 2-methyl-2-butene;
(Step G-4c): a step of reacting the compound obtained in Step G-4b with compound (2) described above publicly known or easily obtained from a publicly known compound in the presence of a condensation reagent; and
(Step G-4d): a step of preparing compound (Ie) by removing $R^g$ group in the presence of a palladium reagent in a —$COOR^g$ group of the compound obtained in Step G-4c.

Step G-4a, Step 4b, Step G-4c and Step G-4d can be carried out in similar manner to Step E-5a, Step E-5c, Step D-2 and Step E-6a, respectively.

(Step G-5)

Step G-5 is a step to prepare compound (If) by reacting compound (Ie) obtained in Step G-4 with compound (25) publicly known or easily obtained from a publicly known compound in the presence of a condensation reagent.

Step G-5 can be carried out in similar manner to Step D-2.
(Method H)

Method H is a method to prepare compound (Ic) in which $R^1$ is —COO(t-Bu), $R^2$ is a hydroxyl group, $R^6$ and $R^7$ are hydrogen atoms, $X^1$ is a group having the formula —O— and $R^8$ is —$X^2COOH$ in the formula (I).
(Step H-1)

Step H-1 is a step to prepare compound (34) by reacting compound (33) publicly known or easily obtained from a publicly known compound with di-tert-butyl dicarbonate [(t-BuOCO)$_2$O] in the presence of an alkyl lithium and a base.

The alkyl lithium used is selected from an alkyl lithium shown in the above base group and is preferably n-butyllithium.

The base used can be a base having the nature of coordinating on a lithium ion, preferably tetramethylethylenediamine.

The solvent used is selected from the above solvent group and is preferably an ether, more preferably diethyl ether.

The reaction temperature is usually from −80 to 50° C., preferably from −50 to 20° C.

The reaction time is usually from 10 minutes to 6 hours, preferably from 30 minutes to 3 hours.
(Step H-2)

Step H-2 is a step to prepare compound (35) by carrying out a removal reaction of a silyl group ($R^h$) in compound (34) obtained in Step H-1.

The reagent used is not particularly limited provided it is usually used for a removal reaction of a silyl group and can include an acid shown in the above acid group, a reagent for producing a fluoride ion ($F^-$) such as tetra-n-butylammonium fluoride and potassium fluoride or a mixture of these, preferably acetic acid, tetra-n-butylammonium fluoride or a mixture of these, and more preferably a mixture of acetic acid and tetra-n-butylammonium fluoride.

The solvent used is selected from the above solvent group and is preferably an ether, more preferably tetrahydrofuran. As a combination of the reagent and the solvent used in Step H-2, a mixture of acetic acid, tetrahydrofuran and water is also preferred.

The reaction temperature is usually from 0 to 150° C., preferably from 20 to 100° C.

The reaction time is usually from 30 minutes to 12 hours, preferably from 1 hour to 6 hours.
(Step H-3)

Step H-3 is a step to prepare compound (36) by reacting compound (35) obtained in Step H-2 with compound (20) in the presence of an azodicarboxylate reagent and a phosphine reagent. Compound (20) is publicly known or easily obtained from a publicly known compound or can be obtained by Method J, Method L or Method M.

Step H-3 can be carried out in similar manner to Step E-4.
(Step H-4)

Step H-4 is a step to prepare compound (37) by carrying out a removal reaction of a methoxymethyl group in compound (36) obtained in Step H-3.

The reagent used is not particularly limited provided it is usually used for a removal reaction of a methoxymethyl group and does not affect to a —COO(t-Bu) group and can include a combination of a silyl halide such as trimethylsilyl chloride and trimethylsilyl bromide and a ammonium halide such as tetra-n-butylammonium chloride and tetra-n-butylammonium bromide, preferably a combination of trimethylsilyl chloride and tetra-n-butylammonium bromide.

The solvent used is selected from the above solvent group and is preferably a halogenated hydrocarbon, more preferably methylene chloride.

The reaction temperature is usually from 0 to 150° C., preferably from 20 to 100° C.

The reaction time is usually from 30 minutes to 24 hours, preferably from 2 hours to 12 hours.

(Step H-5)

Step H-5 is a step to prepare compound (Ic) by carrying out a removal reaction of $R^d$ group in compound (37) obtained in Step H-4.

Step H-5 can be carried out in similar manner to Step E-6b. Further, in the case that $R^d$ of compound (37) is an allyl group, Step H-5 can also be carried out in similar manner to Step E-6a.

(Method I)

Method I is a method to prepare compound (7) used in Step A-4.

(Step I-1)

Step I-1 is a step to prepare compound (7) by reacting compound (10) publicly known or easily obtained from a publicly known compound with compound (8) publicly known or easily obtained from a publicly known compound in the presence of a palladium reagent and a base.

Step I-1 can be carried out in similar manner to Step B-1.

(Method J)

Method J is a method to prepare compound (20) used in Step E-4 or Step H-3.

(Step J-1)

Step J-1 is a step to prepare compound (39) by reacting compound (38) publicly known or easily obtained from a publicly known compound with compound (8) publicly known or easily obtained from a publicly known compound in the presence of a palladium reagent and a base.

Step J-1 can be carried out in similar manner to Step B-1.

(Step J-2)

Step J-2 is a step to prepare compound (41) by reacting compound (39) obtained in Step J-1 with compound (40) publicly known or easily obtained from a publicly known compound in the presence of a palladium reagent and a base.

Step J-2 can be carried out in similar manner to Step A-4.

(Step J-3)

Step J3 is a step to prepare compound (20) by carrying out removal of the $R^i$ group in compound (41) obtained in Step J-2.

Step J-3 can be carried out according to a usual method (for example, a method described in T. H. Greene, P. G. Wuts, Protective Groups in Organic Synthesis. Third Edition, 1999, John Wiley & Sons, Inc. or the like) according to the kind of $R^i$ group.

(Method K)

Method K is a method to prepare compound (41) used in Step J-3.

(Step K-1)

Step K-1 is a step to prepare compound (42) by reacting compound (40) publicly known or easily obtained from a publicly known compound with compound (8) publicly known or easily obtained from a publicly known compound in the presence of a palladium reagent and a base.

Step K-1 can be carried out in similar manner to Step B-1.

(Step K-2)

Step K-2 is a step to prepare compound (41) by reacting compound (42) obtained in Step K-1 with compound (38) publicly known or easily obtained from a publicly known compound in the presence of a palladium catalyst and a base.

Step K-2 can be carried out in similar manner to Step A-4.

(Method L)

Method L is a method to prepare compound (47) in which $X^2$ in compound (20) used in Step E-4 or Step H-3 is a methylene group.

(Step L-1)

Step L-1 is a step to prepare compound (44) by reacting compound (43) publicly known or easily obtained from a publicly known compound with a cyanation reagent.

The cyanation reagent used is not particularly limited provided it is usually used for a cyanation reaction of a halogenated alkyl and can include an alkali metal cyanide, preferably sodium cyanide or potassium cyanide.

The solvent used is selected from the above solvent group and is preferably an alcohol, water or a mixture of these, more preferably ethanol, water or a mixture of these, and further preferably a mixture of ethanol and water.

The reaction temperature is usually from 0 to 150° C., preferably from 20 to 100° C.

The reaction time is usually from 30 minutes to 24 hours, preferably from 2 hours to 12 hours.

(Step L-2)

Step L-2 is a step to prepare compound (46) by reacting compound (44) obtained in Step L-1 with compound (45) publicly known or easily obtained from a publicly known compound in the presence of a palladium catalyst and a base.

Step L-2 can be carried out in similar manner to Step A-4.

(Step L-3)

Step L-3 comprises (Step L-3a): a step of hydrolyzing compound (46) obtained in Step L-2 in the presence of an acid; and (Step L-3b): a step of preparing compound (47) by reacting a compound obtained in Step L-3a with compound $R^d$OH in the presence of an acid.

(Step L-3a)

The acid used is an acid selected from the above acid group or a mixture of these, preferably hydrochloric acid or a mixture of hydrochloric acid and acetic acid, and more preferably a mixture of hydrochloric acid and acetic acid.

The solvent used is selected from the above solvent group and is preferably acetic acid, water or a mixture of these, more preferably water. In Step L-3a, water is necessarily used and only water can also be used as solvent.

The reaction temperature is usually from 20 to 180° C., preferably from 50 to 150° C.

The reaction time is usually from 1 hour to 72 hours, preferably from 2 hours to 48 hours.

Step L-3a can be also carried out in similar manner to Step M-1a.

(Step L-3b)

The acid used is selected from the above acid group and is preferably hydrochloric acid or sulfuric acid, more preferably sulfuric acid.

The solvent used is selected from the above solvent group and is preferably an alcohol. In Step L-3b, compound $R^d$OH is preferably used as a solvent.

The reaction temperature is usually from 20 to 180° C., preferably from 50 to 150° C.

The reaction time is usually from 1 hour to 36 hours, preferably from 2 hours to 24 hours.

Step L-3b can be also carried out in similar manner to Step M-1b.

(Method M)

Method M is a method to prepare compound (47) in which $X^2$ in compound (20) used in Step E-4 or Step H-3 is a methylene group.

(Step M-1)
Step M-1 comprises
(Step M-1a): a step of hydrolyzing compound (44) obtained in Step L-1 in the presence of a base; and
(Step M-1b): a step of preparing compound (48) by reacting the compound obtained in Step M-1a with compound $R^d X^d$ in the presence of a base.
(Step M-1a)
The base used can be an alkali metal hydroxide or an alkaline earth metal hydroxide in the above base group, preferably sodium hydroxide or potassium hydroxide.

The solvent used is selected from the above solvent group and is preferably an alcohol, water or a mixture of these, more preferably a mixture of an alcohol and water, and further preferably a mixture of ethylene glycol and water. In Step M-1a, water is necessarily used and only water can also be used as solvent.

The reaction temperature is usually from 50 to 200° C., preferably from 80 to 160° C.

The reaction time is usually from 1 hour to 72 hours, preferably from 2 hours to 48 hours.

Step M-1a can be also carried out in similar manner to Step L-3a.
(Step M-1b)
The base used is selected from the above base group and is preferably an alkali metal carbonate, an alkali metal hydrogencarbonate or an alkali metal hydride, more preferably an alkali metal carbonate, and further preferably sodium carbonate or potassium carbonate.

The solvent used is selected from the above solvent group and is preferably an amide, more preferably dimethylformamide.

The reaction temperature is usually from 0 to 150° C., preferably from 20 to 100° C.

The reaction time is usually from 1 hour to 24 hours, preferably from 2 hours to 12 hours.

Step M-1b can be also carried out in similar manner to Step L-3b.
(Step M-2)
Step M-2 is a step to prepare compound (47) by reacting compound (48) obtained in Step M-1 with compound (45) publicly known or easily obtained from a publicly known compound in the presence of a palladium catalyst and a base.

Step M-2 can be carried out in similar manner to Step A-4.
(Method N)
Method N is a method to prepare compound (53) in which $X^2$ in compound (20) used in Step E-4 or Step H-3 is a methylene group substituted by $R^j$ and $R^k$.
(Step N-1)
Step N-1 is a step to prepare compound (52) by successively reacting compound (49) publicly known or easily obtained from a publicly known compound with compound (50) and compound (51) in the presence of a base. Step N-1 can also be carried out using compound $X^c$—$R^1$—$X^c$ (wherein $R^1$ represents an ethylene group or a trimethylene group) instead of compound (50) and compound (51).

The base used is selected from the above base group and is preferably an alkali metal hydride, more preferably sodium hydride.

The solvent used is selected from the above solvent group and is preferably an amide, more preferably dimethylformamide.

The reaction temperature is usually from 0 to 150° C., preferably from 20 to 100° C.

The reaction time is usually from 30 minutes to 12 hours, preferably from 1 hour to 6 hours.

(Step N-2)
Step N-2 is a step to prepare compound (53) by reacting compound (52) obtained in Step N-1 with compound (45) publicly known or easily obtained from a publicly known compound in the presence of a palladium catalyst and a base.

Step N-2 can be carried out in similar manner to Step A-4.
(Method O)
Method O is a method to prepare compound (57) in which $R^a$ is a t-butoxy group, $R^2$ is a hydroxyl group and $X^b$ is a group having the formula —O— in compound (6) used in Step A-4 or Step B-1.
(Step O-1)
Step O-1 is a step to prepare compound (55) by reacting compound (19) obtained in Step E-3 with compound (54) in the presence of an azodicarboxylate reagent and a phosphine reagent. Compound (54) is publicly known or easily obtained from a publicly known compound.

Step O-1 can be carried out in similar manner to Step E-4.
(Step O-2)
Step O-2 comprises
(Step O-2a): a step of converting a dimethoxymethyl group to a formyl group and removing a methoxymethyl group in the presence of an acid in compound (55) obtained in Step O-1; and
(Step O-2b): a step of oxidizing the compound obtained in Step O-2a with sodium hypochlorite ($NaClO_2$) in the presence of sodium dihydrogenphosphate and 2-methyl-2-butene.

Step O-2a can be carried out in similar manner to Step E-5a.

Step O-2b can be carried out in similar manner to Step E-5c.
(Step O-3)
Step O-3 comprises
(Step O-3a): a step of reacting compound (56) obtained in Step O-2 with di-tert-butyl dicarbonate [$(tBuOCO)_2O$] in the presence of a base; and
(Step O-3b): a step of removing a Boc group on a hydroxyl group of the compound obtained in Step O-3a in the presence of a base.
(Step O-3a)
The base used is selected from the above base group and is preferably an organic amine, more preferably 4-(N,N-dimethylamino)pyridine.

The solvent used is selected from the above solvent group and is preferably an ether, an alcohol or a mixture of these, more preferably tetrahydrofuran, 2-methyl-2-propanol or a mixture of these.

The reaction temperature is usually from 0 to 150° C., preferably from 20 to 100° C.

The reaction time is usually from 30 minutes to 24 hours, preferably from 1 hour to 12 hours.
(Step O-3b)
The base used is preferably pyrrolidine or piperidine, more preferably pyrrolidine.

The solvent used is selected from the above solvent group and is preferably an ether, more preferably tetrahydrofuran.

The reaction temperature is usually from 0 to 150° C., preferably from 20 to 100° C.

The reaction time is usually from 10 minutes to 12 hours, preferably from 30 minutes to 6 hours.
(Method P)
Method P is a method to prepare compound (Ic) in which $R^1$ is —COO(t-Bu), $R^2$ is a hydroxyl group, $R^6$ and $R^7$ are hydrogen atoms, $X^1$ is a group having the formula —O— and $R^1$ is —$X^2$COOH in the formula (I).

(Step P-1)

Step P-1 is a step to react compound (18) obtained in Step E-2 with methyl iodide in the presence of an alkyl lithium and a base.

Step P-1 can be carried out in similar manner to Step E-3a.

(Step P-2)

Step P-2 comprises (Step P-2a): a step of converting a dimethoxymethyl group to a formyl group and removing a methoxymethyl group in compound (58) obtained in Step P-1 in the presence of an acid; and (Step P-2b): a step of oxidizing the compound obtained in Step P-2a with sodium hypochlorite (NaClO$_2$) in the presence of sodium dihydrogenphosphate and 2-methyl-2-butene.

Step P-2a can be carried out in similar manner to Step P-5a.

Step P-2b can be carried out in similar manner to Step E-5c.

(Step P-3)

Step P-3 comprises (Step P-3a): a step of reacting compound (59) obtained in Step P-2 with ditert-butyl dicarbonate [(tBuOCO)$_2$O] in the presence of a base; and (Step P-3b): a step of preparing compound (60) by halogenating the compound obtained in Step P-3a with a halogenating reagent.

Step P-3a can be carried out in similar manner to Step O-3a.

Step P-3b can be carried out in similar manner to Step A-2.

(Step P-4)

Step P-4 is a step to prepare compound (61) by reacting compound (60) obtained in Step P-3 with compound (20) in the presence of a base. Compound (20) is publicly known or easily obtained from a publicly known compound or can be obtained by Method J, Method L or Method M.

Step P-4 can be carried out in similar manner to Step A-3.

Step P-4 can also be carried out using compound (60a) in which X$^a$ is a methanesulfonyloxy group, a benzenesulfonyloxy group or a p-toluenesulfonyloxy group in compound (60).

(Step P-5)

Step P-5 is a step to remove a Boo group on a hydroxyl group of compound (61) obtained in Step P-4 in the presence of a base.

Step P-5 can be carried out in similar manner to Step O-3b.

(Step P-6)

Step P-6 is a step to prepare compound (Ic) by hydrolysis of compound (62) obtained in Step P-5 in the presence of a base.

Step P-5 can be carried out in similar manner to Step E-6b.

Further, a substituent introduction reaction or the like under the following reaction conditions can be appropriately applied, if necessary, to Method A to Method P described above:

(a) bromination of the 2 position of a thiophene ring: N-bromosuccinimide, acetic acid (Jackson, P. M., J. Chem. Soc., Perkin Trans. 1, 1990, vol. 11, pp. 2909-2918);

(b) introduction of a methoxycarbonylmethyl group to a nitrogen of a pyrazole ring: methyl bromoacetate, potassium carbonate;

(c) introduction of a hydroxymethyl group to the benzyl position: paraformaldehyde, sodium hydrogencarbonate;

(d) introduction of an alkyl group to the benzyl position of a phenyl acetic acid ester:

(d-1) tetra-n-butylammonium hydrogensulfate, lithium bis(trimethylsilyl)amide or lithium diisopropylamide, and (d-2) a halogenated alkyl;

(e) introduction of an alkyl group to the benzyl position of a phenyl acetic acid ester:

(e-1) lithium bis(trimethylsilyl)amide or lithium diisopropylamide, (e-2) an aliphatic aldehyde, and (e-3) sodium cyanoborohydride, acetic acid;

(f) introduction of a dimethylaminomethyl group to the benzyl position of a phenylacetic acid ester:

(f-1) N,N-dimethylformamide, di-tert-butyl acetal, and (f-2) sodium cyanoborohydride, acetic acid.

In the present invention, "arteriosclerosis" includes (i) arteriosclerosis caused by various factors such as smoking or genetic factors (including comprehensive factors); and, (ii) arteriosclerosis caused by diseases capable of leading to arteriosclerosis such as hyperlipemia, hypercholesterolemia, lipid-associated diseases, inflammatory disease, diabetes, obesity and hypertension, including, for example, atherosclerosis, arteriolosclerosis (in thin vessel) and arteriosclerosis obliterans. "Arteriosclerotic heart disease" refers to cardiovascular disease caused by arteriosclerosis, and "cardiovascular disease" includes, for example, ischemic heart disease, cardiac insufficiency, angina pectoris and myocardial infarction.

In the present invention, "inflammatory disease" refers to a disease caused by inflammatory cytokines, and includes, for example, chronic rheumatoid arthritis, osteoarthritis, allergic diseases, asthma, septicemia, psoriasis and osteoporosis. "Auto-immune disease" includes systemic lupus erythematosus, ulcerative colitis and Crohn's disease. "Diabetic complications" include retinopathy, nephropathy, neuropathy and coronary artery disease.

In the case that a compound of the present invention represented by the general formula (I) or a pharmacologically acceptable salt or ester thereof is used as a pharmaceutical, a pharmaceutical composition can be formed containing as an active ingredient a compound represented by the general formula (I) or a pharmacologically acceptable salt or ester thereof and another pharmaceutical described below and such a pharmaceutical composition is included in the present invention. In a pharmaceutical composition described above, each active ingredient can be suitably "administered simultaneously", or can also be "administered separately at different times" if necessary.

In the case that each active ingredient of a pharmaceutical composition described above is "administered simultaneously", there are no particular limitations on the administration form provided it is an administration form in which an administration can be performed at nearly the same time, examples of which include an administration in the form of a combination of a pharmaceutical composition containing a compound represented by the general formula (I) of the present invention or a pharmacologically acceptable salt or ester thereof and a pharmaceutical composition containing another pharmaceutical described below (one or more pharmaceutical compositions in the case of two or more said other pharmaceuticals), namely a combination of separate and different pharmaceutical compositions, and an administration in the form of a combination of a single pharmaceutical composition simultaneously containing a compound represented by the general formula (I) of the present invention or a pharmacologically acceptable salt or ester thereof and another pharmaceutical described below, namely a combination pharmaceutical composition, and preferably an administration in a form of a combination of separate and different pharmaceutical compositions.

In the case that each active ingredient of a pharmaceutical composition described above is "administered separately at different times", there are no particular limitations on the administration form provided it is an administration form in which an administration can be performed separately at different times, examples of which include that a compound represented by the general formula (I) or a pharmacologically acceptable salt or ester thereof is first administered followed by another pharmaceutical described below being administered after a fixed period of time and that another pharmaceutical described below is first administered followed by a compound represented by the general formula (I) or a pharmacologically acceptable salt or ester thereof being administered after a fixed period of time. There are no particular limitations on the period of time from one active ingredient being administered to the other active ingredient being administered, and the other active ingredient is preferably administered while an effect of the active ingredient which is first administered is lasting.

There are no particular limitations on "other pharmaceutical" provided it has a desired effect in accordance with a purpose of use, examples of which include one or more pharmaceutical(s) selected from the group consisting of an HMG-CoA reductase inhibitor, HMG-CoA synthase inhibitor, serum HDL enhancer, cholesterol biosynthesis inhibitor, squalene epoxidase inhibitor, squalene synthase inhibitor, hypercholesterolemia therapeutic medicine, acyl coenzyme A, CETP inhibitor, ACAT inhibitor, probucol, cholesterol absorption inhibitor, bile acid adsorption ion exchange resin, fibrate-based medicine, nicotinic acid derivative, niacin amide, LDL receptor inducing substance, vitamin $B_6$, vitamin $B_{12}$, antioxidative vitamin, angiotensin II inhibitor, angiotensin converting enzyme inhibitor, β-blocker, fibrinogen inhibitor, aspirin and diuretic, preferably one or more pharmaceutical(s) selected from the group consisting of an HMG-CoA reductase inhibitor, CETP inhibitor, ACAT inhibitor, cholesterol absorption inhibitor, bile acid adsorption ion exchange resin, fibrate-based medicine, nicotinic acid derivative, angiotensin II inhibitor and diuretic, more preferably one or more pharmaceutical(s) selected from the group consisting of an HMG-CoA reductase inhibitor, CETP inhibitor and cholesterol absorption inhibitor, even more preferably an HMG-CoA reductase inhibitor, a combination of HMG-CoA reductase inhibitor and CETP inhibitor or a combination of HMG-CoA reductase inhibitor and cholesterol absorption inhibitor, and the most preferably an HMG-CoA reductase inhibitor.

A pharmaceutical composition containing as an active ingredient a compound represented by the general formula (I) of the present invention or a pharmacologically acceptable salt or ester thereof and HMG-CoA reductase inhibitor (said pharmaceutical composition may also contain a CETP inhibitor or cholesterol absorption inhibitor if necessary) has a superior lipid metabolism improvement effect and is useful as a pharmaceutical composition for treating or preventing arteriosclerosis, atherosclerosis, arteriosclerosis caused by diabetes, hyperlipemia, hypercholesterolemia, lipid-associated diseases, arteriosclerotic heart disease, cardiovascular disease, coronary artery disease or cerebrovascular disease, preferably arteriosclerosis, atherosclerosis, arteriosclerosis caused by diabetes, arteriosclerotic heart disease, cardiovascular disease or coronary artery disease, more preferably arteriosclerosis, atherosclerosis or arteriosclerotic heart disease, and most preferably arteriosclerosis. In addition, said pharmaceutical composition is useful as a pharmaceutical composition for a warm-blooded animal (particularly a human).

There are no particular limitations on the HMG-CoA reductase inhibitor described above provided it has an HMG-CoA reductase inhibitory activity and can be used as a pharmaceutical, examples of which include (+)-(3R,5R)-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptanoic acid (pravastatin) described in Japanese Patent Application (Kokai) No. Sho 57-2240 (U.S. Pat. No. 4,346,227) [including a salt of pravastatin such as (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptanoic acid monosodium salt (pravastatin sodium)], (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl (S)-2-methylbutyrate (lovastatin) described in Japanese Patent Application (Kokai) No. She 57-163374 (U.S. Pat. No. 4,231,938), (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl 2,2-dimethylbutyrate (simvastatin) described in Japanese Patent Application (Kokai) No. Sho 56-122375 (U.S. Pat. No. 4,444,784), (O)-(3R*,5S*,6E)-7-[3-(4-fluorophenyl)-1-(1-methylethyl)-1H-indol-2-yl]-3,5-dihydroxy-6-heptanoic acid (fluvastatin) described in Japanese Patent Application (Kokai) No. Sho 60-500015 (U.S. Pat. No. 4,739,073), (3R,5S,6E)-7-[4-(4-fluorophenyl)-2,6-di-(1-methylethyl)-5-methoxymethylpyridin-3-yl]-3,5-dihydroxy-6-heptanoic acid (cerivastatin) described Japanese Patent Application (Kokai) No. Hei 1-216974 (U.S. Pat. No. 5,006,530), (3R,5S)-7-[2-(4-fluorophenyl)-5-(1-methylethyl)-3-phenyl-4-phenylaminocarbonyl-1H-pyrrol-1-yl]-3,5-dihydroxyheptanoic acid (atorvastatin) described in Japanese Patent Application (Kokai) No. Hei 3-58967 (U.S. Pat. No. 5,273,995), (E)-3,5-dihydroxy-7-[4'-(4"-fluorophenyl)-2'-cyclopropylquinolin-3'-yl]-6-heptanoic acid (pitavastatin) described in Japanese Patent Application (Kokai) No. Hei 1-279866 (U.S. Pat. Nos. 5,854,259 and 5,856,336), and (+)-(3R,5S)-7-[4-(4-fluorophenyl)-6-isopropyl-2-(N-methyl-N-methanesulfonylamino)pyrimidin-5-yl]-3,5-dihydroxy-6 (E)-heptanoic acid (rosuvastatin) described in Japanese Patent Application (Kokai) No. He-5-178841 (U.S. Pat. No. 5,260,440) or a pharmacologically acceptable salt thereof, preferable pravastatin, atorvastatin, and rosuvastatin, and more preferable pravastatin.

There are no particular limitations on the CETP inhibitor described above provided it has a CETP inhibitory activity and can be used as a pharmaceutical, examples of which include cis-4-[(3,5-bistrifluoromethylbenzyl)methoxycarbonylamino-2-ethyl-6-trifluoromethyl-3,4-dihydro-2H-quinolin-1-carboxylic acid ethyl ester, or ethyl (2R,4S)-4-[[3,5-bis (trifluoromethyl)benzyl](methoxycarbonyl)amino]-2-ethyl-6-(trifluoromethyl)-3,4-dihydroquinolin-1(2H)-carboxylate described in International Publication WO 00/17164, or 2-methylthiopropionic acid S-[2-[1-(2-ethylbutyl)cyclohexane carbonylamino]phenyl]ester described in Japanese Patent Application (Kokai) No. Hei 11-49743 or Japanese Patent Application (Kokai) No. Hei 11-222428.

There are no particular limitations on the ACAT inhibitor described above provided it has an ACAT inhibitory activity and can be used as a pharmaceutical, examples of which include (±)-N-(1,2-diphenylethyl)-2-(2-octyloxyphenyl)acetamide described in International Publication WO 92/09561 pamphlet, 2,6-bis(1-methylethyl)phenyl N-[[2,4,6-tris(1-methylethyl)phenyl]acetyl]sulfamate described U.S. Pat. No. 5,491,172, U.S. Pat. No. 5,633,287, U.S. Pat. No. 6,093,719, U.S. Pat. No. 6,124,309 or U.S. Pat. No. 6,143,755, (1S,2S)-2-[N-(2,2-dimethylpropyl)-N-nonylcarbamoyl]aminocyclohexan-1-yl 3-[N-(2,2,5,5-tetramethyl-1,3-dixoane-4-carbonyl)amino]propionate described in U.S. Pat. No. 5,120,738, (S)-2',3',5'-trimethyl-4'-hydroxy-α-dodecylthio-α-phenylacetanilide described in U.S. Pat. No. 5,990,173, 2-[3-(2-cyclohexylethyl)-3-(4-dimethylaminophenyl)ureide]-4-methoxy-6-tert-butylphenol and a hydrochloride thereof described in U.S. Pat. No. 5,849,732, (−)-4-{(4R,5R)-2-[3-(2,6-diisopropylphenyl)ureidomethyl]-4,5-dimethyl-1,3-dioxolan-2-yl}phenyl phosphate and a monosodium salt thereof described in International Publication WO 96/26948 pamphlet, N-[2,4-bis(methylthio)-6-methyl-3-pyridyl]-2-[4-[2-(oxazolo[4,5-b]pyridine-2-ylthio)ethyl]piperadin-1-yl]acetamide described in European Patent No. 0987254, N-(2,6-diisopropylphenyl)-2-tetradecylthioacetamide described in U.S. Pat. No. 5,475,130, trans-1,4-bis[{1-cyclohexyl-3-(4-dimethylaminophenyl)ureido]methyl}cyclohexane described in U.S. Pat. No. 5,733,931, 1-benzyl-1-[3-(pyrazol-3-yl)benzyl]-3-[2,4-bis(methylthio)-6-methylpyridin-3-yl]urea described in International Publication WO 96/10559 pamphlet, N-(4,6-dimethyl-1-pentylindolin-7-yl)-2,2-dimethylpropaneamide described in U.S. Pat. No. 5,990,150 or U.S. Pat. No. 6,127,403, N-(1-octyl-5-carboxymethyl-4,6-dimethylindolin-7-yl)-2,2-dimethyl propaneamide and a sulfate thereof described in U.S. Pat. No. 6,063,806 and U.S. Pat. No. 6,200,988, N-[4-(3,4-dimethylphenyl)-1,4-diazacyclohexyl]-(2E)-3-(3,5-dimethoxy-4-octyloxyphenyl)-2-propaneamide, or a pharmaceutically acceptable salt thereof, and preferably N-(1-octyl-5-carboxymethyl-4,6-dimethylindolin-7-yl)-2,2-dimethylpropaneamide and a sulfate thereof.

There are no particular limitations on the angiotensin II inhibitor described above provided it has an angiotensin II inhibitory activity and can be used as a pharmaceutical, examples of which include candesartan or 2-ethoxy-1-[p-(o-1H-tetrazol-5-ylphenyl)benzyl]-7-benzimidazole carboxylic acid 1-(cyclohexyloxycarbonyloxy)ethyl ester (candesartan cilexetil) described in European Patent Application Publication No. 0459136 or European Patent Application Publication No. 0520423, 2-n-butyl-4-spirocyclopentane-1-[({2'-tetrazol-5-yl}biphenyl-4-yl)methyl]-2-imidazolin-5-one (irbesartan) described in International Publication WO 91/14679 pamphlet, olmesartan or (5-methyl-2-oxo-1,3-dioxolen-4-yl) methyl 4-(1-hydroxy-1-methylethyl)-2-propyl-1-[[2'-(1H-tetrazol-5-yl)biphenyl-4-yl]methyl]imidazole-5-carboxylate (olmesartan medoxomil) described in Japanese Patent Application (Kokai) No. Hei 5-78328 (U.S. Pat. No. 5,459,148), 2-propyl-8-oxo-1-[(2'-(1H-tetrazol-5-yl)biphenyl-4-yl)methyl]-4,5,6,7-tetrahydrocycloheptoimidazole (pratosartan) described in Japanese Patent Application (Kokai) No. Hei 1-320139, 4'-[(1,4'-dimethyl-2'-propyl[2,6'-bi-1H-benzimidazol]-1'-yl)methyl]-[1,1'-biphenyl]-2-carboxylic acid (telmisartan) described in European Patent Application Publication No. 0502314, (S)—N-valeryl-N-([2'-(1H-tetrazol-5-yl)biphenyl-4-yl]methyl)valine (valsartan) described in European Patent Application Publication No. 0443983, eprosartan or 3-[1-(4-carboxyphenylmethyl)-2-n-butylimidazol-5-yl]-2-thienylmethyl-2-propenoic acid methane sulfonate (eprosartan mesilate) described in European Patent Application Publication No. 0403159, losartan or 2-butyl-4-chloro-1-[2'-(1H-tetrazol-5-yl)-[1,1'-biphenyl]-4-yl]methyl]-1H-imidazole-5-methanol monopotassium salt (losartan potassium) described in European Patent Application Publication No. 0253310 or European Patent Application Publication No. 0511767, or a pharmaceutically acceptable salt thereof, and preferably olmesartan or olmesartan medoxomil.

There are no particular limitations on the cholesterol absorption inhibitor described above provided it has an activity of inhibiting absorption of dietary cholesterol from the digestive tract and can be used as a pharmaceutical, examples of which include 1-(4-fluorophenyl)-3(R)-[3-(4-fluorophenyl)-3(S)-hydroxypropyl]-4(S)-(4-hydroxyphenyl)-2-azetidinone (ezetimibe).

There are no particular limitations on the bile acid adsorption ion exchange resin described above provided it has an activity increasing excretion of bile acid which serves as an external excretion pathway of cholesterol and can be used as a pharmaceutical, examples of which include colestyramine, cholestimide and colesevelam hydrochloride.

There are no particular limitations on the fibrate-based medicine described above provided it can be used as a pharmaceutical, examples of which include clofibrate, clinofibrate, bezafibrate, fenofibrate and zemfibrate.

There are no particular limitations on the nicotinic acid derivative medicine provided it can be used as a pharmaceutical, examples of which include niceritrol and nicomol.

There are no particular limitations on the diuretic medicine provided it has a diuretic activity and can be used as a pharmaceutical, examples of which include chlorothiazide, hydrochlorothiazide, furosemide, piretanide and azosemide.

In the case that an HMG-CoA reductase inhibitor, CETP inhibitor, ACAT inhibitor, angiotensin II inhibitor, cholesterol absorption inhibitor, fibrate-based medicine, nicotinic acid derivative or diuretic described above can form a salt with an acid or a base, these pharmaceuticals include those salts. In addition, in the case that pharmaceuticals described above have a stereoisomer, these pharmaceuticals include all stereoisomers and a mixture thereof.

In the case that a compound represented by the general formula (I) or a pharmacologically acceptable salt or ester thereof of the present invention is used as a pharmaceutical for treating or preventing diseases described above, it can be administered as it is (in bulk form), or it can be administered orally in a form of a pharmaceutical composition such as a tablet, a capsule, a granule, a powder or syrup, etc. prepared by mixing with a suitable pharmaceutically acceptable vehicle, diluent and so forth or parenterally in a form of a pharmaceutical composition such as an injection, a suppository, a patch or an external composition, etc. prepared in the same manner, and it is preferably orally administered.

These pharmaceutical compositions are prepared by a well known method using an additive such as a vehicle, a lubricant, a binder, a disintegrant, an emulsifier, a stabilizer, a corrigent, a diluent and the like.

A vehicle can be, for example, an organic vehicle or an inorganic vehicle. Examples of an organic vehicle include a sugar derivative such as lactose, sucrose, glucose, mannitol and sorbitol; a starch derivative such as cornstarch, potato starch, α-starch and dextrin; a cellulose derivative such as crystalline cellulose; a gum arabic; a dextran; and, a pullulan. Examples of an inorganic vehicle include a silicate derivative such as light silicic anhydride, synthetic aluminum silicate, calcium silicate and magnesium aluminate metasilicate; a phosphate such as calcium hydrogen phosphate; a carbonate such as calcium carbonate; and, a sulfate such as calcium sulfate.

Examples of a lubricant include stearic acid; a stearic acid metal salt such as calcium stearate and magnesium stearate; a talc; a colloidal silica; a wax such as beeswax and spermaceti; boronic acid; adipic acid; a sulfate such as sodium sulfate; glycol; fumaric acid; sodium benzoate; DL-leucine; a lauryl sulfate such as sodium lauryl sulfate and magnesium lauryl sulfate; a silicic acid such as silicic anhydride and silicic acid hydrate; and a starch derivative as described for a vehicle above.

Examples of a binder include hydroxypropyl cellulose, hydroxypropyl methyl cellulose, polyvinyl pyrrolidone, polyethylene glycol and a derivative as described for a vehicle above.

Examples of a disintegrant include a cellulose derivative such as a lowly-substituted hydroxypropyl cellulose, carboxymethyl cellulose, calcium carboxymethyl cellulose and an internally crosslinked sodium carboxymethyl cellulose; a chemically modified starch-cellulose derivative such as carboxymethyl starch and sodium carboxymethyl starch; and, a crosslinked polyvinyl pyrrolidone.

Examples of an emulsifier include a colloidal clay such as bentonite and bee gum; a metal hydroxide such as magnesium hydroxide and aluminum hydroxide; an anionic surfactant such as sodium lauryl sulfate and calcium stearate; a cationic surfactant such as benzalkonium chloride; and a nonionic surfactant such as a polyoxyethylene alkyl ether, a polyoxyethylene sorbitan fatty acid ester and a sucrose fatty acid ester.

Examples of a stabilizer include a parahydroxybenzoic acid ester such as methyl paraben and propyl paraben; an alcohol such as chlorobutanol, benzyl alcohol and phenyl ethyl alcohol; benzalkonium chloride; a phenol such as phenol and cresol; thimerosal; dehydroacetic acid; and, sorbic acid.

Examples of a corrigent include a sweetener such as sodium saccharin and aspartame; an acidulant such as citric acid, malic acid and tartaric acid; and a fragrance such as menthol, lemon extract and orange extract.

A diluent can be a compound which is usually used as a diluent, examples of which include lactose, mannitol, glucose, sucrose, calcium sulfate, calcium phosphate, hydroxypropyl cellulose, microcrystalline cellulose, water, ethanol, polyethylene glycol, propylene glycol, glycerol, starch, polyvinyl pyrrolidone, magnesium aluminate metasilicate and a mixture thereof.

Although the dose of a compound represented by the general formula (I) or a pharmacologically acceptable salt or ester thereof varies depending on the disease, age of the patient and so forth, administration is preferably performed one to six times per day depending on the disease and symptom thereof, in the case of oral administration at a lower limit dose of 0.01 mg/kg (preferably 0.05 mg/kg) and an upper limit dose of 500 mg/kg (preferably 100 mg/kg) per administration for a human adult and in the case of an intravenous administration at a lower limit dose of 0.001 mg/kg (preferably 0.005 mg/kg) and an upper limit dose of 100 mg/kg (preferably 20 mg/kg) per administration for a human adult.

Effect of the Present Invention

The compound represented by the general formula (I) or a pharmacologically acceptable salt or ester thereof of the present invention has a superior binding activity to LXR, has superior pharmacokinetic properties in terms of absorption, distribution in the body and half-life in the blood, and has a low toxicity against kidney, liver and other organs. Therefore, the compound represented by the general formula (I) or a pharmacologically acceptable salt or ester thereof of the present invention is useful as a pharmaceutical for a warmblooded animal, preferably a human.

The compound represented by the general formula (I) or pharmacologically acceptable salt or ester thereof of the present invention is useful as an LXR modulator, an LXE agonist or an LXR antagonist, preferably as an LXR modulator or an LXR agonist, and more preferably as an LXR modulator. The compound represented by the general formula (I) or a pharmacologically acceptable salt or ester thereof of the present invention is useful as a pharmaceutical for inducing ABCA1 expression or promoting reverse cholesterol transport.

The compound represented by the general formula (I) or a pharmacologically acceptable salt or ester thereof of the present invention is useful as a pharmaceutical for treating or preventing preferably arteriosclerosis, atherosclerosis, arteriosclerosis caused by diabetes, hyperlipemia, hypercholesterolemia, lipid-associated diseases, inflammatory disease, auto-immune disease, arteriosclerotic heart disease, cardiovascular disease, coronary artery disease, cerebrovascular disease, kidney disease, diabetes, diabetic complications, obesity, nephritis, hepatitis, cancer or Alzheimer's disease; more preferably arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease or diabetes; even more preferably arteriosclerosis, atherosclerosis, arteriosclerosis caused by diabetes, arteriosclerotic heart disease, cardiovascular disease or coronary artery disease; still more preferably arteriosclerosis, atherosclerosis or arteriosclerotic heart disease; and most preferably arteriosclerosis.

BEST MODE FOR CARRYING OUT THE INVENTION

In the following, the present invention is explained in more detail by exemplifying Examples, Test Examples and Formulation Examples but the scope of the present invention is not limited to these.

In the following respective Examples, an obtained compound can be purified, if necessary, by recrystallization, reprecipitation, silica gel column chromatography or a combination of these.

EXAMPLE

Example 1

(4'-{[2-(tert-Butoxycarbonyl)-4-fluoro-3-hydroxybenzyl]oxy}-1,1'-biphenyl-4-yl)acetic acid (Exemplification Compound No.: 1-93)

(1-1)

Paraformaldehyde (3.86 g, 133 mmol), magnesium chloride (6.32 g, 66.5 mmol) and triethylamine (11.6 ml, 83.3 mmol) were added to a solution of 2-fluoro-5-methylphenol (4.19 g, 33.3 mmol) in acetonitrile (100 ml), and the mixture was vigorously stirred at 90° C. for 10 days. The reaction mixture was poured into 1N hydrochloric acid and extracted with ethyl acetate. After the organic layer was successively washed with 1N hydrochloric acid, water and a saturated aqueous NaCl solution, and dried with anhydrous sodium sulfate, it was concentrated under reduced pressure. The obtained residue was subjected to silica gel column chromatography (eluting solvent: hexane/ethyl acetate=4/1) to obtain crude 3-fluoro-2-hydroxy-6-methylbenzaldehyde. According to a method similar to Example (28-3) and Example (28-4), from the crude compound obtained in the above, tert-butyl 2-[(tert-butoxycarbonyl)oxy]-3-fluoro-6-methylbenzoate was obtained (624 mg, three-step total yield: 6%).

$^1$H-NMR (500 MHz, CDCl$_3$): δ 7.11-6.96 (2H, m), 2.33 (3H, s), 1.58 (9H, s), 1.54 (9H, s).

(1-2)

According to a method similar to Example (28-5), Example (40-2), Example (33-5) and Example (7), from tert-butyl 2-[(tert-butoxycarbonyl)oxy]-3-fluoro-6-methylbenzoate (624 mg, 1.91 mmol) obtained in Example (1-1), the title compound was obtained as a colorless powder (93 mg, four-step total yield: 34%).

In the step described above corresponding to the Example (40-2), methyl (4'-hydroxy-1,1'-biphenyl-4-yl)acetate obtained in Example (6-2) was used as a phenol derivative.

¹H-NMR (400 MHz, CDCl₃): δ 7.59-7.46 (4H, m), 7.33 (2H, d, J=7.8 Hz), 7.24-7.19 (1H, app t J=9.2 Hz), 7.08 (1H, dd, 8.4, 4.5 Hz), 6.98 (2H, d, J=8.2 Hz), 5.28 (2H, s), 3.68 (2H, s), 1.60 (9H, s).

MS (ESI) (m/z): 451 ([M−H]⁺).

Example 2

(4'-{[2-(tert-Butoxycarbonyl)-4-(trifluoromethyl)benzyl]oxy}-1,1'-biphenyl-3-yl)acetic acid (Exemplification Compound No.: 2-2)

(2-1)

Potassium tert-butoxide (5.40 g, 48.1 mmol) was added to an ice-cooled solution of 2-methyl-5-trifluoromethylbenzoyl chloride (10.5 g, 47.2 mmol) (manufactured by Apollo Scientific Inc.) in tetrahydrofuran (180 ml) in a small portion and the mixture was stirred for 1 hour. After the reaction mixture was poured into water and the mixture was extracted with ethyl acetate, the organic layer was successively washed with a 5% aqueous sodium hydrogencarbonate solution, water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=60/1-20/1) to give tert-butyl 2-methyl-5-(trifluoromethyl)benzoate as a colorless oil (9.90 g, yield: 81%).

¹H-NMR (400 MHz, CDCl₃): δ 8.03 (1H, br s), 7.57 (1H, br d, J=7.8 Hz), 7.31 (1H, d, J=7.8 Hz), 2.62 (3H, s), 1.61 (9H, s).

(2-2)

N-Bromosuccinimide (1.18 g, 6.63 mmol) and 2,2'-azobis(isobutyronitrile) (20 mg) were added to a solution of tert-butyl 2-methyl-5-(trifluoromethyl)benzoate (1.57 g, 6.03 mmol) obtained in Example (2-1) in benzene (25 ml) and the mixture was heated under reflux for 60 minutes. The temperature of the reaction mixture was returned to room temperature and the residue obtained by removing the solvent under reduced pressure was purified by silica gel column chromatography (eluting solvent: n-hexane/ethyl acetate=8/1-6/1) to give tert-butyl 2-(bromomethyl)-5-(trifluoromethyl)benzoate as a white powder (1.08, yield: 53%).

¹H-NMR (400 MHz, CDCl₃): δ 8.12 (1H, br s), 7.69 (1H, br d, J=8.1 Hz), 7.56 (1H, d, J=8.1 Hz), 4.92 (2H, s), 1.65 (9H, s).

(2-3)

Potassium carbonate (1.30 g, 9.41 mmol) was added to a solution of tert-butyl 2-(bromomethyl)-5-(trifluoromethyl)benzoate (2.00 g, 5.90 mmol) obtained in Example (2-2) and 4-iodophenol (1.30 g, 5.91 mmol) in N,N-dimethylformamide (20 ml) under ice-cooling and the mixture was stirred at room temperature for 2 hours. The reaction mixture was poured into water and extracted with ethyl acetate (three times). After the organic layer was successively washed with water (three times) and a saturated aqueous NaCl solution and dried with anhydrous sodium sulfate, it was concentrated under reduced pressure. The obtained residue was purified by silica gel column chromatography (eluting solvent: n-hexane/ethyl acetate=100/1-50/1) to give tert-butyl 2-[(4-iodophenoxy)methyl]-5-(trifluoromethyl)benzoate as a colorless solid (2.65 g, yield: 94%).

¹H-NMR (400 MHz, CDCl₃): δ 8.20 (1H, s), 7.85 (1H, d, J=8.2 Hz), 7.76 (1H, d, J=8.2 Hz), 7.58 (2H, d, J=9.4 Hz), 6.77 (2H, d, J=9.4 Hz), 5.47 (2H, s), 1.61 (9H, s).

(2-4)

After 4,4,4',4',5,5,5',5'-octamethyl-2,2'-bi-1,3,2-dioxaborolane [another name: bis(pinacolate)diborone] (1.00 g, 3.94 mmol), [1,1'-bis(diphenylphosphino)ferrocene]dichloropalladium (II)-dichloromethane adduct (146 mg, 0.179 mmol) and potassium acetate (530 mg, 5.40 mmol) were added to a solution of tert-butyl 2-[(4-iodophenoxy)methyl]-5-(trifluoromethyl)benzoate (1.71 g, 3.59 mmol) obtained in Example (2-3) in dimethyl sulfoxide (15 ml), the mixture was stirred at 80° C. for 4 hours. After the reaction mixture was poured into water and the mixture was extracted with ethyl acetate, the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=20/1-8/1) to give tert-butyl 2-{[4-(4,4,5,5-tetramethyl-1,3,2-dioxaborolan-2-yl}phenoxy]methyl)-5-(trifluoromethyl)benzoate (1.14 g, yield: 66%).

¹H-NMR (400 MHz, CDCl₃): δ 8.20 (1H, br s), 7.88 (1H, d, J=8.8 Hz), 7.79-7.73 (3H, m), 6.98 (2H, d, J=8.8 Hz), 5.52 (2H, s), 1.61 (9H, s), 1.34 (2H, s).

(2-5)

According to a method similar to Example (8-1), from tert-butyl 2-{[4-(4,4,5,5-tetramethyl-1,3,2-dioxaborolan-2-yl)phenoxy]methyl}-5-(trifluoromethyl)benzoate (88 mg, 0.18 mmol) obtained in Example (2-4) and 3-bromophenylacetic acid (50 mg, 0.23 mmol), the title compound was obtained as a yellow powder (4.5 mg, yield: 29%).

¹H-NMR (400 MHz, CDCl₃): δ 8.18 (1H, br a), 7.89 (1H, d, J=7.8 Hz), 7.75 (1H, br d, J=7.8 Hz), 7.50 (2H, d, J=8.6 Hz), 7.47-7.42 (2H, m), 7.36 (1H, t, J=7.8 Hz), 7.22 (1H, br d, J=7.8 Hz), 7.02 (2H, d, J=8.6 Hz), 5.53 (2H, s), 3.70 (2H, s), 1.62 (9H, s).

Example 3

(4'-{[2-(tert-Butoxycarbonyl)-4-(trifluoromethyl)benzyl]oxy}-1,1'-biphenyl-4-yl)acetic acid (Exemplification Compound No.: 1-16)

(3-1)

Concentrated sulfuric acid (30 ml) was added to a solution of (4-bromophenyl)acetic acid (101 g, 468 mmol) in methanol (1000 ml) under ice-cooling and the mixture was stirred at room temperature for 2 hours. After the reaction mixture was concentrated and ethyl acetate was added to the residue, the mixture was successively washed with water, a saturated aqueous sodium hydrogencarbonate solution and a saturated aqueous NaCl solution and dried with anhydrous sodium sulfate. The residue obtained by removing the solvent under reduced pressure was purified by silica gel column chromatography (eluting solvent: n-hexane/ethyl acetate=5/1) to give methyl (4-bromophenyl)acetate (107 g, yield: 100%).

¹H-NMR (400 MHz, CDCl₃): δ 7.43 (2H, d, J=8.6 Hz), 7.14 (2H, d, J=8.6 Hz), 3.69 (3H, s), 3.57 (2H, s).

(3-2)

According to a method similar to Example (8-1), from tert-butyl 2-{[4-(4,4,5,5-tetramethyl-1,3,2-dioxaborolan-2-yl)phenoxy]methyl}-5-(trifluoromethyl)benzoate (100 mg, 0.21 mmol) obtained in Example (2-4) and methyl (4-bromophenyl)acetate (62 mg, 0.27 mmol) obtained in Example (3-1), tert-butyl 2-[({4'-[(methoxycarbonyl)methyl]-1,1'-biphenyl-4-yl}oxy)methyl]-5-(trifluoromethyl)benzoate was obtained (54 mg, yield: 52%).

¹H-NMR (500 MHz, CDCl₃): δ 8.21 (1H, d, J=2.0 Hz), 7.92 (1H, d, J=7.8 Hz), 7.78 (1H, dd, J=7.8, 2.0 Hz), 7.54-7.49

(4H, m), 7.33 (2H, d, J=7.8 Hz), 7.05 (2H, d, J=8.8 Hz), 5.55 (2H, s), 3.71 (3H, s), 3.66 (2H, s), 1.63 (9H, s).

(3-3)

According to a method similar to Example (7), from tert-butyl 2-[({4'-[(methoxycarbonyl)methyl]-1,1'-biphenyl-4-yl}oxy)methyl]-5-(trifluoromethyl)benzoate (52 mg, 0.10 mmol) obtained in Example (3-2), the title compound was obtained as a white powder (41 mg, yield: 82%).

$^1$H-NMR (500 MHz, CDCl$_3$): δ 8.21 (1H, br s), 7.92 (1H, d, J=7.8 Hz), 7.78 (1H, app d, J=7.8 Hz), 7.53 (4H, app d, J=7.8 Hz), 7.35 (2H, d, J=8.8 Hz), 7.05 (2H, d, J=8.8 Hz), 5.55 (2H, s), 3.70 (2H, s), 1.63 (9H, s).

MS (FAB) (m/z): 486 (M$^+$).

Example 4

[5-(4-{[2-(tert-Butoxycarbonyl)-4-(trifluoromethyl) benzyl]oxy}phenyl)-2-thienyl]acetic acid (Exemplification Compound No.: 2-26)

(4-1)

According to a method similar to Example (8-1), from methyl (5-bromo-2-thienyl)acetate which was synthesized from methyl 2-thienylacetate according to the method described in literature (Jackson, P. M. et al., J. Chem. Soc. Perkin Trans. 1, 1990, vol. 11, pp. 2909-2918) and tert-butyl 2-{[4-(4,4,5,5-tetramethyl-1,3,2-dioxaborolan-2-yl)phenoxy]methyl}-5-(trifluoromethyl)benzoate obtained in Example (2-4), tert-butyl 2-[4-({5-[(methoxycarbonyl)methyl]-2-thienyl}phenoxy)methyl]-5-(trifluoromethyl)benzoate was obtained (53 mg, yield: 13%).

$^1$H-NMR (500 MHz, CDCl$_3$): δ 8.20 (1H, br s), 7.89 (1H, d, J=7.8 Hz), 7.77 (1H, d, J=7.8 Hz), 7.50 (2H, d, J=8.8 Hz), 7.05 (1H, d, J=3.4 Hz), 6.98 (2H, d, J=8.8 Hz), 6.87 (1H, d, J=3.4 Hz), 5.52 (2H, s), 3.83 (2H, s), 3.75 (3H, s), 1.62 (9H, s).

(4-2)

According to a method similar to Example 7, from tert-butyl 2-[4-({5-[(methoxycarbonyl)methyl]-2-thienyl}phenoxy)methyl]-5-(trifluoromethyl)benzoate (300 mg, 0.62 mmol) obtained in Example (4-1), the title compound was obtained as a pale yellow powder (53 mg, yield: 17%).

$^1$H-NMR (500 MHz, CDCl$_3$): δ 8.20 (1H, br s), 7.89 (1H, d, J=8.3 Hz), 7.77 (1H, d, J=8.3 Hz), 7.50 (2H, d, J=8.8 Hz), 7.06 (1H, br d, J=2.9 Hz), 6.98 (2H, d, C=8.8 Hz), 6.91 (1H, br d, J=2.9 Hz), 5.52 (2H, s), 3.88 (2H, s), 1.62 (9H, 5).

MS (FAB) (m/z): 492 (M).

Example 5

(4'-{[2-(tert-Butoxycarbonyl)-4-chloro-3-hydroxybenzyl]oxy}-1,1'-biphenyl-4-yl)acetic acid (Exemplification Compound No.: 1-95)

(5-1)

Paraformaldehyde (4.73 g, 163 mmol), magnesium chloride (7.76 g, 81.7 mmol) and triethylamine (14.2 ml, 102 mmol were added to a solution of 2-chloro-5-methylphenol (5.80 g, 40.8 mmol) in acetonitrile (100 ml) and the mixture was vigorously stirred at 90° C. for 10 hours. The reaction mixture was poured into 1N hydrochloric acid and extracted with ethyl acetate. After the organic layer was successively washed with 1N hydrochloric acid, water and a saturated aqueous NaCl solution and dried with anhydrous sodium sulfate, it was concentrated under reduced pressure. The obtained residue was subjected to silica gel column chromatography (eluting solvent: hexane/ethyl acetate=3/1) to give crude 3-chloro-2-hydroxy-6-methylbenzaldehyde. According to a method similar to Example (28-3) and Example (28-4), from the crude compound obtained in the above, tert-butyl 2-[(tert-butoxycarbonyl)oxy]-3-chloro-6-methylbenzoate was obtained (1.82 g, three-step total yield: 13%).

$^1$H-NMR (400 MHz, CDCl$_3$): δ 7.34-7.31 (1H, m), 7.04-7.01 (1H, m) 2.35 (3H, s), 1.59 (9H, s), 1.56 (9H, s).

(5-2)

According to a method similar to Example (28-5), Example (40-2), Example (33-5) and Example (7), from tert-butyl 2-[(tert-butoxycarbonyl)oxy]-3-chloro-6-methylbenzoate (1.82 g, 5.32 mmol) obtained in Example (5-1), the title compound was obtained as a white powder (30 mg, four-step total yield: 1%).

In the step described above corresponding to Example (40-2), methyl (4'-hydroxy-1,1'-biphenyl-4-yl)acetate obtained in Example (6-2) was used as a phenol derivative.

$^1$H-NMR (400 MHz, CDCl$_3$): δ 7.52-7.46 (5H, m), 7.33 (2H, d, J=8.6 Hz), 7.10 (1H, d, J=8.6 Hz), 6.95 (2H, d, J=8.6 Hz), 5.30 (2H, s), 3.68 (2H, s), 1.61 (9H, s).

MS (ESI) (m/z): 467 ([M−H]$^+$).

Example 6 tert-Butyl 2-hydroxy-6-[({4'-[(methoxycarbonyl) methyl]-1,1'-biphenyl-4-yl}oxy}methyl]-3-(trifluoromethyl)benzoate (Exemplification Compound No.: 1-56)

(6-1)

After a 1M aqueous sodium carbonate solution (2.8 ml) and tetrakis(triphenylphosphine)palladium (0) (116 mg, 0.10 mmol) were added to a solution of methyl (4-bromophenyl) acetate (573 mg, 2.50 mmol) obtained in Example (3-1) and 4-methoxyphenylboronic acid (380 mg, 2.50 mmol) in a mixture of toluene-ethanol (6:1, 6 ml), the mixture was heated under reflux for 4 hours. After the temperature of the reaction mixture was returned to room temperature, the mixture was poured into water and extracted with ethyl acetate three times. The organic layer was successively washed with water (twice) and a saturated aqueous NaCl solution and dried with anhydrous sodium sulfate. The solvent was removed under reduced pressure to give a yellow solid. It was purified by silica gel column chromatography (eluting solvent: n-hexane/ethyl acetate=95/5-80/20) to give methyl (4'-methoxy-1,1'-biphenyl-4-yl)acetate as a pale yellow powder (617 mg, yield: 96%).

$^1$H-NMR (400 MHz, CDCl$_3$): δ 7.52 (4H, d, J=8.4 Hz), 7.33 (2H, d, J=8.4 Hz), 6.97 (2H, d, J=8.4 Hz), 3.85 (3H, s), 3.71 (3H, s), 3.66 (2H, s).

(6-2)

After boron trichloride (1.0N methylene chloride solution 2.0 ml, 2.0 mmol) was added to a solution of methyl (4'-methoxy-1,1'-biphenyl-4-yl)acetate (210 mg, 0.82 mmol) obtained in Example (6-1) and tetra-n-butyl ammonium iodide (393 mg, 1.1 mmol) in methylene chloride (5 ml) at −78° C., the temperature of the mixture was raised to room temperature and then the mixture was stirred for 1 hour. After ice was added to the reaction mixture and the mixture was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=1/1) to give methyl (4'-hydroxy-1,1'-biphenyl-4-yl)acetate (155 mg, yield: 78%).

¹H-NMR (400 MHz, CDCl₃): δ 7.45 (2H, d, J=8.2 Hz), 7.40 (2H, d, J=8.6 Hz), 7.29 (2H, d, J=8.2 Hz), 6.83 (2H, d, J=8.6 Hz), 5.25 (1H, s), 3.71 (3H, s), 3.66 (2H, s).

(6-3)

A n-butyl lithium-1.58M n-hexane solution (65.9 ml, 104 mmol) was added dropwise to a solution of 2-[2-(trifluoromethyl)phenoxy]tetrahydro-2H-pyrane (21.4 g, 86.8 mmol) which was synthesized according to the method described in literature (Miller, J. A. et al., J. Org. Chem. 1993, vol. 58, pp. 2637-2639) and N,N,N',N'-tetramethylethylenediamine (15.7 ml, 104 mmol) in diethyl ether (230 ml) at −20° C. over 10 minutes. After the reaction mixture was stirred at −20° C. for 30 minutes, it was further stirred at room temperature for 40 minutes. After the reaction mixture was cooled to −30° C. and N,N-dimethylformamide (13.5 ml, 174 mmol) was added thereto, the mixture was further stirred at room temperature for 1 hour. After the reaction mixture was carefully poured into cooled water and the mixture was extracted with ethyl acetate (three times), the organic layer was successively washed with 1N hydrochloric acid, a 5% aqueous sodium hydrogencarbonate solution, water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=20/1-10/1). The obtained 2-(tetrahydro-2H-pyran-2-yloxy)-3-(trifluoromethyl)benzaldehyde as a pale yellow oil was left to stand at room temperature overnight to give 2-hydroxy-3-(trifluoromethyl)benzaldehyde as a pale yellow solid (31.7 g, yield: 96%).

¹H-NMR (400 MHz, CDCl₃): δ 11.70 (1H, s), 9.93 (1H, s), 7.80 (1H, d, J=7.8 Hz), 7.75 (1H, d, J=7.8 Hz), 7.10 (1H, t, J=7.8 Hz).

¹H-NMR spectrum of 2-(tetrahydro-2H-pyran-2-yloxy)-3-(trifluoromethyl)benzaldehyde which is an intermediate is shown below.

¹H-NMR (400 MHz, CDCl₃): δ 10.33 (1H, s), 8.02 (1H, dd, J=7.8, 1.5 Hz), 7.83 (1H, dd, J=7.8, 1.5 Hz), 7.33 (1H, t, J=7.8 Hz), 4.80 (1H, dd, J=7.4, 2.7 Hz), 4.03-3.96 (1H, m), 3.47-3.39 (1H, m), 2.11-2.03 (1H, m), 2.01-1.80 (2H, m), 1.67-1.50 (3H, m).

(6-4)

After trimethyl orthoformate (130 ml, 1.19 mol) and camphorsulfonic acid (1.55 g, 6.67 mmol) were added to a solution of 2-hydroxy-3-(trifluoromethyl)benzaldehyde (31.7 g, 167 mmol) obtained in Example (6-3) in methanol (50 ml), the mixture was stirred at 50° C. for 6 hours. After the reaction mixture was poured into a 1% aqueous sodium hydrogencarbonate solution and the mixture was extracted with ethyl acetate (three times), the organic layer was successively washed with water (twice) and a saturated aqueous NaCl solution and dried with anhydrous sodium sulfate. The residue obtained by concentrating the organic layer was dissolved in methylene chloride (400 ml) and diisopropylethylamine (50.9 ml, 292 mmol) and chloromethyl methyl ether (15.4 ml, 203 mmol) were successively added thereto under ice-cooling, and the mixture was stirred overnight. After the reaction mixture was poured into water and the mixture was extracted with ethyl acetate (twice), the organic layer was successively washed with 0.5N hydrochloric acid, a 5% aqueous sodium hydrogencarbonate solution, water and a saturated aqueous NaCl solution and dried with anhydrous sodium sulfate. The residue obtained by removing the solvent under reduced pressure was purified by silica gel column chromatography (eluting solvent: n-hexane/ethyl acetate=14/1-10/1) to give 1-(dimethoxymethyl)-2-(methoxymethoxy)-3-(trifluoromethyl)benzene as a pale yellow oil (42.2 g, yield: 93%).

¹H-NMR (400 MHz, CDCl₃): δ 7.77 (1H, dd, J=7.8, 1.6 Hz), 7.59 (1H, dd, J=7.8, 1.6 Hz), 7.24 (1H, t, J=7.8 Hz), 5.67 (1H, s), 5.07 (2H, s), 3.65 (3H, s), 3.38 (6H, s).

(6-5)

A n-butyl lithium-1.59M n-hexane solution (196 ml, 312 mmol) was added dropwise to a solution of 1-(dimethoxymethyl)-2-(methoxymethoxy)-3-(trifluoromethyl)benzene (39.3 g, 140 mmol) obtained in Example (6-4) and N,N,N',N'-tetramethylethylenediamine (46.9 ml, 311 mmol) in diethyl ether (410 ml) at −25° C. over 20 minutes. After the reaction mixture was stirred at 0° C. for 30 minutes, it was further stirred at room temperature for 1.5 hours. After the reaction mixture was cooled to −30° C. and N,N-dimethylformamide (41.9 ml, 541 mmol) was added thereto, the mixture was further stirred at room temperature for 1 hour. After the reaction mixture was carefully poured into cold 0.1N hydrochloric acid and the mixture was extracted with ethyl acetate (four times), the organic layer was successively washed with 0.1N hydrochloric acid, water (three times) and a saturated aqueous NaCl solution and dried with anhydrous sodium sulfate. The solvent was removed under reduced pressure to give crude 2-(dimethoxymethyl)-3-(methoxymethoxy)-4-(trifluoromethyl)benzaldehyde. This compound was used in Example (6-6) without further purification.

¹H-NMR (400 MHz, CDCl₃): δ 10.71 (1H, s), 7.81 (1H, d, J=8.2 Hz), 7.70 (1H, d, J=8.2 Hz), 5.79 (1H, s), 5.07 (2H, s), 3.67 (3H, s), 3.50 (6H, s).

MS (FAB) (+0.1N KIaq.) (m/z): 347 ([M+K]⁺).

(6-6)

Sodium borohydride (5.11 g, 135 mmol) was added to a solution of crude 2-(dimethoxymethyl)-3-(methoxymethoxy)-4-(trifluoromethyl)benzaldehyde obtained in Example (6-5) in a mixture of tetrahydrofuran-methanol (5:1, 100 ml) under ice-cooling and the mixture was stirred overnight. After the reaction mixture was poured into water and the mixture was extracted with ethyl acetate (four times), the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=5/1-2/1) to give [2-(dimethoxymethyl)-3-(methoxymethoxy)-4-(trifluoromethyl)phenyl]methanol as an orange oil (22.6 g, two-step total yield: 52%).

¹H-NMR (400 MHz, CDCl₃): δ 7.59 (1H, d, J=8.2 Hz), 7.31 (1H, d, J=8.2 Hz), 5.81 (1H, s), 5.01 (2H, s), 4.85 (2H, d, J=7.0 Hz), 3.65 (3H, s), 3.50 (6H, s), 3.36 (1H, t, J=7.0 Hz).

MS (FAB) (m/z): 309 ([M−H]⁺).

(6-7)

1,1'-(Azodicarbonyl)dipiperidine (3.10 g, 12.3 mmol) and tri-n-butylphosphine (3.10 ml, 12.4 mmol) were successively added to a solution of [2-(dimethoxymethyl)-3-(methoxymethoxy)-4-(trifluoromethyl)phenyl]methanol (3.20 g, 10.3 mmol) obtained in Example (6-6) and methyl (4'-hydroxy-1,1'-biphenyl-4-yl)acetate (2.50 g, 10.3 mmol) obtained in Example (6-2) in tetrahydrofuran (40 ml) and the mixture was stirred at room temperature for 5 hours. After the formed white precipitate was removed by filtration, the precipitate was washed with ethyl acetate. After the filtrate was poured into water and the mixture was extracted with ethyl acetate (three times), the organic layer was successively washed with a 3N aqueous sodium hydroxide solution, water and a saturated aqueous NaCl solution and dried with anhydrous sodium sulfate. The solvent was removed under reduced pressure and the residue was purified by silica gel column chromatography (eluting solvent: n-hexane/ethyl acetate=4/1) to give methyl (4'-{[2-(dimethoxymethyl)-3-(methoxymethoxy)-4-(trifluoromethyl)benzyl]oxy}-1,1'-biphenyl-4-yl)acetate (3.16 g, yield: 58%).

¹H-NMR (400 MHz, CDCl₃): δ 7.56-7.54 (2H, br s), 7.47 (2H, d, J=7.8 Hz), 7.46 (2H, d, J=9.0 Hz), 7.29 (2H, d, J=7.8 Hz), 7.01 (2H, d, J=9.0 Hz), 5.75 (1H, s), 5.51 (2H, s), 5.03 (2H, s), 3.70 (3H, s), 3.66 (3H, s), 3.64 (2H, s), 3.48 (6H, s)
(6-8)

After p-toluenesulfonic acid monohydrate (1.01 g, 5.31 mmol) was added to a solution of methyl (4'-{[2-(dimethoxymethyl)-3-(methoxymethoxy)-4-(trifluoromethyl)benzyl]oxy}-1,1'-biphenyl-4-yl)acetate (2.38 g, 4.45 mmol) obtained in Example (6-7) in acetone (14 ml), the mixture was stirred at room temperature for 14 hours. After the reaction mixture was poured into water and the mixture was extracted with ethyl acetate, the organic layer was successively washed with water and a saturated aqueous NaCl solution and dried with anhydrous sodium sulfate. The solvent was removed under reduced pressure to give a residue. Potassium carbonate (738 mg, 5.34 mmol) and allyl bromide (0.462 ml, 5.34 mmol) were successively added to a solution of the obtained residue in N,N-dimethylformamide (4 ml) and the mixture was stirred at 50° C. for 2 hours. After the reaction mixture was poured into water and the mixture was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=50/1-2/1) to give methyl (4'-{[3-(allyloxy)-2-formyl-4-(trifluoromethyl)benzyl]oxy}-1,1'-biphenyl-4-yl)acetate (1.81 g, yield: 84%).

¹H-NMR (400 MHz, CDCl₃): δ 10.52 (1H, br a), 7.86 (1H, d, J=8.2 Hz), 7.76 (1H, d, J=8.2 Hz), 7.51 (2H, d, J=8.4 Hz), 7.49 (2H, d, J=8.4 Hz), 7.31 (2H, d, J=8.4 Hz), 7.04 (2H, d, J=8.4 Hz), 6.16-6.04 (1H, m), 5.52-5.44 (3H, m), 5.39-5.34 (1H, m), 4.58 (2H, m), 3.70 (3H, s), 3.66 (2H, s).
(6-9)

After an aqueous solution (7.5 ml) of sodium chlorite (1.28 g, 14.2 mmol) and sodium dihydrogenphosphate monohydrate (1.28 g, 9.28 mmol) was added dropwise to a solution of methyl (4'-([3-(allyloxy)-2-formyl-4-(trifluoromethyl)benzyl]oxy)-1,1'-biphenyl-4-yl)acetate (1.71 g, 3.53 mmol) obtained in Example (6-8) in a mixture of tert-butyl alcohol (15 ml), 1,4-dioxane (3.5 ml) and 2-methyl-2-butene (4.5 ml), the mixture was stirred at room temperature for 4 hours. After a 5% aqueous sodium thiosulfate solution was added to the reaction mixture, the mixture was poured into 0.5N hydrochloric acid and extracted with ethyl acetate (twice). The organic layer was successively washed with water and a saturated aqueous NaCl solution and dried with anhydrous sodium sulfate. The solvent was removed under reduced pressure to give a residue. After the obtained residue was dissolved in toluene (12 ml), N,N-dimethylformamide di-tert-butyl acetal (3.39 ml, 14.1 mmol) was added thereto and the mixture was heated under reflux for 4 hours. After the reaction mixture was poured into water and the mixture was extracted with ethyl acetate (three times), the organic layer was successively washed with water (twice) and a saturated aqueous NaCl solution and dried with anhydrous sodium sulfate. Pyrrolidine (0.500 ml, 5.99 mmol) and tetrakis(triphenylphosphine)palladium (81.6 mg, 70.6 mmol) were added to a solution of the residue obtained by removing the solvent under reduced pressure in a mixture of 1,4-dioxane-water (30:1, 12 ml), and the mixture was stirred at room temperature for 4 hours. After water was poured into the reaction mixture and the mixture was extracted with ethyl acetate, the organic layer was successively washed with water and a saturated aqueous NaCl solution and dried with anhydrous sodium sulfate. The mixture was purified by silica gel column chromatography (eluting solvent: n-hexane/ethyl acetate=98/2-85/15) to give the title compound as a pale yellow powder (1.08 g, yield: 59%).

¹H-NMR (400 MHz, CDCl₃): δ 12.23 (1H, s), 7.68 (1H, d, J=8.2 Hz), 7.50 (2H, d, J=9.0 Hz), 7.48 (2H, d, J=8.2 Hz), 7.30 (2H, d, J=8.2 Hz), 7.25 (1H, d, J=8.2 Hz), 6.95 (2H, d, J=9.0 Hz), 5.35 (2H, a), 3.70 (3H, s), 3.65 (2H, s), 1.63 (9H, s).

Example 7

(4'-{[2-(tert-Butoxycarbonyl)-3-hydroxy-4-(trifluoromethyl)benzyl]oxy}-1,1'-biphenyl-4-yl)acetic acid (Exemplification Compound No.: 1-55)

A 3N aqueous sodium hydroxide solution (0.33 ml, 0.33 mmol) was added to a solution of tert-butyl 2-hydroxy-6-[({4'-[(methoxycarbonyl)methyl]-1,1'-biphenyl-4-yl}oxy)methyl]-3-(trifluoromethyl)benzoate (467 mg, 0.90 mmol) obtained in Example (6-9) in tetrahydrofuran (8 ml), and the mixture was stirred at room temperature for 10 hours. After the reaction mixture was poured into 1N hydrochloric acid and the mixture was extracted with ethyl acetate (three times), the organic layer was successively washed with water and a saturated aqueous NaCl solution and dried with anhydrous sodium sulfate. The solid obtained by removing the solvent under reduced pressure was reprecipitated using n-hexane-ethyl acetate to give the title compound as a white powder (372 mg, yield: 82%).

¹H-NMR (400 MHz, acetone-d₆): δ 12.26 (1H, br), 7.82 (1H, d, J=8.2 Hz), 7.61 (2H, d, J=8.6 Hz), 7.56 (2H, d, J=8.2 Hz), 7.41-7.33 (3H, m), 7.09 (2H, d, J=8.6 Hz), 5.52 (2H, s), 3.66 (2H, s), 1.71 (9H, s).

MS (FAB) (m/z): 502 ([M]⁺).

Example 8 tert-Butyl 2-hydroxy-6-[({3'-[(methoxycarbonyl)methyl]-1,1'-biphenyl-4-yl}oxy)methyl]-3-(trifluoromethyl)benzoate (Exemplification Compound No.: 2-30)

(8-1)
Tetrakis(triphenylphosphine)palladium (0) (1.00 g, 0.88 mmol) and potassium carbonate (4.80 g, 37.0 mmol) were added to a solution of 4-(4,4,5,5-tetramethyl-1,3,2-dioxaborolan-2-yl)phenol (3.84 g, 17.5 mmol) and methyl (3-bromophenyl)acetate (4.00 g, 17.5 mmol) which was synthesized according to the method described in literature (Muller, R. N. et al., Eur. J. Org. Chem., 2002, vol. 23, pp. 3966-3973) in a mixture of N,N-dimethylacetamide-water (10:1, 66 ml), and the mixture was stirred at 110° C. for 6 hours. After the reaction mixture was poured into 0.2N hydrochloric acid and the mixture was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=2/1) to give methyl (4'-hydroxy-1,1'-biphenyl-3-yl)acetate (2.83 g, yield: 67%).

113

¹H-NMR (400 MHz, CDCl₃): δ 7.50-7.43 (4H, m), 7.40-7.35 (1H, m), 7.25-7.20 (1H, m), 6.89 (2H, app d, J=8.6 Hz), 3.71 (3H, s), 3.69 (2H, s).

(8-2)

According to a method similar to Example (6-7), from [2-(dimethoxymethyl)-3-(methoxymethoxy)-4-(trifluoromethyl)phenyl]methanol (1.96 g, 6.32 mmol) obtained in Example (6-6) and methyl (4'-hydroxy-1,1'-biphenyl-3-yl)acetate (1.68 g, 6.95 mmol) obtained in Example (8-1), methyl (4'-{[2-(dimethoxymethyl)-3-(methoxymethoxy)-4-(trifluoromethyl)benzyl]oxy}-1,1'-biphenyl-3-yl)acetate was obtained (1.83 g, yield: 549%).

¹H-NMR (500 MHz, CDCl₃): δ 7.62-7.56 (2H, m), 7.53-7.43 (4H, m), 7.38-7.34 (1H, m), 7.24-7.19 (1H, m), 7.03 (2H, br d, J=8.3 Hz), 5.77 (1H, s), 5.53 (2H, s), 5.04 (2H, s), 3.73-3.66 (8H, m), 3.49 (6H, s).

(8-3)

After p-toluenesulfonic acid monohydrate (0.716 g, 3.77 mmol) was added to a solution of methyl (4'-{[2-(dimethoxymethyl)-3-(methoxymethoxy)-4-(trifluoromethyl)benzyl]oxy}-1,1'-biphenyl-3-yl)acetate (1.83 g, 3.43 mmol) obtained in Example (8-2) in acetone (20 ml), the mixture was stirred at room temperature for 6 hours. After the reaction mixture was poured into water and the mixture was extracted with ethyl acetate (twice), the organic layer was successively washed with water and a saturated aqueous NaCl solution and dried with anhydrous sodium sulfate. The solvent was removed under reduced pressure to give a residue. The obtained residue was purified by silica gel column chromatography (eluting solvent: n-hexane/ethyl acetate=80/20-70/30) to give methyl (4'-{[2-formyl-3-hydroxy-4-(trifluoromethyl)benzyl]oxy}-1,1'-biphenyl-3-yl)acetate (1.26 g, yield: 83%).

¹H-NMR (400 MHz, CDCl₃): δ 12.66 (1H, s), 10.38 (1H, s), 7.82 (1H, br d, J=7.8 Hz), 7.57-7.53 (2H, m), 7.47-7.38 (2H, m), 7.42-7.36 (1H, m), 7.28-7.23 (1H, m), 7.11 (1H, br d, J=7.8 Hz), 7.08-7.03 (2H, m), 5.37 (2H, s), 3.71 (3H, s), 3.69 (2H, s).

(8-4)

According to a method similar to Example (12-5) and Example (6-9), from methyl (4'-{[2-formyl-3-hydroxy-4-(trifluoromethyl)benzyl]oxy}-1,1'-biphenyl-3-yl)acetate (1.26 g, 2.84 mmol) obtained in Example (8-3), the title compound was obtained (609 mg, two-step total yield: 42%).

¹H-NMR (500 MHz, CDCl₃): δ 12.30 (1H, br s), 7.72 (1H, br d, J=8.3 Hz), 7.56 (2H, br d, J=8.3 Hz), 7.51-7.46 (2H, m), 7.43-7.46 (1H, m), 7.30 (1H, br d, J=8.3 Hz), 7.28-7.23 (1H, m), 7.04-6.97 (2H, m), 5.39 (2H, s), 3.72 (3H, s), 3.70 (2H, s), 1.67 (9H, s).

Example 9

(4'-{[2-(tert-Butoxycarbonyl)-3-hydroxy-4-(trifluoromethyl)benzyl]oxy}-1,1'-biphenyl-3-yl)acetic acid (Exemplification Compound No.: 2-29)

According to a method similar to Example 7, from tert-butyl 2-hydroxy-6-[({3'-[(methoxycarbonyl)methyl]-1,1'-biphenyl-3-yl}oxy)methyl]-3-(trifluoromethyl)benzoate (609 mg, 1.18 mmol) obtained in Example (8-4), the title compound was obtained as a colorless amorphous form (469 mg, yield: 79%).

¹H-NMR (400 MHz, CDCl₃): δ 12.28 (1H, br s), 7.69 (1H, br d, J=8.2 Hz), 7.52 (2H, br d, J=8.8 Hz), 7.49-7.45 (2H, m), 7.41-7.35 (1H, m), 7.29-7.21 (2H, m), 6.98 (2H, br d, J=8.8 Hz), 5.36 (2H, s), 3.70 (2H, s) 1.65 (9H, s).

MS (FAB) (m/z): 502 ([M]⁺)

114

Example 10

(4'-{[2-(tert-Butoxycarbonyl)-4-tert-butyl-3-hydroxybenzyl]oxy}-1,1'-biphenyl-4-yl)acetic acid (Exemplification Compound No.: 1-49)

(10-1)

After trimethyl orthoformate (106 ml, 0.972 mol) and camphorsulfonic acid (0.751 g, 3.24 mmol) were added to a solution of 3-tert-butyl-2-hydroxybenzaldehyde (28.8 g, 162 mmol) which was synthesized according to the method described in literature (Hofsløkken, N. U. et al., Acta Chem. Scand., 1999, vol. 53, pp. 258-262) in methanol (20 ml), the mixture was stirred at 50° C. for 6 hours. After the reaction mixture was poured into a 1% aqueous sodium hydrogencarbonate solution and the mixture was extracted with ethyl acetate (three times), the organic layer was successively washed with water (twice) and a saturated aqueous NaCl solution and dried with anhydrous sodium sulfate. The residue obtained by concentrating the organic layer was dissolved in N,N-dimethylformamide (100 ml). After sodium hydride (55% oily, 7.77 g, 178 mmol) was added to the solution under ice-cooling and the mixture was stirred for 30 minutes, chloromethyl methyl ether (13.5 ml, 178 mmol) was added thereto and the mixture was stirred at room temperature for 2 hours. After the reaction mixture was poured into water and the mixture was extracted with ethyl acetate (twice), the organic layer was successively washed with 0.5N hydrochloric acid, a 5% aqueous sodium hydrogencarbonate solution, water and a saturated aqueous NaCl solution and dried with anhydrous sodium sulfate. The residue obtained by removing the solvent under reduced pressure was purified by silica gel column chromatography (eluting solvent: n-hexane/ethyl acetate=14/1-10/1) to give 1-tert-butyl-3-(dimethoxymethyl)-2-(methoxymethoxy)benzene (10.4 g, yield: 24%).

¹H-NMR (500 MHz, CDCl₃): δ 7.44 (1H, dd, J=7.6, 1.6 Hz), 7.33 (1H, dd, J=7.8, 1.6 Hz), 7.08 (1H, app t, J=7.8 Hz), 5.64 (1H, s), 5.06 (2H, s), 3.66 (3H, s), 3.38 (6H, s), 1.41 (9H, s).

(10-2)

A sec-butyl lithium-1.00M cyclohexane-n-hexane mixture solution (29.8 ml, 29.8 mmol) was added dropwise to a solution of 1-tert-butyl-3-(dimethoxymethyl)-2-(methoxymethoxy)benzene (4.00 g, 14.9 mmol) obtained in Example (10-1) and N,N,N',N'-tetramethylethylenediamine (4.72 ml, 31.3 mmol) in diethyl ether (100 ml) at –40° C. over 20 minutes. After the reaction mixture was stirred at room temperature for 1 hour, it was cooled to –20° C. and N,N-dimethylformamide (2.30 ml, 31.3 mmol) was added thereto. After the temperature of the reaction mixture was returned to room temperature and the mixture was further stirred for 1 hour, the mixture was carefully poured into cold 0.1N hydrochloric acid and the mixture was extracted with ethyl acetate (three times). The combined organic layer was successively washed with 0.1N hydrochloric acid, water (three times) and a saturated aqueous NaCl solution and dried with anhydrous sodium sulfate. The solvent was removed under reduced pressure to give a residue. The obtained residue was dissolved in methanol (10 ml) and sodium borohydride (111 mg, 3.00 mmol) was added thereto under ice-cooling, and the mixture was stirred at room temperature overnight. After the reaction mixture was poured into water and the mixture was extracted with ethyl acetate (four times), the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=10/1-3/1) to give [4-tert-butyl-2-(dimethoxymethyl)-3-(methoxymethoxy)phenyl]methanol (350 mg, yield: 8%).

$^1$H-NMR (400 MHz, CDCl$_3$): δ 7.27 (1H, d, J=7.8 Hz), 7.06 (1H, d, J=7.8 Hz), 5.74 (1H, s), 4.95 (2H, s), 4.75 (2H, d, J=6.8 Hz), 3.52 (1H, t, J=6.8 Hz), 3.64 (3H, s), 3.46 (6H, s), 1.39 (9H, s).

(10-3)

According to a method similar to Example (6-7), Example (6-8) and Example (6-9), using [4-tert-butyl-2-(dimethoxymethyl)-3-(methoxymethoxy)phenyl]methanol (161 mg, 0.540 mmol) obtained in Example (10-2) and methyl (4'-hydroxy-1,1'-biphenyl-4-yl)acetate (144 mg, 0.594 mmol) obtained in Example (6-2) as a starting material, tert-butyl 3-tert-butyl-2-hydroxy-6-[({4'-[(methoxycarbonyl)methyl]-1,1'-biphenyl-4-yl}oxy)methyl]benzoate was obtained (52 mg, three-step total yield: 19%).

$^1$H-NMR (400 MHz, CDCl$_3$): δ 12.05 (1H, s), 7.51-7.47 (4H, m), 7.37 (1H, d, J=7.8 Hz), 7.31 (2H, d, J=8.2 Hz), 7.01 (1H, d, J=7.8 Hz), 6.96 (2H, d, J=8.6 Hz), 5.29 (2H, s), 3.70 (3H, s), 3.65 (2H, s), 1.58 (9H, s), 1.42 (9H, s).

(10-4)

According to a method similar to Example 7, from tert-butyl 3-tert-butyl-2-hydroxy-6-[({4'-[(methoxycarbonyl)methyl]-1,1'-biphenyl-4-yl}oxy)methyl]benzoate (52 mg, 0.103 mmol) obtained in Example (10-3), the title compound was obtained as a white powder (44 mg, yield: 87%).

$^1$H-NMR (400 MHz, CDCl$_3$): δ 12.08 (1H, br s), 7.55-7.47 (4H, m), 7.39 (1H, br d, J=8.2 Hz), 7.33 (2H, br d, J=7.8 Hz), 7.03 (1H, br d, J=8.2 Hz), 6.98 (2H, br d, J=8.6 Hz), 5.30 (2H, s), 3.68 (2H, s), 1.58 (9H, s), 1.41 (9H, s).

MS (ESI) (m/z): 489 ([M−H]$^+$).

Example 11

(4'-{[2-(tert-Butoxycarbonyl)-3-hydroxy-4-(trifluoromethyl)benzyl]oxy}-3-fluoro-1,1'-biphenyl-4-yl)acetic acid (Exemplification Compound No.: 2-48)

(11-1)

Potassium cyanide (1.3 g, 20 mmol) was added to a solution of 4-bromo-2-fluorobenzylbromide (5.00 g, 18.7 mmol) in a mixture of ethanol-water (3:1, 40 ml), and the mixture was stirred at 60° C. for 2 hours. After the reaction mixture was poured into water and the mixture was extracted with ethyl acetate, the organic layer was washed with a saturated aqueous NaCl solution and dried with anhydrous sodium sulfate. The residue obtained by removing the solvent under reduced pressure was purified by silica gel column chromatography (eluting solvent: n-hexane/ethyl acetate) to give (4-bromo-2-fluorophenyl)acetonitrile in colorless solid form (3.75 g, yield: 94%).

$^1$H-NMR (400 MHz, CDCl$_3$): δ 7.35-7.26 (3H, m), 3.72 (2H, s).

(11-2)

According to a method similar to Example (8-1), from (4-bromo-2-fluorophenyl)acetonitrile (3.0 g, 14 mmol) obtained in Example (11-1) and 4-(4,4,5,5-tetramethyl-1,3,2-dioxaborolan-2-yl)phenol (3.45 g, 14 mmol), (3-fluoro-4'-hydroxy-1,1'-biphenyl-4-yl)acetonitrile was obtained as a colorless solid (2.9 g, yield: 91%).

$^1$H-NMR (400 MHz, MeOH-d$_4$): δ 7.50-7.34 (5H, m), 6.87 (2H, d, J=8.8 Hz), 3.92 (2H, s).

(11-3)

After acetic acid (10 ml) and concentrated hydrochloric acid (10 ml) were added to (3-fluoro-4'-hydroxy-1,1'-biphenyl-4-yl)acetonitrile (2.4 g, 11 mmol) obtained in Example (11-2), the mixture was stirred at 110° C. for 1 hour. After the reaction mixture was poured into water and the mixture was extracted with ethyl acetate, the organic layer was successively washed with water and a saturated aqueous NaCl solution and dried with anhydrous sodium sulfate. After allyl alcohol (20 ml) and concentrated sulfuric acid (1.5 ml) were successively added to the residue obtained by concentrating under reduced pressure, the mixture was stirred at room temperature for 1 hour. After the reaction mixture was poured into water and the mixture was extracted with ethyl acetate (three times), the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=5/1-2/1) to give allyl (3-fluoro-4'-hydroxy-1,1'-biphenyl-4-yl)acetate as a colorless solid (2.0 g, two-step total yield: 66%).

$^1$H-NMR (400 MHz, CDCl$_3$): δ 7.42 (2H, d, J=8.4 Hz), 7.31-7.21 (3H, m), 6.86 (2H, d, J=8.4 Hz), 5.97-5.88 (1H, m), 5.32 (1H, app d, J=16.4 Hz), 5.24 (1H, app d, J=10.4 Hz), 4.96 (1H, br s), 4.64 (2H, app d, J=6.0 Hz), 3.73 (2H, s).

(11-4)

According to a method similar to Example (6-7), from allyl (3-fluoro-4'-hydroxy-1,1'-biphenyl-4-yl)acetate (3.10 g, 10.9 mmol) obtained in Example (11-3) and [2-(dimethoxymethyl)-3-(methoxymethoxy)-4-(trifluoromethyl)phenyl]methanol (3.70 g, 12.0 mmol) obtained in Example (6-6), allyl (4'-{[2-(dimethoxymethyl)-3-(methoxymethoxy)-4-(trifluoromethyl)benzyl]oxy}-3-fluoro-1,1'-biphenyl-4-yl)acetate was obtained as a pale yellow oil (3.89 g, yield: 61%).

$^1$H-NMR (400 MHz, CDCl$_3$): δ 7.57-7.56 (2H, m), 7.47 (2H, d, J=8.4 Hz), 7.29-7.22 (3H, m), 7.03 (2H, d, J=8.4 Hz), 5.97-5.87 (1H, m), 5.77 (1H, s), 5.53 (2H, s), 5.30 (1H, app d, J=17.2 Hz), 5.23 (1H, app d, J=10.4 Hz), 5.04 (2H, s), 4.63 (2H, app d, J=5.6 Hz), 3.72 (2H, s), 3.67 (3H, s), 3.49 (6H, s).

(11-5)

According to a method similar to Example (12-4) and Example (12-5), from allyl (4'-{[2-(dimethoxymethyl)-3-(methoxymethoxy)-4-(trifluoromethyl)benzyl]oxy}-3-fluoro-1,1'-biphenyl-4-yl)acetate (3.89 g, 6.7 mmol) obtained in Example (11-4), allyl (4'-{[3-(allyloxy)-2-formyl-4-(trifluoromethyl)benzyl]oxy}-3-fluoro-1,1'-biphenyl-4-yl)acetate was obtained as a pale yellow solid (2.52 g, two-step total yield: 71%).

$^1$H-NMR (500 MHz, CDCl$_3$): δ 10.55 (1H, s), 7.88 (1H, d, J=8.5 Hz), 7.78 (1H, d, J=8.5 Hz), 7.52 (2H, d, J=8.5 Hz), 7.33-7.25 (3H, m), 7.06 (2H, d, J=8.5 Hz), 6.16-6.08 (1H, m), 5.96-5.89 (1H, m), 5.52 (2H, s), 5.49 (1H, dd, J=17.5, 1.5 Hz), 5.38 (1H, dd, J=10.0, 1.0 Hz), 5.31 (1H, dd, J=17.0, 1.5 Hz), 5.24 (1H, dd, J=10.0, 1.0 Hz), 4.64 (2H, app d, J=5.5 Hz), 4.60 (2H, app d, J=5.5 Hz), 3.73 (2H, s).

(11-6)

After an aqueous solution (22 ml) of sodium chlorite (2.6 g, 29 mmol) and sodium dihydrogenphosphate monohydrate (2.6 g, 19 mmol) was added dropwise to a solution of allyl (4'-{[3-(allyloxy)-2-formyl-4-(trifluoromethyl)benzyl]oxy}-3-fluoro-1,1'-biphenyl-4-yl)acetate (2.52 g, 4.8 mmol) obtained in Example (11-5) in a mixture of tert-butyl alcohol (51 ml), 1,4-dioxane (17 ml) and 2-methyl-2-butene (17 ml), the mixture was stirred at room temperature for 90 minutes. After a 5% aqueous sodium thiosulfate solution was added to the reaction mixture, the mixture was poured into 1N hydrochloric acid and the mixture was extracted with ethyl acetate (twice). The organic layer was successively washed with water and a saturated aqueous NaCl solution and dried with anhydrous sodium sulfate. The solvent was removed under reduced pressure to give a residue. Methylene chloride (50 ml), 2-methyl-1-propene (150 ml) and sulfuric acid (1 ml) were successively added to the obtained residue and the mixture was stirred at room temperature overnight. After the reaction mixture was poured into a 5% aqueous sodium hydrogencarbonate solution and the mixture was extracted with ethyl acetate (twice), the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=10/1-3/1) to give tert-butyl 2-(allyloxy)-6-{[(4'-{[(allyloxy)carbonyl]methyl}-3'-fluoro-1,1'-biphenyl-4-yl}oxy]methyl}-3-(trifluoromethyl)benzoate as a colorless powder (2.38 g, yield: 83%).

$^1$H-NMR (500 MHz, CDCl$_3$): δ 7.64 (1H, d, J=8.5 Hz), 7.50 (2H, d, J=8.5 Hz), 7.39 (1H, d, J=8.5 Hz), 7.31-7.23 (3H, m), 7.00 (2H, d, J=8.5 Hz), 6.11-6.03 (1H, m), 5.96-5.88 (1H, m), 5.43 (1H, dd, J=17.5, 1.5 Hz), 5.31 (1H, app d, J=17.0 Hz), 5.28 (1H, app d, J=10.0 Hz), 5.24 (1H, app d, J=10.0 Hz), 5.16 (2H, s), 4.64 (2H, app d, J=6.0 Hz), 4.58 (2H, app d, J=5.5 Hz), 3.73 (2H, s), 1.58 (9H, s).

(11-7)

Morpholine (0.27 ml, 3.3 mmol) and tetrakis(triphenylphosphine)palladium (0) (57 mg, 0.049 mmol) were successively added to a solution of tert-butyl 2-(allyloxy)-6-{[(4'-{[(allyloxy)carbonyl]methyl}-3'-fluoro-1,1'-biphenyl-4-yl)oxy]methyl}-3-(trifluoromethyl)benzoate (790 mg, 1.32 mmol) obtained in Example (11-6) in tetrahydrofuran (8 ml), and the mixture was stirred at room temperature for 1 hour. After water was poured into the reaction mixture and the mixture was extracted with ethyl acetate, the organic layer was successively washed with water and a saturated aqueous NaCl solution and dried with anhydrous sodium sulfate. After the residue obtained by removing the solvent under reduced pressure was purified by silica gel column chromatography (eluting solvent: n-hexane/ethyl acetate=3/1-0/1), it was crystallized from a mixture solvent of methylene chloride-ethyl acetate to give the title compound as a colorless powder (323 mg, yield: 47%).

$^1$H-NMR (500 MHz, CDCl$_3$): δ 12.26 (1H, s), 7.71 (1H, d, J=8.5 Hz), 7.52 (2H, d, J=8.5 Hz), 7.32-7.26 (4H, m), 6.98 (2H, d, J=8.5 Hz), 5.38 (2H, s), 3.76 (2H, s), 1.65 (9H, s).

MS (ESI) (m/z): 519 ([M−H]$^+$).

Example 12

(4'-{[2-(tert-Butoxycarbonyl)-3-hydroxy-4-(trifluoromethyl)benzyl]oxy}-3'-fluoro-1,1'-biphenyl-4-yl) acetic acid (Exemplification Compound No.: 2-51)

(12-1)

After 4,4,4',4',5,5,5',5'-octamethyl-2,2'-bi-1,3,2-dioxaborolane [bis(pinacolate)diborone, 21.2 g, 83.6 mmol], [1,1'-bis(diphenylphosphino)ferrocene]dichloropalladium (II)-dichloromethane adduct (3.1 g, 3.8 mmol) and potassium acetate (22.4 g, 228 mmol) were added to a solution of methyl 4-bromophenylacetate (17.4 g, 76.0 mmol) obtained in Example (3-1) in 1,4-dioxane (300 ml), the mixture was stirred at 90° C. for 4 hours. After ethyl acetate was added to the reaction mixture and was filtered through Celite, the filtrate was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=20/1-9/1) to give methyl[4-(4,4,5,5-tetramethyl-1,3,2-dioxaborolan-2-yl)phenyl]acetate as an oil (21.0 g, yield: 100%).

$^1$H-NMR (400 MHz, CDCl$_3$): δ 7.77 (2H, d, J=8.2 Hz), 7.29 (2H, d, J=8.2 Hz), 3.68 (3H, s), 3.64 (2H, s), 1.35-1.32 (12H, m).

(12-2)

According to a method similar to Examples (13-1) and (13-2), using methyl [4-(4,4,5,5-tetramethyl-1,3,2-dioxaborolan-2-yl)phenyl]acetate (1.38 g, 5.0 mmol) obtained in Example (12-1) and 4-bromo-2-fluoro-phenol (1.15 g, 6.0 mmol) as a starting material, allyl (3'-fluoro-4'-hydroxy-1,1'-biphenyl-4-yl)acetate was obtained as a white powder (430 mg, yield: 33%).

$^1$H-NMR (400 MHz, CDCl$_3$): δ 7.50-7.45 (2H, m), 7.37-7.23 (4H, m), 7.08-7.02 (1H, m), 5.98-5.86 (1H, m), 5.34-5.21 (3H, m), 4.65-4.59 (2H, m), 3.69 (2H, s).

(12-3)

According to a method similar to Example (6-7), from allyl (3'-fluoro-4'-hydroxy-1,1'-biphenyl-4-yl)acetate (300 mg, 1.05 mmol) obtained in Example (12-2) and [2-(dimethoxymethyl)-3-(methoxymethoxy)-4-(trifluoromethyl)phenyl]methanol (500 mg, 1.61 mmol) obtained in Example (6-6), allyl (4'-{[2-(dimethoxymethyl)-3-(methoxymethoxy)-4-(trifluoromethyl)benzyl]oxy}-3'-fluoro-1,1'-biphenyl-4-yl)acetate was obtained (618 mg, yield: 93%).

$^1$H-NMR (400 MHz, CDCl$_3$): δ 7.60 (1H, d, J=8.2 Hz), 7.57 (1H, d, J=8.2 Hz), 7.45 (2H, d, J=8.2 Hz), 7.34-7.29 (3H, m), 7.21-7.17 (1H, m), 7.03 (1H, app t, J=8.6 Hz), 5.95-5.84 (1H, m), 5.74 (1H, s), 5.57 (2H, s), 5.31-5.19 (2H, m), 5.03 (2H, s), 4.62-4.68 (2H, m), 3.67 (2H, s), 3.66 (3H, s), 3.47 (6H, s).

(12-4)

p-Toluenesulfonic acid monohydrate (223 mg, 1.18 mmol) was added to a solution of allyl (4'-{[2-(dimethoxymethyl)-3-(methoxymethoxy)-4-(trifluoromethyl)benzyl]oxy}-3'-fluoro-1,1'-biphenyl-4-yl)acetate (618 mg, 1.06 mmol) obtained in Example (12-3) in acetone (10 ml), and the mixture was stirred at 50° C. for 1 hour. The residue obtained by concentrating the reaction mixture was diluted with ethyl acetate. The obtained solution was successively washed with a saturated aqueous sodium hydrogencarbonate solution, water and a saturated aqueous NaCl solution and dried with anhydrous sodium sulfate. The residue obtained by removing the solvent under reduced pressure was purified by silica gel column chromatography (eluting solvent: n-hexane/ethyl acetate=3/1) to give allyl (3'-fluoro-4'-{[2-formyl-3-hydroxy-4-(trifluoromethyl)benzyl]oxy}-1,1'-biphenyl-4-yl) acetate (476 mg, yield: 91%).

$^1$H-NMR (400 MHz, CDCl$_3$): δ 12.68 (1H, s), 10.44 (1H, s), 7.80 (1H, d, J=7.8 Hz), 7.49 (2H, d, J=7.8 Hz), 7.39-7.27 (4H, m), 7.13-7.06 (2H, m), 5.98-5.86 (1H, m), 5.43 (2H, s), 5.34-5.21 (2H, m), 4.64-4.60 (2H, m), 3.69 (2H, s).

(12-5)

Potassium carbonate (148 mg, 1.07 mmol) and allyl bromide (0.091 ml, 1.1 mmol) were successively added to a solution of allyl (3'-fluoro-4'-{[2-formyl-3-hydroxy-4-(trifluoromethyl)benzyl]oxy}-1,1'-biphenyl-4-yl)acetate (476 mg, 0.975 mmol) obtained in Example (12-4) in N,N-dimethylformamide (5 ml), and the mixture was stirred at 50° C. for 1.5 hours. After the reaction mixture was poured into water and the mixture was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=3/

1) to give allyl (4'-{[3-(allyloxy)-2-formyl-4-(trifluoromethyl)benzyl]oxy}-3'-fluoro-1,1'-biphenyl-4-yl)acetate (122 mg, yield: 24%).

$^1$H-NMR (400 MHz, CDCl$_3$): δ 10.54 (1H, s), 7.92 (1H, d, J=8.4 Hz), 7.87 (1H, d, J=8.4 Hz), 7.50 (2H, d, J=7.8 Hz), 7.40-7.25 (4H, m), 7.09 (1H, app t, J=8.6 Hz), 6.18-6.05 (1H, m), 5.97-5.86 (1H, m), 5.56 (2H, s), 5.53-5.19 (4H, m), 4.67-4.56 (4H, m), 3.69 (2H, s).

(12-6)

After an aqueous solution (1.1 ml) of sodium chlorite (125 mg, 1.38 mmol) and sodium dihydrogenphosphate monohydrate (125 mg, 0.91 mmol) was added dropwise to a solution of allyl (4'-{[3-(allyloxy)-2-formyl-4-(trifluoromethyl)benzyl]oxy}-3'-fluoro-1,1'-biphenyl-4-yl)acetate obtained in Example (12-5) in a mixture of tert-butyl alcohol (2.4 ml), 1,4-dioxane (0.8 ml) and 2-methyl-2-butene (0.8 ml), the mixture was stirred at room temperature for 2 hours. After a 5% aqueous sodium thiosulfate solution was added to the reaction mixture, the mixture was poured into 1N hydrochloric acid and extracted with ethyl acetate (twice). The organic layer was successively washed with water and a saturated aqueous NaCl solution and dried with anhydrous sodium sulfate. The solvent was removed under reduced pressure to give a residue. The obtained residue was purified by silica gel column chromatography (eluting solvent: ethyl acetate) to give 2-(allyloxy)-6-{[(4'-{[(allyloxy)carbonyl]methyl}-3-fluoro-1,1'-biphenyl-4-yl)oxy]methyl}-3-(trifluoromethyl) benzoic acid (135 mg, yield: 100%).

$^1$H-NMR (400 MHz, CDCl$_3$): δ 7.74 (1H, d, J=8.2 Hz), 7.54 (1H, d, J=8.2 Hz), 7.42 (2H, d, J=8.2 Hz), 7.34-7.19 (4H, m), 7.00 (1H, app t, J=8.4 Hz), 6.12-6.00 (1H, m), 5.96-5.84 (1H, m), 5.47-5.18 (6H, m), 4.62-4.58 (4H, m), 3.67 (2H, s).

(12-7)

N,N-Dimethylaminopyridine (9.5 mg, 0.077 mmol) and di-tert-butyl dicarbonate [(tBuOCO)$_2$O] (156 mg, 0.715 mmol) were added to a solution of 2-(allyloxy)-6-{[(4'-{[(allyloxy)carbonyl]methyl}-3-fluoro-1',1-biphenyl-4-yl)oxy]methyl}-3-(trifluoromethyl)benzoic acid (135 mg, 0.248 mmol) obtained in Example (12-6) in tert-butyl alcohol (2 ml), and the mixture was stirred at 50° C. for 1 hour. The reaction mixture was concentrated under reduced pressure and the residue was purified by silica gel column chromatography (eluting solvent: n-hexane/ethyl acetate=19/1-4/1) to give tert-butyl 2-(allyloxy)-6-{[(4'-{[(allyloxy)carbonyl]methyl}-3-fluoro-1',1-biphenyl-4-yl)oxy]methyl}-3-(trifluoromethyl)benzoate (65 mg, yield: 44%).

$^1$H-NMR (400 MHz, CDCl$_3$): 7.63 (1H, d, J=8.2 Hz), 7.46 (2H, d, J=8.2 Hz), 7.42 (1H, d, J=8.2 Hz), 7.35-7.29 (3H, m), 7.25-7.21 (1H, m), 6.97 (1H, app t, J=8.6 Hz), 6.10-5.99 (1H, m), 5.95-5.85 (1H, m), 5.45-5.38 (1H, m), 5.31-5.19 (5H, m), 4.62-4.59 (2H, m), 4.58-4.54 (2H, m), 3.68 (2H, s), 1.59 (9H, s).

(12-8)

According to a method similar to Example (11-7), from tert-butyl 2-(allyloxy)-6-{[(4'-{[(allyloxy)carbonyl]methyl}-3-fluoro-1'1-biphenyl-4-yl)oxy]methyl}-3-(trifluoromethyl)benzoate (65 mg, 0.108 mmol) obtained in Example (12-7), the title compound was obtained as a pale yellow powder (45 mg, yield: 80%).

$^1$H-NMR (400 MHz, CDCl$_3$): δ 12.23 (1H, s), 7.71 (1H, d, J=8.2 Hz), 7.48 (2H, d, J=8.2 Hz), 7.37-7.29 (4H, m), 7.26-7.22 (1H, m), 6.92 (1H, app t, J=8.6 Hz), 5.43 (2H, s), 3.70 (2H, s), 1.66 (9H, s).

MS (ESI) (m/z): 519 ([M−H]$^+$).

Example 13

(4'-{[2-(tert-Butoxycarbonyl)-3-hydroxy-4-(trifluoromethyl)benzyl]oxy}-2'-chloro-1,1'-biphenyl-4-yl) acetic acid (Exemplification Compound NO.: 2-60)

(13-1)

After a 2N aqueous sodium carbonate solution (12 ml) and tetrakis(triphenylphosphine)palladium (0) (504 mg, 0.436 mmol) were added to a solution of methyl [4-(4,4,5,5-tetramethyl-1,3,2-dioxaborolan-2-yl)phenyl]acetate (2.41 g, 8.73 mmol) obtained in Example (12-1) and 4-bromo-3-chlorophenol (2.17 g, 10.5 mmol) in a mixture of toluene-ethanol (5:1, 36 ml), the mixture was stirred at 110° C. for 8 hours. After the temperature of the reaction mixture was returned to room temperature and ethanol (12 ml) and a 1N aqueous sodium hydroxide solution (15 ml, 15 mmol) were added thereto, the mixture was stirred at 60° C. for 3 hours. The reaction mixture was poured into 0.5N hydrochloric acid and the mixture was extracted with ethyl acetate (three times). The organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=85/15-50/50) to give (2'-chloro-4'-hydroxy-1,1'-biphenyl-4-yl)acetic acid as a pale yellow powder (1.95 g, yield: 85%).

$^1$H-NMR (400 MHz, CD$_3$OD): δ 7.35-7.28 (4H, m), 7.15 (1H, d, J=7.8 Hz), 6.90 (1H, d, J=2.3 Hz), 6.77 (1H, dd, J=7.8, 2.3 Hz), 3.64 (2H, s).

MS (FAB) (m/z): 262 ([M]$^+$).

(13-2)

After allyl alcohol (7.0 ml, 103 mmol) and concentrated sulfuric acid (0.1 ml) were successively added to a solution of (2'-chloro-4'-hydroxy-1,1'-biphenyl-4-yl)acetic acid (1.93 g, 7.35 mmol) obtained in Example (13-1) in benzene (30 ml), the mixture was heated under reflux for 1 hour. The reaction mixture was poured into water and extracted with ethyl acetate (twice). The organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ ethyl acetate=90/10-65/35) to give allyl (2'-chloro-4'-hydroxy-1,1'-biphenyl-4-yl)acetate as a white powder (1.97 g, yield: 899.

$^1$H-NMR (400 MHz, CDCl$_3$): δ 7.33 (2H, d, J=7.8 Hz), 7.30 (2H, d, J=7.8 Hz), 7.09 (1H, d, J=7.8 Hz), 6.92 (1H, d, J=2.3 Hz), 6.66 (1H, dd, J=7.8, 2.3 Hz), 5.97-5.85 (1H, m), 5.70 (1H, s), 5.29 (1H, dd, J=17.2, 1.6 Hz), 5.23 (1H, br d, J=10.2 Hz), 4.63 (2H, app d, J=5.5 Hz), 3.71 (2H, s).

MS (EI) (m/z): 302 ([M]$^+$).

(13-3)

According to a method similar to Example (6-7), from [2-(dimethoxymethyl)-3-methoxymethoxy)-4-(trifluoromethyl)phenyl]methanol (1.04 g, 3.35 mmol) obtained in Example (6-6) and allyl (2'-chloro-4'-hydroxy-1,1'-biphenyl-4-yl)acetate (1.17 g, 3.86 mmol) obtained in Example (13-2), allyl (2'-chloro-4'-{[2-(dimethoxymethyl)-3-(methoxymethoxy)-4-(trifluoromethyl)benzyl]oxy}-1,1'-biphenyl-4-yl)acetate was obtained as a pale yellow oil (1.88 g, yield: 94%).

$^1$H-NMR (400 MHz, CDCl$_3$): , 7.59 (1H, d, J=8.6 Hz), 7.54 (1H, d, J=8.6 Hz), 7.37 (2H, d, J=8.2 Hz), 7.33 (2H, d, J=8.2 Hz), 7.21 (1H, d, J=8.6 Hz), 7.13 (1H, d, J=2.3 Hz), 6.93 (1H, dd, J=8.6, 2.3 Hz), 5.98-5.87 (1H, m), 5.77 (1H, s), 5.51 (2H, br s), 5.29 (1H, dd, J=17.2, 1.6 Hz), 5.23 (1H, br d, J=10.9 Hz), 5.04 (2H, s), 4.62 (2H, d, J=6.3 Hz), 3.69 (2H, s), 3.67 (3H, s), 3.50 (6H, s).

MS (FAB) (m/z): 594 ([M]$^+$).

(13-4)

4N Hydrochloric acid (3.5 ml) was added to a solution of allyl (2'-chloro-4'-{[2-(dimethoxymethyl)-3-(methoxymethoxy)-4-(trifluoromethyl)benzyl]oxy}-1,1'-biphenyl-4-yl)acetate (1.83 g, 3.08 mmol) obtained in Example (13-3) in tetrahydrofuran (35 ml), and the mixture was stirred at 45° C. for 4 hours. After water was poured into the reaction mixture and the mixture was extracted with ethyl acetate (twice), the organic layer was successively washed with water and a saturated aqueous NaCl solution and dried with anhydrous sodium sulfate. The solvent was removed under reduced pressure to give a crude aldehyde compound. According to a method similar to Example (12-5), Example (12-6) and Example (12-7), using the crude aldehyde compound obtained in the above as a starting material, tert-butyl 2-(allyloxy)-6-{[(4'-{[(allyloxy)carbonyl]methyl}-2-chloro-1,1'-biphenyl-4-yl)oxy]methyl}-3-(trifluoromethyl)benzoate was obtained as a pale yellow oil (967 mg, four-step total yield: 51%).

$^1$H-NMR (400 MHz, CDCl$_3$): δ 7.65 (1H, d, J=7.8 Hz), 7.40-7.32 (1H, overlapped with δ 7.38 or 7.34), 7.38 (2H, d, J=7.8 Hz), 7.34 (2H, d, J=7.8 Hz), 7.24 (1H, d, J=8.6 Hz), 7.06 (1H, d, J=2.3 Hz), 6.89 (1H, dd, J=8.6, 2.3 Hz), 6.14-6.01 (1H, m), 5.99-5.87 (1H, m), 5.43 (1H, d, J=17.2 Hz, 5.33-5.20 (3H, m), 5.15 (2H, s), 4.62 (2H, app d, J=6.3 Hz), 4.58 (2H, br d, J=5.4 Hz), 3.70 (2H, s), 1.59 (9H, s).

MS (FAB) (m/z): 616 ([M]$^+$).

$^1$H-NMR spectrum of the crude aldehyde compound obtained as an intermediate, allyl (2'-chloro-4'-{[2-formyl-3-hydroxy-4-(trifluoromethyl)benzyl]oxy}-1,1'-biphenyl-4-yl)acetate is shown below.

$^1$H-NMR (400 MHz, CDCl$_3$): δ 12.61 (1H, br s), 10.31 (1H, s), 7.80 (1H, d, J=7.8 Hz), 7.36 (2H, d, J=8.6 Hz), 7.32 (2H, d, J=8.6 Hz), 7.26 (1H, d, J=7.8 Hz), 7.10-7.05 (2H, m), 6.90 (1H, dd, J=7.8, 2.3 Hz), 5.97-5.85 (1H, m), 5.34 (2H, s), 5.28 (1H, dd, J=17.2, 1.6 Hz), 5.22 (1H, br d, J=10.2 Hz), 4.61 (2H, app d, J=5.5 Hz), 3.70 (2H, s).

(13-5)

Pyrrolidine (0.525 ml, 6.29 mmol) and tetrakis(triphenylphosphine)palladium (0) (41 mg, 0.035 mmol) were added to a solution of tert-butyl 2-(allyloxy)-6-{[(4'-{[(allyloxy)carbonyl]methyl}-2-chloro-1,1'-biphenyl-4-yl)oxy]methyl}-3-(trifluoromethyl)benzoate (960 mg, 1.56 mmol) obtained in Example (13-4) in a mixture of 1,4-dioxane (9.5 ml) and water (0.5 ml), and the mixture was stirred at room temperature for 3 hours. After water was poured into the reaction mixture and the mixture was extracted with ethyl acetate (three times), the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=75/25-40/60) to give the title compound as a white powder (446 mg, yield: 74%).

$^1$H-NMR (400 MHz, CDCl$_3$): δ 12.26 (1H, br a), 7.73 (1H, d, J=7.8 Hz), 7.40 (2H, d, J=8.2 Hz), 7.35 (2H, d, J=8.2 Hz), 7.28-7.24 (2H, m), 7.06 (1H, d, T=2.7 Hz), 6.88 (1H, dd, J=8.6, 2.7 Hz), 5.36 (2H, s), 3.71 (2H, s), 1.67 (9H, s).

MS (FAB) (m/z): 536 ([M]$^+$).

Example 14

(4'-{[2-(tert-Butoxycarbonyl)-3-hydroxy-4-(trifluoromethyl)benzyl]oxy}-2'-fluoro-1,1'-biphenyl-4-yl) acetic acid (Exemplification Compound No.: 2-54)

(14-1)

After palladium acetate (II) (50 mg, 0.22 mmol), tri-o-tolylphosphine (135 mg, 0.44 mmol) and a 2N aqueous sodium carbonate solution (15 ml) were added to a solution of methyl [4-(4,4,5,5-tetramethyl-1,3,2-dioxaborolan-2-yl)phenyl]acetate (2.04 g, 7.39 mmol) obtained in Example (12-1) and 4-bromo-3-fluorophenol (1.69 g, 8.87 mol) in N,N-dimethylformamide (50 ml), the mixture was stirred at 80° C. for 3 hours. The reaction mixture was poured into 0.5N hydrochloric acid and the mixture was extracted with ethyl acetate (three times). The organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=80/20-50/50) to give methyl (2'-fluoro-4'-hydroxy-1,1'-biphenyl-4-yl)acetate (1.13 g, yield: 59%).

$^1$H-NMR (400 MHz, CDCl$_3$): δ 7.43 (2H, br d, J=8.0 Hz), 7.31 (2H, br d, J=8.0 Hz), 7.26-7.21 (1H, m), 6.66-6.60 (2H, m), 5.25 (1H, br s), 3.71 (3H, s), 3.66 (2H, s).

(14-2)

According to a method similar to Example (6-7), from methyl (2'-fluoro-4'-hydroxy-1,1'-biphenyl-4-yl)acetate (1.02 g, 3.94 mmol) obtained in Example (14-1) and [2-(dimethoxymethyl)-3-(methoxymethoxy)-4-(trifluoromethyl)phenyl]methanol (1.71 g, 5.52 mmol) obtained in Example (6-6), methyl (4'-{[2-(dimethoxymethyl)-3-(methoxymethoxy)-4-(trifluoromethyl)benzyl]oxy}-2'-fluoro-1,1'-biphenyl-4-yl)acetate was obtained (2.01 g, yield: 92%).

$^1$H-NMR (400 MHz, CDCl$_3$): δ 7.58-7.51 (2H, m), 7.45-7.42 (2H, m), 7.33-7.23 (4H, m), 6.83-6.73 (1H, m), 5.75 (1H, s), 5.49 (2H, s), 5.03 (2H, s), 3.70 (3H, s), 3.66 (3H, s), 3.65 (2H, s), 3.48 (6H, s).

(14-3)

According to a method similar to Example (6-8) and Example (6-9), from methyl (4'-{[2-(dimethoxymethyl)-3-(methoxymethoxy)-4-(trifluoromethyl)benzyl]oxy}-2'-fluoro-1,1'-biphenyl-4-yl)acetate (2.01 g, 3.64 mmol) obtained in Example (14-2), tert-butyl 6-[({2-fluoro-4'-[(methoxycarbonyl)methyl]-1,1'-biphenyl-4-yl}oxy)methyl]-2-hydroxy-3-(trifluoromethyl)benzoate was obtained (568 mg, two-step total yield: 29%).

$^1$H-NMR (500 MHz, CDCl$_3$): δ 12.27 (1H, br s), 7.71 (1H, br d, J=8.3 Hz), 7.48 (2H, br d, J=7.8 Hz), 7.40-7.32 (3H, m), 7.24 (1H, br d, J=8.3 Hz), 6.78 (1H, app dd, J=8.6, 2.4 Hz), 6.73 (1H, app dd, J=12.2, 2.4 Hz), 5.35 (2H, s), 3.71 (3H, s), 3.66 (2H, s), 1.65 (9H, s).

(14-4)

According to a method similar to Example 7, from tert-butyl 6-[({2-fluoro-4'-[(methoxycarbonyl)methyl]-1,1'-biphenyl-4-yl}oxy)methyl]-2-hydroxy-3-(trifluoromethyl) benzoate (568 mg, 1.06 mmol) obtained in Example (14-3), the title compound was obtained as a white powder (404 mg, yield: 73%).

$^1$H-NMR (500 MHz, CD$_3$OD): δ 7.65 (1H, br d, J=8.3 Hz), 7.34 (2H, br d, J=8.3 Hz), 7.31 (1H, br d, J=8.3 Hz), 7.23 (2H, br d, J=8.3 Hz), 7.20 (1H, br d, J=8.3 Hz), 6.77 (1H, app dd, J=8.3, 2.4 Hz), 6.74 (1H, app dd, J=12.7, 2.4 Hz), 5.30 (2H, s), 3.52 (2H, s), 1.53 (9H, s).

MS (ESI) (m/z): 519 ([M−H]$^+$).

Example 15

1-(4'-{[2-(tert-Butoxycarbonyl)-3-hydroxy-4-(trifluoromethyl)benzyl]oxy}-1,1'-biphenyl-4-yl)cyclopropanecarboxylic acid (Exemplification Compound No.: 1-64)

(15-1)

After sodium hydride (55% oily) (2.40 g, 55.0 mmol) was added to a solution of methyl (4-bromophenyl)acetate (5.73 g, 25.0 mmol) obtained in Example (3-1) in N,N-dimethylformamide (50 ml) at 0° C., the mixture was stirred at room temperature for 10 minutes. After the reaction mixture was cooled to 0° C. and 1,2-dibromoethane (2.37 ml, 27.5 mmol) was added thereto, the mixture was further stirred at room temperature for 15 hours. After a saturated aqueous ammonium chloride solution was poured into the reaction mixture and the mixture was extracted with ethyl acetate, the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=9/1) to give methyl 1-(4-bromophenyl)cyclopropanecarboxylate as an oil (2.97 g, yield: 47%).

$^1$H-NMR (400 MHz, CDCl$_3$): δ 7.43 (2H, d, J=8.2 Hz), 7.22 (2H, d, J=8.2 Hz), 3.63 (3H, s), 1.63-1.59 (2H, m), 1.18-1.14 (2H, m).

(15-2)

According to a method similar to Example (8-1), from methyl 1-(4-bromophenyl)cyclopropanecarboxylate (2.96 g, 11.6 mmol) obtained in Example (15-1) and 4-(4,4,5,5-tetramethyl-1,3,2-dioxaborolan-2-yl)phenol (2.55 g, 11.6 mmol), methyl 1-(4'-hydroxy-1,1'-biphenyl-4-yl)cyclopropanecarboxylate was obtained as a white powder (2.49 g, yield: 80%).

$^1$H-NMR (400 MHz, CDCl$_3$): δ 7.46 (2H, d, J=8.2 Hz), 7.44 (2H, d, J=8.6 Hz), 7.36 (2H, d, J=8.2 Hz), 6.86 (2H, d, J=8.6 Hz), 4.95 (1H, s), 3.64 (3H, s), 1.65-1.61 (2H, m), 1.24-1.20 (2H, m).

(15-3)

According to a method similar to Example 7 and Example (13-2), from methyl 1-(4'-hydroxy-1,1'-biphenyl-4-yl)cyclopropanecarboxylate (2.49 g, 9.28 mmol) obtained in Example (15-2), allyl 1-(4'-hydroxy-1,1'-biphenyl-4-yl)cyclopropanecarboxylate as a white powder (2.1 g, two-step yield: 77%).

In the present step, the hydrolysis step corresponding to Example (7) was carried out at the reaction temperature of 60° C.

$^1$H-NMR (400 MHz, CDCl$_3$): δ 7.47-7.41 (4H, m), 7.37 (2H, d, J=8.2 Hz), 6.85 (2H, d, J=8.6 Hz), 5.88-5.77 (1H, m), 5.20-5.12 (2H, m), 5.09 (1H, s), 4.57-4.54 (2H, m), 1.67-1.63 (2H, m), 1.27-1.22 (2H, m).

(15-4)

According to a method similar to Example (6-7), Example (12-4), Example (12-5) and Example (12-6), using allyl 1-(4'-hydroxy-1,1'-biphenyl-4-yl)cyclopropanecarboxylate (479 mg, 1.63 mmol) obtained in Example (15-3) and [2-(dimethoxymethyl)-3-(methoxymethoxy)-4-(trifluoromethyl)phenyl]methanol (505 mg, 1.63 mmol) obtained in Example (6-6) as a starting material, 2-(allyloxy)-6-{[(4'-{1-[(allyloxy)carbonyl]cyclopropyl}-1,1'-biphenyl-4-yl)oxy]methyl}-3-(trifluoromethyl)benzoic acid was obtained (175 mg, four-step total yield: 19%).

$^1$H-NMR (400 MHz, CDCl$_3$): δ 7.72 (1H, d, J=8.2 Hz), 7.51-7.45 (3H, m), 7.43 (2H, d, J=8.2 Hz), 7.36 (2H, d, J=8.2 Hz), 6.98 (2H, d, J=8.6 Hz), 6.11-6.00 (1H, m), 5.87-5.76 (1H, m), 5.45-5.38 (1H, m), 5.30-5.23 (3H, m), 5.19-5.10 (2H, m), 4.61-4.58 (2H, m), 4.56-4.53 (2H, m), 1.66-1.62 (2H, m), 1.25-1.21 (2H, m).

(15-5)

2-(Allyloxy)-6-{[(4'-{1-[(allyloxy)carbonyl]cyclopropyl}-1,1'-biphenyl-4-yl-oxy]methyl}-3-(trifluoromethyl)benzoic acid (175 mg, 0.317 mmol) obtained in Example (15-4) and N,N-dimethylformamide di-tert-butylacetal (0.300 ml, 1.27 mmol) were dissolved in toluene (2 ml), and the mixture was heated under reflux for 2 hours. The reaction mixture was concentrated under reduced pressure and the obtained residue was purified by silica gel column chromatography (eluting solvent: n-hexane/ethyl acetate=3/1) to give tert-butyl 2-(allyloxy)-6-{[(4'-{1-[(allyloxy)carbonyl]cyclopropyl}-1,1'-biphenyl-4-yl)oxy]methyl}-3-(trifluoromethyl)benzoate (122 mg, yield: 63%).

$^1$H-NMR (400 MHz, CDCl$_3$): δ 7.62 (1H, d, J=8.2 Hz), 7.50 (2H, d, J=8.6 Hz), 7.47 (2H, d, J=8.6 Hz), 7.40-7.36 (3H, m), 6.97 (2H, d, J=8.6 Hz), 6.11-6.00 (1H, m), 5.88-5.76 (1H, m), 5.45-5.38 (1H, m), 5.29-5.24 (1H, m), 5.19-5.11 (4H, m), 4.58-4.53 (4H, m), 1.67-1.63 (2H, m), 1.58 (9H, s), 1.26-1.21 (2H, m).

(15-6)

According to a method similar to Example (11-7), from tert-butyl 2-(allyloxy)-6-{[(4'-1-[(allyloxy)carbonyl]cyclopropyl)-1,1'-biphenyl-4-yl)oxy]methyl}-3-(trifluoromethyl)benzoate (122 mg, 0.2 mmol) obtained in Example (15-5), the title compound was obtained as a pale yellow powder (63 mg, yield: 59%).

$^1$H-NMR (400 MHz, CDCl$_3$): δ 12.23 (1H, s), 7.68 (1H, d, J=8.2 Hz), 7.50 (2H, d, J=8.6 Hz), 7.48 (2H, d, J=8.2 Hz), 7.39 (2H, d, J=8.2 Hz), 7.25 (1H, d, J=8.2 Hz), 6.95 (2H, d, J=8.6 Hz), 5.36 (2H, s), 1.72-1.68 (2H, m), 1.64 (9H, s), 1.33-1.28 (2H, m).

MS (ESI) (m/z): 527 ([M−H]$^+$).

Example 16

(4'-{[2-(tert-Butoxycarbonyl)-3-hydroxy-4-(trifluoromethyl)benzyl]oxy}-2-fluoro-1,1'-biphenyl-4-yl)acetic acid (Exemplification Compound No.: 2-45)

(16-1)

According to a method similar to Example (17-1), from (4-bromo-3-fluorophenyl)methanol which was synthesized according to the method described in literature (deSolms. et al., J. Med. Chem., 2003, vol. 46, pp. 2973-2984), (4-bromo-3-fluorophenyl)-acetonitrile was obtained as a colorless oil (1.60 g, yield: 75%).

(16-2)

According to a method similar to Example (8-1) and Example (11-3), using (4-bromo-3-fluorophenyl)acetonitrile (1.6 g, 7.5 mmol) obtained in Example (16-1) and 4-(4,4,5,5-tetramethyl-1,3,2-dioxaborolan-2-yl)phenol (1.65 g, 7.5 mmol) as a starting material, allyl (2-fluoro-4'-hydroxy-1,1'-biphenyl-4-yl)acetate was obtained as a colorless solid (0.78 g, three-step total yield: 36%).

$^1$H-NMR (500 MHz, CDCl$_3$): δ 7.45 (2H, d, J=9.0 Hz), 7.24 (1H, app s), 7.14 (1H, app d, J=9.0 Hz), 6.96 (1H, app d, J=9.0 Hz), 6.90 (2H, d, J=9.0 Hz), 5.94-5.89 (1H, m), 5.30 (1H, dd, J=17.5, 1.5 Hz), 5.24 (1H, dd, J=10.0, 1.5 Hz), 4.89 (1H, br s), 4.62 (2H, app d, J=5.5 Hz), 3.69 (2H, s).

MS (ESI) (m/z): 285 ([M−H]$^+$).

(16-3)

According to a method similar to Example (6-7), Example (12-4), Example (12-5), Example (12-6) and Example (12-7), using allyl (2-fluoro-4'-hydroxy-1,1'-biphenyl-4-yl)acetate (650 mg, 2.27 mmol) obtained in Example (16-2) and [2-(dimethoxymethyl)-3-(methoxymethoxy)-4-(trifluoromethyl)phenyl]methanol (987 mg, 3.18 mmol) obtained in Example (6-6) as a starting material, tert-butyl 2-(allyloxy)-6-{[(4'-([(allyloxy)carbonyl]methyl)-2'-fluoro-1,1'-biphenyl-4-yl)oxy]methyl}-3-(trifluoromethyl)benzoate was obtained as a pale yellow oil (360 mg, five-step total yield: 26%).

$^1$H-NMR (500 MHz, CDCl$_3$): δ 7.65 (1H, d, J=8.5 Hz), 7.50 (2H, d, J=9.0 Hz), 7.39 (1H, d, J=8.5 Hz), 7.24 (1H, app s), 7.15 (1H, app d, J=9.5 Hz), 7.00 (2H, d, J=9.0 Hz), 6.96 (1H, app d, J=9.5 Hz), 6.11-6.03 (1H, m), 5.95-5.88 (1H, m), 5.43 (1H, dd, J=17.0, 1.5 Hz), 5.32-5.27 (2H, m), 5.24 (1H, dd, J=10.0, 1.0 Hz), 5.16 (2H, s), 4.62 (2H, app d, J=5.5 Hz), 4.58 (2H, app d, J=5.5 Hz), 3.69 (2H, s), 1.58 (9H, s).

(16-4)

According to a method similar to Example (11-7), from tert-butyl 2-(allyloxy)-6-{[(4'-([(allyloxy)carbonyl]methyl)-2'-fluoro-1,1'-biphenyl-4-yl)oxy]methyl}-3-(trifluoromethyl)benzoate (360 mg, 0.59 mmol) obtained in Example (16-3), the title compound was obtained as a colorless powder (144 mg, yield: 47%).

$^1$H-NMR (400 MHz, CDCl$_3$): δ 12.22, (1H, s), 7.68 (1H, d, J=8.4 Hz), 7.49 (2H, d, J=8.4 Hz), 7.25-7.23 (2H, m), 7.15 (1H, app d, J=9.6 Hz), 6.97-6.94 (3H, m), 5.36 (2H, s), 3.70 (2H, s), 1.64 (9H, s).

MS (FAB) (m/z): 543 ([M+Na]$^+$).

Example 17

(4'-{[2-(tert-Butoxycarbonyl)-3-hydroxy-4-(trifluoromethyl)benzyl]oxy}-3-methyl-1,1'-biphenyl-4-yl)acetic acid (Exemplification Compound No.: 2-47)

(17-1)

After carbon tetrabromide (6.7 g, 20 mmol) and triphenylphosphine (5.2 g, 20 mmol) were added to a solution of (4-bromo-2-methylphenyl)methanol (3.7 g, 18.4 mmol) which was synthesized according to the method described in literature (Dawson, M. I., et al., J. Med. Chem., 1984, vol. 27, pp. 1516-1531) under ice-cooling, the mixture was stirred at room temperature for 1 hour. Hexane was added to the reaction mixture and the insolubles were removed by filtration. After the obtained filtrate was poured into water and the mixture was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=10/0-10/1) to give a crudely purified 4-bromo-1-(bromomethyl)-2-methylbenzene. Potassium cyanide (1.3 g, 20 mmol) was added to a solution of crude 4-bromo-1-(bromomethyl)-2-methylbenzene obtained in the above in a mixture of ethanol-water (3:1, 40 ml), and the mixture was stirred at 60° C. for 1.5 hours. After the reaction mixture was poured into water and the mixture was extracted with ethyl acetate, the organic layer was washed with a saturated aqueous NaCl solution and dried with anhydrous sodium sulfate. The residue obtained by removing the solvent under reduced pressure was purified by silica gel column chromatography (eluting solvent: n-hexane/ethyl acetate=6/1-3/1) to give (4-bromo-2-methylphenyl)acetonitrile as a pale orange solid (2.4 g, two-step total yield: 63%).

$^1$H-NMR (400 MHz, CDCl$_3$): δ 7.38-7.36 (2H, m), 7.23 (1H, app d, J=8.0 Hz), 3.61 (2H, s), 2.33 (3H, s).

(17-2)

Potassium hydroxide (0.60 g, 11 mmol) was added to a solution of (4-bromo-2-methylphenyl)acetonitrile (1.0 g, 4.8 mmol) obtained in Example (17-1) in ethylene glycol (5 ml), and the mixture was stirred at 130° C. for 1.5 hours. After the reaction mixture was cooled to room temperature and concentrated hydrochloric acid was added to acidify the reaction mixture, the mixture was extracted with ethyl acetate. The organic layer was successively washed with water and a saturated aqueous NaCl solution and dried with anhydrous sodium sulfate. After the residue obtained by removing the solvent under reduced pressure was washed with water, it was dried under reduced pressure to give a solid. Potassium carbonate (0.97 g, 7.0 mmol) and methyl iodide (0.37 ml, 5.9 mmol) were added to a solution of the obtained solid in N,N-dimethylformamide (6 ml), and the mixture was stirred at room temperature for 2 hours. The reaction mixture was diluted with ethyl acetate and the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=99/1-10/1) to give crudely purified methyl (4-bromo-2-methylphenyl)acetate as an oil. According to a method similar to Example (8-1), from crude methyl (4-bromo-2-methylphenyl)acetate obtained in the above and 4-(4,4,5,5-tetramethyl-1,3,2-dioxaborolan-2-yl)phenol (814 mg, 3.7 mmol), methyl (4'-hydroxy-3-methyl-1,1'-biphenyl-4-yl)acetate was obtained as a colorless solid (0.70 g, three-step total yield: 56%).

$^1$H-NMR (500 MHz, CDCl$_3$): δ 7.42 (2H, d, J=8.0 Hz), 7.34 (1H, s), 7.31 (1H, app d, J=8.0 Hz), 7.23 (1H, app d, J=8.0 Hz), 6.84 (2H, d, J=8.0 Hz), 5.10 (1H, br s), 3.72 (3H, s), 3.68 (2H, s), 2.36 (3H, s).

(17-3)

According to a method similar to Example (6-7), Example (12-4), Example (12-5) and Example (6-9), using methyl (4'-hydroxy-3-methyl-1,1'-biphenyl-4-yl)acetate (0.60 g, 2.3 mmol) obtained in Example (17-2) and [2-(dimethoxymethyl)-3-(methoxymethoxy)-4-(trifluoromethyl)phenyl]methanol (1.0 g, 3.3 mmol) obtained in Example (6-6) as a starting material, tert-butyl 2-hydroxy-6-[({4'-[(methoxycarbonyl)methyl]-3'-methyl-1,1'-biphenyl-4-yl}oxy)methyl]-3-(trifluoromethyl)benzoate was obtained as a colorless solid (667 mg, four-step total yield: 53%).

In the present step, morpholine was used instead of pyrrolidine in the deprotection step corresponding to Example (6-9). Further, tetrahydrofuran was used as the reaction solvent instead of a mixture of dioxane-water.

$^1$H-NMR (500 MHz, CDCl$_3$): δ 12.27 (1H, s), 7.71 (1H, d, J=8.0 Hz), 7.52 (2H, d, J=9.0 Hz), 7.37 (1H, s), 7.35 (1H, app d, J=8.0 Hz), 7.28 (1H, d, J=8.0 Hz), 7.25 (1H, d, J=8.0 Hz), 6.97 (2H, d, 7=9.0 Hz), 5.37 (2H, s), 3.71 (3H, s), 3.68 (2H, s), 2.37 (3H, s), 1.65 (9H, s).

(17-4)

A 1N aqueous sodium hydroxide solution (3.0 ml, 3.0 mmol) and methanol (0.5 ml) were added to a solution of tert-butyl 2-hydroxy-6-[({4'-[(methoxycarbonyl)methyl]-3'-methyl-1,1'-biphenyl-4-yl}oxy)methyl]-3-(trifluoromethyl)benzoate (667 mg, 1.26 mmol) obtained in Example (17-3) in tetrahydrofuran (8.5 ml), and the mixture was stirred at room temperature for 6 hours. After the reaction mixture was poured into 0.5N hydrochloric acid and the mixture was extracted with ethyl acetate (three times), the organic layer was successively washed with water and a saturated aqueous NaCl solution and dried with anhydrous sodium sulfate. The residue obtained by removing the solvent under reduced pressure was crystallized from a mixture solvent of ethanol-ethyl acetate to give the title compound as a colorless powder (552 mg, yield: 84%).

$^1$H-NMR (500 MHz, CDCl$_3$): δ 12.26, (1H, s), 7.71 (1H, d, J=8.5 Hz), 7.52 (2H, d, J=9.0 Hz), 7.39 (1H, br s), 7.36 (1H, d, J=8.5 Hz), 7.29-7.26 (2H, m), 6.97 (2H, d, J=9.0 Hz), 5.37 (2H, s), 3.72 (2H, s), 2.39 (3H, s), 1.65 (9H, s).

MS (FAB) (m/z): 516 ([M]$^+$).

Example 18

(4'-{[2-(tert-Butoxycarbonyl)-3-hydroxy-4-(trifluoromethyl)benzyl]oxy}-3-chloro-1,1'-biphenyl-4-yl) acetic acid (Exemplification Compound No.: 2-49)

(18-1)

Potassium carbonate (1.38 g, 10 mmol) and methyl iodide (0.623 ml, 10 mmol) were added to a solution of 4-bromo-2-chlorobenzoic acid (2.0 g, 8.5 mmol) in N,N-dimethylformamide (8 ml) under ice-cooling, and the mixture was stirred at room temperature for 3 hours. After the reaction mixture was poured into water and the mixture was extracted with ethyl acetate, the organic layer was successively washed with water and a saturated aqueous NaCl solution and dried with anhydrous sodium sulfate. The solvent was removed under reduced pressure to give an oily residue. After diisobutyl aluminum hydride-11.0M toluene solution (24 ml, 24 mmol) was added dropwise to a solution of the obtained residue in toluene (30 ml) at −78° C., the temperature of the mixture was raised to room temperature over 3 hours. After sodium sulfate decahydrate (12 g) was added to the reaction mixture and the mixture was stirred at room temperature for 30 minutes, Celite (12 g) and anhydrous magnesium sulfate (12 g) were added thereto and the mixture was stirred at room temperature for 30 minutes. After the insolubles were removed by filtration, the solvent was removed from the obtained filtrate under reduced pressure to give crudely purified (4-bromo-2-chlorophenyl)methanol as a solid. According to a method similar to Example (17-1), from crude (4-bromo-2-chlorophenyl) methanol obtained in the above, (4-bromo-2-chlorophenyl) acetonitrile was obtained as a pale yellow solid (1.4 g, yield: 71%).

$^1$H-NMR (400 MHz, CDCl$_3$): δ 7.61 (TH, d, J=1.6 Hz), 7.47 (1H, app d, J=8.0 Hz), 7.40 (1H, d, J=8.0 Hz), 3.79 (2H, s).

(18-2)

According to a method similar to Example (8-1) and Example (11-3), using (4-bromo-2-chlorophenyl)acetonitrile (1.37 g, 5.9 mmol) obtained in Example (18-1) and 4-(4,4,5,5-tetramethyl-1,3,2-dioxaborolan-2-yl)phenol (1.3 g, 5.9 mmol) as a starting material, allyl (3-chloro-4'-hydroxy-1,1'-biphenyl-4-yl)acetate was obtained as a pale yellow solid (698 mg, two-step total yield: 39%).

In the present step, the reaction corresponding to Example (8-1) was carried out at a reaction temperature of 85° C.

$^1$H-NMR (400 MHz, CDCl$_3$): δ 7.56 (1H, d, J=1.6 Hz), 7.44 (2H, d, J=8.8 Hz), 7.39 (1H, app d, J=8.0 Hz), 7.33 (1H, d, J=8.0 Hz), 6.89 (2H, d, J=8.8 Hz), 5.98-5.90 (1H, m), 5.32 (1H, app d, J=16.4 Hz), 5.24 (1H, app d, J=10.8 Hz), 4.88 (1H, br s), 4.65 (2H, app d, J=6.0 Hz), 3.83 (2H, s).

(18-3)

According to a method similar to Example (6-7), Example (12-4), Example (12-5), Example (12-6) and Example (12-7), using allyl (3-chloro-4'-hydroxy-1,1'-biphenyl-4-yl)acetate (560 mg, 1.85 mmol) obtained in Example (18-2) and [2-(dimethoxymethyl)-3-(methoxymethoxy)-4-(trifluoromethyl)phenyl]methanol (807 mg, 2.6 mmol) obtained in Example (6-6) as a starting material, tert-butyl 2-(allyloxy)-6-{[(4'-([(allyloxy)carbonyl]methyl}-3'-chloro-1,1'-biphenyl-4-yl)oxy]methyl)-3-(trifluoromethyl)benzoate was obtained as a colorless solid (622 mg, five-step total yield: 54%).

$^1$H-NMR (400 MHz, CDCl$_3$): δ 7.65 (1H, d, J=8.4 Hz), 7.57 (1H, d, J=1.6 Hz), 7.49 (2H, d, J=8.4 Hz), 7.42-7.38 (2H, m), 7.33 (1H, d, J=8.4 Hz), 7.00 (2H, d, J=8.4 Hz), 6.12-6.02 (1H, m), 5.98-5.88 (1H, m), 5.43 (1H, dd, J=17.2, 1.6 Hz), 5.34-5.27 (2H, m), 5.24 (1H, dd, J=11.2, 1.2 Hz), 5.16 (2H, s), 4.64 (2H, app d, J=6.0 Hz), 4.58 (2H, app d, J=5.6 Hz), 3.83 (2H, s), 1.58 (9H, s).

(18-4)

According to a method similar to Example (11-7), from tert-butyl 2-(allyloxy)-6-{[(4'-{[(allyloxy)carbonyl]methyl}-3'-chloro-1,1'-biphenyl-4-yl)oxy]methyl}-3-(trifluoromethyl)benzoate (622 mg, 1.01 mmol) obtained in Example (18-3), the title compound was obtained as a colorless powder (337 mg, yield: 62%).

$^1$H-NMR (500 MHz, CDCl$_3$): δ 12.26, (1H, s), 7.71 (5H, d, J=8.0 Hz), 7.60 (1H, d, 2.0 Hz), 7.51 (2H, d, J=8.5 Hz), 7.43 (1H, dd, J=8.0, 2.0 Hz), 7.35 (1H, d, J=8.0 Hz), 7.28-7.26 (1H, m), 6.99 (2H, d, J=8.5 Hz), 5.38 (2H, s), 3.86 (2H, s), 1.65 (9H, s).

MS (FAB) (m/z): 536 [M]$^+$).

Anal. calcd. for C$_{27}$H$_{24}$ClF$_3$O$_6$: C, 60.40; H, 4.51; F, 10.62; Cl, 6.60. found: C, 60.20; H, 4.39; F, 10.72; Cl, 6.69.

Example 19

(4'-{[2-(tert-Butoxycarbonyl)-3-hydroxy-4-(trifluoromethyl)benzyl]oxy}-2-methyl-1,1'-biphenyl-4-yl) acetic acid (Exemplification Compound No.: 2-43)

(19-1)

According to a method similar to Example (11-1) and Example (8-1), using 1-bromo-4-(bromomethyl)-2-methylbenzene which was synthesized according to the method described in literature (Hanessian, S. et al., J. Org. Chem., 2003, vol. 68, pp. 7204-7218), (4'-hydroxy-2-methyl-1,1'-biphenyl-4-yl)acetonitrile was obtained as a pale yellow solid (969 mg, yield: 76%).

In the present step, 4-(4,4,5,5-tetramethyl-1,3,2-dioxaborolan-2-yl)phenol was used as the boronic acid ester reagent in the r corresponding to Example (8-1).

$^1$H-NMR (400 MHz, CDCl$_3$): δ 7.23-7.16 (—H, m), 6.89 (2H, d, J=8.4 Hz) 4.6 (1H, br s), 3.75 (2H, s), 2.28 (3H, s).

(19-2)

According to a method similar to Example (11-3), from (4'-hydroxy-2-methyl-1,1'-biphenyl-4-yl) acetonitrile (969 mg, 4.35 ml) obtained in Example (19-1), allyl (4'-hydroxy-2-methyl-1,1'-biphenyl-4-yl)acetate was obtained as a pale yellow oil (1.19 g, yield: 97%).

$^1$H-NMR (400 MHz, CDCl$_3$): δ 7.20-7.13 (5H, m), 6.86 (2H, d, J=8.8 Hz), 5.98-5.89 (1H, m), 5.32 (1H, app dd, J=17.2, 1.6 Hz), 5.24 (1H, app dd, J=10.4, 1.6 Hz), 4.84 (1H, br s), 4.63 (2H, app d, J=5.6 Hz), 3.65 (2H, s), 2.25 (3H, s).

(19-3)

According to a method similar to Example (6-7), Example (12-4), Example (12-5), Example (12-6) and Example (12-7), using allyl (4'-hydroxy-2-methyl-1,1'-biphenyl-4-yl)acetate (1.20 g, 4.3 mmol) obtained in Example (19-2) and [2-(dimethoxymethyl)-3-(methoxymethoxy)-4-(trifluoromethyl)phenyl]methanol (1.84 g, 6.0 mmol) obtained in Example (6-6) as a starting material, tert-butyl 2-(allyloxy)-6-{[(4'-{[(allyloxy)carbonyl]methyl}-2'-methyl-1,1'-biphenyl-4-yl)oxy]methyl}-3-(trifluoromethyl)benzoate was obtained as a colorless oil (1.26 g, five-step total yield: 46%).

$^1$H-NMR (400 MHz, CDCl$_3$): δ 7.66 (1H, d, J=8.4 Hz), 7.42 (1H, d, J=8.4 Hz), 7.23 (2H, d, J=8.4 Hz), 7.18-7.13 (3H, m), 6.97 (2H, d, J=8.4 Hz), 6.12-6.02 (1H, m), 5.98-5.89 (1H, m), 5.43 (1H, dd, J=16.8, 1.2 Hz), 5.34-5.23 (3H, m), 5.16 (2H, s), 4.63 (2H, app d, J=5.6 Hz), 4.58 (2H, app d, J=5.6 Hz), 3.65 (2H, s), 2.25 (3H, s), 1.58 (9H, s).

(19-4)

According to a method similar to Example (11-7), from tert-butyl 2-(allyloxy)-6-{[(4'-{[(allyloxy)carbonyl]methyl}-2'-methyl-1,1'-biphenyl-4-yl)oxy]methyl}-3-(trifluoromethyl)benzoate (1.26 g, 2.1 mmol) obtained in Example (19-3), the title compound was obtained as a colorless powder (652 mg, yield: 60%).

$^1$H-NMR (400 MHz, CDCl$_3$): δ 12.27, (1H, s), 7.72 (1H, d, J=8.0 Hz), 7.30 (1H, d, J=8.0 Hz), 7.26-7.23 (2H, m), 7.20-7.15 (3H, m), 6.95 (2H, d, J=8.8 Hz), 5.38 (2H, s), 3.68 (2H, s), 2.27 (3H, s), 1.65 (9H, s).

MS (FAB) (m/z): 516 ([M]$^+$).

Example 20

1-(4'-{[2-(tert-Butoxycarbonyl)-3-hydroxy-4-(trifluoromethyl)benzyl]oxy}-3-fluoro-1,1'-biphenyl-4-yl)cyclopropanecarboxylic acid (Exemplification Compound No.: 2-70)

(20-1)

According to a method similar to Example (11-1) and Example (11-3), from 4-bromo-2-fluorobenzyl bromide (6.0 g, 22 mmol), methyl (4-bromo-2-fluorophenyl)acetate was obtained (3.41 g, three-step yield: 62%).

Methanol was used instead of allyl alcohol in the esterification step included in the reaction corresponding to Example (11-3) and the reaction was carried out at a reaction temperature of 50° C.

$^1$H-NMR (400 MHz, CDCl$_3$): δ 7.29-7.23 (2H, m), 7.15 (1H, app t, J=8.2 Hz), 3.72 (3H, s), 3.64 (2H, s).

(20-2)

According to a method similar to Example (15-1), Example (15-2), Example 7 and Example (13-2), from methyl (4-bromo-2-fluorophenyl)acetate (1.24 g, 5.02 mmol) obtained in Example (20-1), allyl 1-(3-fluoro-4'-hydroxy-1,1'-biphenyl-4-yl)cyclopropanecarboxylate was obtained as a white powder (1.00 g, yield: 64%).

In the present step, the hydrolysis step corresponding to Example 7 was carried out at a reaction temperature of 60° C.

$^1$H-NMR (400 MHz, CDCl$_3$): δ 7.39 (2H, d, J=8.6 Hz), 7.29-7.15 (3H, m), 6.84 (2H, d, J=8.6 Hz), 5.88-5.76 (1H, m), 5.28 (1H, br s), 5.21-5.11 (2H, m), 4.58-4.55 (2H, m), 1.73-1.69 (2H, m), 1.26-1.22 (2H, m).

(20-3)

According to a method similar to Example (6-7), Example (12-4), Example (12-5), Example (12-6) and Example (12-7), using allyl 1-(3-fluoro-4'-hydroxy-1,1'-biphenyl-4-yl)cyclopropanecarboxylate (303 mg, 0.97 mmol) obtained in Example (20-2) and [2-(dimethoxymethyl)-3-(methoxymethoxy)-4-(trifluoromethyl)phenyl]methanol (421 mg, 1.36 mmol) obtained in Example (6-6) as a starting material, tert-butyl 2-(allyloxy)-6-{[(4'-{1-[(allyloxy)carbonyl]cyclopropyl}-3'-fluoro-1,1'-biphenyl-4-yl)oxy]methyl}-3-(trifluoromethyl)benzoate was obtained (219 mg, five-step total yield: 36%).

$^1$H-NMR (400 MHz, CDCl$_3$): δ 7.62 (1H, d, J=8.2 Hz), 7.48 (2H, d, J=8.6 Hz), 7.37 (1H, d, J=8.2 Hz), 7.30-7.18 (3H, m), 6.98 (2H, d, J=8.6 Hz), 6.10-6.00 (1H, m), 5.86-5.76 (1H, m), 5.45-5.38 (1H, m), 5.29-5.24 (1H, m), 5.19-5.10 (4H, m), 4.58-4.54 (4H, m), 1.72-1.68 (2H, m), 1.57 (9H, s), 1.26-1.21 (2H, m).

(20-4)

According to a method similar to Example (11-7), from tert-butyl 2-(allyloxy)-6-{[(4'-(1-[(allyloxy)carbonyl]cyclopropyl)-3'-fluoro-1,1'-biphenyl-4-yl)oxy]methyl}-3-(trifluoromethyl)benzoate (219 mg, 0.35 mmol) obtained in Example (20-3), the title compound was obtained as a white amorphous solid (121 mg, yield: 63%).

$^1$H-NMR (400 MHz, CDCl$_3$): δ 12.22 (1H, s), 7.69 (1H, d, J=8.2 Hz), 7.49 (2H, d, J=8.6 Hz), 7.32-7.18 (4H, m), 6.96 (2H, d, J=8.6 Hz), 5.36 (2H, s), 1.77-1.72 (2H, m), 1.64 (9H, s), 1.31-1.26 (2H, m).

MS (ESI) (m/z): 545 ([M−H]$^+$).

Example 21

(4'-{[2-(tert-Butoxycarbonyl)-3-hydroxy-4-isopropylbenzyl]oxy}-1,1'-biphenyl-4-yl)acetic acid (Exemplification Compound No.: 1-47)

(21-1)

Trimethyl orthoformate (2.35 ml, 21.4 mmol) and ammonium chloride (52 mg, 0.98 mmol) were added to a solution of 3-isopropyl-2-(methoxymethoxy)benzaldehyde (4.06 g, 19.5 mmol) which was synthesized according to the method described in literature (James, R. et al., J. Med. Chem., 1980, vol. 23, pp. 1350-1357) in methanol (65 ml), and the mixture was stirred under heating with reflux for 1 hour. The solvent was removed under reduced pressure and a saturated aqueous sodium hydrogencarbonate solution was added to the residue, and the mixture was extracted with ethyl acetate. The organic layer was washed with a saturated aqueous NaCl solution and dried with anhydrous sodium sulfate. The residue obtained by removing the solvent under reduced pressure was purified by silica gel column chromatography (eluting solvent: n-hexane/ethyl acetate=12/0-12/1) to give 1-(dimethoxymethyl)-3-isopropyl-2-(methoxymethoxy)benzene as a colorless oil (4.49 g, yield: 91%).

$^1$H-NMR (400 MHz, CDCl$_3$): δ 7.39 (1H, dd, J=7.8, 1.5 Hz), 7.28 (1H, dd, J=7.8, 1.5 Hz), 7.15 (1H, t, J=7.8 Hz), 5.64 (1H, s), 4.99 (2H, s), 3.63 (3H, s), 3.40 (1H, sp, J=6.8 Hz), 3.37 (6H, s), 1.23 (6H, d, J=6.8 Hz).

(21-2)

According to a method similar to Example (6-5), Example (6-6), Example (6-7), Example (6-8) and Example (6-9), from 1-(dimethoxymethyl)-3-isopropyl-2-(methoxymethoxy)benzene (4.49 g, 17.7 mmol) obtained in Example (21-1), tert-butyl 2-hydroxy-3-isopropyl-6-[({4'-[(methoxycarbonyl)methyl]-1,1'-biphenyl-4-yl}oxy)methyl]benzoate was obtained as a yellow oil (432 mg, five-step total yield: 5%).

$^1$H-NMR (400 MHz, CDCl$_3$): δ 11.78 (1H, s), 7.52 (4H, d, J=8.2 Hz), 7.34 (1H, d, J=8.2 Hz), 7.33 (2H, d, J=8.2 Hz), 7.08 (1H, d, J=8.2 Hz), 6.99 (2H, d, J=8.2 Hz), 5.31 (2H, s), 3.71 (2H, s), 3.55 (3H, s), 3.38 (1H, sp, J=7.0 Hz), 1.58 (9H, s), 1.24 (6H, d, J=7.0 Hz).

(21-3)

According to a method similar to Example (7), from tert-butyl 2-hydroxy-3-isopropyl-6-[({4'-[(methoxycarbonyl)methyl]-1,1'-biphenyl-4-yl}oxy)methyl]benzoate (432 mg, 0.880 mmol) obtained in Example (21-2), the title compound was obtained as a white powder (176 mg, yield: 42%).

$^1$H-NMR (400 MHz, CDCl$_3$): δ 11.80 (1H, s), 7.54 (2H, d, J=8.2 Hz), 7.52 (2H, d, J=8.2 Hz), 7.36 (2H, d, J=8.2 Hz), 7.34 (1H, d, J=8.2 Hz), 7.08 (1H, d, J=8.2 Hz), 6.99 (2H, d,

J=8.2 Hz), 5.31 (2H, s), 3.71 (2H, s), 3.38 (1H, sp, J=6.7 Hz), 1.58 (9H, s), 1.24 (6H, d, J=6.7 Hz).

MS (FAB) (m/z): 476 ([M]$^+$).

Example 22

(4'-{[2-(tert-Butoxycarbonyl)-3-hydroxy-4-(trifluoromethyl)benzyl]oxy}-2-methoxy-1,1'-biphenyl-4-yl)acetic acid (Exemplification Compound No.: 2-44)

(22-1)

According to a method similar to Example (6-7), from [2-(dimethoxymethyl)-3-(methoxymethoxy)-4-(trifluoromethyl)phenyl]methanol (3.00 g, 9.66 mmol) obtained in Example (6-6) and 4-bromophenol (2.00 g, 11.6 mmol), 1-[(4-bromophenoxy)methyl]-2-(dimethoxymethyl)-3-(methoxymethoxy)-4-(trifluoromethyl)benzene was obtained (3.46 g, yield: 77%).

$^1$H-NMR (400 MHz, CDCl$_3$): δ 7.56 (1H, d, J=8.6 Hz), 7.49 (1H, d, J=8.6 Hz), 7.35 (2H, d, J=9.0 Hz), 6.86 (2H, d, J=9.0 Hz), 5.75 (1H, s), 5.46 (2H, s), 5.03 (2H, s), 3.66 (3H, s), 3.47 (6H, s).

(22-2)

According to a method similar to Example (8-3) and Example (28-3), from 1-[(4-bromophenoxy)methyl]-2-(dimethoxymethyl)-3-(methoxymethoxy)-4-(trifluoromethyl)benzene (17.6 g, 56.0 mmol) obtained in Example (22-1), 6-[(4-bromophenoxy)methyl]-2-hydroxyl-3-(trifluoromethyl)benzoic acid was obtained (12.0 g, two-step total yield: 55%).

$^1$H-NMR (400 MHz, CDCl$_3$): δ 12.24 (1H, s), 7.77 (1H, d, J=8.0 Hz), 7.40 (2H, d, J=9.0 Hz), 7.29 (1H, d, J=8.0 Hz), 6.80 (2H, d, J=9.0 Hz), 5.38 (2H, s).

(22-3)

According to a method similar to Example (28-4) and Example (33-5), from 6-[(4-bromophenoxy)methyl]-2-hydroxy-3-(trifluoromethyl)benzoic acid (3.22 g, 8.23 mmol) obtained in Example (22-2), tert-butyl 6-[(4-bromophenoxy)methyl]-2-hydroxy-3-(trifluoromethyl)benzoate was obtained (2.26 g, two-step total yield: 61%).

$^1$H-NMR (400 MHz, CDCl$_3$): δ 12.24 (1H, s), 7.69 (1H, d, J=8.2 Hz), 7.40 (2H, d, J=9.0 Hz), 7.21 (1H, d, J=8.2 Hz), 6.80 (2H, d, J=9.0 Hz), 5.30 (2H, s), 1.62 (9H, s).

(22-4)

According to a method similar to Example (2-4), from tert-butyl 6-[(4-bromophenoxy)methyl]-2-hydroxy-3-(trifluoromethyl)benzoate (10.2 g, 22.8 mmol) obtained in Example (22-3), tert-butyl 2-hydroxy-{[4-(4,4,5,5-tetramethyl-1,3,2-dioxaborolan-2-yl)phenoxy]methyl}-3-(trifluoromethyl)benzoate was obtained (11.3 g, yield: 99%).

$^1$H-NMR (400 MHz, CDCl$_3$): δ 12.27 (1H, s), 7.77 (2H, d, J=8.8 Hz), 7.69 (1H, d, J=8.4 Hz), 7.25 (1H, d, J=8.4 Hz), 6.92 (2H, d, J=8.8 Hz), 5.34 (2H, s), 1.33 (9H, s), 1.26 (12H, s).

(22-5)

Pyridine (2.10 ml, 25.9 mmol), anhydrous trifluoromethanesulfonic acid (1.61 ml, 9.53 mmol) and 4-dimethylaminopyridine (30 mg, 0.25 mmol) were added to a solution of methyl (4-hydroxy-3-methoxyphenyl)acetate (1.70 g, 8.66 mmol) in methylene chloride (20 ml) and the mixture was stirred under ice-cooling for 10 minutes and then stirred at room temperature for 20 minutes. After the reaction mixture was poured into water and the mixture was extracted with ethyl acetate, the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=2/1) to give methyl (3-methoxy-4-{[(trifluoromethyl)sulfonyl]oxy}phenyl)acetate (2.84 g, yield: 99%).

$^1$H-NMR (400 MHz, CDCl$_3$): δ 7.14 (1H, d, J=8.2 Hz), 6.96 (1H, s), 6.86 (1H, d, J=8.2 Hz), 3.90 (3H, s), 3.71 (3H, s), 3.62 (2H, s).

(22-6)

After a 2M aqueous sodium carbonate solution (0.5 ml), tris(dibenzylideneacetone)dipalladium (0) (18 mg, 0.02 mmol) and bis(2-diphenylphosphinophenyl)ether (DPEphos) (22 mg, 0.04 mmol) were added to a solution of tert-butyl 2-hydroxy-{[4-(4,4,5,5-tetramethyl-1,3,2-dioxaborolan-2-yl)phenoxy]methyl}-3-(trifluoromethyl)benzoate (100 mg, 0.20 mmol) obtained in Example (22-4) and methyl (3-methoxy-4-{[(trifluoromethyl)sulfonyl]oxy}phenyl)acetate (79 mg, 0.24 mmol) obtained in Example (22-5) in a mixture of toluene-ethanol (6:1, 3.5 ml), the mixture was stirred at 100° C. for 5 hours. After the temperature of the reaction mixture was returned to room temperature, the mixture was poured into water and extracted with ethyl acetate (three times). The organic layer was successively washed with water (twice) and a saturated aqueous NaCl solution and dried with anhydrous sodium sulfate. The compound obtained by removing the solvent under reduced pressure was treated according to a method similar to Example (17-4) to give the title compound as a pale yellow powder (43 mg, yield: 40%).

$^1$H-NMR (400 MHz, DMSO-d$_6$): δ 8.78 (1H, s), 7.79 (1H, d, J=8.4 Hz), 7.39 (2H, d, J=7.2 Hz), 7.27 (1H, d, J=8.4 Hz), 7.17 (1H, d, J=8.0 Hz), 6.99-6.96 (3H, m), 6.86 (1H, dd, J=8.0, 1.2 Hz), 5.34 (2H, s), 3.72 (3H, s), 3.57 (2H, s), 1.55 (9H, s).

MS (ESI) (m/z): 531 ([M−H]$^+$).

Example 23

(4'-{[2-(tert-Butoxycarbonyl)-3-hydroxy-4-(trifluoromethyl)benzyl]oxy}-2-chloro-1,1'-biphenyl-4-yl) acetic acid (Exemplification Compound No.: 2-46)

(23-1)

Sulfuric acid (1 ml) was added dropwise to a solution of 3-chloro-4-hydroxyphenylacetic acid (3.7 g, 20 mmol) in methanol at 0° C. The temperature of the reaction mixture was returned to room temperature and the mixture was stirred for 4 hours. After the solvent was removed under reduced pressure, the residue was poured into water and extracted with ethyl acetate. The organic layer was successively washed with water, a saturated aqueous sodium hydrogencarbonate solution and a saturated aqueous NaCl solution and dried with anhydrous sodium sulfate. The residue obtained by removing the solvent under reduced pressure was subjected to silica gel column chromatography (eluting solvent: ethyl acetate) to obtain give crude methyl (3-chloro-4-hydroxyphenyl)acetate. Pyridine (8 ml, 99 mmol) and trifluoromethanesulfonic anhydride (3.4 ml, 20 mmol) were added dropwise to a solution of the crude compound obtained in the above in methylene chloride (30 ml) under ice-cooling, and the mixture was stirred for 1 hour. The reaction mixture was poured into a 1N aqueous sodium hydroxide solution and extracted with methylene chloride. The organic layer was successively washed with water, diluted hydrochloric acid and a saturated aqueous NaCl solution and dried with anhydrous sodium sulfate. The residue obtained by removing the solvent under reduced pressure was purified by silica gel column chromatography (eluting solvent: n-hexane/ethyl acetate=3/1) to give methyl (3-chloro-4-{[(trifluoromethyl)sulfonyl]oxy}phenyl)acetate as a colorless solid (6.3 g, yield: 95%).

$^1$H-NMR (400 MHz, CDCl$_3$): δ 7.48 (1H, d, J=2.0 Hz), 7.31 (1H, d, J=8.8 Hz), 7.27 (1H, dd, J=8.8, 2.0 Hz), 3.73 (3H, s), 3.64 (2H, s).

(23-2)

After a 2M aqueous sodium carbonate solution (1.5 ml), tris(dibenzylideneacetone)dipalladium (0) (23 mg, 25 μmol) and bis(2-diphenylphosphinophenyl)ether (DPEphos) (28 mg, 52 μmol) were added to a solution of methyl (3-chloro-4-{[(trifluoromethyl)sulfonyl]oxy}phenyl)acetate (317 mg, 1.0 mmol) obtained in Example (23-1) and 4-methoxyphenylboronic acid (152 mg, 1.0 mmol) in a mixture of toluene-ethanol (5:1, 9 ml), the mixture was stirred at 100° C. for 5 hours under stirring. After the temperature of the reaction mixture was returned to room temperature, the mixture was poured into water and extracted with ethyl acetate (three times). The organic layer was successively washed with water (twice) and a saturated aqueous NaCl solution and dried with anhydrous sodium sulfate. The solvent was removed under reduced pressure to give methyl (2-chloro-4'-methoxy-1,1'-biphenyl-4-yl)acetate as a solid (192 mg, yield: 66%).

$^1$H-NMR (400 MHz, CDCl$_3$): δ 7.39-7.36 (3H, m), 7.30-7.28 (1H, m), 7.21 (1H, dd, J=7.6, 1.6 Hz), 6.96 (2H, d, J=8.4 Hz), 3.86 (3H, s), 3.73 (3H, s), 3.64 (2H, s).

(23-3)

After boron trichloride (1.0N methylene chloride solution, 1.8 ml, 1.8 mmol) was added to a solution of methyl (2-chloro-4'-methoxy-1,1'-biphenyl-4-yl)acetate (228 mg, 0.73 mmol) obtained in Example (23-2) and tetra-n-butylammonium iodide (325 mg, 0.88 mmol) in methylene chloride (4 ml) at −78° C., the temperature of the mixture was raised to room temperature and the mixture was stirred for 2 hours. Ice was added to the reaction mixture and the mixture was extracted with ethyl acetate. The organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=10/1-2/1) to give methyl (2-chloro-4'-hydroxy-1,1'-biphenyl-4-yl)acetate as a colorless solid (144 mg, yield: 71%).

$^1$H-NMR (400 MHz, CDCl$_3$): δ 7.39 (1H, s), 7.32 (2H, d, J=8.0 Hz), 7.29-7.26 (1H, m), 7.21 (1H, d, J=7.2 Hz), 6.89 (2H, d, J=8.0 Hz), 4.90 (1H, br a), 3.74 (3H, s), 3.64 (2H, s).

(23-4)

According to a method similar to Example (2-3), Example (33-5) and Example (17-4), from methyl (2-chloro-4'-hydroxy-1,1'-biphenyl-4-yl)acetate (150 mg, 0.54 mmol) obtained in Example (23-3) and tert-butyl 6-(bromomethyl)-2-[(tert-butoxycarbonyl)oxy]-3-(trifluoromethyl)benzoate (455 mg, 1.0 mmol) obtained in Example (28-5), the title compound was obtained as a colorless compound (46 mg, three-step total yield: 15%).

$^1$H-NMR (400 MHz, CDCl$_3$): δ 12.28 (1H, s), 7.72 (1H, d, J=8.0 Hz), 7.42 (1H, d, J=2.0 Hz), 7.39 (2H, d, J=8.4 Hz), 7.32-7.28 (2H, m), 7.24 (1H, dd, J=8.0, 2.0 Hz), 6.97 (2H, d, J=8.4 Hz), 5.39 (2H, s), 3.69 (2H, s), 1.65 (9H, s).

MS (FAB) (m/z): 536 ([M]$^+$).

Example 24

(4'-{[2-(tert-Butoxycarbonyl)-3-hydroxy-4-(trifluoromethyl)benzyl]oxy}-3-methoxy-1,1'-biphenyl-4-yl)acetic acid (Exemplification Compound No.: 2-184)

(24-1)

According to a method similar to Example (17-1), using (4-chloro-2-methoxyphenyl)methanol (2.00 g, 11.6 mmol) as a starting material, (4-chloro-2-methoxyphenyl)acetonitrile was obtained. Acetic acid (6 ml) and concentrated hydrochloric acid (6 ml) were added to the crude compound obtained in the above and the mixture was stirred at 100° C. for 2 hours. The reaction mixture was poured into water and extracted with ethyl acetate. The organic layer was successively washed with water and a saturated aqueous NaCl solution and dried with anhydrous sodium sulfate. The solvent was removed under reduced pressure to give crude (4-chloro-2-methoxyphenyl)acetic acid. Methanol (12 ml) and concentrated sulfuric acid (1.0 ml) were added to the crude compound obtained in the above and the mixture was stirred at 50° C. for 1 hour. The temperature of the reaction mixture was returned to room temperature and the solvent was removed under reduced pressure. After ethyl acetate was added to the residue, the organic layer was successively washed with water, a saturated aqueous sodium hydrogencarbonate solution and a saturated aqueous NaCl solution and dried with anhydrous sodium sulfate. The residue obtained by removing the solvent under reduced pressure was purified by silica gel column chromatography (eluting solvent: n-hexane/ethyl acetate=10/1) to give methyl (4-chloro-2-methoxyphenyl)acetate (1.37 g, yield: 55%).

$^1$H-NMR (400 MHz, CDCl$_3$) δ 7.07 (1H, d, J=8.0 Hz), 6.88 (1H, dd, J=8.0, 2.0 Hz), 6.83 (1H, d, J=2.0 Hz), 3.79 (3H, s), 3.67 (3H, s), 3.57 (2H, s).

(24-2)

After tripotassium phosphate (127 mg, 0.60 mmol), palladium acetate (8 mg, 0.04 mmol) and 2-(dicyclohexylphosphino)-2',6'-dimethoxy-1,1'-biphenyl (S-PHOS) (16 mg, 0.04 mmol) were added to a solution of methyl (4-chloro-2-methoxyphenyl)acetate (43 mg, 0.2 mmol) obtained in Example (24-1) and tert-butyl 2-hydroxy-{[4-(4,4,5,5-tetramethyl-1,3,2-dioxaborolan-2-yl)phenoxy]methyl}-3-(trifluoromethyl)benzoate (100 mg, 0.2 mmol) obtained in Example (22-4) in toluene (2.0 ml), the mixture was stirred at 70° C. for 4 hours. After the temperature of the reaction mixture was returned to room temperature, the mixture was poured into water and extracted with ethyl acetate (three times). The organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=2/1) to give tert-butyl 2-hydroxy-6-[({4'-[(methoxycarbonyl)methyl]-3'-methoxy-1,1'-biphenyl-4-yl}oxy)methyl]-3-(trifluoromethyl)benzoate (100 mg, yield: 60%).

$^1$H-NMR (400 MHz, CDCl$_3$): δ 12.27 (1H, s), 7.71 (1H, d, J=8.2 Hz), 7.53 (2H, d, J=8.6 Hz), 7.28 (1H, d, J=8.2 Hz), 7.23 (1H, d, J=7.6 Hz), 7.10 (1H, dd, j=7.6, 1.6 Hz), 7.03 (1H, d, J=1.6 Hz), 6.98 (2H, d, J=8.6 Hz), 5.38 (2H, s), 3.88 (3H, s), 3.71 (3H, s), 3.67 (2H, s), 1.65 (9H, s).

(24-3)

According to a method similar to Example (17-4), from tert-butyl 2-hydroxy-6-[({4'-[(methoxycarbonyl)methyl]-3'-methoxy-1,1'-biphenyl-4-yl}oxy)methyl]-3-(trifluoromethyl)benzoate (100 mg, 0.18 mmol) obtained in Example (24-2), the title compound was obtained as a white powder (75 mg, yield: 78%).

$^1$H-NMR (400 MHz, DMSO-d$_6$): δ 12.14 (1H, br), 11.45 (1H, br), 7.81 (1H, d, J=8.0 Hz), 7.66 (2H, d, J=8.4 Hz), 7.30 (1H, d, J=8.0 Hz), 7.21 (1H, d, J=7.6 Hz), 7.16 (1H, s), 7.12 (1H, d, J=7.6 Hz), 7.07 (2H, d, J=8.4 Hz), 5.36 (2H, s), 3.84 (3H, s), 3.51 (2H, s), 1.57 (9H, s).

MS (ESI) (m/z): 531 ([M−H]$^+$).

Example 25

(4'-{[2-(tert-Butoxycarbonyl)-3-hydroxy-4-(trifluoromethyl)benzyl]oxy}-2-trifluoromethyl-1,1'-biphenyl-4-yl)acetic acid (Exemplification Compound No.: 2-185)

(25-1)

According to a method similar to Example (17-1), using [4-chloro-3-(trifluoromethyl)phenyl]methanol (2.00 g, 5.59 mmol) as a starting material, [4-chloro-3-(trifluoromethyl)phenyl]acetonitrile was obtained. Acetic acid (6 ml) and concentrated hydrochloric acid (6 ml) were added to the obtained [4-chloro-3-(trifluoromethyl)phenyl]acetonitrile and the mixture was stirred at 100° C. for 2 hours. After the temperature of the reaction mixture was returned to room temperature, the mixture was poured into water and extracted with ethyl acetate. The organic layer was successively washed with water and a saturated aqueous NaCl solution and dried with anhydrous sodium sulfate. The solvent was removed under reduced pressure to give crude [4-chloro-3-(trifluoromethyl)phenyl]acetic acid. Methanol (12 ml) and concentrated sulfuric acid (1.0 ml) were added to the crude product obtained in the above and the mixture was stirred at 50° C. for 1 hour. The temperature of the reaction mixture was returned to room temperature and the solvent was removed under reduced pressure. After ethyl acetate was added thereto, the organic layer was successively washed with a saturated aqueous sodium hydrogencarbonate solution and a saturated aqueous NaCl solution and dried with anhydrous sodium sulfate. The residue obtained by removing the solvent under reduced pressure was purified by silica gel column chromatography (eluting solvent: n-hexane/ethyl acetate=10/1) to give methyl[4-chloro-3-(trifluoromethyl)phenyl]acetate (1.08 g, two-step total yield: 45%).

$^1$H-NMR (400 MHz, CDCl$_3$): δ 7.58 (1H, d, J=2.0 Hz), 7.45 (1H, d, J=8.0 Hz), 7.37 (1H, dd, j=8.0, 2.0 Hz), 3.70 (3H, s), 3.64 (2H, s).

(25-2)

According to a method similar to Example (24-2) and Example (17-4), from methyl [4-chloro-3-(trifluoromethyl)phenyl]acetate (51 mg, 0.20 mmol) obtained in Example (25-1) and tert-butyl 2-hydroxy-{[4-(4,4,5,5-tetramethyl-1,3,2-dioxaborolan-2-yl)phenoxy]methyl}-3-(trifluoromethyl)benzoate (100 mg, 0.20 mmol) obtained in Example (22-4), the title compound was obtained as a pale yellow powder (24 mg, two-step total yield: 44%).

$^1$H-NMR (400 MHz, CDCl$_3$): δ 12.27 (1H, s), 7.71 (1H, d, J=8.0 Hz), 7.65 (1H, s), 7.48 (1H, d, J=7.6 Hz), 7.31-7.24 (4H, m), 6.94 (2H, d, J=8.4 Hz), 5.36 (2H, s), 3.75 (2H, s), 1.62 (9H, s).

MS (ESI) (m/z): 569 ([M−H]$^+$).

Example 26 tert-Butyl 6-[({2'-ethyl-4'-[(methoxycarbonyl)methyl]-1,1'-biphenyl-4-yl}oxy)methyl]-2-hydroxy-3-(trifluoromethyl)benzoate (Exemplification Compound No.: 2-189)

(26-1)

N,N-Dimethylformamide (75 ml) was added to 3-bromo-4-methoxybenzyl cyanide (9.0 g, 40 mmol), [1,1'-bis(diphenylphosphino)ferrocene]dichloropalladium (II)-dichloromethane adduct (400 mg, 0.49 mmol) and potassium carbonate (24.0 g, 174 mmol) at room temperature. Further, triethylborane (1M n-hexane solution, 50 ml, 50 mmol) was added dropwise thereto and the reaction mixture was stirred at 70° C. for 5 hours. After the temperature of the reaction mixture was returned to room temperature, the mixture was poured into water and extracted with ethyl acetate. The organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=8/1-5/1) to give (3-ethyl-4-methoxyphenyl)acetonitrile (2.6 g, yield: 38%) as an oil.

$^1$H-NMR (400 MHz, CDCl$_3$): δ 7.11 (1H, d, J=8.4 Hz), 7.08 (1H, s), 6.81 (1H, d, J=8.4 Hz), 3.83 (3H, s), 3.67 (2H, s), 2.63 (2H, q, J=7.6 Hz), 1.19 (3H, t, J=7.6 Hz).

(26-2)

According to a method similar to Example (6-2) and Example (22-5), from (3-ethyl-4-methoxyphenyl)acetonitrile (6.10 g, 34.8 mmol) obtained in Example (26-1), 4-(cyanomethyl)-2-ethylphenyl trifluoromethanesulfonate was obtained as an oil (8.1 g, two-step total yield: 78%).

$^1$H-NMR (500 MHz, CDCl$_3$): δ 7.32 (1H, d, J=2.0 Hz), 7.28-7.23 (2H, m), 3.77 (2H, s), 2.76 (2H, q, J=7.5 Hz), 1.28 (3H, t, J=7.5 Hz).

(26-3)

After toluene (150 ml), ethanol (30 ml) and distilled water (30 ml) were added to 4-(cyanomethyl)-2-ethylphenyl trifluoromethanesulfonate (9.7 g, 33 mmol) obtained in Example (26-2), 4-methoxyphenylboronic acid (5.3 g, 35 mmol), [1,1'-bis(diphenylphosphino)ferrocene]dichloropalladium (II)-dichloromethane adduct (2.7 g, 3.3 mol) and sodium carbonate (10.0 g, 94 mmol), the mixture was stirred at 80° C. for 4 hours. After the reaction mixture was cooled to room temperature, the insolubles were removed by filtration. The obtained filtrate was poured into water and extracted with ethyl acetate. The organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=7/1-6/1) to give (2-ethyl-4'-methoxy-1,1'-biphenyl-4-yl)acetonitrile as an oil (5.5 g, yield: 66%).

$^1$H-NMR (400 MHz, CDCl$_3$): δ 7.25-7.17 (5H, m), 6.95 (2H, d, J=8.8 Hz), 3.86 (3H, s), 3.77 (2H, s), 2.61 (2H, q, J=7.6 Hz), 1.10 (3H, t, J=7.6 Hz).

(26-4)

Acetic acid (55 ml) and hydrobromic acid (55 ml) were added to (2-ethyl-4'-methoxy-1,1'-biphenyl-4-yl)acetonitrile (5.5 g, 22 mmol) obtained in Example (26-3), and the mixture was stirred at 100° C. for 10 hours. After the reaction mixture was cooled to room temperature, ethyl acetate was added thereto and the mixture was successively washed with water and a saturated aqueous NaCl solution and dried with anhydrous sodium sulfate. After methanol (150 ml) was added to the residue obtained by removing the solvent under reduced pressure, sulfuric acid (3 ml) was added to the mixture under ice-cooling. After the mixture was stirred at room temperature for 1 hour, the solvent was removed under reduced pressure. After ethyl acetate was added to the obtained residue, the mixture was washed with a saturated aqueous NaCl solution and dried with anhydrous sodium sulfate. The residue obtained by removing the solvent under reduced pressure was purified by silica gel column chromatography (eluting solvent: n-hexane/ethyl acetate=5/1-2/1) to give methyl (2-ethyl-4'-hydroxy-1,1'-biphenyl-4-yl)acetate as a colorless solid (5.0 g, yield: 85%).

¹H-NMR (400 MHz, CDCl₃): δ 7.20-7.13 (5H, m), 6.86 (2H, d, J=8.0 Hz), 4.76 (1H, br s), 3.73 (3H, s), 3.65 (2H, s), 2.58 (2H, q, J=7.2 Hz), 1.09 (3H, t, J=7.2 Hz).

(26-5)

Triethylamine (2.74 ml, 19.7 mmol) was added to a solution of [2-(dimethoxymethyl)-3-(methoxymethoxy)-4-(trifluoromethyl)phenyl]methanol (5.09 g, 16.4 mmol) obtained in Example (6-6) in ethyl acetate (50 ml). After methanesulfonyl chloride (1.33 ml, 17.2 mmol) was added dropwise to the mixture under ice-cooling, the reaction mixture was stirred at the same temperature for 30 minutes. The reaction mixture was filtered through Celite. The filtrate was successively washed with a saturated aqueous sodium hydrogencarbonate solution, water and a saturated aqueous NaCl solution and dried with anhydrous sodium sulfate. n-Hexane was added to the residue obtained by removing the solvent under reduced pressure. The precipitated crystals were filtered to give 2-(dimethoxymethyl)-3-(methoxymethoxy)-4-(trifluoromethyl)benzyl methanesulfonate as a pale yellow compound (5.37 g, yield: 84%).

¹H-NMR (400 MHz, CDCl₃): δ 7.64 (1H, d, J=8.2 Hz), 7.49 (1H, d, J=8.2 Hz), 5.72 (1H, s), 5.65 (2H, s), 5.01 (2H, s), 3.65 (3H, s), 3.45 (6H, s), 3.06 (3H, s).

(26-6)

According to a method similar to Example (40-2) and Example (8-3), from methyl (2-ethyl-4'-hydroxy-1,1'-biphenyl-4-yl)acetate (4.90 g, 18.1 mmol) obtained in Example (26-4) and 2-(dimethoxymethyl)-3-(methoxymethoxy)-4-(trifluoromethyl)benzyl methanesulfonate (8.35 g, 21.5 mmol) obtained in Example (26-5), methyl (2-ethyl-4'-{[2-formyl-3-hydroxy-4-(trifluoromethyl)benzyl]oxy}-1,1'-biphenyl-4-yl)acetate was obtained as a colorless solid (6.77 g, two-step total yield: 79%).

¹H-NMR (400 MHz, CDCl₃): δ 12.66 (1H, s), 10.40 (1H, s), 7.83 (1H, d, J=8.0 Hz), 7.26 (2H, d, J=8.0 Hz), 7.21 (1H, s), 7.14 (2H, br s), 7.11 (1H, d, J=8.0 Hz), 7.00 (2H, d, J=8.0 Hz), 3.73 (3H, s), 3.66 (2H, s), 2.58 (2H, q, J=7.6 Hz), 1.10 (3H, t, J=7.6 Hz).

(26-7)

According to a method similar to Example (28-3), Example (28-4) and Example (33-5), from methyl (2-ethyl-4'-{[2-formyl-3-hydroxy-4-(trifluoromethyl)benzyl]oxy}-1,1'-biphenyl-4-yl)acetate (6.77 g, 14.3 mmol) obtained in Example (26-6), the title compound was obtained as a colorless solid (5.87 g, three-step total yield: 76%).

¹H-NMR (400 MHz, CDCl₃): δ 12.22 (1H, s), 7.69 (1H, d, J=8.4 Hz), 7.28 (1H, d, J=8.4 Hz), 7.21 (2H, d, J=8.4 Hz), 7.18 (1H, s), 7.12 (2H, br s), 6.92 (2H, d, J=8.4 Hz), 5.36 (2H, s), 3.72 (3H, s), 3.64 (2H, s), 2.58 (2H, q, J=7.6 Hz), 1.64 (9H, s), 1.09 (3H, t, J=7.6 Hz).

ESI (ES−) (m/z): 543 ([M−H]⁺).

Example 27

(4'-{[2-(tert-Butoxycarbonyl)-3-hydroxy-4-(trifluoromethyl)benzyl]oxy}-2-fluoro-1,1'-biphenyl-3-yl)acetic acid (Exemplification Compound No.: 2-32)

According to a method similar to Example (24-2) and Example (7), from tert-butyl 2-{[4-(4,4,5,5-tetramethyl-1,3,2-dioxaborolan-2-yl)phenoxy]methyl}-5-(trifluoromethyl) benzoate (450 mg, 0.910 mmol) obtained in Example (22-4) and methyl (3-chloro-2-fluorophenyl)acetate (184 mg, 0.910 mmol), the title compound was obtained as a white powder (25 mg, two-step total yield: 5%).

¹H-NMR (400 MHz, CDCl₃): δ 12.27 (1H, s), 7.71 (1H, d, J=8.6 Hz), 7.43 (2H, d, J=8.6 Hz), 7.36 (1H, td, J=7.4, 1.6 Hz), 7.29 (1H, d, J=8.6 Hz), 7.26-7.22 (1H, m), 7.17 (1H, t, J=7.4 Hz), 6.99 (2H, d, J=8.6 Hz), 5.38 (2H, s), 3.79 (2H, s), 1.65 (9H, s).

MS (FAB) (m/z): 520 ([M]⁺).

Example 28

[5-(4-{[2-(tert-Butoxycarbonyl)-3-hydroxy-4-(trifluoromethyl)benzyl]oxy}phenyl)-2-thienyl]acetic acid (Exemplification Compound No.: 2-113)

(28-1)

A n-butyllithium-1.59M n-hexane solution (40.0 ml, 64.4 mmol) was added dropwise to a solution of 1-(dimethoxymethyl)-2-(methoxymethoxy)-3-(trifluoromethyl)benzene (12.0 g, 42.9 mmol) obtained in Example (6-4) and N,N,N',N'-tetramethylethylenediamine (9.70 ml, 64.4 mmol) in tetrahydrofuran (100 ml) at −40° C. over 5 minutes. The reaction mixture was stirred at 0° C. for 15 minutes. After the reaction mixture was cooled to −40° C., methyl iodide (5.3 ml, 85.85 mmol) was added thereto and the mixture was further stirred at room temperature for 30 minutes. A saturated aqueous ammonium chloride solution was poured into the reaction mixture and the mixture was extracted with ethyl acetate. The organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=5/1) to give 2-(dimethoxymethyl)-3-(methoxymethoxy)-1-methyl-4-(trifluoromethyl)benzene as an oil (7.19 g, yield: 57%).

¹H-NMR (400 MHz, CDCl₃): δ 7.44 (1H, d, J=8.2 Hz), 7.04 (1H, d, J=8.2 Hz), 5.70 (1H, s), 4.99 (2H, s), 3.64 (3H, s), 3.43 (6H, s), 2.55 (3H, s).

(28-2)

According to a method similar to Example (8-3), from 2-(dimethoxymethyl)-3-(methoxymethoxy)-1-methyl-4-(trifluoromethyl)benzene (7.19 g, 24.4 mmol) obtained in Example (28-1), 2-hydroxy-6-methyl-3-(trifluoromethyl) benzaldehyde was obtained (4.65 g, yield: 93%).

¹H-NMR (400 MHz, CDCl₃): δ 12.58 (1H, s), 10.32 (1H, s), 7.65 (1H, d, J=7.8 Hz), 6.79 (1H, d, J=7.8 Hz), 2.67 (3H, s).

(28-3)

After an aqueous solution (40 ml) of sodium chlorite (6.0 g, 66.3 mmol) and sodium dihydrogenphosphate monohydrate (6.0 g, 43.5 mmol) was added dropwise to a solution of 2-hydroxy-6-methyl-3-(trifluoromethyl)benzaldehyde (4.65 g, 22.8 mmol) obtained in Example (28-2) in a mixture of tert-butyl alcohol (90 ml), 1,4-dioxane (30 ml) and 2-methyl-2-butene (30 ml), the mixture was stirred at room temperature for 1 hour. After the reaction mixture was cooled with ice and a 5% aqueous sodium thiosulfate solution was added thereto, the mixture was poured into 0.5N hydrochloric acid and extracted with ethyl acetate (twice). The organic layer was successively washed with water and a saturated aqueous NaCl solution and dried with anhydrous sodium sulfate. The residue obtained by removing the solvent under reduced pressure was crystallized using ethyl acetate and n-hexane to give 2-hydroxy-6-methyl-3-(trifluoromethyl)benzoic acid as a colorless compound (4.21 g, yield: 84%).

¹H-NMR (400 MHz, CDCl₃): δ 11.73 (1H, s), 7.63 (1H, d, J=7.8 Hz), 6.84 (1H, d, J=7.8 Hz), 2.67 (3H, s).

(28-4)

N,N-Dimethylaminopyridine (0.7 g, 5.7 mmol) and di-tert-butyl dicarbonate [(tBuOCO)₂O] (16.7 g, 76.5 mmol) were added to a solution of 2-hydroxy-6-methyl-3-(trifluoromethyl)benzoic acid (4.21 g, 19.1 mmol) obtained in Example (28-3) in a mixture of tert-butyl alcohol-tetrahydrofuran (2:1, 60 ml), and the mixture was stirred at 60° C. for 3 hours. The reaction mixture was concentrated under reduced pressure and the residue was purified by silica gel column chromatography (eluting solvent: n-hexane/ethyl acetate=9/1) to give tert-butyl 2-[(tert-butoxycarbonyl)oxy]-6-methyl-3-(trifluoromethyl)benzoate (6.27 g, yield: 87%).

$^1$H-NMR (400 MHz, CDCl$_3$): δ 7.53 (1H, d, J=7.8 Hz), 7.17 (1H, d, J=7.8 Hz), 2.43 (3H, s), 1.59 (9H, s), 1.53 (9H, s).

(28-5)

N-Bromosuccinimide (9.70 g, 54.5 mmol) and benzoyl peroxide (0.7 g) were added to a solution of tert-butyl 2-[(tert-butoxycarbonyl)oxy]-6-methyl-3-(trifluoromethyl)benzoate (18.6 g, 49.6 mmol) obtained in Example (28-4) in carbon tetrachloride (400 ml), and the mixture was heated under reflux for 5 hours. The temperature of the reaction mixture was returned to room temperature and the solvent was removed under reduced pressure. After n-hexane was added to the obtained residue and the mixture was filtered, the filtrate was concentrated under reduced pressure. The obtained residue was purified by silica gel column chromatography (eluting solvent: toluene) to give tert-butyl 6-(bromomethyl)-2-[(tert-butoxycarbonyl)oxy]-3-(trifluoromethyl)benzoate (11.66 g, yield: 52%).

$^1$H-NMR (400 MHz, CDCl$_3$): δ 7.64 (1H, d, J=8.2 Hz), 7.40 (1H, d, J=8.2 Hz), 4.60 (2H, s), 1.63 (9H, s), 1.52 (9H, s).

(28-6)

After tris(dibenzylideneacetone)dipalladium (0) (110 mg, 0.12 mmol), tri-o-tolylphosphine (61 mg, 0.2 mmol) and 2N aqueous sodium carbonate solution (4 ml) were added to a solution of 4-(4,4,5,5-tetramethyl-1,3,2-dioxaborolan-2-yl)phenol (0.8 g, 3.65 mmol) and ethyl (5-bromo-2-thienyl)acetate (1.00 g, 4.01 mmol) which was synthesized according to the method described in literature (Jackson, P. M. et al., J. Chem. Soc. Perkin Trans. 1, 1990, vol. 11, pp. 2909-2918) in a mixture of toluene-ethanol (5:1, 24 ml), the mixture was stirred at 80° C. for 3 hours. After water was poured into the reaction mixture and the mixture was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=3/1) to give ethyl [5-(4-hydroxyphenyl)-2-thienyl]acetate (0.73 g, yield: 77%).

$^1$H-NMR (400 MHz, CDCl$_3$): δ 7.41 (2H, d, J=8.6 Hz), 7.00 (1H, d, J=3.5 Hz), 6.85 (1H, d, J=3.5 Hz), 6.80 (2H, d, J=8.6 Hz), 4.89 (1H, s), 4.19 (2H, q, J=7.0 Hz), 3.80 (2H, s), 1.29 (3H, t, J=7.0 Hz).

(28-7)

According to a method similar to Example (2-3), Example (33-5) and Example (17-4), from tert-butyl 6-(bromomethyl)-2-[(tert-butoxycarbonyl)oxy]-3-(trifluoromethyl)benzoate (366 mg, 0.8 mmol) obtained in Example (28-5) and ethyl [5-(4-hydroxyphenyl)-2-thienyl]acetate (211 mg, 0.8 mmol) obtained in Example (28-6), the title compound was obtained as a colorless powder (56 mg, three-step total yield: 14%).

$^1$H-NMR (400 MHz, DMSO-d$_6$): δ 12.58 (1H, s), 11.44 (1H, s), 7.82 (1H, d, J=7.8 Hz), 7.56 (2H, d, J=7.8 Hz), 7.29 (1H, d, J=7.8 Hz), 7.23 (1H, d, J=3.5 Hz), 7.02 (2H, d, J=7.8 Hz), 6.91 (1H, d, J=3.5 Hz), 5.35 (2H, s), 3.81 (2H, s), 1.56 (9H, s).

MS (ESI) (m/z): 507 ([M–H]$^+$).

Example 29 tert-Butyl 2-hydroxy-6-{[(4'-{[(methylamino)sulfonyl]methyl}-1,1'-biphenyl-4-yl)oxy]methyl}-3-(trifluoromethyl)benzoate (Exemplification Compound No.: 1-113)

(29-1)

An aqueous solution (40 ml) of sodium sulfite (2.52 g, 20.0 mmol) was added to a solution of 4-bromobenzyl bromide (5.00 g, 20.0 mmol) in acetone (40 ml), and the mixture was heated under reflux for 48 hours. The reaction mixture was concentrated and the precipitated crystals were filtered and washed with a small amount of acetone to give white crystals. The obtained crystals were suspended in methylene chloride (36 ml) and oxalyl chloride (0.742 ml, 8.65 mmol) and N,N-dimethylformamide (0.1 ml) were added thereto, and the mixture was stirred at room temperature overnight. The solvent was removed under reduced pressure and ethyl acetate was added to the residue. After the insolubles were removed by filtration, the solvent was removed under reduced pressure to give a reaction mixture (1.94 g). A part of the obtained reaction mixture (150 mg) was dissolved in a mixture of tetrahydrofuran (3 ml) and tert-butanol (1.5 ml) and a 40% aqueous methylamine solution (130 µl) was added thereto, and the mixture was stirred at room temperature for 2 hours. After the reaction mixture was poured into a saturated aqueous sodium hydrogencarbonate solution and the mixture was extracted with ethyl acetate, the organic layer was successively washed with water and a saturated aqueous NaCl solution and dried with anhydrous sodium sulfate. The solvent was removed under reduced pressure to give 1-(4-bromophenyl)-N-methylmethanesulfonamide as a yellow solid (80 mg).

$^1$H-NMR (400 MHz, CDCl$_3$): δ 7.53 (2H, d, J=8.2 Hz), 7.28 (2H, d, J=8.2 Hz), 4.21 (2H, s), 4.03-3.99 (1H, m), 2.73 (3H, d, J=4.7 Hz).

(29-2)

Tetrakis(triphenylphosphine)palladium (0) (10 mg, 8.9 µmol) and a 2N aqueous sodium carbonate solution (0.33 ml) were added to a solution of 1-(4-bromophenyl)-N-methylmethanesulfonamide (80 mg, 0.30 mmol) obtained in Example (29-1) and tert-butyl 2-{[4-(4,4,5,5-tetramethyl-1,3,2-dioxaborolan-2-yl)phenoxy]methyl}-5-(trifluoromethyl)benzoate (147 mg, 0.30 mmol) obtained in Example (22-4) in a mixture of toluene-ethanol (6:1, 1.2 ml), and the mixture was stirred with heating under reflux for 8 hours. Ethyl acetate and water were added to the reaction mixture and the insolubles were removed by filtration through Celite. After the obtained filtrate was extracted with ethyl acetate, the organic layer was successively washed with water and a saturated aqueous NaCl solution and dried with anhydrous sodium sulfate. The residue obtained by removing the solvent under reduced pressure was purified by silica gel preparative thin layer chromatography (developing solvent: methylene chloride/methanol=50/1) to give the title compound as a pale yellow powder (7 mg, yield: 4%).

$^1$H-NMR (400 MHz, CDCl$_3$): δ 12.25 (1H, s), 7.71 (1H, d, J=8.2 Hz), 7.58 (2H, d, J=8.2 Hz), 7.54 (2H, d, J=8.6 Hz), 7.45 (2H, d, J=8.2 Hz), 7.28 (1H, d, J=8.2 Hz), 7.00 (2H, d, J=8.6 Hz), 5.39 (2H, s), 4.30 (2H, s), 4.01 (1H, q, J=5.1 Hz), 2.77 (3H, d, J=5.1 Hz), 1.65 (9H, s).

MS (FAB) (m/z): 551 ([M]$^+$).

Example 30

[2-(4-{[2-(tert-Butoxycarbonyl)-3-hydroxy-4-(trifluoromethyl)benzyl]oxy}phenyl)-1,3-thiazol-5-yl]acetic acid (Exemplification Compound No.: 2-187)

(30-1)
4-Methoxythiobenzamide (1.62 g, 9.7 mmol) and ethyl 3-bromo-4-oxobutanoate (2.02 g, 9.7 mmol) were suspended in 1,2-dichloroethane (25 ml), and the mixture was heated under reflux for 3 hours. The reaction mixture was diluted with ethyl acetate, successively washed with a saturated aqueous sodium hydrogencarbonate solution and a saturated aqueous NaCl solution and dried with anhydrous sodium sulfate. The residue obtained by removing the solvent under reduced pressure was purified by silica gel column chromatography (eluting solvent: n-hexane/ethyl acetate=2/1) to give ethyl [2-(4-methoxyphenyl)-1,3-thiazol-5-yl]acetate (1.79 g, yield: 67%).
$^1$H-NMR (400 MHz, CDCl$_3$): δ 7.83 (2H, d, J=8.6 Hz), 7.56 (1H, s) 6.93 (2H, d, J=8.6 Hz), 4.20 (2H, q, J=7.0 Hz), 3.85-3.83 (5H, m), 1.29 (3H, t, J=7.0 Hz).

(30-2)
According to a method similar to Example (26-4), from ethyl [2-(4-methoxyphenyl)-1,3-thiazol-5-yl]acetate (303 mg, 1.1 mmol) obtained in Example (30-1), allyl[2-(4-hydroxyphenyl)-1,3-thiazol-5-yl]acetate was obtained (195 mg, yield: 65°).

In the present step, allyl alcohol was used instead of methanol in the esterification step.
$^1$H-NMR (400 MHz, CDCl$_3$): δ 8.00 (1H, br s), 7.69 (2H, d, J=8.6 Hz), 7.57 (1H, s), 6.79 (2H, d, J=8.6 Hz), 5.96-5.86 (1H, m), 5.36-5.23 (2H, m), 4.66-4.63 (2H, n), 3.88 (2H, s).

(30-3)
According to a method similar to Example (2-3), Example (33-5) and Example (11-7), from tert-butyl 6-(bromomethyl)-2-[(tert-butoxycarbonyl)oxy]-3-(trifluoromethyl)benzoate (314 mg, 0.69 mmol) obtained in Example (28-5) and allyl[2-(4-hydroxyphenyl)-1,3-thiazol-5-yl]acetate (190 mg, 0.69 mmol) obtained in Example (30-2), the title compound was obtained as a colorless powder (33 mg, three-step total yield: 9%).
$^1$H-NMR (400 MHz, DMSO-d): δ 12.69 (1H, s), 11.40 (1H, s), 7.85 (2H, d, J=9.0 Hz), 7.80 (1H, d, J=8.2 Hz), 7.62 (1H, s), 7.27 (1H, d, J=8.2 Hz), 7.08 (2H, d, J=9.0 Hz), 5.37 (2H, s), 3.91 (2H, s), 1.54 (9H, s).
MS (ESI) (m/z): 508 ([M−H]$^+$).

Example 31 tert-Butyl 2-hydroxy-6-({[3'-(methylsulfonyl)-1,1'-biphenyl-4-yl]oxy}methyl)-3-(trifluoromethyl)benzoate (Exemplification Compound No.: 2-188)

After a 2M aqueous sodium carbonate solution (1.0 ml) and [1,1'-bis(diphenylphosphino)ferrocene]dichloropalladium (II)-dichloromethane adduct (81 mg, 0.1 mmol) were added to a solution of 3-bromophenylmethylsulfone (235 mg, 1.0 mmol) and tert-butyl 2-hydroxy-{[4-(4,4,5,5-tetramethyl-1,3,2-dioxaborolan-2-yl)phenoxy]methyl}-3-(trifluoromethyl)benzoate (494 mg, 1.0 mmol) obtained in Example (22-4) in dioxane (5.0 ml), the mixture was stirred at 50° C. for 2 hours. After the temperature of the reaction mixture was returned to room temperature, the mixture was poured into water and extracted with ethyl acetate (three times). The organic layer was successively washed with water (twice) and a saturated aqueous NaCl solution and dried with anhydrous sodium sulfate. The solvent was removed under reduced pressure to give tert-butyl 2-hydroxy-6-{[3'-(methylsulfonyl)-1,1'-biphenyl-4-yl]oxy}methyl)-3-(trifluoromethyl)benzoate as a solid (80 mg, yield: 15%).
$^1$H-NMR (400 MHz, DMSO-d$_6$): δ 11.44 (1H, s), 8.12 (1H, s), 8.00 (1H, d, J=8.0 Hz), 7.86 (1H, d, J=8.0 Hz), 7.82 (1H, d, J=8.0 Hz), 7.76 (2H, d, J=8.0 Hz), 7.71 (1H, t, J=8.0 Hz), 7.31 (1H, d, J=8.8 Hz), 7.13 (2H, d, J=8.0 Hz), 5.39 (2H, s), 3.29 (3H, s), 1.56 (9H, s).
MS (ESI) (m/z): 521 ([M−H]$^+$).

Example 32

(4'-{[2-(tert-Butoxycarbonyl)-3-hydroxy-4-(trifluoromethyl)benzyl]oxy}-2-ethyl-1,1'-biphenyl-4-yl)acetic acid (Exemplification Compound No.: 2-186)

According to a method similar to Example (17-4), from tert-Butyl 2-hydroxy-6-[({2'-ethyl-4'-[(methoxycarbonyl)methyl]-1,1'-biphenyl-4-yl}oxy)methyl]-3-(trifluoromethyl)benzoate (5.0 g, 9.2 mmol) obtained in Example (26-7), the title compound was obtained as a colorless solid (4.79 g, yield: 97%).
$^1$H-NMR (400 MHz, CDCl$_3$): δ 12.27 (1H, s), 7.72 (1H, d, J=8.0 Hz), 7.30 (1H, d, J=8.0 Hz), 7.26-7.22 (3H, m), 7.16 (2H, br s), 6.95 (2H, d, J=8.0 Hz), 5.38 (2H, s), 3.70 (2H, s), 2.60 (2H, q, J=7.6 Hz), 1.65 (9H, s), 1.10 (3H, t, J=7.6 Hz).
ESI (ES−)(m/z): 529 ([M−H]$^+$).
Anal. calcd. for C$_{29}$H$_{29}$F$_3$O$_6$: C, 65.65; H, 5.51; F, 10.74. found: C, 65.63; H, 5.53; F, 10.78.

Example 33

(4'-{[2-(tert-Butoxycarbonyl)-3-hydroxy-4-(trifluoromethyl)benzyl]oxy}-2-methyl-1,1'-biphenyl-3-yl)acetic acid (Exemplification Compound No.: 2-31)

(33-1)
An aqueous solution (2 ml) of sodium nitrite (1.92 g, 11.6 mmol) was added dropwise to a solution of (3-amino-2-methylphenyl)acetic acid (1.20 g, 17.2 mmol) which was synthesized according to the method described in literature (Askam, V. et al., J. Chem. Soc. C; 1969, pp. 1935-1936) in 10% sulfuric acid (72 ml) under ice-cooling. After the mixture was stirred at room temperature for 1 hour, the reaction mixture was added dropwise to an aqueous solution (11 ml) of potassium iodide (3.66 g, 22.0 mmol). The temperature of the reaction mixture was raised to 90° C. and the mixture was stirred for 2.5 hours. The reaction mixture was extracted with ethyl acetate and the organic layer was successively washed with a 10% aqueous sodium sulfite solution and a saturated aqueous NaCl solution and dried with anhydrous sodium sulfate. According to a method similar to Example (3-1), from the reaction mixture obtained by removing the solvent under reduced pressure, methyl (3-iodo-2-methylphenyl)acetate was obtained (2.23 g, yield: 66%).
$^1$H-NMR (400 MHz, CDCl$_3$): δ 7.02 (1H, t, J=7.8 Hz), 6.80 (1H, d, J=7.8 Hz), 6.70 (1H, d, J=7.8 Hz), 3.70 (2H, s), 3.65 (3H, s), 2.19 (3H, s).

(33-2)
After palladium acetate (II) (37 mg, 0.16 mmol), tri-o-tolylphosphine (100 mg, 0.327 mmol) and a 2N aqueous sodium carbonate solution (2.5 ml) were added to a solution of methyl (3-iodo-2-methylphenyl)acetate (950 mg, 3.27 mmol) obtained in Example (33-1) and 4-methoxyphenylboronic acid (498 mg, 3.27 mmol) in N,N-dimethylformamide (8 ml), the mixture was stirred at 80° C. for 5 hours. After the reaction mixture was diluted with ethyl acetate and water, the insolubles were removed by filtration through Celite. After the obtained filtrate was extracted with ethyl acetate, the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=9/1) to give methyl (4'-methoxy-2-methyl-1,1'-biphenyl-3-yl)acetate as a yellow powder (59 mg, yield: 7%).

$^1$H-NMR (400 MHz, CDCl$_3$): δ 7.23-7.12 (5H, m), 6.92 (2H, d, T=8.6 Hz), 3.84 (3H, s), 3.71 (2H, s), 3.70 (3H, s), 2.18 (3H, s).

(33-3)

According to a method similar to Example (6-2), from methyl (4'-methoxy-2-methyl-1,1'-biphenyl-3-yl)acetate (59 mg, 0.22 mmol) obtained in Example (33-2), methyl (4'-hydroxy-2-methyl-1,1'-biphenyl-3-yl)acetate was obtained (28 mg, yield: 50%).

$^1$H-NMR (400 MHz, CDCl$_3$): δ 7.45-7.39 (1H, m), 7.18-7.12 (4H, m), 6.84 (2H, d, J=8.6 Hz), 4.90 (1H, s), 3.71 (5H, s), 2.18 (3H, s).

(33-4)

According to a method similar to Example (40-2), from methyl (4'-hydroxy-2-methyl-1,1'-biphenyl-3-yl)acetate (28 mg, 0.11 mmol) obtained in Example (33-3), tert-butyl 2-[(tert-butoxycarbonyl)oxy]-6-[({3'-[(methoxycarbonyl)methyl]-2'-methyl-1,1'-biphenyl-4-yl}oxy)methyl]-3-(trifluoromethyl)benzoate was obtained as a colorless oil (19 mg, yield: 28%).

$^1$H-NMR (400 MHz, CDCl$_3$): δ 7.73 (1H, d, J=8.6 Hz), 7.62 (1H, d, J=8.6 Hz), 7.22 (2H, d, J=8.6 Hz), 7.24-7.12 (5H, m), 6.97 (2H, d, J=8.6 Hz), 5.27 (2H, s), 3.72 (2H, s), 3.71 (3H, s), 2.17 (3H, s), 1.58 (9H, s), 1.54 (9H, s).

(33-5)

Pyrrolidine (3 μl, 0.036 mmol) was added to a solution of tert-butyl 2-[(tert-butoxycarbonyl)oxy]-6-[({3'-[(methoxycarbonyl)methyl]-2'-methyl-1,1'-biphenyl-4-yl}oxy)methyl]-3-(trifluoromethyl)benzoate (19 mg, 0.030 mmol) obtained in Example (33-4) in tetrahydrofuran (1 ml), and the mixture was stirred at 40° C. for 1 hour. The residue obtained by removing the solvent under reduced pressure was purified by silica gel preparative thin layer chromatography (developing solvent: n-hexane/ethyl acetate=3/1) to give tert-butyl 2-hydroxy-6-[({3'-[(methoxycarbonyl)methyl]-2'-methyl-1,1'-biphenyl-4-yl}oxy)methyl]-3-(trifluoromethyl)benzoate as a colorless oil (16 mg, yield: 100%).

$^1$H-NMR (400 MHz, CDCl$_3$): δ 12.27 (1H, s), 7.72 (1H, d, J=8.2 Hz), 7.31 (1H, d, J=8.2 Hz), 7.24 (2H, d, 8=8.61 Hz), 7.25-7.13 (5H, m), 6.95 (2H, d, J=8.6 Hz), 5.38 (2H, s), 3.72 (5H, s), 2.19 (3H, s), 1.65 (9H, s).

(33-6)

According to a method similar to Example (7), from tert-butyl 2-hydroxy-6-[({3'-[(methoxycarbonyl)methyl]-2'-methyl-1,1'-biphenyl-4-yl}-oxy)methyl]-3-(trifluoromethyl)benzoate (16 mg, 0.030 mmol) obtained in Example (33-5), the compound was obtained as a brown powder (12 mg, yield: 77%).

$^1$H-NMR (500 MHz, CDCl$_3$): δ 12.27 (1H, s), 7.72 (1H, d, J=8.3 Hz), 7.31 (1H, d, J=8.3 Hz), 7.24 (2H, d, 7=8.3 z), 7.25-7.15 (5H, m), 6.96 (2H, d, J=8.3 Hz, 5.38 (2H, s), 3.76 (2H, s), 2.21 (3H, s), 1.65 (9H, s).

MS (FAB) (m/z): 516 ([M]$^+$).

Example 34

[2-(4-{[2-(tert-Butoxycarbonyl)-3-hydroxy-4-(trifluoromethyl)benzyl]oxy}phenyl)-5-pyrimidinyl]acetic acid (Exemplification Compound No.: 2-151)

(34-1)

According to a method similar to Example (2-3) and Example (33-5), from tert-butyl 6-(bromomethyl)-2-[(tert-butoxycarbonyl)oxy]-3-(trifluoromethyl)benzoate (412 mg, 0.92 mmol) obtained in Example (28-5) and allyl [2-(4-hydroxyphenyl)-5-pyrimidinyl]acetate (250 mg, 0.92 mmol), tert-butyl 6-{[4-(5-{[(allyloxy)carbonyl]methyl}-2-pyrimidinyl)phenoxy]methyl}-2-hydroxy-3-(trifluoromethyl)benzoate was obtained (140 mg, two-step total yield: 28%).

$^1$H-NMR (400 MHz, CDCl$_3$): δ 12.24 (1H, s), 8.67 (2H, s), 8.38 (2H, d, J=9.0 Hz), 7.69 (1H, d, J=7.8 Hz), 7.25 (1H, d, J=7.8 Hz), 7.01 (2H, d, J=9.0 Hz), 5.96-5.85 (1H, m), 5.38 (2H, s), 5.34-5.23 (2H, m), 4.64-4.61 (2H, m), 3.66 (2H, s), 1.63 (9H, s).

(34-2)

According to a method similar to Example (11-7), from tert-butyl 6-{[4-(5-{[(allyloxy)carbonyl]methyl}-2-pyrimidinyl) phenoxy]methyl}-2-hydroxy-3-(trifluoromethyl)benzoate (140 mg, 0.26 mmol) obtained in Example (34-1), the title compound was obtained as a colorless powder (94 mg, yield: 72%).

$^1$H-NMR (400 MHz, DMSO-d$_6$): δ 12.62 (1H, s), 11.42 (1H, s), 8.72 (2H, s), 8.34 (2H, d, J=9.0 Hz), 7.80 (1H, d, J=8.2 Hz), 7.28 (1H, d, J=8.2 Hz), 7.11 (2H, d, 7=9.0 Hz), 5.39 (2H, s), 3.70 (2H, s), 1.54 (9H, s).

MS (ESI) (m/z): 505 ([M+H]$^+$).

Example 35 tert-Butyl 2-hydroxy-6-[({3'-[(methylsulfonyl)amino]-1,1'-biphenyl-4-yl}oxy)methyl]-3-(trifluromethyl)benzoate (Exemplification Compound No.: 2-190)

(35-1)

According to a method similar to Example (26-5), from 3-iodoaniline (500 mg, 2.28 mmol), N-(3-iodophenyl)methanesulfonamide was obtained as a pale yellow solid (490 mg, yield: 72%).

$^1$H-NMR (400 MHz, CDCl$_3$): δ 7.56 (1H, s), 7.53 (1H, d, J=7.8 Hz), 7.22 (1H, d, J=7.8 Hz), 7.08 (1H, t, J=7.8 Hz), 3.04 (3H, s).

(35-2)

According to a method similar to Example (31), from N-(3-iodophenyl)methanesulfonamide (134 mg, 0.45 mmol) obtained in Example (35-1) and tert-butyl 2-hydroxy-6-{[4-(4,4,5,5-tetramethyl-1,3,2-dioxaborolan-2-yl)phenoxy]methyl}-3-(trifluoromethyl)benzoate (250 mg, 0.51 mmol) obtained in Example (22-4), the title compound was obtained as a pale violet powder (20 mg, yield: 8%).

$^1$H-NMR (400 MHz, DMSO-d$_6$): δ 11.40 (1H, s), 9.76 (1H, s), 7.79 (1H, d, J=8.6 Hz), 7.55 (2H, d, J=8.6 Hz), 7.40-7.26 (4H, m), 7.14 (1H, d, J=7.0 Hz), 7.07 (2H, d, J=8.6 Hz), 5.36 (2H, s), 3.01 (3H, s), 1.56 (9H, s).

MS (FAB+) (m/z): 537 (M$^{+-}$).

Example 36

[4-(5-{[2-(tert-Butoxycarbonyl)-3-hydroxy-4-(trifluoromethyl)benzyl]oxy}-2-pyridinyl)phenyl]acetic acid (Exemplification Compound No.: 2-164)

(36-1)
Tetrakis(triphenylphosphine)palladium (0) (220 mg, 0.193 mmol) and a 2N aqueous sodium carbonate solution (4.63 ml) were added to a solution of methyl [4-(4,4,5,5-tetramethyl-1,3,2-dioxaborolan-2-yl(phenyl]acetate (1.07 g, 3.86 mmol) obtained in Example (12-1, and 2-chloro-5-hydroxypyridine (500 mg, 3.86 mmol) in dimethoxyethane (20 ml), and the mixture was stirred under heating with reflux overnight. The reaction mixture was diluted with ethyl acetate and water, and the insolubles were removed by filtration through Celite. After the obtained filtrate was extracted with ethyl acetate, the organic layer was washed with a saturated aqueous NaCl solution and dried with anhydrous sodium sulfate. The residue obtained by removing the solvent under reduced pressure was purified by silica gel column chromatography (eluting solvent: n-hexane/ethyl acetate=2/1-1/1) to give methyl [4-(5-hydroxy-2-pyridinyl)phenyl]acetate (230 mg, yield: 24%).

$^1$H-NMR (500 MHz, CDCl$_3$): δ 8.30 (1H, s), 7.85 (2H, d, J=8.3 Hz), 7.59 (1H, d, J=8.3 Hz), 7.36 (2H, d, J=8.3 Hz), 7.21 (1H, d, J=8.3 Hz), 3.71 (3H, s), 3.67 (2H, s).

(36-2)
According to a method similar to Example (40-2), Example (33-5) and Example (7), from methyl [4-(5-hydroxy-2-pyridinyl)phenyl]acetate (64 mg, 0.26 mmol) obtained in Example (36-1), the title compound was obtained as a white powder (74 mg, three-step total yield: 67%).

$^1$H-NMR (500 MHz, CDCl$_3$): δ 12.26 (1H, s), 8.44 (1H, d, J=7.8 Hz), 7.87 (2H, d, J=7.8 Hz), 7.73 (1H, d, J=8.6 Hz), 7.67 (1H, d, J=8.6 Hz), 7.39 (2H, d, J=7.8 Hz), 7.31-7.25 (2H, m), 5.43 (2H, s), 3.71 (2H, s), 1.66 (9H, s).

MS (FAB) (m/z): 504 ([M+H]$^+$).

Example 37

(4'-{[2-(tert-Butoxycarbonyl)-3-hydroxy-4-(trifluoromethyl)benzyl]oxy}-2-nitro-1,1'-biphenyl-4-yl)acetic acid (Exemplification Compound No.: 2-191)

(37-1)
According to a method similar to Example (29-2), Example (2-2), Example (11-1) and Example (26-4), from 4-methoxyphenylboric acid (17.0 g, 112 mmol) and 4-bromo-2-nitrotoluene (22.1 g, 102 mmol), methyl (4'-hydroxy-2-nitro-1,1'-biphenyl-4-yl)acetate was obtained (3.53 g, four-step total yield: 12%).

$^1$H-NMR (500 MHz, CDCl$_3$): δ 7.73-7.69 (1H, m), 7.52-7.47 (1H, m), 7.41-7.36 (1H, m), 7.18-7.10 (2H, m), 6.94-6.86 (2H, m), 3.80-3.67 (5H, m).

(37-2)
According to a method similar to Example (40-2), Example (33-5) and Example (17-4), from methyl (4'-hydroxy-2-nitro-1,1'-biphenyl-4-yl)acetate (1.71 g, 3.76 mmol) obtained in Example (37-1) and tert-butyl 6-(bromomethyl)-2-[(tert-butoxycarbonyl)oxy]-3-(trifluoromethyl)benzoate (1.08 g, 3.76 mmol) obtained in Example (28-5), the title compound was obtained as a yellow oil (138 mg, three-step total yield: 7%).

$^1$H-NMR (400 MHz, CDCl$_3$): δ 7.75 (1H, d, J=1.2 Hz), 7.69 (1H, d, J=8.0 Hz), 7.50 (1H, dd, J=8.0, 1.2 Hz), 7.38 (1H, d, J=8.0 Hz), 7.26-7.19 (3H, m), 6.94 (2H, d, J=8.0 Hz), 5.35 (2H, s), 3.76 (2H, s), 1.63 (9H, s).

MS (FAB) (m/z): 547 ([M]$^+$).

Example 38

(2-Amino-4'-{[2-(tert-butoxycarbonyl)-3-hydroxy-4-(trifluoromethyl)benzyl]oxy}-1,1'-biphenyl-4-yl)acetic acid (Exemplification Compound No.: 2-192)

Rhodium-alumina (Rh 5%) (100 mg) was added to a solution of (4'-{[2-(tert-butoxycarbonyl)-3-hydroxy-4-(trifluoromethyl)benzyl]oxy}-2-nitro-1,1'-biphenyl-4-yl)acetic acid (130 mg, 0.237 mmol) obtained in Example (37-2) in methanol (4 ml), and the mixture was stirred at room temperature under a hydrogen atmosphere for 2 days. The insolubles were removed by filtration through Celite and the filtrate was concentrated. The obtained residue was purified by silica gel preparative thin layer chromatography (developing solvent: methylene chloride/methanol=20/1) to give the title compound as a yellow amorphous compound (63 mg, yield: 51%).

$^1$H-NMR (400 MHz, CDCl$_3$): δ 7.69 (1H, d, J=8.0 Hz), 7.35 (2H, d, J=8.6 Hz), 7.26 (1H, d, J=8.0 Hz), 7.04 (1H, d, J=8.0 Hz), 6.96 (2S, d, J=8.6 Hz), 6.71 (1H, d, J=8.0 Hz), 6.69 (1H, br s), 5.36 (2H, s), 3.58 (2H, s), 1.65 (9H, s).

MS (ESI) (m/z): 516 ([M−H]$^+$).

Example 39

[4'-{[2-(tert-Butoxycarbonyl)-3-hydroxy-4-(trifluoromethyl)benzyl]oxy}-2-(dimethylamino)-1,1'-biphenyl-4-yl]acetic acid (Exemplification Compound No.: 2-193)

36% aqueous formaline solution (0.5 ml), acetic acid (100 μl) and cyano sodium borohydride (36 mg, 0.59 mmol) were successively added to a solution of (2-amino-4'-{[2-(tert-butoxycarbonyl)-3-hydroxy-4-(trifluoromethyl)benzyl]oxy}-1,1'-biphenyl-4-yl)acetic acid (50 mg, 0.096 mmol) obtained in Example 38 in acetonitrile (4 ml), and the mixture was stirred at room temperature overnight. After the reaction mixture was poured into water and extracted with ethyl acetate, the organic layer was successively washed with water and a saturated aqueous NaCl solution and dried with anhydrous sodium sulfate. The residue obtained by removing the solvent under reduced pressure was purified by silica gel preparative thin layer chromatography (developing solvent: methylene chloride/methanol=20/1) to give the title compound as a yellow oil (48 mg, yield: 92%.)

$^1$H-NMR (400 MHz, CDCl$_3$): δ 7.68 (1H, d, J=8.2 Hz), 7.48 (2H, d, J=8.6 Hz), 7.27 (1H, d, J=8.2 Hz), 7.12 (1H, d, J=8.2 Hz), 6.93-6.87 (4H, m), 5.34 (2H, s), 3.63 (2H, s), 2.53 (6H, s), 1.63 (9H, s).

MS (ESI) (m/z): 544 ([M−H]$^+$).

Example 40

(2-Acetyl-4'-{[2-(tert-butoxycarbonyl)-3-hydroxy-4-(trifluoromethyl)benzyl]oxy}-1,1'-biphenyl-4-yl)acetic acid (Exemplification Compound No.: 2-194)

(40-1)
According to a method similar to Examples (22-5) and (26-3), from methyl (3-acetyl-4-hydroxyphenyl)acetate (1.02 g, 4.90 mmol) which was synthesized according to the method described in literature (Watanabe, T. et al., Chem.

Pharm. Bull., 1998, vol. 46, pp. 53-68), methyl (2-acetyl-4'-hydroxy-1,1'-biphenyl-4-yl)acetate was obtained (644 mg, two-step total yield: 51%).

In the present step, 4-(4,4,5,5-tetramethyl-1,3,2-dioxaborolan-2-yl)phenol was used as the boronic acid ester reagent in the reaction corresponding to Example (26-3).

$^1$H-NMR (400 MHz, CDCl$_3$): δ 7.45-7.39 (2H, m), 7.36-7.30 (1H, m), 7.19-7.12 (2H, m), 6.90-6.83 (2H, m), 3.74 (3H, s), 3.70 (2H, s), 2.01 (3H, s).

(40-2)

Cesium carbonate (209 mg, 0.644 mmol) was added to a solution of methyl (2-acetyl-4'-hydroxy-1,1'-biphenyl-4-yl)acetate (122 mg, 0.429 mmol) obtained in Example (40-1) and tert-butyl 6-(bromomethyl)-2-[(tert-butoxycarbonyl)oxy]-3-(trifluoromethyl)benzoate (181 mg, 0.429 mmol) obtained in Example (28-5) in N,N-dimethylformamide (4 ml), and the mixture was stirred at room temperature overnight. The reaction mixture was poured into water and extracted with ethyl acetate (three times). After the organic layer was successively washed with water (three times) and a saturated aqueous NaCl solution and dried with anhydrous sodium sulfate, it was concentrated under reduced pressure. The obtained residue was purified by silica gel preparative thin layer chromatography (developing solvent: hexane/ethyl acetate=3/1) to give tert-butyl 6-[({2'-acetyl-4'-[(methoxycarbonyl)methyl]-1,1'-biphenyl-4-yl}oxy)methyl]-2-[(tert-butoxycarbonyl)oxy]-3-(trifluoromethyl)benzoate (93 mg, yield: 34%).

$^1$H-NMR (400 MHz, CDCl$_3$): δ 7.70 (1H, d, J=8.2 Hz), 7.57 (1H, d, J=8.2 Hz), 7.43-7.37 (2H, m), 7.31 (1H, d, J=8.2 Hz), 7.26-7.21 (2H, m), 6.97 (2H, d, J=8.6 Hz), 5.24 (2H, s), 3.71 (3H, s), 3.68 (2H, s), 1.99 (3H, s), 1.56 (9H, s), 1.53 (9H, s).

(40-3)

According to a method similar to Example (33-5) and Example (17-4), from tert-butyl 6-[({2'-acetyl-4'-[(methoxycarbonyl)methyl]-1,1'-biphenyl-4-yl}oxy)methyl]-2-[(tert-butoxycarbonyl)oxy]-3-(trifluoromethyl)benzoate (93 mg, 0.14 mmol) obtained in Example (40-2), the title compound was obtained as a yellow oil (48 mg, two-step total yield: 61%).

$^1$H-NMR (400 MHz, CDCl$_3$): δ 7.70 (1H, d, J=8.0 Hz), 7.46-7.38 (2H, m), 7.32 (1H, d, J=8.0 Hz), 7.29-7.19 (3H, m), 6.97 (2H, d, J=9.0 Hz), 5.36 (2H, s), 3.68 (2H, s), 2.00 (3H, s), 1.63 (9H, s).

MS (ESI) (m/z): 543 ([M−H]$^+$).

Example 41

2-(4'-{[2-(tert-Butoxycarbonyl)-3-hydroxy-4-(trifluoromethyl)benzyl]oxy}-1,1'-biphenyl-4-yl)-3-hydroxypropanoic acid (Exemplification Compound No.: 1-114).

(41-1)

Dimethyl sulfoxide (3 ml), paraformaldehyde (90% purity, 300 mg) and sodium hydrogencarbonate (300 mg, 3.57 mmol) were added to tert-butyl 2-hydroxy-6-[({4'-[(methoxycarbonyl)methyl]-1,1'-biphenyl-4-yl}oxy)methyl]-3-(trifluoromethyl)benzoate (400 mg, 0.77 mmol) obtained in Example (6-9), and the mixture was stirred at 60° C. for 3 hours. After the reaction mixture was cooled to room temperature, it was diluted with ethyl acetate. The organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=4/1-1/3) to give tert-butyl 2-hydroxy-6-[({4'-[2-hydroxy-1-(methoxycarbonyl)ethyl]-1,1'-biphenyl-4-yl}oxy)methyl]-3-(trifluoromethyl)benzoate as a colorless solid (246 mg, yield: 58%), tert-butyl 2-hydroxy-6-[({4'-[1-(methoxycarbonyl)vinyl]-1,1'-biphenyl-4-yl}oxy)methyl]-3-(trifluoromethyl)benzoate (37 mg, yield: 9%) and tert-butyl 2-hydroxy-6-[({4'-[2-hydroxy-1-hydroxymethyl-1-(methoxycarbonyl)ethyl]-1,1'-biphenyl-4-yl}oxy)methyl]-3-(trifluoromethyl)benzoate (112 mg, yield: 25%).

$^1$H-NMR spectra of the obtained compounds are shown below. tert-Butyl 2-hydroxy-6-[({4'-[2-hydroxy-1-(methoxycarbonyl)ethyl]-1,1'-biphenyl-4-yl}oxy)methyl]-3-(trifluoromethyl)benzoate $^1$H-NMR (500 MHz, CDCl$_3$) δ 12.26 (1H, s), 7.71 (1H, d, J=8.0 Hz), 7.53 (2H, d, J=8.0 Hz), 7.52 (2H, d, J=9.0 Hz), 7.32 (2H, d, J=8.0 Hz), 7.28-7.26 (1H, m), 6.98 (2H, d, J=9.0 Hz), 5.38 (2H, s), 4.18-4.14 (1H, m), 3.91-3.84 (2H, m), 3.74 (3H, s), 2.26-2.23 (1H, m), 1.65 (9H, s).

tert-Butyl 2-hydroxy-6-[({4'-[1-(methoxycarbonyl)vinyl]-1,1'-biphenyl-4-yl}oxy)methyl]-3-(trifluoromethyl)benzoate $^1$H-NMR (500 MHz, CDCl$_3$) δ 12.26 (1H, s), 7.71 (1H, d, J=8.5 Hz), 7.56 (2H, d, J=8.5 Hz), 7.55 (2H, d, J=8.5 Hz), 7.48 (2H, d, J=8.5 Hz), 7.28 (1H, d, J=8.5 Hz), 6.99 (2H, d, J=8.5 Hz), 6.38 (1H, s), 5.95 (1H, s), 5.38 (2H, s), 3.85 (3H, s), 1.65 (9H, s).

tert-Butyl 2-hydroxy-6-[({4'-[2-hydroxy-1-hydroxymethyl-1-(methoxycarbonyl)ethyl]-1,1'-biphenyl-4-yl}oxy)methyl]-3-(trifluoromethyl)benzoate $^1$H-NMR (500 MHz, CDCl$_3$): δ 12.25 (1H, s), 7.71 (1H, d, J=8.5 Hz), 7.53 (2H, d, J=9.0 Hz), 7.51 (2H, d, J=8.5 Hz), 7.28-7.23 (3H, m), 6.98 (2H, d, J=9.0 Hz), 5.38 (2H, s), 4.39-4.35 (2H, m), 4.21-4.17 (2H, m), 3.83 (3H, s), 2.89-2.86 (2H, m), 1.64 (9H, s).

(41-2)

According to a method similar to Example (17-4), from tert-butyl 2-hydroxy-6-[({4'-[2-hydroxy-1-(methoxycarbonyl)ethyl]-1,1'-biphenyl-4-yl}oxy)methyl]-3-(trifluoromethyl)benzoate obtained in Example (41-1), 2-(4'-{[2-(tert-butoxycarbonyl)-3-hydroxy-4-(trifluoromethyl)benzyl]oxy}-1,1'-biphenyl-4-yl)-3-hydroxypropanoic acid was obtained as a colorless solid (65 mg).

In the present step, 1,4-dioxane was used as the reaction solvent instead of tetrahydrofuran.

$^1$H-NMR (400 MHz, CDCl$_3$) δ 12.26 (1H, s), 7.71 (1H, d, J=8.0 Hz), 7.55 (2H, d, J=8.0 Hz), 7.52 (2H, d, J=8.8 Hz), 7.36 (2H, d, J=8.0 Hz), 7.29-7.26 (1H, m), 6.98 (2H, d, J=8.8 Hz), 5.38 (2H, s), 4.21-4.17 (1H, m), 3.97-3.91 (2H, m), 1.65 (9H, s).

ESI (ES−) (m/z): 531 ([M−H]$^+$).

Example 42

(4'-{[2-(tert-Butoxycarbonyl)-3-hydroxy-4-(trifluoromethyl)benzyl]oxy}-2-isopropyl-1,1'-biphenyl-4-yl)acetic acid (Exemplification Compound No.: 2-195)

(42-1)

An isopropylmagnesium bromide-0.63M tetrahydrofuran solution (3.2 ml, 2.0 mmol) was added dropwise to a solution of zinc bromide (473 mg, 2.1 mmol) in tetrahydrofuran (2 ml)

under ice-cooling. After the mixture was stirred for 15 minutes, the reaction mixture was cooled to −78° C. After 3-bromo-4-methoxybenzyl cyanide (226 mg, 1.0 mmol) and [1,1'-bis(diphenylphosphino)ferrocene]dichloropalladium (II)-dichloromethane adduct (32 mg, 0.04 mmol) were added to the mixture at −78° C., the temperature of the reaction mixture was raised to room temperature and the mixture was further stirred for 5 hours. 1N Hydrochloric acid was added to the reaction mixture and the mixture was extracted with ethyl acetate. The organic layer was successively washed with water and a saturated aqueous NaCl solution and dried with anhydrous sodium sulfate. The residue obtained by removing the solvent under reduced pressure was subjected to silica gel column chromatography (eluting solvent: n-hexane/ethyl acetate=8/1-6/1) to give crude (3-isopropyl-4-methoxyphenyl)acetonitrile (158 mg).

$^1$H-NMR (400 MHz, CDCl$_3$): δ 7.12-7.11 (2H, m), 6.83 (1H, d, J=9.2 Hz), 3.83 (3H, s), 3.69 (2H, s), 3.34-3.27 (1H, m), 1.21 (3H, d, J=6.8 Hz), 1.20 (3H, d, J=6.8 Hz).

(42-2)

According to a method similar to Example (26-4), from crudely purified (3-isopropyl-4-methoxyphenyl)acetonitrile (158 mg) obtained in Example (42-1), crude methyl (4-hydroxy-3-isopropylphenyl)acetate was obtained (163 mg).

$^1$H-NMR (400 MHz, CDCl$_3$): δ 7.08 (1H, s), 6.98 (1H, d, J=8.0 Hz), 6.70 (1H, d, J=8.0 Hz), 4.64 (1H, hr s), 3.69 (3H, s), 3.55 (2H, s), 3.21-3.15 (1H, m), 1.25 (6H, d, J=6.8 Hz).

(42-3)

According to a method similar to Example (22-5), Example (29-2) and Example (26-4), from crude methyl (4-hydroxy-3-isopropylphenyl)acetate (163 mg) obtained in Example (42-2), crude methyl (4'-hydroxy-2-isopropyl-1,1'-biphenyl-4-yl)acetate was obtained (147 mg).

In the present step, 4-methoxyphenylboronic acid was used instead of tert-butyl 2-{[4-(4,4,5,5-tetramethyl-1,3,2-dioxaborolan-2-yl)phenoxy]methyl}-5-(trifluoromethyl)benzoate in the Suzuki coupling step corresponding to Example (29-2).

$^1$H-NMR (400 MHz, CDCl$_3$) δ 7.26-7.12 (5H, m), 6.87-6.82 (2H, m), 3.74 (3H, s), 3.67 (2H, s), 3.09-3.02 (1H, m), 1.15 (6H, d, J=6.8 Hz).

(42-4)

According to a method similar to Example (40-2) and Example (8-3), from crudely purified methyl (4'-hydroxy-2-isopropyl-1,1-biphenyl-4-yl)acetate (147 mg) obtained in Example (42-3) and 2-(dimethoxymethyl)-3-(methoxymethoxy)-4-(trifluoromethyl)benzyl methanesulfonate (252 mg, 0.65 mmol) obtained in Example (26-5), crude methyl (4'-{[2-formyl-3-hydroxy-4-(trifluoromethyl)benzyl]oxy}-2-isopropyl-1,1'-biphenyl-4-yl)acetate was obtained (169 mg).

$^1$H-NMR (500 MHz, CDCl$_3$) δ 12.66 (1H, s), 10.39 (1H, s), 7.83 (1H, d, J=8.0 Hz), 7.26-7.23 (3H, m), 7.12-7.10 (3H, m), 7.00 (2H, d, J=8.5 Hz), 5.37 (2H, s), 3.73 (3H, s), 3.67 (2H, s), 3.05-3.02 (1H, m), 1.16 (6H, d, J=6.5 Hz).

(42-5)

According to a method similar to Example (28-3), Example (28-4) and Example (33-5), from crudely purified methyl (4'-{[2-formyl-3-hydroxy-4-(trifluoromethyl)benzyl]oxy}-2-isopropyl-1,1'-biphenyl-4-yl)acetate (169 mg) obtained in Example (42-4), tert-butyl 2-hydroxy-6-[({2'-isopropyl-4'-[(methoxycarbonyl)methyl]-1,1'-biphenyl-4-yl}oxy)methyl]-3-(trifluoromethyl)benzoate was obtained (91 mg, 0.16 mmol).

In the present step, purification of the compound was carried out using high performance liquid chromatography (column: G. L. Science, inert sil ODS-3; eluent: acetonitrile: water=93/7-98/2) subsequent to silica gel column chromatography in the step corresponding to Example (33-5).

$^1$H-NMR (500 MHz, CDCl$_3$): δ 12.26 (1H, s), 7.72 (1H, d, J=8.0 Hz), 7.32-7.26 (2H, m), 7.21 (2H, d, J=8.5 Hz), 7.12 (2H, br s), 6.94 (2H, d, J=8.5 Hz), 5.38 (2H, s), 3.73 (3H, s), 3.67 (2H, s), 3.09-3.04 (1H, m), 1.65 (9H, s), 1.15 (6H, d, J=6.5 Hz).

(42-6)

According to a method similar to Example (17-4), from tert-butyl 2-hydroxy-6-[({2'-isopropyl-4'-[(methoxycarbonyl)methyl]-1,1'-biphenyl-4-yl}oxy)methyl]-3-(trifluoromethyl)benzoate (91 mg, 0.16 mmol) obtained in Example (42-5), the title compound was obtained as a colorless solid (84 g, yield: 94%).

In the present step, 1,4-dioxane was used as the reaction solvent instead of tetrahydrofuran.

$^1$H-NMR (400 MHz, CDCl$_3$): δ 12.23 (1H, s), 7.70 (1H, d, J=8.4 Hz), 7.28 (1H, d, J=8.4 Hz), 7.25-7.24 (1H, m), 7.19 (2H, d, J=8.8 Hz), 7.12 (2H, br s), 6.92 (2H, d, J=8.8 Hz), 5.36 (2H, s), 3.69 (2H, s), 3.07-3.04 (1H, m), 1.65 (9H, s), 1.15 (6H, d, J=6.8 Hz).

ESI (ES−) (m/z): 543 ([M−H]$^+$).

Example 43

4'-{[2-(tert-Butoxycarbonyl)-3-hydroxy-4-(trifluoromethyl)benzyl]oxy}-1,1'-biphenyl-4-carboxylic acid (Exemplification Compound No.: 1-54)

(43-1)

According to a method similar to Example (13-2), from 4'-hydroxy-1,1'-biphenyl-4-carboxylic acid (820 mg, 3.82 mmol), allyl 4'-hydroxy-1,1'-biphenyl-4-carboxylate was obtained as a grayish white solid (582 mg, yield: 60%).

$^1$H-NMR (400 MHz, CDCl$_3$): δ 8.08 (2H, d, J=8.6 Hz), 7.59 (2H, d, J=8.6 Hz), 7.50 (2H, d, J=8.6 Hz), 6.91 (2H, d, J=8.6 Hz), 6.10-5.99 (1H, m), 5.44-5.20 (1H, m), 5.31-5.26 (1H, m), 5.01 (1H, s), 4.83 (2H, d, J=5.5 Hz).

(43-2)

According to a method similar to Example (40-2), Example (33-5) and Example (13-5), using allyl 4'-hydroxy-1,1'-biphenyl-4-carboxylate (190 mg, 0.75 mmol) obtained in Example (43-1) and tert-butyl 6-(bromomethyl)-2-[(tert-butoxycarbonyl)oxy]-3-(trifluoromethyl)benzoate (400 mg, 0.88 mmol) obtained in Example (28-5), the title compound was obtained as a colorless powder (293 mg, three-step total yield: 80%).

$^1$H-NMR (500 MHz, DMSO-d$_6$): δ 12.9 (1H, br s), 11.4 (1H, br s), 7.98 (2H, d, J=8.8 Hz), 7.82 (1H, d, J=8.8 Hz), 7.76 (2H, d, J=8.8 Hz), 7.72 (2H, d, J=8.8 Hz), 7.30 (1H, d, J=8.8 Hz), 7.11 (2H, d, J=8.8 Hz), 5.39 (2H, s), 1.57 (9H, s).

MS (FAB+) (m/z): 489 ([M+H]$^+$).

Example 44

(4'-{[2-(tert-Butoxycarbonyl)-3-hydroxy-4-(trifluoromethyl)benzyl]oxy}-3-trifluoromethyl-1,1'-biphenyl-4-yl)acetic acid (Exemplification Compound No.: 2-196)

(44-1)

After N-bromosuccinimide (1.49 g, 6.63 mmol) and 2,2'-azobis(isbutyronitrile) (20 mg) were added to a solution of 4-bromo-1-methyl-2-(trifluoromethyl)benzene (2.0 g, 8.4 mmol) in carbon tetrachloride (20 ml), the mixture was heated under reflux for 5 hours. The temperature of the reaction mixture was returned to room temperature and the residue obtained by removing the solvent under reduced pressure was subjected to silica gel column chromatography (eluting solvent: n-hexane) to give crude 4-bromo-1-bromomethyl-2-(trifluoromethyl)benzene. Potassium cyanide (365 mg, 5.6 mmol) was added to a solution of crude 4-bromo-1-bromomethyl-2-(trifluoromethyl)benzene obtained in the above in a mixture of ethanol-water (3:1, 12 ml), and the mixture was stirred at 70° C. for 3 hours. After the reaction mixture was poured into water and extracted with ethyl acetate, the organic layer was washed with a saturated aqueous NaCl solution and dried with anhydrous sodium sulfate. The residue obtained by removing the solvent under reduced pressure was purified by silica gel column chromatography (eluting solvent: n-hexane/ethyl acetate=10/1-5/1) to give [4-bromo-2-(trifluoromethyl)phenyl]acetonitrile as a solid (1.14 g, total yield: 52%).

$^1$H-NMR (400 MHz, CDCl$_3$): δ 7.80 (1H, d, J=2.0 Hz), 7.65 (1H, dd, J=8.0, 2.0 Hz), 7.27 (1H, d, J=8.0 Hz), 3.78 (2H, s), 3.70 (3H, s).

(44-2)

According to a method similar to Example (24-2) and Example (17-4), from methyl [4-chloro-3-(trifluoromethyl)phenyl]acetate (51 mg, 0.20 mmol) obtained in Example (44-1) and tert-butyl 2-hydroxy-{[4-(4,4,5,5-tetramethyl-1,3,2-dioxaborolan-2-yl)phenoxy]methyl}-3-(trifluoromethyl)benzoate (100 mg, 0.20 mmol) obtained in Example (22-4), the title compound was obtained as a pale yellow powder (24 mg, two-step total yield: 44%).

$^1$H-NMR (400 MHz, DMSO-d$_6$): δ 12.50 (1H, s), 11.44 (1H, s), 7.90-7.86 (2H, m), 7.82 (1H, d, J=8.4 Hz), 7.73 (2H, d, J=7.2 Hz), 7.56 (1H, d, J=8.0 Hz), 7.31 (1H, d, J=8.4 Hz), 7.11 (2H, d, J=7.2 Hz), 5.38 (2H, 9), 3.81 (2H, s), 1.57 (9H, s).

Example 45

(4'-{[2-(tert-Butoxycarbonyl)-3-hydroxy-4-(trifluoromethyl)benzyl]oxy}-2-formyl-1,1'-biphenyl-4-yl)acetic acid (Exemplification Compound No.: 2-197)

(45-1)

According to a method similar to Example (1-1), Example (22-5) and Example (26-3), from methyl 4-hydroxyphenylacetate (15.6 g, 110 mmol), methyl)-2-formyl-4'-hydroxy-1,1'-biphenyl-4-yl)acetate was obtained (6.32 g, three-step total yield: 21%).

In the present step, the reaction time was 12 hours in the reaction corresponding to Example (1-1). In the reaction corresponding to Example (26-3), 4-(4,4,5,5-tetramethyl-1,3,2-dioxaborolan-2-yl)phenol was used as the boronic acid ester reagent.

$^1$H-NMR (500 MHz, CDCl$_3$): δ 9.96 (1H, s), 7.88 (1H, s), 7.55 (1H, app d, J=7.8 Hz), 7.40 (1H, d, J=7.8 Hz), 7.20 (2H, d, J=8.3 Hz), 6.92 (2H, d, J=8.3 Hz), 3.75-3.71 (5H, m).

(45-2)

According to a method similar to Example (2-3), from tert-butyl 6-(bromomethyl)-2-[(tert-butoxycarbonyl)oxy]-3-(trifluoromethyl)benzoate (3.60 g, 8.56 mmol) obtained in Example (28-5) and methyl (2-formyl-4'-hydroxy-1,1'-biphenyl-4-yl)acetate (2.10 g, 7.78 mmol) obtained in Example (45-1), tert-butyl 2-[(tert-butoxycarbonyl)oxy]-6-[({2'-formyl-4'-[(methoxycarbonyl)methyl]-1,1'-biphenyl-4-yl}oxy)methyl]-3-(trifluoromethyl)benzoate was obtained (3.06 g, yield: 61%).

In the present step, acetone was used as the reaction solvent instead of N,N-dimethylformamide.

$^1$H-NMR (400 MHz, CDCl$_3$): δ 9.93 (1H, s), 7.87 (1H, s), 7.71 (1H, d, J=8.2 Hz), 7.58 (1H, d, J=8.2 Hz), 7.54 (1H, d, J=7.8 Hz), 7.38 (1H, d, J=7.8 Hz), 7.28 (2H, d, J=8.2 Hz), 7.01 (2H, d, J=8.2 Hz), 5.27 (2H, s), 3.75-3.70 (5H, m), 1.58 (9H, s), 1.54 (9H, s).

(45-3)

According to a method similar to Example (33-5) and Example (17-4), from tert-butyl 2-[(tert-butoxycarbonyl)oxy]-6-[({2'-formyl-4'-[(methoxycarbonyl)methyl]-1,1'-biphenyl-4-yl}oxy)methyl]-3-(trifluoromethyl)benzoate (88 mg, 0.14 mmol) obtained in Example (45-2), the title compound was obtained as a white powder (28 mg, two-step total yield 38%).

$^1$H-NMR (400 MHz, CDCl$_3$): δ 12.23 (1H, s), 9.94 (1H, s), 7.89 (1H, d, J=2.0 Hz), 7.70 (1H, d, J=8.2 Hz), 7.55 (1H, dd, J=7.8, 2.0 Hz), 7.40 (1H, d, J=7.8 Hz), 7.29 (2H, d, J=8.6 Hz), 7.26 (1H, d, J=8.2 Hz), 7.00 (2H, d, J=8.6 Hz), 5.38 (2H, s), 3.76 (2H, s), 1.65 (9H, s).

ESI (ES−) (m/z): 529 ([M−H]$^+$).

Example 46

(4'-{[2-(tert-Butoxycarbonyl)-3-hydroxy-4-(trifluoromethyl)benzyl]oxy}-2-(hydroxymethyl)-1,1'-biphenyl-4-yl)acetic acid (Exemplification Compound No.: 2-198)

According to a method similar to Example (6-6), Example (33-5) and Example (17-4), from tert-butyl 2-[(tert-butoxycarbonyl)oxy]-6-[({2'-formyl-4'-[(methoxycarbonyl)methyl]-1,1'-biphenyl-4-yl}oxy)methyl]-3-(trifluoromethyl)benzoate (200 mg, 0.371 mmol) obtained in Example (45-2), the title compound was obtained as a white powder (62 mg, three-step total yield: 31%).

$^1$H-NMR (400 MHz, CDCl$_3$): δ 12.22 (1H, s), 7.68 (1H, d, J=8.2 Hz), 7.44 (1H, s), 7.30-7.18 (5H, m), 6.93 (2H, d, J=8.2 Hz), 5.35 (2H, s), 4.59 (2H, s), 3.70 (2H, s), 1.64 (9H, s).

ESI (ES−) (m/z): 531 ([M−H]$^+$).

Example 47

(4'-{[2-(tert-Butoxycarbonyl)-3-hydroxy-4-(trifluoromethyl)benzyl]oxy}-2-cyano-1,1'-biphenyl-4-yl)acetic acid (Exemplification Compound No.: 2-199)

(47-1)

Pyridine (49 μl, 0.62 mmol) and hydroxylamine hydrochloride (42 mg, 0.62 mmol) were added to a solution of tert-butyl 2-[(tert-butoxycarbonyl)oxy]-6-[({2'-formyl-4'-[(methoxycarbonyl)methyl]-1,1'-biphenyl-4-yl}oxy)methyl]-3-(trifluoromethyl)benzoate (198 mg, 0.307 mmol) obtained in Example (45-2) in ethanol (4 ml), and the mixture was stirred at room temperature for 4 hours. The reaction mixture was diluted with ethyl acetate, successively washed with water and a saturated aqueous NaCl solution and dried with anhydrous sodium sulfate. The residue obtained by removing the solvent under reduced pressure was subjected to silica gel preparative thin layer chromatography (developing solvent: n-hexane/ethyl acetate=2/1) to give crude tert-butyl 2-[(tert-butoxycarbonyl)oxy]-6-[({2'-[(hydroxyimino)methyl]-4'-[(methoxycarbonyl)methyl]-1,1'-biphenyl-4-yl}oxy)methyl]-3-(trifluoromethyl)benzoate (170 mg).

Triethylamine (71 μl, 0.51 mmol) and methanesulfonyl chloride (23 μl, 0.31 mmol) were added to a solution of crude tert-butyl 2-[(tert-butoxycarbonyl)oxy]-6-[({2'-[(hydroxyimino)methyl]-4'-[(methoxycarbonyl)methyl]-1,1'-biphenyl-4-yl}oxy)methyl]-3-(trifluoromethyl)benzoate (170 mg) obtained in the above in dichloromethane (4 ml), and the mixture was stirred at room temperature for 1 hour. The reaction mixture was diluted with ethyl acetate, successively washed with a saturated aqueous sodium hydrogencarbonate solution, water and a saturated aqueous NaCl solution and dried with anhydrous sodium sulfate. The solvent was removed under reduced pressure. Triethylamine (71 μl, 0.51 mmol) was added to a solution of the obtained residue in ethanol (4 ml) and the mixture was heated under reflux for 14 hours. The solvent was removed under reduced pressure and the obtained residue was subjected to silica gel preparative thin layer chromatography (developing solvent: n-hexane/ethyl acetate=2/1) to give crude tert-butyl 2-[(tert-butoxycarbonyl)oxy]-6-[({2'-cyano-4'-[(methoxycarbonyl)methyl]-1,1'-biphenyl-4-yl}oxy)methyl]-3-(trifluoromethyl)benzoate (125 mg).

Pyrrolidine (33 μl, 0.39 mmol) was added to a solution of crude tert-butyl 2-[(tert-butoxycarbonyl)oxy]-6-[({2'-cyano-4'-[(methoxycarbonyl)methyl]-1,1'-biphenyl-4-yl}oxy)methyl]-3-(trifluoromethyl)benzoate (125 mg) obtained in the above in 1,4-dioxane (4 ml), and the mixture was stirred at 50° C. for 2 hours. The residue obtained by removing the solvent under reduced pressure was purified by silica gel preparative thin layer chromatography (developing solvent: n-hexane/ethyl acetate=5/1) to give tert-butyl 6-[({2'-cyano-4'-[(methoxycarbonyl)methyl]-1,1'-biphenyl-4-yl}oxy)methyl]-2-hydroxy-3-(trifluoromethyl)benzoate (100 mg, 60%).

$^1$H-NMR (400 MHz, CDCl$_3$): δ 12.30 (1H, s), 7.71 (1H, d, J=8.6 Hz), 7.67 (1H, d, J=1.8 Hz), 7.55 (1H, dd, J=8.6, 1.8 Hz), 7.51 (2H, d, J=8.6 Hz), 7.46 (1H, d, J=8.6 Hz), 7.27 (1H, d, J=8.6 Hz), 7.03 (2H, d, J=8.6 Hz), 5.40 (2H, s), 3.74 (3H, s), 3.70 (2H, s), 1.65 (9H, s).

(47-2)

According to a method similar to Example (17-4), from tert-butyl 6-[({2'-cyano-4'-[(methoxycarbonyl)methyl]-1,1'-biphenyl-4-yl}oxy)methyl]-3-(trifluoromethyl)benzoate (100 mg, 0.184 mmol) obtained in Example (47-1), the title compound was obtained as a white amorphous compound (80 mg, 829).

$^1$H-NMR (400 MHz, CDCl$_3$): δ 12.29 (1H, s), 7.71 (1H, d, J=8.0 Hz), 7.68 (1H, d, J=1.6 Hz), 7.55 (1H, dd, J=8.0, 1.6 Hz), 7.51 (2H, d, J=8.6 Hz), 7.47 (1H, d, J=8.0 Hz), 7.27 (1H, d, J=8.0 Hz), 7.02 (2H, d, J=8.6 Hz), 5.40 (2H, s), 3.74 (2H, s), 1.65 (9H, s).

MS (FAB) (m/z): 528 ([M+H]$^+$).

Example 48

(4'-{[2-(tert-Butoxycarbonyl)-3-hydroxy-4-(trifluoromethyl)benzyl]oxy}-2'-methyl-1,1'-biphenyl-4-yl) acetic acid (Exemplification Compound No.: 2-53)

According to a method similar to Example (6-7), Example (6-8), Example (6-9) and Example (7), from [2-(dimethoxymethyl)-3-(methoxymethoxy)-4-(trifluoromethyl)phenyl]methanol (985 mg, 3.18 mmol) obtained in Example (6-6) and methyl (4'-hydroxy-2'-methyl-1,1'-biphenyl-4-yl)acetate (626 mg, 2.44 mmol), the title compound was obtained as a colorless crystal (198 mg, four-step total yield: 16%).

$^1$H-NMR (400 MHz, CDCl$_3$): δ 12.26 (1H, s), 7.69 (1H, d, J=8.2 Hz), 7.31 (2H, d, J=8.2 Hz), 7.27-7.24 (3H, m), 7.13 (1H, d, J=8.2 Hz), 6.83 (1H, d, J=2.7 Hz), 6.98 (1H, dd, J=8.2, 2.7 Hz), 5.35 (2H, s), 3.70 (2H, s), 2.26 (3H, s), 1.66 (9H, s).

MS (FAB) (m/z): 516 ([M]$^+$).

Example 49 tert-Butyl 6-[({4'-[2-(dimethylamino)-2-oxoethyl]-1,1'-biphenyl-4-yl}oxy)methyl]-2-hydroxy-3-(trifluoromethyl)benzoate (Exemplification Compound No.: 1-61)

Dimethylamine hydrochloride (41 mg, 0.502 mmol), N-ethyl-N'-(3-dimethylaminopropyl)carbodiimide hydrochloride (96 mg, 0.50 mmol), hydroxybenzotriazole (77 mg, 0.50 mmol) and triethylamine (0.10 ml) were added to a solution of (4'-{[2-(tert-butoxycarbonyl)-3-hydroxy-4-(trifluoromethyl)benzyl]oxy}-1,1'-biphenyl-4-yl)acetic acid (168 mg, 0.334 mmol) obtained in Example (7) in acetonitrile (10 ml). After the mixture was stirred for 10 hours, a saturated aqueous ammonium chloride solution was added thereto and the mixture was extracted with ethyl acetate. The organic layer was successively washed with water and a saturated aqueous NaCl solution and dried with anhydrous sodium sulfate. The residue obtained by removing the solvent under reduced pressure was purified by silica gel column chromatography (eluting solvent: hexane/ethyl acetate=3/1-methylene chloride/methanol=15/1) to give the title compound as a pale yellow crystal (303 mg, yield: 34%).

$^1$H-NMR (400 MHz, CDCl$_3$): δ 12.23 (1H, s), 7.68 (1H, d, J=8.6 Hz), 7.51-7.47 (4H, m), 7.29-7.24 (3H, m), 6.96 (2H, d, J=8.6 Hz), 5.35 (2H, s), 3.74 (2H, s), 3.03 (3H, s), 2.98 (3H, s), 1.64 (9H, s).

MS (530) (m/z): 530 ([M+H]$^+$).

Example 50 tert-Butyl 2-hydroxy-6-[({4'-[2-(methylamino)-2-oxoethyl]-1,1'-biphenyl-4-yl}oxy)methyl]-3-trifluoromethylbenzoate (Exemplification Compound No.: 1-60)

According to a method similar to Example (49), from (4'-([2-(tert-butoxycarbonyl)-3-hydroxy-4-(trifluoromethyl)benzyl]oxy)-1,1'-biphenyl-4-yl)acetic acid (216 mg, 0.431 mmol) obtained in Example (7) and methylamine hydrochloride (50 mg, 0.74 mmol), the title compound was obtained as a colorless crystal (160 mg, yield: 72%).

$^1$H-NMR (400 MHz, CDCl$_3$): δ 12.27 (1H, s), 7.71 (1H, d, J=8.2 Hz), 7.56-7.53 (4H, m), 7.32-7.27 (3H, m), 7.00 (2H, d, J=7.0 Hz), 5.38 (2H, s), 3.61 (2H, s), 2.79 (3H, d, J=5.0 Hz), 1.65 (9H, s).

MS (516) (m/z): 516 ([M+H]$^+$).

Example 51

(4'-{[2-(tert-Butoxycarbonyl)-3-hydroxy-4-methoxybenzyl]oxy}-1,1'-biphenyl-4-yl)acetic acid (Exemplification Compound No.: 1-85)

(51-1)

According to a method similar to Example (40-2), from tert-butyl 6-(bromomethyl)-3-methoxy-2-(methoxymethyl)benzoate (1.20 g, 2.33 mmol) and methyl (4'-hydroxy-1,1'-biphenyl-4-yl)acetate (619 mg, 2.56 mmol) obtained in Example (6-2), tert-butyl 3-methoxy-2-(methoxymethoxy)-6-[({4'-[(methoxycarbonyl)methyl]-1,1'-biphenyl-4-yl}oxy)methyl]benzoate was obtained (306 mg, yield: 25%).

$^1$H-NMR (400 MHz, CDCl$_3$): δ 7.55-7.46 (4H, m), 7.32 (2H, d, J=8.2 Hz), 7.19 (1H, d, J=8.4 Hz), 7.00 (2H, d, J=8.6 Hz), 6.92 (1H, d, J=8.4 Hz), 5.17 (2H, s), 5.06 (2H, s), 3.85 (3H, s), 3.71 (3H, s), 3.66 (2H, s), 3.59 (3H, s), 1.54 (9H, s).

(51-2)

After trimethylsilyl bromide (55 µl, 0.414 mmol) was added to a solution of tert-butyl 3-methoxy-2-(methoxymethoxy)-6-[({4'-[(methoxycarbonyl)methyl]-1,1'-biphenyl-4-yl}oxy)methyl]benzoate (180 mg, 0.344 mmol) obtained in Example (51-1) in dichloromethane (4.0 ml), the mixture was stirred at room temperature for 12 hours. The reaction mixture was poured into an aqueous sodium hydrogencarbonate solution and the mixture was extracted with ethyl acetate. The organic layer was successively washed with water and a saturated aqueous NaCl solution and dried with anhydrous sodium sulfate. The residue obtained by removing the solvent under reduced pressure was purified by silica gel preparative thin layer chromatography (developing solvent: n-hexane/ethyl acetate=2/1) to give tert-butyl 2-hydroxy-3-methoxy-6-[({4'-[(methoxycarbonyl)methyl]-1,1'-biphenyl-4-yl}oxy)methyl]benzoate (146 mg, yield: 89%).

$^1$H-NMR (400 MHz, CDCl$_3$): δ 11.61 (1H, s), 7.55-7.43 (5H, m), 7.35-7.30 (2H, m), 7.06-6.95 (3H, m), 5.27 (2H, s), 3.91 (3H, s), 3.71 (3H, s), 3.66 (2H, s), 1.57 (9H, s).

(51-3)

According to a method similar to Example (17-4), from tert-butyl 2-hydroxy-3-methoxy-6-[({4'-[(methoxycarbonyl)methyl]-1,1'-biphenyl-4-yl}oxy)methyl]benzoate (146 mg, 0.305 mmol) obtained in Example (51-2), the title compound was obtained as a colorless amorphous compound (110 mg, yield: 78%).

$^1$H-NMR (500 MHz, CDCl$_3$): δ 7.56-7.46 (4H, m), 7.36-7.31 (2H, m), 7.11-6.91 (4H, m), 5.27 (2H, s), 3.91 (3H, s), 3.69 (2H, s), 1.57 (9H, s).

ESI (ES−) (m/z): 463 ([M−H]$^+$).

Example 52

(4'-{[2-(tert-Butoxycarbonyl)-3-hydroxy-4-(trifluoromethyl)benzyl]oxy}-6-fluoro-1,1'-biphenyl-3-yl) acetic acid (Exemplification Compound No.: 2-41)

According to a method similar to Example (6-1) and Example (7), from tert-butyl 2-hydroxy-{[4-(4,4,5,5-tetramethyl-1,3,2-dioxaborolan-2-yl)phenoxy]methyl}-3-(trifluoromethyl)benzoate (424 mg, 0.858 mmol) obtained in Example (22-4) and methyl (3-bromo-4-fluorophenyl)acetate (200 mg, 0.858 mmol), the title compound was obtained as a white powder (220 mg, two-step total yield: 38%).

$^1$H-NMR (400 MHz, CDCl$_3$): δ 12.27 (1H, s), 7.71 (1H, d, J=8.2 Hz), 7.50 (2H, d, J=8.6 Hz), 7.33 (1H, d, J=7.4 Hz), 7.27 (1H, d, J=8.2 Hz), 7.23-7.19 (1H, m), 7.11 (1H, dd, J=10.2, 8.6 Hz), 6.99 (2H, d, J=8.6 Hz), 5.38 (2H, s), 3.68 (2H, s), 1.65 (9H, s).

MS (FAB) (m/z): 520 ([M]).

Example 53

(4'-{[2-(tert-Butoxycarbonyl)-3-hydroxy-4-(trifluoromethyl)benzyl]oxy}-1,1'-biphenyl-4-yl)(hydroxy) acetic acid (Exemplification Compound No.: 1-115)

According to a method similar to Example (31) and Example (17-4), from methyl (4-bromophenyl)(hydroxy)acetate (100 mg, 0.41 mmol) and tert-butyl 2-hydroxy-6-{[4-(4,4,5,5-tetramethyl-1,3,2-dioxaborolan-2-yl)phenoxy]methyl}-3-(trifluoromethyl)benzoate (170 mg, 0.34 mmol) obtained in Example (22-4), the title compound was obtained as a grayish white powder (14 mg, yield: 8%).

$^1$H-NMR (400 MHz, DMSO-d$_6$): δ 12.57 (1H, br), 11.40 (1H, br, s), 7.79 (1H, d, J=8.6 Hz), 7.60 (2H, d, J=9.4 Hz), 7.57 (2H, d, J=8.6 Hz), 7.44 (2H, d, J=8.6 Hz), 7.27 (1H, d, J=8.6 Hz), 7.05 (2H, d, J=9.4 Hz), 5.85 (1H, br), 5.35 (2H, s), 5.04 (1H, s), 1.56 (9H, s).

MS (FAB+) (m/z): 518 (M$^{+-}$).

Example 54

(4'-{[2-(tert-Butoxycarbonyl)-3-hydroxy-4-(trifluoromethyl)benzyl]oxy}-1,1'-biphenyl-4-yl)(ethoxy) acetic acid (Exemplification Compound No.: 1-116)

According to a method similar to Example (31) and Example (17-4), from methyl (4-bromophenyl)(ethoxy)acetate (110 mg, 0.4 mmol) and tert-butyl 2-hydroxy-6-{[4-(4,4,5,5-tetramethyl-1,3,2-dioxaborolan-2-yl)phenoxy]methyl}-3-(trifluoromethyl)benzoate (170 mg, 0.34 mmol) obtained in Example (22-4), the title compound was obtained as a grayish white powder (35 mg, yield: 19%).

$^1$H-NMR (400 MHz, DMSO-d$_6$): δ 12.76 (1H, br, s), 11.41 (1H, br, s) 7.79 (1H, d, J=8.6 Hz), 7.62-7.58 (4H, m), 7.42 (2H, d, J=8.6 Hz), 7.28 (1H, d, J=8.6 Hz), 7.05 (2H, d, J=9.4 Hz), 5.36 (2H, s), 4.87 (1H, s), 3.61-3.52 (1H, m), 3.46-3.38 (1H, m), 1.56 (9H, s), 1.16 (3H, t, J=7.0 Hz).

MS (FAB+) (m/z): 546 (M$^{+-}$).

Example 55

3-(4'-{[2-(tert-Butoxycarbonyl)-3-hydroxy-4-(trifluoromethyl)benzyl]oxy}-1,1'-biphenyl-3-yl)propanoic acid (Exemplification Compound No.: 2-200)

According to a method similar to Example (6-1) and Example (7), from tert-butyl 2-hydroxy-{[4-(4,4,5,5-tetramethyl-1,3,2-dioxaborolan-2-yl)phenoxy]methyl}-3-(trifluoromethyl)benzoate (300 mg, 0.607 mmol) obtained in Example (22-4) and methyl 3-(3-bromophenyl)propanoate (148 mg, 0.607 mmol), the title compound was obtained as a white powder (111 mg, two-step total yield: 35%).

$^1$H-NMR (400 MHz, CDCl$_3$): δ 12.27 (1H, s), 7.71 (1H, d, J=8.2 Hz), 7.53 (2H, d, J=9.0 Hz), 7.41 (1H, d, J=7.4 Hz), 7.40 (1H, s), 7.35 (1H, t, J=7.4 Hz), 7.28 (1H, d, J=8.2 Hz), 7.17 (1H, d, J=7.4 Hz), 6.99 (2H, d, J=9.0 Hz), 5.38 (2H, s), 3.03 (2H, t, J=7.8 Hz), 2.74 (2H, t, J=7.8 Hz), 1.65 (9H, s).

MS (FAB) (m/z): 516 ([M]$^+$).

Example 56

(4'-{[2-(tert-Butoxycarbonyl)-3-hydroxy-4-(trifluoromethyl)benzyl]oxy}-5-fluoro-1,1'-biphenyl-3-yl) acetic acid (Exemplification Compound No.: 2-38)

According to a method similar to Example (24-2) and Example (7), from tert-butyl 2-hydroxy-{[4-(4,4,5,5-tetramethyl-1,3,2-dioxaborolan-2-yl)phenoxy]methyl}-3-(trifluoromethyl)benzoate (400 mg, 0.809 mmol) obtained in Example (22-4) and methyl (3-chloro-5-fluorophenyl)acetate (164 mg, 0.809 mmol), the title compound was obtained as a white powder (59 mg, two-step total yield: 14%).

$^1$H-NMR (400 MHz, CDCl$_3$): δ 12.26 (1H, s), 7.71 (1H, d, J=8.2 Hz), 7.52 (2H, d, J=8.6 Hz), 7.28-7.20 (2H, m), 7.18 (1H, ddd, J=10.2, 2.0, 1.6 Hz), 7.00-6.96 (1H, m), 6.99 (2H, d, J=8.6 Hz), 5.38 (2H, s), 3.71 (2H, s), 1.65 (9H, s).

MS (FAB) (m/z): 520 ([M]⁺).

Example 57 tert-Butyl 6-{[4'-{[(dimethylamino)sulfonyl]methyl}-1,1'-biphenyl-4-yl]oxy}methyl)-2-hydroxy-3-(trifluoromethyl)benzoate (Exemplification Compound No.: 1-120)

According to a method similar to Example (29-1) and Example (29-2), from 4-bromobenzyl bromide, the title compound was obtained as a white powder (6 mg).

In the present step, dimethylamine was used instead of the 40% aqueous methylamine solution in the step corresponding to Example (29-1).

¹H-NMR (400 MHz, CDCl₃): δ 12.26 (1H, s), 7.71 (1H, d, J=8.2 Hz), 7.57 (2H, d, J=8.2 Hz), 7.55 (2H, d, J=8.6 Hz), 7.45 (2H, d, J=8.2 Hz), 7.27 (1H, d, J=8.2 Hz), 7.00 (2H, d, J=8.6 Hz), 5.39 (2H, s), 4.25 (2H, s), 2.78 (6H, s), 1.65 (9H, s).

MS (FAB) (m/z): 565 ([M]⁺).

Example 58 tert-Butyl 2-hydroxy-6-{[(3'-{[(methylsulfonyl)amino]methyl}-1,1'-biphenyl-4-yl)oxy]methyl}-3-(trifluoromethyl)benzoate (Exemplification Compound No.: 2-201)

According to a method similar to Example (31), from N-(3-bromobenzyl)methanesulfonamide (119 mg, 0.45 mmol) and tert-butyl 2-hydroxy-6-{[4-(4,4,5,5-tetramethyl-1,3,2-dioxaborolan-2-yl)phenoxy]methyl}-3-(trifluoromethyl)benzoate (250 mg, 0.51 mmol) obtained in Example (22-4), the title compound was obtained as a pale brown powder (49 mg, yield: 20%).

¹H-NMR (400 MHz, DMSO-d₆): δ 11.31 (1H, br s), 7.79 (1H, d, J=7.8 Hz), 7.62-7.49 (5H, m), 7.39 (1H, t, J=7.8 Hz), 7.32-7.25 (2H, m), 7.06 (2H, d, J=8.6 Hz), 5.36 (2H, s), 4.20 (2H, d, J=6.3 Hz), 3.31 (3H, s), 1.56 (9H, s).

MS (FAB+) (m/z): 551 (M⁺⁻).

Example 59 tert-Butyl 6-[({4'-[2-(ethylamino) 2-oxoethyl]-1,1'-biphenyl-4-yl}oxy)methyl]-2-hydroxy-3-(trifluoromethyl)benzoate (Exemplification Compound No.: 1-121)

According to a method similar to Example (49), from (4'-{[2-(tert-butoxycarbonyl)-3-hydroxy-4-(trifluoromethyl)benzyl]oxy}-1,1'-biphenyl-4-yl)acetic acid (187 mg, 0.374 mmol) obtained in Example (7) and ethylamine hydrochloride (61 mg, 0.75 mmol), the title compound was obtained as a colorless powder (129 mg, yield: 65%).

¹H-NMR (400 MHz, CDCl₃): δ 12.22 (1H, s), 7.68 (1H, d, J=7.8 Hz), 7.54-7.50 (4H, m), 7.29 (2H, d, J=8.2 Hz), 7.25 (1H, d, J=7.8 Hz), 6.97 (2H, d, J=8.2 Hz), 5.37 (2H, s), 3.58 (2H, s), 3.30-3.22 (2H, m), 1.65 (9H, s), 1.08 (3H, t, J=7.4 Hz).

MS (530) (m/z): 530 ([M+H]⁺).

Example 60 tert-Butyl 2-hydroxy-6-[({4'-[(methylsulfonyl)methyl]-1,1'-biphenyl-4-yl}oxy)methyl]-3-(trifluoromethyl)benzoate (Exemplification Compound No.: 1-123)

According to a method similar to Example (24-3), from 1-chloro-4-[(methylsulfonyl)methyl]benzene (204 mg, 1.0 mmol) and tert-butyl 2-hydroxy-{[4-(4,4,5,5-tetramethyl-1,3,2-dioxaborolan-2-yl)phenoxy]methyl}-3-(trifluoromethyl)benzoate (494 mg, 1.0 mmol) obtained in Example (22-4), the title compound was obtained (62 mg, yield: 12%).

¹H-NMR (400 MHz, DMSO-d₆): δ 11.41 (1H, s), 7.79 (1H, d, J=8.2 Hz), 7.65-7.63 (4H, m), 7.44 (2H, d, J=8.2 Hz), 7.27 (1H, d, J=8.2 Hz), 7.06 (2H, d, J=8.2 Hz), 5.36 (2H, s), 4.50 (2H, s), 2.92 (3H, s), 2.08 (9H, s).

MS (EI) (m/z): 535 ([M–H]⁻).

Example 61

[4'-{[2-(tert-Butoxycarbonyl)-3-hydroxy-4-(trifluoromethyl)benzyl]oxy}-3-(methylsulfonyl)-1,1'-biphenyl-4-yl]acetic acid (Exemplification Compound No.: 2-203)

According to a method similar to Example (6-1) and Example (7), from tert-butyl 2-hydroxy-{[4-(4,4,5,5-tetramethyl-1,3,2-dioxaborolan-2-yl)phenoxy]methyl}-3-(trifluoromethyl)benzoate (150 mg, 0.30 mmol) obtained in Example (22-4) and methyl [4-bromo-2-(methylsulfonyl)phenyl]acetate (93 mg, 0.30 mmol), the title compound was obtained as a yellow crystal (93 mg, two-step total yield: 53%).

¹H-NMR (400 MHz, CDCl₃): δ 12.26 (1H, s), 8.25 (1H, d, J=2.0 Hz), 7.79 (1H, dd, J=7.8, 2.0 Hz), 7.72 (1H, d, J=8.2 Hz), 7.58 (2H, d, J=8.6 Hz), 7.46 (1H, d, J=7.8 Hz), 7.27 (1H, d, J=8.2 Hz), 7.03 (2H, d, J=8.6 Hz), 5.39 (2H, s), 4.27 (2H, s), 3.17 (3H, s), 1.65 (9H, s).

MS (FAB) (m/z): 580 ([M]⁺).

Example 62 tert-Butyl 2-hydroxy-6-[({3'-[methyl(methylsulfonyl)amino]-1,1'-biphenyl-4-yl}oxy)methyl]-3-(trifluoromethyl)benzoate (Exemplification Compound No.: 2-204)

After [1,1'-bis(diphenylphosphino)ferrocene]dichloropalladium (II)-dichloromethane adduct (82 mg, 0.1 mmol), 1,1'-bis(diphenylphosphino)ferrocene (166 mg, 0.3 mmol) and cesium carbonate (460 mg, 3 mmol) were added to a solution of N-(3-iodophenyl)-N-methylmethanesulfonamide (310 mg, 1 mmol) and tert-butyl 2-hydroxy-6-{[4-(4,4,5,5-tetramethyl-1,3,2-dioxaborolan-2-yl)phenoxy]methyl}-3-(trifluoromethyl)benzoate (494 mg, 1 mmol) obtained in Example (22-4) in 1,4-dioxane (5 ml) and the mixture was stirred under heating at 60° C. for 4 hours, the mixture was left to stand at room temperature overnight. N,N-dimethylformamide (5 ml) was added to the reaction mixture and the mixture was stirred under heating at 70° C. for 9 hour and left to stand at room temperature for one week. The reaction mixture was poured into water and extracted with ethyl acetate (twice). The organic layer was successively washed with water and a saturated aqueous NaCl solution (twice) and dried with anhydrous magnesium sulfate. After the residue obtained by removing the solvent under reduced pressure was purified by silica gel column chromatography (eluting solvent: n-hexane/ethyl acetate=3/1), recrystallization was carried out using tetrahydrofuran and diisopropyl ether to give the title compound as a grayish white crystal (115 mg, yield: 21%).

$^1$H-NMR (500 MHz, DMSO-d$_6$): δ 11.43 (1H, br s), 7.81 (1H, d, J=7.8 Hz), 7.66 (2H, d, J=8.8 Hz), 7.64 (1H, s), 7.57 (1H, d, J=7.8 Hz), 7.46 (1H, t, J=7.8 Hz), 7.35 (1H, d, J=7.8 Hz), 7.30 (1H, d, J=7.8 Hz), 7.09 (2H, d, J=8.8 Hz), 5.38 (2H, s), 3.29 (3H, s), 2.97 (3H, s), 1.57 (9H, s).

MS (FAB+) (m/z): 551 (M$^{+-}$).

Example 63

6-(4-{[2-(tert-Butoxycarbonyl)-3-hydroxy-4-(trifluoromethyl)benzyl]oxy}phenyl)nicotinic acid (Exemplification Compound No.: 2-206)

According to a method similar to Example (8-1), Example (40-2), Example (33-5) and Example (17-4), from methyl 6-chloronicotinate (177 mg, 1.02 mmol), the title compound was obtained as a colorless powder (220 mg, four-step total yield: 44%).

$^1$H-NMR (400 MHz, DMSO-d$_6$): δ 13.25 (1H, s), 11.41 (1H, s), 9.07 (1H, dd, J=2.0, 0.8 Hz), 8.25 (1H, dd, J=8.6, 2.0 Hz), 8.14 (2H, d, J=9.0 Hz), 8.03 (1H, dd, J=8.6, 0.8 Hz), 7.80 (1H, d, J=8.2 Hz), 7.28 (1H, d, J=8.2 Hz), 7.12 (2H, d, J=9.0 Hz), 5.39 (2H, s), 1.55 (9H, s).

ESI (ES−) (m/z): 488 ([M−H]$^+$).

Example 64

[5-(4-{[2-(tert-Butoxycarbonyl)-3-hydroxy-4-(trifluoromethyl)benzyl]oxy}phenyl)-3-pyridinyl]acetic acid (Exemplification Compound No.: 2-95)

According to a method similar to Example (8-1), Example (40-2), Example (33-5) and Example (17-4), from methyl (5-bromo-3-pyridinyl)acetate (397 mg, 1.72 mmol), the title compound was obtained as a colorless powder (86 mg, four-step total yield: 10%).

$^1$H-NMR (400 MHz, DMSO-d$_6$): δ 12.48 (1H, s), 11.41 (1H, s), 8.71 (1H, d, J=2.0 Hz), 8.38 (1H, d, J=2.0 Hz), 7.91 (1H, t, J=2.0 Hz), 7.80 (1H, d, J=8.2 Hz), 7.67 (2H, d, J=9.0 Hz), 7.28 (1H, d, J=8.2 Hz), 7.10 (2H, d, J=9.0 Hz), 5.37 (2H, s), 3.69 (2H, s), 1.56 (9H, s).

ESI (ES−) (m/z): 502 ([M−H]$^+$).

Example 65

3-(4'-{[2-(tert-Butoxycarbonyl)-3-hydroxy-4-(trifluoromethyl)benzyl]oxy}-1,1'-biphenyl-4-yl)propanoic acid (Exemplification Compound No.: 1-67)

According to a method similar to Example (31) and Example (17-4), from methyl 3-(4-bromophenyl)propionate (131 mg, 0.51 mmol) and tert-butyl 2-hydroxy-6-{[4-(4,4,5,5-tetramethyl-1,3,2-dioxaborolan-2-yl)phenoxy]methyl}-3-(trifluoromethyl)benzoate (250 mg, 0.51 mmol) obtained in Example (22-4), the title compound was obtained as a colorless powder (26 mg, yield: 10%).

$^1$H-NMR (400 MHz, DMSO-d$_6$): δ 12.09 (1H, br), 11.40 (1H, br), 7.79 (1H, d, J=7.8 Hz), 7.58 (2H, d, J=8.6 Hz), 7.50 (2H, d, J=8.6 Hz), 7.28-7.24 (3H, m), 7.03 (2H, d, J=8.6 Hz), 5.35 (2H, s), 2.83 (2H, t, J=7.8 Hz), 2.55 (2H, t, J=7.8 Hz), 1.56 (9H, s).

MS (FAB+) (m/z): 516 (M$^{+-}$).

Example 66

(4'-{[2-(tert-Butoxycarbonyl)-3-hydroxy-4-(trifluoromethyl)benzyl]oxy}-2-propyl-1,1'-biphenyl-4-yl)acetic acid (Exemplification Compound No.: 2-208)

According to a method similar to Example (40-2), Example (33-5) and Example (17-4), from methyl (4'-hydroxy-2-propyl-1,1'-biphenyl-4-yl)acetate (140 mg, 0.493 mmol) and tert-butyl 6-(bromomethyl)-2-[(tert-butoxycarbonyl)oxy]-3-(trifluoromethyl)benzoate (228 mg, 0.542 mmol) obtained in Example (28-5), the title compound was obtained as a yellow amorphous compound (128 mg, yield: 48%).

$^1$H-NMR (400 MHz, CDCl$_3$): δ 7.69 (1H, d, J=8.2 Hz), 7.27 (1H, d, J=8.2 Hz), 7.24-7.10 (5H, m), 6.93 (2H, d, J=8.6 Hz), 5.36 (2H, s), 3.66 (2H, s), 2.57-2.50 (2H, m), 1.64 (9H, s), 1.53-1.43 (2H, m), 0.81 (3H, t, J=7.2 Hz).

MS (ESI) (m/z): 543 ([M−H]$^+$).

Example 67 tert-Butyl 6-{[(3'-acetyl-1,1'-biphenyl-4-yl)oxy]methyl}-2-hydroxy-3-(trifluoromethyl)benzoate (Exemplification Compound No.: 2-209)

According to a method similar to Example (8-1), Example (40-2) and Example (33-5), from 1-(3-bromophenyl)ethanone (231 mg, 1.16 mmol), the title compound was obtained as a colorless powder (205 mg, three-step total yield: 36%).

$^1$H-NMR (400 MHz, CDCl$_3$): δ 12.23 (1H, s), 8.14-8.12 (1H, m), 7.89-7.85 (1H, m), 7.75-7.71 (1H, m), 7.69 (1H, d, J=8.2 Hz), 7.56 (2H, d, J=8.6 Hz), 7.50 1H, dd, J=7.8, 7.4 Hz), 7.26 (1H, d, J=8.2 Hz), 7.00 (2H, d, J=8.6 Hz), 5.37 (2H, s), 2.65 (3H, s), 1.65 (9H, s).

ESI (ES−) (m/z): 485 ([M−H]$^+$).

Example 68 tert-Butyl 6-{[(3'-chloro-4'-[(methoxycarbonyl)methyl]-1,1'-biphenyl-4-yl)oxy]methyl}-2-hydroxy-3-(trifluoromethyl)benzoate (Exemplification Compound No.: 2-211)

A trimethylsilyldiazomethane-0.6M hexane solution (0.20 ml, 0.12 mmol) was added to a solution of (4'-{[2-(tert-butoxycarbonyl)-3-hydroxy-4-(trifluoromethyl)benzyl]oxy}-3-chloro-1,1'-biphenyl-4-yl)acetic acid (60 mg, 0.11 mmol) obtained in Example (18-4) in a mixture of benzene-methanol (4:1, 2.5 ml), and the mixture was stirred for 1 hour. The residue obtained by removing the solvent under reduced pressure was purified by silica gel preparative thin layer chromatography (developing solvent: hexane/methylene chloride/ethyl acetate=9/1/1) to give the title compound (45 mg, yield: 73%).

$^1$H-NMR (500 MHz, CDCl$_3$): δ 12.25 (1H, s), 7.71 (1H, d, J=8.1 Hz), 7.58 (1H, d, J=1.8 Hz), 7.52 (2H, d, J=8.8 Hz), 7.42 (1H, dd, J=8.1, 1.8 Hz), 7.33 (1H, d, J=8.1 Hz), 7.27 (1H, d, J=8.1 Hz), 6.99 (2H, d, J=8.8 Hz), 5.38 (2H, s), 3.81 (2H, s) 3.74 (3H, s), 1.65 (9H, s).

ESI (ES−) (m/z): 549 ([M−H]$^+$).

Example 69

(4'-{[2-(tert-Butoxycarbonyl)-3-hydroxy-4-(trifluoromethyl)benzyl]oxy}-2-propionyl-1,1'-biphenyl-4-yl)acetic acid (Exemplification Compound No.: 2-212)

According to a method similar to Example (40-2), Example (33-5) and Example (17-4), from tert-butyl 6-(bromomethyl)-2-[(tert-butoxycarbonyl)oxy]-3-(trifluoromethyl)benzoate (289 mg, 0.688 mmol) obtained in Example (28-5) and methyl (4'-hydroxy-2-propionyl-1,1'-biphenyl-4-yl)acetate (174 mg, 0.626 mmol), the title compound was obtained as a colorless amorphous compound (194 mg, yield: 53%).

$^1$H-NMR (400 MHz, CDCl$_3$): δ 7.68 (2H, d, J=8.2 Hz), 7.35-7.30 (2H, m), 7.28-7.20 (3H, m), 6.94 (2H, d, J=8.2 Hz), 5.34 (2H, s), 3.69 (2H, s), 2.27 (2H, q, J=7.3 Hz), 1.63 (9H, s) 0.90 (3H, t, J=7.3 Hz).

ESI (ES–) (m/z): 557 ([M–H]$^+$).

Example 70

2-(4'-{[2-(tert-Butoxycarbonyl)-3-hydroxy-4-(trifluoromethyl)benzyl]oxy}-1,1'-biphenyl-4-yl)acrylic acid (Exemplification Compound No.: 1-124)

According to a method similar to Example (17-4), from tert-butyl 2-hydroxy-6-[({4'-[1-(methoxycarbonyl)vinyl]-1,1'-biphenyl-4-yl}oxy)methyl]-3-(trifluoromethyl)benzoate (29 mg, 0.055 mmol) obtained in Example (41-1), the title compound was obtained as a colorless solid (7.3 mg, yield: 25%).

In the present step, 1,4-dioxane was used as the reaction solvent instead of tetrahydrofuran.

$^1$H-NMR (400 MHz, CDCl$_3$): δ 12.26 (1H, s) 7.7 (1H, d, J=8.4 Hz), 7.58-7.50 (6H, m), 7.28 (1H, d, J=8.4 Hz), 6.99 (2H, d, J=9.2 Hz), 6.53 (1H, s), 6.08 (s), 5.39 (2H, s), 1.65 (9H, s)

ESI (ES–) (m/z): 513 ([M–H]+).

Example 71

[6-(4-{[2-(tert-Butoxycarbonyl)-3-hydroxy-4-(trifluoromethyl)benzyl]oxy}phenyl)-5-methyl-3-pyridinyl]acetic acid (Exemplification Compound No.: 2-85)

(71-1)
According to a method similar to Example (76-1), Example (76-2), Example (6-6), Example (26-5) and Example (11-1), from 2,5-dibromo-3-methylpyridine (2.64 g, 10.5 mmol), [6-(4-methoxyphenyl)-5-methyl-3-pyridinyl]acetonitrile was obtained (320 mg, five-step total yield: 13%).

$^1$H-NMR (400 MHz, CDCl$_3$): δ 8.44 (1H, d, J=2.0 Hz), 7.60 (1H, d, J=2.0 Hz), 7.48 (2H, d, J=8.6 Hz), 6.99 (2H, d, J=8.6 Hz), 3.87 (3H, s), 3.77 (2H, s), 2.41 (3H, s).

(71-2)
[6-(4-Methoxyphenyl)-5-methyl-3-pyridinyl]acetonitrile (314 mg, 1.32 mmol) obtained in Example (71-1) was added to 47% hydrobromic acid (5 ml), and the mixture was stirred at 120° C. for 8 hours. The solvent was removed under reduced pressure and azeotropic distillation was carried out with methanol (twice). The residue was dissolved in methanol (5 ml) again and the mixture was stirred at room temperature overnight. The solvent was removed under reduced pressure and a saturated aqueous sodium hydrogencarbonate solution was added to the residue and the mixture was extracted with ethyl acetate. The organic layer was washed with a saturated aqueous NaCl solution and dried with anhydrous sodium sulfate. The residue obtained by removing the solvent under reduced pressure was purified by silica gel column chromatography (eluting solvent: n-hexane/ethyl acetate=1/1-1/4) to give methyl [6-(4-hydroxyphenyl)-5-methyl-3-pyridinyl]acetate (240 mg, yield: 71%).

$^1$H-NMR (400 MHz, CDCl$_3$): δ 8.97 (1H, br), 8.38 (1H, d, J=2.0 Hz), 7.57 (1H, d, J=2.0 Hz), 7.27 (2H, d, J=8.6 Hz), 6.66 (2H, d, J=8.6 Hz), 3.74 (3H, s), 3.64 (2H, s), 2.34 (3H, s).

(71-3)
According to a method similar to Example (40-2), Example (33-5) and Example (17-4), from methyl [6-(4-hydroxyphenyl)-5-methyl-3-pyridinyl]acetate (330 mg, 1.28 mmol) obtained in Example (71-2), the title compound was obtained as a colorless powder (240 mg, three-step total yield: 37%).

$^1$H-NMR (400 MHz, DMSO-d$_6$): δ 12.50 (1H, s), 11.45 (1H, s), 8.33 (1H, d, J=2.0 Hz), 7.83 (1H, d, J=8.2 Hz), 7.58 (1H, d, J=2.0 Hz), 7.52 (2H, d, J=8.6 Hz), 7.32 (1H, d, J=8.2 Hz), 7.07 (2H, d, J=8.6 Hz), 5.38 (2H, s), 3.68 (2H, s), 2.32 (3H, s), 1.56 (9H, s).

ESI (ES–) (m/z): 516 ([M–H]$^+$).

Example 72

(4'-{[3-Hydroxy-2-(isopropoxycarbonyl)-4-(trifluoromethyl)benzyl]oxy}-1,1'-biphenyl-4-yl)acetic acid (Exemplification Compound No.: 1-5)

(72-1)
Diethyl azodicarboxylate (108 μl, 0.68 mmol) was added to a solution of 2-(allyloxy)-6-{[(4'-{[(allyloxy)carbonyl]methyl}-1,1'-biphenyl-4-yl)oxy]methyl}-3-(trifluoromethyl)benzoic acid (150 mg, 0.29 mmol), 2-propanol (26 μl, 0.34 mmol) and triphenylphosphine (180 mg, 0.68 mmol) in tetrahydrofuran (3 ml) at room temperature. After the mixture was stirred at room temperature for 1 hour, the solvent of the reaction mixture was removed under reduced pressure. The obtained residue was purified by silica gel preparative thin layer chromatography (developing solvent: n-hexane/ethyl acetate=4/1) to give isopropyl 2-(allyloxy)-6-{[(4'-{[(allyloxy)carbonyl]methyl}-1,1'-biphenyl-4-yl)oxy]methyl}-3-(trifluoromethyl)benzoate (141 mg, yield: 87%).

$^1$H-NMR (400 MHz, CDCl$_3$): δ 7.67 (1H, d, J=8.2 Hz), 7.51 (2H, d, J=8.2 Hz), 7.50 (2H, d, J=8.2 Hz), 7.40 (1H, d, J=8.2 Hz), 7.34 (2H, d, J=8.2 Hz), 6.99 (2H, d, J=8.2 Hz), 6.10-6.00 (1H, m), 5.97-5.87 (1H, m), 5.32-5.22 (5H, m), 5.16 (2H, s), 4.62 (2H, d, J=5.9 Hz), 4.57 (2H, d, J=5.9 Hz), 3.68 (2H, s), 1.34 (6H, d, J=6.3 Hz).

(72-2)
According to a method similar to Example (13-5), from isopropyl 2-(allyloxy)-6-{[(4'-{[(allyloxy)carbonyl]methyl}-1,1'-biphenyl-4-yl)oxy]methyl}-3-(trifluoromethyl)benzoate (141 mg, 0.248 mmol) obtained in Example (72-1), the title compound was obtained as a yellow crystal (111 mg, yield: 92%).

$^1$H-NMR (400 MHz, CDCl$_3$): δ 12.22 (1H, s), 7.74 (1H, d, J=8.2 Hz), 7.53 (4H, d, J=8.6 Hz), 7.35 (2H, d, J=8.6 Hz), 7.30 (1H, d, J=8.2 Hz), 6.99 (2H, d, J=8.6 Hz), 5.40 (2H, s), 5.39 (1H, sp, J=6.3 Hz), 3.71 (2H, s), 1.41 (6H, d, J=6.3 Hz).

MS (FAB) (m/z): 488 ([M]$^+$).

Example 73

[4'-({3-Hydroxy-4-(trifluoromethyl)-2-[(2,2,2-trifluoro-1-methylethoxy)carbonyl]benzyl}oxy)-1,1'-biphenyl-4-yl]acetic acid (Exemplification Compound No.: 1-126)

According to a method similar to Example (72-1) and Example (13-5), from 2-(allyloxy)-6-{[(4'-{[(allyloxy)carbonyl]methyl}-1,1'-biphenyl-4-yl)oxy]methyl}-3-(trifluoromethyl)benzoic acid (150 mg, 0.29 mmol) and 1,1,1-trifluoro-2-propanol (31 µl, 0.34 mmol), the title compound was obtained as a yellow crystal (68 mg, two-step total yield: 43%).

¹H-NMR (400 MHz, CDCl₃): δ 11.66 (1H, s), 7.82 (1H, d, J=8.2 Hz), 7.55 (2H, d, J=8.6 Hz), 7.54 (2H, d, J=7.8 Hz), 7.44 (1H, d, J=8.2 Hz), 7.36 (2H, d, J=7.8 Hz), 7.01 (2H, d, J=8.6 Hz), 5.65 (1H, qq, J=6.6, 6.3 Hz), 5.44 (1H, d, J=15.3 Hz), 5.32 (1H, d, J=15.3 Hz), 3.71 (2H, s), 1.58 (6H, d, J=6.6 Hz).

MS (FAB) (m/z): 542 ([M]⁺).

Example 74

6-(4-{[2-(tert-Butoxycarbonyl)-3-hydroxy-4-(trifluoromethyl)benzyl]oxy}phenyl)-2,3-dihydro-1-benzofuran-3-carboxylic acid (Exemplification Compound No.: 2-213)

(74-1)

1-(4-Chloro-2-methoxyphenyl)-2-methoxy-2-oxoethanediazonium

A solution of methyl (4-chloro-2-methoxyphenyl)acetate (410 mg, 1.91 mmol) and 1,8-diazabicyclo[5.4.0]-7-undecene (871 mg, 5.73 mmol) in acetonitrile (6 ml) was added dropwise to a solution of 4-(acetylamino)benzensulfonylazide (580 mg, 2.4 mmol) in acetonitrile (3 ml) at room temperature, and the mixture was stirred for 4 hours. The reaction mixture was poured into water and extracted with ethyl acetate (twice). The organic layer was washed with a saturated aqueous NaCl solution and dried with anhydrous magnesium sulfate. The residue obtained by removing the solvent under reduced pressure was purified by silica gel column chromatography (eluting solvent: n-hexane/ethyl acetate=2/1) to give the title compound as a yellow solid (400 mg, yield: 87%).

¹H-NMR (500 MHz, CDCl₃): δ 7.49 (1H, d, J=7.8 Hz), 7.00 (1H, dd, J=7.8 Hz, 2.0 Hz), 6.78 (1H, d, J=2.0 Hz), 3.83 (3H, s), 3.85 (3H, s).

(74-2)

Methyl 6-chloro-2,3-dihydro-1-benzofuran-3-carboxylate

A nitrogen gas was blown into a solution of 1-(4-chloro-2-methoxyphenyl)-2-methoxy-2-oxoethanediazonium (200 mg, 0.83 mmol) obtained in Example (74-1) in toluene (5 ml) at room temperature for 5 minutes. The reaction mixture was heated to 80° C. while blowing a nitrogen gas into the mixture and tetrakis(triphenylacetate)dirhodium (II) (1 mg) was added thereto, and the mixture was stirred for 15 minutes. The reaction mixture was cooled to room temperature and the residue obtained by removing the solvent under reduced pressure was purified by silica gel column chromatography (eluting solvent: n-hexane/ethyl acetate=5/1) to give the title compound as a pale yellow oil (127 mg, yield: 72%).

¹H-NMR (500 MHz, CDCl₃): δ 7.27 (1H, d, J=7.8 Hz), 6.87 (1H, dd, J=7.8 Hz, 2.0 Hz), 6.82 (1H, d, J=2.0 Hz), 4.97 (1H, dd, J=9.8 Hz, 5.8 Hz), 4.70 (1H, t, J=9.8 Hz), 4.29 (1H, dd, J=9.8 Hz, 5.8 Hz), 3.78 (3H, s).

(74-3)

6-(4-{[2-(tert-Butoxycarbonyl)-3-hydroxy-4-(trifluoromethyl)benzyl]oxy}phenyl)-2,3-dihydro-1-benzofuran-3-carboxylic acid According to a method similar to Example (24-2) and Example (17-4), from methyl 6-chloro-2,3-dihydro-1-benzofuran-3-carboxylate (125 mg, 0.59 mmol) obtained in Example (74-2) and tert-butyl 2-hydroxy-6-{[4-(4,4,5,5-tetramethyl-1,3,2-dioxoborolan-2-yl)phenoxy]methyl}-3-(trifluoromethyl)benzoate (350 mg, 0.71 mmol) obtained in Example (22-4), the title compound was obtained as a grayish white powder (22 mg, yield: 8%).

In the present step, 1,4-dioxane was used as the reaction solvent instead of toluene in the step corresponding to Example (24-2).

¹H-NMR (500 MHz, DMSO-d₆): δ 12.89 (1H, br, s), 11.43 (1H, br, s), 7.81 (1H, d, J=7.8 Hz), 7.59 (2H, d, J=8.8 Hz), 7.37 (1H, d, J=7.8 Hz), 7.29 (1H, d, J=7.8 Hz), 7.13 (1H, d, J=7.8 Hz), 7.06-7.03 (3H, m), 5.37 (2H, s), 4.79 (1H, dd, J=9.8 Hz, 5.8 Hz), 4.67 (1H, t, J=9.8 Hz), 4.38 (1H, dd, J=9.8 Hz, 5.8 Hz), 1.57 (9H, s).

MS (FAB+) (m/z): 530 (M⁺⁻).

Example 75 tert-Butyl 2-hydroxy-6-({4-[5-(methylsulfonyl)-3-pyridinyl]phenoxy}methyl)-3-(trifluoromethyl)benzoate (Exemplification Compound No.: 2-215)

(75-1)

tert-Butyl 2-[(tert-butoxycarbonyl)oxy]-6-({4-[5-(methylthio)-3-pyridinyl]phenoxy}methyl)-3-(trifluoromethyl) benzoate (410 mg, 0.69 mmol) which was obtained using 4-[5-(methylthio)-3-pyridinyl]phenol (200 mg, 0.92 mmol) as a starting material according to a similar method to Example (40-2) was dissolved in a mixture of methylene chloride-methanol (1:1, 10 ml). After magnesium monoperoxyphthalate hexahydrate (860 mg, 1.39 mmol) was added to the solution under ice-cooling, the mixture was stirred at room temperature for 30 minutes. After the reaction mixture was cooled with ice and a 5% aqueous sodium thiosulfate solution was added thereto, the mixture was extracted with ethyl acetate (twice). The organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=7/3-0/10) to give tert-butyl 2-[(tert-butoxycarbonyl)oxy]-6-({4-[5-(methylsulfonyl)-3-pyridinyl]phenoxy}methyl)-3-(trifluoromethyl)benzoate (350 mg, two-step total yield: 61%).

¹H-NMR (400 MHz, CDCl₃): δ 9.05 (1H, d, J=2.3 Hz), 9.04 (1H, d, J=2.3 Hz), 8.32 (1H, t, J=2.3 Hz), 7.71 (1H, d, J=8.2 Hz), 7.58-7.53 (3H, m), 7.07 (2H, d, J=9.0 Hz), 5.28 (2H, s), 3.15 (3H, s), 1.58 (9H, s), 1.54 (9H, s).

ESI (ES+) (m/z): 624 ([M+H]⁺).

(75-2)

According to a method similar to Example (33-5), from tert-butyl 2-[(tert-butoxycarbonyl)oxy]-6-({4-[5-(methylsulfonyl)-3-pyridinyl]phenoxy}methyl)-3-(trifluoromethyl)benzoate (350 mg, 0.56 mmol) obtained in Example (75-1), the title compound was obtained as a colorless powder (215 mg, yield: 73%).

¹H-NMR (400 MHz, CDCl₃): δ 12.21 (1H, s), 9.06-9.04 (2H, m), 8.33 (1H, d, J=2.4 Hz), 7.70 (1H, d, J=8.2 Hz), 7.58 (2H, d, J=9.0 Hz), 7.24 (1H, d, J=8.2 Hz), 7.05 (2H, d, J=9.0 Hz), 5.39 (2H, s), 3.15 (3H, s), 1.65 (9H, s).

ESI (ES−) (m/z): 522 ([M−H]⁺).

Example 76

[5-(4-{[2-(tert-Butoxycarbonyl)-3-hydroxy-4-(trifluoromethyl)benzyl]oxy}phenyl)-4-methyl-3-pyridinyl]acetic acid (Exemplification Compound No.: 2-216)

(76-1)
Tetrakis(triphenylphosphine)palladium (0) (1.03 g, 0.89 mmol) and potassium carbonate (8.22 g, 59.5 mmol) were added to a solution of 3,5-dibromo-4-methylpyridine (7.46 g, 29.73 mmol) which was synthesized according to the method described in literature (Gu, Y. G. and Bayburt, E. K., Tetrahedron Lett., vol.: 37, 1966, pp. 2565-2568) and 4-methoxyphenylboronic acid (4.52 g, 29.73 mmol) in a mixture of N,N-dimethylacetamide-water (20:1, 100 ml), and the mixture was stirred at 80° C. for 4 hours. After the temperature of the reaction mixture was set to room temperature and ethyl acetate was added thereto, the insolubles were removed by filtration. The obtained filtrate was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=4/1) to give 3-bromo-5-(4-methoxyphenyl)-4-methylpyridine (3.83 g, yield: 46%).
$^1$H-NMR (400 MHz, CDCl$_3$): δ 8.63 (1H, s), 8.32 (1H, s), 7.22 (2H, d, J=8.6 Hz), 6.99 (2H, d, J=8.6 Hz), 3.87 (3H, s), 2.35 (3H, s).

(76-2)
A n-butyllithium-1.58M n-hexane solution (3.9 ml, 6.13 mmol) was added dropwise to a solution of 3-bromo-5-(4-methoxyphenyl)-4-methylpyridine (1.55 g, 5.57 mmol) obtained in Example (76-1) in tetrahydrofuran (20 ml) at −78° C., and the mixture was stirred for 5 minutes. N,N-Dimethylformamide (0.87 ml, 11.2 mmol) was added dropwise thereto at the same temperature and the mixture was stirred for 30 minutes. A saturated aqueous ammonium chloride solution was added to the reaction mixture and the temperature of the mixture was raised to room temperature, and the mixture was extracted with ethyl acetate. The organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=4/1-2/3) to give 5-(4-methoxyphenyl)-4-methylnicotinaldehyde (0.56 g, yield: 44%).
$^1$H-NMR (400 MHz, CDCl$_3$): δ 10.34 (1H, s), 8.88 (1H, s), 8.58 (1H, s), 7.21 (2H, d, J=9.0 Hz), 7.00 (2H, d, J=9.0 Hz), 3.87 (3H, s), 2.58 (3H, s).

(76-3)
According to a method similar to Example (6-6), Example (90-4) and Example (11-1), from 5-(4-methoxyphenyl)-4-methylnicotinaldehyde (406 mg, 1.79 mmol) obtained in Example (76-2), [5-(4-methoxyphenyl)-4-methyl-3-pyridinyl]acetonitrile was obtained (227 mg, three-step total yield: 53%).
$^1$H-NMR (400 MHz, CDCl$_3$): δ 8.46 (1H, s), 8.42 (1H, s), 7.20 (2H, d, J=8.6 Hz), 6.98 (2H, d, J=8.6 Hz), 3.86 (3H, s), 3.73 (2H, s), 2.30 (3H, s).

(76-4)
According to a method similar to Example (71-2), from [5-(4-methoxyphenyl)-4-methyl-3-pyridinyl]acetonitrile (300 mg, 1.26 mmol) obtained in Example (76-3), methyl [5-(4-methoxyphenyl)-4-methyl-3-pyridinyl]acetate was obtained (0.31 g, yield: 96%).

$^1$H-NMR (400 MHz, CDCl$_3$): δ 8.34 (2H, s), 7.94 (1H, br), 7.14 (2H, d, J=8.6 Hz), 6.92 (2H, d, J=8.6 Hz), 3.73 (5H, s), 2.24 (3H, s).

(76-5)
According to a method similar to Example (40-2), Example (33-5) and Example (17-4), from methyl [5-(4-methoxyphenyl)-4-methyl-3-pyridinyl]acetate (150 mg, 0.58 mmol) obtained in Example (76-4), the title compound was obtained as a colorless powder (95 mg, three-step total yield: 44%).
$^1$H-NMR (400 MHz, DMSO-d$_6$): δ 12.49 (1H, s), 11.42 (1H, s), 8.30 (1H, s), 8.22 (1H, s), 7.81 (1H, d, J=8.2 Hz), 7.30 (1H, d, J=8.2 Hz), 7.29 (2H, d, J=8.6 Hz), 7.07 (2H, d, J=8.6 Hz), 5.37 (2H, s) 3.72 (2H, s), 2.13 (3H, s), 1.56 (9H, s).
ESI (ES−) (m/z): 516 ([M−H]$^+$).

Example 77

2-(4'-{[2-(tert-Butoxycarbonyl)-3-hydroxy-4-(trifluoromethyl)benzyl]oxy}-1,1'-biphenyl-4-yl)-3-methoxypropanoic acid (Exemplification Compound No.: 1-127)

Silver oxide (120 mg, 0.52 mmol) and methyl iodide (180 μl, 2.9 mmol) were added to a solution of tert-butyl 2-(allyloxy)-6-{[(4'-{1-[(allyloxy)carbonyl]-2-(hydroxyethyl)}-1,1'-biphenyl-4-yl)oxy]methyl}-3-(trifluoromethyl)benzoate (61 mg, 0.1 mmol) in toluene (1 ml), and the mixture was stirred at 70° C. for 17 hours. After the mixture was cooled to room temperature, the reaction mixture was subjected to silica gel column chromatography (eluting solvent: n-hexane/ethyl acetate=10/1-3/1) to give crude tert-butyl 2-(allyloxy)-6-{[(4'-{1-[(allyloxy)carbonyl]-2-(methoxyethyl)}-1,1'-biphenyl-4-yl)oxy]methyl}-3-(trifluoromethyl)benzoate.
According to a method similar to Example (11-7), from the compound obtained in the above, the title compound was obtained as a colorless solid (39 mg, two-step total yield: 71%).
$^1$H-NMR (400 MHz, CDCl$_3$): δ 12.26 (1H, s), 7.71 (1H, d, J=8.0 Hz), 7.53 (2H, d, J=8.8 Hz), 7.52 (2H, d, J=8.8 Hz), 7.39 (2H, d, J=8.8 Hz), 7.28-7.25 (1H, m), 6.98 (2H, d, J=8.8 Hz), 5.38 (2H, s), 4.02-3.95 (2H, m), 3.72-3.69 (1H, m), 3.43 (3H, s), 1.65 (9H, s).
ESI (ES−) (m/z): 545 ([M−H]+).

Example 78

2-(4'-{[2-(tert-Butoxycarbonyl)-3-hydroxy-4-(trifluoromethyl)benzyl]oxy}-2-ethyl-1,1'-biphenyl-4-yl)-3-hydroxypropanoic acid (Exemplification Compound No.: 2-218)

According to a method similar to Example (41-1) and Example (17-4), from tert-butyl 6-[({2'-ethyl-4'-[(methoxycarbonyl)methyl]-1,1'-biphenyl-4-yl}oxy)methyl]-2-hydroxy-3-(trifluoromethyl)benzoate (200 mg, 0.36 mmol) obtained in Example (26-7), the title compound was obtained as a colorless solid (110 mg, two-step total yield: 54%).
In the present step, 1,4-dioxane was used as the reaction solvent instead of tetrahydrofuran in the hydrolysis step corresponding to Example (17-4).
$^1$H-NMR (400 MHz, CDCl$_3$): δ 12.26 (1H, s), 7.72 (1H, d, J=8.0 Hz), 7.29 (1H, d, J=8.0 Hz), 7.24-7.14 (5H, m), 6.95 (2H, d, J=8.4 Hz), 5.38 (2H, s), 4.22-4.16 (1H, m), 3.95-3.89 (2H, m), 2.60 (2H, q, J=7.6 Hz), 1.65 (9H, s), 1.09 (3H, t, J=7.6 Hz).
ESI (ES−) (m/z): 559 ([M−H]+).

Example 79

2-(4'-{[2-(tert-Butoxycarbonyl)-3-hydroxy-4-(trifluoromethyl)benzyl]oxy}-3-fluoro-1,1'-biphenyl-4-yl)-3-hydroxypropanoic acid (Exemplification Compound No.: 2-219)

According to a method similar to Example (41-1) and Example (11-7), from tert-butyl 2-(allyloxy)-6-{[(4'-{[(allyloxy)carbonyl]methyl}-3'-fluoro-1,1'-biphenyl-4-yl)oxy]methyl}-3-(trifluoromethyl)benzoate (200 mg, 0.33 mmol) obtained in Example (11-6), the title compound was obtained as a colorless solid (107 mg, two-step total yield: 53%).

$^1$H-NMR (400 MHz, CDCl$_3$): δ 12.25 (1H, s), 7.70 (1H, d, J=8.0 Hz), 7.50 (2H, d, J=8.4 Hz), 7.37-7.26 (4H, m), 6.98 (2H, d, J=8.4 Hz), 5.37 (2H, s), 4.19-4.15 (2H, m), 3.91-3.90 (1H, m), 1.64 (9H, s).

ESI (ES−) (m/z): 549 ([M−H]+).

Example 80

(4'-{[2-(tert-Butoxycarbonyl)-3-hydroxy-4-(trifluoromethyl)benzyl]oxy}-2-hydroxy-1,1'-biphenyl-4-yl)acetic acid (Exemplification Compound No.: 2-220)

According to a method similar to Example (40-2), Example (51-2), Example (33-5) and Example (17-4), from tert-butyl 6-(bromomethyl)-2-[(tert-butoxycarbonyl)oxy]-3-(trifluoromethyl)benzoate (1.66 g, 3.93 mmol) obtained in Example (28-5) and methyl [4'-hydroxy-2-(methoxymethoxy)-1,1'-biphenyl-4-yl]acetate (990 mg, 3.28 mmol), the title compound was obtained as a colorless amorphous compound (111 mg, yield: 7%).

$^1$H-NMR (500 MHz, CDCl$_3$): δ 7.71 (1H, d, J=8.3 Hz), 7.53 (2H, d, J=8.8 Hz), 7.32 (1H, d, J=8.3 Hz), 7.21 (1H, d, J=7.3 Hz), 7.00-6.95 (2H, m), 6.90-6.80 (2H, m), 5.39 (2H, s), 3.57 (2H, s), 1.67 (9H, s).

ESI (ES−) (m/z): 517 ([M−H]$^+$).

Example 81

2-(4'-{[2-(tert-Butoxycarbonyl)-3-hydroxy-4-(trifluoromethyl)benzyl]oxy}-1,1'-biphenyl-4-yl)propanoic acid (Exemplification Compound No.: 1-62)

According to a method similar to Example (24-2) and Example (17-4) to obtain the title compound in colorless solid form (65 mg, two-step total yield: 25%) from methyl 2-(4-chlorophenyl)propanoate (119 mg, 0.6 mmol) and tert-butyl 2-hydroxy-{[4-(4,4,5,5-tetramethyl-1,3,2-dioxaborolan-2-yl)phenoxy]methyl}-3-(trifluoromethyl)benzoate (250 mg, 0.5 mmol) obtained in Example (22-4).

In the present step, toluene/methanol/water (25/1/1) was used as a solvent instead of toluene in the Suzuki-Miyaura coupling reaction corresponding to Example (24-2). Further, in the hydrolysis reaction corresponding to Example (17-4), 1,4-dioxane was used as the reaction solvent instead of tetrahydrofuran.

$^1$H-NMR (500 MHz, CDCl$_3$): δ 12.26 (1H, s), 7.71 (1H, d, J=8.5 Hz), 7.52 (2H, d, J=8.5 Hz), 7.52 (2H, d, J=8.5 Hz), 7.38 (2H, d, J=8.5 Hz), 7.28 (11, d, J=8.5 Hz), 6.98 (28, d, J=8.5 Hz), 5.38 (2H, s), 3.81 (1H, q, J=7.5 Hz), 1.65 (9H, s), 1.56 (381, d, J=7.5 Hz).

ESI (ES−) (m/z): ([M−H]+).

Example 82

(4'-{[2-(tert-Butoxycarbonyl)-3-hydroxy-4-(trifluoromethyl)benzyl]oxy}-2-cyclopropyl-1,1'-biphenyl-4-yl)acetic acid (Exemplification Compound No.: 2-221)

(82-1)

Methyl (3-cyclopropyl-4-{[(trifluoromethyl)sulfonyl]oxy}phenyl)acetate

According to a method similar to Example (42-1), Example (6-2) and Example (22-5), from methyl (3-bromo-4-methoxyphenyl)acetate (1.2 g, 4.7 mmol), methyl (3-cyclopropyl-4-{[(trifluoromethyl)sulfonyl]oxy}phenyl)acetate was obtained as an oil (288 mg, three-step total yield: 18%).

In the present step, a cyclopropylmagnesium bromide-0.5M tetrahydrofuran solution was used as the Grignard reagent in the step corresponding to Example (42-1).

$^1$H-NMR (400 MHz, CDCl$_3$): δ 7.18 (1H, d, J=8.4 Hz), 7.14 (1H, dd, J=8.4, 1.6 Hz), 6.92 (1H, d, J=1.6 Hz), 3.70 (3H, s), 3.59 (2H, s), 2.11-2.05 (1H, m), 1.09-1.04 (2H, m), 0.78-0.73 (2H, m).

(82-2)

Methyl (2-cyclopropyl-4'-hydroxy-1,1'-biphenyl-4-yl)acetate

According to a method similar to Example (26-3) and Example (6-2), from (3-cyclopropyl-4-{[(trifluoromethyl)sulfonyl]oxy}phenyl)acetate (288 mg, 0.85 mmol) obtained in Example (82-1), methyl (2-cyclopropyl-4'-hydroxy-1,1'-biphenyl-4-yl)acetate was obtained as an oil (120 mg, two-step total yield: 49%).

In the present step, tetrakis(triphenylphosphine)palladium (0) was used as the catalyst instead of [1,1'-bis(diphenylphosphino)ferrocene]dichloropalladium (II)-dichloromethane adduct in the Suzuki-Miyaura coupling reaction corresponding to Example (26-3).

$^1$H-NMR (400 MHz, CDCl$_3$): δ 7.23 (2H, d, J=8.6 Hz), 7.15 (1H, d, J=8.6 Hz), 6.94 (1H, d, J=8.6 Hz), 6.91 (1H, s), 6.83 (2H, d, J=8.6 Hz), 4.78 (1H, s), 3.70 (3H, s), 3.59 (2H, s), 2.11-2.05 (1H, m), 1.09-1.04 (2H, m), 0.77-0.73 (2H, m).

(82-3)

(4'-{[2-(tert-Butoxycarbonyl)-3-hydroxy-4-(trifluoromethyl)benzyl]oxy}-2-cyclopropyl-1,1'-biphenyl-4-yl)acetic acid According to a method similar to Example (2-3), Example (33-5) and Example (17-4), from tert-butyl 6-(bromomethyl)-2-[(tert-butoxycarbonyl)oxy]-3-(trifluoromethyl)benzoate (256 mg, 0.55 mmol) obtained in Example (28-5) and (methyl (2-cyclopropyl-4'-hydroxy-1,1'-biphenyl-4-yl)acetate (120 mg, 0.43 mmol) obtained in Example (82-2), the title compound was obtained in colorless solid form (91 mg, three-step total yield: 38%).

In the present step, piperidine was used instead of morpholine in the step corresponding to Example (33-5). Further, 1,4-dioxane was used as the reaction solvent instead of tetrahydrofuran in the step corresponding to Example (17-4).

$^1$H-NMR (400 MHz, CDCl$_3$): δ 12.27 (1H, s), 7.72 (1H, d, J=8.0 Hz), 7.37 (2H, d, J=8.4 Hz), 7.30 (1H, d, J=8.0 Hz), 7.19 (1H, d, J=8.0 Hz), 7.14 (1H, d, J=8.0 Hz), 6.96 (2H, d,

J=8.4 Hz), 6.85 (1H, s), 5.38 (2H, s), 3.66 (2H, s), 1.91-1.85 (1H, m), 1.65 (9H, s), 0.87-0.82 (2H, m), 0.71-0.67 (2H, m).

Example 83

(4'-{[2-(tert-Butoxycarbonyl)-3-hydroxy-4-(trifluoromethyl)benzyl]oxy}-3-nitro-1,1'-biphenyl-4-yl)acetic acid (Exemplification Compound No.: 2-222)

According to a method similar to Examples (24-2) and (17-4), from tert-butyl 2-hydroxy-([4-(4,4,5,5-tetramethyl-1,3,2-dioxaborolan-2-yl)phenoxy]methyl)-3-(trifluoromethyl)benzoate (313 mg, 0.634 mmol) obtained in Example (22-4) and methyl (4-bromo-2-nitrophenyl)acetate (173 mg, 0.634 mmol), the title compound was obtained as a pale yellow powder (33 mg, yield: 9%).

$^1$H-NMR (400 MHz, CD$_3$OD): δ 8.26 (1H, d, J=2.0 Hz), 7.85 (1H, dd, J=7.8, 2.0 Hz), 7.72 (1H, d, J=8.2 Hz), 7.64 (2H, d, J=8.7 Hz), 7.47 (1H, d, J=7.8 Hz), 7.29 (1H, d, J=8.2 Hz), 7.08 (2H, d, J=8.7 Hz), 5.41 (2H, s), 4.02 (2H, s), 1.63 (9H, s).
MS (FAB) (m/z): 547 ([M]$^+$).

Example 84

[4-(5-{[2-(tert-Butoxycarbonyl)-3-hydroxy-4-(trifluoromethyl)benzyl]oxy}-2-pyridinyl)-3-methylphenyl]acetic acid (Exemplification Compound No.: 2-165)

(84-1)
According to a method similar to Example (2-3) and Example (33-5), from tert-butyl 6-(bromomethyl)-2-[(tert-butoxycarbonyl)oxy]-3-(trifluoromethyl)benzoate (6.22 g, 13.7 mmol) obtained in Example (28-5) and 6-chloro-3-pyridinol (1.77 g, 13.7 mmol), tert-butyl 6-{[(6-chloro-3-pyridinyl)oxy]methyl}-2-hydroxy-3-(trifluoromethyl)benzoate was obtained (4.61 g, two-step total yield: 84%).

$^1$H-NMR (400 MHz, CDCl$_3$): δ 12.23 (1H, s), 8.11 (1H, dd, J=3.1, 0.8 Hz), 7.72 (1H, d, J=8.2 Hz), 7.29-7.20 (3H, m), 5.37 (2H, s), 1.64 (9H, s).
(84-2)
(4-Bromo-3-methylphenyl)acetonitrile (2.59 g, 12.3 mmol) that was obtained according to a method similar to Example (11-1) from 1-bromo-4-(bromomethyl)-2-methylbenzene which was synthesized according to the method described in literature (Hanessian, S. et al., J. Org. Chem., 2003, vol. 68, pp. 7204-7218) was dissolved in acetic acid (10 ml). 6N Hydrochloric acid (10 ml) was added to the solution and the mixture was heated under reflux for 3 hours. The solvent was removed under reduced pressure and azeotropic distillation with toluene (twice) was carried out. The residue was dissolved in methanol (10 ml) and conc. sulfuric acid (2 ml) was added thereto under ice-cooling, and the mixture was stirred at room temperature overnight. The solvent was removed under reduced pressure and water was added to the residue, and the mixture was extracted with ethyl acetate. The organic layer was washed with a saturated aqueous sodium hydrogencarbonate solution and a saturated aqueous NaCl solution and dried with anhydrous sodium sulfate. The residue obtained by removing the solvent under reduced pressure was purified by silica gel column chromatography (eluting solvent: n-hexane/ethyl acetate=9/1) to give methyl (4-bromo-3-methylphenyl)acetate (2.45 g, yield: 82%).

$^1$H-NMR (400 MHz, CDCl$_3$): δ 7.45 (1H, d, J=8.2 Hz), 7.13 (1H, d, J=2.0 Hz), 6.94 (1H, dd, J=8.2, 2.0 Hz), 3.68 (3H, s), 3.54 (2H, s), 2.37 (3H, s).

(84-3)
After 4,4,4',4',5,5,5',5'-octamethyl-2,2'-bi-1,3,2-dioxaborolane (another name: bis(pinacolate)diboron) (1.15 g, 4.52 mmol), [1,1'-bis(diphenylphosphino)ferrocene]dichloropalladium (II)-dichloromethane adduct (168 mg, 0.21 mmol) and potassium acetate (1.21 mg, 12.34 mmol) were added to a solution of methyl (4-bromo-3-methylphenyl)acetate (1.0 g, 4.11 mmol) obtained in Example (84-2) in dioxane (20 ml), the mixture was stirred at 90° C. for 3 hours. The temperature of the reaction mixture was returned to room temperature, ethyl acetate was added thereto and the mixture was filtered through Celite. The filtrate was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=9/1) to give methyl [3-methyl-4-(4,4,5,5-tetramethyl-1,3,2-dioxaborolan-2-yl)phenyl]acetate (0.9 g, yield: 75%).

$^1$H-NMR (400 MHz, CDCl$_3$): δ 7.73 (1H, d, J=7.8 Hz), 7.10-7.06 (2H, m), 3.67 (3H, s), 3.59 (2H, s), 2.52 (3H, s), 1.33 (12H, s).
(84-4)
According to a method similar to Example (76-1), from tert-butyl 6-{[(6-chloro-3-pyridinyl)oxy]methyl}-2-hydroxy-3-(trifluoromethyl)benzoate (240 mg, 0.59 mmol) obtained in Example (84-1) and methyl [3-methyl-4-(4,4,5,5-tetramethyl-1,3,2-dioxaborolan-2-yl)phenyl]acetate (224 mg, 0.77 mmol) obtained in Example (84-3), tert-butyl 2-hydroxy-6-{[(6-{4-[(methoxycarbonyl)methyl]-2-methylphenyl}-3-pyridinyl)oxy]methyl}-3-(trifluoromethyl)benzoate was obtained (157 mg, yield: 50%).

$^1$H-NMR (400 MHz, CDCl$_3$): δ 12.22 (1H, s), 8.41 (1H, d, J=2.4 Hz), 7.72 (1H, d, J=8.2 Hz), 7.34-7.23 (4H, m), 7.18-7.14 (2H, m), 5.42 (2H, s), 3.69 (3H, s), 3.63 (2H, s), 2.35 (3H, s), 1.65 (9H, s).
(84-5)
According to a method similar to Example (17-4), from tert-butyl 2-hydroxy-6-{[(6-{4-[(methoxycarbonyl)methyl]-2-methylphenyl}-3-pyridinyl)oxy]methyl}-3-(trifluoromethyl)benzoate (157 mg, 0.30 mmol) obtained in Example (84-4), the title compound was obtained as a colorless powder (110 mg, yield: 72%).

$^1$H-NMR (400 MHz, DMSO-d$_6$): δ 12.34 (1H, s), 11.49 (1H, s), 8.45-8.42 (1H, m), 7.84 (1H, d, J=8.2 Hz), 7.50-7.48 (2H, m), 7.33 (1H, d, J=8.2 Hz), 7.31 (1H, d, J=7.4 Hz), 7.18-7.13 (2H, m), 5.45 (2H, s), 3.57 (2H, s), 2.30 (3H, s), 1.56 (9H, s).
ESI (ES−) (m/z): 516 ([M−H]$^+$).

Example 85

(4'-{[2-(tert-Butoxycarbonyl)-3-hydroxy-4-(trifluoromethyl)benzyl]oxy}-3-ethyl-1,1'-biphenyl-4-yl)acetic acid (Exemplification Compound No.: 2-223)

(85-1)
According to a method similar to Example (11-1) and Example (26-4), from 4-bromo-2-iodobenzyl bromide (2.01 g, 6.24 mmol) which was synthesized according to the method described in literature (Nishide, H. et al., Bull. Chem. Soc. Jpn., vol. 69, 1996, pp. 499-508), methyl (4-bromo-2-iodophenyl)acetate was obtained (1.90 g, two-step total yield: 86%).

$^1$H-NMR (400 MHz, CDCl$_3$): δ 7.94 (1H, d, J=2.4 Hz), 7.43 (1H, dd, J=8.6, 2.4 Hz), 7.13 (1H, d, J=8.6 Hz), 3.76 (2H, s), 3.69 (3H, s).

(85-2)

Trimethylsilylacetylene (0.319 ml, 2.25 mmol), palladium acetate (12 mg, 56.3 μmol), triphenylphosphine (30 mg, 0.113 mmol), n-butylamine (0.334 ml, 3.38 mmol) and copper iodide (43 mg, 0.225 mmol) were added to a solution of methyl (4-bromo-2-iodophenyl)acetate (400 mg, 1.13 mmol) obtained in Example (85-1) in tetrahydrofuran (6 ml), and the mixture was stirred at room temperature for 3 hours. The solvent was removed under reduced pressure and the obtained residue was purified by silica gel column chromatography (developing solvent: hexane/ethyl acetate=15/1) to give crude methyl (4-bromo-2-trimethylsilanylethynylphenyl)acetate (434 mg).

Potassium carbonate (368 mg, 2.67 mmol) was added to a solution of the crude product obtained in the above in methanol (9 ml) and the mixture was stirred at room temperature for 4 hours. After water was added to the reaction mixture and the mixture was extracted with ethyl acetate, the organic layer was washed with a saturated aqueous NaCl solution and dried with anhydrous sodium sulfate. The solvent was removed under reduced pressure and the obtained residue was purified by silica gel column chromatography (developing solvent: hexane/ethyl acetate=10/1) to give methyl (4-bromo-2-ethynylphenyl)acetate (177 mg, two-step total yield: 62%).

$^1$H-NMR (400 MHz, CDCl$_3$): δ 7.65 (1H, d, J=2.4 Hz), 7.45 (1H, dd, J=8.6, 2.41 Hz), 7.17 (1H, d, J=8.6 Hz), 3.80 (2H, s), 3.71 (3H, s), 3.32 (1H, s).

(85-3)

Chlorotris(triphenylphosphine)rhodium (65 mg, 69.9 μmol) was added to a solution of methyl (4-bromo-2-ethynylphenyl)acetate (177 mg, 0.699 mmol) obtained in Example (85-2) in methanol (6 ml), and the mixture was stirred at room temperature under hydrogen atmosphere for 16 hours. The solvent was removed under reduced pressure and the obtained residue was purified by silica gel column chromatography (developing solvent: hexane/ethyl acetate=15/1) to give methyl (4-bromo-2-ethylphenyl)acetate (138 mg, yield: 77%).

$^1$H-NMR (400 MHz, CDCl$_3$): δ 7.35 (1H, d, J=2.4 Hz), 7.29 (1H, dd, J=8.6, 2.4 Hz), 7.07 (1H, d, J=8.6 Hz), 3.68 (2H, s), 3.61 (3H, s), 2.62 (2H, q, J=7.4 Hz), 1.20 (3H, t, J=7.4 Hz).

(85-4)

According to a method similar to Example (26-3), from methyl (4-bromo-2-ethylphenyl)acetate (138 mg, 0.537 mmol) synthesized in Example (85-3) and 4-(4,4,5,5-tetramethyl-1,3,2-dioxaborolan-2-yl)phenol (142 mg, 0.644 mmol), methyl (3-ethyl-4'-hydroxy-1,1'-biphenyl-4-yl)acetate was obtained (122 mg, yield: 84%).

$^1$H-NMR (500 MHz, CDCl$_3$): δ 7.46 (2H, d, J=8.8 Hz), 7.37 (1H, d, J=2.0 Hz), 7.33 (1H, dd, J=8.8, 2.0 Hz), 7.25 (1H, d, J=8.8 Hz), 6.88 (2H, d, J=8.8 Hz), 4.95 (1H, s), 3.71 (2H, s), 3.70 (3H, s), 2.71 (2H, q, J=7.8 Hz), 1.25 (3H, t, J=7.8 Hz).

(85-5)

According to a method similar to Example (40-2), Example (33-5) and Example (17-4), from methyl (3-ethyl-4'-hydroxy-1,1'-biphenyl-4-yl)acetate (122 mg, 0.45 mmol) synthesized in Example (85-4) and tert-butyl 6-(bromomethyl)-2-[(tert-butoxycarbonyl)oxy]-3-(trifluoromethyl)benzoate (226 mg, 0.50 mmol) obtained in Example (28-5), the title compound was obtained (107 mg, three-step total yield: 46%).

$^1$H-NMR (400 MHz, CDCl$_3$): δ 12.3 (1H, s), 7.71 (1H, d, J=8.8 Hz), 7.53 (2H, d, J=8.6 Hz), 7.41 (1H, d, J=1.6 Hz), 7.28 (2H, dd, J=8.8, 1.6 Hz), 6.98 (2H, d, J=8.6 Hz), 5.38 (2H, s), 3.74 (2H, s), 2.72 (2H, q, J=7.8 Hz), 1.65 (9H, s), 1.23 (3H, t, J=7.8 Hz).

MS (FAB) (m/z): 569 ([M+K]$^+$).

Example 86

[4-(5-{[2-(tert-Butoxycarbonyl)-3-hydroxy-4-(trifluoromethyl)benzyl]oxy}-2-pyridinyl)-2-chlorophenyl]acetic acid (Exemplification Compound No.: 2-168)

According to a method similar to Example (84-2) and Example (84-3), from (4-bromo-2-chlorophenyl)acetonitrile (205 mg, 0.89 mmol) obtained in Example (18-1), methyl [2-chloro-4-(4,4,5,5-tetramethyl-1,3,2-dioxaborolan-2-yl)phenyl]acetate was obtained.

According to a method similar to Example (76-1) and Example (17-4), from the compound obtained in the above and tert-butyl 6-{[(6-chloro-3-pyridinyl)oxy]methyl}-2-hydroxy-3-(trifluoromethyl)benzoate obtained in Example (84-1), the title compound was obtained as a colorless powder (192 mg, four-step total yield: 40%).

$^1$H-NMR (400 MHz, DMSO-d$_6$): δ 12.46 (1H, s), 11.45 (1H, s), 8.42 (1H, s), 8.06 (1H, s), 8.00 (1H, d, J=9.0 Hz), 7.92 (1H, d, J=9.0 Hz), 7.81 (1H, d, J=8.2 Hz), 7.51 (1H, d, J=8.2 Hz), 7.45 (1H, d, J=8.2 Hz), 7.29 (1H, d, J=8.2 Hz), 5.45 (2H, s), 3.74 (2H, s), 1.56 (9H, s).

ESI (ES−) (m/z): 537 ([M−H]$^+$).

Example 87

(4'-{[2-(tert-Butoxycarbonyl)-3,6-dihydroxy-4-(trifluoromethyl)benzyl]oxy}-1,1'-biphenyl-4-yl)acetic acid (Exemplification Compound No.: 1-129)

(87-1)

According to a method similar to Example (28-5), from tert-butyl 2,5-bis(methoxymethoxy)-6-methyl-3-(trifluoromethyl)benzoate (225 mg, 0.70 mmol), tert-butyl 2-(bromomethyl)-3,6-bis(methoxymethoxy)-5-(trifluoromethyl)benzoate was obtained (164 mg, yield: 519%).

$^1$H-NMR (400 MHz, CDCl$_3$): δ 7.38 (1H, s), 5.28 (2H, s), 5.07 (2H, s), 4.53 (2H, s), 3.57 (3H, s), 3.52 (3H, s), 1.66 (9H, s).

(87-2)

According to a method similar to Example (40-2), Example (8-3) and Example (17-4), from tert-butyl 2-(bromomethyl)-3,6-bis(methoxymethoxy)-5-(trifluoromethyl)benzoate (154 mg, 0.34 mmol) obtained in Example (87-1) and methyl (4'-hydroxy-1,1'-biphenyl-4-yl)acetate (80 mg, 0.33 mmol) obtained in Example (6-2), the title compound was obtained (25 mg, three-step total yield: 17%).

$^1$H-NMR (400 MHz, CDCl$_3$): δ 10.98 (1H, s), 7.55-7.51 (4H, m), 7.35 (2H, d, J=8.2 Hz), 7.33 (1H, s), 7.03 (2H, d, J=8.2 Hz), 5.57 (2H, s), 3.70 (2H, s), (1.59 (9H, s).

MS (EI) (m/z): 517 ([M−H]$^-$).

Example 88

(4'-{[2-(tert-Butoxycarbonyl)-3-hydroxy-4-(trifluoromethyl)benzyl]oxy}-2-(1-hydroxyethyl)-1,1'-biphenyl-4-yl)acetic acid (Exemplification Compound No.: 2-225)

(88-1)

According to a method similar to Example (6-6), from methyl (2-acetyl-4'-hydroxy-1,1'-biphenyl-4-yl)acetate (170 mg, 0.599 mmol) obtained in Example (40-1), methyl [4'-hydroxy-2-(1-hydroxyethyl)-1,1'-biphenyl-4-yl]acetate was obtained (93 mg, yield: 54%).

$^1$H-NMR (400 MHz, CDCl$_2$): δ 7.53 (1H, d, J=1.6 Hz), 7.19 (1H, dd, J=7.8, 1.6 Hz), 7.12 (1H, d, J=7.8 Hz), 7.06 (2H, d, J=8.6 Hz), 6.77 (2H, d, J=8.6 Hz), 4.98 (1H, q, J=6.7 Hz), 3.72 (3H, s), 3.68 (2H, s), 1.37 (3H, d, J=6.7 Hz).

(88-2)

According to a method similar to Example (40-2), Example (33-5) and Example (17-4), from tert-butyl 6-(bromomethyl)-2-[(tert-butoxycarbonyl)oxy]-3-(trifluoromethyl)benzoate (137 mg, 0.325 mmol) obtained in Example (28-5) and methyl [4'-hydroxy-2-(1-hydroxyethyl)-1,1'-biphenyl-4-yl]acetate (93 mg, 0.325 mmol) obtained in Example (88-1), the title compound was obtained as a pale yellow oil (60 mg, yield: 34%).

$^1$H-NMR (500 MHz, CDCl$_3$): δ 7.71 (1H, d, J=−7.8 Hz), 7.57 (1H, d, J=1.5 Hz), 7.29 (1H, d, J=7.8 Hz), 7.25-7.20 (3H, m), 7.15 (1H, d, J=7.8 Hz), 6.95 (2H, d, J=8.8 Hz), 5.38 (2H, s), 4.99 (1H, q, J=6.4 Hz), 3.70 (2H, s), 1.65 (9H, s), 1.39 (3H, d, J=6.4 Hz).

ESI (ES−) (m/z): 545 ([M−H]$^+$).

Example 89

(4'-{[2-(tert-Butoxycarbonyl)-3-hydroxy-4-(trifluoromethyl)benzyl]oxy}-3-[(dimethylamino)carbonyl]-1,1'-biphenyl-4-yl)acetic acid (Exemplification Compound No.: 2-226)

(89-1)

According to a method similar to Example (26-3) and Example (68), from methyl {4-bromo-2-[(dimethylamino)carbonyl]phenyl}acetate (102 mg, 0.340 mmol) and 4-(4,4,5,5-tetramethyl-1,3,2-dioxaborolan-2-yl)phenol (90 mg, 0.408 mol), methyl {3-[(dimethylamino)carbonyl]-4'-hydroxy-1,1'-biphenyl-4-yl}acetate was obtained (82 mg, two-step total yield: 77%).

$^1$H-NMR (500 MHz, CDCl$_3$): δ 7.49 (1H, d, J=7.8 Hz), 7.39-7.32 (3H, m), 6.87-6.79 (3H, m), 4.95 (1H, s), 3.75 (2H, s), 3.70 (3H, s), 3.15 (3H, s), 2.93 (3H, s).

(89-2)

According to a method similar to Example (2-3), Example (33-5) and Example (17-4), from methyl {3-[(dimethylamino)carbonyl]-4'-hydroxy-1,1'-biphenyl-4-yl}acetate (82 mg, 0.262 mmol) obtained in Example (89-1) and tert-butyl 6-(bromomethyl)-2-[(tert-butoxycarbonyl)oxy]-3-(trifluoromethyl)benzoate (131 mg, 0.288 mmol) obtained in Example (28-5), the title compound was obtained (100 mg, three-step total yield: 67%).

In the present step, methyl ethyl ketone was used as the reaction solvent instead of N,N-dimethylformamide in the step corresponding to Example (2-3).

$^1$H-NMR (500 MHz, CDCl$_3$): δ 12.2 (1H, s), 7.71 (5H, d, J=7.8 Hz), 7.61 (1H, dd, J=7.8, 2.0 Hz), 7.56-7.48 (3H, m), 7.45, (1H, d, J=2.0 Hz), 7.27-7.25 (1H, m), 7.02-6.98 (2H, m), 5.39 (2H, s), 3.66 (2H, s), 3.24 (3H, s), 3.11 (3H, s), 1.65 (9H, s).

Example 90

(4'-{[2-(tert-Butoxycarbonyl)-3-hydroxy-4-(trifluoromethyl)benzyl]oxy}-2-ethyl-1,1'-biphenyl-3-yl) acetic acid (Exemplification Compound No.: 2-227)

(90-1)

A n-butyllithium-1.58M n-hexane solution (36.2 ml, 57.2 mmol) was added dropwise to a solution of diisopropylamine (8.02 ml, 57.2 mmol) in tetrahydrofuran (114 ml) under ice-cooling, and the mixture was further stirred for 30 minutes. After the reaction mixture was cooled to −50° C., a solution of 3-iodo-2-methylbenzoic acid (5.00 g, 19.1 mmol) in tetrahydrofuran (38 ml) was added thereto. After the mixture was stirred for 1 hour, iodomethane (9.51 ml, 153 mmol) was added thereto and the temperature of the mixture was raised from −50° C. to −20° C. over 1 hour. The reaction mixture was poured into 1N hydrochloric acid and extracted with ethyl acetate. The organic layer was successively washed with 1N hydrochloric acid, water and a saturated aqueous NaCl solution and dried with anhydrous sodium sulfate. The solvent was removed under reduced pressure to give 3-iodo-2-ethylbenzoic acid (5.48 g, yield: 100%).

$^1$H-NMR (400 MHz, CDCl$_3$): δ 8.05 (1H, d, J=7.8 Hz), 7.93 (1H, d, J=7.8 Hz), 6.97 (1H, t, J=7.8 Hz), 3.17 (2H, q, J=7.4 Hz), 1.23 (3H, t, J=7.4 Hz).

(90-2)

Potassium carbonate (3.17 g, 22.9 mmol) and methyl iodide (1.43 ml, 22.9 mmol) were added to a solution of 3-iodo-2-ethylbenzoic acid (5.48 g, 19.1 mmol) obtained in Example (90-1) in N,N-dimethylformamide (38 ml) under ice-cooling, and the mixture was stirred at room temperature overnight. After the reaction mixture was poured into water and the mixture was extracted with ethyl acetate, the organic layer was successively washed with water and a saturated aqueous NaCl solution and dried with anhydrous sodium sulfate, and the solvent was removed under reduced pressure. According to a method similar to Example (14-1), from the residue obtained in the above and 4-methoxyphenylboronic acid (2.90 g, 19.1 mmol), methyl 2-ethyl-4'-methoxy-1,1'-biphenyl-3-carboxylate was obtained (4.83 g, yield: 94%, two-step total yield).

$^1$H-NMR (400 MHz, CDCl$_3$): δ 7.72 (1H, d, J=7.4 Hz), 7.28 (1H, d, J=7.4 Hz), 7.21 (1H, t, J=7.4 Hz), 7.17 (2H, d, J=8.6 Hz), 6.92 (2H, d, J=8.6 Hz), 3.90 (3H, s), 3.85 (3H, s), 2.86 (2H, q, J=7.4 Hz), 1.00 (3H, t, J=7.4 Hz).

(90-3)

After methyl 2-ethyl-4'-methoxy-1,1'-biphenyl-3-carboxylate (4.83 g, 17.9 mmol) obtained in Example (90-2) was added to a suspension of lithium aluminum hydride (1.02 g, 26.8 mmol) in tetrahydrofuran (90 ml) under ice-cooling, the mixture was stirred at room temperature for 30 minutes. The reaction mixture was cooled with ice and water (1 ml) was added dropwise thereto. After the mixture was stirred for 5 minutes, a 3N aqueous sodium hydroxide solution (1 ml) was added thereto at room temperature and the mixture was stirred for 5 minutes. Further, water (3 ml) was added thereto and the mixture was stirred for 20 minutes. After the insolubles were removed by filtration using Celite, the solvent was removed under reduced pressure. The obtained residue was purified by silica gel column chromatography (eluting solvent: n-hexane/ethyl acetate=4/1-3/1) to give (2-ethyl-4'-methoxy-1,1'-biphenyl-3-yl)methanol (4.39 g, yield: 100%).

$^1$H-NMR (400 MHz, CDCl$_3$): δ 7.41 (1H, d, J=7.4 Hz), 7.23 (1H, t, J=7.4 Hz), 7.21 (2H, d, J=8.2 Hz), 7.14 (1H, d, J=7.4 Hz), 6.92 (2H, d, J=8.2 Hz), 4.81 (2H, s), 3.86 (3H, s), 2.66 (2H, q, J=7.4 Hz), 0.99 (3H, t, J=7.4 Hz).

(90-4)

After thionyl chloride (4 ml) was added to a solution of (2-ethyl-4'-methoxy-1,1'-biphenyl-3-yl)methanol (4.39 g, 17.9 mmol) obtained in Example (90-3) in methylene chloride (18 ml) under ice-cooling, the mixture was stirred at room temperature for 7 hours. The residue obtained by removing the solvent under reduced pressure was diluted with ethyl acetate and the mixture was successively washed with water, a saturated aqueous sodium hydrogencarbonate solution and a saturated aqueous NaCl solution and dried with anhydrous sodium sulfate. The solvent was removed under reduced pressure to give 3'-(chloromethyl)-2'-ethyl-1,1'-biphenyl-4-yl methyl ether (3.32 g, yield: 71%).

$^1$H-NMR (400 MHz, CDCl$_3$): δ 7.36 (1H, dd, J=7.8, 1.6 Hz), 7.22 (2H, d, J=9.0 Hz), 7.21 (1H, t, J=7.8 Hz), 7.15 (1H, dd, J=7.8, 1.6 Hz), 6.94 (2H, d, J=9.0 Hz), 3.86 (3H, s), 2.71 (2H, q, J=7.4 Hz), 1.03 (3H, t, J=7.4 Hz).

(90-5)

An aqueous solution (7 ml) of potassium cyanide (829 mg, 12.7 mmol) was added dropwise to a solution of 3'-(chloromethyl)-2'-ethyl-1,1'-biphenyl-4-yl methyl ether (3.32 g, 12.7 mmol) obtained in Example (90-4) in N,N-dimethyl sulfoxide (7 ml) at 80° C., and the mixture was stirred at the same temperature for 3 hours. The reaction mixture was diluted with ethyl acetate and the organic layer was successively washed with water and a saturated aqueous NaCl solution and dried with anhydrous sodium sulfate. The residue obtained by removing the solvent under reduced pressure was purified by silica gel column chromatography (eluting solvent: n-hexane/ethyl acetate=9/1-3/1) to give (2-ethyl-4'-methoxy-1,1'-biphenyl-3-yl)acetonitrile (2.65 g, yield: 83%).

$^1$H-NMR (400 MHz, CDCl$_3$): δ 7.40 (1H, d, J=7.4 Hz), 7.24 (1H, t, J=7.4 Hz), 7.19 (2H, d, J=8.6 Hz), 7.17 (1H, d, J=7.4 Hz), 6.95 (2H, d, J=8.6 Hz), 3.86 (3H, s), 3.80 (2H, s), 2.60 (2H, q, J=7.4 Hz), 1.00 (3H, t, J=7.4 Hz).

(90-6)

According to a method similar to Example (26-4), from (2-ethyl-4'-methoxy-1,1'-biphenyl-3-yl)acetonitrile (2.65 g, 10.5 mmol) obtained in Example (90-5), allyl (2-ethyl-4'-hydroxy-1,1'-biphenyl-3-yl)acetate was obtained (2.57 g, yield: 83%).

Allyl alcohol was used instead of methanol in the esterification reaction.

$^1$H-NMR (400 MHz, CDCl$_3$): δ 7.24 (1H, dd, J=7.8, 1.6 Hz), 7.17 (1H, t, J=7.8 Hz), 7.16 (2H, d, J=8.6 Hz), 7.09 (1H, dd, J=7.8, 1.6 Hz), 6.85 (2H, d, J=8.6 Hz), 5.97-5.87 (1H, m), 5.82-5.21 (2H, m), 4.86 (1H, s), 4.64-4.61 (2H, m), 3.76 (2H, s), 2.60 (2H, q, J=7.4 Hz), 0.95 (3H, t, J=7.4 Hz).

(90-7)

According to a method similar to Example (40-2), Example (33-5) and Example (13-5), from allyl (2-ethyl-4'-hydroxy-1,1'-biphenyl-3-yl)acetate (200 mg, 0.675 mmol) obtained in Example (90-6), the title compound was obtained as a white solid (222 mg, three-step total yield: 62%).

$^1$H-NMR (400 MHz, CDCl$_3$): δ 12.22 (1H, s), 7.70 (1H, d, J=8.2 Hz), 7.28 (1H, d, J=8.2 Hz), 7.24-7.20 (1H, m), 7.21 (2H, d, J=8.6 Hz), 7.17 (1H, t, J=7.4 Hz), 7.09 (1H, d, J=7.4 Hz), 6.92 (2H, d, J=8.6 Hz), 5.36 (2H, s), 3.77 (2H, s), 2.60 (2H, q, J=7.8 Hz), 1.64 (9H, s), 0.96 (3H, t, J=7.8 Hz).

MS (FAB) (m/z): 530 ([M]$^+$).

Example 91

(4'-{[2-(tert-Butoxycarbonyl)-3-hydroxy-4-(trifluoromethyl)benzyl]oxy}-2,3-difluoro-1,1'-biphenyl-4-yl)acetic acid (Exemplification Compound No.: 2-228).

(91-1)

According to a method similar to Example (22-5), Example (26-3), Example (2-2), Example (90-5) and Example (26-4), from 2,3-difluoro-4-methylphenol (2.50 g, 17.3 mmol), methyl (2,3-difluoro-4'-hydroxy-1,1'-biphenyl-4-yl)acetate was obtained as a brown powder (654 mg, five-step total yield: 14%).

$^1$H-NMR (400 MHz, CDCl$_3$): δ 7.42 (2H, d, J=8.3 Hz), 7.12 (1H, dd, J=8.0, 6.8 Hz), 7.05 (1H, dd, J=8.0, 6.8 Hz), 6.91 (2H, d, J=8.3 Hz), 4.91 (1H, s), 3.75 (3H, s), 3.73 (2H, s).

(91-2)

According to a method similar to Example (40-2), Example (33-5) and Example (17-4), from methyl (2,3-difluoro-4'-hydroxy-1,1'-biphenyl-4-yl)acetate (200 mg, 0.72 mmol) obtained in Example (91-1), the title compound was obtained as a white powder (16 mg, three-step total yield: 4%).

$^1$H-NMR (400 MHz, CDCl$_3$): δ 12.22 (1H, s), 7.69 (1H, d, J=8.2 Hz), 7.47 (2H, d, J=8.6 Hz), 7.25 (1H, d, J=8.2 Hz), 7.13 (1H, dd, J=8.0, 6.7 Hz), 7.05 (1H, dd, J=8.0, 6.7 Hz), 6.97 (2H, d, J=8.6 Hz), 5.37 (2H, s), 3.77 (2H, s), 1.65 (9H, s).

MS (FAB) (m/z): 538 ([M]$^+$).

Example 92

(4'-{[2-(tert-Butoxycarbonyl)-3-hydroxy-4-(trifluoromethyl)benzyl]oxy}-2,3-dimethyl-1,1'-biphenyl-4-yl)acetic acid (Exemplification Compound No.: 2-229)

(92-1)

According to a method similar to Example (26-4), from 2,3-dimethyl-4-methoxyphenylacetonitrile (800 mg, 4.57 mmol), methyl (4-methoxy-2,3-dimethylphenyl)acetate was obtained (857 mg, 85.3%).

$^1$H-NMR (400 MHz, CDCl$_3$): δ 7.01 (1H, d, J=7.8 Hz), 6.69 (1H, dd, J=7.8 Hz), 3.80 (3H, s), 3.68 (3H, s), 3.62 (2H, s), 2.20 (3H, s), 2.17 (3H, s).

(92-2)

According to a method similar to Example (6-2), from methyl (4-methoxy-2,3-dimethylphenyl)acetate (857 mg, 4.12 mmol) obtained in Example (92-1), methyl (4-hydroxy-2,3-dimethylphenyl)acetate was obtained (477 mg, 59.7%).

$^1$H-NMR (400 MHz, CDCl$_3$): δ 6.90 (1H, d, J=7.8 Hz), 6.59 (1H, d, J=7.8 Hz), 4.75-4.70 (1H, br s), 3.68 (3H, s), 3.60 (2H, s), 2.19 (3H, s), 2.18 (3H, s).

(92-3)

According to a method similar to Example (22-5) and Example (26-3), from methyl (4-hydroxy-2,3-dimethylphenyl)acetate (477 mg, 2.46 mmol) obtained in Example (92-2), methyl (4'-hydroxy-2,3-dimethyl-1,1'-biphenyl-4-yl)acetate was obtained (282 mg, two-step total yield: 42.5%).

In the present step, 4-(4,4,5,5-tetramethyl-1,3,2-dioxaborolan-2-yl)phenol was used instead of 4-methoxyphenylboronic acid in the Suzuki coupling step corresponding to Example (26-3).

$^1$H-NMR (400 MHz, CDCl$_3$): δ 7.14 (2H, d, J=8.6 Hz), 7.07 (1H, d, J=7.8 Hz), 7.02 (1H, d, J=7.8 Hz), 6.84 (2H, d, J=8.6 Hz), 4.99-4.95 (1H, br s), 3.72 (3H, s), 3.71 (2H, s), 2.26 (3H, s), 2.16 (3H, s).

(92-4)

According to a method similar to Example (40-2), Example (33-5) and Example (17-4), from methyl (4'-hydroxy-2,3-dimethyl-1,1'-biphenyl-4-yl)acetate (282 mg, 1.04 mmol) synthesized in Example (92-3), the title compound was obtained (256 mg, three-step total yield: 46.3%).

$^1$H-NMR (400 MHz, CDCl$_3$): δ 12.26 (1H, s), 7.72 (1H, d, J=8.2 Hz), 7.30 (1H, d, J=8.2 Hz), 7.23-7.17 (2H, m), 7.09 (1H, d, J=7.8 Hz), 7.04 (1H, d, J=7.8 Hz), 6.96-6.90 (2H, m), 5.30 (2H, s), 3.76 (2H, s), 2.28 (3H, s), 2.18 (3H, s), 1.65 (9H, s).

MS (FAB) (m/z): 530 ([M]$^+$).

Example 93

2-(4'-{[2-(tert-Butoxycarbonyl)-3-hydroxy-4-(trifluoromethyl)benzyl]oxy}-3-fluoro-1,1'-biphenyl-4-yl)-3-(dimethylamino)propanoic acid (Exemplification Compound No.: 2-230)

(93-1)

tert-Butyl 2-(allyloxy)-6-{[(4'-{[(allyloxy)carbonyl]methyl}-3'-fluoro-1,1'-biphenyl-4-yl)oxy]methyl}-3-(trifluoromethyl)benzoate (200 mg, 0.33 mmol) obtained in Example (11-6) was dissolved in toluene (3 ml) and N,N-dimethylformamide di-tert-butyl acetal (0.4 ml, 1.7 mmol) was added thereto, and the mixture was heated under reflux for 3 hours. After the reaction mixture was poured into water and the mixture was extracted with ethyl acetate (three times), the organic layer was successively washed with water (twice) and a saturated aqueous NaCl solution and dried with anhydrous sodium sulfate. The residue obtained by removing the solvent under reduced pressure was purified by silica gel column chromatography (eluting solvent: n-hexane/ethyl acetate=10/1-1/1) to give tert-butyl 2-(allyloxy)-6-{[(4'-{1-[(allyloxy)carbonyl]-2-(dimethylamino)vinyl}-3'-fluoro-1,1'-biphenyl-4-yl)oxy]methyl}-3-(trifluoromethyl)benzoate (141 mg, yield: 65%).

$^1$H-NMR (400 MHz, CDCl$_3$): δ 7.69 (1H, s), 7.64 (1H, d, J=0.8 Hz), 7.53 (2H, d, J=8.8 Hz), 7.39 (1H, d, J=8.8 Hz), 7.29-7.20 (3H, m), 7.00 (2H, d, J=8.8 Hz), 6.11-6.08 (1H, m), 5.93-5.85 (1H, m), 5.43 (1H, d, J=15.6 Hz), 5.28 (1H, d, J=10.4 Hz), 5.21-5.10 (2H, m), 5.17 (2H, s), 4.59-4.58 (4H, m), 2.78 (6H, s), 1.58 (9H, s).

(93-2)

Morpholine (0.02 ml, 0.23 mmol) and tetrakis(triphenylphosphine)palladium (0) (6 mg, 0.005 mmol) were successively added to a solution of tert-butyl 2-(allyloxy)-6-{[(4'-{1-[(allyloxy)carbonyl]-2-(dimethylamino)vinyl}-3'-fluoro-1,1'-biphenyl-4-yl)oxy]methyl}-3-(trifluoromethyl)benzoate (67 mg, 0.10 mmol) obtained in Example (93-1) in tetrahydrofuran (1 ml), and the mixture was stirred at room temperature for 1 hour. After the reaction mixture was poured into water and the mixture was extracted with ethyl acetate, the organic layer was successively washed with water and a saturated aqueous NaCl solution and dried with anhydrous sodium sulfate. The residue obtained by removing the solvent under reduced pressure was subjected to silica gel column chromatography (eluting solvent: n-hexane/ethyl acetate=10/1-1/>99) to give crude tert-butyl 2-hydroxy-6-{[(4'-{1-[(allyloxy)carbonyl]-2-(dimethylamino)vinyl}-3'-fluoro-1,1'-biphenyl-4-yl)oxy]methyl}-3-(trifluoromethyl)benzoate (42 mg).

After a neutral phosphate pH standard solution (pH 6.86, 0.2 ml) and sodium cyanoborohydride (15 mg, 0.24 mmol) were successively added to a solution of the compound obtained in the above in acetonitrile (1 ml) and the mixture was stirred at room temperature for 1.5 hours, sodium cyanoborohydride (15 mg, 0.24 mmol) and a small amount of acetic acid were successively added thereto and the mixture was stirred at room temperature for 3 hours. After an aqueous sodium hydrogencarbonate solution was added to the reaction mixture and the mixture was extracted with ethyl acetate, it was dried with anhydrous sodium sulfate. The residue obtained by removing the solvent under reduced pressure was subjected to silica gel column chromatography (eluting solvent: ethyl acetate/methanol=>99/1-5/1) to give crude tert-butyl 6-{[(4'-{1-[(allyloxy)carbonyl]-2-(dimethylamino)ethyl}-3'-fluoro-1,1'-biphenyl-4-yl)oxy]methyl}-2-hydroxy-3-(trifluoromethyl)benzoate.

Morpholine (0.012 ml, 0.13 mmol) and tetrakis(triphenylphosphine)palladium (0) (6 mg, 0.005 mmol) were successively added to a solution of the compound obtained in the above in tetrahydrofuran (1 ml), and the mixture was stirred at room temperature for 1 hour. The solvent was removed under reduced pressure and the residue was diluted with ethyl acetate. A neutral phosphate pH standard solution (pH 6.86) and a saturated aqueous NaCl solution were added to the solution and the mixture was extracted with ethyl acetate. The organic layer was washed with a saturated aqueous NaCl solution and dried with anhydrous sodium sulfate. The residue obtained by removing the solvent under reduced pressure was purified by high performance liquid chromatography (column: G.L. science, inert sil ODS-3; eluting solvent: acetonitrile:water=85/15-98/2) to give the title compound as a colorless solid (12 mg, three-step total yield: 20%).

$^1$H-NMR (400 MHz, CDCl$_3$): δ 12.25 (1H, s), 7.71 (1H, d, J=8.0 Hz), 7.49 (2H, d, J=8.8 Hz), 7.39-7.23 (4H, m), 6.98 (2H, d, J=8.8 Hz), 5.38 (2H, s), 4.08-4.05 (1H, m), 3.36 (1H, t, J=12.4 Hz), 2.74-2.71 (1H, m), 2.68 (3H, s), 2.68 (3H, s), 1.65 (9H, s).

MS (ESI) (m/z): 576 ([M−H]$^+$).

Example 94

2-(4'-{[2-(tert-Butoxycarbonyl)-3-hydroxy-4-(trifluoromethyl)benzyl]oxy}-2-ethyl-1,1'-biphenyl-4-yl)propanoic acid (Exemplification Compound No.: 2-231)

(94-1)

After lithium bis(trimethylsilyl)amide (1M n-hexane solution, 0.32 ml, 0.32 mmol) was added to a solution of tert-butyl 2-(allyloxy)-6-[({2'-ethyl-4'-[(methoxycarbonyl)methyl]-1,1'-biphenyl-4-yl}oxy)methyl]-3-(trifluoromethyl)benzoate (105 mg, 0.19 mmol) in tetrahydrofuran (2 ml) at −78° C. under nitrogen atmosphere and the mixture was stirred for 0.5 hours, methyl iodide (30 μl, 0.48 mmol) was added thereto and the mixture was stirred for 1 hour. After a saturated aqueous NaCl solution was added to the reaction mixture and the mixture was extracted with ethyl acetate, the organic layer was washed with a saturated aqueous NaCl solution and dried with anhydrous sodium sulfate. The residue obtained by removing the solvent under reduced pressure was purified by silica gel preparative thin layer chromatography (developing solvent: hexane/ethyl acetate=5/1) to give tert-butyl 2-(allyloxy)-6-[({2'-ethyl-4'-[1-(methoxycarbonyl)ethyl]-1,1'-biphenyl-4-yl}oxy)methyl]-3-(trifluoromethyl)benzoate as an oil (30 mg, yield: 27%).

$^1$H-NMR (500 MHz, CDCl$_3$): δ 7.66 (1H, d, J=8.0 Hz), 7.42 (1H, d, J=8.0 Hz), 7.26-7.20 (3H, m), 7.14-7.13 (2H, m), 6.96 (2H, d, J=8.5 Hz), 6.11-6.03 (1H, m), 5.43 (1H, dd, J=17.0, 1.5 Hz), 5.28 (1H, dd, J=10.5, 1.5 Hz), 5.16 (2H, s), 4.58 (2H, d, J=5.5 Hz), 3.75 (1H, q, J=7.0 Hz), 3.69 (3H, s), 2.58 (2H, q, J=7.5 Hz), 1.57 (9H, s), 1.53 (3H, d, J=7.0 Hz), 1.08 (3H, t, J=7.5 Hz).

(94-2)

According to a method similar to Example (11-7) and Example (17-4), from tert-butyl 2-(allyloxy)-6-[({2'-ethyl-4'-[1-(methoxycarbonyl)ethyl]-1,1'-biphenyl-4-yl}oxy)methyl]-3-(trifluoromethyl)benzoate (64 mg, 0.11 mmol) obtained in Example (94-1), the title compound was obtained as a colorless solid (31 mg, two-step total yield: 52%).

$^1$H-NMR (500 MHz, CD$_3$OD): δ 7.77 (1H, d, J=8.0 Hz), 7.34 (1H, d, J=8.0 Hz), 7.23-7.22 (3H, m), 7.16 (1H, dd, J=8.0, 2.0 Hz), 7.08 (1H, d, J=8.0 Hz), 7.02 (2H, d, J=9.0 Hz), 5.41 (2H, s), 3.70 (1H, q, J=7.5 Hz), 2.58 (2H, q, J=7.5 Hz), 1.63 (9H, s), 1.46 (3H, d, J=7 Hz), 1.04 (3H, t, J=7.5 Hz).
MS (ESI) (m/z): 543 ([M–H]$^+$).

Example 95 tert-Butyl 2-hydroxy-6-({[4'(1H-tetrazol-5-yl)-1,1'-biphenyl-4-yl]oxy}methyl)-3-(trifluoromethyl)benzoate (Exemplification Compound No.: 1-68)

(95-1)
Chloromethyl methyl ether (0.5 ml, 6.59 mmol) and diisopropylethylamine (1.44 ml, 8.24 mmol) were added to a solution of 4'-hydroxy-1,1'-biphenyl-4-carbonitrile (1.07 g, 5.49 mmol) in methylene chloride (10 ml), and the mixture was stirred at room temperature for 16 hours. After water was added to the reaction mixture and the mixture was extracted with ethyl acetate, the organic layer was washed with a saturated aqueous NaCl solution and dried with anhydrous sodium sulfate. The residue obtained by removing the solvent under reduced pressure was purified by silica gel column chromatography (developing solvent: hexane/ethyl acetate=5/1) to give 4'-methoxymethoxy-1,1'-biphenyl-4-carbonitrile (1.03 g, yield: 78%).
$^1$H-NMR (400 MHz, CDCl$_3$): δ 7.70 (2H, d, J=7.8 Hz), 7.64 (2H, d, J=7.8 Hz), 7.56-7.51 (2H, m), 7.17-7.12 (2H, m), 5.23 (2H, s), 3.51 (3H, s).
(95-2)
Sodium azide (531 mg, 8.16 mmol) and ammonium chloride (435 mg, 8.16 mmol) were added to a solution of 4'-methoxymethoxy-1,1'-biphenyl-4-carbonitrile (500 mg, 2.09 mmol) obtained in Example (95-1) in N,N-dimethylformamide (10 ml), and the mixture was stirred at 120° C. for one week. A saturated aqueous sodium hydrogencarbonate solution was added to the reaction mixture and the aqueous layer was washed with ethyl acetate. After the aqueous layer was acidified with a 1N aqueous hydrochloric acid solution and the mixture was extracted with ethyl acetate, the organic layer was washed with a saturated aqueous NaCl solution and dried with anhydrous sodium sulfate. The solvent was removed under reduced pressure to give crude 5-(4'-methoxymethoxy-1,1'-biphenyl-9-yl)-1H-tetrazole (600 mg).
Allyl bromide (0.27 ml, 3.13 mmol) and cesium carbonate (1.02 g, 3.13 mmol) were added to a solution of the obtained compound in N,N-dimethylformamide (5 ml), and the mixture was stirred at room temperature for 1 hour. After water was added to the reaction mixture and the mixture was extracted with ethyl acetate, the organic layer was washed with a saturated aqueous NaCl solution and dried with anhydrous sodium sulfate. The residue obtained by removing the solvent under reduced pressure was purified by silica gel column chromatography (developing solvent: hexane/ethyl acetate=2/1) to give a mixture of 1-allyl-5-(4'-methoxymethoxy-1,1'-biphenyl-4-yl)-1H-tetrazole and 2-allyl-5-(4'-methoxymethoxy-1,1'-biphenyl-4-yl)-2H-tetrazole (504 mg, two-step total yield: 71%).
$^1$H-NMR (400 MHz, CDCl$_3$): δ 8.20 (2H, d, J=7.8 Hz), 7.68 (2H, d, J=7.8 Hz), 7.59 (2H, d, J=8.6 Hz), 7.14 (2H, d, J=8.6 Hz), 6.21-6.09 (1H, m), 5.44 (1H, s), 5.41 (1H, d, J=5.9 Hz), 5.28 (2H, d, J=5.9 Hz), 5.23 (2H, s), 3.51 (3H, s).
(95-3)
A 4N hydrochloric acid-dioxane solution (0.75 ml, 3.00 mmol) was added to a solution of a mixture of 1-allyl-5-(4'-methoxymethoxy-1,1'-biphenyl-4-yl)-1H-tetrazole and 2-allyl-5-(4'-methoxymethoxy-1,1'-biphenyl-4-yl)-2H-tetrazole (504 mg, 1.50 mmol) obtained in Example (95-2) in methanol (5 ml), and the mixture was stirred at 50° C. for 2 hours. After a saturated aqueous sodium hydrogencarbonate solution was added to the reaction mixture and the mixture was extracted with ethyl acetate, the organic layer was washed with a saturated aqueous NaCl solution and dried with anhydrous sodium sulfate. The solvent was removed under reduced pressure to give a crude mixture of 1-allyl-5-(4'-hydroxy-1,1'-biphenyl-4-yl)-1H-tetrazole and 2-allyl-5-(4'-hydroxy-1,1'-biphenyl-4-yl)-2H-tetrazole (463 mg).
According to a method similar to Example (40-2) and Example (33-5), from a crude mixture (463 mg, 1.50 mmol) obtained in the above and tert-butyl 6-(bromomethyl)-2-[(tert-butoxycarbonyl)oxy]-3-(trifluoromethyl)benzoate (900 mg, 1.80 mmol) obtained in Example (28-5), a mixture of tert-butyl 6-({[4'-(1-allyl-1H-tetrazol-5-yl)-1,1'-biphenyl-4-yl]oxy}methyl)-2-hydroxy-3-(trifluoromethyl)benzoate and tert-butyl 6-({[4'-(2-allyl-2H-tetrazol-5-yl)-1,1'-biphenyl-4-yl]oxy}methyl)-2-hydroxy-3-(trifluoromethyl)benzoate was obtained (712 mg, three-step total yield: 86%).
$^1$H-NMR (400 MHz, CDCl$_3$): δ 12.28-12.24 (1H, s), 8.22-8.18 (2H, m), 7.80-7.65 (3H, m), 7.63-7.59 (2H, m), 7.32-7.27 (1H, m), 7.05-7.00 (2H, m), 6.25-6.20 (1H, m), 5.46-5.38 (4H, m), 5.29-5.26 (2H, m), 1.66 (9H, s).
(95-4)
Tetrakis(triphenylphosphine)palladium (0) (74 mg, 64.4 μmol), acetic acid (0.4 ml, 6.44 mmol) and phenylsilane (0.397 ml, 3.22 mmol) were added to a solution of the mixture (712 mg, 1.29 mmol) obtained in Example (95-3) in methylene chloride (6 ml) under a nitrogen atmosphere, and the mixture was stirred at room temperature for 3 hours. The formed solid was filtered and washed with methylene chloride to give the title compound (469 mg, yield: 71%).
$^1$H-NMR (400 MHz, DMSO-d$_6$): δ 11.45 (1H, s), 8.10 (2H, d, J=7.8 Hz), 7.89 (2H, d, J=8.3 Hz), 7.82 (1H, d, J=8.8 Hz), 7.76 (2H, d, J=8.3 Hz), 7.31 (1H, d, J=7.8 Hz), 7.12 (2H, d, J=8.8 Hz), 5.40 (2H, s), 1.57 (9H, s).

Example 96

[5-(4-([2-(tert-Butoxycarbonyl)-3-hydroxy-4-(trifluoromethyl)benzyl]oxy)phenyl)-4-methyl-2-thienyl]acetic acid (Exemplification Compound No.: 2-232)

(96-1)
Phosphoryl chloride (5.3 ml, 0.57 mmol) was added dropwise to N,N-dimethylformamide (8.8 ml, 0.11 mmol) under ice-cooling, and the mixture was stirred at room temperature for 30 minutes. 2-Bromo-3-methylthiophene (5.00 g, 28.2 mmol) was added dropwise thereto under ice-cooling and the mixture was stirred at 50° C. for 6 hours. The reaction mixture was neutralized with a 2N aqueous sodium hydroxide solution under ice-cooling. The reaction mixture was extracted with diethyl ether and the organic layer was dried with anhydrous sodium sulfate. The residue obtained by removing the solvent under reduced pressure was purified by silica gel column chromatography (eluting solvent: n-hexane/ethyl acetate=5/1) to give 5-bromo-4-methyl-2-thiophenecarbaldehyde (1.41 g, yield: 24%).
$^1$H-NMR (400 MHz, CDCl$_3$): δ 9.74 (1H, s), 7.44 (1H, s), 2.25 (3H, s).
(96-2)
According to a method similar to Example (6-6), Example (26-5) and Example (11-1), from 5-bromo-4-methyl-2-thiophenecarbaldehyde (1.41 g, 6.88 mmol) obtained in Example (96-1), (5-bromo-4-methyl-2-thienyl)acetonitrile was obtained (0.19 g, three-step total yield: 13%).
In the present step, acetone was used instead of ethanol in the cyanation step corresponding to Example (11-1).

¹H-NMR (400 MHz, CDCl₃): δ 6.76 (1H, s), 3.79 (2H, s), 2.16 (3H, s).

(96-3)

According to a method similar to Example (28-6), from (5-bromo-4-methyl-2-thienyl)acetonitrile (280 mg, 1.3 mmol) obtained in Example (96-2), [5-(4-hydroxyphenyl)-4-methyl-2-thienyl]acetonitrile was obtained (131 mg, yield: 44%).

¹H-NMR (400 MHz, CDCl₃): δ 7.30 (2H, d, J=8.6 Hz), 6.88 (2H, d, J=8.6 Hz), 6.87 (1H, s), 4.99 (1H, s), 3.86 (2H, s), 2.24 (3H, s).

(96-4)

According to a method similar to Example (84-2), from [5-(4-hydroxyphenyl)-4-methyl-2-thienyl]acetonitrile (131 mg, 0.57 mmol) obtained in Example (96-3), methyl [5-(4-hydroxyphenyl)-4-methyl-2-thienyl]acetate was obtained (133 mg, yield: 87%).

¹H-NMR (400 MHz, CDCl₃): δ 7.29 (2H, d, J=8.2 Hz), 6.85 (2H, d, J=8.2 Hz), 6.74 (1H, s), 5.18 (1H, s), 3.78 (2H, s), 3.75 (3H, s), 2.22 (3H, s).

(96-5)

According to a method similar to Example (2-3), Example (33-5) and Example (17-4), from methyl [5-(4-hydroxyphenyl)-4-methyl-2-thienyl]acetate (133 mg, 0.51 mmol) obtained in Example (96-4) and tert-butyl 6-(bromomethyl)-2-[(tert-butoxycarbonyl)oxy]-3-(trifluoromethyl)benzoate (254 mg, 0.56 mmol) obtained in Example (28-5), the title compound was obtained as a pale yellow crystal (35 mg, three-step total yield: 13%).

¹H-NMR (400 MHz, CDCl₃): δ 12.26 (1H, s), 7.71 (1H, d, J=8.2 Hz), 7.37 (2H, d, J=9.0 Hz), 7.27 (1H, d, J=8.2 Hz), 6.94 (2H, d, J=9.0 Hz), 6.78 (1H, s), 5.36 (2H, s), 3.83 (2H, s), 2.25 (3H, s), 1.64 (9H, s).

ESI (ES−) (m/z): 521 ([M−H]⁺).

Example 97

2-(4'-{[2-(tert-Butoxycarbonyl)-3-hydroxy-4-(trifluoromethyl)benzyl]oxy}-3-chloro-1,1'-biphenyl-4-yl)propanoic acid (Exemplification Compound No.: 2-65)

(97-1)

tetra-n-Butylammonium hydrogensulfate (21 mg, 0.062 mmol), a 2N aqueous sodium hydroxide solution (0.06 ml, 0.12 mmol) and methyl iodide (10 μl, 0.16 mmol) were added to a solution of tert-butyl 2-(allyloxy)-6-{[(4'-{[(allyloxy)carbonyl]methyl}-3'-chloro-1,1'-biphenyl-4-yl)oxy]methyl}-3-(trifluoromethyl)benzoate (19 mg, 0.03 mmol) obtained in Example (18-3) in dichloromethane (0.4 ml), and the mixture was stirred at room temperature for 1.5 hours. A 2N aqueous sodium hydroxide solution (0.03 ml, 0.06 mmol) and methyl iodide (7 μl, 0.11 mmol) were added to the reaction mixture and the mixture was further stirred for 1 hour. The residue obtained by removing the solvent under reduced pressure was purified by silica gel preparative thin layer chromatography (developing solvent: hexane/ethyl acetate=5/1) to give tert-butyl 2-(allyloxy)-6-{[(4'-{1-[(allyloxy)carbonyl]ethyl}-3'-chloro-1,1'-biphenyl-4-yl)oxy]methyl}-3-(trifluoromethyl)benzoate (8 mg, yield: 42%).

¹H-NMR (500 MHz, CDCl₃): δ 7.64 (1H, d, J=8.0 Hz), 7.56 (1H, d, J=2.0 Hz), 7.49 (2H, d, J=8.5 Hz), 7.42 (1H, dd, J=8.0, 2.0 Hz), 7.39 (1H, d, J=8.0 Hz), 7.36 (1H, d, J=8.0 Hz), 7.00 (2H, d, J=8.5 Hz), 6.11-6.03 (1H, m), 5.92-5.84 (1H, m), 5.43 (1H, dd, J=17.0, 1.5 Hz), 5.29-5.18 (3H, m), 5.16 (2H, s), 4.61 (2H, dd, J=5.5, 1.5 Hz), 4.58 (2H, d, J=5.5 Hz), 4.27 (1H, q, J=7.0 Hz), 1.58 (9H, s), 1.54 (3H, d, J=7.0 Hz).

(97-2)

According to a method similar to Example (11-7), from tert-butyl 2-(allyloxy)-6-([(4'-{1-[(allyloxy)carbonyl]ethyl)-3'-chloro-1,1'-biphenyl-4-yl)oxy]methyl}-3-(trifluoromethyl)benzoate obtained in Example (97-1), the title compound was obtained as a colorless solid.

¹H-NMR (400 MHz, CD₃OD): δ 7.76 (1H, d, J=8.0 Hz), 7.61 (1H, d, J=1.2 Hz), 7.59 (2H, d, J=8.4 Hz), 7.53-7.50 (1H, m), 7.43 (1H, d, J=8.0 Hz), 7.32 (1H, d, J=8.0 Hz), 7.06 (2H, d, J=8.4 Hz), 5.42 (2H, s), 4.18 (1H, q, J=7.2 Hz), 1.64 (9H, s), 1.48 (3H, d, J=7.2 Hz).

MS (ESI) (m/z): 549 ([M−H]⁺).

Example 98

2-(4'-{[2-(tert-Butoxycarbonyl)-3-hydroxy-4-(trifluoromethyl)benzyl]oxy}-2-methyl-1,1'-biphenyl-3-yl)propanoic acid (Exemplification Compound No.: 2-233)

(98-1)

According to a method similar to Example (26-4), from methyl (4'-methoxy-2-methyl-1,1'-biphenyl-3-yl)acetate (780 mg, 2.88 mmol) obtained in Example (33-2), allyl (4'-hydroxy-2-methyl-1,1'-biphenyl-3-yl)acetate was obtained as a brown oil (830 mg, yield: 86%).

In the present step, allyl alcohol was used instead of methanol in the reaction of esterification.

¹H-NMR (400 MHz, CDCl₃): δ 7.19-7.12 (3H, m), 7.16 (2H, d, J=8.6 Hz), 6.86 (2H, d, J=8.6 Hz), 5.96-5.87 (1H, m), 5.31-5.21 (2H, m), 4.81 (1H, s), 4.62 (2H, d, J=5.9 Hz), 3.74 (2H, s), 2.18 (3H, s).

(98-2)

tert-Butyl(dimethyl)silyl chloride (370 mg, 2.48 mmol) was added to a solution of allyl (4'-hydroxy-2-methyl-1,1'-biphenyl-3-yl)acetate (830 mg, 2.48 mmol) obtained in Example (98-1) and imidazole (170 mg, 2.48 mmol) in N,N-dimethylformamide (12 ml), and the mixture was stirred at room temperature for 1 hour. After the reaction mixture was diluted with ethyl acetate and successively washed with water and a saturated aqueous NaCl solution, it was dried with anhydrous sodium sulfate. The residue obtained by removing the solvent under reduced pressure was purified by silica gel column chromatography (eluting solvent: n-hexane/ethyl acetate=95/5-90/10) to give allyl (4'-{[tert-butyl(dimethyl)silyl]oxy}-2-methyl-1,1'-biphenyl-3-yl)acetate (675 mg, yield: 69%).

¹H-NMR (400 MHz, CDCl₃): δ 7.19-7.12 (3H, m), 7.13 (2H, d, J=8.6 Hz), 6.86 (2H, d, J=8.6 Hz), 5.96-5.86 (1H, m), 5.30-5.20 (2H, m), 4.62 (2H, d, J=5.9 Hz), 3.73 (2H, s), 2.18 (3H, s), 1.01 (9H, s), 0.24 (6H, s).

(98-3)

A bis(trimethylsilyl)amide lithium-11.0M tetrahydrofuran solution (2.47 ml, 2.47 mmol) was added dropwise to a solution of allyl (4'-{[tert-butyl(dimethyl)silyl]oxy}-2-methyl-1,1'-biphenyl-3-yl)acetate (675 mg, 1.70 mmol) obtained in Example (98-2) in tetrahydrofuran (6 ml) at −78° C. After the mixture was stirred for 30 minutes, methyl iodide (512 μl, 8.22 mmol) was added thereto and the mixture was stirred at −78° C. for 1 hour. Water was added to the reaction mixture and the mixture was extracted with ethyl acetate. The organic layer was washed with a saturated aqueous NaCl solution and dried with anhydrous sodium sulfate. The residue obtained by removing the solvent under reduced pressure was dissolved in tetrahydrofuran (5 ml). A tetra-n-butylammonium fluoride-1.0M tetrahydrofuran solution (2.04 ml, 2.04 mmol was added to the solution and the mixture was stirred at room temperature overnight. The reaction mixture was poured into water and extracted with ethyl acetate. The organic layer was washed with a saturated aqueous NaCl solution and dried with anhydrous sodium sulfate. The residue obtained by removing the solvent under reduced pressure was purified by silica gel preparative thin layer chromatography (developing solvent: n-hexane/ethyl acetate=3/1) to give allyl 2-(4'-hydroxy-2-methyl-1,1'-biphenyl-3-yl)propanoate (457 mg, yield: 91%).

$^1$H-NMR (400 MHz, CDCl$_3$): δ 7.27 (1H, dd, J=7.4, 1.6 Hz), 7.20 (1H, t, J=7.4 Hz), 7.16 (2H, d, J=8.6 Hz), 7.11 (1H, dd, J=7.4, 1.6 Hz), 6.87 (2H, d, J=8.6 Hz), 5.93-5.83 (1H, m), 5.25-5.16 (2H, m), 4.84 (1H, s), 4.65-4.55 (2H, m), 4.08 (1H, q, J=7.4 Hz), 2.24 (3H, s), 1.53 (3H, d, J=7.4 Hz).

(98-4)

According to a method similar to Example (40-2), Example (33-5) and Example (17-4), from allyl 2-(4'-hydroxy-2-methyl-1,1'-biphenyl-3-yl)propanoate (150 mg, 0.506 mmol) obtained in Example (98-3), the title compound was obtained as a white powder (107 mg, three-step total yield: 40%).

$^1$H-NMR (400 MHz, CDCl$_3$): δ 12.27 (1H, s), 7.72 (1H, d, J=8.2 Hz), 7.31 (1H, d, J=8.2 Hz), 7.31 (1H, d, J=7.8 Hz), 7.24 (1H, t, J=7.8 Hz), 7.23 (2H, d, J=8.6 Hz), 7.14 (1H, d, J=7.8 Hz), 6.96 (2H, d, J=8.6 Hz), 5.38 (2H, s), 4.10 (1H, q, J=7.0 Hz), 2.26 (3H, s), 1.65 (9H, s), 1.55 (3H, d, J=7.0 Hz).

MS (FAB) (m/z): 530 ([M]$^+$).

Example 99

2-(4'-{[2-(tert-Butoxycarbonyl)-3-hydroxy-4-(trifluoromethyl)benzyl]oxy}-2-ethyl-1,1'-biphenyl-3-yl) propanoic acid (Exemplification Compound No.: 2-234)

(99-1)

According to a method similar to Example (98-2) and Example (98-3), from allyl (2-ethyl-4'-hydroxy-1,1'-biphenyl-3-yl)acetate (400 mg, 1.35 mmol) obtained in Example (90-6), allyl 2-(2-ethyl-4'-hydroxy-1,1'-biphenyl-3-yl)propanoate was obtained as a pale yellow powder (434 mg, two-step total yield: 100%).

$^1$H-NMR (400 MHz, CDCl$_3$): δ 7.31 (1H, dd, J=7.8, 1.2 Hz), 7.18 (1H, t, J=7.8 Hz), 7.16 (2H, d, J=8.6 Hz), 7.05 (1H, dd, J=7.8, 1.2 Hz), 6.86 (2H, d, J=8.6 Hz), 5.92-5.82 (1H, m), 5.24-5.15 (2H, m), 4.80 (1H, s), 4.65-4.52 (2H, m), 4.09 (1H, q, J=7.0 Hz), 2.75-2.65 (1H, m), 2.62-2.53 (1H, m), 1.53 (3H, d, J=7.0 Hz), 1.05 (3H, t, J=7.4 Hz).

(99-2)

According to a method similar to Example (40-2), Example (33-5) and Example (17-4), from allyl 2-(2-ethyl-4'-hydroxy-1,1'-biphenyl-3-yl)propanoate (150 mg, 0.48 mmol) obtained in Example (99-1), the title compound was obtained as a pale brown powder (97 mg, three-step total yield: 43%).

$^1$H-NMR (400 MHz, CDCl$_3$): δ 12.27 (1H, s), 7.73 (1H, d, J=8.2 Hz), 7.34 (1H, dd, J=7.8, 1.2 Hz), 7.31 (1H, d, J=8.2 Hz), 7.23 (2H, d, J=8.6 Hz), 7.21 (1H, t, J=7.8 Hz), 7.08 (1H, dd, J=7.8, 1.2 Hz), 6.95 (2H, d, J=8.6 Hz), 5.38 (2H, s), 4.10 (1H, q, J=7.0 Hz), 2.75-2.66 (1H, m), 2.63-2.54 (1H, m), 1.54 (3H, d, J=7.0 Hz), 1.06 (3H, t, J=7.4 Hz).

MS (FAB) (m/z): 544 ([M]$^+$).

Example 100

2-(4'-{[2-(tert-Butoxycarbonyl)-3-hydroxy-4-(trifluoromethyl)benzyl]oxy}-3-fluoro-1,1'-biphenyl-4-yl)propanoic acid (Exemplification Compound No.: 2-64)

According to a method similar to Example (97-1) and Example (11-7), from tert-butyl 2-(allyloxy)-6-{[(4'-{[(allyloxy)carbonyl]methyl}-3'-fluoro-1,1'-biphenyl-4-yl)oxy]methyl}-3-(trifluoromethyl)benzoate obtained in Example (11-6), the title compound was obtained as a colorless solid.

$^1$H-NMR (500 MHz, CDCl$_3$): δ 12.26 (1H, s), 7.71 (1H, d, J=8.5 Hz), 7.51 (2H, d, J=8.5 Hz), 7.38-7.22 (4H, m), 6.98 (2H, d, J=8.5 Hz), 5.38 (2H, s), 4.10 (1H, q, J=7.0 Hz), 1.65 (9H, s), 1.57 (3H, d, J=7.0 Hz).

MS (ESI) (m/z): 533 ([M−H]$^+$).

Example 101

2-(4'-{[2-(tert-Butoxycarbonyl)-3-hydroxy-4-(trifluoromethyl)benzyl]oxy}-2-nitro-1,1'-biphenyl-4-yl) propanoic acid (Exemplification Compound No.: 2-235)

(101-1)

Potassium carbonate (147 mg, 1.06 mmol) was added to a solution of methyl (4'-hydroxy-2-nitro-1,1'-biphenyl-4-yl) acetate (203 mg, 0.71 mmol) obtained in Example (37-1) and tert-butyl 6-(bromomethyl)-2-[(tert-butoxycarbonyl)oxy]-3-(trifluoromethyl)benzoate (330 mg, 0.781 mmol) obtained in Example (28-5) in acetone (15 ml), and the mixture was stirred at 70° C. for 8 hours. The reaction mixture was poured into water and extracted with ethyl acetate. The organic layer was successively washed with water and a saturated aqueous NaCl solution and dried with anhydrous sodium sulfate. The residue obtained by removing the solvent under reduced pressure was subjected to silica gel column chromatography (eluting solvent: hexane/ethyl acetate=4/1) to give crude tert-butyl 2-[(tert-butoxycarbonyl)oxy]-6-[({4'-[(methoxycarbonyl)methyl]-2'-nitro-1,1'-biphenyl-4-yl}oxy)methyl]-3-(trifluoromethyl)benzoate.

After a lithium diisopropylamide-2.0M heptane/tetrahydrofuran/ethylbenzene solution (192 µl, 0.386 mmol) was added to a solution of the compound in tetrahydrofuran (4 ml) at −78° C., methyl iodide (24 µl, 0.386 mmol was added dropwise thereto and the mixture was stirred for 1 hour. The temperature of the reaction mixture was raised to room temperature and the reaction mixture was poured into water, and the mixture was extracted with ethyl acetate. The organic layer was successively washed with water and a saturated aqueous NaCl solution and dried with anhydrous sodium sulfate. The residue obtained by removing the solvent under reduced pressure was purified by silica gel preparative thin layer chromatography (developing solvent: hexane/ethyl acetate=4/1) to give tert-butyl 2-[(tert-butoxycarbonyl)oxy]-6-[({4'-[1-(methoxycarbonyl)ethyl]-2'-nitro-1,1'-biphenyl-4-yl}oxy)methyl]-3-(trifluoromethyl)benzoate (84 mg, 17%).

$^1$H-NMR (400 MHz, CDCl$_3$): δ 7.76 (1H, d, J=1.6 Hz), 7.72 (1H, d, J=8.2 Hz), 7.59 (1H, d, J=8.2 Hz), 7.53 (1H, dd, J=7.9, 1.6 Hz), 7.37 (1H, d, J=7.9 Hz), 7.23 (2H, d, J=8.6 Hz), 6.97 (2H, d, J=8.6 Hz), 5.25 (2H, s), 3.83 (1H, q, J=7.3 Hz), 3.71 (3H, s), 1.57 (3H, d, J=7.3 Hz), 1.57 (9H, s), 1.54 (9H, s).

(101-2)

According to a method similar to Example (33-5) and Example (17-4), from tert-butyl 2-[(tert-butoxycarbonyl)oxy]-6-[({4'-[1-(methoxycarbonyl)ethyl]-2'-nitro-1,1'-biphenyl-4-yl}oxy)methyl]-3-(trifluoromethyl)benzoate (84 mg, 0.146 mmol) obtained in Example (101-1), the title compound was obtained as a yellow oil (47 mg, 64%).

$^1$H-NMR (500 MHz, CDCl$_3$): δ 12.28 (1H, s), 7.79 (1H, d, J=1.6 Hz), 7.71 (1H, d, J=8.3 Hz), 7.57 (1H, dd, J=7.9, 1.6 Hz), 7.40 (1H, d, J=7.9 Hz), 7.28-7.23 (3H, m), 6.96 (2H, d, J=8.8 Hz), 5.37 (2H, s), 3.87 (1H, q, J=7.3 Hz), 1.64 (9H, s), 1.61 (3H, d, J=7.3 Hz).

MS (FAB) (m/z): 561 ([M]$^+$).

Example 102

2-[4-(5-{[2-(tert-Butoxycarbonyl)-3-hydroxy-4-(trifluoromethyl)benzyl]oxy}-2-pyridinyl)-3-methylphenyl]propanoic acid (Exemplification Compound No.: 2-236)

(102-1)

According to a method similar to Example (104-1), from methyl [3-methyl-4-(4,4,5,5-tetramethyl-1,3,2-dioxaborolan-2-yl)phenyl]acetate (640 mg, 2.21 mmol) obtained in Example (84-3), methyl 2-[3-methyl-4-(4,4,5,5-tetramethyl-1,3,2-dioxaborolan-2-yl)phenyl]propanoate was obtained (223 mg, yield: 33%).

$^1$H-NMR (400 MHz, CDCl$_3$): δ 7.73 (1H, d, J=8.2 Hz), 7.11-7.06 (2H, m), 3.68 (1H, q, J=7.0 Hz), 3.64 (3H, s), 2.53 (3H, s), 1.47 (3H, d, J=7.0 Hz), 1.32 (12H, s).

(102-2)

According to a method similar to Example (76-1) and Example (17-4), from methyl 2-[3-methyl-4-(4,4,5,5-tetramethyl-1,3,2-dioxaborolan-2-yl)phenyl]propanoate (223 mg, 0.73 mmol) obtained in Example (102-1), the title compound was obtained as an amorphous compound (63 mg, two-step total yield: 17%).

In the present step, tert-butyl 6-{[(6-chloro-3-pyridinyl)oxy]methyl}-2-hydroxy-3-(trifluoromethyl)benzoate obtained in Example (84-1) was used as a halogenated compound in the Suzuki coupling step corresponding to Example (76-1).

$^1$H-NMR (400 MHz, CDCl$_3$): δ 12.30 (1H, s), 8.50 (1H, d, J=2.7 Hz), 7.75 (1H, d, J=8.2 Hz), 7.38-7.27 (4H, m), 7.17-7.13 (2H, m), 5.45 (2H, s), 3.70 (1H, q, J=7.0 Hz), 2.29 (3H, s), 1.67 (9H, s), 1.51 (3H, d, J=7.0 Hz).

ESI (ES−) (m/z): 530 ([M−H]$^+$).

Example 103

2-(4'-{[2-(tert-Butoxycarbonyl)-3-hydroxy-4-(trifluoromethyl)benzyl]oxy}-3-ethyl-1,1'-biphenyl-4-yl)propanoic acid (Exemplification Compound No.: 2-237)

(103-1)

According to a method similar to Example (98-2) and Example (104-1), from methyl (3-ethyl-4'-hydroxy-1,1'-biphenyl-4-yl)acetate (100 mg, 0.370 mmol) obtained in Example (85-4), methyl 2-(4'-{[tert-butyl(dimethyl)silyl]oxy}-3-ethyl-1,1'-biphenyl-4-yl)propionate was obtained (104 mg, two-step total yield: 71%).

$^1$H-NMR (400 MHz, CDCl$_3$): δ 7.46-7.42 (2H, m), 7.38-7.35 (2H, m), 7.33-7.30 (1H, m), 6.90-6.86 (2H, m), 4.01 (1H, q, J=7.0 Hz), 3.67 (3H, s), 2.84-2.70 (2H, m), 1.50 (3H, d, J=7.0 Hz), 1.28 (3H, t, J=7.8 Hz), 1.00 (9H, s), 0.22 (6H, s).

(103-2)

A tetra-n-butylammonium fluoride-1.0M tetrahydrofuran solution (0.39 ml, 0.391 mmol) was added to a solution of methyl 2-(4'-{[tert-butyl(dimethyl)silyl]oxy}-3-ethyl-1,1'-biphenyl-4-yl)propionate (104 mg, 283 mmol) obtained in Example (103-1) in tetrahydrofuran (5 ml), and the mixture was stirred at room temperature for 1.5 hours. After water was added to the reaction mixture and the mixture was extracted with ethyl acetate, the organic layer was washed with a saturated aqueous NaCl solution and dried with anhydrous sodium sulfate. The residue obtained by removing the solvent under reduced pressure was purified by silica gel column chromatography (developing solvent: hexane/ethyl acetate=3/1) to give methyl 2-(3-ethyl-4'-hydroxy-1,1'-biphenyl-4-yl)propionate (76 mg, 1009).

$^1$H-NMR (400 MHz, CDCl$_3$): δ 7.49-7.42 (2H, m), 7.37-7.33 (1H, m), 7.33-7.29 (1H, m), 7.26-7.21 (1H, m), 6.91-6.86 (2H, m), 4.78 (1H, br s), 4.01 (1H, q, J=7.0 Hz), 3.67 (3H, s), 2.82-2.69 (2H, m), 1.50 (3H, d, J=7.0 Hz), 1.26 (3H, t, J=7.8 Hz).

(103-3)

According to a method similar to Example (40-2), Example (33-5) and Example (17-4), from methyl 2-(3-ethyl-4'-hydroxy-1,1'-biphenyl-4-yl)propionate (76 mg, 0.269 mmol) obtained in Example (103-2), the title compound was obtained (57.5 mg, three-step total yield: 39%).

In the present step, the step corresponding to Example (17-4) was carried out at the reaction temperature of 40° C.

$^1$H-NMR (400 MHz, DMSO-d$_6$): δ 12.2 (1H, s), 7.79 (1H, d, J=8.0 Hz), 7.56-7.50 (2H, m), 7.41-7.35 (2H, m), 7.30-7.25 (2H, m), 7.07-7.03 (2H, m), 5.35 (2H, s), 3.90 (1H, q, J=7.1 Hz), 2.79-2.65 (2H, m), 1.56 (9H, s), 1.36 (3H, d, J=7.1 Hz), 1.21 (3H, t, J=7.5 Hz).

Example 104

2-(4'-{[2-(tert-Butoxycarbonyl)-3-hydroxy-4-(trifluoromethyl)benzyl]oxy}-2,5-dimethyl-1,1'-biphenyl-4-yl)propanoic acid (Exemplification Compound No.: 2-238)

(104-1)

After a lithium bis(trimethylsilyl)amide 1.0M-tetrahydrofuran solution (3.86 ml, 3.86 mmol) was added to a solution of methyl (4'-methoxy-2,5-dimethyl-1,1'-biphenyl-4-yl)acetate (730 mg, 2.57 mmol) obtained in Example (105-1) in tetrahydrofuran (6 ml) at −78° C., methyl iodide (800 μl, 12.9 mmol) was added dropwise thereto and the mixture was stirred for 1 hour. A saturated aqueous ammonium chloride solution was poured into the reaction mixture and the mixture was extracted with ethyl acetate (twice). The organic layer was successively washed with water and a saturated aqueous NaCl solution and dried with anhydrous sodium sulfate. The residue obtained by removing the solvent under reduced pressure was purified by silica gel column chromatography (eluting solvent: hexane/ethyl acetate=95/5-15/1) to give methyl 2-(4'-methoxy-2,5-dimethyl-1,1'-biphenyl-4-yl)propanoate as a colorless oil (620 mg, 81%).

$^1$H-NMR (400 MHz, CDCl$_3$): δ 7.24 (2H, d, J=8.6 Hz), 7.12 (1H, s), 7.02 (1H, s), 6.94 (2H, d, J=8.6 Hz), 3.95 (1H, q, J=7.0 Hz), 3.85 (3H, s), 3.69 (3H, s), 2.34 (3H, s), 2.23 (3H, s), 1.50 (3H, d, J=7.0 Hz).

(104-2)

According to a method similar to Example (6-2), from methyl 2-(4'-methoxy-2,5-dimethyl-1,1'-biphenyl-4-yl)propanoate (617 mg, 2.07 mmol) obtained in Example (104-1), methyl 2-(4'-hydroxy-2,5-dimethyl-1,1'-biphenyl-4-yl)propanoate was obtained (400 mg, yield: 68%).

¹H-NMR (400 MHz, CDCl₃): δ 7.20-7.10 (3H, m), 7.00 (1H, s), 6.84 (2H, d, J=7.8 Hz), 3.97 (1H, q, J=7.0 Hz), 3.70 (3H, s), 2.33 (3H, s), 2.20 (3H, s), 1.51 (3H, d, J=7.0 Hz).

(104-3)

According to a method similar to Example (40-2), Example (33-5) and Example (17-4), from methyl 2-(4'-hydroxy-2,5-dimethyl-1,1'-biphenyl-4-yl)propanoate (400 mg, 1.40 mmol) obtained in Example (104-2), the title compound was obtained as a colorless powder (308 mg, yield: 40%).

¹H-NMR (400 MHz, CDCl₃): δ 12.27 (1H, s), 7.71 (1H, d, J=8.4 Hz), 7.29 (1H, d, J=8.4 Hz), 7.25 (2H, d, J=8.8 Hz), 7.17 (1H, s), 7.03 (1H, s), 6.94 (2H, d, J=8.8 Hz), 5.37 (2H, s), 3.99 (1H, q, J=7.0 Hz), 2.36 (3H, s), 2.24 (3H, s), 1.65 (9H, s), 1.53 (3H, d, J=7.0 Hz).

MS (ESI) (m/z): 543 ([M−H]⁺).

Example 105

(4'-{[2-(tert-Butoxycarbonyl)-3-hydroxy-4-(trifluoromethyl)benzyl]oxy}-2,5-dimethyl-1,1'-biphenyl-4-yl)acetic acid (Exemplification Compound No.: 2-239)

(105-1)

According to a method similar to Example (26-4), Example (22-5) and Example (26-3), from (4-hydroxy-2,5-dimethylphenyl)acetonitrile (1.52 g, 8.68 mmol), methyl (4'-methoxy-2,5-dimethyl-1,1'-biphenyl-4-yl)acetate was obtained (1.79 g, three-step total yield: 73%).

¹H-NMR (400 MHz, CDCl₃): δ 7.24 (2H, d, J=8.6 Hz), 7.08 (1H, s), 7.04 (1H, s), 6.94 (2H, d, J=8.6 Hz), 3.85 (3H, s), 3.72 (3H, s), 3.64 (2H, s), 2.29 (3H, s), 2.23 (3H, s).

(105-2)

According to a method similar to Example (26-4), from methyl (4'-methoxy-2,5-dimethyl-1,1'-biphenyl-4-yl)acetate (652 mg, 2.29 mmol) obtained in Example (105-1), methyl (4'-hydroxy-2,5-dimethyl-1,1'-biphenyl-4-yl)acetate was obtained (556 mg, yield: 90%).

¹H-NMR (400 MHz, CDCl₃): δ 7.17 (2H, d, J=8.6 Hz), 7.08 (1H, s), 7.03 (1H, s), 6.84 (2H, d, J=8.6 Hz), 5.05 (1H, br s), 3.73 (3H, s), 3.65 (2H, s), 2.29 (3H, s), 2.21 (3H, s).

(105-3)

According to a method similar to Example (40-2), Example (33-5) and Example (17-4), from methyl (4'-hydroxy-2,5-dimethyl-1,1'-biphenyl-4-yl)acetate (320 mg, 1.18 mmol) obtained in Example (105-2), the title compound was obtained as a colorless powder (370 mg, yield: 59%).

¹H-NMR (400 MHz, CDCl₃): δ 12.27 (1H, s), 7.70 (1H, d, J=8.2 Hz), 7.29 (1H, d, J=8.2 Hz), 7.25 (2H, d, J=8.6 Hz), 7.09 (1H, s), 7.05 (1H, s), 6.94 (2H, d, J=8.6 Hz), 5.37 (2H, s), 3.67 (2H, s), 2.31 (3H, s), 2.23 (3H, s), 1.65 (9H, s).

MS (ESI) (m/z): 529 ([M−H]⁺).

Example 106

2-(4'-{[2-(tert-Butoxycarbonyl)-3-hydroxy-4-(trifluoromethyl)benzyl]oxy}-2-chloro-1,1'-biphenyl-4-yl)propanoic acid (Exemplification Compound No.: 2-62)

Diisopropylethylamine (936 μl, 5.37 mmol) and chloromethyl methyl ether (303 μl, 4.02 mmol) were successively added to a solution of methyl (2-chloro-4'-hydroxy-1,1'-biphenyl-4-yl)acetate (650 mg, 2.68 mmol) obtained in Example (23-3) in methylene chloride (10 ml) under ice-cooling, and the mixture was stirred for 3 hours. After the reaction mixture was poured into water and the mixture was extracted with ethyl acetate, the organic layer was successively washed with water and a saturated aqueous NaCl solution and dried with anhydrous sodium sulfate. The solvent was removed under reduced pressure to give crude methyl [2-chloro-4'-(methoxymethoxy)-1,1'-biphenyl-4-yl]acetate. According to a method similar to Example (104-1), Example (12-4), Example (40-2), Example (33-5) and Example (17-4), from the compound obtained in the above, the title compound was obtained as a colorless powder (260 mg, six-step total yield: 18%).

¹H-NMR (400 MHz, CDCl₃): δ 12.27 (1H, s), 7.71 (1H, d, J=8.4 Hz), 7.43 (1H, d, J=1.6 Hz), 7.37 (2H, d, J=8.6 Hz), 7.32-7.23 (3H, m), 6.96 (2H, d, J=8.6 Hz), 5.38 (2H, s), 3.76 (1H, q, J=7.0 Hz), 1.65 (9H, s), 1.56 (3H, d, J=7.0 Hz).

MS (ESI) (m/z): 549 ([M−H]⁺).

Example 107

2-(4'-{[2-(tert-Butoxycarbonyl)-3-hydroxy-4-(trifluoromethyl)benzyl]oxy}-2-methyl-1,1'-biphenyl-4-yl)propanoic acid (Exemplification Compound No.: 2-61)

(107-1)

According to a method similar to Example (104-1) and Example (76-1), from methyl (4-bromo-3-methylphenyl)acetate (0.64 g, 2.63 mmol) obtained in Example (84-2), methyl 2-(4'-hydroxy-2-methyl-1,1'-biphenyl-4-yl)propanoate was obtained (337 mg, two-step total yield: 53%).

In the present step, tert-butyl 2-{[4-(4,4,5,5-tetramethyl-1,3,2-dioxaborolan-2-yl)phenoxy]methyl}-5-(trifluoromethyl)benzoate was used instead of 4-methoxyphenylboronic acid in the Suzuki coupling step corresponding to Example (76-1).

¹H-NMR (400 MHz, CDCl₃): δ 7.20-7.14 (5H, m), 6.86 (2H, d, J=8.6 Hz), 4.93 (1H, s), 3.74 (1H, q, J=7.0 Hz), 3.70 (3H, s), 2.26 (3H, s), 1.53 (3H, d, J=7.0 Hz).

(107-2)

According to a method similar to Example (2-3), Example (33-5) and Example (17-4), from methyl 2-(4'-hydroxy-2-methyl-1,1'-biphenyl-4-yl)propanoate (224 mg, 0.83 mmol) obtained in Example (107-1) and tert-butyl 6-(bromomethyl)-2-[(tert-butoxycarbonyl)oxy]-3-(trifluoromethyl)benzoate (415 mg, 0.91 mmol) obtained in Example (28-5), the title compound was obtained as a colorless powder (235 mg, three-step total yield: 53%).

¹H-NMR (400 MHz, DMSO-d₆): δ 12.29 (1H, s), 11.45 (1H, s), 7.83 (1H, d, J=8.2 Hz), 7.31 (1H, d, J=8.2 Hz), 7.28 (2H, d, J=8.6 Hz), 7.20-7.12 (3H, m), 7.04 (2H, d, J=8.6 Hz), 5.37 (2H, s), 3.66 (1H, q, J=7.0 Hz), 2.21 (3H, s), 1.56 (9H, s), 1.38 (3H, d, J=7.0 Hz).

ESI (ES−) (m/z): 529 ([M−H]⁺).

Example 108

2-[4'-{[2-(tert-Butoxycarbonyl)-3-hydroxy-4-(trifluoromethyl)benzyl)]oxy}-2-(trifluoromethyl)-1,1'-biphenyl-4-yl]propanoic acid (Exemplification Compound No.: 2-241)

According to a method similar to Example (97-1) and Example (11-7), from tert-butyl 2-(allyloxy)-6-({[4'-{[(allyloxy)carbonyl]methyl}-2'-(trifluoromethyl)-1,1'-biphenyl-4-yl]oxy}methyl)-3-(trifluoromethyl)benzoate (75 mg, 0.12 mmol), crude tert-butyl 2-hydroxy-6-[({4'-[1-(methoxycarbonyl)ethyl]-2'-(trifluoromethyl)-1,1'-biphenyl-4-yl}oxy) methyl]-3-(trifluoromethyl)benzoate was obtained. According to a method similar to Example (17-4), from the compound obtained in the above, the title compound was obtained as a colorless solid (6.7 mg, three-step total yield: 10%).

$^1$H-NMR (400 MHz, CD$_3$OD): δ 7.77 (1H, d, J=8.0 Hz), 7.70 (1H, s), 7.58 (1H, d, J=8.0 Hz), 7.33 (1H, d, J=8.0 Hz), 7.32 (1H, d, J=8.0 Hz), 7.26 (2H, d, J=8.8 Hz), 7.02 (2H, d, J=8.8 Hz), 5.41 (2H, s), 3.86 (1H, q, J=6.8 Hz), 1.62 (9H, s), 1.52 (3H, d, J=6.8 Hz).

MS (ESI) (m/z): 583 ([M−H]$^+$).

Example 109

2-(4'-{[2-(tert-Butoxycarbonyl)-3-hydroxy-4-(trifluoromethyl)benzyl]oxy}-2-isopropyl-1,1'-biphenyl-4-yl)propanoic acid (Exemplification Compound No.: 2-242)

(109-1)

According to a method similar to Example (42-1), from 3-bromo-4-methoxybenzylcyanide (8.7 g, 38.5 mmol) and an isopropenylmagnesium bromide-0.5M tetrahydrofuran solution (100 ml, 50 mmol), (3-isopropenyl-4-methoxyphenyl)acetonitrile was obtained (4.42 g, yield: 61%).

$^1$H-NMR (400 MHz, CDCl$_3$): δ 7.20 (1H, dd, J=8.6, 2.3 Hz), 7.12 (1H, d, J=2.3 Hz), 6.86 (1H, d, J=8.6 Hz), 5.18-5.16 (1H, m), 5.06-5.04 (1H, m), 3.84 (3H, s), 3.68 (2H, s), 2.10 (3H, t, J=1.2 Hz).

(109-2)

(3-Isopropenyl-4-methoxyphenyl)acetonitrile (4.42 g, 23.61 mmol) obtained in Example (109-1) was dissolved in ethanol (50 ml) and 10% palladium-carbon (1 g) was added thereto, and the mixture was stirred at room temperature under a hydrogen atmosphere for 30 minutes. The reaction mixture was filtered, and the filtrate was concentrated under reduced pressure. The residue obtained was purified by silica gel column chromatography (developing solvent: hexane/ethyl acetate=4/1) to give (3-isopropyl-4-methoxyphenyl)acetonitrile (4.08 g, yield: 91%).

$^1$H-NMR (400 MHz, CDCl$_3$): δ 7.11-7.07 (2H, m), 6.80 (1H, d, J=9.0 Hz), 3.82 (3H, s), 3.67 (2H, s), 3.35-3.24 (1H, m), 1.20 (6H, d, J=6.7 Hz).

(109-3)

According to a method similar to Example (26-4), Example (22-5), Example (76-1), Example (98-2) and Example (98-3), from (3-isopropyl-4-methoxyphenyl)acetonitrile (900 mg, 4.76 mmol) obtained in Example (109-2), methyl 2-(4'-hydroxy-2-isopropyl-1,1'-biphenyl-4-yl)propanoate was obtained (290 mg, five-step total yield: 20%).

In the present step, 4-(4,4,5,5-tetramethyl-1,3,2-dioxaborolan-2-yl)phenol was used instead of 4-methoxyphenylboronic acid in the Suzuki coupling step corresponding to Example (76-1).

$^1$H-NMR (400 MHz, CDCl$_3$): δ 7.26 (1H, s), 7.17-7.09 (4H, m), 6.85 (2H, d, J=8.6 Hz), 4.88 (1H, br), 3.76 (1H, q, J=7.0 Hz), 3.70 (3H, s), 3.12-3.01 (1H, m), 1.54 (3H, d, J=7.0 Hz), 1.15 (3H, d, J=6.6 Hz), 1.14 (3H, d, J=6.6 Hz)

(109-4)

According to a method similar to Example (2-3), Example (33-5) and Example (17-4), from methyl 2-(4'-hydroxy-2-isopropyl-1,1'-biphenyl-4-yl)propanoate (290 mg, 0.97 mmol) obtained in Example (107-1) and tert-butyl 6-(bromomethyl)-2-[(tert-butoxycarbonyl)oxy]-3-(trifluoromethyl)benzoate (487 mg, 1.07 mmol) obtained in Example (28-5), the title compound was obtained as a colorless powder (246 mg, three-step total yield: 45%).

$^1$H-NMR (400 MHz, DMSO-d$_6$): δ 12.30 (1H, s), 11.46 (1H, s), 7.83 (1H, d, J=8.2 Hz), 7.32 (1H, d, J=8.2 Hz), 7.30 (1H, d, J=2.0 Hz), 7.22 (2H, d, J=9.0 Hz), 7.12 (1H, dd, J=7.8, 2.0 Hz), 7.06 (1H, d, J=7.8 Hz), 7.04 (2H, d, J=9.0 Hz), 5.37 (2H, s), 3.70 (1H, q, J=7.0 Hz), 3.02-2.94 (1H, m), 1.56 (9H, s), 1.38 (3H, d, J=7.0 Hz), 1.11 (3H, d, J=6.7 Hz), 1.10 (3H, d, J=6.7 Hz).

ESI (ES−) (m/z): 557 ([M−H]$^+$).

Example 110

2-(4'-{[2-(tert-Butoxycarbonyl)-3-hydroxy-4-(trifluoromethyl)benzyl]oxy}-2,3-difluoro-1,1'-biphenyl-4-yl)propanoic acid (Exemplification Compound No.: 2-243)

According to a method similar to Example (40-2), Example (33-5) and Example (17-4), from methyl 2-(2,3-difluoro-4'-hydroxy-1,1'-biphenyl-4-yl)propanoate (193 mg, 0.661 mmol) and tert-butyl 6-(bromomethyl)-2-[(tert-butoxycarbonyl)oxy]-3-(trifluoromethyl)benzoate (306 mg, 0.726 mmol) obtained in Example (28-5), the title compound was obtained as a white powder (45 mg, yield: 12%).

$^1$H-NMR (500 MHz, CDCl$_3$): δ 12.27 (1H, s), 7.71 (1H, d, J=8.3 Hz), 7.49 (2H, d, J=8.8 Hz), 7.27 (1H, d, J=8.3 Hz), 7.18-7.08 (2H, m), 6.99 (2H, d, J=8.8 Hz), 5.39 (2H, s), 3.78-3.73 (1H, m), 1.65 (9H, s), 1.58 (3H, d, J=7.3 Hz).

MS (ESI) (m/z): 551 ([M−H]$^+$).

Example 111

2-(4'-{[2-(tert-Butoxycarbonyl)-3-hydroxy-4-(trifluoromethyl)benzyl]oxy}-2,3-dimethyl-1,1'-biphenyl-4-yl)propanoic acid (Exemplification Compound No.: 2-244)

According to a method similar to Example (12-5), Example (104-1), Example (13-5) and Example (17-4), title compound was obtained as a colorless oil (8.0 mg, yield: 7%) from (4'-{[2-(tert-butoxycarbonyl)-3-hydroxy-4-(trifluoromethyl)benzyl]oxy}-2,3-dimethyl-1,1'-biphenyl-4-yl)acetic acid (105 mg, 0.198 mmol) obtained in Example (92-4).

$^1$H-NMR (500 MHz, CDCl$_3$): δ 12.27 (1H, s), 7.72 (1H, d, J=8.3 Hz), 7.30 (1H, d, J=8.3 Hz), 7.22 (2H, d, J=8.8 Hz), 7.17 (1H, d, J=7.8 Hz), 7.08 (1H, d, J=7.8 Hz), 6.94 (2H, d, J=8.8 Hz), 5.38 (2H, s), 3.78-3.70 (1H, m), 2.34 (3H, s), 2.19 (3H, s), 1.65 (9H, s), 1.55 (3H, d, J=7.3 Hz).

Example 112

2-(4'-{[2-(tert-Butoxycarbonyl)-3-hydroxy-4-(trifluoromethyl)benzyl]oxy}-2-cyclopropyl-1,1'-biphenyl-4-yl)propanoic acid (Exemplification Compound No.: 2-245)

(112-1)

According to a method similar to Example (84-2), Example (104-1), Example (42-1), Example (6-2), Example (22-5) and Example (76-1), from 3-bromo-4-methoxybenzyl cyanide (2.4 g, 10.62 mmol), methyl 2-(2-cyclopropyl-4'-hydroxy-1,1'-biphenyl-4-yl)propanoate was obtained (135 mg, six-step total yield: 4%).

In the present step, a cyclopropyl magnesium bromide-0.5M tetrahydrofuran solution was used as the Grignard reagent in the step corresponding to Example (42-1). Further, 4-(4,4,5,5-tetramethyl-1,3,2-dioxaborolan-2-yl)phenol was used instead of 4-methoxyphenylboronic acid in the Suzuki coupling step corresponding to Example (76-1).

$^1$H-NMR (400 MHz, CDCl$_3$): δ 7.31 (2H, d, J=8.6 Hz), 7.17 (1H, d, J=7.8 Hz), 7.13 (1H, dd, J=7.8, 2.0 Hz), 6.87 (2H, d, J=8.6 Hz), 6.83 (1H, d, J=2.0 Hz), 4.84 (1H, s), 3.71 (1H, q, J=7.0 Hz), 3.68 (3H, s), 1.93-1.84 (1H, m), 1.51 (3H, d, J=7.0 Hz), 0.86-0.81 (2H, m), 0.71-0.65 (2H, m).

(112-2)

According to a method similar to Example (2-3), Example (33-5) and Example (17-4), from methyl 2-(2-cyclopropyl-4'-hydroxy-1,1'-biphenyl-4-yl)propanoate (135 mg, 0.46 mmol) obtained in Example (112-1) and tert-butyl 6-(bromomethyl)-2-[(tert-butoxycarbonyl)oxy]-3-(trifluoromethyl)benzoate (249 mg, 0.55 mmol) obtained in Example (28-5), the title compound was obtained as a colorless powder (115 mg, three-step total yield: 45%).

$^1$H-NMR (400 MHz, DMSO-d$_6$): δ 12.28 (1H, s), 11.45 (1H, s), 7.83 (1H, d, J=8.2 Hz), 7.36 (2H, d, J=8.6 Hz), 7.31 (1H, d, J=8.2 Hz), 7.14-7.09 (2H, m), 7.05 (2H, d, J=8.6 Hz), 6.86 (1H, s), 5.37 (2H, s), 3.66 (1H, q, J=7.0 Hz), 1.87-1.79 (1H, m), 1.56 (9H, s), 1.35 (3H, d, J=7.0 Hz), 0.85-0.79 (2H, m), 0.64-0.59 (2H, m).

ESI (ES−) (m/z): 555 ([M−H]$^+$).

Example 113

2-[4'-{[2-(tert-Butoxycarbonyl)-3-hydroxy-4-(trifluoromethyl)benzyl]oxy}-1,1'-biphenyl-4-yl]butanoic acid (Exemplification Compound No.: 1-132)

(113-1)

Methyl 2-(4'-hydroxy-1,1'-biphenyl-4-yl)butanoate

According to a method similar to Example (98-2) and Example (98-3), from methyl (4'-hydroxy-1,1'-biphenyl-4-yl)acetate (266 mg, 1.1 mmol) obtained in Example (6-2), methyl 2-(4'-hydroxy-1,1'-biphenyl-4-yl)butanoate was obtained (94 mg, two-step total yield: 32%).

In the present step, ethyl iodide was used instead of methyl iodide in the step corresponding to Example (98-3).

$^1$H-NMR (400 MHz, CDCl$_3$): δ 7.49 (2H, d, J=8.4 Hz), 7.46 (2H, d, J=8.4 Hz), 7.34 (2H, d, J=8.4 Hz), 6.89 (2H, d, J=8.4 Hz), 4.86 (1H, bs), 3.67 (3H, s), 3.49 (1H, t, 7.6 Hz), 2.17-2.05 (1H, m), 1.86-1.79 (1H, m), 0.92 (3H, t, J=7.2 Hz).

(113-2)

According to a method similar to Example (40-2), Example (33-5) and Example (17-4), from methyl 2-(4'-hydroxy-1,1'-biphenyl-4-yl)butanoate (94 mg, 0.347 mmol) obtained in Example (113-1), the title compound was obtained as a white powder (99 mg, three-step total yield: 53%).

In the present step, 1,4-dioxane was used as the reaction solvent instead of tetrahydrofuran in the step corresponding to Example (17-4).

$^1$H-NMR (400 MHz, CDCl$_3$): δ 12.25 (1H, s), 7.71 (1H, d, J=−8.8 Hz), 7.52 (2H, d, J=8.8 Hz), 7.52 (2H, d, J=8.8 Hz), 7.37 (2H, d, J=8.8 Hz), 7.29-7.25 (1H, m), 6.98 (2H, d, J=8.8 Hz), 5.37 (2H, s), 3.53 (1H, t, J=7.6 Hz), 2.21-2.10 (1H, m), 1.91-1.80 (1H, m), 1.64 (9H, s), 0.95 (3H, t, J=7.2 Hz).

MS (ESI) (m/z): 529 ([M−]$^+$).

Example 114

(4'-{[2-(tert-Butoxycarbonyl)-3-hydroxy-4-(trifluoromethyl)benzyl]oxy}-2-methoxy-1,1'-biphenyl-3-yl)acetic acid (Exemplification Compound No.: 2-246)

(114-1)

10% Palladium-carbon (300 mg) was added to a solution of 2-hydroxy-3-nitrobenzoic acid (6.00 g, 32.8 mmol) in methanol (164 ml), and the mixture was stirred at room temperature under a nitrogen atmosphere for 5.5 hours. The insolubles were removed by filtration using Celite and the filtrate was concentrated. An aqueous sodium nitrite (3.40 g, 49.2 mmol) solution (49 ml) was added dropwise to a solution of the obtained residue in 10% sulfuric acid (164 ml) under ice-cooling. After the mixture was stirred at room temperature for 1 hour, an aqueous potassium iodide (10.4 g, 62.3 mmol) solution (31 ml) was added dropwise to the reaction mixture. The reaction mixture was heated to 90° C. and stirred for 2 hours. The reaction mixture was extracted with ethyl acetate and the organic layer was successively washed with a 10% aqueous sodium sulfite solution and a saturated aqueous NaCl solution and dried with anhydrous sodium sulfate. The solvent was removed under reduced pressure and potassium carbonate (10.1 g, 78.7 mmol) and methyl iodide (4.90 ml, 78.7 mmol) were added to a solution of the obtained residue in N,N-dimethylformamide (60 ml) under ice-cooling. After the reaction mixture was stirred at room temperature for 3 hours, the reaction mixture was poured into water and extracted with ethyl acetate. The organic layer was successively washed with water and a saturated aqueous NaCl solution and dried with anhydrous sodium sulfate.

After a diisobutyl aluminum hydride-1.0M toluene solution (49.0 ml, 48.6 mmol) was added dropwise to a solution of the residue obtained by removing the solvent under reduced pressure in toluene (100 ml) at −78° C., the temperature of the reaction mixture was raised to −20° C. over 2 hours. 2N Hydrochloric acid was added to the reaction mixture and the mixture was stirred at room temperature for 30 minutes. After the reaction mixture was extracted with ethyl acetate, the organic layer was successively washed with water and a saturated aqueous NaCl solution and dried with anhydrous sodium sulfate. The residue obtained by removing the solvent under reduced pressure was subjected to silica gel column chromatography (eluting solvent: hexane/ethyl acetate=3/1) to give crude (3-iodo-2-methoxyphenyl)methanol.

According to a method similar to Example (90-4), Example (90-5), Example (84-2) and Example (14-1), from the compound obtained in the above, methyl (4'-hydroxy-2-methoxy-1,1'-biphenyl-3-yl)acetate was obtained as a yellow oil (792 mg, seven-step total yield: 9%).

In the present step, 4-(4,4,5,5-tetramethyl-1,3,2-dioxaborolan-2-yl)phenol was used instead of methyl [4-(4,4,5,5-tetramethyl-1,3,2-dioxaborolan-2-yl)phenyl]acetate in the Suzuki coupling step corresponding to Example (14-1).

$^1$H-NMR (500 MHz, CDCl$_3$): δ 7.46 (2H, d, J=8.3 Hz), 7.25 (1H, dd, J=7.3, 1.5 Hz), 7.20 (1H, dd, J=7.3, 1.5 Hz), 7.11 (1H, t, J=7.3 Hz), 6.89 (2H, d, J=8.3 Hz), 5.06 (1H, s), 3.73 (2H, s), 3.72 (3H, s), 3.34 (3H, s).

(114-2)

According to a method similar to Example (2-3), from methyl (4'-hydroxy-2-methoxy-1,1'-biphenyl-3-yl)acetate (792 mg, 2.91 mmol) obtained in Example (114-1) and tert-butyl 6-(bromomethyl)-2-[(tert-butoxycarbonyl)oxy]-3-(trifluoromethyl)benzoate (1.32 g, 2.91 mmol) obtained in Example (28-5), tert-butyl 2-[(tert-butoxycarbonyl)oxy]-6-

[({2'-methoxy-3'-[(methoxycarbonyl)methyl]-1,1'-biphenyl-4-yl}oxy)methyl]-3-(trifluoromethyl)benzoate was obtained as a yellow oil (1.20 g, yield: 64%).

$^1$H-NMR (400 MHz, CDCl$_3$): δ 7.73 (1H, d, J=7.8 Hz), 7.62 (1H, d, J=7.8 Hz), 7.51 (2H, d, J=8.0 Hz), 7.24 (1H, dd, J=7.4, 1.2 Hz), 7.20 (1H, dd, I=7.4, 1.2 Hz), 7.11 (1H, t, J=7.4 Hz), 6.99 (2H, d, J=8.0 Hz), 5.26 (2H, s), 3.72 (5H, s), 3.33 (3H, s), 1.57 (9H, s), 1.54 (9H, s).

(114-3)

According to a method similar to Example (33-5) and Example (17-4), from tert-butyl 2-[(tert-butoxycarbonyl)oxy]-6-[({2'-methoxy-3'-[(methoxycarbonyl)methyl]-1,1'-biphenyl-4-yl}oxy)methyl]-3-(trifluoromethyl)benzoate (150 mg, 0.23 mmol) obtained in Example (114-2), the title compound was obtained as a yellow oil (58 mg, two-step total yield: 47%).

$^1$H-NMR (400 MHz, CDCl$_3$): δ 12.26 (1H, s), 7.72 (1H, d, J=8.2 Hz), 7.53 (2H, d, J=8.6 Hz), 7.30 (1H, d, J=8.2 Hz), 7.27 (1H, dd, J=7.4, 1.6 Hz), 7.22 (1H, dd, J=7.4, 1.6 Hz), 7.14 (1H, t, J=7.4 Hz), 6.98 (2H, d, J=8.6 Hz), 5.37 (2H, s), 3.77 (2H, s), 3.38 (3H, s), 1.64 (9H, s).

MS (FAB) (m/z): 532 ([M]$^+$).

Example 115

2-(4'-{[2-(tert-Butoxycarbonyl)-3-hydroxy-4-(trifluoromethyl)benzyl]oxy}-2-methoxy-1,1'-biphenyl-3-yl)propanoic acid (Exemplification Compound No.: 2-63)

(115-1)

According to a method similar to Example (94-1), from tert-butyl 2-[(tert-butoxycarbonyl)oxy]-6-[({2'-methoxy-3'-[(methoxycarbonyl)methyl]-1,1'-biphenyl-4-yl}oxy)methyl]-3-(trifluoromethyl)benzoate (300 mg, 0.46 mmol) obtained in Example (115-1), tert-butyl 2-[(tert-butoxycarbonyl)oxy]-6-[({2'-methoxy-3'-[1-(methoxycarbonyl)ethyl]-1,1'-biphenyl-4-yl}oxy)methyl]-3-(trifluoromethyl)benzoate was obtained as a white amorphous compound (212 mg, yield: 69%).

$^1$H-NMR (500 MHz, CDCl$_3$): δ 7.73 (1H, d, J=7.8 Hz), 7.62 (1H, d, J=7.8 Hz), 7.52 (2H, d, J=8.8 Hz), 7.24 (1H, dd, J=7.8, 1.5 Hz), 7.22 (1H, dd, J=7.8, 1.5 Hz), 7.14 (1H, t, J=7.8 Hz), 6.99 (2H, d, J=8.8 Hz), 5.27 (2H, s), 4.19 (1H, q, J=7.3 Hz), 3.69 (3H, s), 3.34 (3H, s), 1.57 (9H, s), 1.54 (9H, s), 1.51 (3H, d, J=7.3 Hz).

(115-2)

According to a method similar to Example (33-5) and Example (17-4), from tert-butyl 2-[(tert-butoxycarbonyl)oxy]-6-[({2'-methoxy-3'-[1-(methoxycarbonyl)ethyl]-1,1'-biphenyl-4-yl}oxy)methyl]-3-(trifluoromethyl)benzoate (212 mg, 0.32 mmol) obtained in Example (115-1), the title compound was obtained as a white amorphous compound (70 mg, two-step total yield: 40%).

$^1$H-NMR (400 MHz, CDCl$_3$): δ 12.26 (1H, s), 7.71 (1H, d, J=8.2 Hz), 7.53 (2H, d, J=8.6 Hz), 7.30 (1H, d, J=8.2 Hz), 7.27 (1H, dd, J=7.4, 1.6 Hz), 7.25 (1H, dd, J=7.4, 1.6 Hz), 7.16 (1H, t, J=7.4 Hz), 6.98 (2H, d, J=8.6 Hz), 5.37 (2H, s), 4.20 (1H, q, J=7.0 Hz), 3.38 (3H, s), 1.64 (9H, s), 1.55 (3H, d, J=7.0 Hz).

MS (FAB) (m/z): 546 ([M]$^+$).

Test Example 1

Co-Transfection Assay

The effect of activating or inhibiting LXR transcription activity of a test compound can be measured by a co-transfection which is a cell-based assay. LXR is known to function by forming a heterodimer with RXR. In a co-transfection assay, LXR and RXR expression plasmids and a luciferase reporter expression plasmid containing three copies of an LXR-RXR heterodimer-responding DNA sequence are first inserted into mammalian cells by transient transfection. Next, when the transfected cells are treated with a test compound having LXR agonist activity, the transcription activating effect of LXR is enhanced, and the LXR agonist activity of a test compound can be measured as an increase in luciferase activity. Similarly, LXR antagonist activity of a test compound can be measured by determining the degree to which a test compound competitively inhibits activation of transcription by an LXR agonist.

[1] Substances Used (1) CV-1 African green monkey kidney cells (ATCC CCL-70)
(2) Co-transfection expression plasmid, pcDNA-hLXRα or pcDNA-hLXRβ, reporter (LXREx3-pTAL-Luc Vector)
(3) Lipofect AMINE, Plus Reagent (Invitrogen) transfection reagent
(4) Cell lysis buffer [Passive lysis buffer; 5× (Promega Corporation) is diluted with distilled water]
(5) Luciferase assay reagent (Promega Corporation)
(6) Medium (Dulbecco's Modified Eagle Medium (Gibco) 500 ml, Gentamicin Reagent Solution (Gibco) 2.5 ml, 2 mM L-Gluta Max I Supplement (Gibco) 5.0 ml, MEM Sodium pyruvate solution (Gibco) 5.0 ml, penicillin-streptomycin (Gibco) 5.0 ml, charcoal/dextran-treated FBS (HyClone) 50 ml)
(7) OPTI-MEM I Reduced-Serum Medium (Gibco)

[2] Adjustment of Screening Reagents

The aforementioned CV-1 cells were disseminated into a 96-well assay plate (Costar 3610) to a concentration of 2×10$^4$ cells/100 μM/well followed by incubating overnight at 37° C.

DNA transfection was carried out according to the protocol provided with the transfection reagent. 10 μl of OPTI-MEM I Reduced-Serum Medium (Gibco) and 0.5 μl of Lipofect AMINE (Invitrogen) were added to two 50 ml tubes followed by shaking the mixed solutions to obtain Solution A. The substances of (1) below were respectively added to each tube followed by shaking the mixed solutions and allowing to stand undisturbed for 15 minutes to obtain Solution B. In addition, Solution C was obtained by carrying out the same procedure using the substances of (2) below.

(1) 10 μl of OPTI-MEM I Reduced-Serum Medium, 1 μl of Plus Reagent (Invitrogen) and 0.1 μg of DNA [PCMX-LXRα (33 ng) and LXRE (66 ng)];
(2) 10 μl of OPTI-MEM I Reduced-Serum Medium, 1 μl of Plus Reagent (Invitrogen) and 0.1 μg of DNA [PCMX-LXRβ (33 ng) and LXRE (66 ng)].

The entire amount of the aforementioned Solution A was respectively added to the aforementioned Solution B followed by shaking and allowing to stand undisturbed for 15 minutes to obtain LXRα solution. In addition, LXRβ solution was obtained by carrying out the same procedure using the aforementioned Solutions C and A.

After removing the medium from the 96-well assay plate used to Incubate the CV-1 cells as described above by decanting, and completely removing any moisture, 50 μl/well of OPTI-MEM I Reduced-Serum Medium were added to each well followed by addition of the aforementioned LXRα solution or LXRβ solution to each well at 20 μl/well and incubating for 3 hours at 37° C.

Three hours later, 20% charcoal FBS-DMEM was added to each well at 70 μl/well. FBS-DMEM used for the medium was prepared by mixing charcoal and dextran-treated FBS at a ratio of 9:1. Next, test compounds adjusted to concentrations of 1 mM, 0.3 mM, 0.1 mM, 30 μM, 10 μM, 3 μM, 1 μM or 0 μM with DMSO were added to each well at 1.4 μl/well. The actual concentrations of test compounds in the wells at this time were 1/100 of the concentrations indicated above. The CV-1 cells contained in each well prepared in the manner described above were incubated overnight at 37° C.

[3] Measurement Procedure

The CV-1 cells were observed microscopically following the aforementioned incubation. After removing the medium by decantation and removing sufficiently any moisture, a white seal was affixed to the bottom of each well. Passive lysis buffer (5×) (Promega corporation) diluted 5-fold with distilled water was added to each well at 20 μl/well, and the CV-1 cells were lysed over the course of 15 minutes using a plate shaker. Luciferase assay reagent (Promega Corporation) was added to each well at 100 μl/well followed by measurement of luciferase activity using the Wallac ARVO HTS 1429 Multilabel Counter (registered trademark: Perkin Elmer) or the Analyst HT (registered trademark: BioSystems).

$EC_{50}$ values, which indicate the strength of activity of the test compounds, and efficacy, which represents the %: activation ability of the test compounds, were able to be determined by LXR/LXRE co-transfection assay. Efficacy is represented by the relative activation ability based on a control compound having LXR agonist activity or a control (DMSO/solvent) not having LXR agonist activity. In this assay, N-(2,2,2-trifluoroethyl)-N-[4-[2,2,2-trifluoro-1-hydroxy-1-(trifluoromethyl)ethyl]phenyl]benzene sulfonamide (Compound 12 described on page 55 of International Patent Publication WO2000/054759; referred to as Compound D) was used as a control compound having LXR agonist activity.

A concentration-response curve was prepared from the measured values at a total of 8 points of dilution series concentrations in (½)Log units. The measured value at each concentration was calculated as the mean of the values of 4 wells in the 96-well plate for a single concentration. The data of this assay was fitted to the following equations to calculate $EC_{50}$ values.

$$Y = \text{Bottom} + (\text{Top} - \text{Bottom})/(I + 10^Z)$$

$$Z = (\log EC_{50} - X) * \text{HillSlope}$$

The $EC_{50}$ value is defined as the concentration at which a test compound provides the intermediate value between the maximum response (top) and baseline (bottom) (see "Fitting to Sigmoidal dose-response (variable slope)" (Graph Pad PRISM Version 3.02)). The value for relative efficacy or % control based on the control compound as an LXR agonist was determined by a comparison with the maximum response value indicated by Compound D used as the control compound.

[4] Result

In the case of testing with this assay, the compounds of Examples 1 to 5, 7 to 12, 14, 15, 17 to 29, 31 to 47, 49, 50, 52, 54 to 67, 69 to 72, 74 to 79, 81 to 102 or 104 to 115 had an $EC_{50}$ value of 5 μM or less against LXRα. The compound of Examples 1 to 115 had an $EC_{50}$ value of 3 μM or less against LXRβ.

From the result described above, the compound of the present invention has a superior binding activity to LXRα and LXRβ and LXR transcripting activity and is useful as a pharmaceutical for treating or preventing a disease such as arteriosclerosis, atherosclerosis, arteriosclerosis caused by diabetes, inflammatory disease, arteriosclerotic heart disease, cardiovascular disease, coronary artery disease and cerebrovascular disease.

Test Example 2

Anti-Inflammatory Effect

The animal and reagent used in this test example is as indicated below unless specifically indicated otherwise.

CD1 mice (6 to 10 weeks age, male and female) are purchased from Japan Charles River, housed at controlled temperature and humidity, and given unlimited access to feed and drinking water. The animals are grouped into groups of 5 animals per group and used in an experiment after an acclimation period of 5 days.

Phorbol 12-myristate 13-acetate (TPA) induces irritative contact dermatitis. 10 μl of a 0.03% (w/v) TPA/acetone solution is respectively applied to the inside and outside of the left ear of a test mouse (total of 20 μl). Only acetone is applied to the right ear. 20 μl of a test compound (10 mM acetone solution) is applied to both sides of both ears 45 minutes and 4 hours after the application of TPA. An animal of a control group is treated in the same manner with only acetone used as a solvent.

Allergic contact dermatitis is induced by sensitizing by applying 20 μl of a 15% (w/v) 4-ethoxymethylene-2-phenyl-2-oxazolin-5-one (oxazolone)/acetone solution to the shaved backs of a CD1 female mouse once a day for 2 days, followed by applying 10 μl of a 2% oxazolone/acetone solution to both sides of the left ear on day 7. Only acetone is applied to the right ear. 20 μl of a test compound (10 mM acetone solution) or acetone is applied in the same manner as described above 45 minutes and 4 hours after the application of oxazolone to the ear.

The degree of inflammation is evaluated by measuring the rate of increase in ear thickness and/or ear weight of the left ear treated with a test compound and the right ear treated with a solvent 18 hours after inducing inflammation with TPA or oxazolone. Ear thickness is measured with a digital caliper, and a tissue sample is obtained using a 6 mm punch to measure a change in ear weight. The degree of inflammation is quantified using the following equation:

Ear enlargement rate(%) = 100 × [(a) − (b)/(b)]

[wherein (a) is thickness or weight of the left ear treated with a test compound, and (b) is thickness or weight of the right ear serving as a control].

In the case of testing according to this method, the compound of the present invention has a superior anti-inflammatory activity and is useful as a pharmaceutical for inflammatory disease.

Test Example 3

Blood Glucose Lowering Effect

Blood sugar lowering effect of a compound of the present invention is measured in the manner described below.

A blood sample is collected from a tail vein of a KK mouse (4 to 5 months age) purchased from Nippon Clea. After centrifuging the blood samples, plasma glucose concentration is measured using a glucose analyzer (Glucoloader-GXT, A&T). These diabetic mice are grouped (3 or 4 animals per group) and given powdered rodent diet (F-2, Funabashi Farm) containing a test compound at 0.1 to 0.001% (w/w) for 7 days. A mouse group given a test compound is designated as a test compound administration group, while a mouse group given powdered rodent diet not containing a test compound is designated as a control group. After 7 days, a blood sample is collected from a tail vein of each mouse and plasma glucose concentration is measured. The plasma glucose lowering rate is calculated according to the following equation:

Plasma glucose lowering rate(%)=(average plasma glucose concentration of control group−average plasma glucose concentration of test compound administration group)×100/plasma glucose concentration of control group.

In the case of testing according to this method, the compound of the present invention has a superior blood glucose lowering effect and is useful as a pharmaceutical for diabetes.

Formulation Example 1

Hard Capsules

A hard capsule is prepared by filling the powdered compound of Example 1 (100 mg), lactose (150 mg), cellulose (50 mg) and magnesium stearate (6 mg) into a standard two-piece hard gelatin capsule, washed and dried.

Formulation Example 2

Soft Capsules

A soft capsule is prepared by injecting a mixture of a digestable oil such as soybean oil or olive oil and the compound of Example 2 into gelatin so as to contain 100 mg of active ingredient, washed and dried.

Formulation Example 3

Tablet

A tablet is prepared according to a usual method using the compound of Example 3 (100 mg), colloidal silicon dioxide (0.2 mg), magnesium stearate (5 mg), microcrystalline cellulose (275 mg), starch (11 mg) and lactose (98.8 mg). The obtained tablet can be coated if necessary.

Formulation Example 4

Suspension

A suspension is prepared so as to contain the finely powdered compound of Example 4 (100 mg), sodium carboxymethyl cellulose (100 mg), sodium benzoate (5 mg), sorbitol solution (Japanese Pharmacopoeia, 1.0 g) and vanillin (0.025 ml) in 5 ml of the suspension.

Formulation Example 5

Cream

A cream is prepared by mixing the finely powdered compound of Example 5 (100 mg) into 5 g of a cream consisting of white petrolatum (40 wt %), microcrystalline wax (3 wt %), lanolin (10 wt %), sorbitan monolaurate (5 wt %), 0.3% polyoxyethylene (20) sorbitan monolaurate (0.3 wt %) and water (41.7 wt %).

INDUSTRIAL APPLICABILITY

The compound represented by the general formula (I) or a pharmacologically acceptable salt or ester thereof of the present invention has a superior binding activity to LXR, has superior pharmacokinetic properties in terms of absorption, distribution in the body and half-life in the blood, and has a low toxicity against kidney, liver and other organs. Therefore, the compound represented by the general formula (I) or a pharmacologically acceptable salt or ester thereof of the present invention is useful as a pharmaceutical for a warm-blooded animal, preferably a human.

The compound represented by the general formula (I) or a pharmacologically acceptable salt or ester thereof of the present invention is useful as an LXR modulator, an LXR agonist or an LXR antagonist, preferably as an LXR modulator or an LXR agonist, and more preferably as an LXR modulator. The compound represented by the general formula (I) or a pharmacologically acceptable salt or ester thereof of the present invention is useful as a pharmaceutical for inducing ABCA1 expression or promoting reverse cholesterol transport.

The compound represented by the general formula (I) or a pharmacologically acceptable salt or ester thereof of the present invention is useful as a pharmaceutical for treating or preventing preferably arteriosclerosis, atherosclerosis, arteriosclerosis caused by diabetes, hyperlipemia, hypercholesterolemia, lipid-associated diseases, inflammatory disease, auto-immune disease, arteriosclerotic heart disease, cardiovascular disease, coronary artery disease, cerebrovascular disease, kidney disease, diabetes, diabetic complications, obesity, nephritis, hepatitis, cancer or Alzheimer's disease; more preferably arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease or diabetes; even more preferably arteriosclerosis, atherosclerosis, arteriosclerosis caused by diabetes, arteriosclerotic heart disease, cardiovascular disease or coronary artery disease; still more preferably arteriosclerosis, atherosclerosis or arteriosclerotic heart disease; and most preferably arteriosclerosis.

The invention claimed is:
1. A compound represented by the general formula (I) or a pharmacologically acceptable salt or ester thereof:

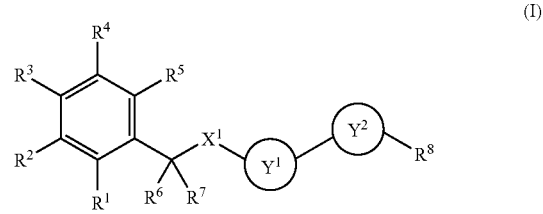

(I)

[wherein $R^1$ represents a group having the formula —$COR^9$ [wherein $R^9$ represents a $C_1$-$C_{10}$ alkyl group, a $C_1$-$C_{10}$ alkoxy group, a halogeno $C_1$-$C_{10}$ alkoxy group (wherein said halogeno $C_1$-$C_{10}$ alkoxy group represents a $C_1$-$C_{10}$ alkoxy group substituted with 1 to 7 halogeno groups), a phenyl-($C_1$-$C_{10}$ alkoxy) group, a $C_1$-$C_{10}$ alkylamino group or a di($C_1$-$C_{10}$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)];
$R^2$ represents a hydrogen atom, a halogeno $C_1$-$C_4$ alkyl group (wherein said halogeno $C_1$-$C_4$ alkyl group represents a $C_1$-$C_4$ alkyl group substituted with 1 to 5 halogeno groups), a hydroxyl group, a $C_1$-$C_4$ alkoxy group, an amino group, a $C_1$-$C_4$ alkylamino group, a di($C_1$-$C_4$ alkyl)amino group (wherein said alkyl groups may be the same or different) or a halogeno group;

$R^3$ represents a hydrogen atom, a $C_1$-$C_6$ alkyl group, a halogeno $C_1$-$C_6$ alkyl group (wherein said halogeno $C_1$-$C_6$ alkyl group represents a $C_1$-$C_6$ alkyl group substituted with 1 to 7 halogeno groups), a ($C_1$-$C_4$ alkoxy)-($C_1$-$C_4$ alkyl) group, a ($C_1$-$C_4$ alkylthio)-($C_1$-$C_4$ alkyl) group, a ($C_1$-$C_4$ alkylsulfinyl)-($C_1$-$C_4$ alkyl) group, a ($C_1$-$C_4$ alkylsulfonyl)-($C_1$-$C_4$ alkyl) group, a ($C_1$-$C_4$ alkylamino)-($C_1$-$C_4$ alkyl) group, a [di($C_1$-$C_4$ alkyl)amino]-($C_1$-$C_4$ alkyl) group (wherein said alkyl groups may be the same or different), a $C_3$-$C_6$ cycloalkyl group, a $C_2$-$C_6$ alkenyl group, a $C_2$-$C_6$ alkynyl group, a hydroxyl group, a $C_1$-$C_6$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a ($C_1$-$C_6$ alkoxy)carbonyl group, a cyano group, a nitro group or a halogeno group;

$R^4$ and $R^5$ may be the same or different and each represents a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_6$ cycloalkyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups) or a halogeno group;

$R^6$ and $R^7$ may be the same or different and each represents a hydrogen atom or a $C_1$-$C_3$ alkyl group;

$R^8$ represents a group having the formula —$X^2R^{10}$ [wherein $R^{10}$ represents a group having the formula —$COR^{11}$ [wherein $R^{11}$ represents a $C_1$-$C_6$ alkyl group, a hydroxyl group, a $C_1$-$C_6$ alkoxy group, a ($C_3$-$C_8$ cycloalkyl)-($C_1$-$C_6$ alkyl)oxy group, a $C_3$-$C_8$ cycloalkyloxy group, an amino group, a $C_1$-$C_6$ alkylamino group, a [($C_3$-$C_8$ cycloalkyl)-($C_1$-$C_6$ alkyl)]amino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di[($C_3$-$C_8$ cycloalkyl)-($C_1$-$C_6$ alkyl)]amino group, a di($C_3$-$C_8$ cycloalkyl)amino group, a N—[($C_3$-$C_8$ cycloalkyl)-($C_1$-$C_6$ alkyl)]-N—($C_1$-$C_6$ alkyl)amino group, a N—($C_3$-$C_8$ cycloalkyl)-N—($C_1$-$C_6$ alkyl)amino group, a N—[($C_3$-$C_8$ cycloalkyl)-($C_1$-$C_6$ alkyl)]-N—($C_3$-$C_8$ cycloalkyl) amino group, a hydroxylamino group or a hydroxyl($C_1$-$C_6$ alkyl)amino group], a group having the formula —$SO_2R^{12}$ [wherein $R^{12}$ represents a $C_1$-$C_6$ alkyl group, a ($C_3$-$C_8$ cycloalkyl)-($C_1$-$C_6$ alkyl) group, a $C_3$-$C_8$ cycloalkyl group, an amino group, a $C_1$-$C_6$ alkylamino group, a [($C_3$-$C_8$ cycloalkyl)-($C_1$-$C_6$ alkyl)]amino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di[($C_3$-$C_8$ cycloalkyl)-($C_1$-$C_6$ alkyl)] amino group, a di($C_3$-$C_8$ cycloalkyl)amino group, a N—[($C_3$-$C_8$ cycloalkyl)-($C_1$-$C_6$ alkyl)]-N—($C_1$-$C_6$ alkyl)amino group, a N—($C_3$-$C_8$ cycloalkyl)-N—($C_1$-$C_6$ alkyl)amino group or a N—[($C_3$-$C_8$ cycloalkyl)-($C_1$-$C_6$ alkyl)]-N—($C_3$-$C_8$ cycloalkyl)amino group], a group having the formula —$N(R^{13})COR^{14}$ [wherein $R^{13}$ represents a hydrogen atom, a $C_1$-$C_6$ alkyl group, a ($C_3$-$C_8$ cycloalkyl)-($C_1$-$C_6$ alkyl) group or a $C_3$-$C_8$ cycloalkyl group, and $R^{14}$ represents a hydrogen atom, a $C_1$-$C_6$ alkyl group, a ($C_3$-$C_8$ cycloalkyl)-($C_1$-$C_6$ alkyl) group or a $C_3$-$C_8$ cycloalkyl group], a group having the formula —$N(R^{13})SO_2R^{15}$ [wherein $R^{13}$ is the same as previously defined, and $R^{15}$ represents a $C_1$-$C_6$ alkyl group, a ($C_3$-$C_8$ cycloalkyl)-($C_1$-$C_6$ alkyl) group or a $C_3$-$C_8$ cycloalkyl group], or a tetrazol-5-yl group, and $X^2$ represents a single bond, a $C_1$-$C_4$ alkylene group or a substituted $C_1$-$C_4$ alkylene group (wherein said substituents may be the same or different and are one or two groups selected from Substituent group γ, or two of said substituents may together form a methylene group, an ethylene group or a trimethylene group)];

$X^1$ represents a group having the formula —NH— or —$NR^{16}$— (wherein $R^{16}$ represents a $C_1$-$C_4$ alkyl group), —O—, —S—, —SO— or —$SO_2$—;

$Y^1$ represents a phenyl group, a substituted phenyl group (wherein said substituents may be the same or different and are 1 to 3 groups selected from Substituent group α);

$Y^2$ represents a 6- to 10-membered aryl group, a substituted 6- to 10-membered aryl group (wherein said substituents may be the same or different and are 1 to 3 groups selected from Substituent group β), a 9- or 10-membered unsaturated cyclic hydrocarbon group (provided that $Y^1$ is bonded to a benzene ring part in said unsaturated cyclic hydrocarbon group), a substituted 9- or 10-membered unsaturated cyclic hydrocarbon group (provided that $Y^1$ is bonded to a benzene ring part in said unsaturated cyclic hydrocarbon group, and said substituents may be the same or different and are 1 to 3 groups selected from Substituent group β);

Substituent group α represents the group consisting of a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a hydroxyl group, a $C_1$-$C_4$ alkoxy group and a halogeno group;

Substituent group β represents the group consisting of a $C_1$-$C_6$ alkyl group, a hydroxy($C_1$-$C_6$ alkyl) group, a carboxy($C_1$-$C_6$ alkyl) group, a ($C_1$-$C_6$ alkoxy)carbonyl-($C_1$-$C_6$ alkyl) group, a halogeno $C_1$-$C_6$ alkyl group (wherein said halogeno $C_1$-$C_6$ alkyl group represents a $C_1$-$C_6$ alkyl group substituted with 1 to 7 halogeno atoms), a ($C_3$-$C_8$ cycloalkyl)-($C_1$-$C_6$ alkyl) group, a $C_2$-$C_7$ alkenyl group, a $C_2$-$C_7$ alkynyl group, a $C_3$-$C_8$ cycloalkyl group, a hydroxyl group, a $C_1$-$C_6$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylthio group, a $C_1$-$C_6$ alkylsulfinyl group, a $C_1$-$C_6$ alkylsulfonyl group, an amino group, a $C_1$-$C_6$ alkylamino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di($C_3$-$C_8$ cycloalkyl)amino group, a N—($C_3$-$C_8$ cycloalkyl)-N—($C_1$-$C_6$ alkyl)amino group, a formylamino group, a ($C_1$-$C_6$ alkyl)carbonylamino group, a ($C_3$-$C_8$ cycloalkyl)carbonylamino group, a N—[($C_1$-$C_6$ alkyl)carbonyl]-N—($C_1$-$C_6$ alkyl)amino group, a N—[($C_3$-$C_8$ cycloalkyl)carbonyl]-N—($C_1$-$C_6$ alkyl) amino group, a $C_1$-$C_6$ alkylsulfonylamino group, a N—($C_1$-$C_6$ alkylsulfonyl)-N—($C_1$-$C_6$ alkyl)amino group, a N—($C_1$-$C_6$ alkylsulfonyl)-N—($C_3$-$C_8$ cycloalkyl)amino group, a formyl group, a ($C_1$-$C_6$ alkyl) carbonyl group, a carboxyl group, a ($C_1$-$C_6$ alkoxy)carbonyl group, a carbamoyl group, a ($C_1$-$C_6$ alkylamino) carbonyl group, a ($C_3$-$C_8$ cycloalkylamino)carbonyl group, a di($C_1$-$C_6$ alkyl)aminocarbonyl group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a N—($C_3$-$C_8$ cycloalkyl)-N—($C_1$-$C_6$ alkyl)aminocarbonyl group, a cyano group, a nitro group and a halogeno group; and, Substituent group γ represents the group consisting of a $C_1$-$C_6$ alkyl group, a hydroxy($C_1$-$C_6$ alkyl) group, a ($C_1$-$C_6$ alkoxy)-($C_1$-$C_6$ alkyl) group, a mercapto($C_1$-$C_6$ alkyl) group, a ($C_1$-$C_6$ alkylthio)-($C_1$-$C_6$ alkyl) group, a ($C_1$-$C_6$ alkylsulfinyl)-($C_1$-$C_6$ alkyl) group, a ($C_1$-$C_6$ alkylsulfonyl)-($C_1$-$C_6$ alkyl) group, an amino($C_1$-$C_6$ alkyl) group, a ($C_1$-$C_6$ alkylamino)-($C_1$-$C_6$ alkyl) group, a ($C_3$-$C_8$ cycloalkylamino)-($C_1$-$C_6$ alkyl) group, a di($C_1$-$C_6$ alkyl)amino-($C_1$-$C_6$ alkyl) group (wherein said alkyl groups may be the same or different and two of said alkyl groups of the di($C_1$-$C_6$ alkyl)amino moiety may, together with the nitrogen atom of said amino group, form a 5- to 7-membered saturated heterocyclyl group containing 1 to 3 atoms selected from the group consisting of a nitrogen atom, an oxygen atom and a sulfur atom), a di($C_3$-$C_8$ cycloalkyl)amino-($C_1$-$C_6$ alkyl) group, a [N—($C_3$-$C_8$ cycloalkyl)-N—($C_1$-$C_6$ alkyl) amino]-($C_1$-$C_6$ alkyl) group, a hydroxyl group, a $C_1$-$C_6$ alkoxy group, a $C_3$-$C_8$ cycloalkyloxy group, a mercapto group, a $C_1$-$C_6$ alkylthio group, a $C_3$-$C_8$ cycloalkylthio group, a $C_1$-$C_6$ alkylsulfinyl group, a $C_3$-$C_8$ cycloalkylsulfinyl group, a $C_1$-$C_6$ alkylsulfonyl group, a $C_3$-$C_8$ cycloalkylsulfonyl group, an amino group, a $C_1$-$C_6$ alkylamino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di($C_3$-$C_8$ cycloalkyl)amino group, a N—($C_3$-$C_8$ cycloalkyl)-N—($C_1$-$C_6$ alkyl)amino group and a halogeno group].

2. A compound or a pharmacologically acceptable salt or ester thereof according to claim 1, wherein $R^1$ is a group having the formula —$COR^{9a}$ [wherein $R^{9a}$ represents a $C_1$-$C_6$ alkyl group, a $C_1$-$C_8$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylamino group, or a di($C_1$-$C_6$ alkyl) amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)].

3. A compound or a pharmacologically acceptable salt or ester thereof according to claim 1, wherein $R^1$ is a group having the formula —$COR^{9b}$ [wherein $R^{9b}$ represents a $C_1$-$C_6$ alkoxy group or a halogeno $C_1$-$C_4$ alkoxy group (wherein said halogeno $C_1$-$C_4$ alkoxy group represents a $C_1$-$C_4$ alkoxy group substituted with 1 to 5 halogeno groups)].

4. A compound or a pharmacologically acceptable salt or ester thereof according to claim 1, wherein $R^1$ is a group having the formula —$COR^{9c}$ (wherein $R^{9c}$ represents a $C_3$-$C_5$ alkoxy group).

5. A compound or a pharmacologically acceptable salt or ester thereof according to claim 1, wherein $R^1$ is a group having the formula —$COR^{9d}$ (wherein $R^{9d}$ represents a 2-methyl-2-propoxy group).

6. A compound or a pharmacologically acceptable salt or ester thereof according to claim 1, wherein $R^2$ is a hydrogen atom, a trifluoromethyl group, a 2,2,2-trifluoroethyl group, a pentafluoroethyl group, a hydroxyl group, a fluoro group or a chloro group.

7. A compound or a pharmacologically acceptable salt or ester thereof according to claim 1, wherein $R^2$ is a hydrogen atom or a hydroxyl group.

8. A compound or a pharmacologically acceptable salt or ester thereof according to claim 1, wherein $R^2$ is a hydroxyl group.

9. A compound or a pharmacologically acceptable salt or ester thereof according to claim 1, wherein $R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_2$-$C_4$ alkenyl group, a $C_2$-$C_4$ alkynyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a fluoro group, a chloro group or a bromo group.

10. A compound) or a pharmacologically acceptable salt or ester thereof according to claim 1, wherein $R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_2$-$C_4$ alkenyl group, a $C_1$-$C_4$ alkoxy group, a fluoro group or a chloro group.

11. A compound or a pharmacologically acceptable salt or ester thereof according to claim 1, wherein $R^3$ is a methyl group, an ethyl group, a 2-propyl group, a 2-methyl-2-propyl group, a trifluoromethyl group, a 2,2,2-trifluoroethyl group, a methoxy group, a fluoro group or a chloro group.

12. A compound or a pharmacologically acceptable salt or ester thereof according to claim 1, wherein $R^3$ is a 2-propyl group, a 2-methyl-2-propyl group, a trifluoromethyl group or a chloro group.

13. A compound or a pharmacologically acceptable salt or ester thereof according to claim 1, wherein $R^3$ is a trifluoromethyl group.

14. A compound or a pharmacologically acceptable salt or ester thereof according to claim 1, wherein $R^4$ and $R^5$ may be the same or different and each is a hydrogen atom, a methyl group, an ethyl group, a trifluoromethyl group, a cyclopropyl group, a hydroxyl group, a methoxy group, a fluoro group, a chloro group or a bromo group.

15. A compound or a pharmacologically acceptable salt or ester thereof according to claim 1, wherein $R^4$ is a hydrogen atom, and $R^5$ is a hydrogen atom or a hydroxyl group.

16. A compound or pharmacologically acceptable salt or ester thereof according to claim 1, wherein $R^4$ and $R^5$ are hydrogen atoms.

17. A compound or a pharmacologically acceptable salt or ester thereof according to claim 1, wherein $R^6$ and $R^7$ may be the same or different and each is a hydrogen atom or a methyl group.

18. A compound or a pharmacologically acceptable salt or ester thereof according to claim 1, wherein $R^6$ and $R^7$ are hydrogen atoms.

19. A compound or a pharmacologically acceptable salt or ester thereof according to claim 1, wherein $R^8$ is a group having the formula —$X^{2a}R^{10a}$ [wherein $R^{10a}$ represents a group having the formula —$COR^{11a}$ [wherein $R^{11a}$ represents a hydroxyl group, a $C_1$-$C_4$ alkoxy group, a ($C_3$-$C_6$ cycloalkyl)-($C_1$-$C_4$ alkyl)oxy group, a $C_3$-$C_6$ cycloalkyloxy group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a hydroxylamino group or a hydroxyl($C_1$-$C_4$ alkyl)]amino group], a group having the formula —$SO_2R^{12a}$ [wherein $R^{12a}$ represents a $C_1$-$C_4$ alkyl group, a ($C_3$-$C_6$ cycloalkyl)-($C_1$-$C_4$ alkyl) group, a $C_3$-$C_6$ cycloalkyl group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group or a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], a group having the formula —$N(R^{13a})COR^{14a}$ [wherein $R^{13a}$ represents a hydrogen atom, a $C_1$-$C_4$ alkyl group, a ($C_3$-$C_5$ cycloalkyl)-($C_1$-$C_2$ alkyl) group or a $C_3$-$C_5$ cycloalkyl group, and $R^{14a}$ represents a hydrogen atom, a $C_1$-$C_4$ alkyl group, a ($C_3$-$C_5$ cycloalkyl)-($C_1$-$C_2$ alkyl) group or a $C_3$-$C_5$ cycloalkyl group], a group having the formula —$N(R^{13a})SO_2R^{15a}$ [wherein $R^{13a}$ is the same as previously defined, and $R^{15a}$ represents a $C_1$-$C_4$ alkyl group, a ($C_3$-$C_5$ cycloalkyl)-($C_1$-$C_2$ alkyl) group or a $C_3$-$C_5$ cycloalkyl group], or a tetrazol-5-yl group, and $X^{2a}$ represents a single bond, a $C_1$-$C_2$ alkylene group or a substituted $C_1$-$C_2$ alkylene group (wherein said substituents may be the same or different and are one or two groups selected from Substituent group γ1, or two of said substituents may together form a methylene group, an ethylene group or a trimethylene group)]; and, Substituent group γ1 is the group consisting of a methyl group, an ethyl group, a hydroxymethyl group, a hydroxyethyl group, a methoxymethyl group, a methoxyethyl group, a methylthiomethyl group, a methylthioethyl group, an aminomethyl group, an aminoethyl group, a methylaminomethyl group, an ethylaminomethyl group, a methylaminoethyl group, a cyclopropylaminomethyl group, a cyclopropylaminoethyl group, a dimethylaminomethyl group, a dimethylaminoethyl group, a (N-methyl-N-ethylamino)methyl group, a dicyclopropylaminomethyl group, a hydroxyl group, a methoxy group, an ethoxy group, a cyclopropyloxy group, a methylthio group, an ethylthio group, a cyclopropylthio group, an amino group, a methylamino group, an ethylamino group, a cyclopropylamino group, a cyclobutylamino group, a dimethylamino group, a diethylamino group, a dicyclopropylamino group, a N-cyclopropyl-N-methylamino group, a fluoro group and a chloro group.

20. A compound or a pharmacologically acceptable salt or ester thereof according to claim 1, wherein $R^8$ is a group having the formula —$X^{2b}R^{10b}$ [wherein $R^{10b}$ represents a group having the formula —$COR^{11b}$ [wherein $R^{11b}$ represents a hydroxyl group, a $C_1$-$C_4$ alkoxy group, a ($C_3$-$C_5$ cycloalkyl)-($C_1$-$C_2$ alkyl)oxy group, a $C_3$-$C_5$ cycloalkyloxy group, an amino group, a methylamino group, an ethylamino group, a dimethylamino group, a diethylamino group, a methylethylamino group or a hydroxylamino group], a group having the formula —$SO_2R^{12b}$ [wherein $R^{12b}$ represents a $C_1$-$C_4$ alkyl group, a ($C_3$-$C_5$ cycloalkyl)-($C_1$-$C_2$ alkyl) group or a $C_3$-$C_5$ cycloalkyl group], or a tetrazol-5-yl group, and $X^{2b}$ represents a single bond, a methylene group, an ethylene group or a substituted methylene group or a substituted ethylene group (wherein said substituents may be the same or different and are one or two groups selected from Substituent group γ2, or two of said substituents may together form an ethylene group or a trimethylene group)]; and, Substituent group γ2 represents the group consisting of a methyl group, an ethyl group, a hydroxymethyl group, a methoxymethyl group, an aminomethyl group, a methylaminomethyl group, a dimethylaminomethyl group, a (N-methyl-N-ethylamino)methyl group, a methoxy group, an ethoxy group, a methylamino group, a dimethylamino group, a fluoro group and a chloro group.

21. A compound or a pharmacologically acceptable salt or ester thereof according to claim 1, wherein $R^8$ is a group having the formula —$X^{2c}R^{10c}$ [wherein $R^{10c}$ represents a group having the formula —$COR^{11c}$ (wherein $R^{11c}$ represents a hydroxyl group or a methoxy group), or a group having the formula —$SO_2R^{12c}$ (wherein $R^{12c}$ represents a methyl group), and $X^{2c}$ represents a single bond, a methylene group or a substituted methylene group (wherein said substituent is a group selected from Substituent group γ3, or two of said substituents may together form an ethylene group)]; and, Substituent group γ3 is the group consisiting of a methyl group, an ethyl group, a hydroxymethyl group, a dimethylaminomethyl group, a methoxy group and an ethoxy group.

22. A compound or a pharmacologically acceptable salt or ester thereof according to claim 1, wherein $R^8$ is a group having the formula —$X^{2d}R^{10d}$ [wherein $R^{10d}$ represents a group having the formula —$COR^{11d}$ (wherein $R^{11d}$ represents a hydroxyl group), and $X^{2d}$ represents a methylene group or a substituted methylene group (wherein said substituent is a group selected from Substituent group γ4, or two of said substituents may together form an ethylene group)]; and, Substituent group γ4 is the group consisting of a methyl group, an ethyl group and a hydroxymethyl group.

23. A compound or a pharmacologically acceptable salt or ester thereof according to claim 1, wherein $R^8$ is a group having the formula $—X^{2e}R^{10e}$ [wherein $R^{10e}$ represents a group having the formula $—COR^{11e}$ (wherein $R^{11e}$ represents a hydroxyl group), and $X^{2e}$ represents a methylene group or a substituted methylene group (wherein said substituent is a methyl group)].

24. A compound or a pharmacologically acceptable salt or ester thereof according to claim 1, wherein $R^8$ is a group having the formula $—X^{2f}R^{10f}$ [wherein $R^{10f}$ represents a group having the formula $—SO_2R^{12f}$ (wherein $R^{12f}$ represents a methyl group), and $X^{2f}$ represents a single bond].

25. A compound or a pharmacologically acceptable salt or ester thereof according to claim 1, wherein $X^1$ is a group having the formula $—NH—$, $—O—$ or $—S—$.

26. A compound or a pharmacologically acceptable salt or ester thereof according to claim 1, wherein $X^1$ is a group having the formula $—O—$.

27. A compound or a pharmacologically acceptable salt or ester thereof according to claim 1, wherein $Y^1$ is a phenyl group or a substituted phenyl group (wherein said substituents may be the same or different and are one or two groups selected from Substituent group α1), and Substituent group α1 is the group consisting of a methyl group, an ethyl group, a trifluoromethyl group, a methoxy group, an ethoxy group, a fluoro group and a chloro group.

28. A compound or a pharmacologically acceptable salt or ester thereof according to claim 1, wherein $Y^1$ is a phenyl group (wherein the substitution positions where $X^1$ and $Y^2$ are bonded to said phenyl group are the 1 and 3 positions or the 1 and 4 positions, respectively) or a substituted phenyl group (wherein said substituent is a group selected from Substituent group α2, and the substitution positions where $X^1$ and $Y^2$ are bonded to said phenyl group are the 1 and 3 positions or the 1 and 4 positions, respectively), and Substituent group α2 is the group consisting of a methyl group, a fluoro group and a chloro group.

29. A compound or a pharmacologically acceptable salt or ester thereof according to claim 1, wherein $Y^1$ is a phenyl group (wherein the substitution positions where $X^1$ and $Y^2$ are bonded to said phenyl group are the 1 and 4 positions).

30. A compound or a pharmacologically acceptable salt or ester thereof according to claim 1, wherein $Y^2$ is a phenyl group, a substituted phenyl group (wherein said substituents may be the same or different and are 1 to 3 groups selected from Substituent group β1), an indanyl group or a tetrahydronaphthyl group (provided that $Y^1$ is bonded to a benzene ring part in said indanyl or tetrahydronaphthyl group), a substituted indanyl group or a substituted tetrahydronaphthyl group (provided that $Y^1$ is bonded to a benzene ring part in said indanyl or tetrahydronaphthyl group, and said substituents may be the same or different and are 1 to 3 groups selected from Substituent group β1); and, Substituent group β1 is the group consisting of a $C_1$-$C_6$ alkyl group, a hydroxy($C_1$-$C_4$ alkyl) group, a carboxy ($C_1$-$C_4$ alkyl) group, a ($C_1$-$C_4$ alkoxy)carbonyl-($C_1$-$C_4$ alkyl) group, a halogeno $C_1$-$C_4$ alkyl group (wherein said halogeno $C_1$-$C_4$ alkyl group represents a $C_1$-$C_4$ alkyl group substituted with 1 to 5 halogeno atoms), a ($C_3$-$C_6$ cycloalkyl)-($C_1$-$C_4$ alkyl) group, a $C_2$-$C_5$ alkenyl group, a $C_2$-$C_5$ alkynyl group, a $C_3$-$C_6$ cycloalkyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a $C_3$-$C_6$ cycloalkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a formylamino group, a ($C_1$-$C_4$ alkyl)carbonylamino group, a ($C_3$-$C_6$ cycloalkyl)carbonylamino group, a N—[($C_1$-$C_4$ alkyl)carbonyl]-N—($C_1$-$C_4$ alkyl)amino group, a N—[($C_3$-$C_6$ cycloalkyl)carbonyl]-N—($C_1$-$C_4$ alkyl)amino group, a $C_1$-$C_4$ alkylsulfonylamino group, a N—($C_1$-$C_4$ alkylsulfonyl)-N—($C_1$-$C_4$ alkyl)amino group, a formyl group, a ($C_1$-$C_4$ alkyl)carbonyl group, a carboxyl group, a ($C_1$-$C_4$ alkoxy)carbonyl group, a carbamoyl group, a ($C_1$-$C_4$ alkylamino)carbonyl group, a di($C_1$-$C_4$ alkyl)aminocarbonyl group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a cyano group, a nitro group, a fluoro group, a chloro group and a bromo group.

31. A compound or a pharmacologically acceptable salt or ester thereof according to claim 1, wherein $Y^2$ is a phenyl group (wherein the substitution positions where $Y^1$ and $R^8$ are bonded to said phenyl group are the 1 and 3 positions or the 1 and 4 positions, respectively), a substituted phenyl group (wherein said substituents may be the same or different and represent one or two groups selected from Substituent group β2, and the substitution positions where $Y^1$ and $R^8$ are bonded to said phenyl group are the 1 and 3 positions or the 1 and 4 positions, respectively); and, Substituent group β2 is the group consisting of a $C_1$-$C_4$ alkyl group, a hydroxymethyl group, a 1-hydroxyethyl group, a trifluoromethyl group, a 2,2,2-trifluoroethyl group, a pentafluoroethyl group, a $C_2$-$C_4$ alkenyl group, a $C_2$-$C_4$ alkynyl group, a $C_3$-$C_4$ cycloalkyl group, a hydroxyl group, a methoxy group, an ethoxy group, a methanesulfonyl group, an ethanesulfonyl group, an amino group, a methylamino group, an ethylamino group, a dimethylamino group, a diethylamino group, a formyl group, a methylcarbonyl group, an ethylcarbonyl group, a cyano group, a nitro group, a fluoro group and a chloro group.

32. A compound or a pharmacologically acceptable salt or ester thereof according to claim 1, wherein $Y^2$ is a phenyl group (wherein the substitution positions where $Y^1$ and $R^8$ are bonded to said phenyl group are the 1 and 4 positions, respectively), a substituted phenyl group (wherein said substituents may be the same or different and are one or two groups selected from Substituent group β3, and the substitution positions where $Y^1$ and $R^8$ are bonded to said phenyl group are the 1 and 4 positions, respectively); and, Substituent group β3 is the group consisting of a methyl group, an ethyl group, a 2-propyl group, a hydroxymethyl group, a trifluoromethyl group, a cyclopropyl group, a methoxy group, a methanesulfonyl group, an amino group, a methylamino group, a dimethylamino group, a methylcarbonyl group, an ethylcarbonyl group, a cyano group, a nitro group, a fluoro group and a chloro group.

33. A compound or a pharmacologically acceptable salt or ester thereof according to claim 1, wherein $Y^2$ is a phenyl group (wherein the substitution positions where $Y^1$ and $R^8$ are bonded to said phenyl group are the 1 and 4 positions, respectively), a substituted phenyl group (wherein said substituents may be the same or different and are a group selected from Substituent group β3 or two groups selected from Substituent group β4, and the substitution positions where $Y^1$ and $R^8$ are bonded to said phenyl group are the 1 and 4 positions, respectively); and, Substituent group β4 is the group consisting of a methyl group, an ethyl group and a fluoro group.

34. A compound or a pharmacologically acceptable salt or ester thereof according to claim 1, wherein $Y^2$ is a phenyl group (wherein the substitution positions where $Y^1$ and $R^8$ are bonded to said phenyl group are the 1 and 4 positions, respectively), or a substituted phenyl group (wherein said substituent is a group selected from Substituent group β5, two methyl groups or two fluoro groups, and the substitution positions where $Y^1$ and $R^8$ are bonded to said phenyl group are the 1 and 4 positions, respectively); and, Substituent group β5 is the group consisting of a methyl group, an ethyl group, a 2-propyl group, a trifluoromethyl group, a nitro group, a fluoro group and a chloro group.

35. A compound or a pharmacologically acceptable salt or ester thereof according to claim 1, wherein $Y^2$ is a phenyl group (wherein the substitution positions where $Y^1$ and $R^8$ are bonded to said phenyl group are the 1 and 3 positions, respectively), a substituted phenyl group (wherein said substituent is a group selected from Substituent group β6, and the substitution positions where $Y^1$, $R^8$ and the substituent are bonded to said phenyl group are the 1, 3 and 2 positions, respectively); and, Substituent group β6 is the group consisting of a $C_1$-$C_4$ alkyl group, a methoxy group, a fluoro group and a chloro group.

36. A compound or a pharmacologically acceptable salt or ester thereof according to claim 1, wherein $Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β7, and the substitution positions where $Y^1$, $R^8$ and the substituent are bonded to said phenyl group are the 1, 3 and 2 positions, respectively); and, Substituent group β7 is the group consisting of a methyl group, an ethyl group, a methoxy group and a fluoro group.

37. A compound or a pharmacologically acceptable salt or ester thereof according to claim 1, wherein $R^1$ is a group having the formula —$COR^{9a}$ [wherein $R^{9a}$ represents a $C_1$-$C_6$ alkyl group, a $C_1$-$C_8$ alkoxy group, a halogeno $C_1$-$C_6$ alkoxy group (wherein said halogeno $C_1$-$C_6$ alkoxy group represents a $C_1$-$C_6$ alkoxy group substituted with 1 to 7 halogeno groups), a $C_1$-$C_6$ alkylamino group or a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)];

$R^2$ is a hydrogen atom, a trifluoromethyl group, a 2,2,2-trifluoroethyl group, a pentafluoroethyl group, a hydroxyl group, a fluoro group or a chloro group;

$R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_2$-$C_4$ alkenyl group, a $C_2$-$C_4$ alkynyl group, a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a fluoro group, a chloro group or a bromo group;

$R^4$ and $R^5$ may be the same or different and each is a hydrogen atom, a methyl group, an ethyl group, a trifluoromethyl group, a cyclopropyl group, a hydroxyl group, a methoxy group, a fluoro group, a chloro group or a bromo group;

$R^6$ and $R^7$ may be the same or different and each is a hydrogen atom or a methyl group;

$R^8$ is a group having the formula —$X^{2a}R^{10a}$ [wherein $R^{10a}$ represents a group having the formula —$COR^{11a}$ [wherein $R^{11a}$ represents a hydroxyl group, a $C_1$-$C_4$ alkoxy group, a ($C_3$-$C_6$ cycloalkyl)-($C_1$-$C_4$ alkyl)oxy group, a $C_3$-$C_6$ cycloalkyloxy group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group, a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a hydroxylamino group or a hydroxyl($C_1$-$C_4$ alkyl)amino group], a group having the formula —$SO_2R^{12a}$ [wherein $R^{12a}$ represents a $C_1$-$C_4$ alkyl group, a ($C_3$-$C_6$ cycloalkyl)-($C_1$-$C_4$ alkyl) group, a $C_3$-$C_6$ cycloalkyl group, an amino group, a $C_1$-$C_4$ alkylamino group, a [($C_3$-$C_6$ cycloalkyl)-($C_1$-$C_4$ alkyl)]amino group, a $C_3$-$C_6$ cycloalkylamino group or a di($C_1$-$C_4$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], a group having the formula —$N(R^{13a})COR^{14a}$ [wherein $R^{13a}$ represents a hydrogen atom, a $C_1$-$C_4$ alkyl group, a ($C_3$-$C_5$ cycloalkyl)-($C_1$-$C_2$ alkyl) group or a $C_3$-$C_5$ cycloalkyl group, and $R^{14a}$ represents a hydrogen atom, a $C_1$-$C_4$ alkyl group, a ($C_3$-$C_5$ cycloalkyl)-($C_1$-$C_2$ alkyl) group or a $C_3$-$C_5$ cycloalkyl group], a group having the formula —$N(R^{13a})SO_2R^{15a}$ [wherein $R^{13a}$ is the same as previously defined, and $R^{15a}$ represents a $C_1$-$C_4$ alkyl group, a ($C_3$-$C_5$ cycloalkyl)-($C_1$-$C_2$ alkyl) group or a $C_3$-$C_5$ cycloalkyl group], or a tetrazol-5-yl group, and $X^{2a}$ represents a single bond, a $C_1$-$C_2$ alkylene group or a substituted $C_1$-$C_2$ alkylene group (wherein said substituents may be the same or different and are one or two groups selected from Substituent group γ1, or two of said substituents may together form a methylene group, an ethylene group or a trimethylene group)];

$X^1$ is a group having the formula —NH—, —O— or —S—;

$Y^1$ is a phenyl group or a substituted phenyl group (wherein said substituents may be the same or different and are one or two groups selected from Substituent group α1); and, $Y^2$ is a phenyl group, a substituted phenyl group (wherein said substituents may be the same or different and are 1 to 3 groups selected from Substituent group β1), an indanyl or tetrahydronaphthyl group (provided that $Y^1$ is bonded to a benzene ring part in said indanyl or tetrahydronaphthyl group), a substituted indanyl group or a substituted tetrahydronaphthyl group (provided that $Y^1$ is bonded to a benzene ring part in said indanyl or tetrahydronaphthyl group, and said substituents may be the same or different and are 1 to 3 groups selected from Substituent group β1).

38. A compound or a pharmacologically acceptable salt or ester thereof according to claim 1, wherein $R^1$ is a group having the formula —COR$^{9b}$ [wherein R$^{9b}$ represents a $C_1$-$C_6$ alkoxy group or a halogeno $C_1$-$C_4$ alkoxy group (wherein said halogeno $C_1$-$C_4$ alkoxy group represents a $C_1$-$C_4$ alkoxy group substituted with 1 to 5 halogeno groups)];

$R^2$ is a hydrogen atom or a hydroxyl group;

$R^3$ is a hydrogen atom, a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a $C_3$-$C_5$ cycloalkyl group, a $C_2$-$C_4$ alkenyl group, a $C_1$-$C_4$ alkoxy group, a fluoro group or a chloro group;

$R^4$ is a hydrogen atom and $R^5$ is a hydrogen atom or a hydroxyl group;

$R^6$ and $R^7$ are hydrogen atoms;

$R^8$ is a group having the formula —X$^{2b}$R$^{10b}$ [wherein R$^{10b}$ represents a group having the formula —COR$^{11b}$ [wherein R$^{11b}$ represents a hydroxyl group, a $C_1$-$C_4$ alkoxy group, a ($C_3$-$C_5$ cycloalkyl)-($C_1$-$C_2$ alkyl)oxy group, a $C_3$-$C_5$ cycloalkyloxy group, an amino group, a methylamino group, an ethylamino group, dimethylamino group, a diethylamino group, a methylethylamino group or a hydroxylamino group], a group having the formula —SO$_2$R$^{12b}$ [wherein R$^{12b}$ represents a $C_1$-$C_4$ alkyl group, a ($C_3$-$C_5$ cycloalkyl)-($C_1$-$C_2$ alkyl) group or a $C_3$-$C_5$ cycloalkyl group], or a tetrazol-5-yl group, and $X^{2b}$ represents a single bond, a methylene group, an ethylene group or a substituted methylene group or a substituted ethylene group (wherein said substituents may be the same or different and are one or two groups selected from Substituent group γ2, or two of said substituents may together form an ethylene group or a trimethylene group)];

$X^1$ is a group having the formula —O—;

$Y^1$ is a phenyl group (wherein the substitution positions where $X^1$ and $Y^2$ are bonded to said phenyl group are the 1 and 3 positions or the 1 and 4 positions, respectively), a substituted phenyl group (wherein said substituents represent a group selected from Substituent group α2, and the substitution positions where $X^1$ and $Y^2$ are bonded to said phenyl group are the 1 and 3 positions or the 1 and 4 positions, respectively); and, $Y^2$ is a phenyl group (wherein the substitution positions where $Y^1$ and $R^8$ are bonded to said phenyl group are the 1 and 3 positions or the 1 and 4 positions, respectively), a substituted phenyl group (wherein said substituents may be the same or different and are one or two groups selected from Substituent group β2, and the substitution positions where $Y^1$ and $R^8$ are bonded to said phenyl group are the 1 and 3 positions or the 1 and 4 positions, respectively).

39. A compound or a pharmacologically acceptable salt or ester thereof according to claim 1, wherein $R^1$ is a group having the formula —COR$^{9c}$ (wherein R$^{9c}$ represents a $C_3$-$C_5$ alkoxy group);

$R^2$ is a hydroxyl group;

$R^3$ is a methyl group, an ethyl group, a 2-propyl group, a 2-methyl-2-propyl group, a trifluoromethyl group, a 2,2,2-trifluoroethyl group, a methoxy group, a fluoro group or a chloro group;

$R^4$ and $R^5$ are hydrogen atoms;

$R^6$ and $R^7$ are hydrogen atoms;

$R^8$ is a group having the formula —X$^{2c}$R$^{10c}$ [wherein R$^{10c}$ represents a group having the formula —COR$^{11c}$ (wherein R$^{11c}$ represents a hydroxyl group or a methoxy group), or a group having the formula —SO$_2$R$^{12c}$ (wherein R$^{12c}$ represents a methyl group), and $X^{2c}$ represents a single bond, a methylene group or a substituted methylene group (wherein said substituent is a group selected from Substituent group γ3, or two of said substituents may together form an ethylene group)];

$X^1$ is a group having the formula —O—;

$Y^1$ is a phenyl group (wherein the substitution positions where $X^1$ and $Y^2$ are bonded to said phenyl group are the 1 and 4 positions, respectively); and, $Y^2$ is a phenyl group (wherein the substitution positions where $Y^1$ and $R^8$ are bonded to said phenyl group are the 1 and 3 positions or the 1 and 4 positions, respectively) or a substituted phenyl group (wherein said substituents may be the same or different and are one or two groups selected from Substituent group β2, and the substitution positions where $Y^1$ and $R^8$ are bonded to said phenyl group are the 1 and 3 positions or the 1 and 4 positions, respectively).

40. A compound or a pharmacologically acceptable salt or ester thereof according to claim 1, wherein $R^1$ is a group having the formula —COR$^{9d}$ (wherein R$^{9d}$ represents a 2-methyl-2-propoxy group);

$R^2$ is a hydroxyl group;

$R^3$ is a 2-propyl group, a 2-methyl-2-propyl group, a trifluoromethyl group or a chloro group;

$R^4$ and $R^5$ are hydrogen atoms;

$R^6$ and $R^7$ are hydrogen atoms;

$R^8$ is a group having the formula —X$^{2d}$R$^{10d}$ [wherein R$^{10d}$ represents a group having the formula —COR$^{11d}$ (wherein R$^{11d}$ represents a hydroxyl group), and $X^{2d}$ is a methylene group or a substituted methylene group (wherein said substituent is a group selected from Substituent group γ4, or two of said substituents may together form an ethylene group)];

$X^1$ is a group having the formula —O—;

$Y^1$ is a phenyl group (wherein the substitution positions where $X^1$ and $Y^2$ are bonded to said phenyl group are the 1 and 4 positions, respectively); and, $Y^2$ is a phenyl group (wherein the substitution positions where $Y^1$ and $R^8$ are bonded to said phenyl group are the 1 and 4 positions, respectively) or a substituted phenyl group (wherein said substituents may be the same or different and are one or two groups selected from Substituent group β3, and the substitution positions where $Y^1$ and $R^8$ are bonded to said phenyl group are the 1 and 4 positions, respectively).

41. A compound or a pharmacologically acceptable salt or ester thereof according to claim 1, wherein
$R^1$ is a group having the formula —$COR^{9d}$ (wherein $R^{9d}$ represents a 2-methyl-2-propoxy group);
$R^2$ is a hydroxyl group;
$R^3$ is a trifluoromethyl group;
$R^4$ and $R^5$ are hydrogen atoms;
$R^6$ and $R^7$ are hydrogen atoms;
$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];
$X^1$ is a group having the formula —O—;
$Y^1$ is a phenyl group (wherein the substitution positions where $X^1$ and $Y^2$ are bonded to said phenyl group are the 1 and 4 positions); and,
$Y^2$ is a phenyl group (wherein the substitution positions where $Y^1$ and $R^8$ are bonded to said phenyl group are the 1 and 4 positions, respectively), a substituted phenyl group (wherein said substituents may be the same or different and are a group selected from Substituent group β3 or two groups selected from Substituent group β4, and the substitution positions where $Y^1$ and $R^8$ are bonded to said phenyl group are the 1 and 4 positions, respectively).

42. A compound or a pharmacologically acceptable salt or ester thereof according to claim 1, wherein
$R^1$ is a group having the formula —$COR^{9d}$ (wherein $R^{9d}$ represents a 2-methyl-2-propoxy group);
$R^2$ is a hydroxyl group;
$R^3$ is a trifluoromethyl group;
$R^4$ and $R^5$ are hydrogen atoms;
$R^6$ and $R^7$ are hydrogen atoms;
$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];
$X^1$ is a group having the formula —O—;
$Y^1$ is a phenyl group (wherein the substitution positions where $X^1$ and $Y^2$ are bonded to said phenyl group are the 1 and 4 positions); and,
$Y^2$ is a phenyl group (wherein the substitution positions where $Y^1$ and $R^8$ are bonded to said phenyl group are the 1 and 4 positions, respectively) or a substituted phenyl group (wherein said substituent is a group selected from Substituent group β5, two methyl groups or two fluoro groups, and the substitution positions where $Y^1$ and $R^8$ are bonded to said phenyl group are the 1 and 4 positions, respectively).

43. A compound or a pharmacologically acceptable salt or ester thereof according to claim 1, wherein
$R^1$ is a group having the formula —$COR^{9d}$ (wherein $R^{9d}$ represents a 2-methyl-2-propoxy group);
$R^2$ is a hydroxyl group;
$R^3$ is a trifluoromethyl group;
$R^4$ and $R^5$ are hydrogen atoms;
$R^6$ and $R^7$ are hydrogen atoms;
$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];
$X^1$ is a group having the formula —O—;
$Y^1$ is a phenyl group (wherein the substitution positions where $X^1$ and $Y^2$ are bonded to said phenyl group are the 1 and 4 positions); and,
$Y^2$ is a phenyl group (wherein the substitution positions where $Y^1$ and $R^8$ are bonded to said phenyl group are the 1 and 3 positions, respectively), a substituted phenyl group (wherein said substituent is a group selected from Substituent group β6, and the substitution positions where $Y^1$, $R^8$ and the substituent are bonded to said phenyl group are the 1, 3 and 2 positions, respectively).

44. A compound or a pharmacologically acceptable salt or ester thereof according to claim 1, wherein
$R^1$ is a group having the formula —$COR^{9d}$ (wherein $R^{9d}$ represents a 2-methyl-2-propoxy group);
$R^2$ is a hydroxyl group;
$R^3$ is a trifluoromethyl group;
$R^4$ and $R^5$ are hydrogen atoms;
$R^6$ and $R^7$ are hydrogen atoms;
$R^8$ is a group having the formula —$X^{2e}R^{10e}$ [wherein $R^{10e}$ represents a group having the formula —$COR^{11e}$ (wherein $R^{11e}$ represents a hydroxyl group), and $X^{2e}$ represents a methylene group or a substituted methylene group (wherein said substituent is a methyl group)];
$X^1$ is a group having the formula —O—;
$Y^1$ is a phenyl group (wherein the substitution positions where $X^1$ and $Y^2$ are bonded to said phenyl group are the 1 and 4 positions); and,
$Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β7, and the substitution positions where $Y^1$, $R^8$ and the substituent are bonded to said phenyl group are the 1, 3 and 2 positions, respectively).

45. A compound or a pharmacologically acceptable salt or ester thereof according to claim 1, wherein
$R^1$ is a group having the formula —$COR^{9d}$ (wherein $R^{9d}$ represents a 2-methyl-2-propoxy group);
$R^2$ is a hydroxyl group;
$R^3$ is a trifluoromethyl group;
$R^4$ and $R^5$ are hydrogen atoms;
$R^6$ and $R^7$ are hydrogen atoms;
$R^8$ is a group having the formula —$X^{2f}R^{10f}$ [wherein $R^{10f}$ represents a group having the formula —$SO_2R^{12f}$ (wherein $R^{12f}$ represents a methyl group), and $X^{2f}$ represents a single bond];
$X^1$ is a group having the formula —O—;
$Y^1$ is a phenyl group (wherein the substitution positions where $X^1$ and $Y^2$ are bonded to said phenyl group are the 1 and 4 positions); and,
$Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β6, and the substitution positions where $Y^1$, $R^8$ and the substituent are bonded to said phenyl group are the 1, 3 and 2 positions, respectively).

46. A compound or a pharmacologically acceptable salt or ester thereof according to claim 1, wherein
$R^1$ is a group having the formula —$COR^{9d}$ (wherein $R^{9d}$ represents a 2-methyl-2-propoxy group);
$R^2$ is a hydroxyl group;
$R^3$ is a trifluoromethyl group;
$R^4$ and $R^5$ are hydrogen atoms;

213

$R^6$ and $R^7$ are hydrogen atoms;

$R^8$ is a group having the formula —$X^{2f}R^{10f}$ [wherein $R^{10f}$ represents a group having the formula —$SO_2R^{12f}$ (wherein $R^{12f}$ represents a methyl group), and $X^{2f}$ represents a single bond];

$X^1$ is a group having the formula —O—;

$Y^1$ is a phenyl group (wherein the substitution positions where $X^1$ and $Y^2$ are bonded to said phenyl group are the 1 and 4 positions); and, $Y^2$ is a phenyl group (wherein the substitution positions where $Y^1$ and $R^8$ are bonded to said phenyl group are the 1 and 3 positions, respectively) or a substituted phenyl group (wherein said substituent is a group selected from Substituent group β7, and the substitution positions where $Y^1$, $R^8$ and the substituent are bonded to said phenyl group are the 1, 3 and 2 positions, respectively).

47. A compound or a pharmacologically acceptable salt or ester thereof according to claim 1 selected from the group consisting of (4'-{[2-(tert-butoxycarbonyl)-3-hydroxy-4-(trifluoromethyl)benzyl]oxy}-1,1'-biphenyl-4-yl)acetic acid, 2-(4'-{[2-(tert-butoxycarbonyl)-3-hydroxy-4-(trifluoromethyl)benzyl]oxy}-1,1'-biphenyl-4-yl)propanoic acid, 1-(4'-{[2-(tert-butoxycarbonyl)-3-hydroxy-4-(trifluoromethyl)benzyl]oxy}-1,1'-biphenyl-4-yl)cyclopropanecarboxylic acid, 2-(4'-{[2-(tert-butoxycarbonyl)-3-hydroxy-4-(trifluoromethyl)benzyl]oxy}-1,1'-biphenyl-4-yl)-3-hydroxypropanoic acid, 2-[4'-{[2-(tert-butoxycarbonyl)-3-hydroxy-4-(trifluoromethyl)benzyl]oxy}-1,1'-biphenyl-4-yl]butanoic acid, (4'-{[2-(tert-butoxycarbonyl)-3-hydroxy-4-(trifluoromethyl)benzyl]oxy}-2-methyl-1,1'-biphenyl-3-yl)acetic acid, (4'-{[2-(tert-butoxycarbonyl)-3-hydroxy-4-(trifluoromethyl)benzyl]oxy}-2-methyl-1,1'-biphenyl-4-yl)acetic acid, (4'-{[2-(tert-butoxycarbonyl)-3-hydroxy-4-(trifluoromethyl)benzyl]oxy}-2-chloro-1,1'-biphenyl-4-yl)acetic acid, (4'-{[2-(tert-butoxycarbonyl)-3-hydroxy-4-(trifluoromethyl)benzyl]oxy}-3-fluoro-1,1'-biphenyl-4-yl)acetic acid, (4'-{[2-(tert-butoxycarbonyl)-3-hydroxy-4-(trifluoromethyl)benzyl]oxy}-3-chloro-1,1'-biphenyl-4-yl)acetic acid, 2-(4'-{[2-(tert-butoxycarbonyl)-3-hydroxy-4-(trifluoromethyl)benzyl]oxy}-2-methoxy-1,1'-biphenyl-3-yl)propanoic acid, 2-(4'-{[2-(tert-butoxycarbonyl)-3-hydroxy-4-(trifluoromethyl)benzyl]oxy}-3-fluoro-1,1'-biphenyl-4-yl)propanoic acid, 1-(4'-{[2-(tert-butoxycarbonyl)-3-hydroxy-4-(trifluoromethyl)benzyl]oxy}-3-fluoro-1,1'-biphenyl-4-yl)cyclopropanecarboxylic acid, (4'-{[2-(tert-butoxycarbonyl)-3-hydroxy-4-(trifluoromethyl)benzyl]oxy}-3-methoxy-1,1'-biphenyl-4-yl)acetic acid, (4'-{[2-(tert-butoxycarbonyl)-3-hydroxy-4-(trifluoromethyl)benzyl]oxy}-2-trifluoromethyl-1,1'-biphenyl-4-yl)acetic acid, (4'-{[2-(tert-butoxycarbonyl)-3-hydroxy-4-(trifluoromethyl)benzyl]oxy}-2-ethyl-1,1'-biphenyl-4-yl)acetic acid, tert-butyl 6-[({2'-ethyl-4'-[(methoxycarbonyl)methyl]-1,1'-biphenyl-4-yl}oxy)methyl]-2-hydroxy-3-(trifluoromethyl)benzoate, (4'-{[2-(tert-butoxycarbonyl)-3-hydroxy-4-(trifluoromethyl)benzyl]oxy}-2-nitro-1,1'-biphenyl-4-yl)acetic acid,

214

(2-amino-4'-{[2-(tert-butoxycarbonyl)-3-hydroxy-4-(trifluoromethyl)benzyl]oxy}-1,1'-biphenyl-4-yl)acetic acid, (4'-{[2-(tert-butoxycarbonyl)-3-hydroxy-4-(trifluoromethyl)benzyl]oxy}-2-isopropyl-1,1'-biphenyl-4-yl)acetic acid, (4'-{[2-(tert-butoxycarbonyl)-3-hydroxy-4-(trifluoromethyl)benzyl]oxy}-2-formyl-1,1'-biphenyl-4-yl)acetic acid, (4'-{[2-(tert-butoxycarbonyl)-3-hydroxy-4-(trifluoromethyl)benzyl]oxy}-2-(hydroxymethyl)-1,1'-biphenyl-4-yl)acetic acid, (4'-{[2-(tert-butoxycarbonyl)-3-hydroxy-4-(trifluoromethyl)benzyl]oxy}-2-cyano-1,1'-biphenyl-4-yl)acetic acid, (4'-{[2-(tert-butoxycarbonyl)-3-hydroxy-4-(trifluoromethyl)benzyl]oxy}-2-cyclopropyl-1,1'-biphenyl-4-yl)acetic acid, (4'-{[2-(tert-butoxycarbonyl)-3-hydroxy-4-(trifluoromethyl)benzyl]oxy}-3-ethyl-1,1'-biphenyl-4-yl)acetic acid, (4'-{[2-(tert-butoxycarbonyl)-3-hydroxy-4-(trifluoromethyl)benzyl]oxy}-2-ethyl-1,1'-biphenyl-3-yl)acetic acid, 2-(4'-{[2-(tert-butoxycarbonyl)-3-hydroxy-4-(trifluoromethyl)benzyl]oxy}-3-fluoro-1,1'-biphenyl-4-yl)-3-(dimethylamino)propanoic acid, 2-(4'-{[2-(tert-butoxycarbonyl)-3-hydroxy-4-(trifluoromethyl)benzyl]oxy}-2-ethyl-1,1'-biphenyl-4-yl)propanoic acid, 2-(4'-{[2-(tert-butoxycarbonyl)-3-hydroxy-4-(trifluoromethyl)benzyl]oxy}-2-nitro-1,1'-biphenyl-4-yl)propanoic acid, 2-(4'-{[2-(tert-butoxycarbonyl)-3-hydroxy-4-(trifluoromethyl)benzyl]oxy}-2-isopropyl-1,1'-biphenyl-4-yl)propanoic acid, 2-(4'-{[2-(tert-butoxycarbonyl)-3-hydroxy-4-(trifluoromethyl)benzyl]oxy}-2,3-dimethyl-1,1'-biphenyl-4-yl)propanoic acid, and 2-(4'-{[2-(tert-butoxycarbonyl)-3-hydroxy-4-(trifluoromethyl)benzyl]oxy}-2-cyclopropyl-1,1'-biphenyl-4-yl)propanoic acid.

48. A compound or a pharmacologically acceptable salt or ester thereof according to claim 1, wherein $R^{11}$ in the group having the formula —$COR^{11}$ represented in $R^{10}$ of the group having the formula —$X^2R^{10}$ in $R^8$ is a hydroxyl group, a $C_1$-$C_6$ alkoxy group, a ($C_3$-$C_8$ cycloalkyl)-($C_1$-$C_6$ alkyl)oxy group, a $C_3$-$C_8$ cycloalkyloxy group, an amino group, a $C_1$-$C_6$ alkylamino group, a [($C_3$-$C_8$ cycloalkyl)-($C_1$-$C_6$ alkyl)] amino group, a $C_3$-$C_8$ cycloalkylamino group, a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom), a di[($C_3$-$C_8$ cycloalkyl)-($C_1$-$C_6$ alkyl)]amino group, a di($C_3$-$C_8$ cycloalkyl)amino group, a N—[($C_3$-$C_8$ cycloalkyl)-($C_1$-$C_6$ alkyl)]-N—($C_1$-$C_6$ alkyl)amino group, a N—($C_3$-$C_8$ cycloalkyl)-N—($C_1$-$C_6$ alkyl)amino group, a N—[($C_3$-$C_8$ cycloalkyl)-($C_1$-$C_6$ alkyl)]-N—($C_3$-$C_8$ cycloalkyl)amino group, a hydroxylamino group or a hydroxyl($C_1$-$C_6$ alkyl)amino group, and $X^2$ in the group having the formula —$X^2R^{10}$ is $R^8$ is a single bond, a $C_1$-$C_4$ alkylene group or a substituted $C_1$-$C_4$ alkylene group (wherein said substituents may be the same or different and are one or two groups selected from Substituent group γ, or two of said substituents may together form an ethylene group or a trimethylene group).

49. A compound or a pharmacologically acceptable salt or ester thereof according to claim 1, wherein $R^8$ is a group having the formula $-X^{2g}R^{10g}$ [wherein $R^{10g}$ represents a group having the formula $-COR^{11g}$ [wherein $R^{11g}$ represents a hydroxyl group, a $C_1$-$C_6$ alkoxy group, an amino group, a $C_1$-$C_6$ alkylamino group or a di($C_1$-$C_6$ alkyl)amino group (wherein said alkyl groups may be the same or different and two of said alkyl groups may, together with the nitrogen atom of said amino group, form a 5- to 7-membered saturated heterocyclyl group containing 1 to 3 atoms selected from the group consisting of a nitrogen atom, an oxygen atom and a sulfur atom)], or a tetrazol-5-yl group, and $X^{2g}$ represents a single bond, a $C_1$-$C_4$ alkylene group or a substituted $C_1$-$C_4$ alkylene group (wherein said substituents may be the same or different and are one or two groups selected from a group consisting of a $C_1$-$C_4$ alkyl group and a halogeno group, and two of said substituents may together form a methylene group or a trimethylene group)];

$Y^1$ is a phenyl group or a substituted phenyl group (wherein said substituents may be the same or different and are 1 to 3 groups selected from Substituent group δ);

$Y^2$ is a phenyl group or a substituted phenyl group (wherein said substituents may be the same or different and are 1 to 3 groups selected from Substituent group δ); and, Substituent group δ is the group consisting of a $C_1$-$C_4$ alkyl group, a halogeno $C_1$-$C_4$ alkyl group (wherein said halogeno $C_1$-$C_4$ alkyl group represents a $C_1$-$C_4$ alkyl group substituted with 1 to 5 halogeno groups), a hydroxyl group, a $C_1$-$C_4$ alkoxy group, a halogeno $C_1$-$C_4$ alkoxy group (wherein said halogeno $C_1$-$C_4$ alkoxy group represents a $C_1$-$C_4$ alkoxy group substituted with 1 to 5 halogeno groups), a $C_1$-$C_4$ alkylthio group, a $C_1$-$C_4$ alkylsulfinyl group, a $C_1$-$C_4$ alkylsulfonyl group, an amino group, a $C_1$-$C_4$ alkylamino group, a di($C_1$-$C_4$ alkyl)amino group (wherein said alkyl groups may be the same or different), a carboxyl group, a ($C_1$-$C_4$ alkoxy)carbonyl group, a cyano group and a halogeno group.

50. An LXR modulator comprising a compound represented by the general formula (I) or a pharmacologically acceptable salt or ester thereof according to claim 1.

51. An LXR agonist comprising a compound represented by the general formula (I) or a pharmacologically acceptable salt or ester thereof according to claim 1.

52. A pharmaceutical composition comprising as an active ingredient a compound represented by the general formula (I) or a pharmacologically acceptable salt or ester thereof according to claim 1.

53. A pharmaceutical composition according to claim 52 for inducing ABCA1 expression.

54. A pharmaceutical composition according to claim 52 for promoting reverse cholesterol transport.

55. A pharmaceutical composition according to claim 52 for treating arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease or diabetes.

56. A pharmaceutical composition according to claim 52 for treating arteriosclerosis, atherosclerosis, arteriosclerosis caused by diabetes, arteriosclerotic heart disease, cardiovascular disease or coronary artery disease.

57. A pharmaceutical composition according to claim 52 for treating arteriosclerosis.

58. A pharmaceutical composition according to claim 52 for treating arteriosclerotic heart disease.

59. A method for inducing ABCA1 expression by administering an effective amount of a compound represented by the general formula (I) or a pharmacologically acceptable salt or ester thereof according to claim 1 to a warm-blooded animal.

60. A method for promoting reverse cholesterol transport by administering an effective amount of a compound represented by the general formula (I) or a pharmacologically acceptable salt or ester thereof according to claim 1 to a warm-blooded animal.

61. A method for treating arteriosclerosis, atherosclerosis, arteriosclerosis caused by diabetes, hyperlipemia, hypercholesterolemia, lipid-associated diseases, inflammatory disease, arteriosclerotic heart disease, cardiovascular disease, coronary artery disease or diabetes by administering an effective amount of a compound represented by the general formula (I) or a pharmacologically acceptable salt or ester thereof according to claim 1, to a warm-blooded animal.

62. A method according to claim 61, wherein the disease is arteriosclerosis.

63. A method according to claim 61, wherein the disease is arteriosclerotic heart disease.

64. A pharmaceutical composition comprising as an active ingredient a compound represented by the general formula (I) or a pharmacologically acceptable salt or ester thereof according to claim 1; and one or more pharmaceutical(s) selected from the group consisting of an HMG-CoA reductase inhibitor, CETP inhibitor, ACAT inhibitor, cholesterol absorption inhibitor, bile acid adsorption ion exchange resin, fibrate-based medicine, nicotinic acid derivative, angiotensin II inhibitor and diuretic.

65. A pharmaceutical composition comprising as an active ingredient a compound represented by the general formula (I) or pharmacologically acceptable salt or ester thereof according to claim 1; and one or more pharmaceutical(s) selected from the group consisting of an HMG-CoA reductase inhibitor, CETP inhibitor and cholesterol absorption inhibitor.

66. A pharmaceutical composition comprising as an active ingredient a compound represented by the general formula (I) or a pharmacologically acceptable salt or ester thereof according to claim 1 and an HMG-CoA reductase inhibitor.

67. A pharmaceutical composition according to claim 66, wherein the HMG-CoA reductase inhibitor is pravastatin, lovastatin, simvastatin, fluvastatin, cerivastatin, atorvastatin, pitavastatin or rosuvastatin.

68. A pharmaceutical composition according to claim 66, wherein the HMG-CoA reductase inhibitor is pravastatin, atorvastatin or rosuvastatin.

69. A method according to claim 59, wherein the warm-blooded animal is a human.

70. A method according to claim 60, wherein the warm-blooded animal is a human.

71. A method according to claim 61, wherein the warm-blooded animal is a human.

72. A method according to claim 61, wherein the disease is arteriosclerosis, atherosclerosis, arteriosclerosis caused by diabetes, arteriosclerotic heart disease, cardiovascular disease or coronary artery disease.

73. A method according to claim 62, wherein the warm-blooded animal is a human.

74. A method according to claim 63, wherein the warm-blooded animal is a human.

75. A method according to claim 72, wherein the warm-blooded animal is a human.

* * * * *